(12) United States Patent
Swayze et al.

(10) Patent No.: US 9,220,500 B2
(45) Date of Patent: Dec. 29, 2015

(54) TISSUE THICKNESS COMPENSATOR COMPRISING STRUCTURE TO PRODUCE A RESILIENT LOAD

(75) Inventors: Jeffrey S. Swayze, Hamilton, OH (US); Frederick E. Shelton, IV, Hillsboro, OH (US); Tamara Widenhouse, Clarksville, OH (US); Christopher W. Widenhouse, Clarksville, OH (US); Taylor W. Aronhalt, Loveland, OH (US); Charles J. Scheib, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 659 days.

(21) Appl. No.: 13/433,148

(22) Filed: Mar. 28, 2012

(65) Prior Publication Data

US 2012/0241501 A1 Sep. 27, 2012

Related U.S. Application Data

(63) Continuation-in-part of application No. 13/097,891, filed on Apr. 29, 2011, now Pat. No. 8,864,009, which is a continuation-in-part of application No. 12/894,377, filed on Sep. 30, 2010, now Pat. No. 8,393,514.

(51) Int. Cl.
*A61B 17/072* (2006.01)
*A61B 17/064* (2006.01)
(Continued)

(52) U.S. Cl.
CPC ....... *A61B 17/0643* (2013.01); *A61B 17/00491* (2013.01); *A61B 17/072* (2013.01);
(Continued)

(58) Field of Classification Search
CPC ............. A61B 17/11; A61B 17/07207; A61B 17/0644
USPC ........... 227/175.1, 176.1, 178.1, 179.1, 180.1
See application file for complete search history.

(56) References Cited

U.S. PATENT DOCUMENTS 66,052 A 6/1867 Smith
662,587 A 11/1900 Blake
(Continued)

FOREIGN PATENT DOCUMENTS

AU 2008207624 A1 3/2009
AU 2010214687 A1 9/2010
(Continued)

OTHER PUBLICATIONS

ASTM procedure D2240-00, "Standard Test Method for Rubber Property-Durometer Hardness," (Published Aug. 2000).
(Continued)

*Primary Examiner* — Nathaniel Chukwurah

(57) ABSTRACT

A fastener cartridge assembly for an end effector of a surgical instrument can comprise a cartridge body, a deformable tube, and a fastener moveable between an initial position and a fired position. The deformable tube can be longitudinally positioned along a length of the cartridge body. When the fastener is moved to the fired position, the fastener can compress a portion of the deformable tube. The deformable tube can comprise a resilient material such that deformation of the deformable tube generates a restoring force. The deformable tube can comprise a lattice of strands woven together to form a tube wall. Further, the deformable tube can be bioabsorbable and can hold a therapeutic agent. The fastener cartridge assembly can comprise multiple, substantially parallel deformable tubes positioned side-by-side and/or within each other.

20 Claims, 143 Drawing Sheets

(51) Int. Cl.
*A61B 17/00* (2006.01)
*A61B 17/115* (2006.01)
*A61B 17/29* (2006.01)
*A61B 17/32* (2006.01)

(52) U.S. Cl.
CPC ..... *A61B17/07207* (2013.01); *A61B 17/07292* (2013.01); *A61B 17/1155* (2013.01); *A61B 17/0644* (2013.01); *A61B 17/2909* (2013.01); *A61B 2017/00004* (2013.01); *A61B 2017/0053* (2013.01); *A61B 2017/00314* (2013.01); *A61B 2017/00327* (2013.01); *A61B 2017/00526* (2013.01); *A61B 2017/00818* (2013.01); *A61B 2017/07228* (2013.01); *A61B 2017/07235* (2013.01); *A61B 2017/07242* (2013.01); *A61B 2017/07264* (2013.01); *A61B 2017/07271* (2013.01); *A61B 2017/07278* (2013.01); *A61B 2017/2908* (2013.01); *A61B 2017/2919* (2013.01); *A61B 2017/2923* (2013.01); *A61B 2017/2927* (2013.01); *A61B 2017/2933* (2013.01); *A61B 2017/2936* (2013.01); *A61B 2017/320052* (2013.01)

(56) References Cited

U.S. PATENT DOCUMENTS

| | | | |
|---|---|---|---|
| 670,748 A | 3/1901 | Weddeler | |
| 951,393 A | 3/1910 | Hahn | |
| 1,306,107 A | 6/1919 | Elliott | |
| 1,314,601 A | 9/1919 | McCaskey | |
| 1,677,337 A | 7/1928 | Grove | |
| 2,037,727 A | 4/1936 | La Chapelle | |
| 2,132,295 A | 10/1938 | Hawkins | |
| 2,161,632 A | 6/1939 | Nattenheimer | |
| 2,211,117 A | 8/1940 | Hess | |
| 2,214,870 A | 9/1940 | West | |
| 2,441,096 A | 5/1948 | Happe | |
| 2,526,902 A | 10/1950 | Rublee | |
| 2,674,149 A | 4/1954 | Benson | |
| 2,804,848 A | 9/1957 | O'Farrell et al. | |
| 2,808,482 A | 10/1957 | Zanichkowsky et al. | |
| 2,853,074 A | 9/1958 | Olson | |
| 2,959,974 A | 11/1960 | Emrick | |
| 3,032,769 A | 5/1962 | Palmer | |
| 3,075,062 A | 1/1963 | Iaccarino | |
| 3,078,465 A | 2/1963 | Bobrov | |
| 3,079,606 A | 3/1963 | Bobrov et al. | |
| 3,166,072 A | 1/1965 | Sullivan, Jr. | |
| 3,196,869 A * | 7/1965 | Scholl | 602/30 |
| 3,266,494 A | 8/1966 | Brownrigg et al. | |
| 3,269,630 A | 8/1966 | Fleischer | |
| 3,275,211 A | 9/1966 | Hirsch et al. | |
| 3,317,103 A | 5/1967 | Cullen et al. | |
| 3,317,105 A | 5/1967 | Astafjev et al. | |
| 3,357,296 A | 12/1967 | Lefever | |
| 3,490,675 A | 1/1970 | Green et al. | |
| 3,494,533 A | 2/1970 | Green et al. | |
| 3,499,591 A | 3/1970 | Green | |
| 3,551,987 A | 1/1971 | Wilkinson | |
| 3,572,159 A | 3/1971 | Tschanz | |
| 3,598,943 A | 8/1971 | Barrett | |
| 3,643,851 A | 2/1972 | Green et al. | |
| 3,662,939 A | 5/1972 | Bryan | |
| 3,717,294 A | 2/1973 | Green | |
| 3,734,207 A | 5/1973 | Fishbein | |
| 3,740,994 A | 6/1973 | DeCarlo, Jr. | |
| 3,744,495 A | 7/1973 | Johnson | |
| 3,746,002 A | 7/1973 | Haller | |
| 3,751,902 A | 8/1973 | Kingsbury et al. | |
| 3,819,100 A | 6/1974 | Noiles et al. | |
| 3,821,919 A | 7/1974 | Knohl | |
| 3,841,474 A | 10/1974 | Maier | |
| 3,851,196 A | 11/1974 | Hinds | |
| 3,885,491 A | 5/1975 | Curtis | |
| 3,892,228 A | 7/1975 | Mitsui | |
| 3,894,174 A | 7/1975 | Cartun | |
| 3,940,844 A | 3/1976 | Colby et al. | |
| 3,955,581 A | 5/1976 | Spasiano et al. | |
| RE28,932 E | 8/1976 | Noiles et al. | |
| 3,981,051 A | 9/1976 | Brumlik | |
| 4,054,108 A | 10/1977 | Gill | |
| 4,060,089 A | 11/1977 | Noiles | |
| 4,106,446 A | 8/1978 | Yamada et al. | |
| 4,111,206 A | 9/1978 | Vishnevsky et al. | |
| 4,129,059 A | 12/1978 | Van Eck | |
| 4,169,990 A | 10/1979 | Lerdman | |
| 4,198,734 A | 4/1980 | Brumlik | |
| 4,198,982 A | 4/1980 | Fortner et al. | |
| 4,207,898 A | 6/1980 | Becht | |
| 4,213,562 A | 7/1980 | Garrett et al. | |
| 4,226,242 A | 10/1980 | Jarvik | |
| 4,244,372 A | 1/1981 | Kapitanov et al. | |
| 4,250,436 A | 2/1981 | Weissman | |
| 4,261,244 A | 4/1981 | Becht et al. | |
| 4,272,002 A | 6/1981 | Moshofsky | |
| 4,272,662 A | 6/1981 | Simpson | |
| 4,274,304 A | 6/1981 | Curtiss | |
| 4,275,813 A | 6/1981 | Noiles | |
| 4,289,133 A | 9/1981 | Rothfuss | |
| 4,305,539 A | 12/1981 | Korolkov et al. | |
| 4,312,685 A | 1/1982 | Riedl | |
| 4,317,451 A | 3/1982 | Cerwin et al. | |
| 4,321,002 A | 3/1982 | Froehlich | |
| 4,328,839 A | 5/1982 | Lyons et al. | |
| 4,331,277 A | 5/1982 | Green | |
| 4,340,331 A | 7/1982 | Savino | |
| 4,347,450 A | 8/1982 | Colligan | |
| 4,349,028 A | 9/1982 | Green | |
| 4,353,371 A | 10/1982 | Cosman | |
| 4,379,457 A | 4/1983 | Gravener et al. | |
| 4,380,312 A | 4/1983 | Landrus | |
| 4,382,326 A | 5/1983 | Rabuse | |
| 4,383,634 A | 5/1983 | Green | |
| 4,393,728 A | 7/1983 | Larson et al. | |
| 4,396,139 A | 8/1983 | Hall et al. | |
| 4,397,311 A | 8/1983 | Kanshin et al. | |
| 4,402,445 A | 9/1983 | Green | |
| 4,408,692 A | 10/1983 | Siegel et al. | |
| 4,409,057 A | 10/1983 | Molenda et al. | |
| 4,415,112 A | 11/1983 | Green | |
| 4,416,276 A | 11/1983 | Newton et al. | |
| 4,428,376 A | 1/1984 | Mericle | |
| 4,429,695 A | 2/1984 | Green | |
| 4,434,796 A | 3/1984 | Karapetian et al. | |
| 4,438,659 A | 3/1984 | Desplats | |
| 4,442,964 A | 4/1984 | Becht | |
| 4,451,743 A | 5/1984 | Suzuki et al. | |
| 4,454,887 A | 6/1984 | Krüger | |
| 4,467,805 A | 8/1984 | Fukuda | |
| 4,473,077 A | 9/1984 | Noiles et al. | |
| 4,475,679 A | 10/1984 | Fleury, Jr. | |
| 4,485,816 A | 12/1984 | Krumme | |
| 4,486,928 A | 12/1984 | Tucker et al. | |
| 4,488,523 A | 12/1984 | Shichman | |
| 4,489,875 A | 12/1984 | Crawford et al. | |
| 4,500,024 A | 2/1985 | DiGiovanni et al. | |
| 4,505,272 A | 3/1985 | Utyamyshev et al. | |
| 4,505,273 A | 3/1985 | Braun et al. | |
| 4,505,414 A | 3/1985 | Filipi | |
| 4,506,671 A | 3/1985 | Green | |
| 4,520,817 A | 6/1985 | Green | |
| 4,522,327 A | 6/1985 | Korthoff et al. | |
| 4,526,174 A | 7/1985 | Froehlich | |
| 4,527,724 A | 7/1985 | Chow et al. | |
| 4,530,453 A | 7/1985 | Green | |
| 4,531,522 A | 7/1985 | Bedi et al. | |
| 4,532,927 A | 8/1985 | Miksza, Jr. | |
| 4,548,202 A | 10/1985 | Duncan | |
| 4,565,109 A | 1/1986 | Tsay | |
| 4,565,189 A | 1/1986 | Mabuchi | |
| 4,566,620 A | 1/1986 | Green et al. | |
| 4,571,213 A | 2/1986 | Ishimoto | |

(56) References Cited

U.S. PATENT DOCUMENTS

| | | |
|---|---|---|
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,585,153 A | 4/1986 | Failla et al. |
| 4,589,416 A | 5/1986 | Green |
| 4,591,085 A | 5/1986 | Di Giovanni |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,646,722 A | 3/1987 | Silverstein et al. |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,834,720 A | 5/1989 | Blinkhorn |
| 4,844,068 A | 7/1989 | Arata et al. |
| 4,848,637 A | 7/1989 | Pruitt |
| 4,865,030 A | 9/1989 | Polyak |
| 4,869,414 A | 9/1989 | Green et al. |
| 4,869,415 A | 9/1989 | Fox |
| 4,873,977 A | 10/1989 | Avant et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,896,678 A | 1/1990 | Ogawa |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,941,623 A | 7/1990 | Pruitt |
| 4,944,443 A | 7/1990 | Oddsen et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |
| 4,988,334 A | 1/1991 | Hornlein et al. |
| 5,002,543 A | 3/1991 | Bradshaw et al. |
| 5,002,553 A | 3/1991 | Shiber |
| 5,009,661 A | 4/1991 | Michelson |
| 5,014,899 A | 5/1991 | Presty et al. |
| 5,015,227 A | 5/1991 | Broadwin et al. |
| 5,024,671 A | 6/1991 | Tu et al. |
| 5,027,834 A | 7/1991 | Pruitt |
| 5,031,814 A | 7/1991 | Tompkins et al. |
| 5,038,109 A | 8/1991 | Goble et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |

(56) References Cited

U.S. PATENT DOCUMENTS

| | | |
|---|---|---|
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,945 A | 2/1994 | Brinkerhoff et al. |
| 5,289,963 A | 3/1994 | McGarry et al. |
| 5,292,053 A | 3/1994 | Bilotti et al. |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller née Degwitz et al. |
| 5,318,221 A | 6/1994 | Green et al. |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,344,060 A | 9/1994 | Gravener et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,370,645 A | 12/1994 | Klicek et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,409,498 A | 4/1995 | Braddock et al. |
| 5,411,508 A | 5/1995 | Bessler et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Schichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |

(56) References Cited

U.S. PATENT DOCUMENTS

| | | |
|---|---|---|
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,542,949 A | 8/1996 | Yoon |
| 5,543,119 A | 8/1996 | Sutter et al. |
| 5,547,117 A | 8/1996 | Hamblin et al. |
| 5,549,621 A | 8/1996 | Bessler et al. |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A * | 11/1996 | Cooper et al. ................ 606/151 |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |

(56) References Cited

U.S. PATENT DOCUMENTS

| | | | |
|---|---|---|---|
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A * | 10/1997 | D'Alessio et al. ............ 424/423 |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A * | 6/1998 | Kingwell ...................... 606/151 |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,800,379 A | 9/1998 | Edwards |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |

(56) References Cited

U.S. PATENT DOCUMENTS

| | | |
|---|---|---|
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,122 A | 12/1998 | Riza |
| 5,843,132 A | 12/1998 | Ilvento |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,693 A | 5/1999 | Dicesare et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,947,984 A | 9/1999 | Whipple |
| 5,948,030 A | 9/1999 | Miller et al. |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,774 A | 10/1999 | McKean et al. |
| 5,971,916 A | 10/1999 | Koren |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,003,517 A | 12/1999 | Sheffield et al. |
| 6,004,319 A | 12/1999 | Goble et al. |
| 6,010,054 A | 1/2000 | Johnson et al. |
| 6,010,513 A | 1/2000 | Törmälä et al. |
| 6,012,494 A | 1/2000 | Balazs |
| 6,013,076 A | 1/2000 | Goble et al. |
| 6,015,406 A | 1/2000 | Goble et al. |
| 6,017,322 A | 1/2000 | Snoke et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,047,861 A | 4/2000 | Vidal et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,062,360 A | 5/2000 | Shields |
| 6,063,097 A | 5/2000 | Oi et al. |
| 6,063,098 A | 5/2000 | Houser et al. |
| 6,065,919 A | 5/2000 | Peck |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,286 A | 6/2000 | Cuschieri et al. |
| 6,079,606 A | 6/2000 | Milliman et al. |
| 6,082,577 A | 7/2000 | Coates et al. |
| 6,083,191 A | 7/2000 | Rose |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,149,660 A | 11/2000 | Laufer et al. |
| 6,152,935 A | 11/2000 | Kammerer et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,897 B1 | 3/2001 | Jamiolkowski et al. |
| 6,210,403 B1 | 4/2001 | Klicek |
| 6,213,999 B1 | 4/2001 | Platt, Jr. et al. |

(56) References Cited

U.S. PATENT DOCUMENTS

| | | |
|---|---|---|
| 6,214,028 B1 | 4/2001 | Yoon et al. |
| 6,220,368 B1 | 4/2001 | Ark et al. |
| 6,223,835 B1 | 5/2001 | Habedank et al. |
| 6,224,617 B1 | 5/2001 | Saadat et al. |
| 6,228,081 B1 | 5/2001 | Goble |
| 6,228,083 B1 | 5/2001 | Lands et al. |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,248,117 B1 | 6/2001 | Blatter |
| 6,249,076 B1 | 6/2001 | Madden et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,306,149 B1 | 10/2001 | Meade |
| 6,309,403 B1 | 10/2001 | Minor et al. |
| 6,315,184 B1 | 11/2001 | Whitman |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,383,201 B1 | 5/2002 | Dong |
| 6,387,113 B1 | 5/2002 | Hawkins et al. |
| 6,387,114 B2 | 5/2002 | Adams |
| 6,391,038 B2 | 5/2002 | Vargas et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,409,724 B1 | 6/2002 | Penny et al. |
| H2037 H | 7/2002 | Yates et al. |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| RE37,814 E | 8/2002 | Allgeyer |
| 6,428,070 B1 | 8/2002 | Takanashi et al. |
| 6,429,611 B1 | 8/2002 | Li |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,447,518 B1 | 9/2002 | Krause et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,468,275 B1 | 10/2002 | Wampler et al. |
| 6,471,106 B1 | 10/2002 | Reining |
| 6,478,210 B2 | 11/2002 | Adams et al. |
| 6,482,200 B2 | 11/2002 | Shippert |
| 6,485,490 B2 | 11/2002 | Wampler et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,527,785 B2 | 3/2003 | Sancoff et al. |
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,583,533 B2 | 6/2003 | Pelrine et al. |
| 6,585,144 B2 | 7/2003 | Adams et al. |
| 6,588,643 B2 | 7/2003 | Bolduc et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 * | 7/2003 | Nelson et al. .................. 424/426 |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |

(56) References Cited

U.S. PATENT DOCUMENTS

| | | |
|---|---|---|
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,777,838 B2 | 8/2004 | Miekka et al. |
| 6,780,151 B2 | 8/2004 | Grabover et al. |
| 6,780,180 B2 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,838,493 B2 | 1/2005 | Williams et al. |
| 6,840,423 B2 | 1/2005 | Adams et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,858,005 B2 | 2/2005 | Ohline et al. |
| RE38,708 E | 3/2005 | Bolanos et al. |
| 6,861,142 B1 * | 3/2005 | Wilkie et al. .................. 428/373 |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,905,057 B2 | 6/2005 | Swayze et al. |
| 6,905,497 B2 | 6/2005 | Truckai et al. |
| 6,908,472 B2 | 6/2005 | Wiener et al. |
| 6,911,033 B2 | 6/2005 | de Guillebon et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |

(56) References Cited

U.S. PATENT DOCUMENTS

| | | |
|---|---|---|
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,994,708 B2 | 2/2006 | Manzo |
| 6,995,729 B2 | 2/2006 | Govari et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,018,357 B2 | 3/2006 | Emmons |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,125,409 B2 | 10/2006 | Truckai et al. |
| 7,126,303 B2 | 10/2006 | Farritor et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,213,736 B2 | 5/2007 | Wales et al. |
| 7,214,224 B2 | 5/2007 | Goble |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |

(56) References Cited

U.S. PATENT DOCUMENTS

| | | | |
|---|---|---|---|
| 7,278,563 B1 | 10/2007 | Green | |
| 7,278,949 B2 | 10/2007 | Bader | |
| 7,278,994 B2 | 10/2007 | Goble | |
| 7,282,048 B2 | 10/2007 | Goble et al. | |
| 7,287,682 B1 | 10/2007 | Ezzat et al. | |
| 7,293,685 B2 | 11/2007 | Ehrenfels et al. | |
| 7,295,907 B2 | 11/2007 | Lu et al. | |
| 7,296,722 B2 | 11/2007 | Ivanko | |
| 7,296,724 B2 | 11/2007 | Green et al. | |
| 7,297,149 B2 | 11/2007 | Vitali et al. | |
| 7,300,450 B2 | 11/2007 | Vleugels et al. | |
| 7,303,106 B2 | 12/2007 | Milliman et al. | |
| 7,303,107 B2 | 12/2007 | Milliman et al. | |
| 7,303,108 B2 | 12/2007 | Shelton, IV | |
| 7,303,502 B2 | 12/2007 | Thompson | |
| 7,303,556 B2 | 12/2007 | Metzger | |
| 7,308,998 B2 | 12/2007 | Mastri et al. | |
| 7,322,975 B2 | 1/2008 | Goble et al. | |
| 7,322,994 B2 | 1/2008 | Nicholas et al. | |
| 7,324,572 B2 | 1/2008 | Chang | |
| 7,326,203 B2 | 2/2008 | Papineau et al. | |
| 7,326,213 B2 | 2/2008 | Benderev et al. | |
| 7,328,828 B2 | 2/2008 | Ortiz et al. | |
| 7,328,829 B2 | 2/2008 | Arad et al. | |
| 7,330,004 B2 | 2/2008 | DeJonge et al. | |
| 7,331,340 B2 | 2/2008 | Barney | |
| 7,334,717 B2 | 2/2008 | Rethy et al. | |
| 7,334,718 B2 | 2/2008 | McAlister et al. | |
| 7,335,199 B2 | 2/2008 | Goble et al. | |
| 7,336,048 B2 | 2/2008 | Lohr | |
| 7,336,184 B2 | 2/2008 | Smith et al. | |
| 7,338,513 B2 | 3/2008 | Lee et al. | |
| 7,341,591 B2 | 3/2008 | Grinberg | |
| 7,343,920 B2 | 3/2008 | Toby et al. | |
| 7,344,532 B2 | 3/2008 | Goble et al. | |
| 7,348,763 B1 | 3/2008 | Reinhart et al. | |
| RE40,237 E | 4/2008 | Bilotti et al. | |
| 7,351,258 B2 | 4/2008 | Ricotta et al. | |
| 7,354,447 B2 | 4/2008 | Shelton, IV et al. | |
| 7,354,502 B2 | 4/2008 | Polat et al. | |
| 7,357,287 B2 | 4/2008 | Shelton, IV et al. | |
| 7,357,806 B2 | 4/2008 | Rivera et al. | |
| 7,361,195 B2 | 4/2008 | Schwartz et al. | |
| 7,364,060 B2 | 4/2008 | Milliman | |
| 7,364,061 B2 | 4/2008 | Swayze et al. | |
| 7,377,918 B2 | 5/2008 | Amoah | |
| 7,377,928 B2 | 5/2008 | Zubik et al. | |
| 7,380,695 B2 | 6/2008 | Doll et al. | |
| 7,380,696 B2 | 6/2008 | Shelton, IV et al. | |
| 7,386,730 B2 | 6/2008 | Uchikubo | |
| 7,388,217 B2 | 6/2008 | Buschbeck et al. | |
| 7,391,173 B2 | 6/2008 | Schena | |
| 7,396,356 B2 | 7/2008 | Mollenauer | |
| 7,397,364 B2 | 7/2008 | Govari | |
| 7,398,907 B2 | 7/2008 | Racenet et al. | |
| 7,398,908 B2 | 7/2008 | Holsten et al. | |
| 7,401,721 B2 | 7/2008 | Holsten et al. | |
| 7,404,508 B2 | 7/2008 | Smith et al. | |
| 7,404,509 B2 | 7/2008 | Ortiz et al. | |
| 7,404,822 B2 | 7/2008 | Viart et al. | |
| 7,407,074 B2 | 8/2008 | Ortiz et al. | |
| 7,407,075 B2 | 8/2008 | Holsten et al. | |
| 7,407,076 B2 | 8/2008 | Racenet et al. | |
| 7,407,077 B2 | 8/2008 | Ortiz et al. | |
| 7,407,078 B2 | 8/2008 | Shelton, IV et al. | |
| 7,410,086 B2 | 8/2008 | Ortiz et al. | |
| 7,413,563 B2 | 8/2008 | Corcoran et al. | |
| 7,416,101 B2 | 8/2008 | Shelton, IV et al. | |
| 7,418,078 B2 | 8/2008 | Blanz et al. | |
| RE40,514 E | 9/2008 | Mastri et al. | |
| 7,419,080 B2 | 9/2008 | Smith et al. | |
| 7,419,081 B2 | 9/2008 | Ehrenfels et al. | |
| 7,419,495 B2 | 9/2008 | Menn et al. | |
| 7,422,136 B1 | 9/2008 | Marczyk | |
| 7,422,139 B2 | 9/2008 | Shelton, IV et al. | |
| 7,424,965 B2 | 9/2008 | Racenet et al. | |
| 7,427,607 B2 | 9/2008 | Suzuki | |
| 7,431,188 B1 | 10/2008 | Marczyk | |
| 7,431,189 B2 | 10/2008 | Shelton, IV et al. | |
| 7,431,694 B2 | 10/2008 | Stefanchik et al. | |
| 7,431,730 B2 | 10/2008 | Viola | |
| 7,434,715 B2 | 10/2008 | Shelton, IV et al. | |
| 7,434,717 B2 | 10/2008 | Shelton, IV et al. | |
| 7,438,209 B1 | 10/2008 | Hess et al. | |
| 7,438,718 B2 | 10/2008 | Milliman et al. | |
| 7,439,354 B2 | 10/2008 | Lenges et al. | |
| 7,441,684 B2 | 10/2008 | Shelton, IV et al. | |
| 7,441,685 B1 | 10/2008 | Boudreaux | |
| 7,442,201 B2 | 10/2008 | Pugsley et al. | |
| 7,448,525 B2 | 11/2008 | Shelton, IV et al. | |
| 7,451,904 B2 | 11/2008 | Shelton, IV | |
| 7,455,208 B2 | 11/2008 | Wales et al. | |
| 7,455,676 B2 | 11/2008 | Holsten et al. | |
| 7,455,682 B2 | 11/2008 | Viola | |
| 7,461,767 B2 | 12/2008 | Viola et al. | |
| 7,462,187 B2 | 12/2008 | Johnston et al. | |
| 7,464,846 B2 | 12/2008 | Shelton, IV et al. | |
| 7,464,847 B2 | 12/2008 | Viola et al. | |
| 7,464,849 B2 | 12/2008 | Shelton, IV et al. | |
| 7,467,740 B2 | 12/2008 | Shelton, IV et al. | |
| 7,467,849 B2 | 12/2008 | Silverbrook et al. | |
| 7,472,814 B2 | 1/2009 | Mastri et al. | |
| 7,472,815 B2 | 1/2009 | Shelton, IV et al. | |
| 7,472,816 B2 | 1/2009 | Holsten et al. | |
| 7,473,253 B2 | 1/2009 | Dycus et al. | |
| 7,473,263 B2 | 1/2009 | Johnston et al. | |
| 7,479,608 B2 | 1/2009 | Smith | |
| 7,481,347 B2 | 1/2009 | Roy | |
| 7,481,348 B2 | 1/2009 | Marczyk | |
| 7,481,349 B2 | 1/2009 | Holsten et al. | |
| 7,481,824 B2 | 1/2009 | Boudreaux et al. | |
| 7,485,133 B2 | 2/2009 | Cannon et al. | |
| 7,485,142 B2 | 2/2009 | Milo | |
| 7,487,899 B2 | 2/2009 | Shelton, IV et al. | |
| 7,490,749 B2 | 2/2009 | Schall et al. | |
| 7,494,039 B2 | 2/2009 | Racenet et al. | |
| 7,494,499 B2 | 2/2009 | Nagase et al. | |
| 7,500,979 B2 | 3/2009 | Hueil et al. | |
| 7,501,198 B2 | 3/2009 | Barlev et al. | |
| 7,503,474 B2 | 3/2009 | Hillstead et al. | |
| 7,506,790 B2 | 3/2009 | Shelton, IV | |
| 7,506,791 B2 | 3/2009 | Omaits et al. | |
| 7,507,202 B2 | 3/2009 | Schoellhorn | |
| 7,510,107 B2 | 3/2009 | Timm et al. | |
| 7,510,566 B2 | 3/2009 | Jacobs et al. | |
| 7,513,408 B2 | 4/2009 | Shelton, IV et al. | |
| 7,517,356 B2 | 4/2009 | Heinrich | |
| 7,524,320 B2 | 4/2009 | Tierney et al. | |
| 7,530,984 B2 | 5/2009 | Sonnenschein et al. | |
| 7,530,985 B2 | 5/2009 | Takemoto et al. | |
| 7,546,939 B2 | 6/2009 | Adams et al. | |
| 7,546,940 B2 | 6/2009 | Milliman et al. | |
| 7,547,312 B2 | 6/2009 | Bauman et al. | |
| 7,549,563 B2 | 6/2009 | Mather et al. | |
| 7,549,564 B2 | 6/2009 | Boudreaux | |
| 7,549,998 B2 | 6/2009 | Braun | |
| 7,552,854 B2 | 6/2009 | Wixey et al. | |
| 7,556,185 B2 | 7/2009 | Viola | |
| 7,556,186 B2 | 7/2009 | Milliman | |
| 7,556,647 B2 | 7/2009 | Drews et al. | |
| 7,559,449 B2 | 7/2009 | Viola | |
| 7,559,450 B2 | 7/2009 | Wales et al. | |
| 7,559,452 B2 | 7/2009 | Wales et al. | |
| 7,563,862 B2 | 7/2009 | Sieg et al. | |
| 7,565,993 B2 | 7/2009 | Milliman et al. | |
| 7,566,300 B2 | 7/2009 | Devierre et al. | |
| 7,567,045 B2 | 7/2009 | Fristedt | |
| 7,568,603 B2 | 8/2009 | Shelton, IV et al. | |
| 7,568,604 B2 | 8/2009 | Ehrenfels et al. | |
| 7,568,619 B2 | 8/2009 | Todd et al. | |
| 7,575,144 B2 | 8/2009 | Ortiz et al. | |
| 7,588,174 B2 | 9/2009 | Holsten et al. | |
| 7,588,175 B2 | 9/2009 | Timm et al. | |
| 7,588,176 B2 | 9/2009 | Timm et al. | |

(56) References Cited

U.S. PATENT DOCUMENTS

| | | |
|---|---|---|
| 7,588,177 B2 | 9/2009 | Racenet |
| 7,591,783 B2 | 9/2009 | Boulais et al. |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,519 B2 | 1/2010 | Lee et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,682,307 B2 | 3/2010 | Danitz et al. |
| 7,686,201 B2 | 3/2010 | Csiky |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,106 B2 | 4/2010 | Schenberger et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,714,239 B2 | 5/2010 | Smith |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shelton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,748,587 B2 | 7/2010 | Haramiishi et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,886 B2 | 10/2010 | Whitfield et al. |
| 7,823,592 B2 | 11/2010 | Bettuchi et al. |
| 7,824,401 B2 | 11/2010 | Manzo et al. |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |

(56) References Cited

U.S. PATENT DOCUMENTS

| | | |
|---|---|---|
| 7,837,694 B2 | 11/2010 | Tethrake et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,850,642 B2 | 12/2010 | Moll et al. |
| 7,850,982 B2 | 12/2010 | Stopek et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,891,531 B1 | 2/2011 | Ward |
| 7,891,532 B2 | 2/2011 | Mastri et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,191 B2 | 3/2011 | Baker et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,376 B1 | 4/2011 | Knodel et al. |
| 7,918,377 B2 | 4/2011 | Measamer et al. |
| 7,918,848 B2 | 4/2011 | Lau et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,927,328 B2 | 4/2011 | Orszulak et al. |
| 7,931,660 B2 | 4/2011 | Aranyi et al. |
| 7,931,695 B2 | 4/2011 | Ringeisen |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,257 B2 | 6/2011 | Frasier et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,963 B2 | 6/2011 | Francischelli et al. |
| 7,963,964 B2 | 6/2011 | Santilli et al. |
| 7,966,799 B2 | 6/2011 | Morgan et al. |
| 7,967,180 B2 | 6/2011 | Scirica |
| 7,967,181 B2 | 6/2011 | Viola et al. |
| 7,967,839 B2 | 6/2011 | Flock et al. |
| 7,972,298 B2 | 7/2011 | Wallace et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,757 B2 | 8/2011 | Wheeler et al. |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,034,077 B2 | 10/2011 | Smith et al. |
| 8,034,363 B2 | 10/2011 | Li et al. |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,047,236 B2 | 11/2011 | Perry |
| 8,056,787 B2 | 11/2011 | Boudreaux et al. |
| 8,056,788 B2 | 11/2011 | Mastri et al. |
| 8,057,508 B2 | 11/2011 | Shelton, IV |
| 8,061,576 B2 | 11/2011 | Cappola |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,070,743 B2 | 12/2011 | Kagan et al. |
| 8,075,571 B2 | 12/2011 | Vitali et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,091,756 B2 | 1/2012 | Viola |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,105,350 B2 | 1/2012 | Lee et al. |
| 8,108,072 B2 | 1/2012 | Zhao et al. |
| 8,109,426 B2 | 2/2012 | Milliman et al. |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,766 B2 | 2/2012 | Bauman et al. |
| 8,123,767 B2 | 2/2012 | Bauman et al. |

(56) References Cited

U.S. PATENT DOCUMENTS

| | | |
|---|---|---|
| 8,127,975 B2 | 3/2012 | Olson et al. |
| 8,128,624 B2 | 3/2012 | Couture et al. |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,136,712 B2 | 3/2012 | Zingman |
| 8,136,713 B2 | 3/2012 | Hathaway et al. |
| 8,140,417 B2 | 3/2012 | Shibata |
| 8,141,762 B2 | 3/2012 | Bedi et al. |
| 8,141,763 B2 | 3/2012 | Milliman |
| 8,146,790 B2 | 4/2012 | Milliman |
| 8,152,041 B2 | 4/2012 | Kostrzewski |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,167,898 B1 | 5/2012 | Schaller et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,180,458 B2 | 5/2012 | Kane et al. |
| 8,181,840 B2 | 5/2012 | Milliman |
| 8,186,555 B2 | 5/2012 | Shelton, IV et al. |
| 8,186,560 B2 | 5/2012 | Hess et al. |
| 8,191,752 B2 | 6/2012 | Scirica |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 | 6/2012 | Zemlok et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,257,251 B2 | 9/2012 | Shelton, IV et al. |
| 8,257,356 B2 | 9/2012 | Bleich et al. |
| 8,257,391 B2 | 9/2012 | Orban, III et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,286,845 B2 | 10/2012 | Perry et al. |
| 8,287,561 B2 | 10/2012 | Nunez et al. |
| 8,292,151 B2 | 10/2012 | Viola |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,323,789 B2 | 12/2012 | Rozhin et al. |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,764 B2 | 12/2012 | Francischelli et al. |
| 8,336,753 B2 | 12/2012 | Olson et al. |
| 8,348,123 B2 | 1/2013 | Scirica et al. |
| 8,348,127 B2 | 1/2013 | Marczyk |
| 8,348,129 B2 | 1/2013 | Bedi et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,973 B1 | 2/2013 | White et al. |
| 8,365,976 B2 | 2/2013 | Hess et al. |
| 8,366,559 B2 | 2/2013 | Papenfuss et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,044 B2 | 2/2013 | Coe et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,673 B2 | 3/2013 | Hinchliffe et al. |
| 8,403,138 B2 | 3/2013 | Weisshaupt et al. |
| 8,403,198 B2 | 3/2013 | Sorrentino et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Oakamoto et al. |
| 8,409,174 B2 | 4/2013 | Omori |
| 8,409,222 B2 | 4/2013 | Whitfield et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,430,292 B2 | 4/2013 | Patel et al. |
| 8,430,898 B2 | 4/2013 | Wiener et al. |

(56) References Cited

U.S. PATENT DOCUMENTS

| | | | |
|---|---|---|---|
| 8,439,246 B1 | 5/2013 | Knodel et al. |
| 8,444,036 B2 | 5/2013 | Shelton, IV |
| 8,444,549 B2 | 5/2013 | Viola et al. |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,474,677 B2 | 7/2013 | Woodard, Jr. et al. |
| 8,475,453 B2 | 7/2013 | Marczyk et al. |
| 8,475,474 B2 | 7/2013 | Bombard et al. |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,500,762 B2 | 8/2013 | Sholev et al. |
| 8,506,557 B2 | 8/2013 | Zemlok et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,881 B2 | 9/2013 | Cabiri et al. |
| 8,529,588 B2 | 9/2013 | Ahlberg et al. |
| 8,529,600 B2 | 9/2013 | Woodard, Jr. et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,579,176 B2 | 11/2013 | Smith et al. |
| 8,579,937 B2 | 11/2013 | Gresham |
| 8,584,919 B2 | 11/2013 | Hueil et al. |
| 8,585,721 B2 | 11/2013 | Kirsch |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,603,135 B2 | 12/2013 | Mueller |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,736 B2 | 1/2014 | Yates et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,178 B2 | 2/2014 | Hueil et al. |
| 8,663,192 B2 | 3/2014 | Hester et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,678,263 B2 | 3/2014 | Viola |
| 8,679,137 B2 | 3/2014 | Bauman et al. |
| 8,679,454 B2 | 3/2014 | Guire et al. |
| 8,684,253 B2 | 4/2014 | Giordano et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,213 B2 | 4/2014 | Shelton, IV et al. |
| 8,720,766 B2 | 5/2014 | Hess et al. |
| 8,721,666 B2 | 5/2014 | Schroeder et al. |
| 8,727,197 B2 | 5/2014 | Hess et al. |
| 8,733,613 B2 | 5/2014 | Huitema et al. |
| 8,734,478 B2 | 5/2014 | Widenhouse et al. |
| 8,746,529 B2 | 6/2014 | Shelton, IV et al. |
| 8,746,530 B2 | 6/2014 | Giordano et al. |
| 8,747,238 B2 | 6/2014 | Shelton, IV et al. |
| 8,752,747 B2 | 6/2014 | Shelton, IV et al. |
| 8,752,749 B2 | 6/2014 | Moore et al. |
| 8,758,235 B2 | 6/2014 | Jaworek |
| 8,758,391 B2 | 6/2014 | Swayze et al. |
| 8,763,875 B2 | 7/2014 | Morgan et al. |
| 8,763,879 B2 | 7/2014 | Shelton, IV et al. |
| 8,783,541 B2 | 7/2014 | Shelton, IV et al. |
| 8,783,543 B2 | 7/2014 | Shelton, IV et al. |
| 8,784,404 B2 | 7/2014 | Doyle et al. |
| 8,789,739 B2 | 7/2014 | Swensgard |
| 8,789,740 B2 | 7/2014 | Baxter, III et al. |
| 8,794,497 B2 | 8/2014 | Zingman |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,820,603 B2 | 9/2014 | Shelton, IV et al. |
| 8,820,605 B2 | 9/2014 | Shelton, IV |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,858,571 B2 | 10/2014 | Shelton, IV et al. |
| 8,858,590 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,946 B2 | 11/2014 | Boudreaux et al. |
| 8,899,465 B2 | 12/2014 | Shelton, IV et al. |
| 8,899,466 B2 | 12/2014 | Baxter, III et al. |
| 8,911,471 B2 | 12/2014 | Spivey et al. |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 2001/0025183 A1 | 9/2001 | Shahidi |
| 2001/0044637 A1 | 11/2001 | Jacobs et al. |
| 2002/0022836 A1 | 2/2002 | Goble et al. |
| 2002/0029036 A1 | 3/2002 | Goble et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0134811 A1 | 9/2002 | Napier et al. |
| 2002/0165541 A1 | 11/2002 | Whitman |
| 2002/0193808 A1 | 12/2002 | Belef et al. |
| 2003/0023316 A1* | 1/2003 | Brown et al. ............... 623/23.72 |
| 2003/0078647 A1* | 4/2003 | Vallana et al. ............... 623/1.11 |
| 2003/0084983 A1 | 5/2003 | Rangachari et al. |
| 2003/0093103 A1 | 5/2003 | Malackowski et al. |
| 2003/0096158 A1 | 5/2003 | Takano et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |

(56) References Cited

U.S. PATENT DOCUMENTS

| | | |
|---|---|---|
| 2003/0153908 A1 | 8/2003 | Goble et al. |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2003/0236505 A1 | 12/2003 | Bonadio et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0024457 A1* | 2/2004 | Boyce et al. ............... 623/13.17 |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068224 A1 | 4/2004 | Couvillon, Jr. et al. |
| 2004/0068307 A1 | 4/2004 | Goble |
| 2004/0070369 A1 | 4/2004 | Sakahibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin, III et al. |
| 2004/0108357 A1 | 6/2004 | Milliman et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne, Jr. et al. |
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0247415 A1 | 12/2004 | Mangone, Jr. |
| 2004/0254566 A1 | 12/2004 | Plicchi et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2004/0267362 A1* | 12/2004 | Hwang et al. ............... 623/13.15 |
| 2005/0010213 A1 | 1/2005 | Stad et al. |
| 2005/0032511 A1 | 2/2005 | Malone et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0143769 A1 | 6/2005 | White et al. |
| 2005/0145675 A1 | 7/2005 | Hartwick et al. |
| 2005/0154258 A1 | 7/2005 | Tartaglia et al. |
| 2005/0154406 A1 | 7/2005 | Bombard et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0274768 A1 | 12/2005 | Cummins et al. |
| 2005/0283188 A1 | 12/2005 | Loshakove et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079115 A1 | 4/2006 | Aranyi et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0135992 A1* | 6/2006 | Bettuchi et al. ............... 606/219 |
| 2006/0142772 A1 | 6/2006 | Ralph et al. |
| 2006/0149163 A1 | 6/2006 | Hibner et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0178556 A1 | 8/2006 | Hasser et al. |

(56) References Cited

U.S. PATENT DOCUMENTS

| | | |
|---|---|---|
| 2006/0180634 A1 | 8/2006 | Shelton, IV et al. |
| 2006/0185682 A1 | 8/2006 | Marczyk |
| 2006/0200123 A1 | 9/2006 | Ryan |
| 2006/0201989 A1 | 9/2006 | Ojeda |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252993 A1 | 11/2006 | Freed et al. |
| 2006/0253069 A1 | 11/2006 | Li et al. |
| 2006/0258904 A1 | 11/2006 | Stefanchik et al. |
| 2006/0258910 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010838 A1 | 1/2007 | Shelton, IV et al. |
| 2007/0023476 A1 | 2/2007 | Whitman et al. |
| 2007/0023477 A1 | 2/2007 | Whitman et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027472 A1 | 2/2007 | Hiles et al. |
| 2007/0027551 A1 | 2/2007 | Farnsworth et al. |
| 2007/0034668 A1 | 2/2007 | Holsten et al. |
| 2007/0049966 A1 | 3/2007 | Bonadio et al. |
| 2007/0051375 A1 | 3/2007 | Milliman |
| 2007/0055219 A1 | 3/2007 | Whitman et al. |
| 2007/0066981 A1 | 3/2007 | Meagher |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0093869 A1 | 4/2007 | Bloom et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0135686 A1 | 6/2007 | Pruitt, Jr. et al. |
| 2007/0135803 A1 | 6/2007 | Belson |
| 2007/0155010 A1* | 7/2007 | Farnsworth et al. .......... 435/399 |
| 2007/0158358 A1 | 7/2007 | Mason, II et al. |
| 2007/0170225 A1 | 7/2007 | Shelton, IV et al. |
| 2007/0173687 A1 | 7/2007 | Shima et al. |
| 2007/0173806 A1 | 7/2007 | Orszulak et al. |
| 2007/0173813 A1 | 7/2007 | Odom |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0219571 A1 | 9/2007 | Balbierz et al. |
| 2007/0221700 A1 | 9/2007 | Ortiz et al. |
| 2007/0225562 A1 | 9/2007 | Spivey et al. |
| 2007/0233163 A1 | 10/2007 | Bombard et al. |
| 2007/0239028 A1 | 10/2007 | Houser et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0249999 A1 | 10/2007 | Sklar et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0287993 A1 | 12/2007 | Hinman et al. |
| 2007/0288044 A1 | 12/2007 | Jinno et al. |
| 2007/0299427 A1 | 12/2007 | Yeung et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemlok et al. |
| 2008/0085296 A1 | 4/2008 | Powell et al. |
| 2008/0086078 A1 | 4/2008 | Powell et al. |
| 2008/0114315 A1 | 5/2008 | Voegele et al. |
| 2008/0114385 A1 | 5/2008 | Byrum et al. |
| 2008/0128469 A1 | 6/2008 | Dalessandro et al. |
| 2008/0129253 A1 | 6/2008 | Shiue et al. |
| 2008/0140115 A1 | 6/2008 | Stopek |
| 2008/0154299 A1 | 6/2008 | Linvneh |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200835 A1 | 8/2008 | Monson et al. |
| 2008/0200933 A1 | 8/2008 | Bakos et al. |
| 2008/0200949 A1 | 8/2008 | Hiles et al. |
| 2008/0228029 A1 | 9/2008 | Mikkaichi et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0283570 A1 | 11/2008 | Boyden et al. |
| 2008/0287944 A1 | 11/2008 | Pearson et al. |
| 2008/0290134 A1 | 11/2008 | Bettuchi et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2008/0315829 A1 | 12/2008 | Jones et al. |
| 2009/0001121 A1 | 1/2009 | Hess et al. |
| 2009/0001122 A1 | 1/2009 | Prommersberger et al. |
| 2009/0001130 A1 | 1/2009 | Hess et al. |
| 2009/0005807 A1 | 1/2009 | Hess et al. |
| 2009/0005809 A1 | 1/2009 | Hess et al. |
| 2009/0012534 A1 | 1/2009 | Madhani et al. |
| 2009/0018553 A1 | 1/2009 | McLean et al. |
| 2009/0020958 A1 | 1/2009 | Soul |
| 2009/0047329 A1 | 2/2009 | Stucky et al. |
| 2009/0048589 A1 | 2/2009 | Takashino et al. |
| 2009/0048612 A1 | 2/2009 | Farritor et al. |
| 2009/0054908 A1 | 2/2009 | Zand et al. |
| 2009/0076506 A1 | 3/2009 | Baker |
| 2009/0078736 A1 | 3/2009 | Van Lue |

(56) References Cited

U.S. PATENT DOCUMENTS

| | | |
|---|---|---|
| 2009/0082789 A1 | 3/2009 | Milliman et al. |
| 2009/0088774 A1 | 4/2009 | Swarup et al. |
| 2009/0090763 A1 | 4/2009 | Zemlok et al. |
| 2009/0092651 A1 | 4/2009 | Shah et al. |
| 2009/0093728 A1 | 4/2009 | Hyde et al. |
| 2009/0099579 A1 | 4/2009 | Nentwick et al. |
| 2009/0099876 A1 | 4/2009 | Whitman |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0119011 A1 | 5/2009 | Kondo et al. |
| 2009/0143805 A1 | 6/2009 | Palmer et al. |
| 2009/0143855 A1 | 6/2009 | Weber et al. |
| 2009/0149871 A9 | 6/2009 | Kagan et al. |
| 2009/0157067 A1 | 6/2009 | Kane et al. |
| 2009/0157087 A1 | 6/2009 | Wei et al. |
| 2009/0171147 A1 | 7/2009 | Lee et al. |
| 2009/0177226 A1 | 7/2009 | Reinprecht et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0213685 A1 | 8/2009 | Mak et al. |
| 2009/0242610 A1 | 10/2009 | Shelton, IV et al. |
| 2009/0247901 A1 | 10/2009 | Zimmer |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0270895 A1 | 10/2009 | Churchill et al. |
| 2009/0277947 A1* | 11/2009 | Viola .................... 227/176.1 |
| 2009/0277949 A1 | 11/2009 | Viola et al. |
| 2009/0292283 A1 | 11/2009 | Odom |
| 2009/0308907 A1 | 12/2009 | Nalagatla et al. |
| 2010/0010511 A1 | 1/2010 | Harris et al. |
| 2010/0012704 A1 | 1/2010 | Tarinelli Racenet et al. |
| 2010/0023024 A1 | 1/2010 | Zeiner et al. |
| 2010/0036370 A1 | 2/2010 | Mirel et al. |
| 2010/0049084 A1 | 2/2010 | Nock et al. |
| 2010/0057087 A1 | 3/2010 | Cha |
| 2010/0057107 A1 | 3/2010 | Sorrentino et al. |
| 2010/0069942 A1 | 3/2010 | Shelton, IV |
| 2010/0072254 A1 | 3/2010 | Aranyi et al. |
| 2010/0076475 A1 | 3/2010 | Yates et al. |
| 2010/0076483 A1 | 3/2010 | Imuta |
| 2010/0076489 A1 | 3/2010 | Stopek et al. |
| 2010/0087840 A1 | 4/2010 | Ebersole et al. |
| 2010/0094289 A1 | 4/2010 | Taylor et al. |
| 2010/0096431 A1 | 4/2010 | Smith et al. |
| 2010/0100124 A1 | 4/2010 | Calabrese et al. |
| 2010/0108740 A1 | 5/2010 | Pastorelli et al. |
| 2010/0108741 A1 | 5/2010 | Hessler et al. |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0179022 A1 | 7/2010 | Shirokoshi |
| 2010/0179540 A1 | 7/2010 | Marczyk et al. |
| 2010/0186219 A1 | 7/2010 | Smith |
| 2010/0193566 A1 | 8/2010 | Scheib et al. |
| 2010/0200637 A1 | 8/2010 | Beetel |
| 2010/0204717 A1 | 8/2010 | Knodel |
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0249519 A1 | 9/2010 | Park et al. |
| 2010/0258611 A1 | 10/2010 | Smith et al. |
| 2010/0267662 A1 | 10/2010 | Fielder et al. |
| 2010/0268030 A1 | 10/2010 | Viola et al. |
| 2010/0274160 A1 | 10/2010 | Yachi et al. |
| 2010/0276471 A1 | 11/2010 | Whitman |
| 2010/0292540 A1 | 11/2010 | Hess et al. |
| 2010/0294827 A1 | 11/2010 | Boyden et al. |
| 2010/0298636 A1 | 11/2010 | Casto et al. |
| 2010/0305552 A1 | 12/2010 | Shelton, IV et al. |
| 2010/0312261 A1 | 12/2010 | Suzuki et al. |
| 2010/0320252 A1 | 12/2010 | Viola et al. |
| 2010/0331856 A1 | 12/2010 | Carlson et al. |
| 2010/0331880 A1 | 12/2010 | Stopek |
| 2011/0003528 A1 | 1/2011 | Lam |
| 2011/0006099 A1 | 1/2011 | Hall et al. |
| 2011/0006101 A1 | 1/2011 | Hall et al. |
| 2011/0011916 A1 | 1/2011 | Levine |
| 2011/0017799 A1 | 1/2011 | Whitman et al. |
| 2011/0017801 A1 | 1/2011 | Zemlok et al. |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0034918 A1 | 2/2011 | Reschke |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0045047 A1 | 2/2011 | Bennett et al. |
| 2011/0060363 A1 | 3/2011 | Hess et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0118754 A1 | 5/2011 | Dachs, II et al. |
| 2011/0118778 A1 | 5/2011 | Burbank |
| 2011/0125176 A1 | 5/2011 | Yates et al. |
| 2011/0125177 A1 | 5/2011 | Yates et al. |
| 2011/0144430 A1 | 6/2011 | Spivey et al. |
| 2011/0144640 A1 | 6/2011 | Heinrich et al. |
| 2011/0147433 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0174099 A1 | 7/2011 | Ross et al. |
| 2011/0174861 A1 | 7/2011 | Shelton, IV et al. |
| 2011/0178536 A1 | 7/2011 | Kostrzewski |
| 2011/0184459 A1 | 7/2011 | Malkowski et al. |
| 2011/0192882 A1 | 8/2011 | Hess et al. |
| 2011/0210156 A1 | 9/2011 | Smith et al. |
| 2011/0253765 A1 | 10/2011 | Nicholas et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0282446 A1 | 11/2011 | Schulte et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290856 A1 | 12/2011 | Shelton, IV et al. |
| 2011/0293690 A1 | 12/2011 | Griffin et al. |
| 2011/0295242 A1 | 12/2011 | Spivey et al. |
| 2011/0295269 A1 | 12/2011 | Swensgard et al. |
| 2011/0295295 A1 | 12/2011 | Shelton, IV et al. |
| 2011/0315413 A1 | 12/2011 | Fisher et al. |
| 2012/0004636 A1 | 1/2012 | Lo |
| 2012/0022523 A1 | 1/2012 | Smith et al. |
| 2012/0022630 A1 | 1/2012 | Wübbeling |
| 2012/0029272 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |

(56) References Cited

U.S. PATENT DOCUMENTS

| | | |
|---|---|---|
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0089131 A1 | 4/2012 | Zemlok et al. |
| 2012/0138658 A1 | 6/2012 | Ullrich et al. |
| 2012/0150192 A1 | 6/2012 | Dachs, II et al. |
| 2012/0160721 A1 | 6/2012 | Shelton, IV et al. |
| 2012/0175398 A1 | 7/2012 | Sandborn et al. |
| 2012/0187179 A1 | 7/2012 | Gleiman |
| 2012/0199632 A1 | 8/2012 | Spivey et al. |
| 2012/0209289 A1 | 8/2012 | Duque et al. |
| 2012/0223123 A1 | 9/2012 | Baxter, III et al. |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234895 A1 | 9/2012 | O'Connor et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0238823 A1 | 9/2012 | Hagerty et al. |
| 2012/0238824 A1 | 9/2012 | Widenhouse et al. |
| 2012/0239010 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0253329 A1 | 10/2012 | Zemlok et al. |
| 2012/0265176 A1 | 10/2012 | Braun |
| 2012/0273550 A1 | 11/2012 | Scirica |
| 2012/0283707 A1 | 11/2012 | Giordano et al. |
| 2012/0283748 A1 | 11/2012 | Ortiz et al. |
| 2012/0289979 A1 | 11/2012 | Eskaros et al. |
| 2012/0292367 A1 | 11/2012 | Morgan et al. |
| 2012/0296333 A1 | 11/2012 | Twomey |
| 2012/0298719 A1 | 11/2012 | Shelton, IV et al. |
| 2012/0298722 A1 | 11/2012 | Hess et al. |
| 2012/0310255 A1 | 12/2012 | Brisson et al. |
| 2012/0310256 A1 | 12/2012 | Brisson |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325892 A1 | 12/2012 | Kostrzewski |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037596 A1 | 2/2013 | Bear et al. |
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0098970 A1 | 4/2013 | Racenet et al. |
| 2013/0103024 A1 | 4/2013 | Monson et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0123822 A1 | 5/2013 | Wellman et al. |
| 2013/0126581 A1 | 5/2013 | Yates et al. |
| 2013/0126582 A1 | 5/2013 | Shelton, IV et al. |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0150832 A1 | 6/2013 | Belson et al. |
| 2013/0153633 A1 | 6/2013 | Casasanta, Jr. et al. |
| 2013/0153634 A1 | 6/2013 | Carter et al. |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0161374 A1 | 6/2013 | Swayze et al. |
| 2013/0161375 A1 | 6/2013 | Huitema et al. |
| 2013/0168435 A1 | 7/2013 | Huang et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0186936 A1 | 7/2013 | Shelton, IV |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0200132 A1 | 8/2013 | Moore et al. |
| 2013/0206814 A1 | 8/2013 | Morgan et al. |
| 2013/0214030 A1 | 8/2013 | Aronhalt et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0248576 A1 | 9/2013 | Laurent et al. |
| 2013/0248577 A1 | 9/2013 | Leimbach et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |

(56) References Cited

U.S. PATENT DOCUMENTS

| | | |
|---|---|---|
| 2013/0256376 A1 | 10/2013 | Barton et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0270322 A1 | 10/2013 | Scheib et al. |
| 2013/0277412 A1 | 10/2013 | Gresham et al. |
| 2013/0310873 A1 | 11/2013 | Stopek et al. |
| 2013/0313303 A1 | 11/2013 | Shelton, IV et al. |
| 2013/0313304 A1 | 11/2013 | Shelton, IV et al. |
| 2013/0313306 A1 | 11/2013 | Shelton, IV et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334278 A1 | 12/2013 | Kerr et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0000411 A1 | 1/2014 | Shelton, IV et al. |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005661 A1 | 1/2014 | Shelton, IV et al. |
| 2014/0005662 A1 | 1/2014 | Shelton, IV |
| 2014/0005676 A1 | 1/2014 | Shelton, IV et al. |
| 2014/0005678 A1 | 1/2014 | Shelton, IV et al. |
| 2014/0005679 A1 | 1/2014 | Shelton, IV et al. |
| 2014/0005680 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005702 A1 | 1/2014 | Timm et al. |
| 2014/0005703 A1 | 1/2014 | Stulen et al. |
| 2014/0005708 A1 | 1/2014 | Shelton, IV |
| 2014/0005718 A1 | 1/2014 | Shelton, IV et al. |
| 2014/0008414 A1 | 1/2014 | Shelton, IV et al. |
| 2014/0014705 A1 | 1/2014 | Baxter, III |
| 2014/0042205 A1 | 2/2014 | Baxter, III et al. |
| 2014/0048582 A1 | 2/2014 | Shelton, IV et al. |
| 2014/0061279 A1 | 3/2014 | Laurent et al. |
| 2014/0097227 A1 | 4/2014 | Aronhalt et al. |
| 2014/0107640 A1 | 4/2014 | Yates et al. |
| 2014/0128850 A1 | 5/2014 | Kerr et al. |
| 2014/0151433 A1 | 6/2014 | Shelton, IV et al. |
| 2014/0151434 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0175155 A1 | 6/2014 | Shelton, IV et al. |
| 2014/0191014 A1 | 7/2014 | Shelton, IV |
| 2014/0191015 A1 | 7/2014 | Shelton, IV |
| 2014/0197223 A1 | 7/2014 | Hess et al. |
| 2014/0205637 A1 | 7/2014 | Widenhouse et al. |
| 2014/0207166 A1 | 7/2014 | Shelton, IV et al. |
| 2014/0224686 A1 | 8/2014 | Aronhalt et al. |
| 2014/0224857 A1 | 8/2014 | Schmid |
| 2014/0236184 A1 | 8/2014 | Leimbach et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252067 A1 | 9/2014 | Moore et al. |
| 2014/0252068 A1 | 9/2014 | Shelton, IV et al. |
| 2014/0252069 A1 | 9/2014 | Moore et al. |
| 2014/0252071 A1 | 9/2014 | Moore et al. |
| 2014/0259591 A1 | 9/2014 | Shelton, IV et al. |
| 2014/0263537 A1 | 9/2014 | Leimbach et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263564 A1 | 9/2014 | Leimbach et al. |
| 2014/0263565 A1 | 9/2014 | Lytle, IV et al. |
| 2014/0263571 A1 | 9/2014 | Morgan et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291381 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0299649 A1 | 10/2014 | Shelton, IV et al. |
| 2014/0303645 A1 | 10/2014 | Morgan et al. |
| 2014/0303646 A1 | 10/2014 | Morgan et al. |
| 2014/0305986 A1 | 10/2014 | Hall et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305993 A1 | 10/2014 | Timm et al. |
| 2014/0305994 A1 | 10/2014 | Parihar et al. |
| 2014/0305995 A1 | 10/2014 | Shelton, IV et al. |
| 2014/0309665 A1 | 10/2014 | Parihar et al. |
| 2014/0309666 A1 | 10/2014 | Shelton, IV et al. |
| 2014/0326777 A1 | 11/2014 | Zingman |
| 2014/0330161 A1 | 11/2014 | Swayze et al. |
| 2014/0352463 A1 | 12/2014 | Parihar |
| 2014/0353358 A1 | 12/2014 | Shelton, IV et al. |
| 2014/0353359 A1 | 12/2014 | Hall et al. |
| 2014/0367447 A1 | 12/2014 | Woodard, Jr. et al. |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |

FOREIGN PATENT DOCUMENTS

| | | |
|---|---|---|
| AU | 2012200178 B2 | 7/2013 |
| CA | 2458946 A1 | 3/2003 |
| CA | 2512960 A1 | 1/2006 |
| CA | 2514274 A1 | 1/2006 |
| CA | 2639177 A1 | 2/2009 |
| CN | 2488482 Y | 5/2002 |
| CN | 1523725 A | 8/2004 |

(56) References Cited

FOREIGN PATENT DOCUMENTS

| | | |
|---|---|---|
| CN | 1634601 A | 7/2005 |
| CN | 1726874 A | 2/2006 |
| CN | 1868411 A | 11/2006 |
| CN | 1915180 A | 2/2007 |
| CN | 1960679 A | 5/2007 |
| CN | 101011286 A | 8/2007 |
| CN | 101095621 A | 1/2008 |
| CN | 101023879 B | 3/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 A1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |

(56) References Cited

FOREIGN PATENT DOCUMENTS

| | | | |
|---|---|---|---|
| EP | 1426012 | A1 | 6/2004 |
| EP | 0833593 | B2 | 7/2004 |
| EP | 1442694 | A1 | 8/2004 |
| EP | 0888749 | B1 | 9/2004 |
| EP | 0959786 | B1 | 9/2004 |
| EP | 1459695 | A1 | 9/2004 |
| EP | 1254636 | B1 | 10/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1520521 | A1 | 4/2005 |
| EP | 1520522 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 0906764 | B1 | 12/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621145 | A2 | 2/2006 |
| EP | 1621151 | A2 | 2/2006 |
| EP | 1034746 | B1 | 3/2006 |
| EP | 1201196 | B1 | 3/2006 |
| EP | 1632191 | A2 | 3/2006 |
| EP | 1647231 | A1 | 4/2006 |
| EP | 1065981 | B1 | 5/2006 |
| EP | 1082944 | B1 | 5/2006 |
| EP | 1230899 | B1 | 5/2006 |
| EP | 1652481 | A2 | 5/2006 |
| EP | 1382303 | B1 | 6/2006 |
| EP | 1253866 | B1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1736105 | A1 | 12/2006 |
| EP | 1011494 | B1 | 1/2007 |
| EP | 1479346 | B1 | 1/2007 |
| EP | 1484024 | B1 | 1/2007 |
| EP | 1749485 | A1 | 2/2007 |
| EP | 1754445 | A2 | 2/2007 |
| EP | 1759812 | A1 | 3/2007 |
| EP | 1767157 | A1 | 3/2007 |
| EP | 1767163 | A1 | 3/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1790294 | A1 | 5/2007 |
| EP | 1563793 | B1 | 6/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1330991 | B1 | 9/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1679096 | B1 | 11/2007 |
| EP | 1857057 | A2 | 11/2007 |
| EP | 1402821 | B1 | 12/2007 |
| EP | 1872727 | A1 | 1/2008 |
| EP | 1550410 | B1 | 2/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943959 | A1 | 7/2008 |
| EP | 1943962 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1980213 | A2 | 10/2008 |
| EP | 1759645 | B1 | 11/2008 |
| EP | 1987780 | A2 | 11/2008 |
| EP | 1990014 | A2 | 11/2008 |
| EP | 1552795 | B1 | 12/2008 |
| EP | 1693008 | B1 | 12/2008 |
| EP | 1759640 | B1 | 12/2008 |
| EP | 1997439 | A2 | 12/2008 |
| EP | 2000102 | A2 | 12/2008 |
| EP | 2005894 | A2 | 12/2008 |
| EP | 2005901 | A1 | 12/2008 |
| EP | 2008595 | A2 | 12/2008 |
| EP | 1736104 | B1 | 3/2009 |
| EP | 1749486 | B1 | 3/2009 |
| EP | 1782743 | B1 | 3/2009 |
| EP | 2039302 | A2 | 3/2009 |
| EP | 2039308 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 2055243 | A2 | 5/2009 |
| EP | 1550409 | B1 | 6/2009 |
| EP | 1550413 | B1 | 6/2009 |
| EP | 1719461 | B1 | 6/2009 |
| EP | 1834594 | B1 | 6/2009 |
| EP | 1709911 | B1 | 7/2009 |
| EP | 2077093 | A2 | 7/2009 |
| EP | 1745748 | B1 | 8/2009 |
| EP | 2090231 | A1 | 8/2009 |
| EP | 2090237 | A1 | 8/2009 |
| EP | 2090241 | A1 | 8/2009 |
| EP | 2090244 | A2 | 8/2009 |
| EP | 2090245 | A1 | 8/2009 |
| EP | 2090254 | A1 | 8/2009 |
| EP | 2090256 | A2 | 8/2009 |
| EP | 2095777 | A2 | 9/2009 |
| EP | 2098170 | A2 | 9/2009 |
| EP | 2110082 | A1 | 10/2009 |
| EP | 2110084 | A2 | 10/2009 |
| EP | 2111803 | A2 | 10/2009 |

(56) References Cited

FOREIGN PATENT DOCUMENTS

| | | |
|---|---|---|
| EP | 1762190 B8 | 11/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2286738 A2 | 2/2011 |
| EP | 1690502 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 2353545 A1 | 8/2011 |
| EP | 2361562 A1 | 8/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2399538 A2 | 12/2011 |
| EP | 1785102 B1 | 1/2012 |
| EP | 2090253 B1 | 3/2012 |
| EP | 2430986 A2 | 3/2012 |
| EP | 2446834 A1 | 5/2012 |
| EP | 2455007 A2 | 5/2012 |
| EP | 2457519 A1 | 5/2012 |
| EP | 2462880 A2 | 6/2012 |
| EP | 1813204 B1 | 7/2012 |
| EP | 2189121 B1 | 7/2012 |
| EP | 2005895 B1 | 8/2012 |
| EP | 2090248 B1 | 8/2012 |
| EP | 2481359 A1 | 8/2012 |
| EP | 1935351 B1 | 9/2012 |
| EP | 2497431 A1 | 9/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 1884206 B1 | 3/2013 |
| EP | 2090238 B1 | 4/2013 |
| EP | 1982657 B1 | 7/2013 |
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2700367 A1 | 2/2014 |
| EP | 1772105 B1 | 5/2014 |
| EP | 2446835 B1 | 1/2015 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| FR | 2815842 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GR | 93100110 A | 11/1993 |
| JP | 50-33988 U | 4/1975 |
| JP | S 58500053 A | 1/1983 |
| JP | 60-100955 A | 6/1985 |
| JP | 61-98249 A | 5/1986 |
| JP | S 61502036 A | 9/1986 |
| JP | S 63-59764 A | 3/1988 |
| JP | S 63-147449 A | 6/1988 |
| JP | 63-203149 | 8/1988 |
| JP | H 02-279149 A | 11/1990 |
| JP | 3-12126 A | 1/1991 |
| JP | H 05-084252 A | 4/1993 |
| JP | 5-212039 A | 8/1993 |
| JP | 6007357 A | 1/1994 |
| JP | H 6-30945 A | 2/1994 |
| JP | H 06-26812 U | 4/1994 |
| JP | H 6-121798 A | 5/1994 |
| JP | H 06-197901 A | 7/1994 |
| JP | H 06-237937 A | 8/1994 |
| JP | 7-31623 A | 2/1995 |
| JP | 7051273 A | 2/1995 |
| JP | 7-124166 A | 5/1995 |
| JP | H 7-163574 A | 6/1995 |
| JP | 07-171163 | 7/1995 |
| JP | 7-255735 A | 10/1995 |
| JP | H 7-285089 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H 09-501081 A | 2/1997 |
| JP | H 09-501577 A | 2/1997 |
| JP | H 09-164144 A | 6/1997 |
| JP | H 10-118090 A | 5/1998 |
| JP | 10-512469 A | 12/1998 |
| JP | 2000-14632 | 1/2000 |
| JP | 2000033071 A | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-046384 A | 2/2001 |
| JP | 2001-87272 A | 4/2001 |

(56) References Cited

FOREIGN PATENT DOCUMENTS

| | | |
|---|---|---|
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002143078 A | 5/2002 |
| JP | 2002-528161 A | 9/2002 |
| JP | 2002369820 A | 12/2002 |
| JP | 2003-500153 A | 1/2003 |
| JP | 2003-504104 A | 2/2003 |
| JP | 2003-135473 A | 5/2003 |
| JP | 2003-164066 | 6/2003 |
| JP | 2003-521301 A | 7/2003 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344663 | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005505322 T | 2/2005 |
| JP | 2005-103280 A | 4/2005 |
| JP | 2005-103281 A | 4/2005 |
| JP | 2005-511131 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-137919 A | 6/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-521109 A | 7/2005 |
| JP | 2005-523105 A | 8/2005 |
| JP | 4461008 B2 | 8/2005 |
| JP | 2005524474 A | 8/2005 |
| JP | 2005-296412 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-34977 A | 2/2006 |
| JP | 2006-034978 A | 2/2006 |
| JP | 2006-034980 A | 2/2006 |
| JP | 2006-506106 A | 2/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-334417 A | 12/2006 |
| JP | 2006-346445 A | 12/2006 |
| JP | 2007-61628 A | 3/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-222615 A | 6/2007 |
| JP | 2007-203051 A | 8/2007 |
| JP | 2007-203057 A | 8/2007 |
| JP | 2007-524435 A | 8/2007 |
| JP | 2007-229448 A | 9/2007 |
| JP | 4001860 B2 | 10/2007 |
| JP | 2007-325922 A | 12/2007 |
| JP | 2008-68073 A | 3/2008 |
| JP | 2008-206967 A | 9/2008 |
| JP | 2008-212637 A | 9/2008 |
| JP | 2008-212638 A | 9/2008 |
| JP | 2008-259860 A | 10/2008 |
| JP | 2008-264535 A | 11/2008 |
| JP | 2008-283459 A | 11/2008 |
| JP | 2009-502351 A | 1/2009 |
| JP | 2009-506799 A | 2/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189838 A | 8/2009 |
| JP | 2009-539420 A | 11/2009 |
| JP | 2010-098844 A | 4/2010 |
| JP | 4549018 B2 | 9/2010 |
| JP | 4783373 B2 | 7/2011 |
| JP | 5140421 B2 | 2/2013 |
| JP | 5162595 B2 | 3/2013 |
| JP | 2013-128791 A | 7/2013 |
| JP | 5333899 B2 | 11/2013 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |

(56) References Cited

FOREIGN PATENT DOCUMENTS

| | | |
|---|---|---|
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 | 12/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A2 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |

(56) References Cited

FOREIGN PATENT DOCUMENTS

| | | |
|---|---|---|
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/109125 A1 | 9/2008 |
| WO | WO 2008/124748 A1 | 10/2008 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2010/028332 A2 | 3/2010 |
| WO | WO 2010/030434 A1 | 3/2010 |
| WO | WO 2010/050771 A2 | 5/2010 |
| WO | WO 2010/054404 A1 | 5/2010 |
| WO | WO 2010/063795 A1 | 6/2010 |
| WO | WO 2010/098871 A2 | 9/2010 |
| WO | WO 2011/008672 A2 | 1/2011 |
| WO | WO 2011/044343 A2 | 4/2011 |
| WO | WO 2011/060311 A2 | 5/2011 |
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/058213 A2 | 5/2012 |
| WO | WO 2012/068156 A2 | 5/2012 |
| WO | WO 2012/148667 A2 | 11/2012 |
| WO | WO 2012/148703 A2 | 11/2012 |
| WO | WO 2013/043707 A2 | 3/2013 |
| WO | WO 2013/043717 A1 | 3/2013 |

OTHER PUBLICATIONS

ASTM procedure D2240-05, "Standard Test Method for Rubber Property-Durometer Hardness," (Published Apr. 2010).
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
U.S. Appl. No. 13/763,054, filed Feb. 8, 2013.
International Search Report for PCT/US2011/053542, dated Jan. 18, 2012 (6 pages).
Written Opinion for PCT/US2011/053542, dated Jan. 18, 2012 (8 pages).
Partial European Search Report for 13161457.0, dated Jul. 31, 2013 (6 pages).
European Search Report for 13161481.0, dated Jul. 30, 2013 (9 pages).
European Search Report for 13161485.1, dated Jul. 26, 2013 (7 pages).
European Search Report for 13161397.8, dated Jul. 29, 2013 (5 pages).
Partial European Search Report for 13161459.6, dated Aug. 1, 2013 (11 pages).
Partial European Search Report for 13161352.3, dated Jul. 29, 2013 (9 pages).
European Search Report for 13161352.3, dated Nov. 18, 2013 (12 pages).
European Search Report for 13161457.0, dated Nov. 18, 2013 (10 pages).
European Search Report for 12166178.9, dated Oct. 17, 2013 (8 pages).
European Search Report for 13161472.9, dated Sep. 23, 2013 (5 pages).
European Search Report for 13161450.5, dated Sep. 25, 2013 (8 pages).

(56) References Cited

OTHER PUBLICATIONS

European Search Report for 13161431.5, dated Sep. 30, 2013 (7 pages).
European Search Report for 13161438.0, dated Sep. 5, 2013 (8 pages).
International Search Report for PCT/US2013/046513, dated Nov. 6, 2013 (6 pages).
International Search Report for PCT/US2013/046500, dated Nov. 6, 2013 (6 pages).
International Search Report for PCT/US2013/034019, dated Nov. 19, 2013 (9 pages).
Written Opinion for PCT/US2013/034019, dated Nov. 19, 2013 (10 pages).
International Search Report for PCT/US2013/034021, dated Jul. 31, 2013 (4 pages).
Written Opinion for PCT/US2013/034004, dated Jul. 26, 2013 (8 pages).
International Search Report for PCT/U52013/034004, dated Jul. 26, 2013 (4 pages).
International Search Report for PCT/US2013/034011, dated Sep. 5, 2013 (6 pages).
International Search Report for PCT/US2013/034008, dated Dec. 6, 2013 (6 pages).
Written Opinion for PCT/US2013/034008, dated Dec. 6, 2013 (6 pages).
International Search Report for PCT/US2013/034002, dated Sep. 27, 2013 (7 pages).
International Search Report for PCT/US2013/033999, dated Sep. 20, 2013 (10 pages).
Written Opinion for PCT/US2013/033999, dated Sep. 20, 2013 (15 pages).
International Search Report for PCT/US2013/033997, dated Sep. 20, 2013 (8 pages).
Written Opinion for PCT/US2013/033997, dated Sep. 20, 2013 (8 pages).
International Search Report for PCT/US2013/046525, dated Nov. 6, 2013 (6 pages).
Written Opinion for PCT/US2013/046525, dated Nov. 6, 2013 (8 pages).
International Search Report for PCT/US2013/046516, dated Nov. 6, 2013 (6 pages).
Written Opinion for PCT/US2013/046516, dated Nov. 6, 2013 (8 pages).
International Search Report for PCT/US2013/034048, dated Jan. 14, 2014 (10 pages).
Written Opinion for PCT/US2013/034048, dated Jan. 14, 2014 (12 pages).
International Search Report for PCT/US2013/034040, dated Sep. 17, 2013 (7 pages).
International Search Report for PCT/US2013/034025, dated Dec. 3, 2013 (9 pages).
Written Opinion for PCT/US2013/034025, dated Dec. 3, 2013 (8 pages).
International Search Report for PCT/US2012/032976, dated Oct. 17, 2013 (7 pages).
International Preliminary Report on Patentability for PCT/US2012/032976, dated Oct. 29, 2013 (9 pages).
International Preliminary Report on Patentability for PCT/US2011/053542, dated Apr. 2, 2013 (8 pages).
European Search Report for 13161459.6, dated Nov. 28, 2013 (15 pages).
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
U.S. Appl. No. 14/540,731, filed Nov. 13, 2014.
U.S. Appl. No. 14/540,779, filed Nov. 13, 2014.
U.S. Appl. No. 14/540,807, filed Nov. 13, 2014.
U.S. Appl. No. 14/549,098, filed Nov. 20, 2014.

U.S. Appl. No. 14/549,219, filed Nov. 20, 2014.
U.S. Appl. No. 14/518,652, filed Oct. 20, 2014.
U.S. Appl. No. 14/578,909, filed Dec. 22, 2014.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
U.S. Appl. No. 14/498,070, filed Sep. 26, 2014.
U.S. Appl. No. 14/498,087, filed Sep. 26, 2014.
U.S. Appl. No. 14/498,105, filed Sep. 26, 2014.
U.S. Appl. No. 14/498,107, filed Sep. 26, 2014.
U.S. Appl. No. 14/498,121, filed Sep. 26, 2014.
U.S. Appl. No. 14/498,145, filed Sep. 26, 2014.
U.S. Appl. No. 14/318,996, filed Jun. 30, 2014.
U.S. Appl. No. 14/319,006, filed Jun. 30, 2014.
U.S. Appl. No. 14/319,014, filed Jun. 30, 2014.
U.S. Appl. No. 14/318,991, filed Jun. 30, 2014.
U.S. Appl. No. 14/319,004, filed Jun. 30, 2014.
U.S. Appl. No. 14/319,008, filed Jun. 30, 2014.
U.S. Appl. No. 14/318,997, filed Jun. 30, 2014.
U.S. Appl. No. 14/319,002, filed Jun. 30, 2014.
U.S. Appl. No. 14/319,013, filed Jun. 30, 2014.
U.S. Appl. No. 14/319,016, filed Jun. 30, 2014.
U.S. Appl. No. 13/974,166, filed Aug. 23, 2013.
U.S. Appl. No. 14/138,481, filed Dec. 23, 2013.

(56) References Cited

OTHER PUBLICATIONS

U.S. Appl. No. 13/974,215, filed Aug. 23, 2013.
U.S. Appl. No. 13/974,202, filed Aug. 23, 2013.
U.S. Appl. No. 13/974,205, filed Aug. 23, 2013.
U.S. Appl. No. 13/974,224, filed Aug. 23, 2013.
U.S. Appl. No. 13/974,169, filed Aug. 23, 2013.
U.S. Appl. No. 13/974,206, filed Aug. 23, 2013.
U.S. Appl. No. 13/974,227, filed Aug. 23, 2013.
U.S. Appl. No. 13/974,174, filed Aug. 23, 2013.
U.S. Appl. No. 13/974,177, filed Aug. 23, 2013.
U.S. Appl. No. 13/974,182, filed Aug. 23, 2013.
U.S. Appl. No. 13/974,208, filed Aug. 23, 2013.
U.S. Appl. No. 13/974,209, filed Aug. 23, 2013.
U.S. Appl. No. 14/559,172, filed Dec. 3, 2014.
U.S. Appl. No. 14/559,188, filed Dec. 3, 2014.
U.S. Appl. No. 14/559,224, filed Dec. 3, 2014.
U.S. Appl. No. 14/559,251, filed Dec. 3, 2014.
U.S. Appl. No. 14/595,645, filed Jan. 13, 2015.
U.S. Appl. No. 12/031,573, filed Feb. 14, 2008.
U.S. Appl. No. 14/187,383, filed Feb. 24, 2014.
U.S. Appl. No. 14/187,386, filed Feb. 24, 2014.
U.S. Appl. No. 14/187,390, filed Feb. 24, 2014.
U.S. Appl. No. 14/187,385, filed Feb. 24, 2014.
U.S. Appl. No. 14/187,384, filed Feb. 24, 2014.
U.S. Appl. No. 14/187,389, filed Feb. 24, 2014.
U.S. Appl. No. 14/226,142, filed Mar. 26, 2014.
U.S. Appl. No. 14/226,106, filed Mar. 26, 2014.
U.S. Appl. No. 14/226,099, filed Mar. 26, 2014.
U.S. Appl. No. 14/226,094, filed Mar. 26, 2014.
U.S. Appl. No. 14/226,117, filed Mar. 26, 2014.
U.S. Appl. No. 14/226,075, filed Mar. 26, 2014.
U.S. Appl. No. 14/226,093, filed Mar. 26, 2014.
U.S. Appl. No. 14/226,116, filed Mar. 26, 2014.
U.S. Appl. No. 14/226,071, filed Mar. 26, 2014.
U.S. Appl. No. 14/226,097, filed Mar. 26, 2014.
U.S. Appl. No. 14/226,126, filed Mar. 26, 2014.
U.S. Appl. No. 14/226,133, filed Mar. 26, 2014.
U.S. Appl. No. 14/226,081, filed Mar. 26, 2014.
U.S. Appl. No. 14/226,076, filed Mar. 26, 2014.
U.S. Appl. No. 14/226,111, filed Mar. 26, 2014.
U.S. Appl. No. 14/226,125, filed Mar. 26, 2014.

* cited by examiner

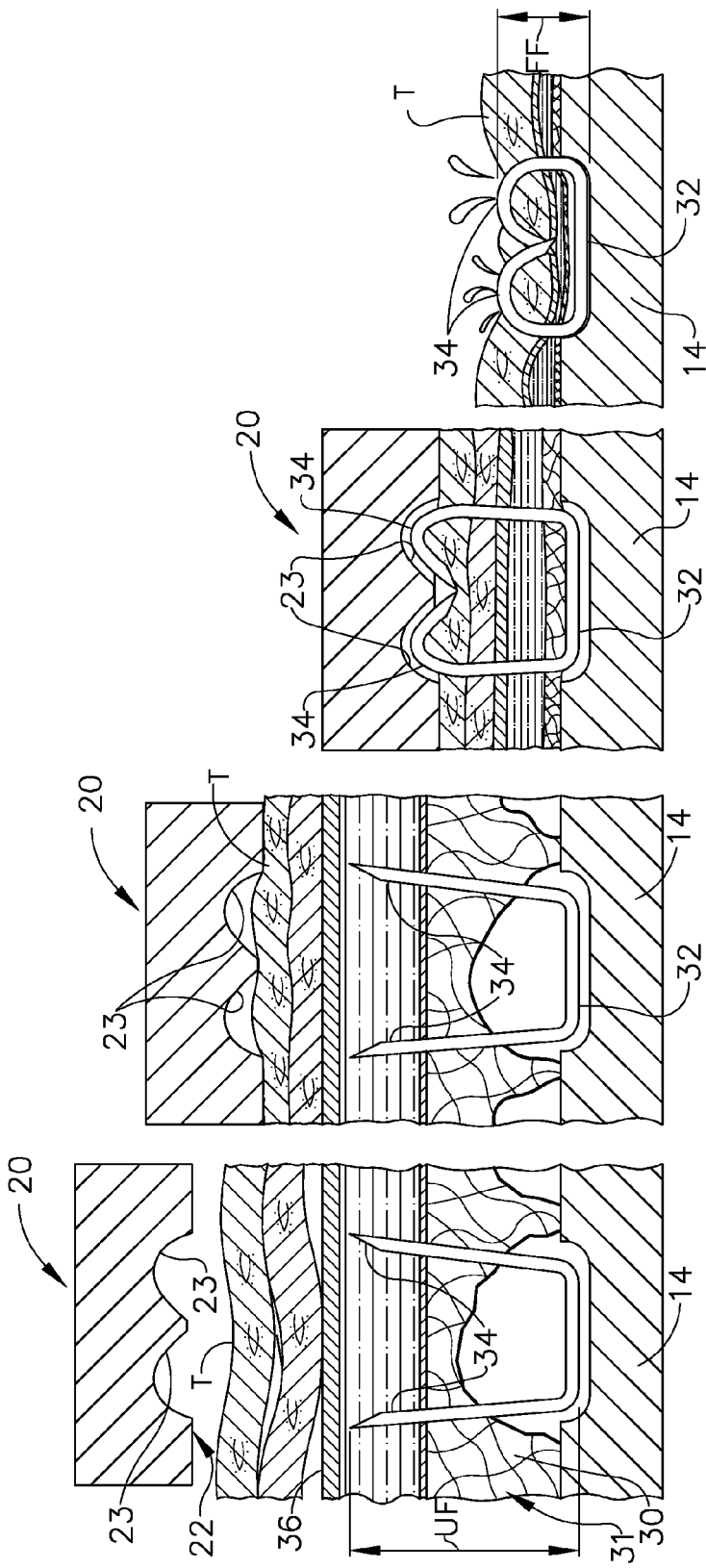

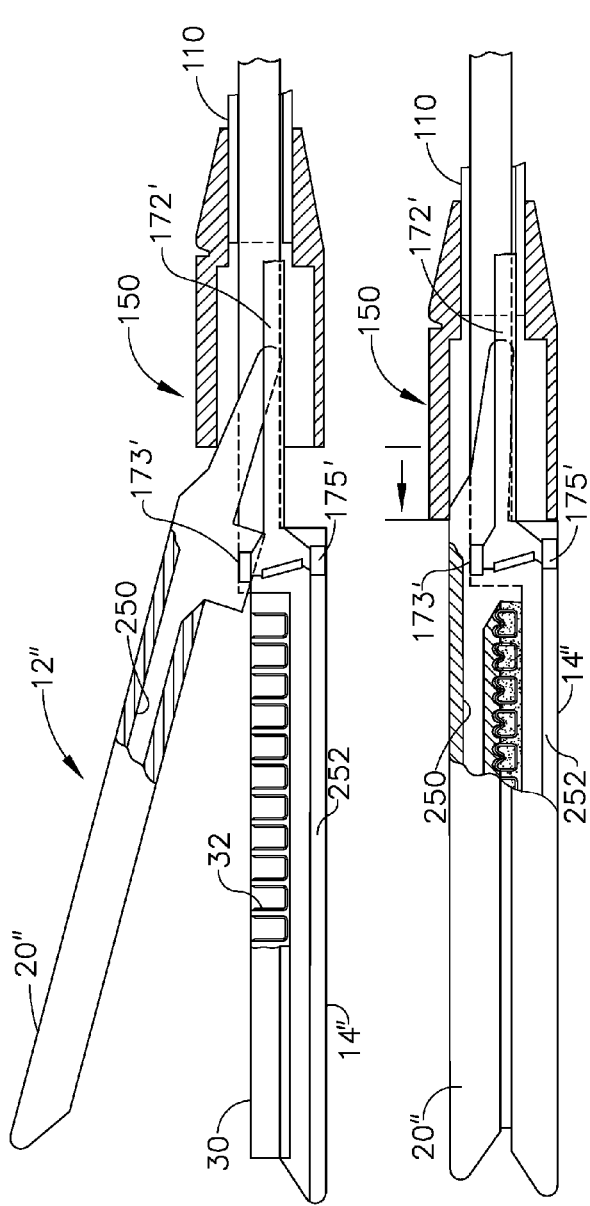
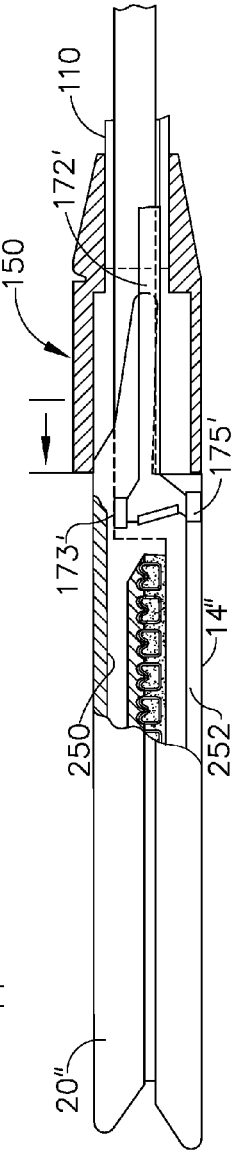
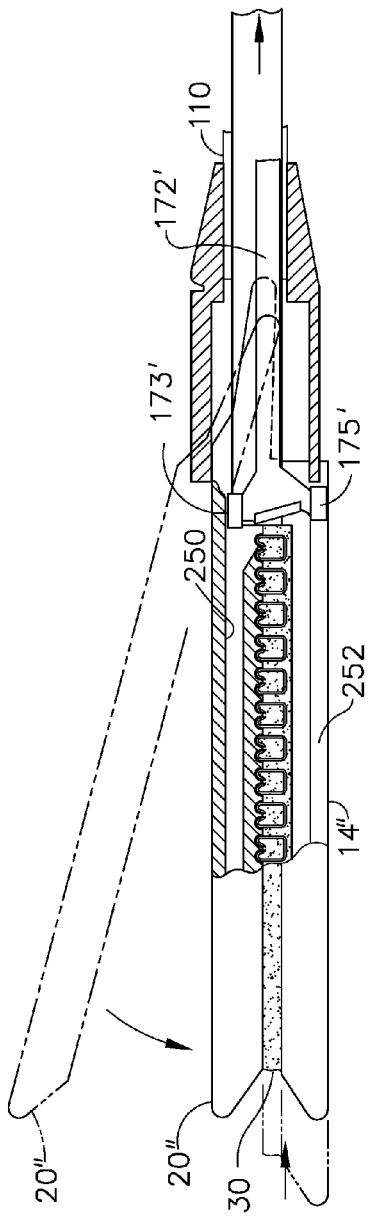
FIG. 2
FIG. 3
FIG. 4

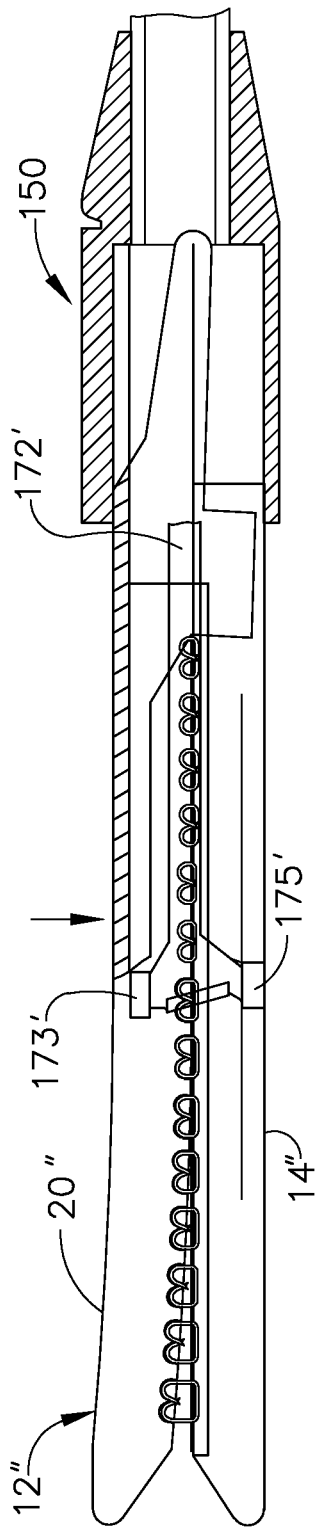

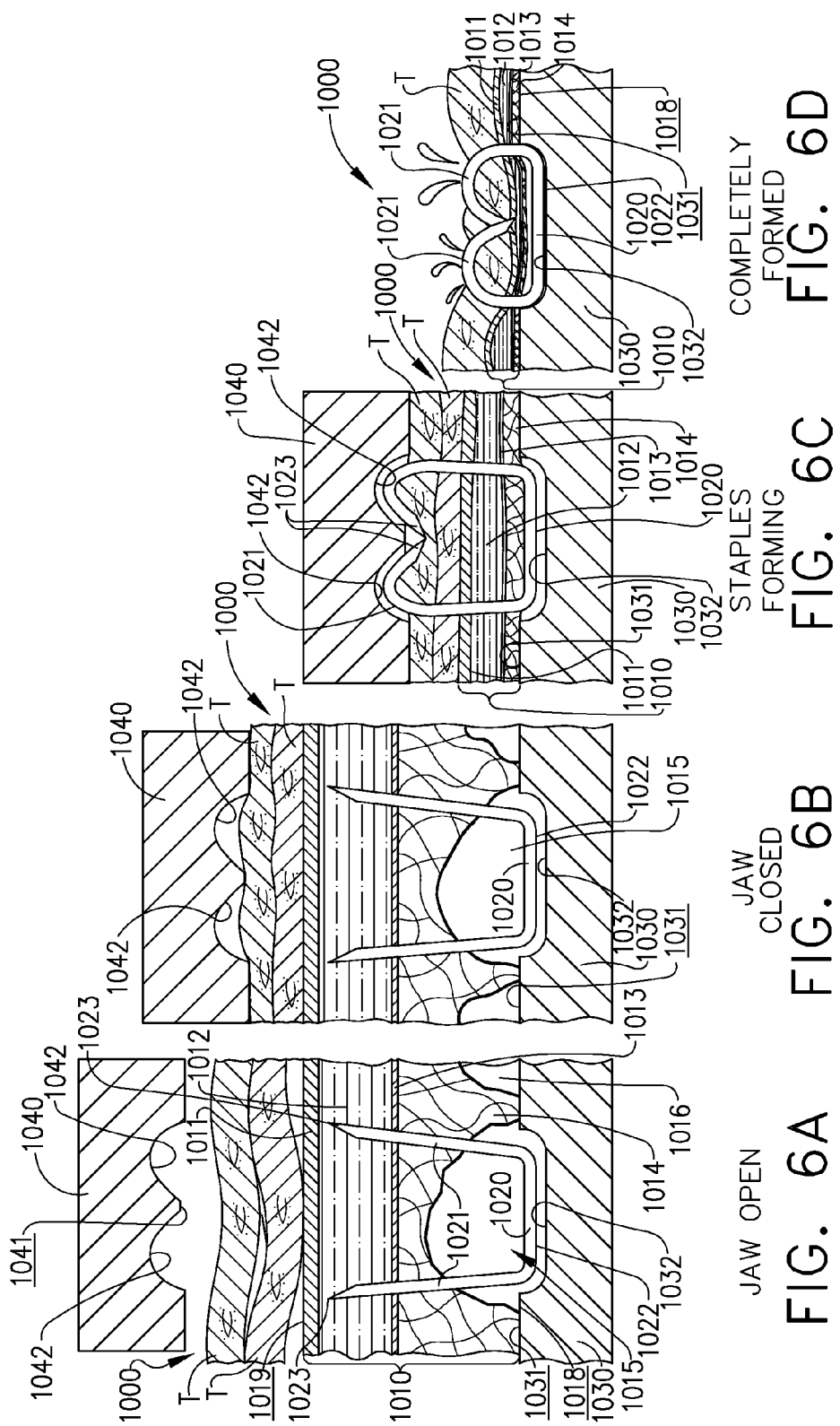

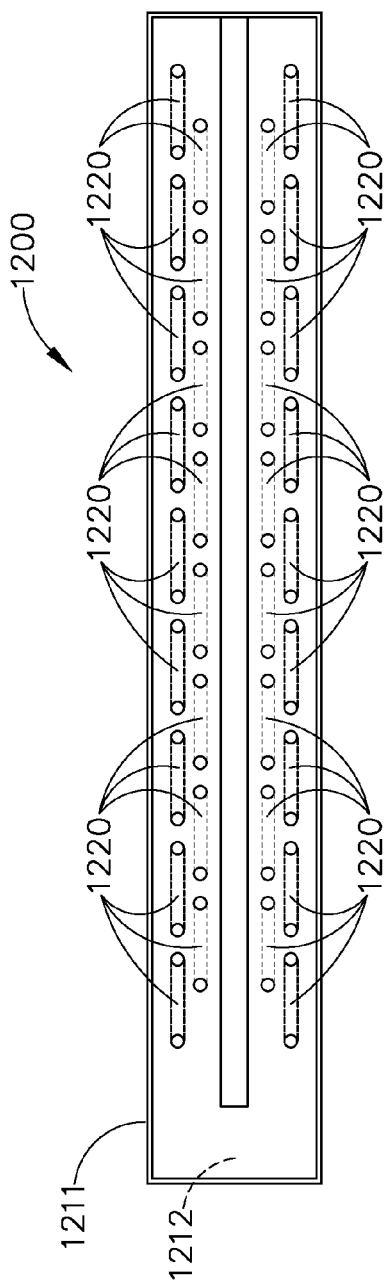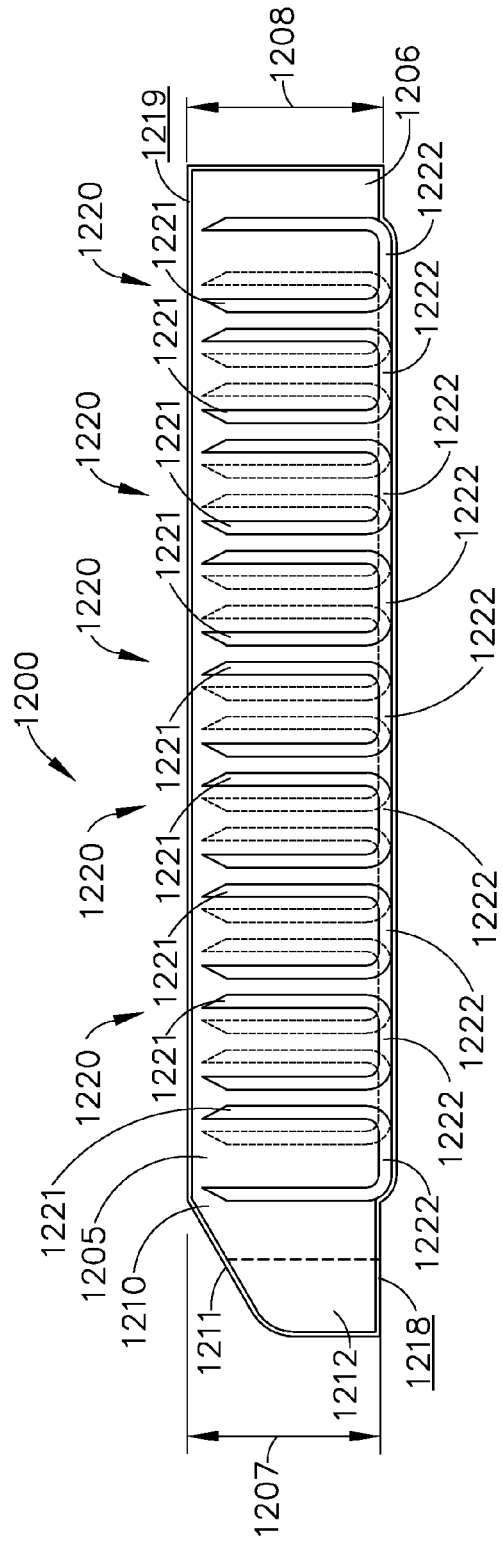
FIG. 8
FIG. 9

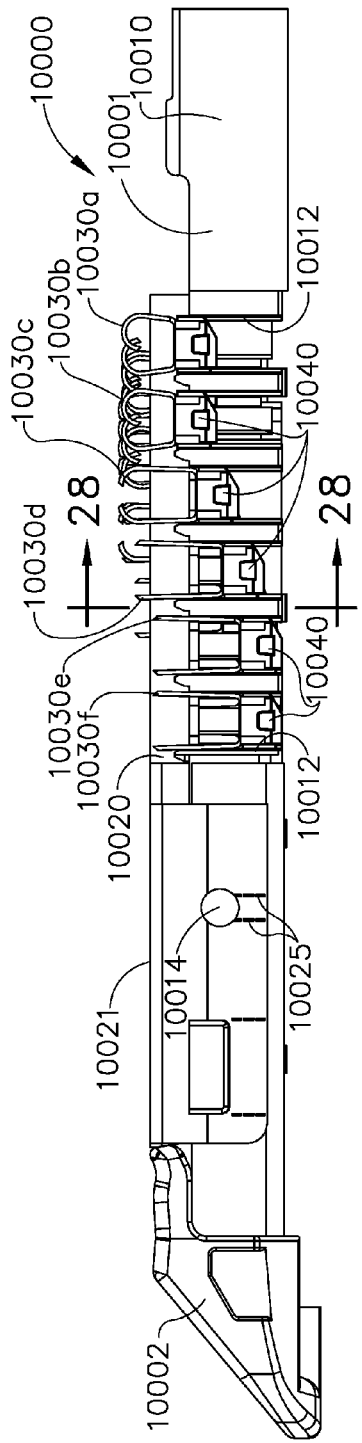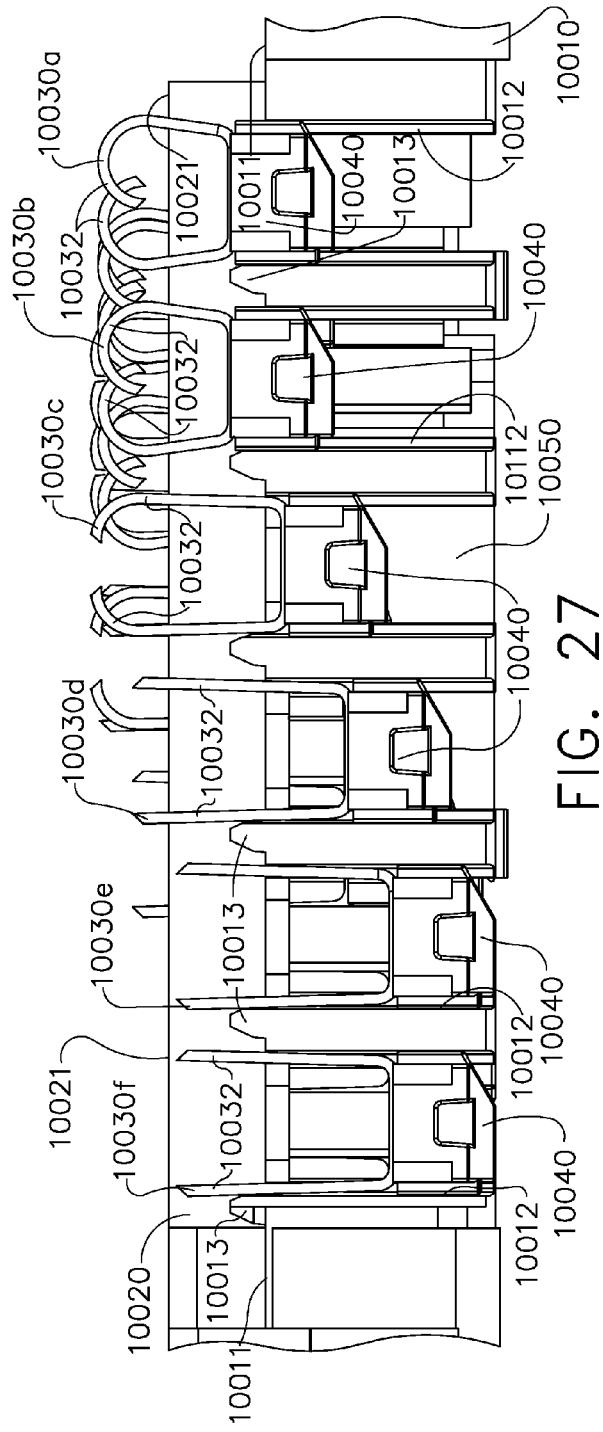

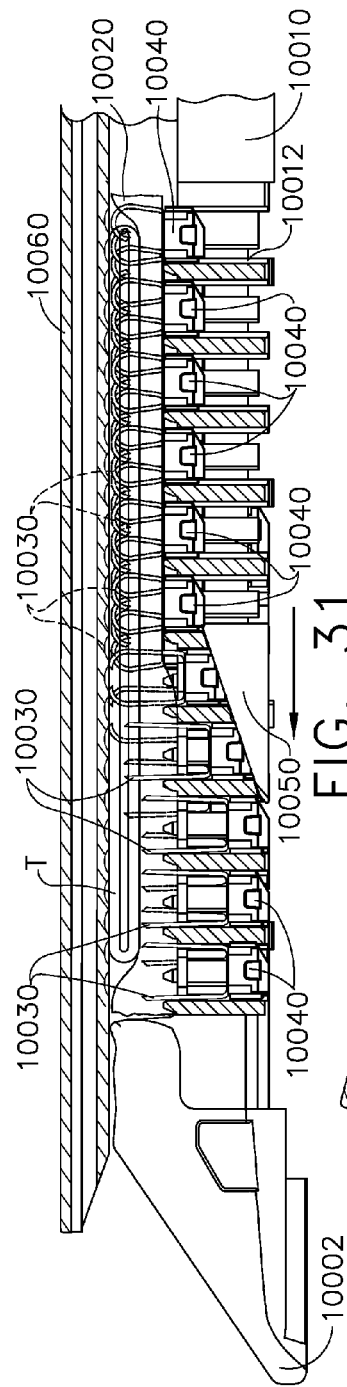
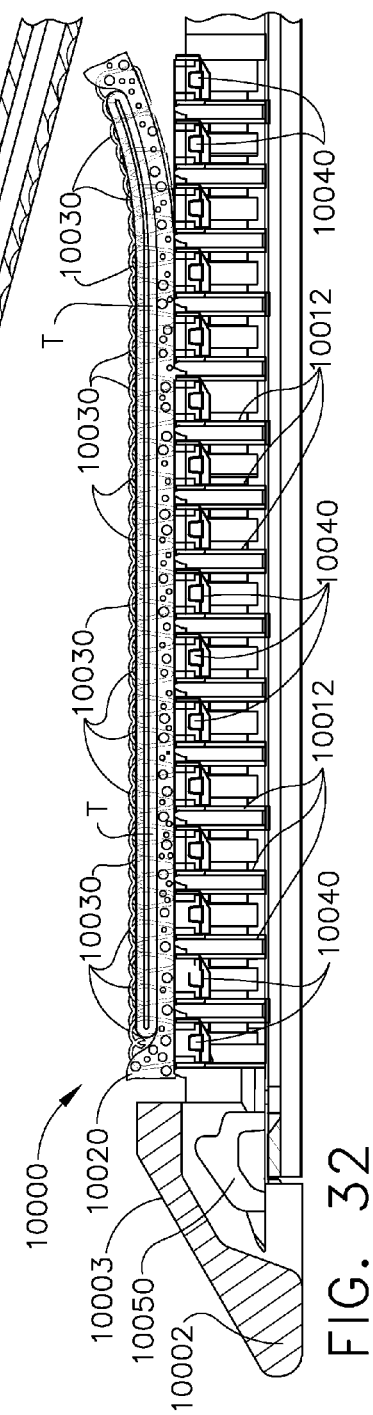

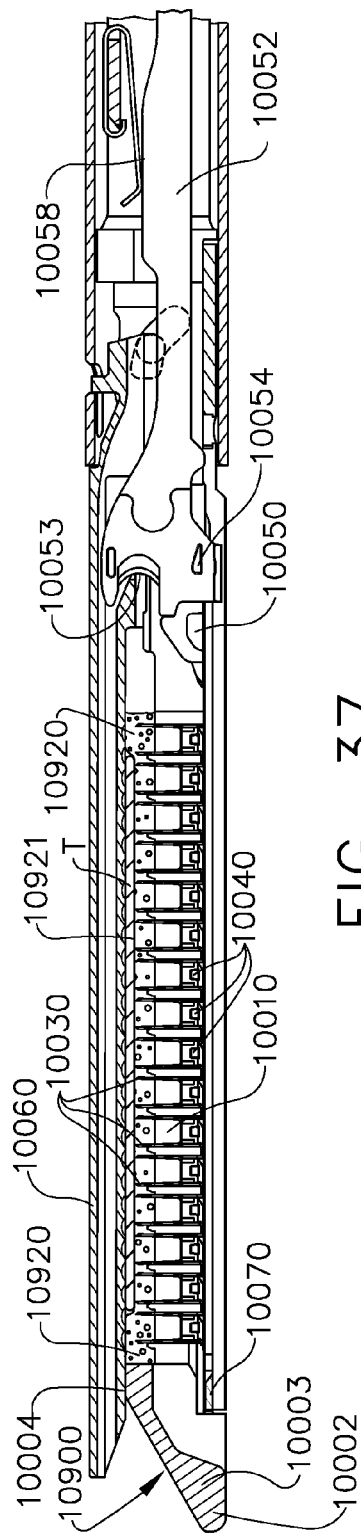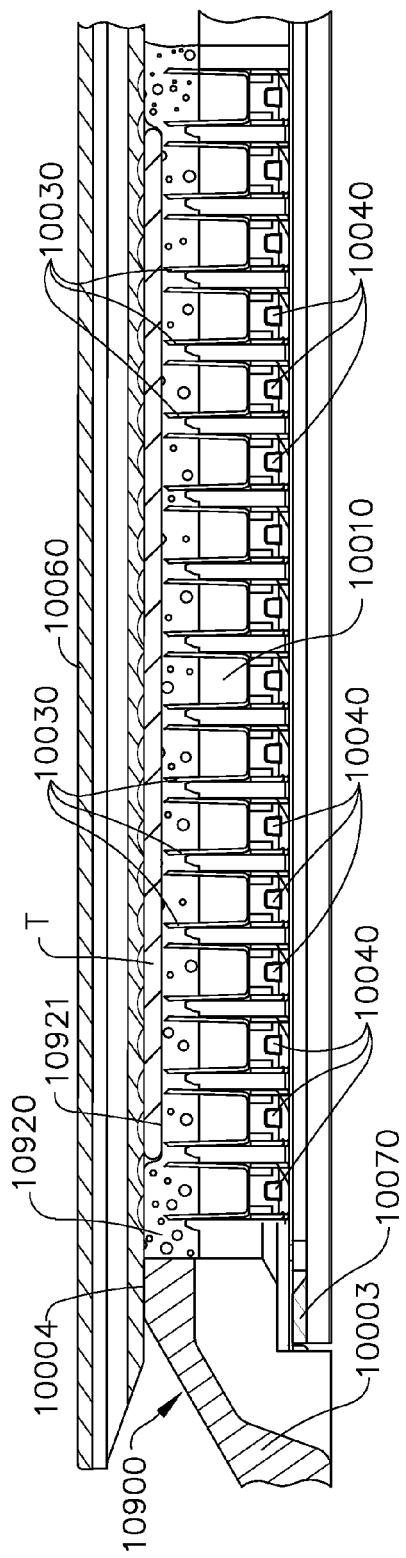

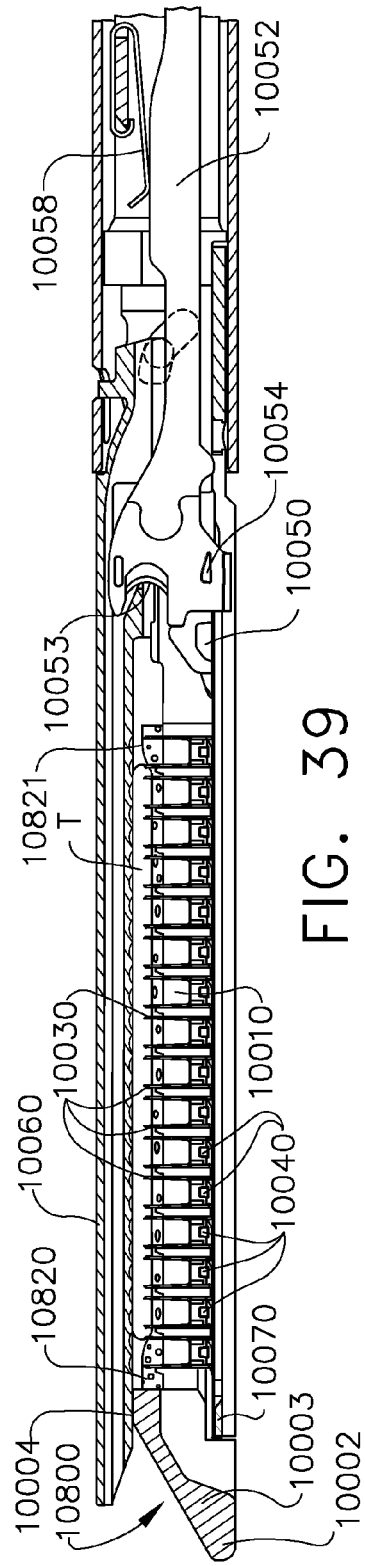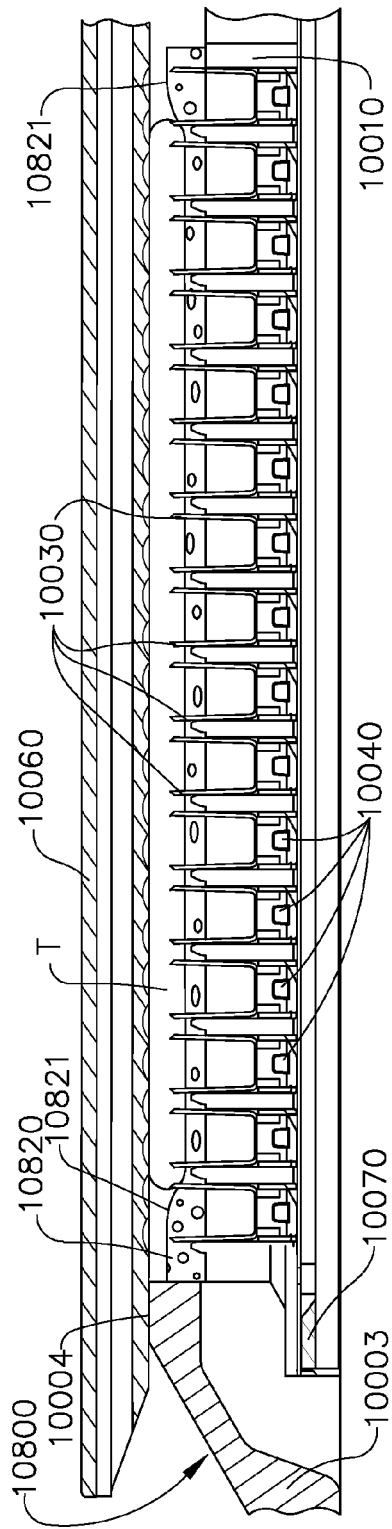

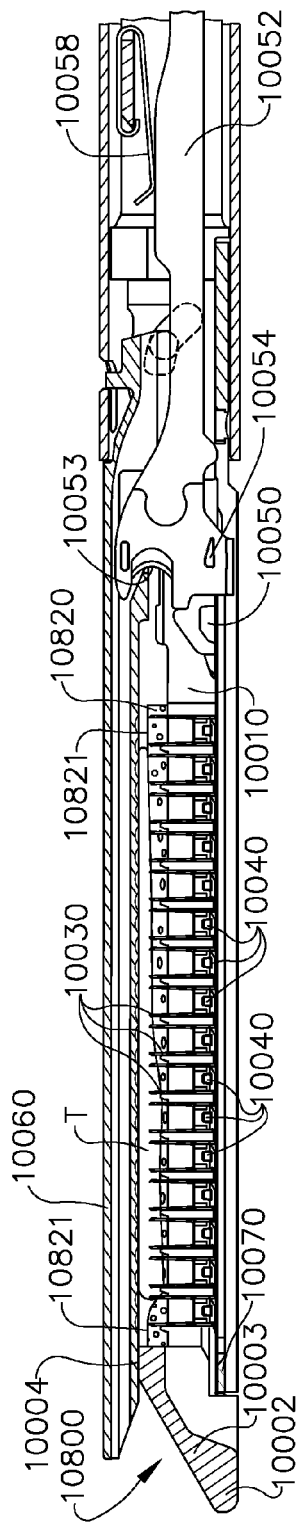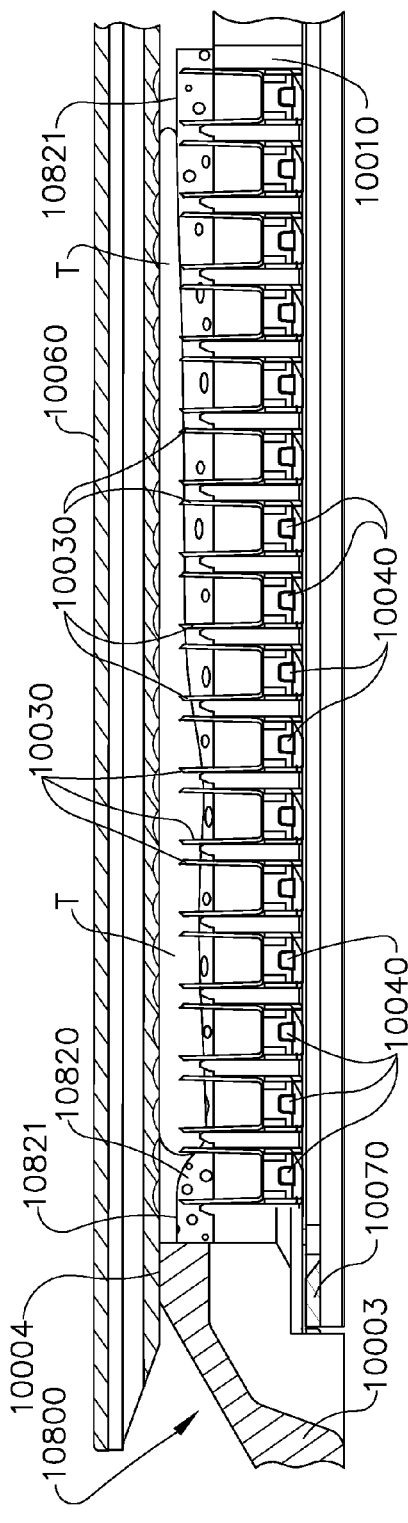

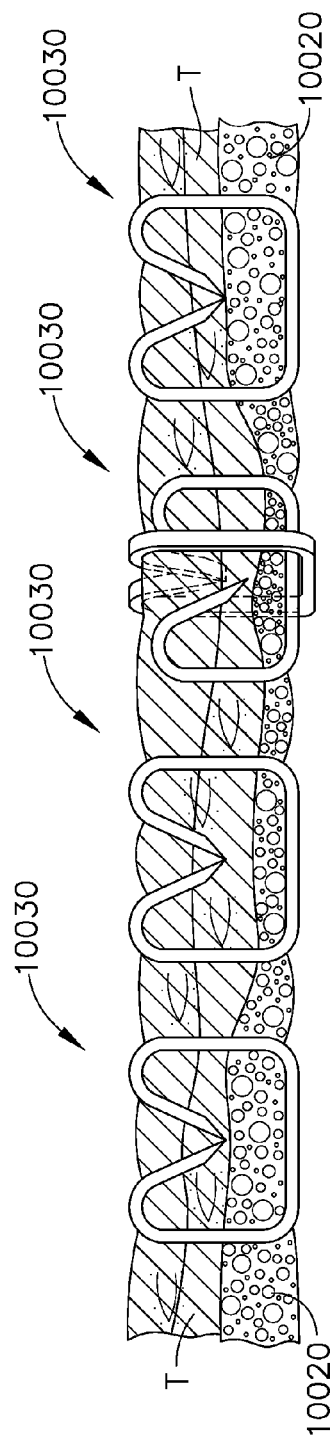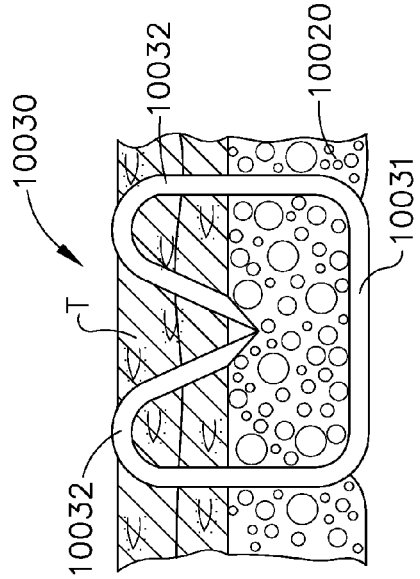
FIG. 47
FIG. 49
FIG. 48

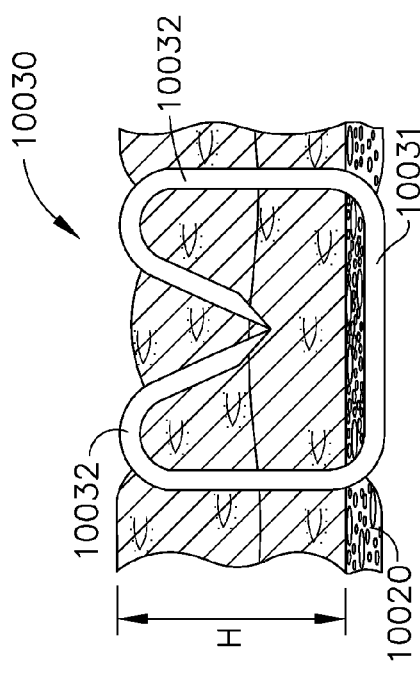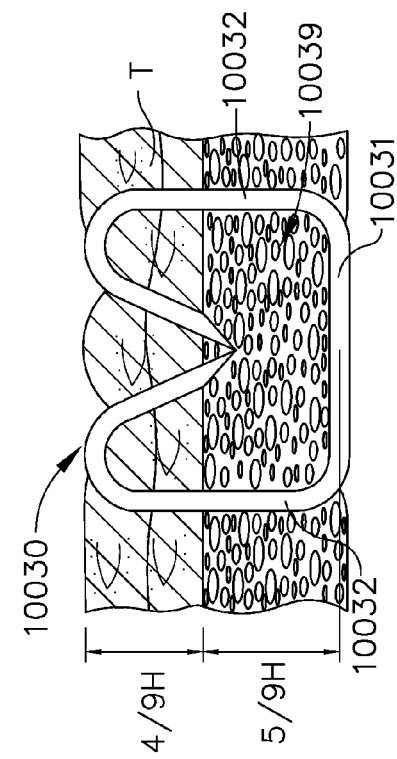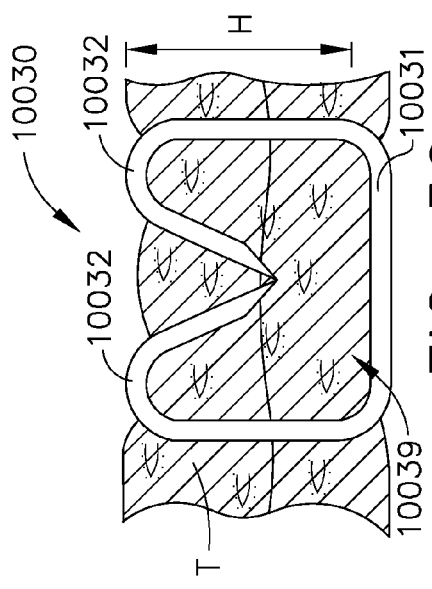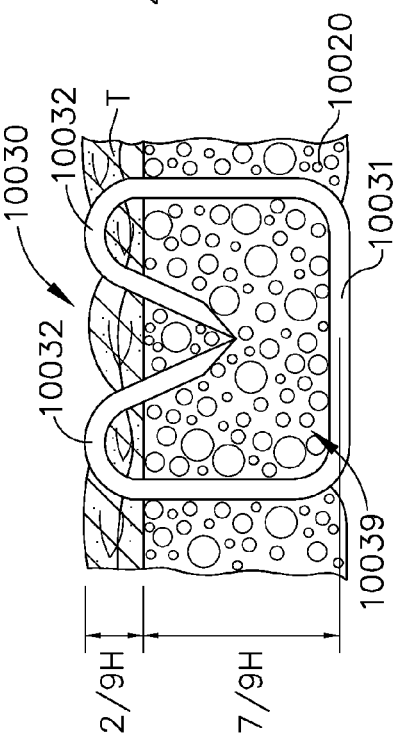
FIG. 50
FIG. 51
FIG. 52
FIG. 53

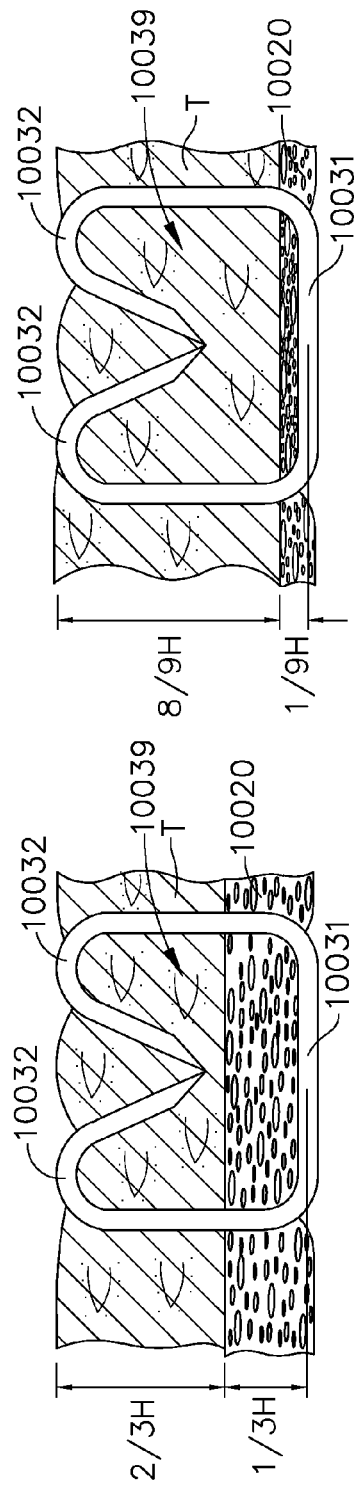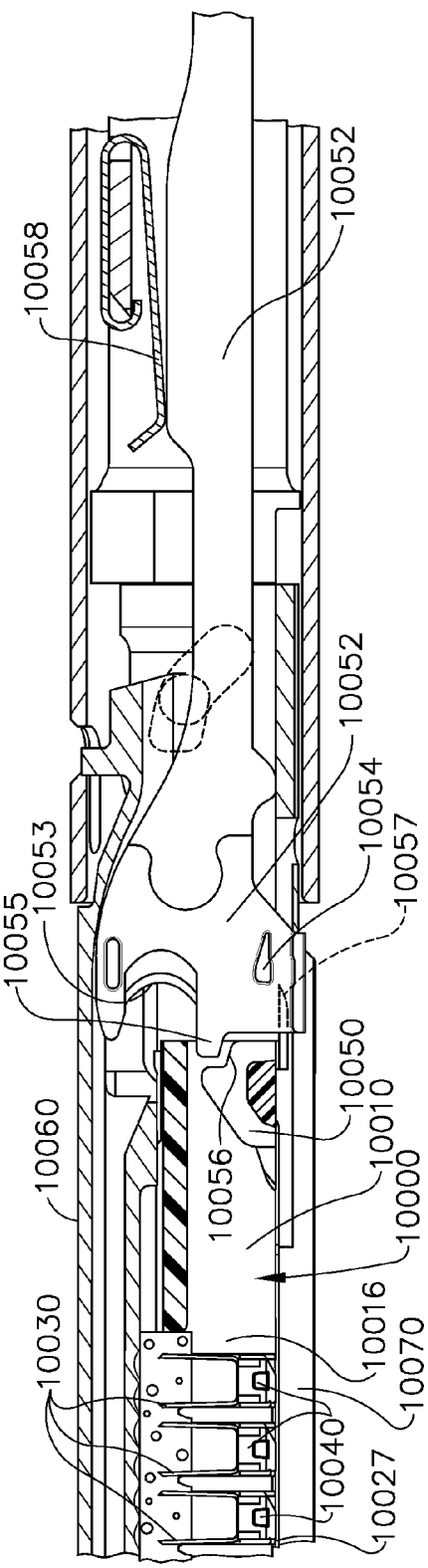

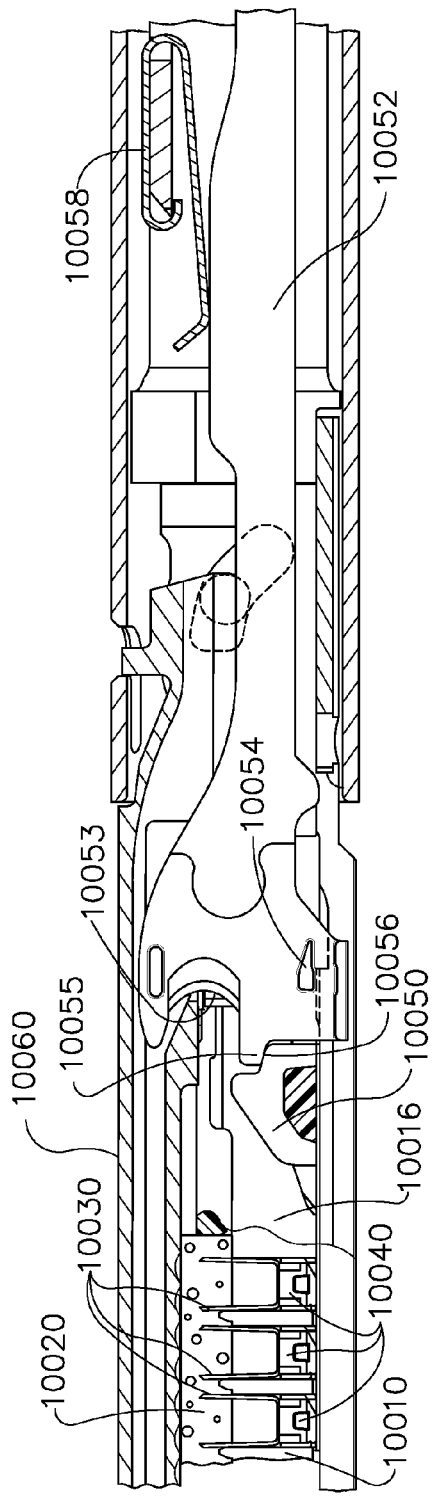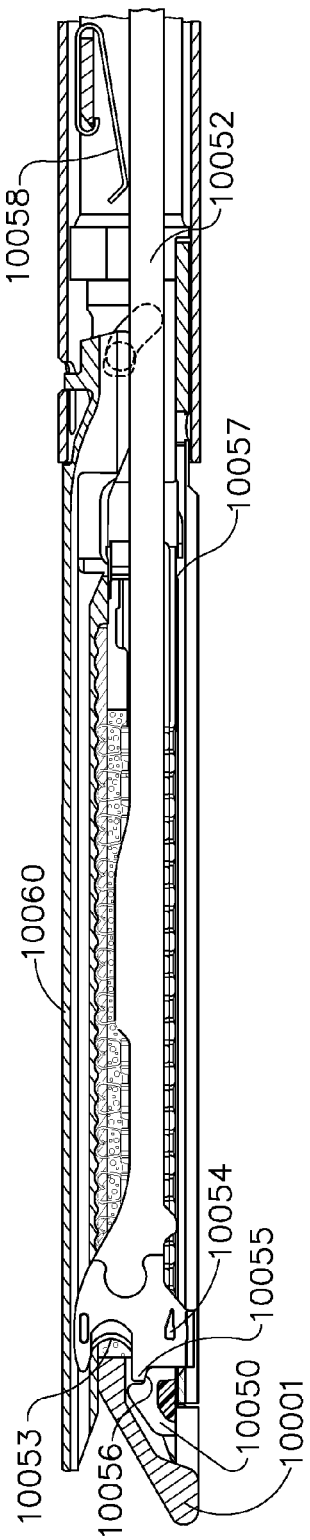

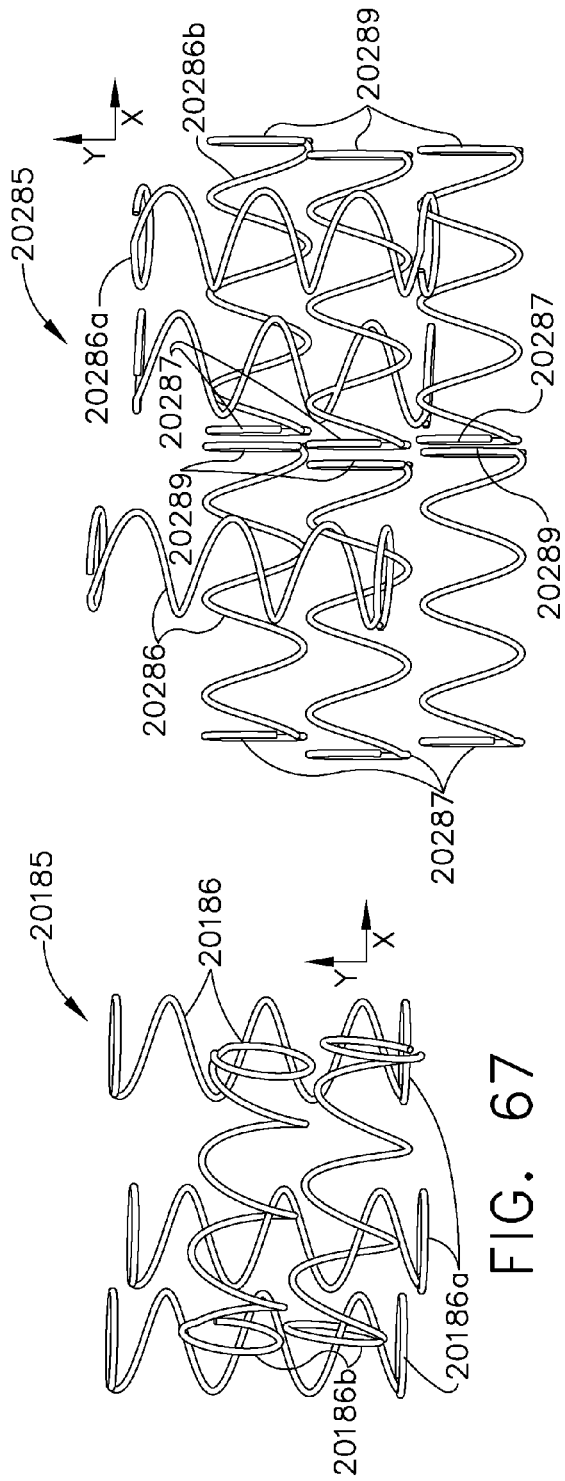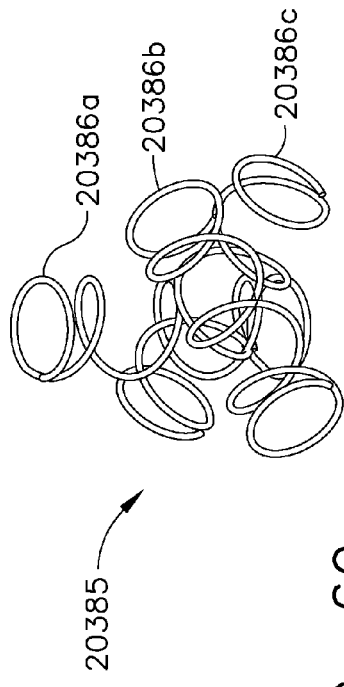

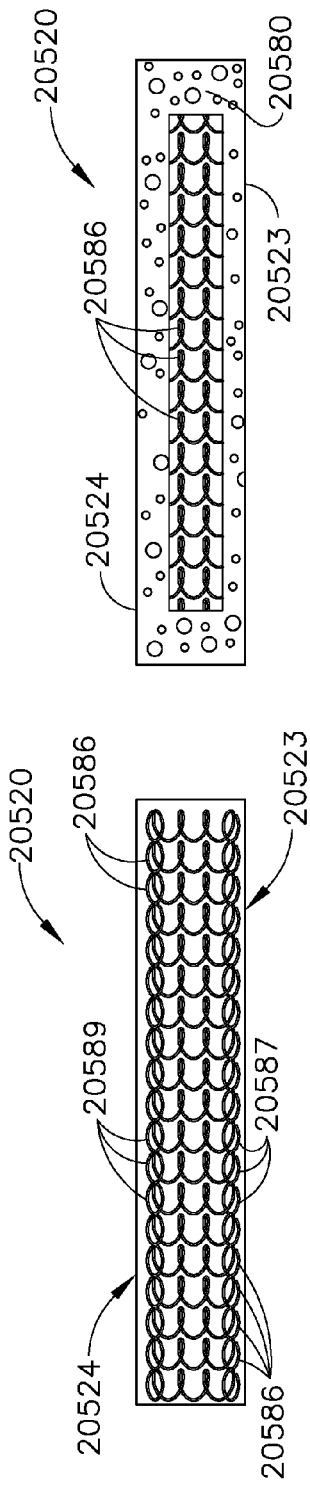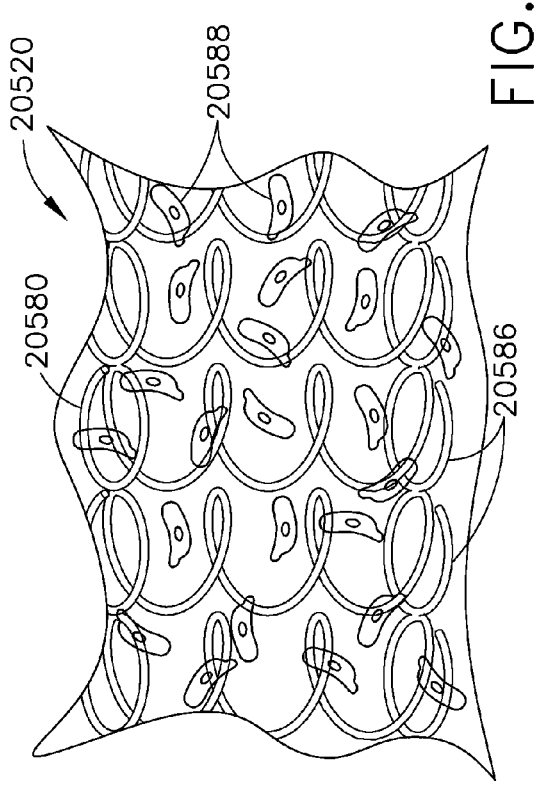

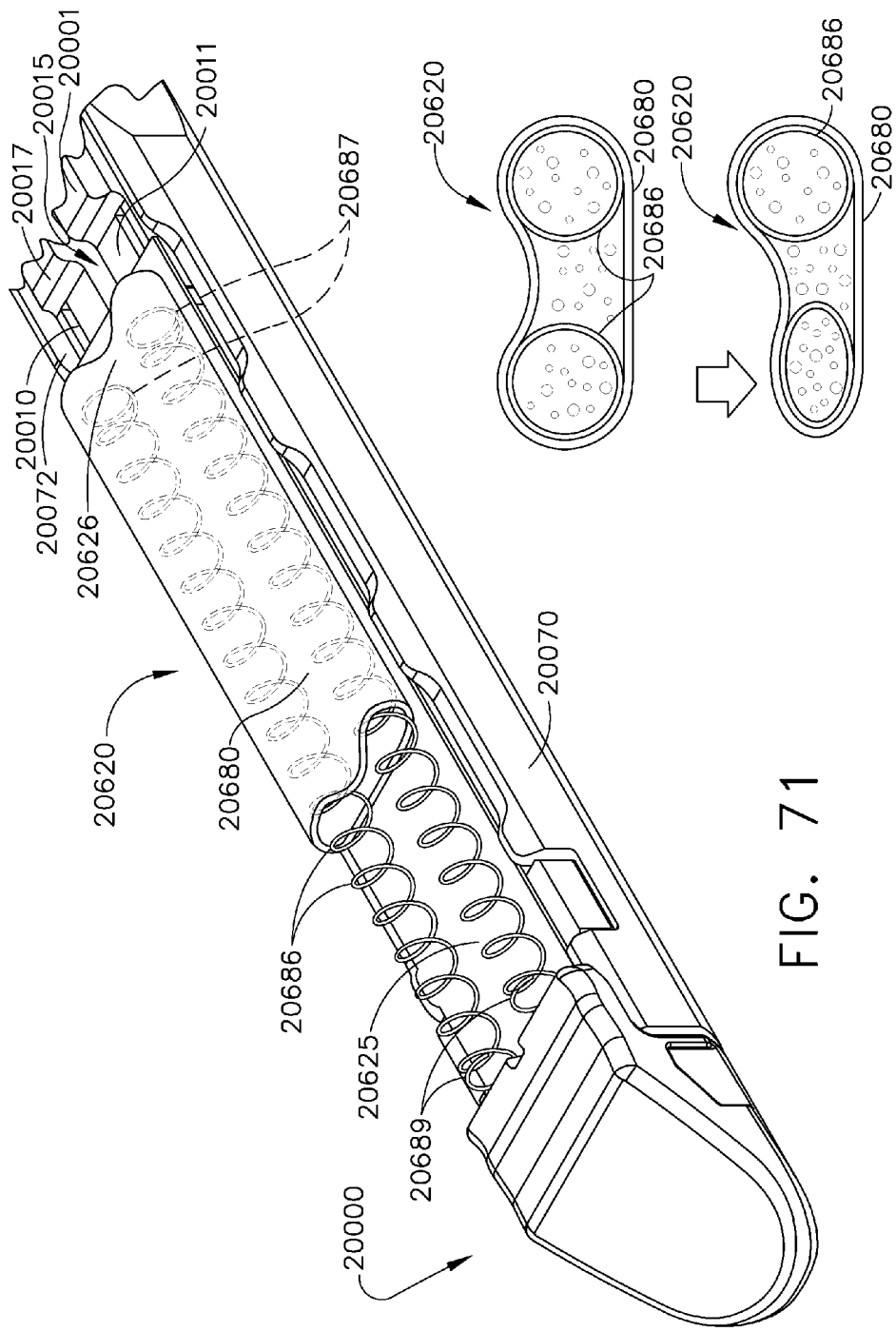

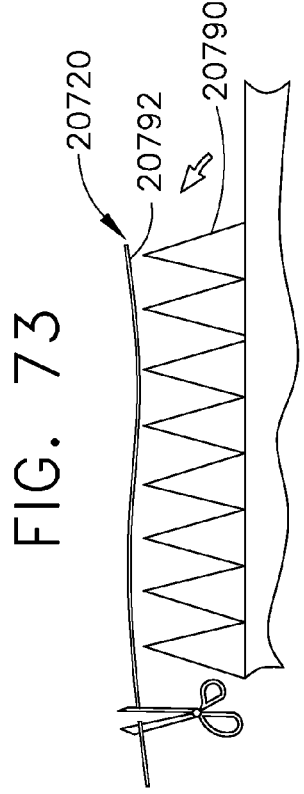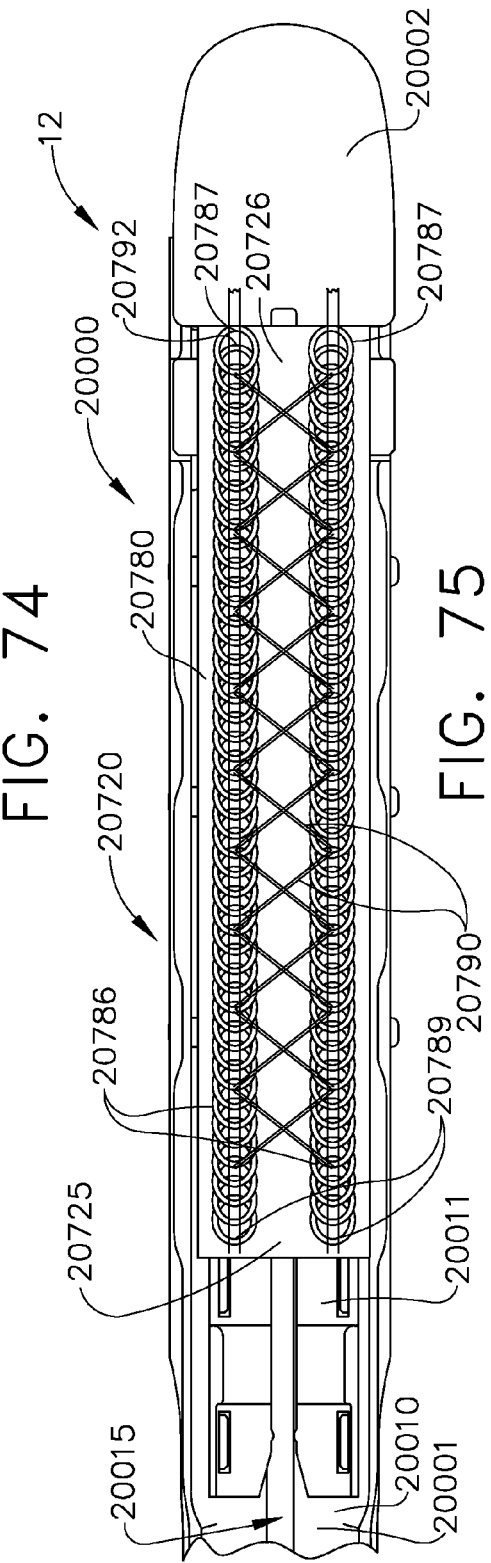

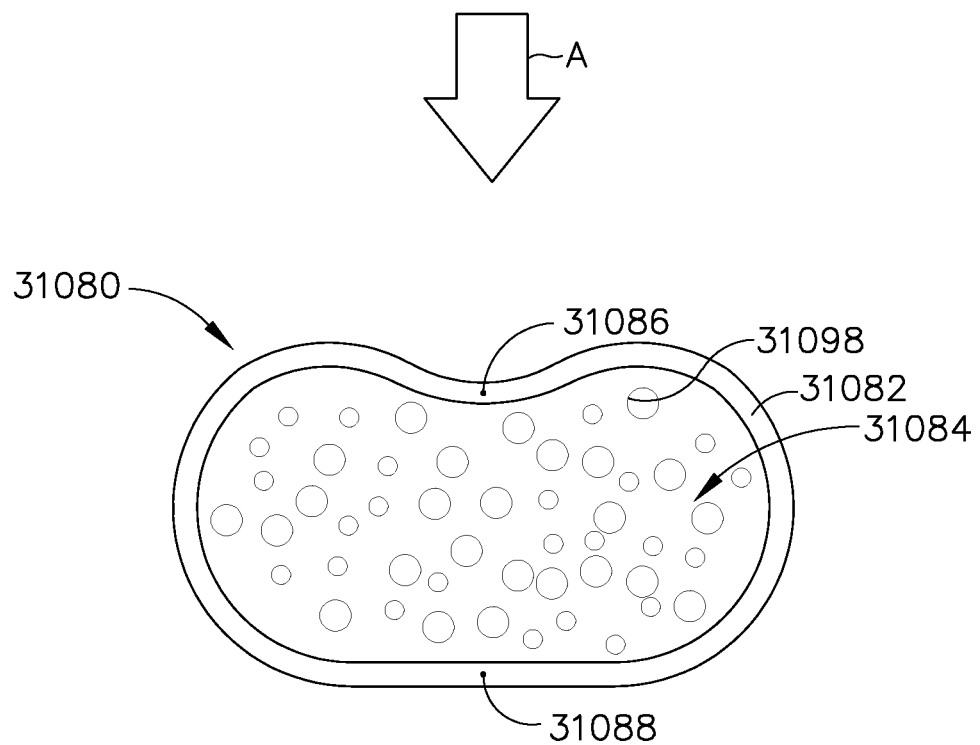
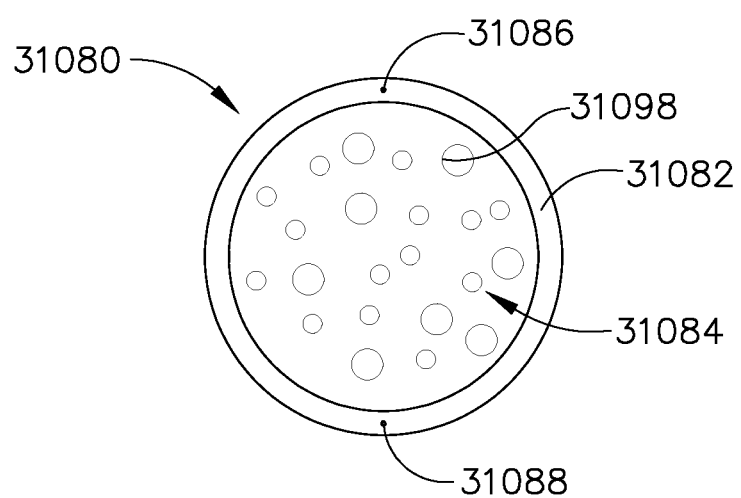
FIG. 87

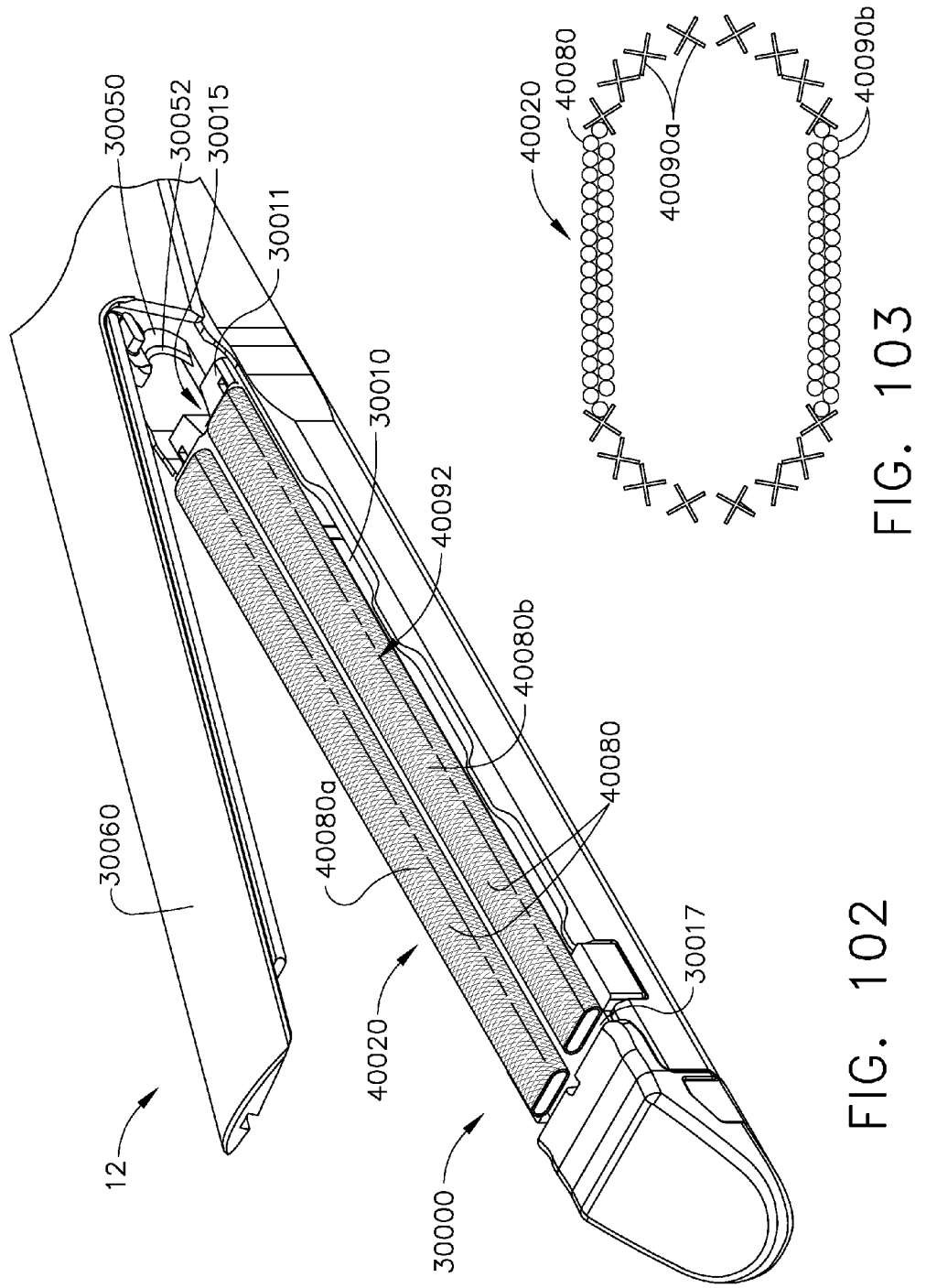

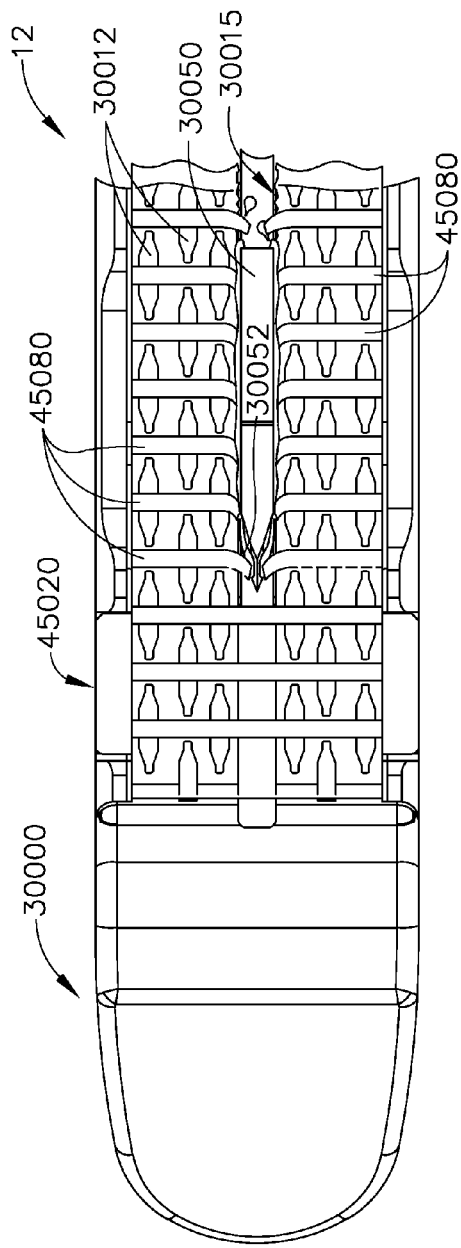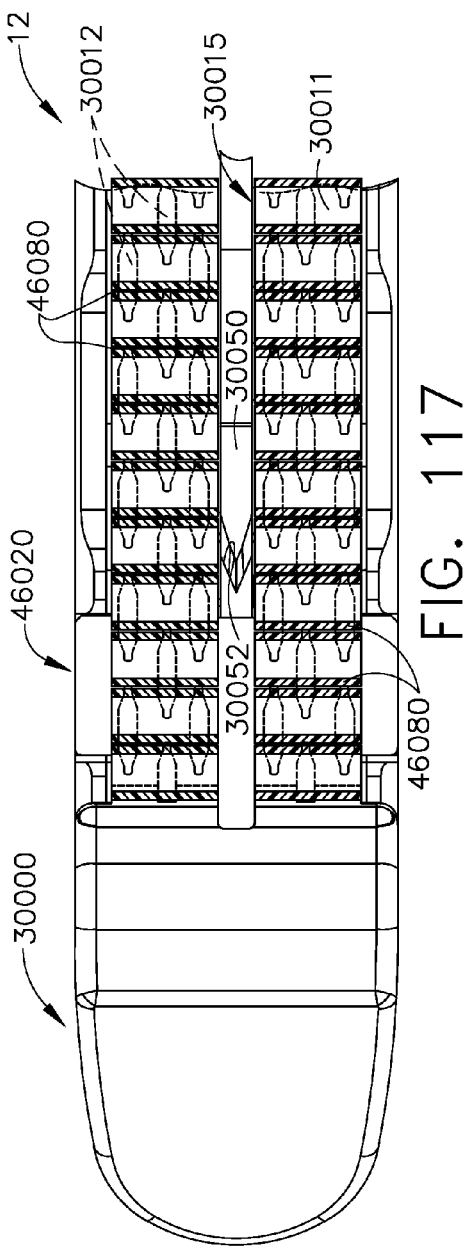

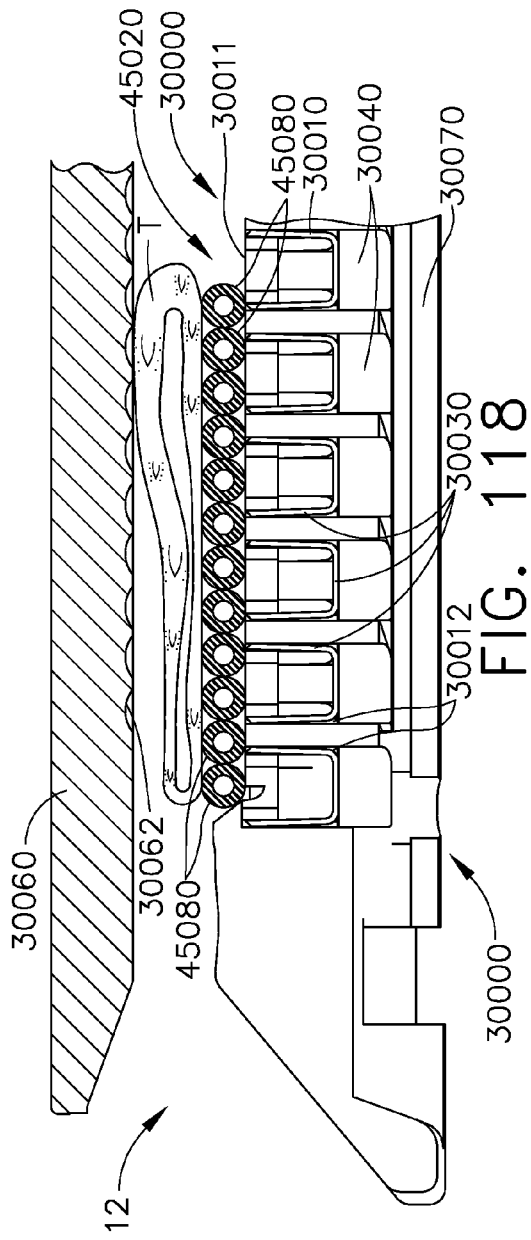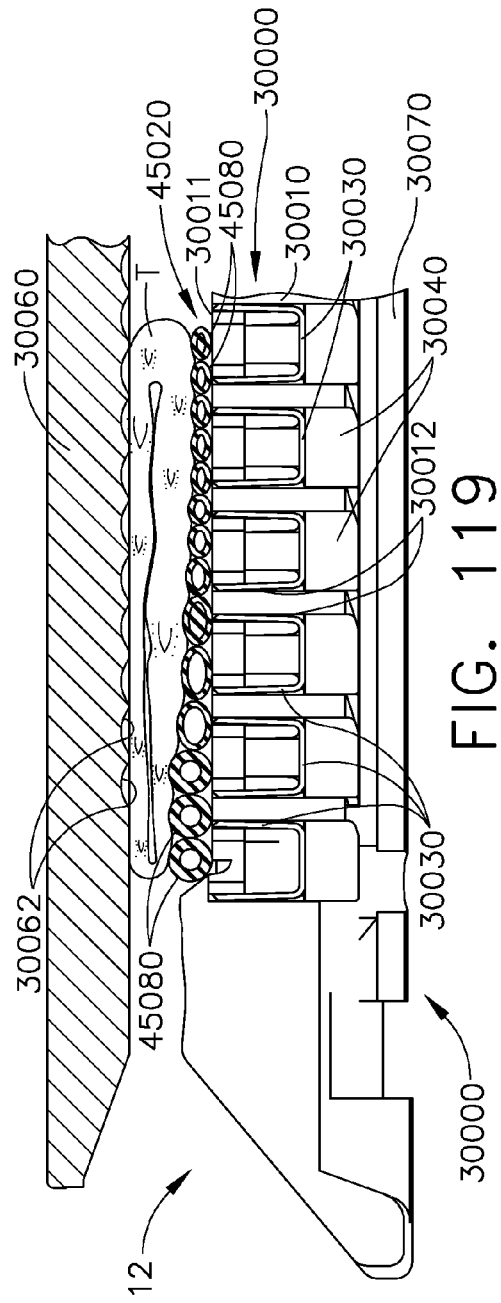

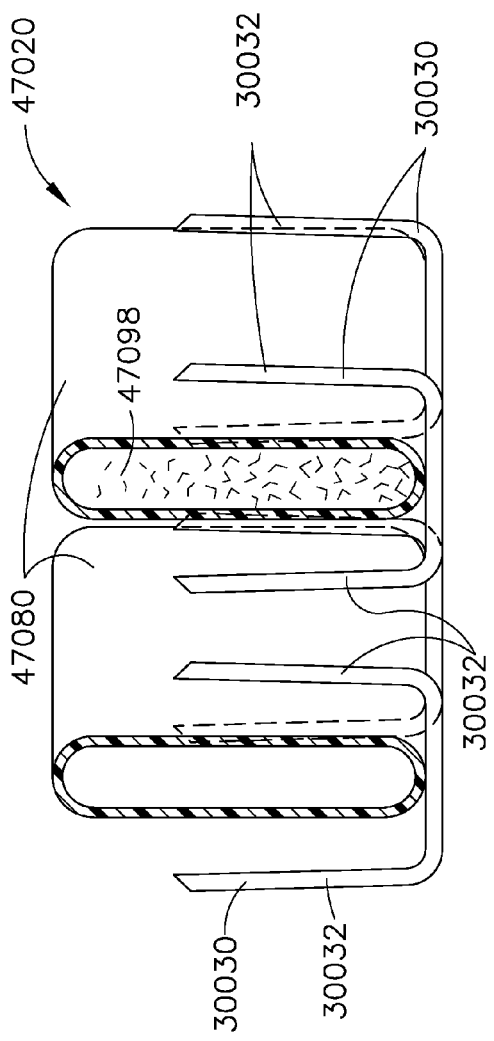
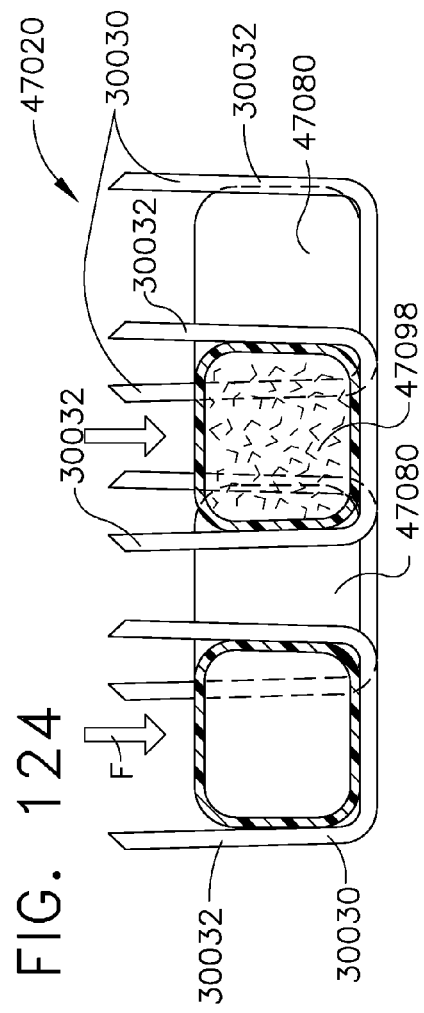
FIG. 124
FIG. 125

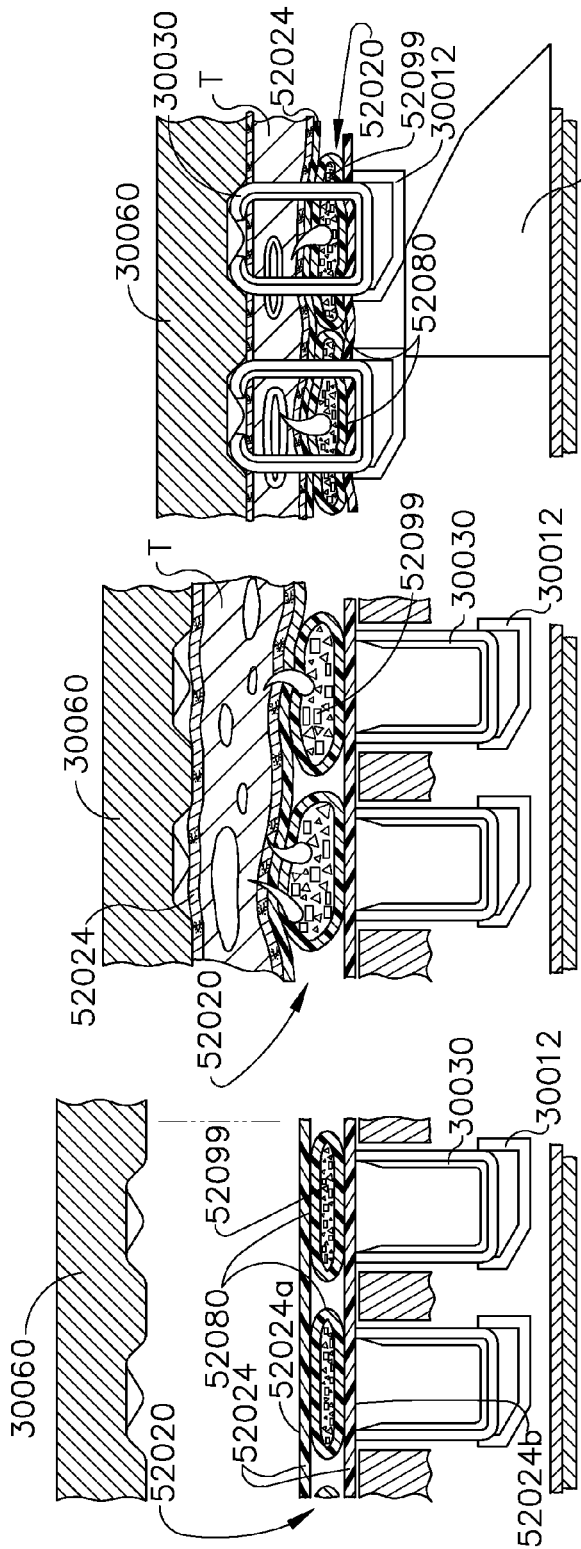

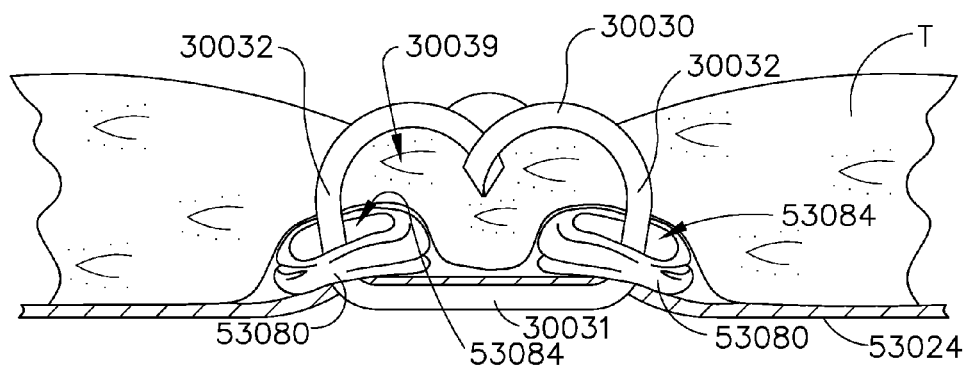
FIG. 152
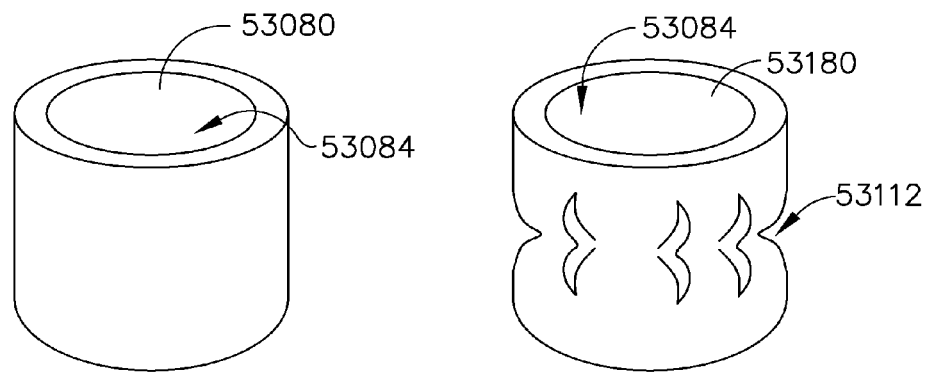
FIG. 153
FIG. 154

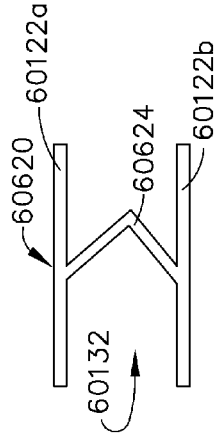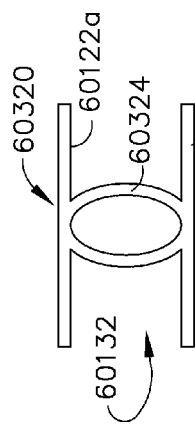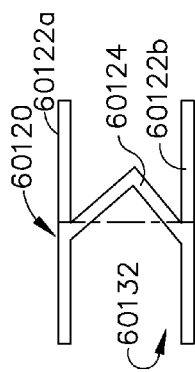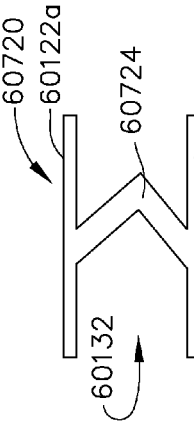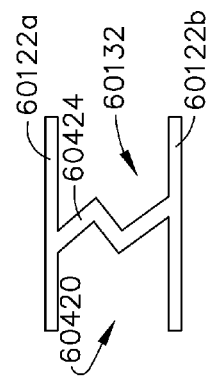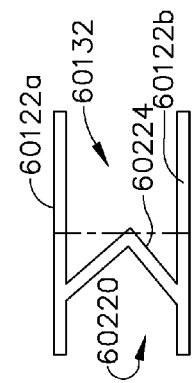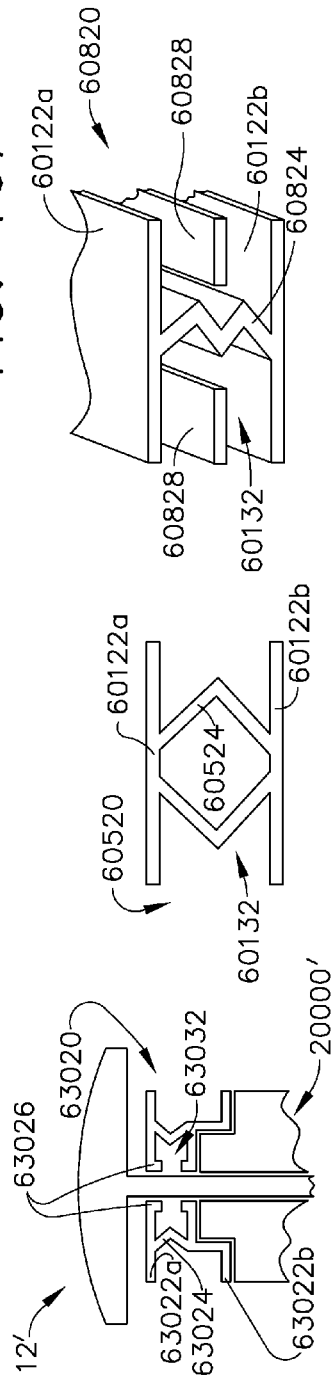

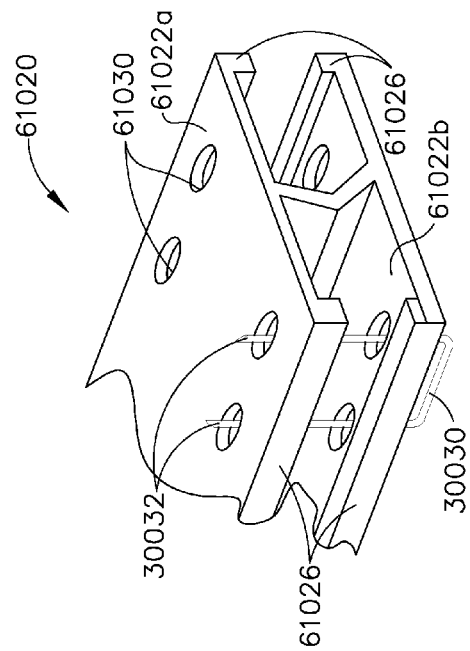
FIG. 170
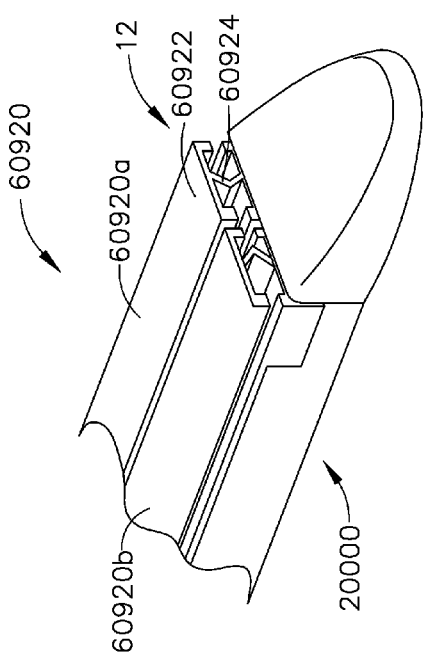
FIG. 169
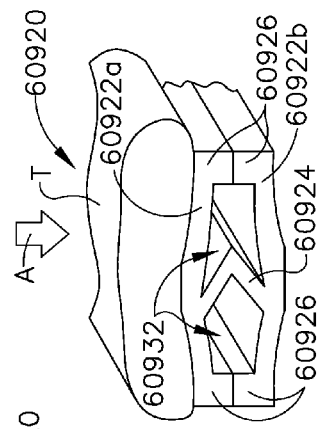
FIG. 173
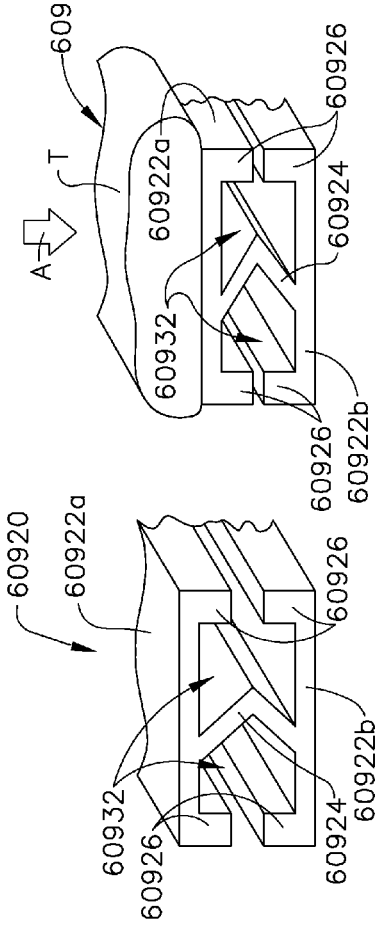
FIG. 172
FIG. 171

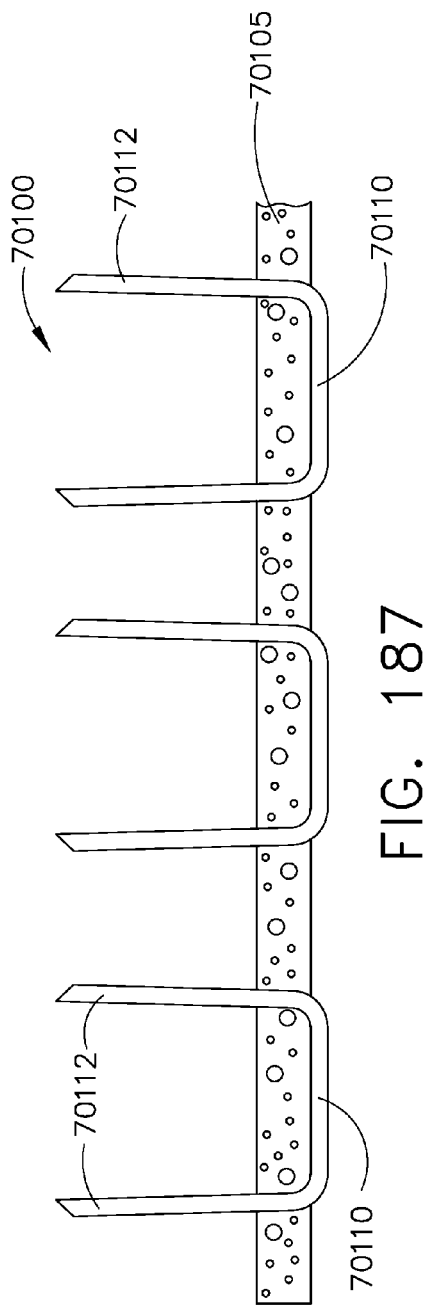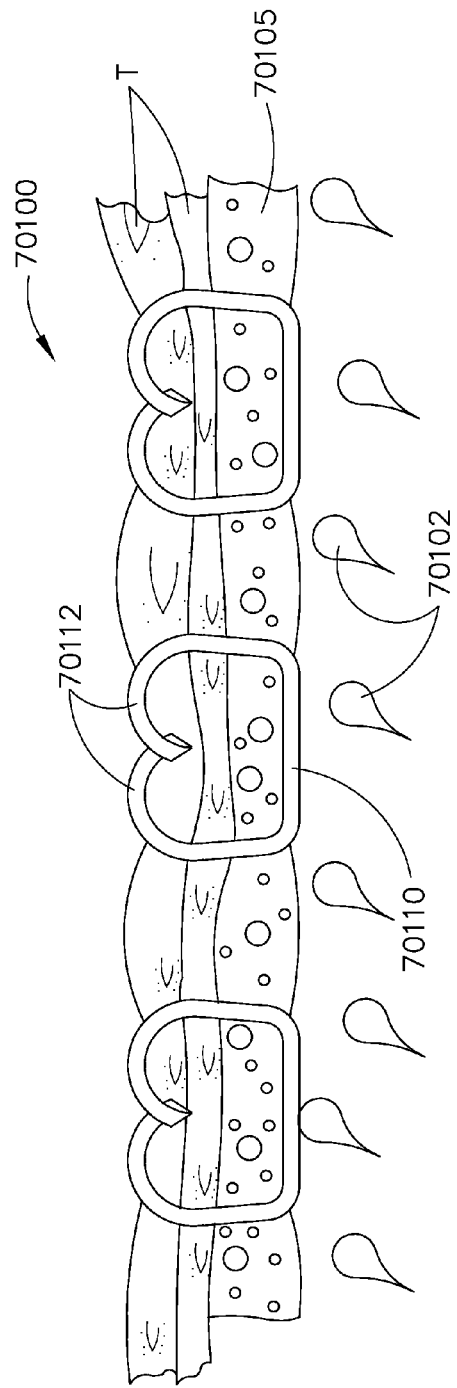

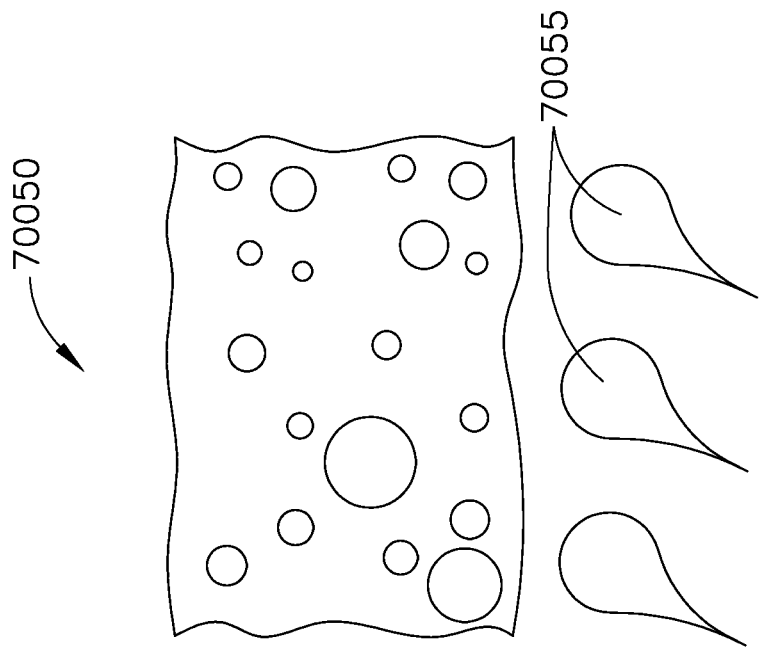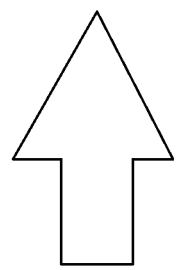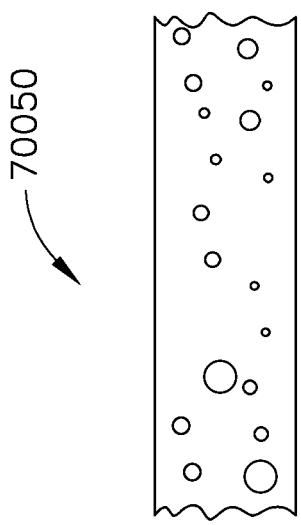
FIG. 190

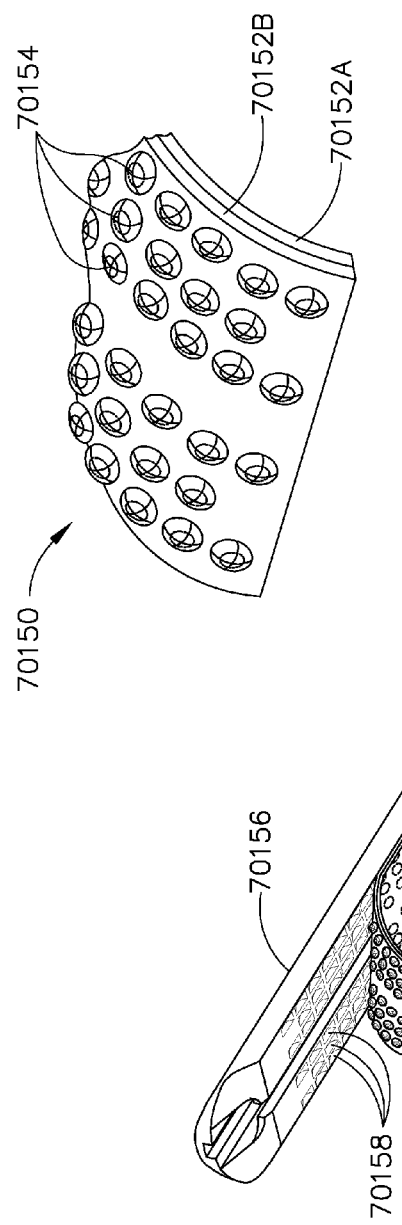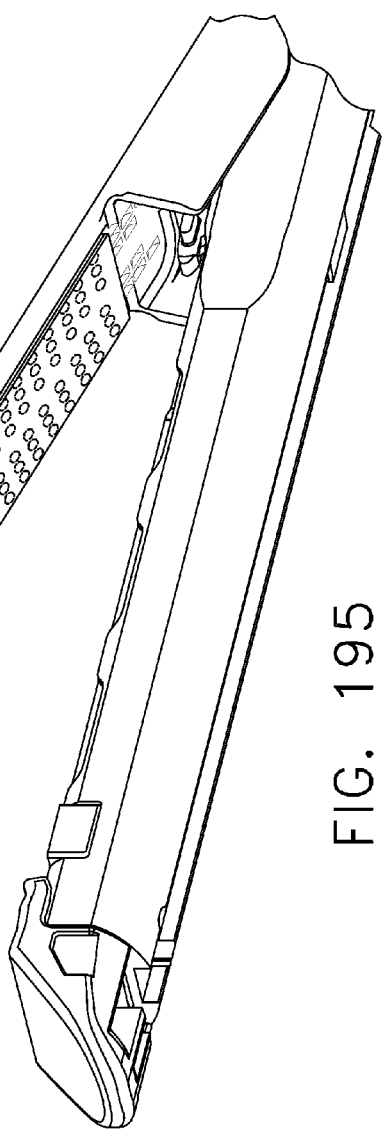
FIG. 194
FIG. 195

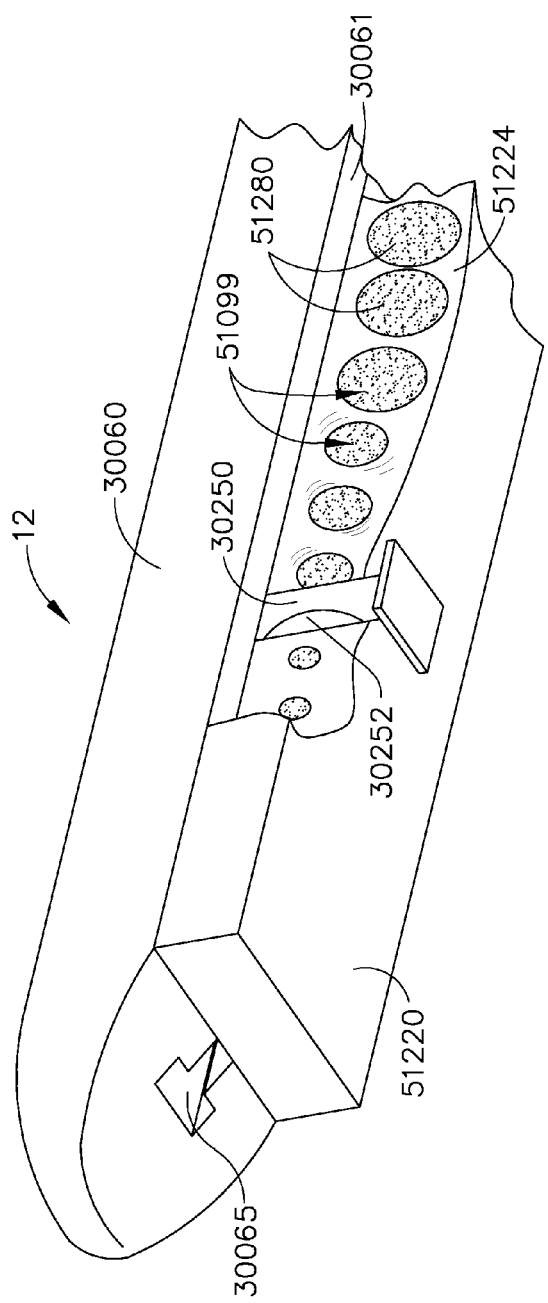
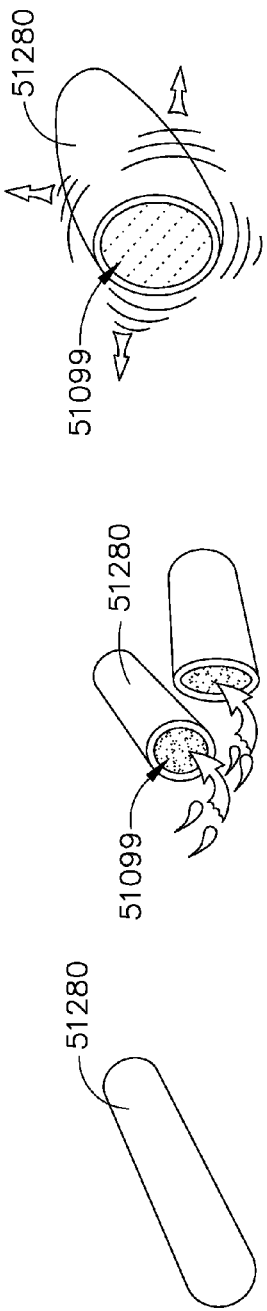
FIG. 208
FIG. 209
FIG. 210
FIG. 211

TISSUE THICKNESS COMPENSATOR COMPRISING STRUCTURE TO PRODUCE A RESILIENT LOAD

CROSS-REFERENCE TO RELATED APPLICATIONS

This non-provisional patent application is a continuation-in-part application under 35 U.S.C. §120 of U.S. patent application Ser. No. 13/097,891, entitled "Tissue Thickness Compensator For A Surgical Stapler Comprising An Adjustable Anvil, filed on Apr. 29, 2011, which issued on Oct. 21, 2014 as U.S. Pat. No. 8,864,009, which is a continuation-in-part application under 35 U.S.C. §120 of U.S. patent application Ser. No. 12/894,377, entitled "Selectively Orientable Implantable Fastener Cartridge", filed on Sep. 30, 2010, which issued on Mar. 12, 2013 as U.S. Pat. No. 8,393,514, the entire disclosures of which are hereby incorporated by reference herein.

BACKGROUND

The present invention relates to surgical instruments and, in various embodiments, to surgical cutting and stapling instruments and staple cartridges therefor that are designed to cut and staple tissue.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIGS. 1B-1E illustrate portions of an end effector clamping and stapling tissue with an implantable staple cartridge;

FIG. 2 is a partial cross-sectional side view of another end effector coupled to a portion of a surgical instrument with the end effector supporting a surgical staple cartridge and with the anvil thereof in an open position;

FIG. 3 is another partial cross-sectional side view of the end effector of FIG. 2 in a closed position;

FIG. 4 is another partial cross-sectional side view of the end effector of FIGS. 2 and 3 as the knife bar is starting to advance through the end effector;

FIG. 5 is another partial cross-sectional side view of the end effector of FIGS. 2-4 with the knife bar partially advanced therethrough;

FIGS. 6A-6D diagram the deformation of a surgical staple positioned within a collapsible staple cartridge body in accordance with at least one embodiment;

FIG. 8 is a top view of a staple cartridge in accordance with at least one embodiment comprising staples embedded in a collapsible staple cartridge body;

FIG. 9 is an elevational view of the staple cartridge of FIG. 8;

FIG. 26 is an elevational view of the staple cartridge of FIG. 25;

FIG. 27 is a detail elevational view of the staple cartridge of FIG. 25;

FIG. 31 is a longitudinal cross-sectional view of an anvil in a closed position and a staple cartridge comprising a rigid support portion and a compressible tissue thickness compensator illustrated with staples being moved from an unfired position to a fired position during a first sequence;

FIG. 32 is another cross-sectional view of the anvil and the staple cartridge of FIG. 31 illustrating the anvil in an open position after the firing sequence has been completed;

FIG. 37 is an elevational view of an anvil in a closed position and a staple cartridge comprising a rigid support portion and a compressible tissue thickness compensator illustrating the staples in an unfired position and tissue captured between the anvil and the tissue thickness compensator;

FIG. 38 is a detail view of the anvil and staple cartridge of FIG. 37;

FIG. 39 is an elevational view of an anvil in a closed position and a staple cartridge comprising a rigid support portion and a compressible tissue thickness compensator illustrating the staples in an unfired position illustrating thicker tissue positioned between the anvil and the staple cartridge;

FIG. 40 is a detail view of the anvil and staple cartridge of FIG. 39;

FIG. 41 is an elevational view of the anvil and staple cartridge of FIG. 39 illustrating tissue having different thicknesses positioned between the anvil and the staple cartridge;

FIG. 42 is a detail view of the anvil and staple cartridge of FIG. 39 as illustrated in FIG. 41;

FIG. 47 is a diagram illustrating a tissue thickness compensator positioned in a region of tissue in which multiple staples lines have intersected;

FIG. 48 is a diagram illustrating tissue captured within a staple;

FIG. 49 is a diagram illustrating tissue and a tissue thickness compensator captured within a staple;

FIG. 50 is a diagram illustrating tissue captured within a staple;

FIG. 51 is a diagram illustrating thick tissue and a tissue thickness compensator captured within a staple;

FIG. 52 is a diagram illustrating thin tissue and a tissue thickness compensator captured within a staple;

FIG. 53 is a diagram illustrating tissue having an intermediate thickness and a tissue thickness compensator captured within a staple;

FIG. 54 is a diagram illustrating tissue having another intermediate thickness and a tissue thickness compensator captured within a staple;

FIG. 55 is a diagram illustrating thick tissue and a tissue thickness compensator captured within a staple;

FIG. 56 is a partial cross-sectional view of an end effector of a surgical stapling instrument illustrating a firing bar and staple-firing sled in a retracted, unfired position;

FIG. 57 is another partial cross-sectional view of the end effector of FIG. 56 illustrating the firing bar and the staple-firing sled in a partially advanced position;

FIG. 58 is a cross-sectional view of the end effector of FIG. 56 illustrating the firing bar in a fully advanced, or fired, position;

FIG. 67 is a schematic depicting an arrangement of crimped fibers according to at least one embodiment;

FIG. 68 is a schematic depicting an arrangement of crimped fibers according to at least one embodiment;

FIG. 69 is a schematic depicting an arrangement of crimped fibers according to at least one embodiment;

FIG. 70 is a plan cross-sectional view of coiled fibers in a tissue thickness compensator according to at least one embodiment;

FIG. 70A is a plan cross-sectional view of the coiled fibers of FIG. 70;

FIG. 70B is a cross-sectional detail view of the tissue thickness compensator of FIG. 70;

FIG. 71 is a perspective view of a tissue thickness compensator in an end effector of a surgical instrument according to at least one embodiment;

FIG. 72 is a diagram depicting deformation of the tissue thickness compensator of FIG. 71;

FIG. 73 is a schematic of woven suture for a tissue thickness compensator depicting the woven suture in a loaded configuration according to at least one embodiment;

FIG. 74 is a schematic of the woven suture of FIG. 73 depicting the woven suture in a released configuration;

FIG. 75 is a plan view of a tissue thickness compensator having the woven suture of FIG. 73 in an end effector of a surgical instrument;

FIG. 87 is a diagram depicting deformation of a deformable tube of a tissue thickness compensator according to at least one embodiment;

FIG. 102 is a perspective view of a tissue thickness compensator positioned in an end effector of a surgical instrument according to at least one embodiment;

FIG. 103 is an elevational view of a tubular element of the tissue thickness compensator of FIG. 102;

FIG. 111 is a perspective view of a tissue thickness compensator positioned in an end effector of a surgical instrument according to at least one embodiment;

FIG. 112 is an elevational cross-sectional view of a tissue thickness compensator positioned in an end effector of a surgical instrument according to at least one embodiment;

FIG. 113 is an elevational cross-sectional view of a tissue thickness compensator positioned in an end effector of a surgical instrument according to at least one embodiment;

FIG. 114 is an elevational cross-sectional view of a tissue thickness compensator positioned in an end effector of a surgical instrument according to at least one embodiment;

FIG. 115 is an elevational cross-sectional view of a tissue thickness compensator positioned in an end effector of a surgical instrument according to at least one embodiment;

FIG. 116 is a partial plan view of a tissue thickness compensator positioned in an end effector of a surgical instrument according to at least one embodiment;

FIG. 117 is a partial plan view of a tissue thickness compensator positioned in an end effector of a surgical instrument according to at least one embodiment;

FIG. 118 is a partial elevational cross-sectional view of the tissue thickness compensator and the end effector of FIG. 116 depicting the end effector in an unclamped configuration;

FIG. 119 is a partial elevational cross-sectional view of the tissue thickness compensator and the end effector of FIG. 116 depicting the end effector in a clamped configuration;

FIG. 120 is a perspective view of a tissue thickness compensator in an end effector of a surgical instrument according to at least one embodiment;

FIG. 121 is an elevational view of the tissue thickness compensator and the end effector of FIG. 120;

FIG. 122 is a perspective view of the tissue thickness compensator and the end effector of FIG. 120 depicting the anvil of the end effector moving towards a clamped configuration;

Figure 120:
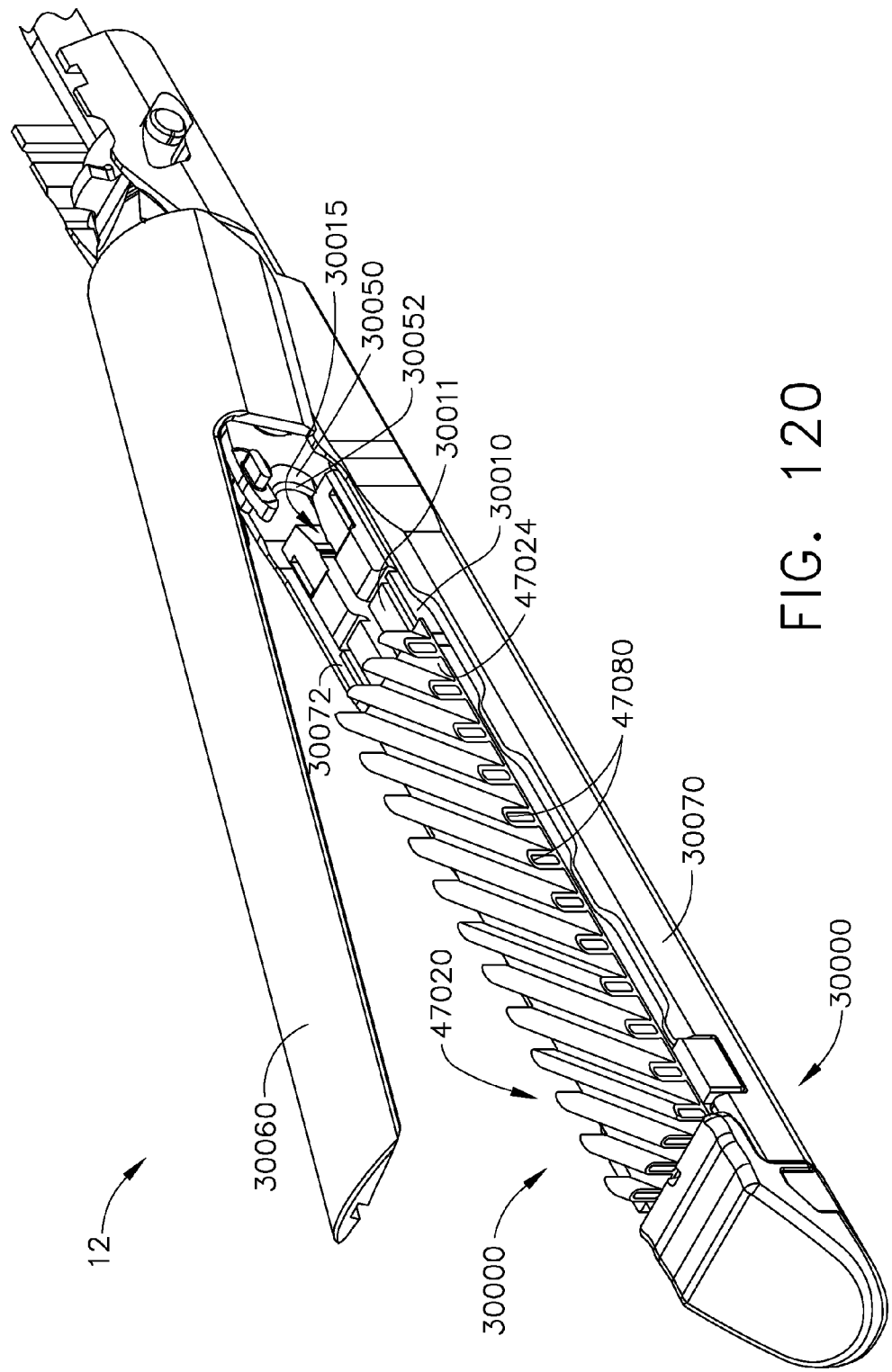
Figure 121:
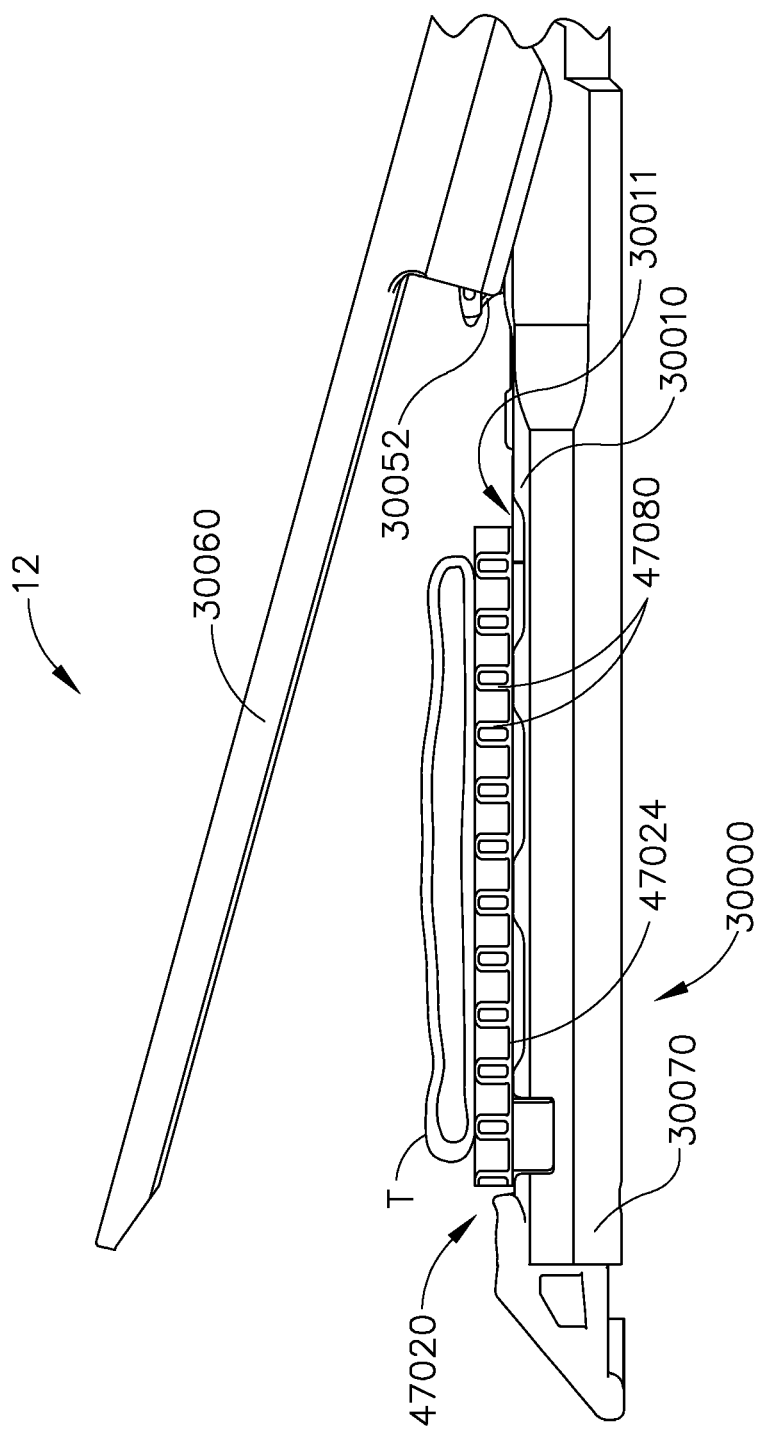
Figure 122:
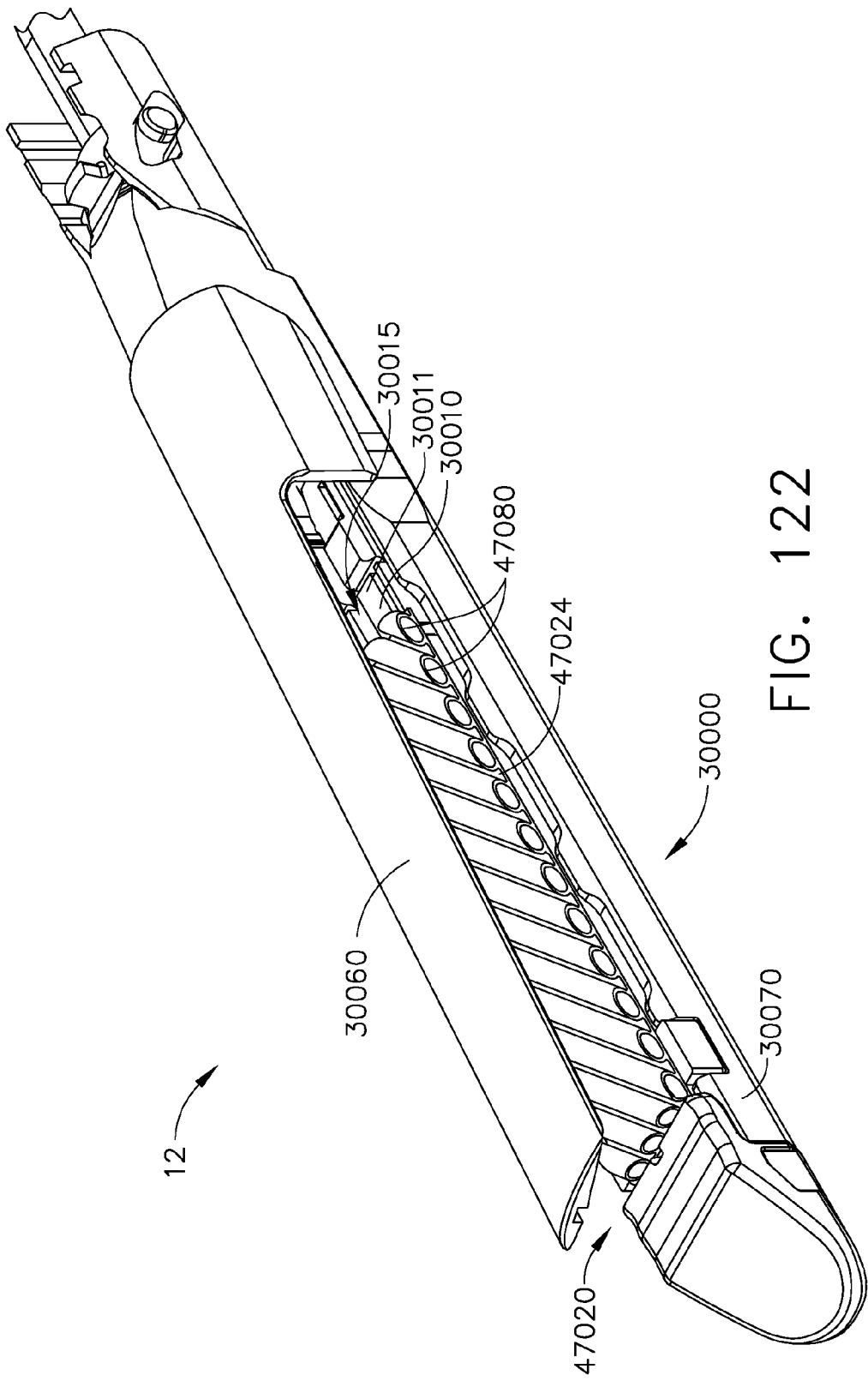
Figure 123:
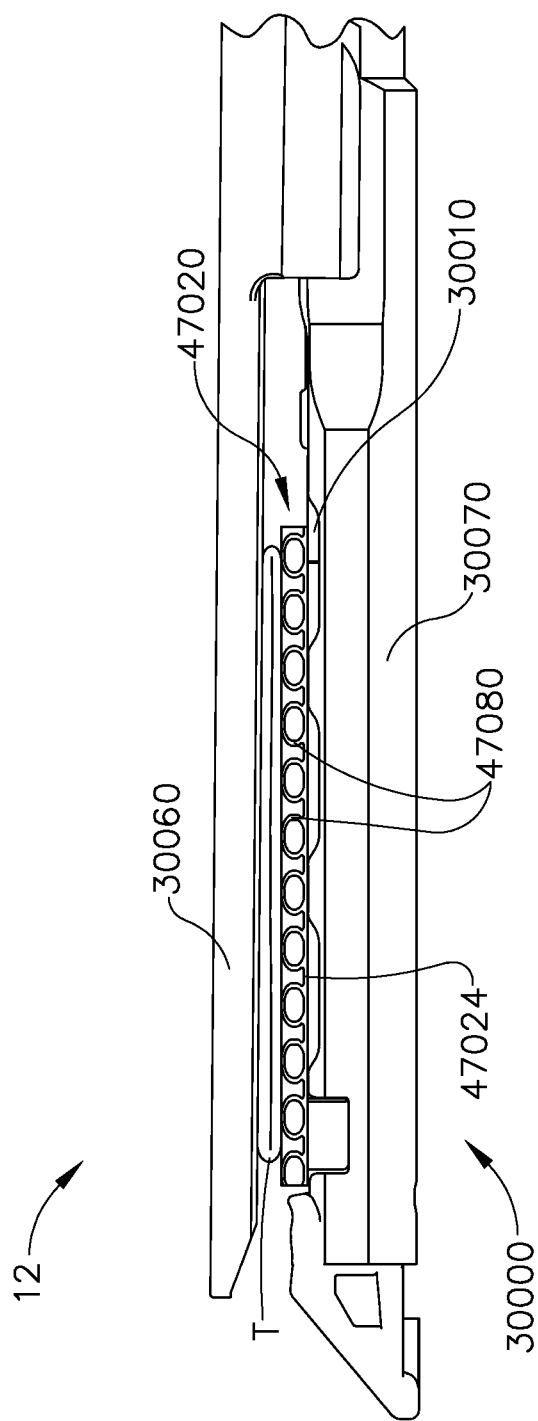
Figure 126:
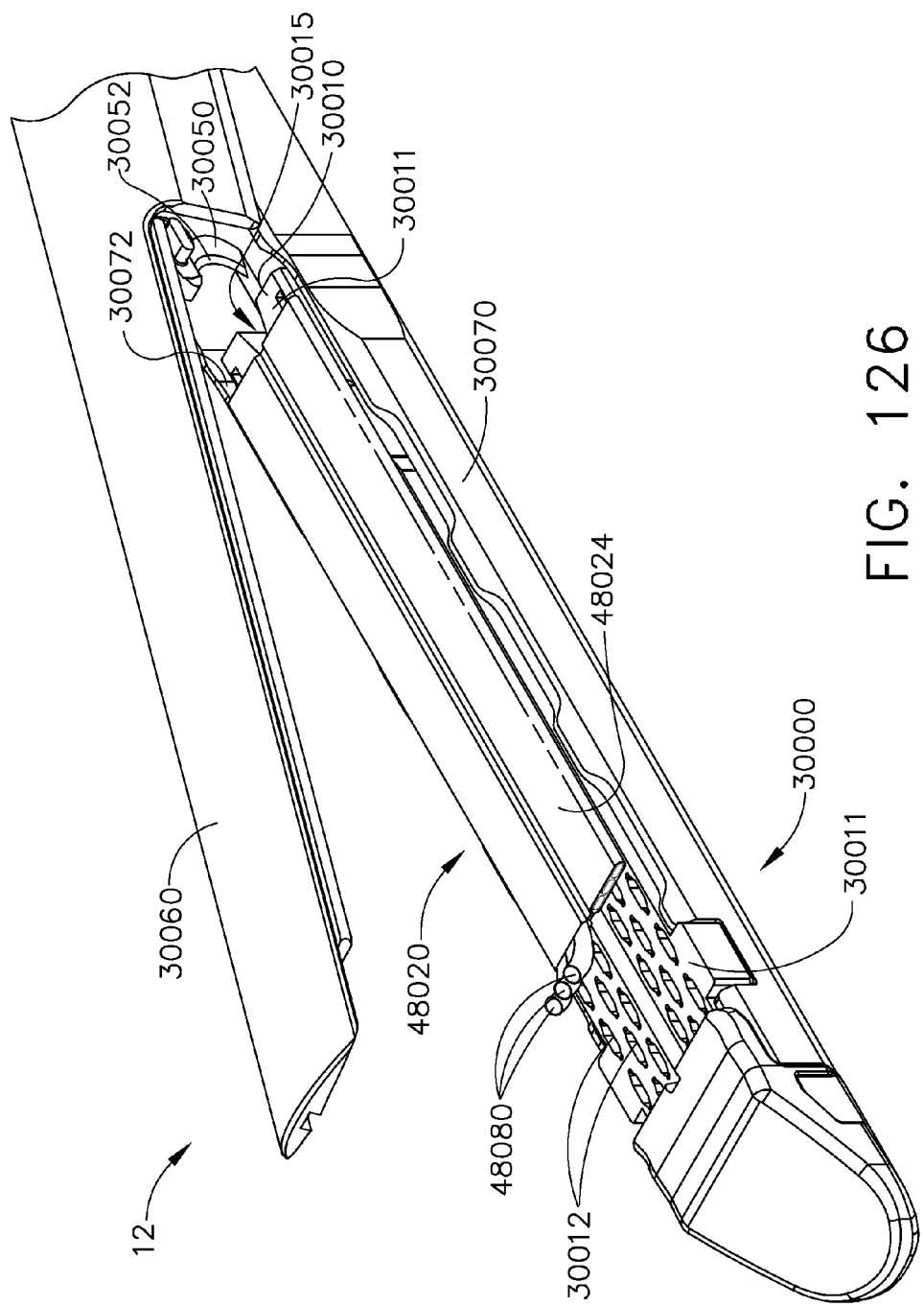
Figure 127:
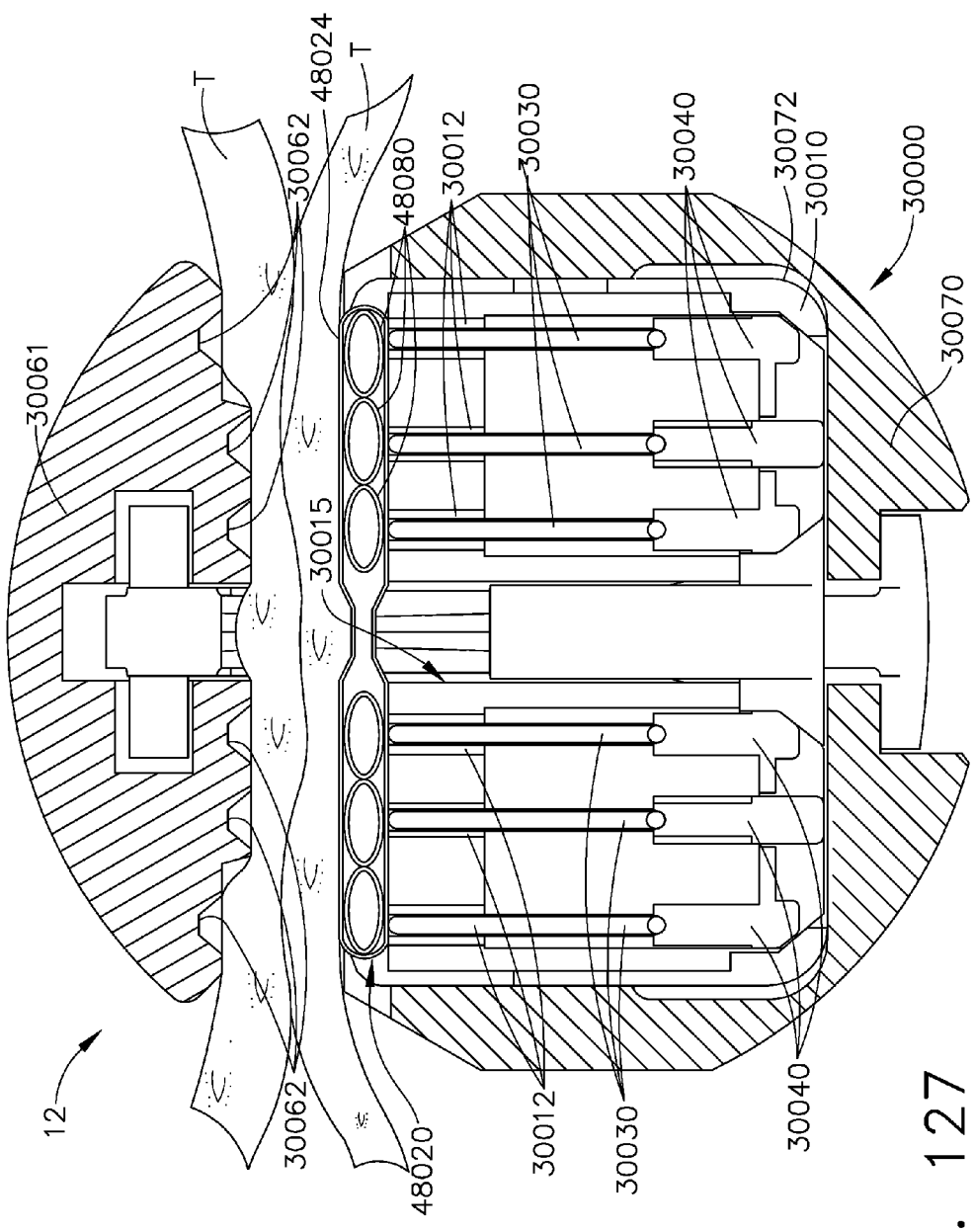
Figure 128:
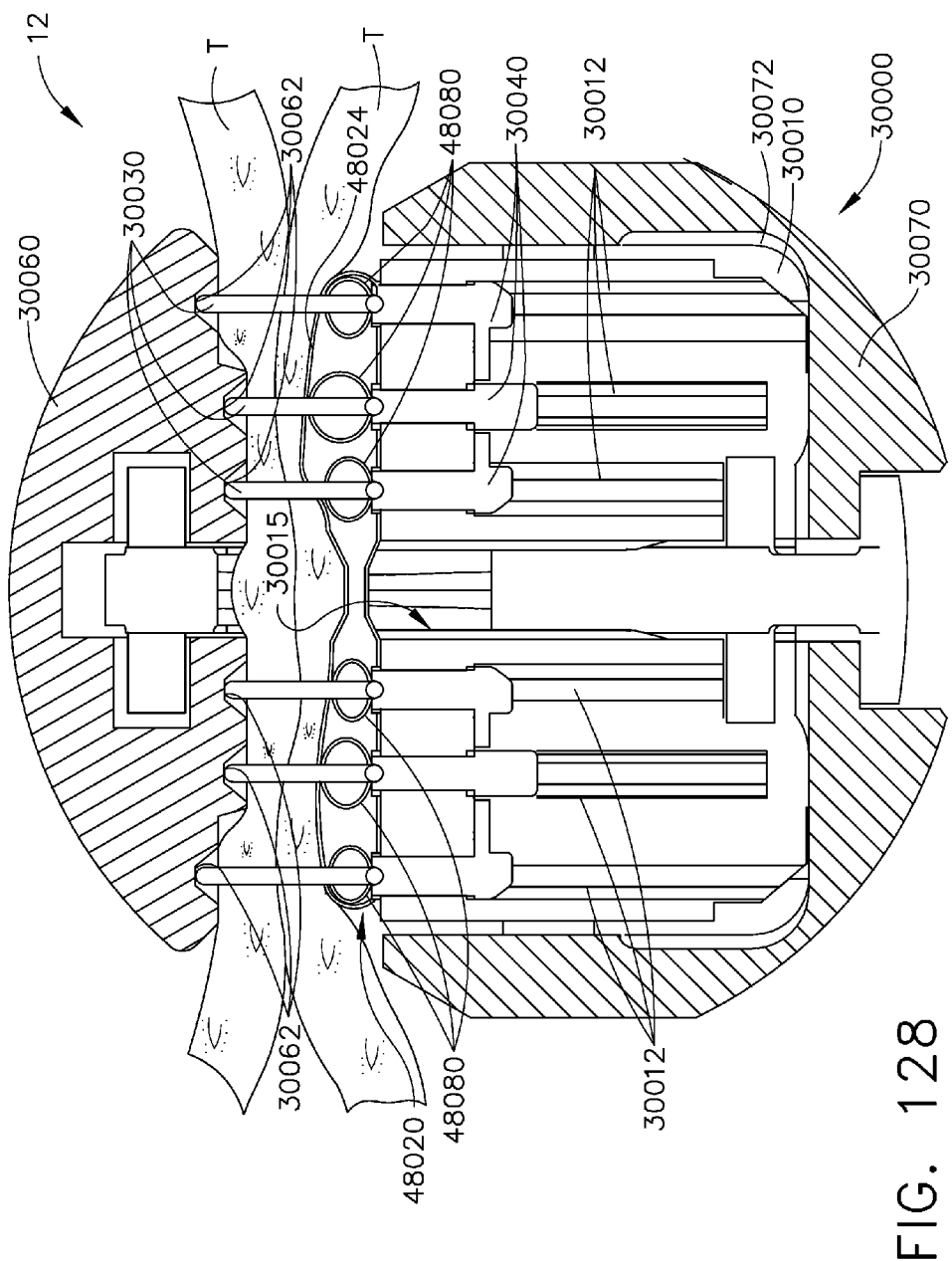
Figure 129:
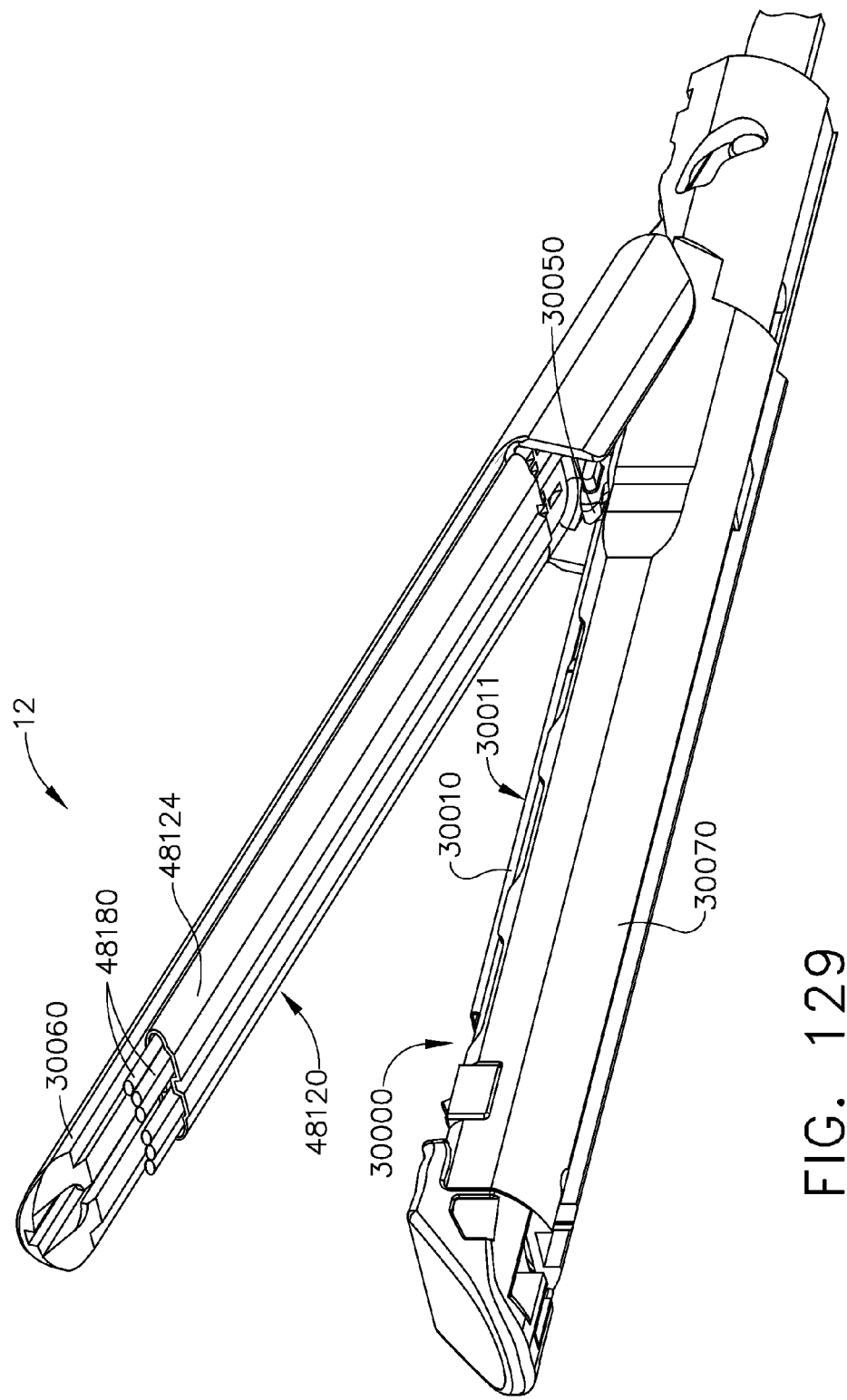
Figure 130:
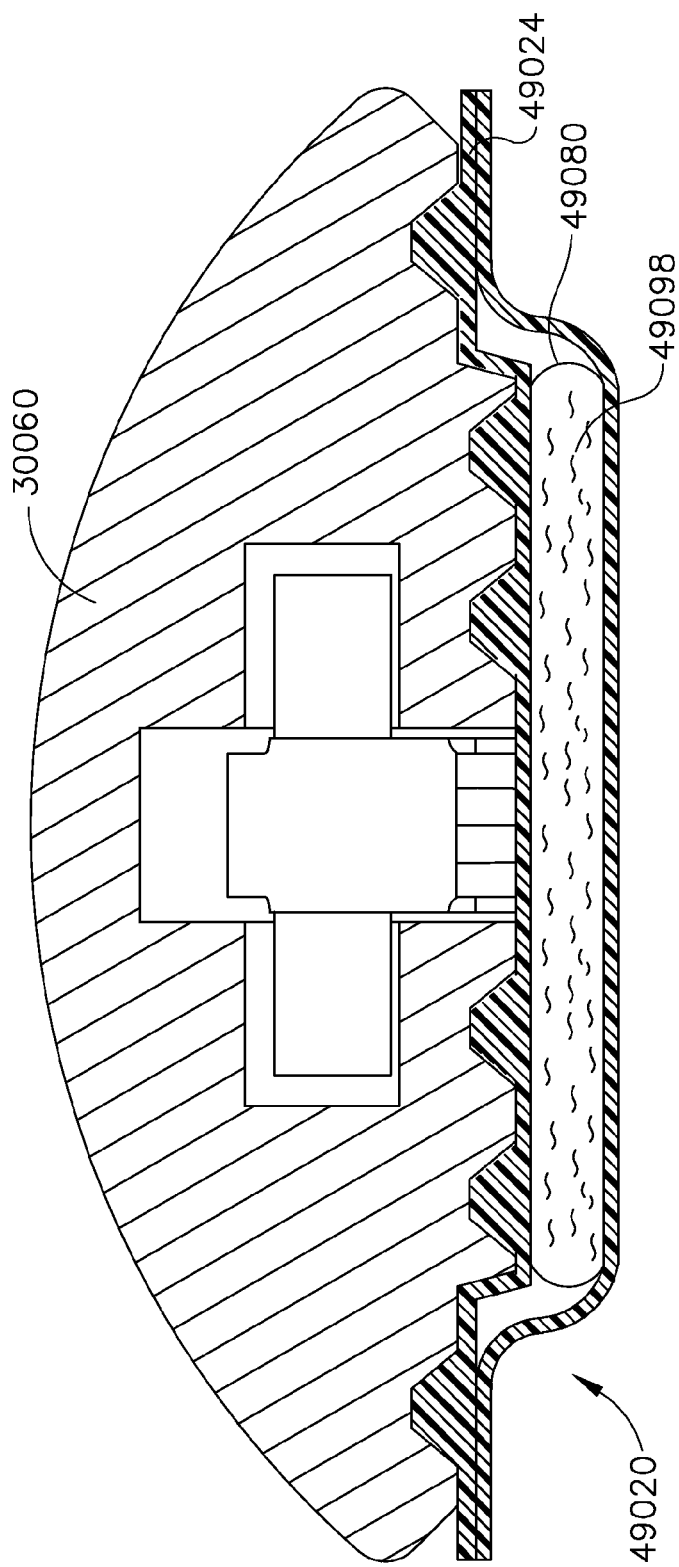
Figure 131:
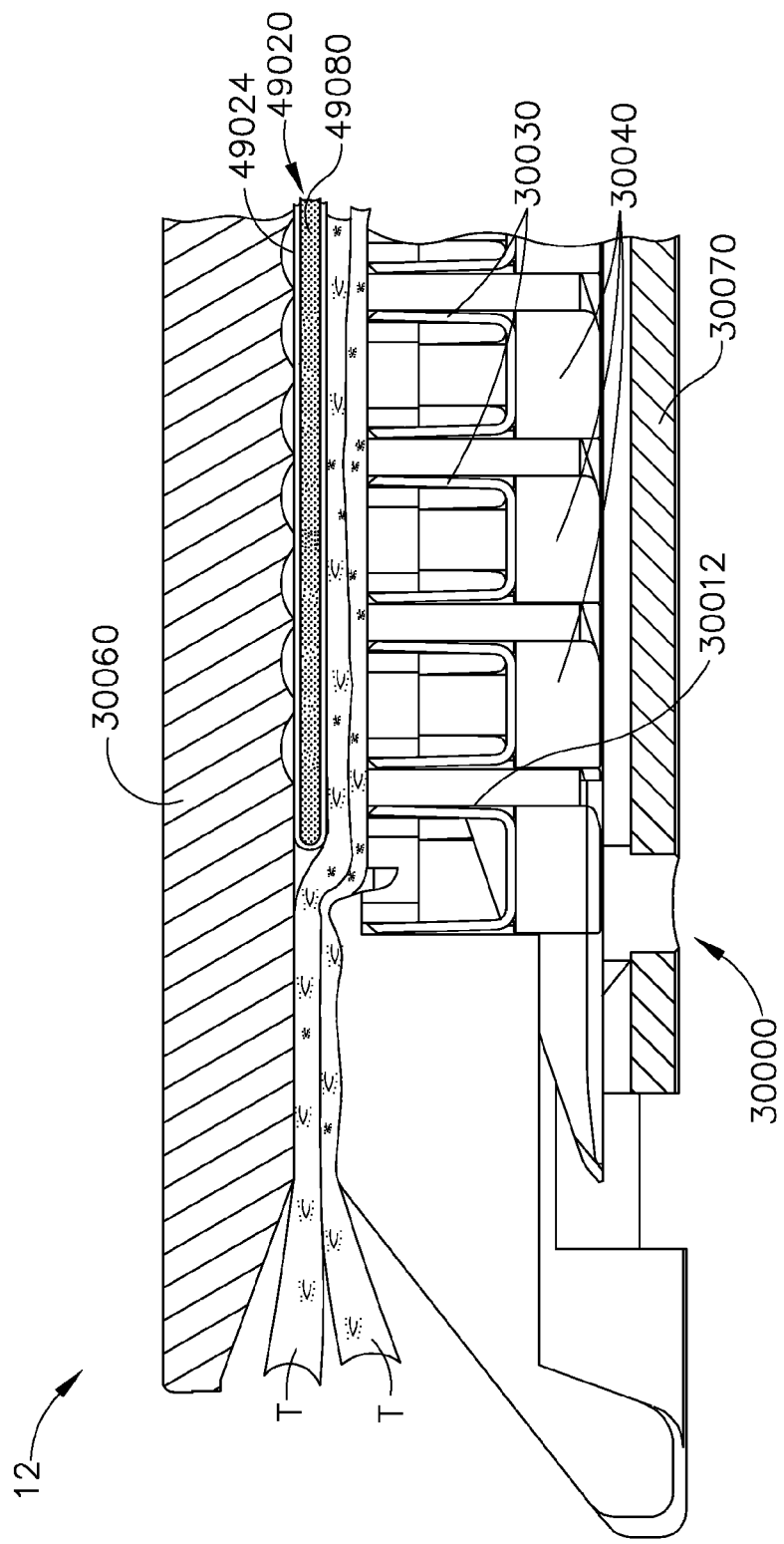
Figure 132:
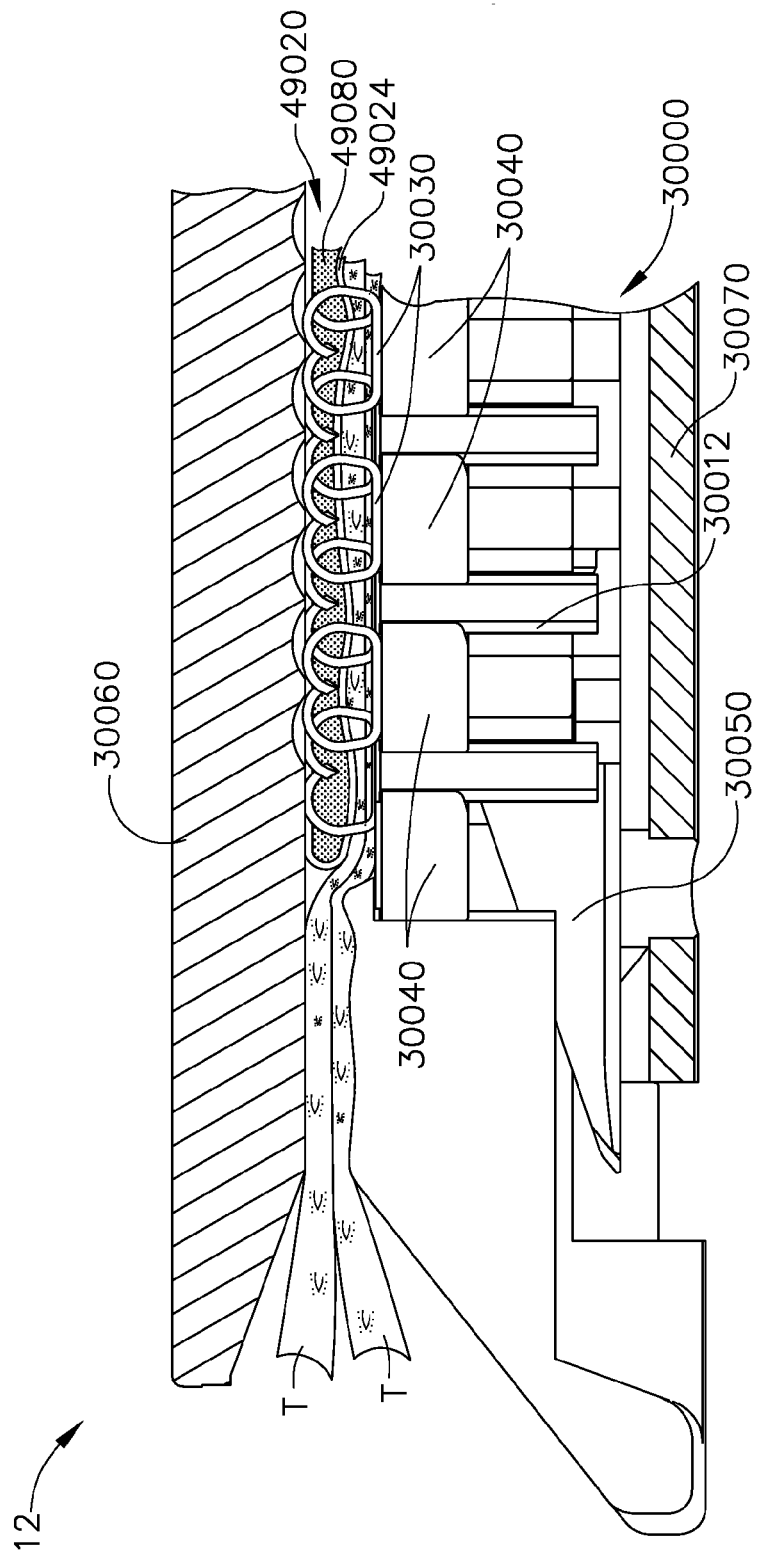
Figure 133:
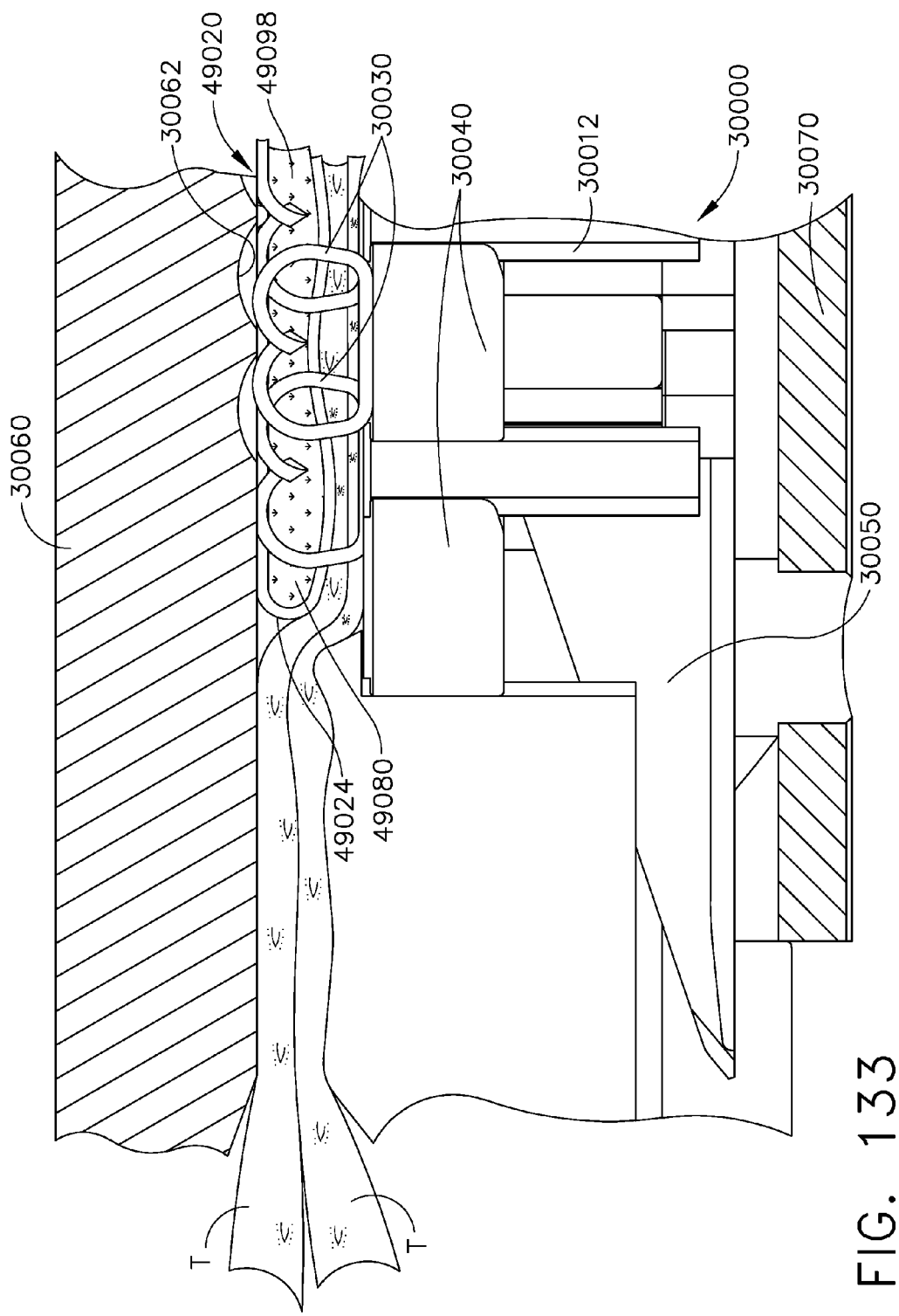
Figure 134:
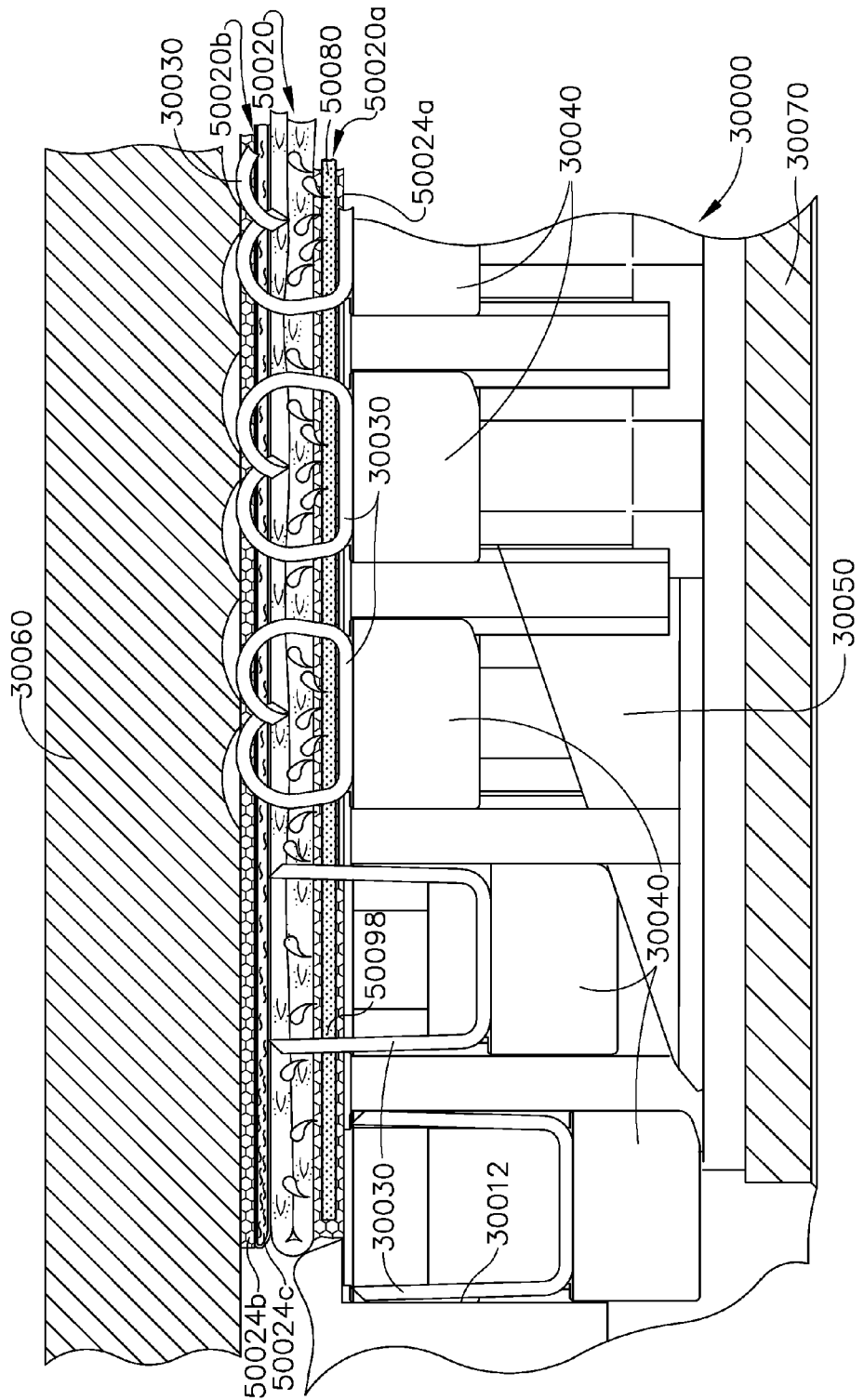
Figure 135:
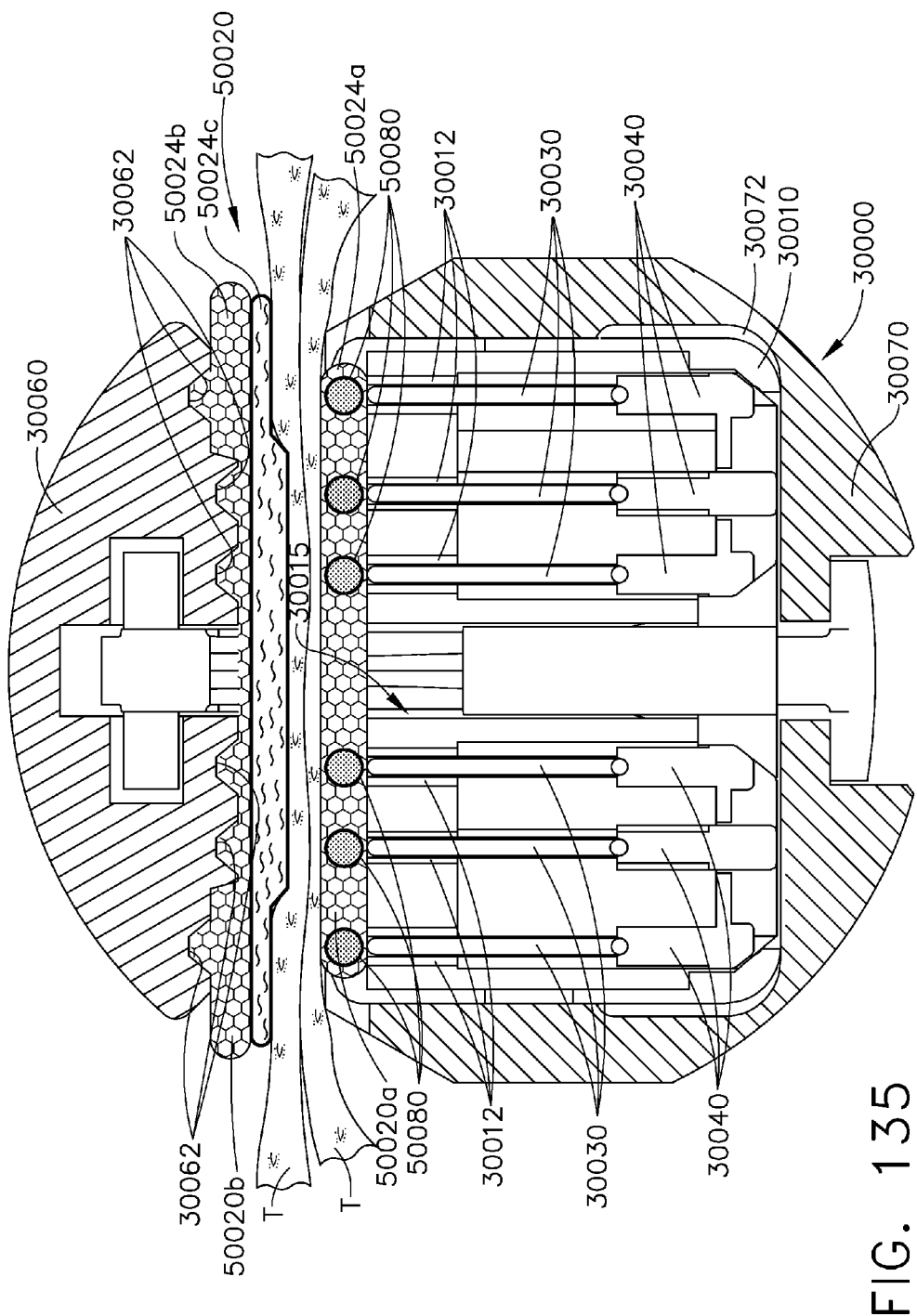
Figure 136:
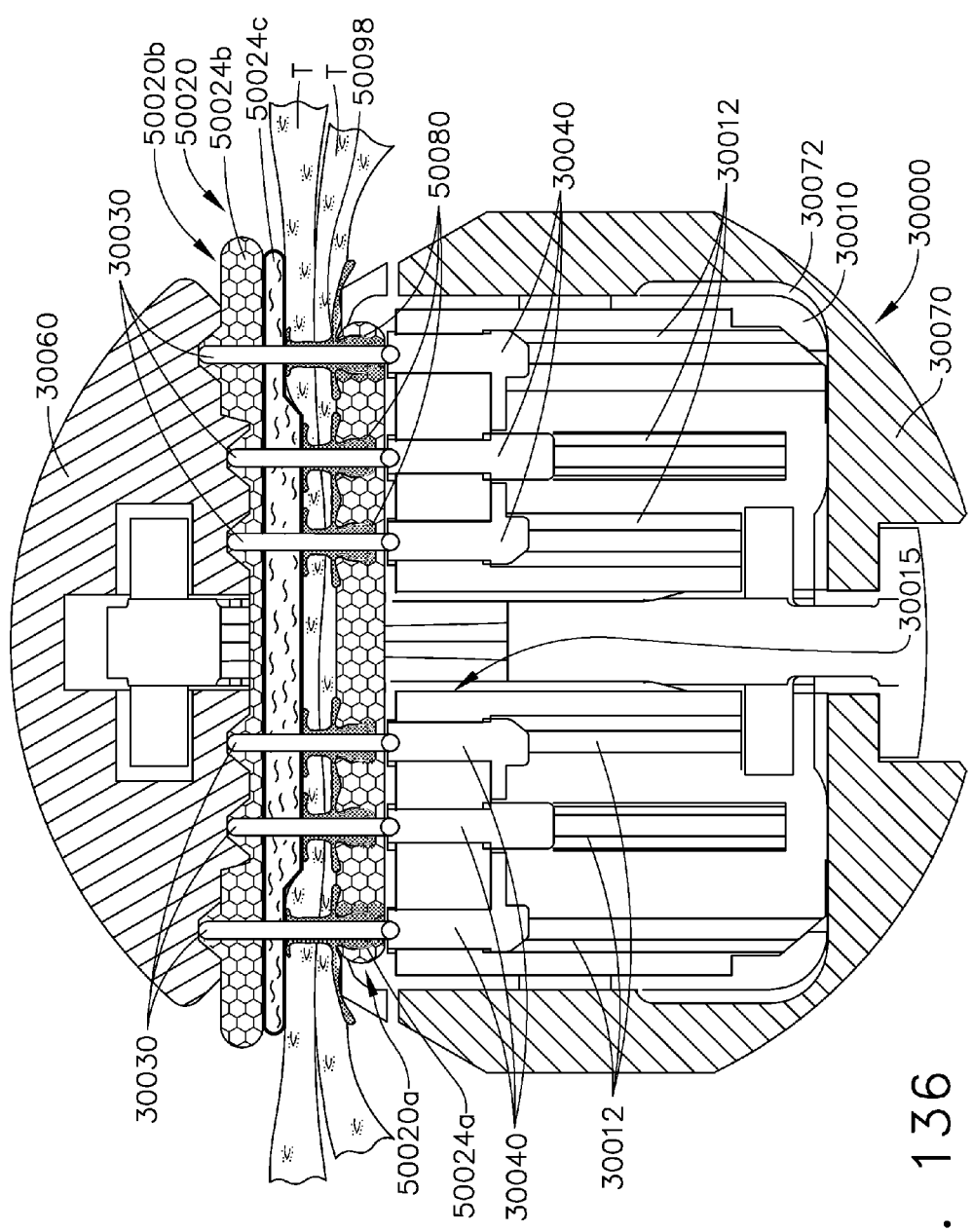
Figure 137:
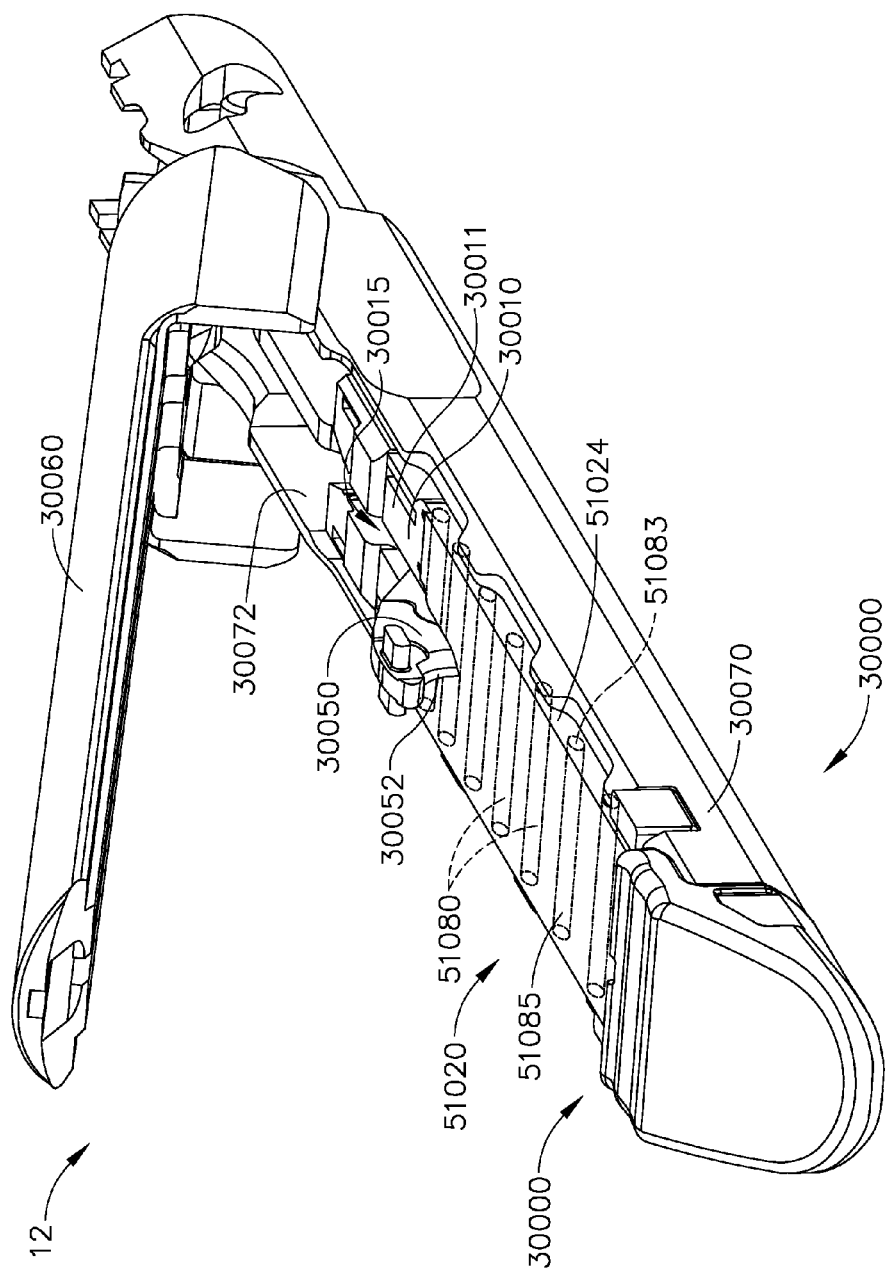
Figure 138:
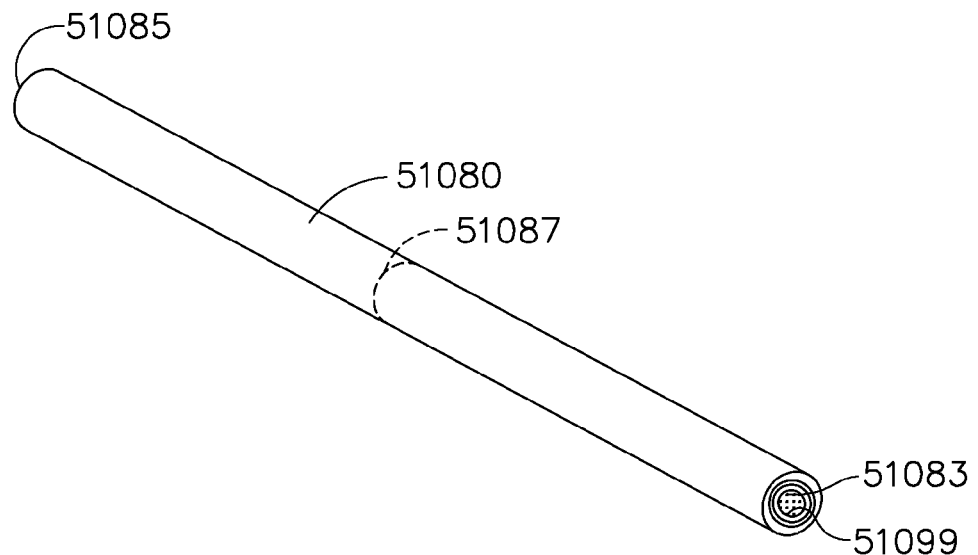
Figure 139:
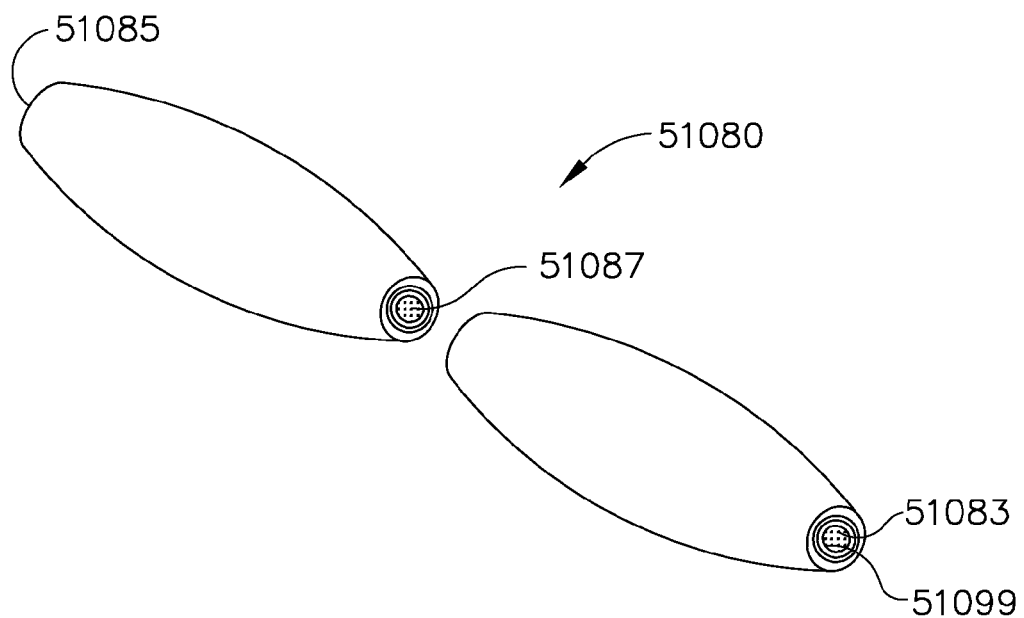
Figure 140:
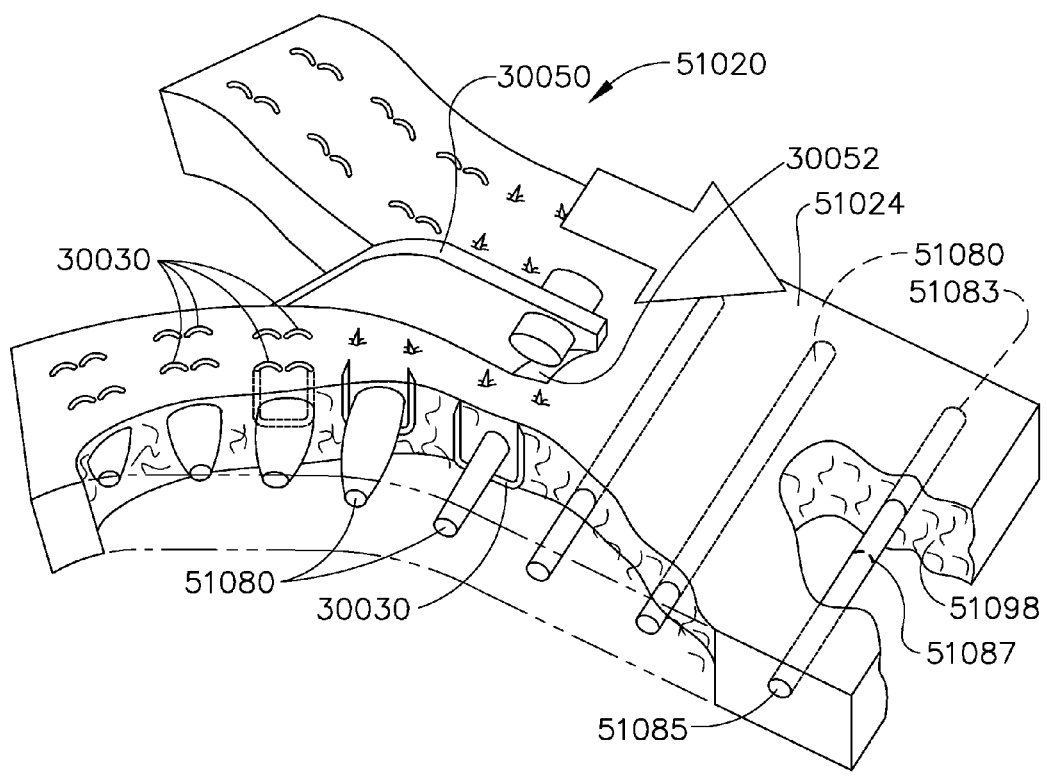
Figure 141:
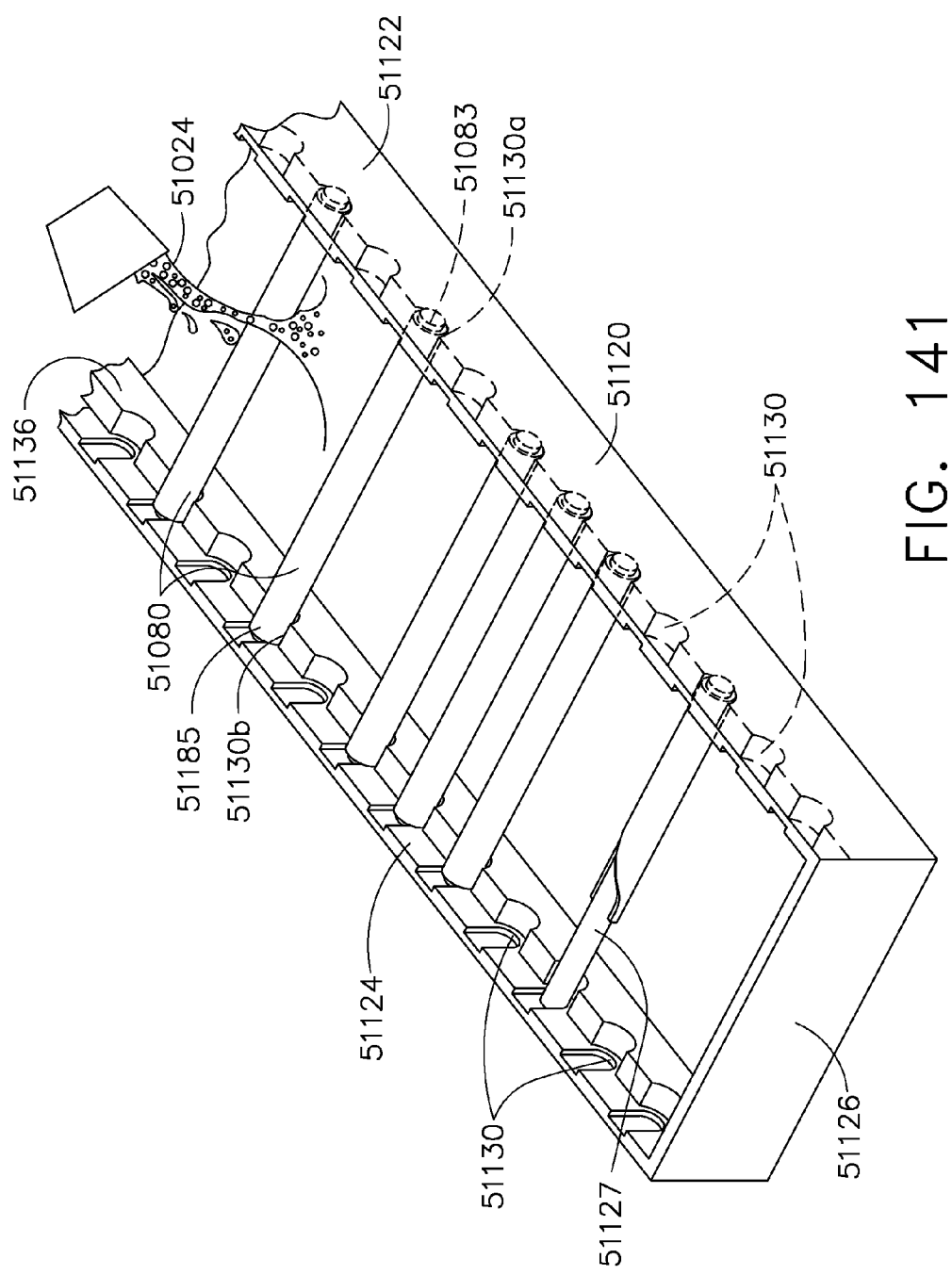
Figure 142:
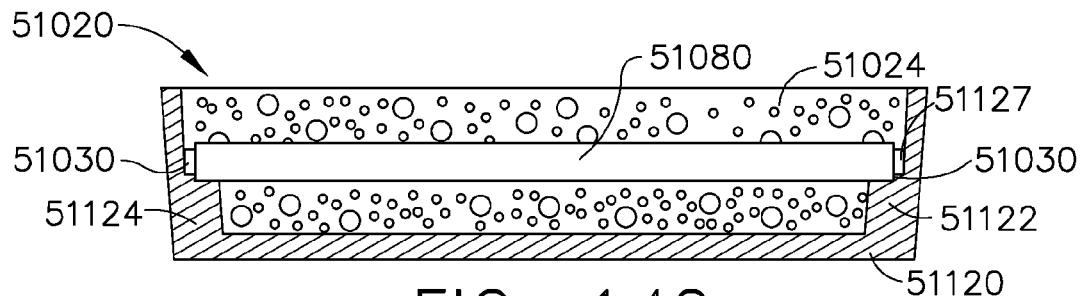
Figure 143:
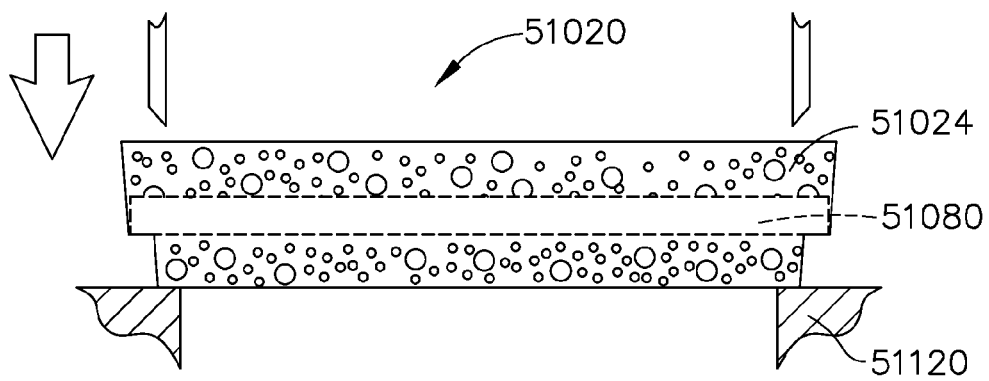
Figure 144:
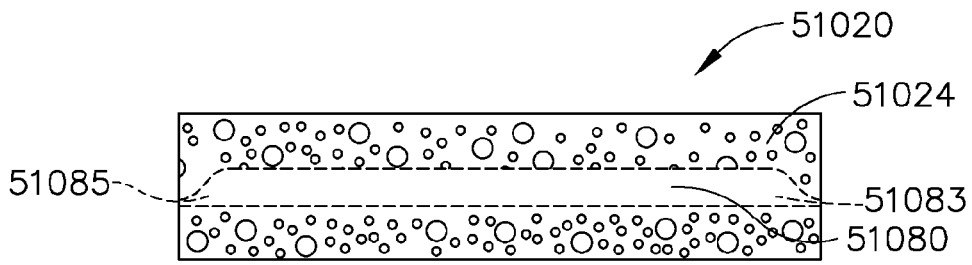
Figure 145:
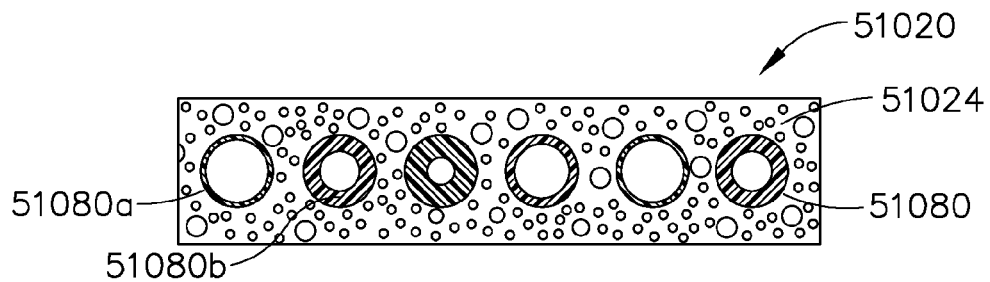
Figure 146:
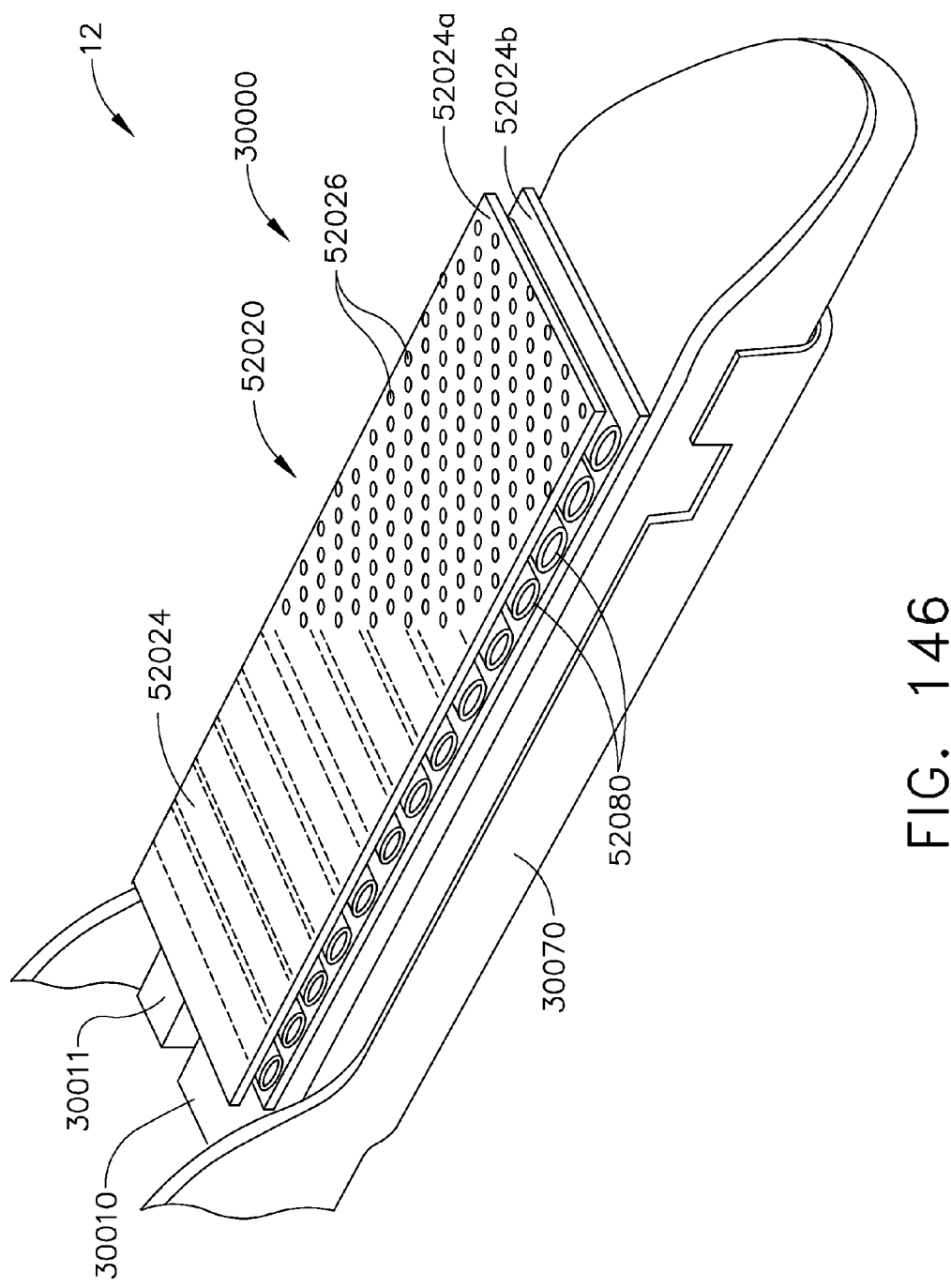
Figure 147:
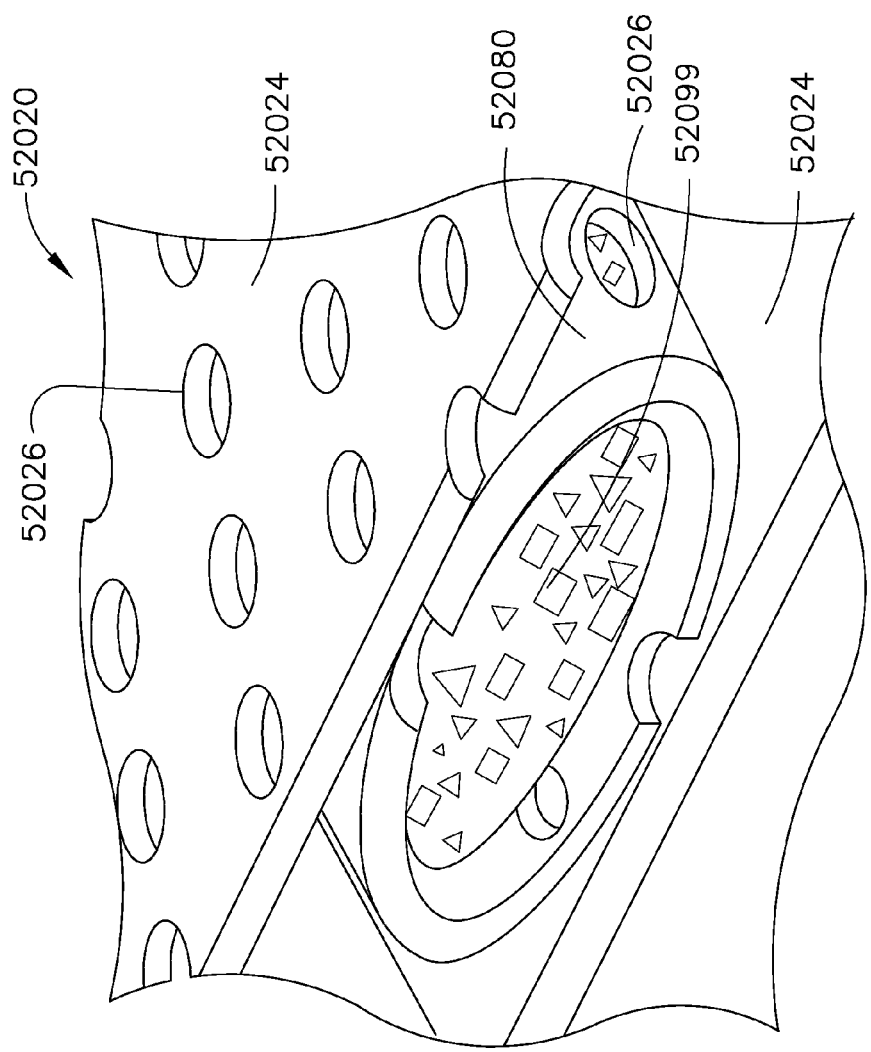
Figure 149:
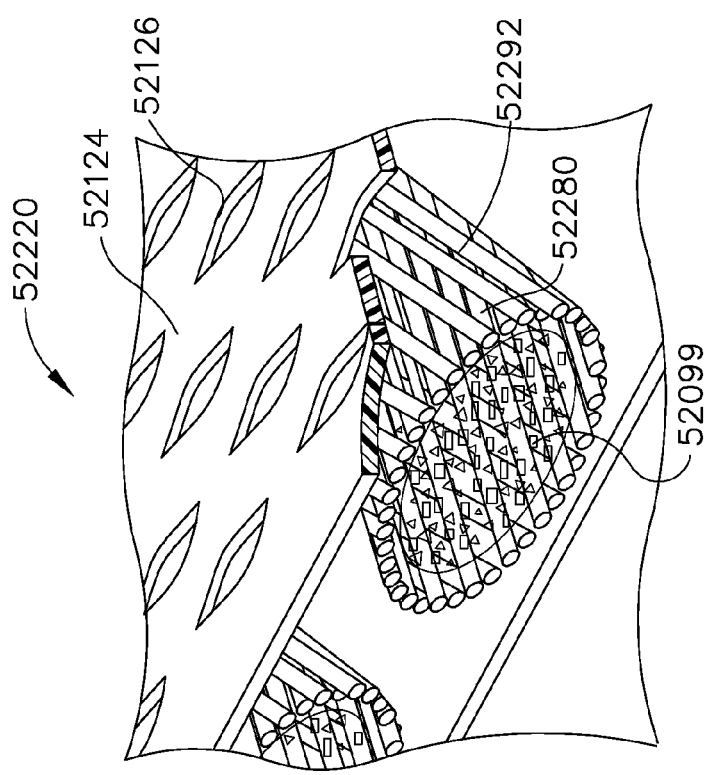
Figure 148:
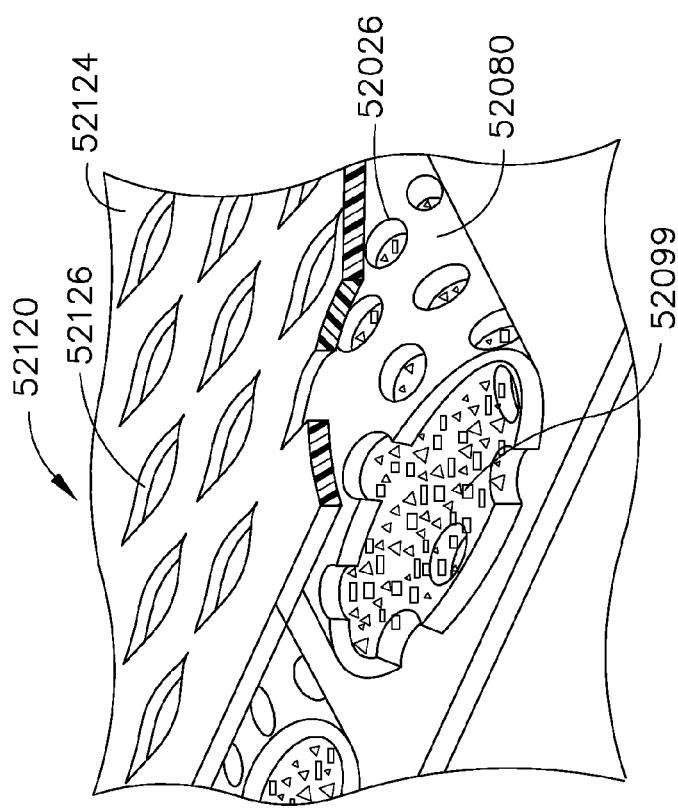
Figure 151:
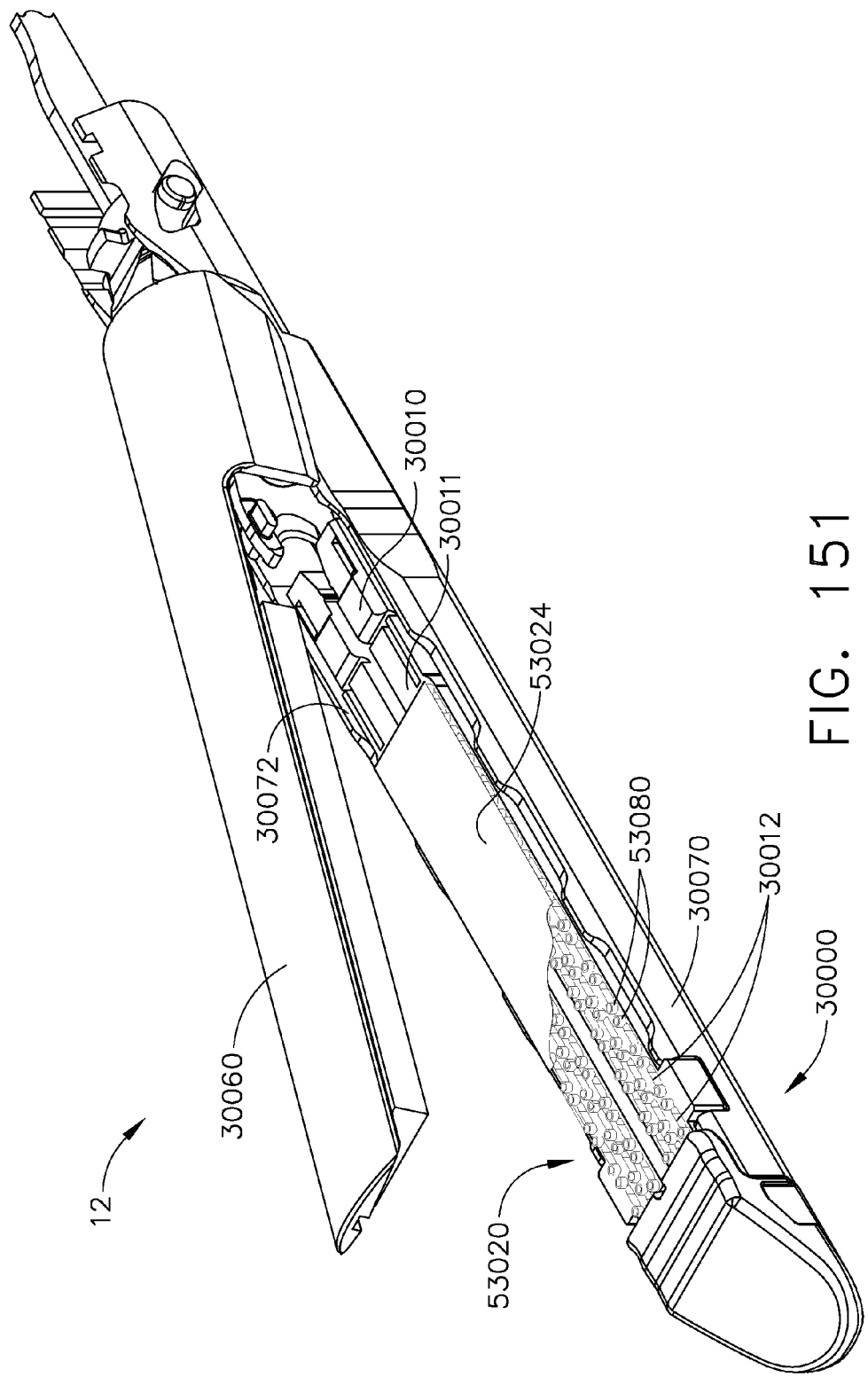
Figure 155:
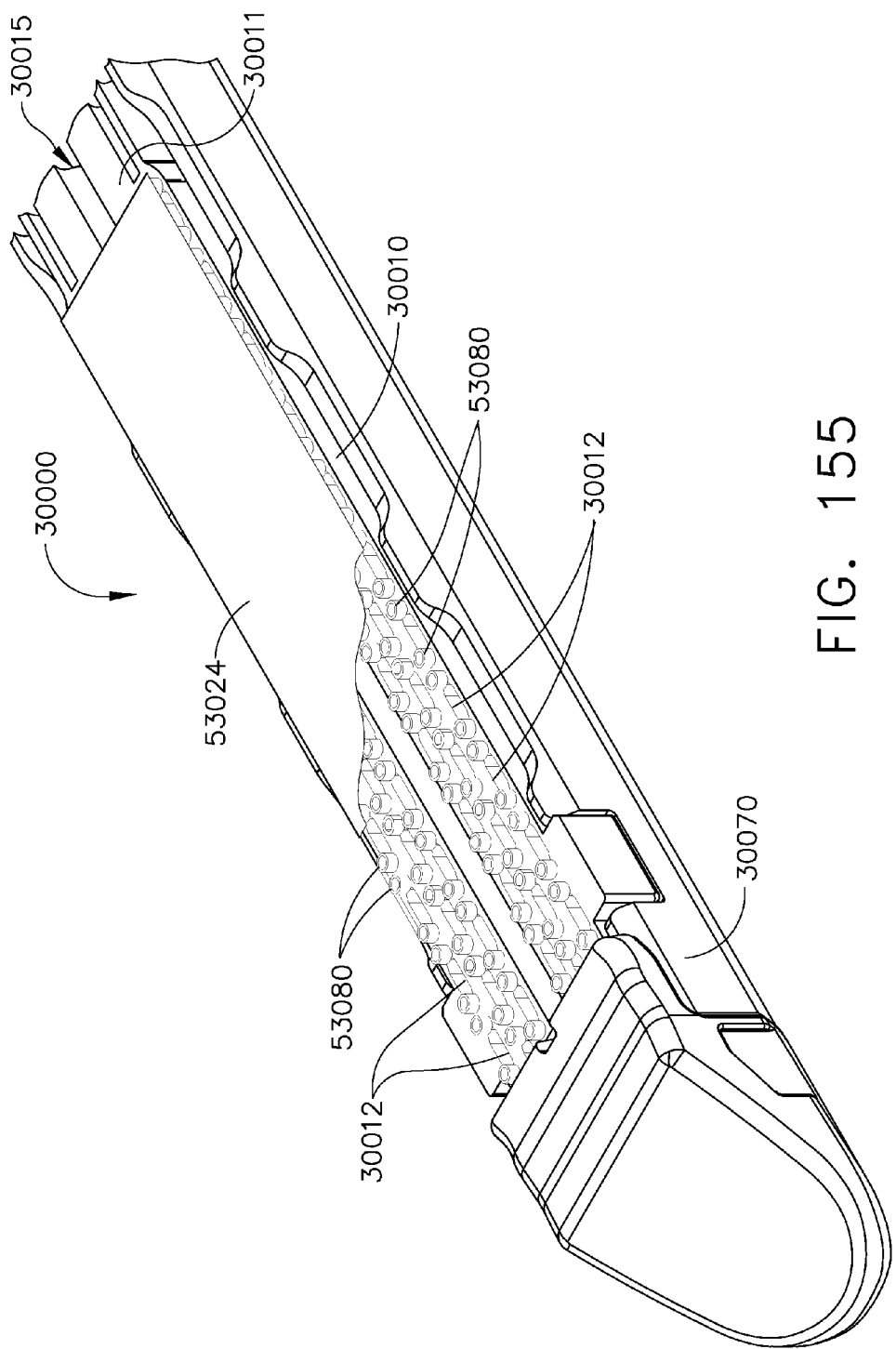
Figure 156:
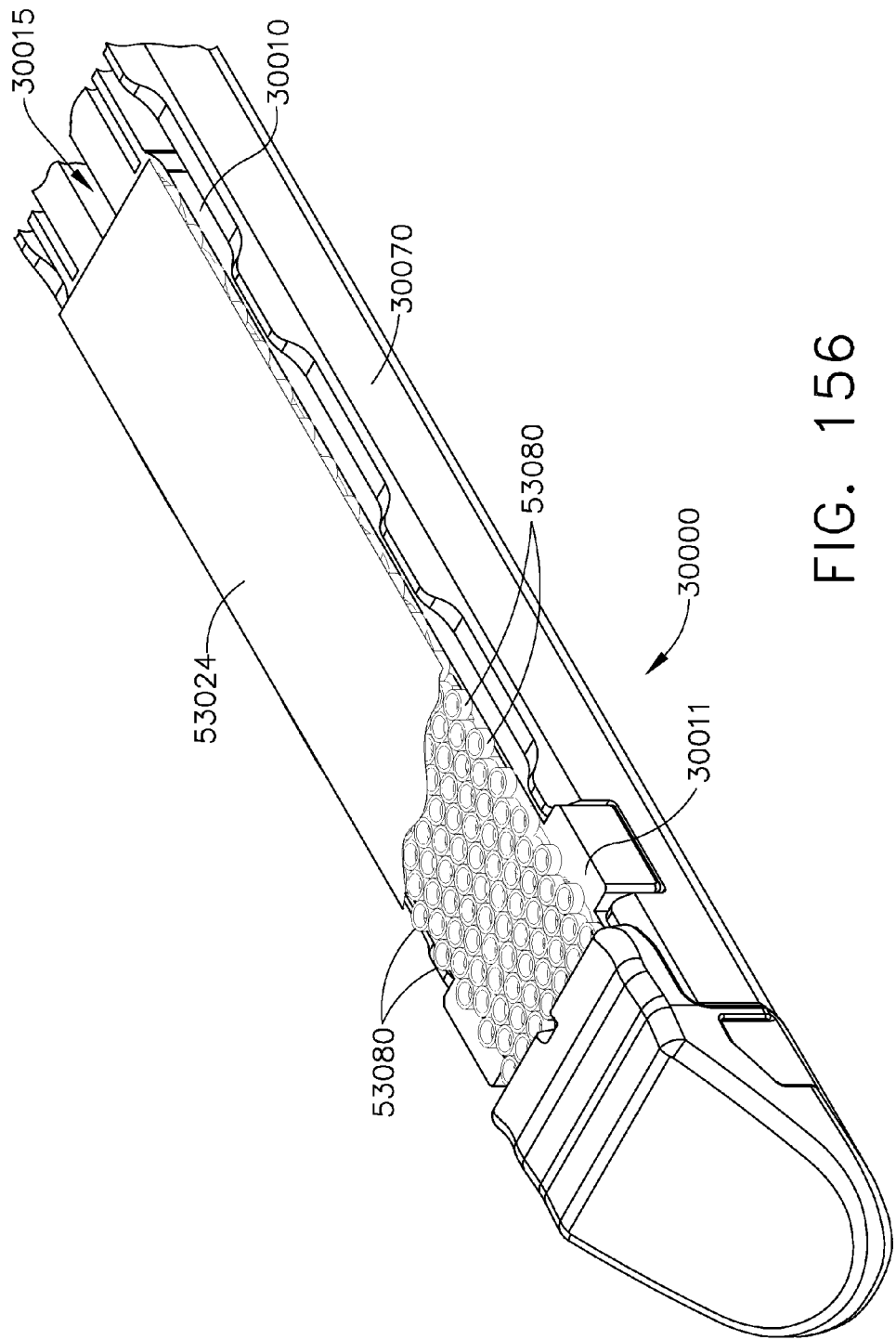
Figure 157:
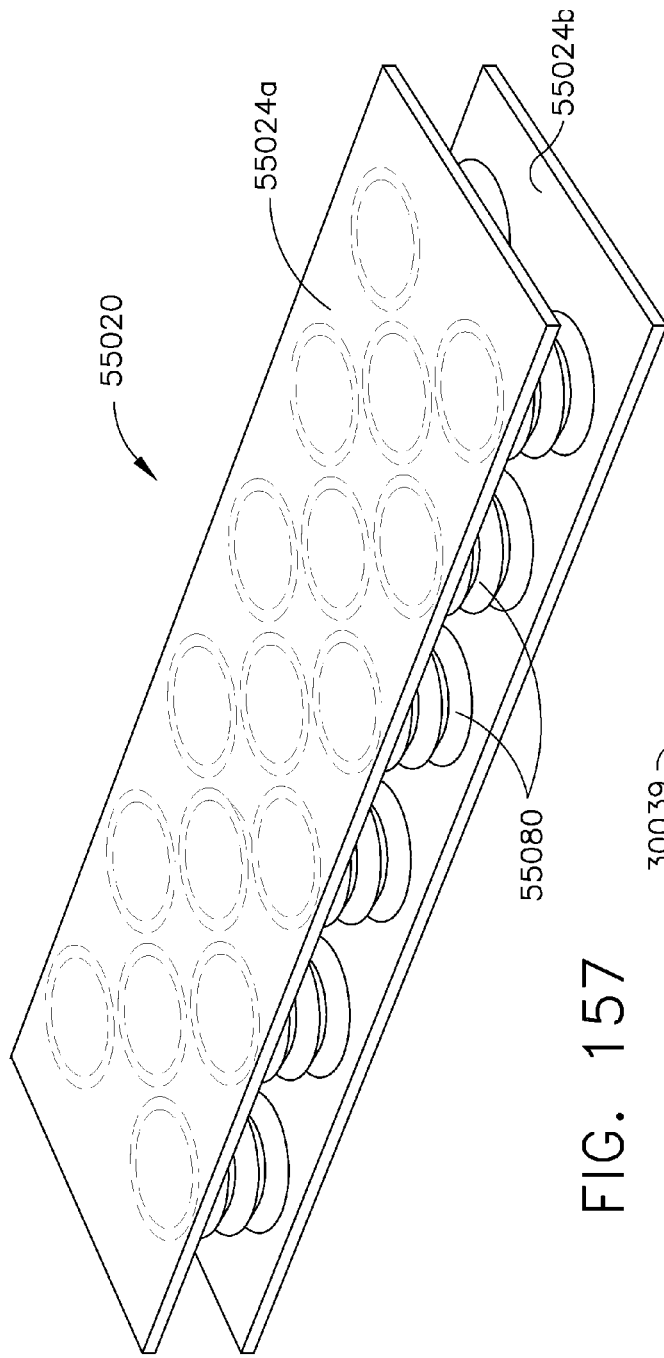
Figure 158:
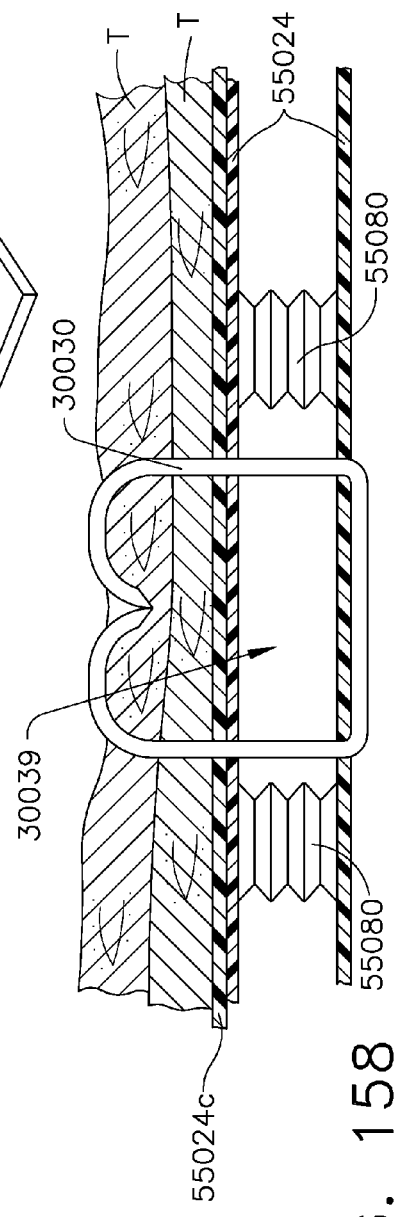
Figure 159:
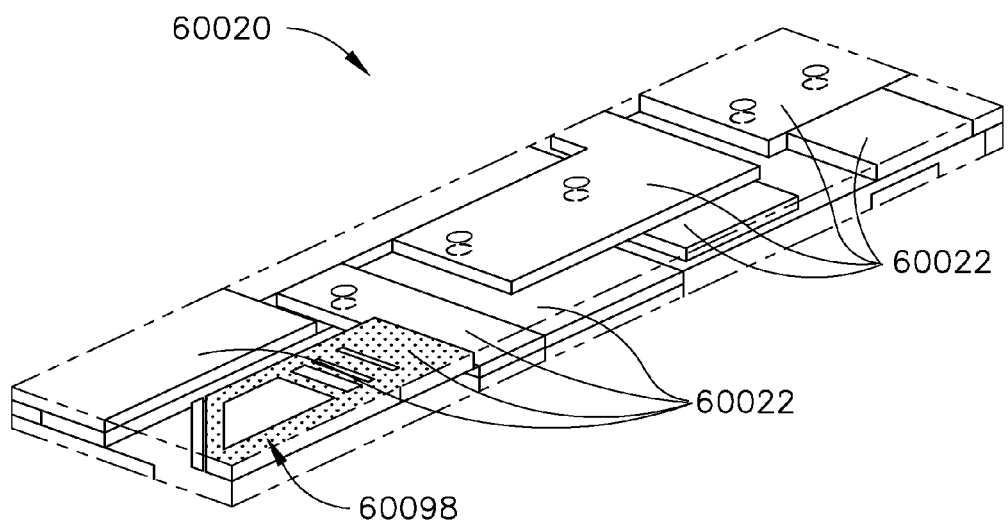
Figure 174:
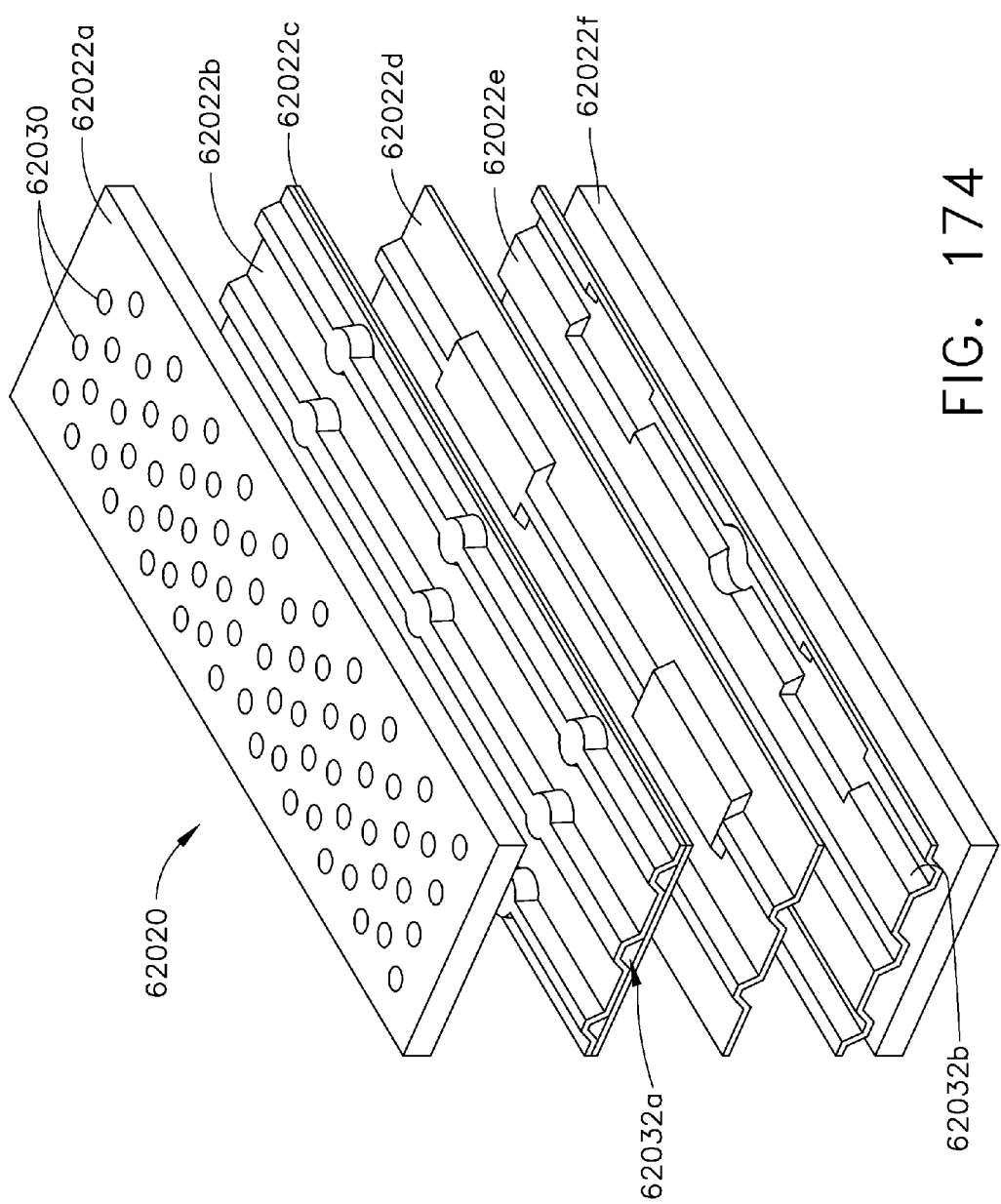
Figure 175:
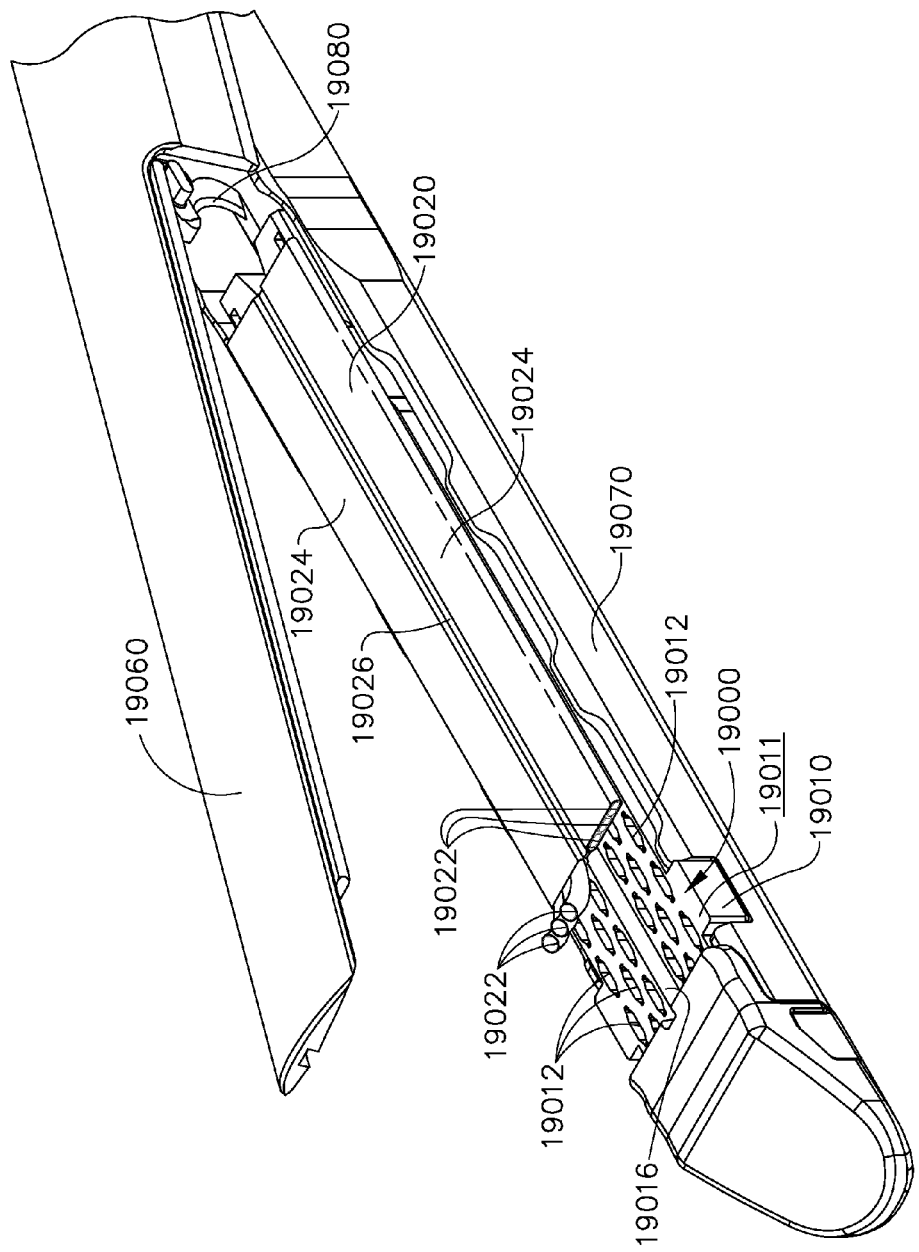
Figure 176:
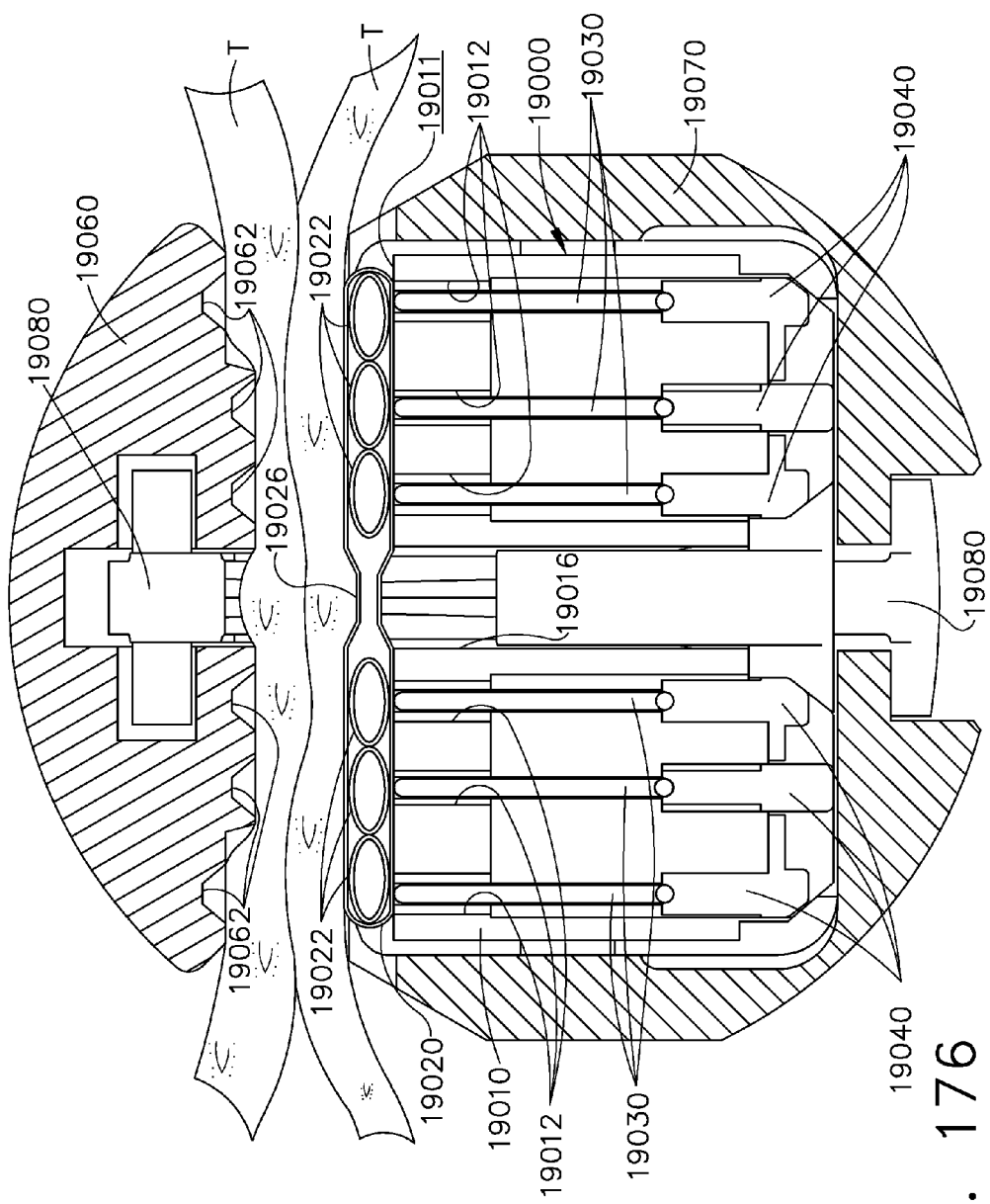
Figure 177:
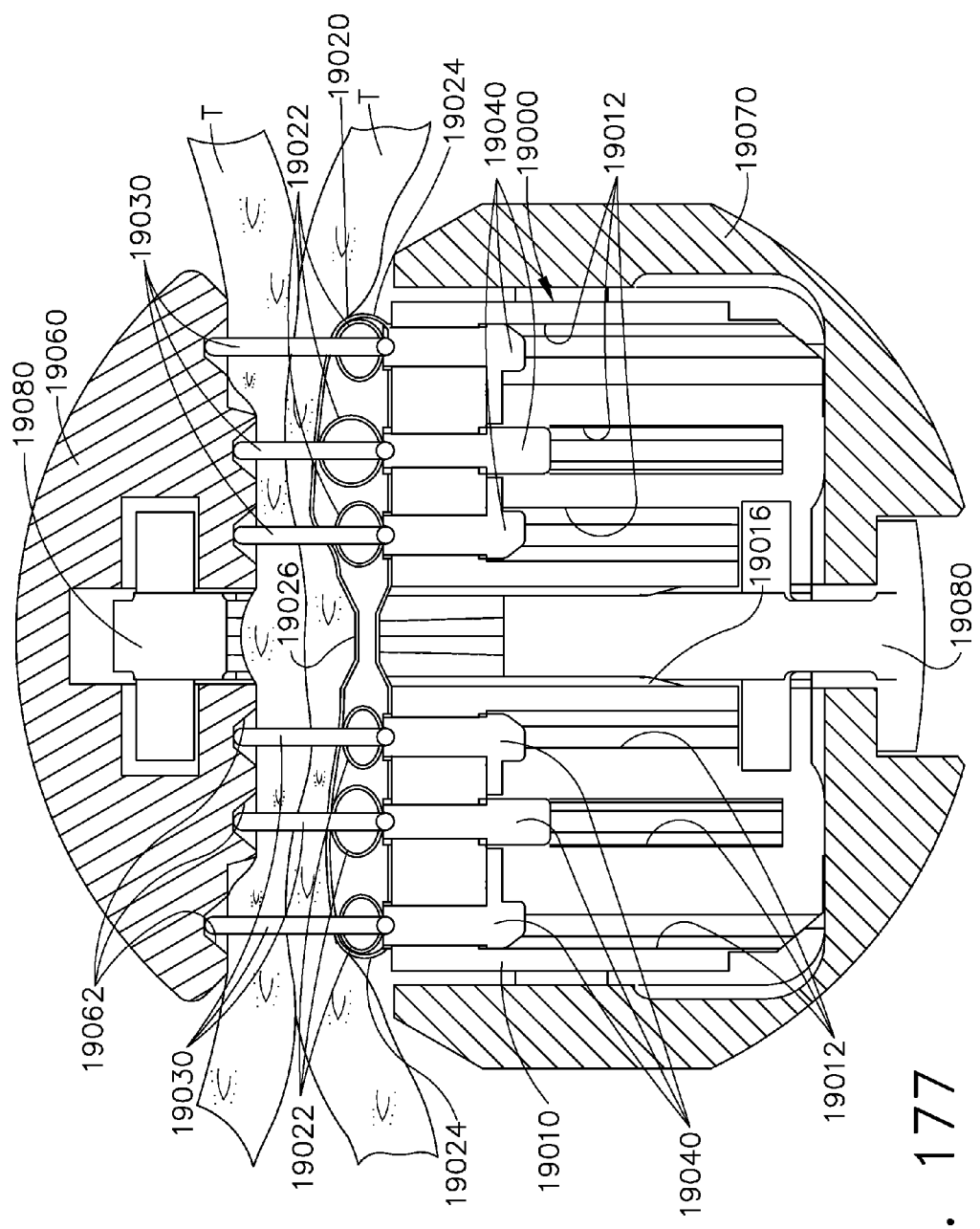
Figure 178:
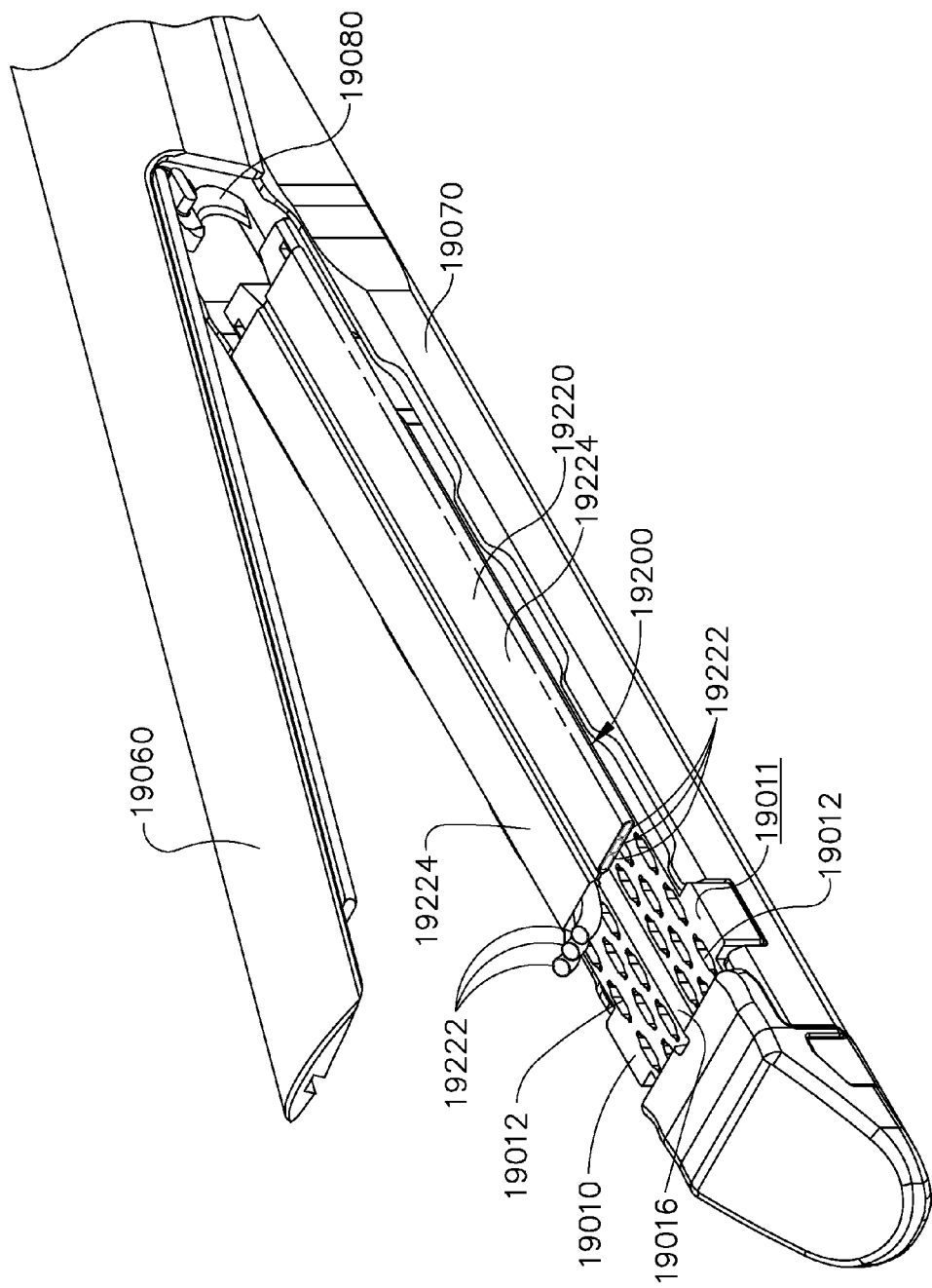
Figure 179:
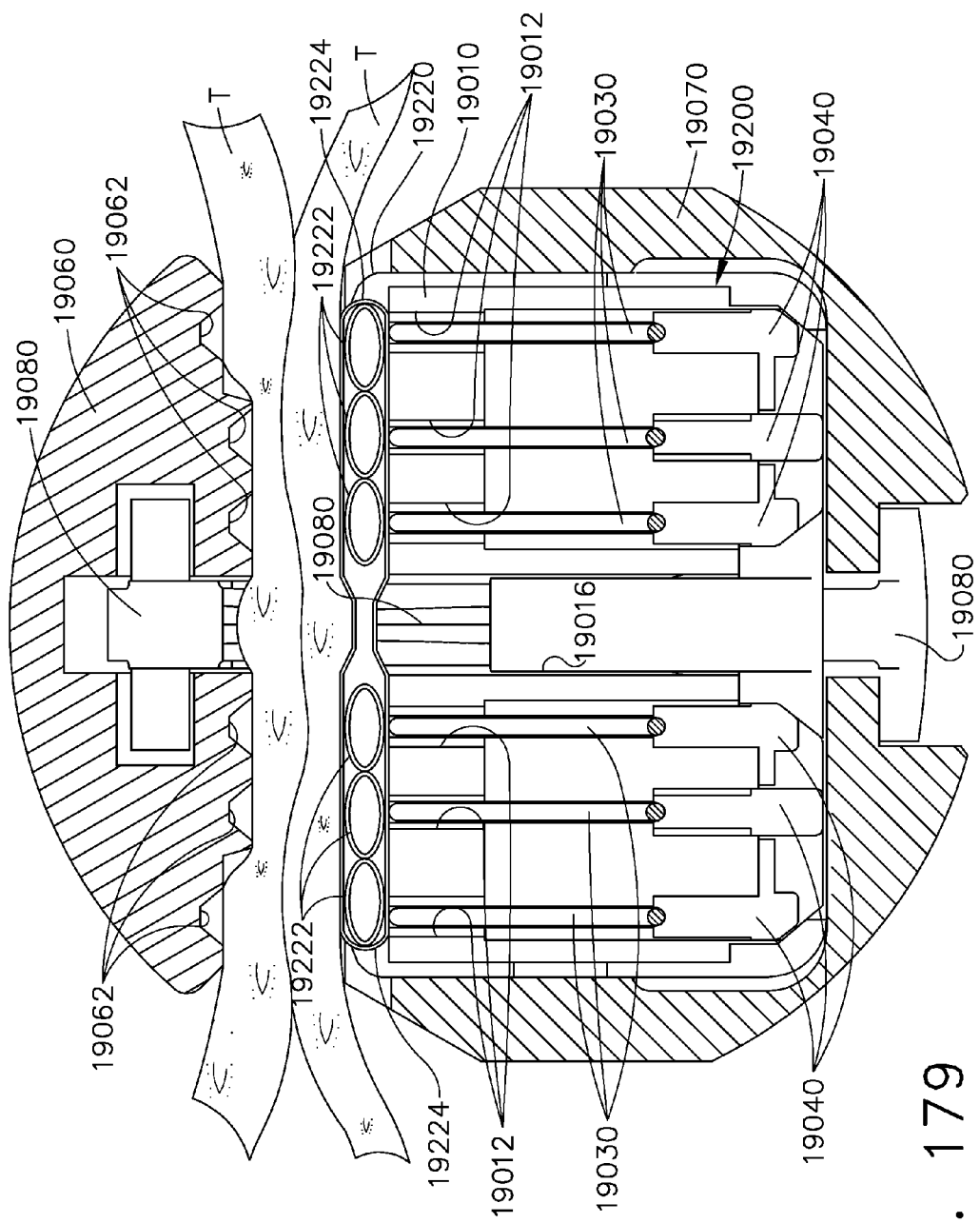
Figure 180:
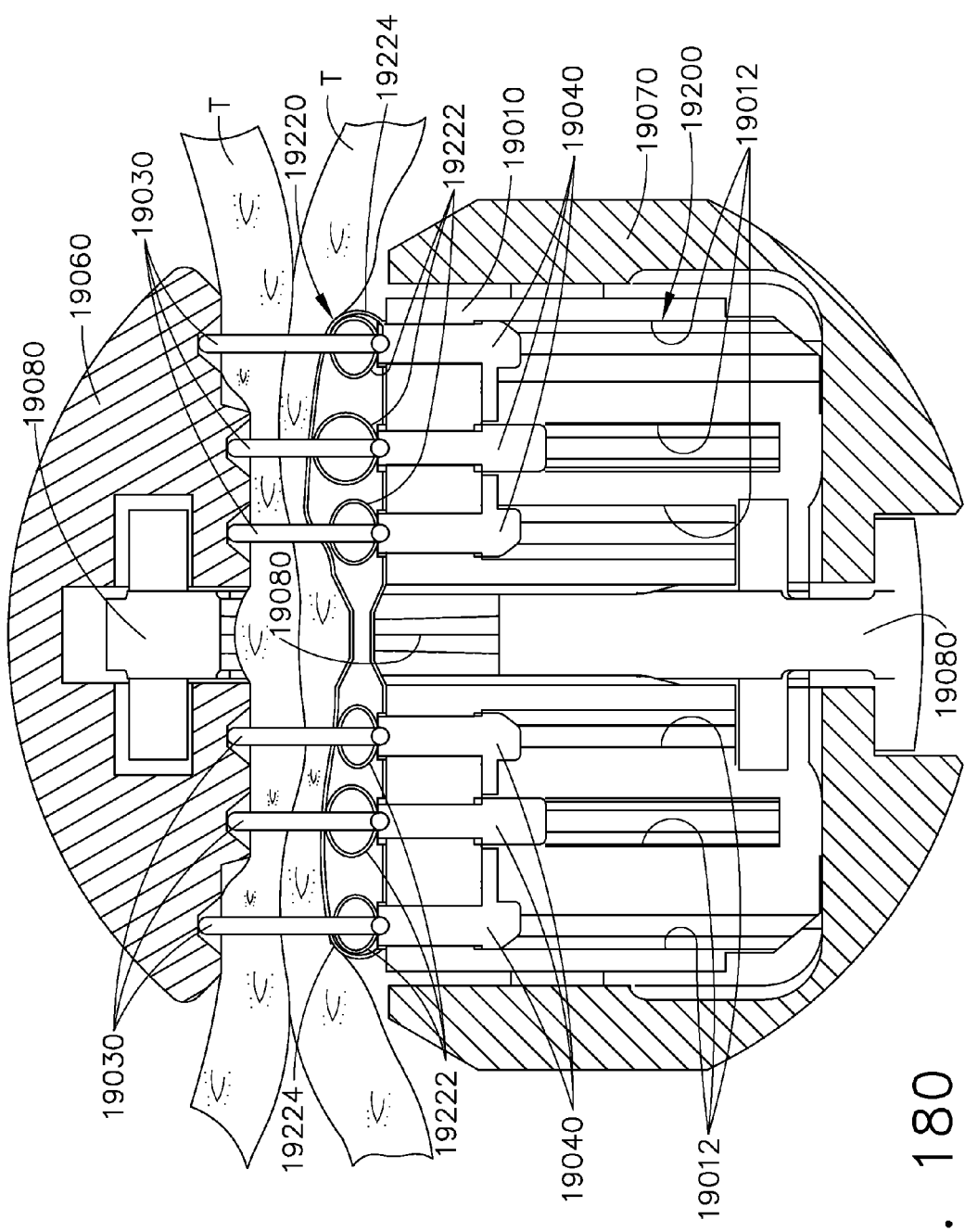
Figure 181:
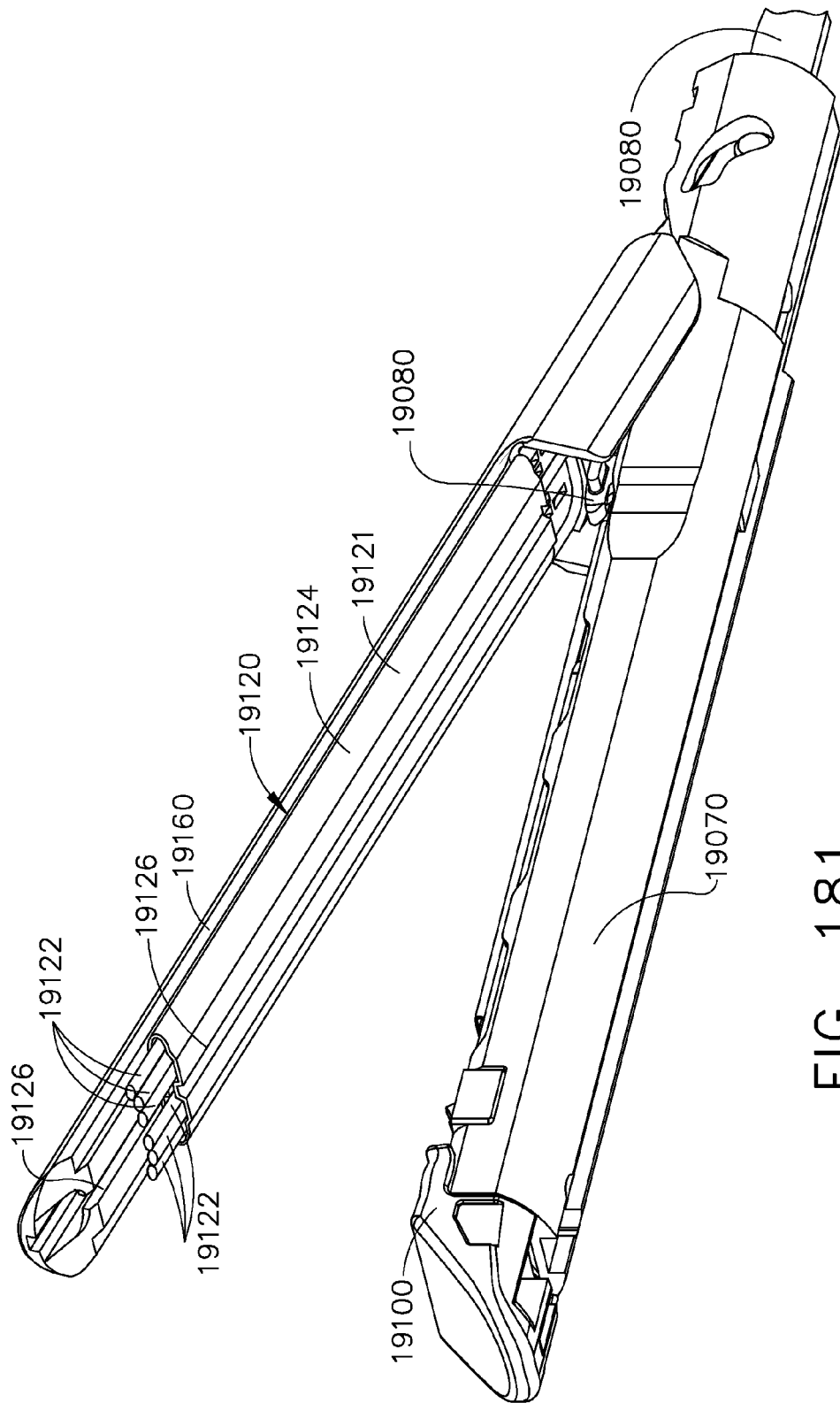
Figure 182:
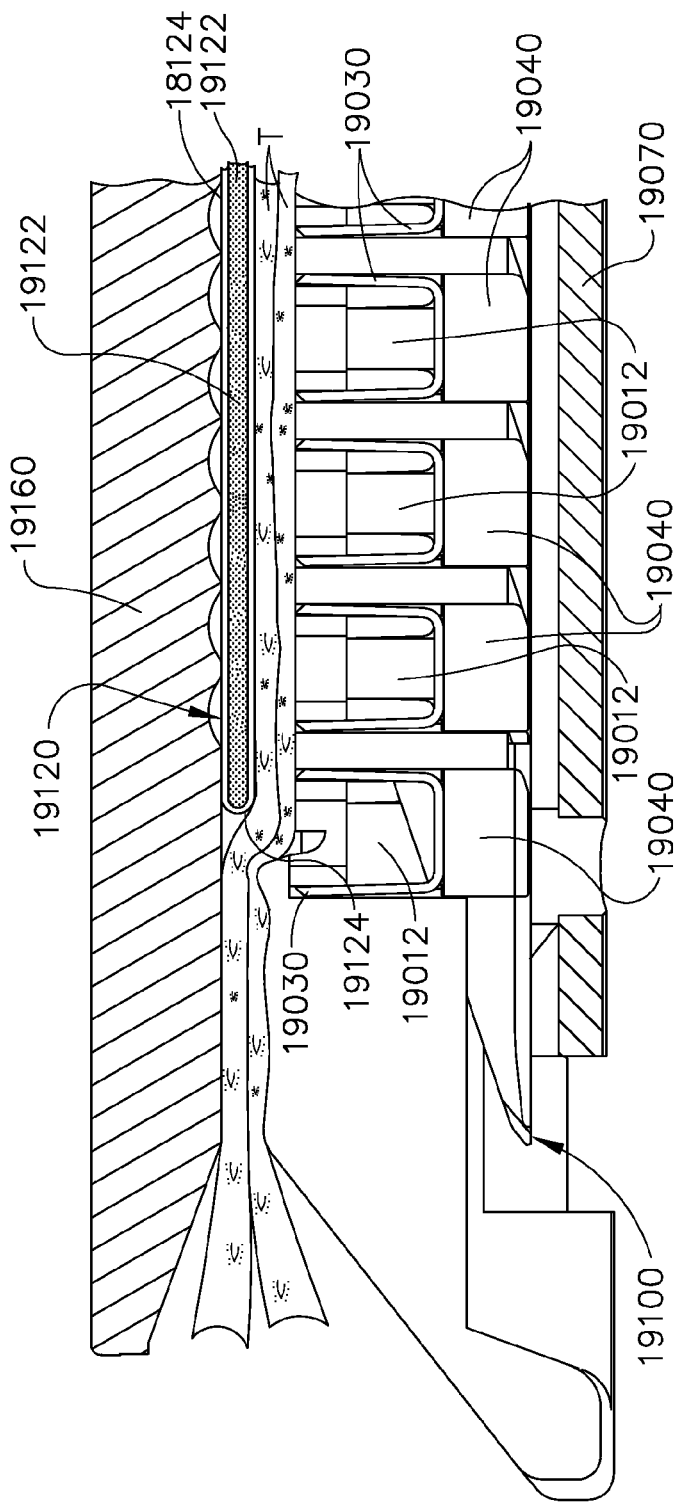
Figure 183:
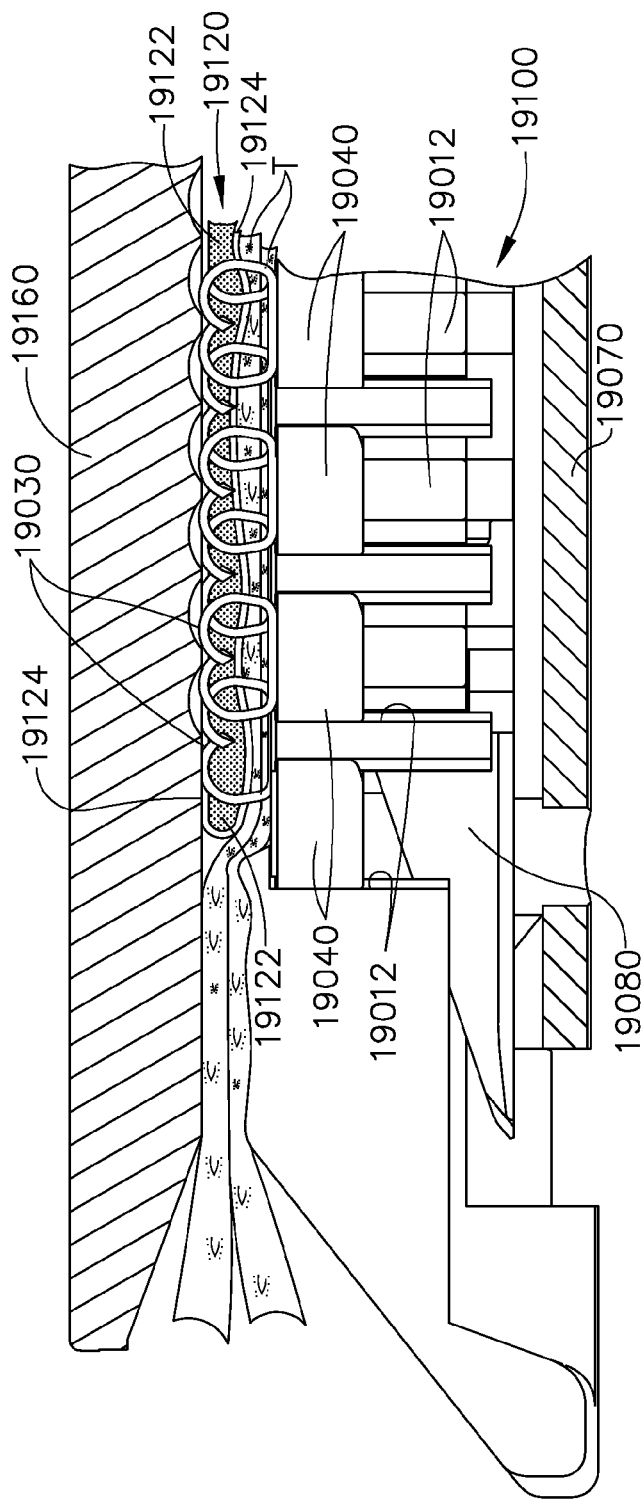
Figure 184:
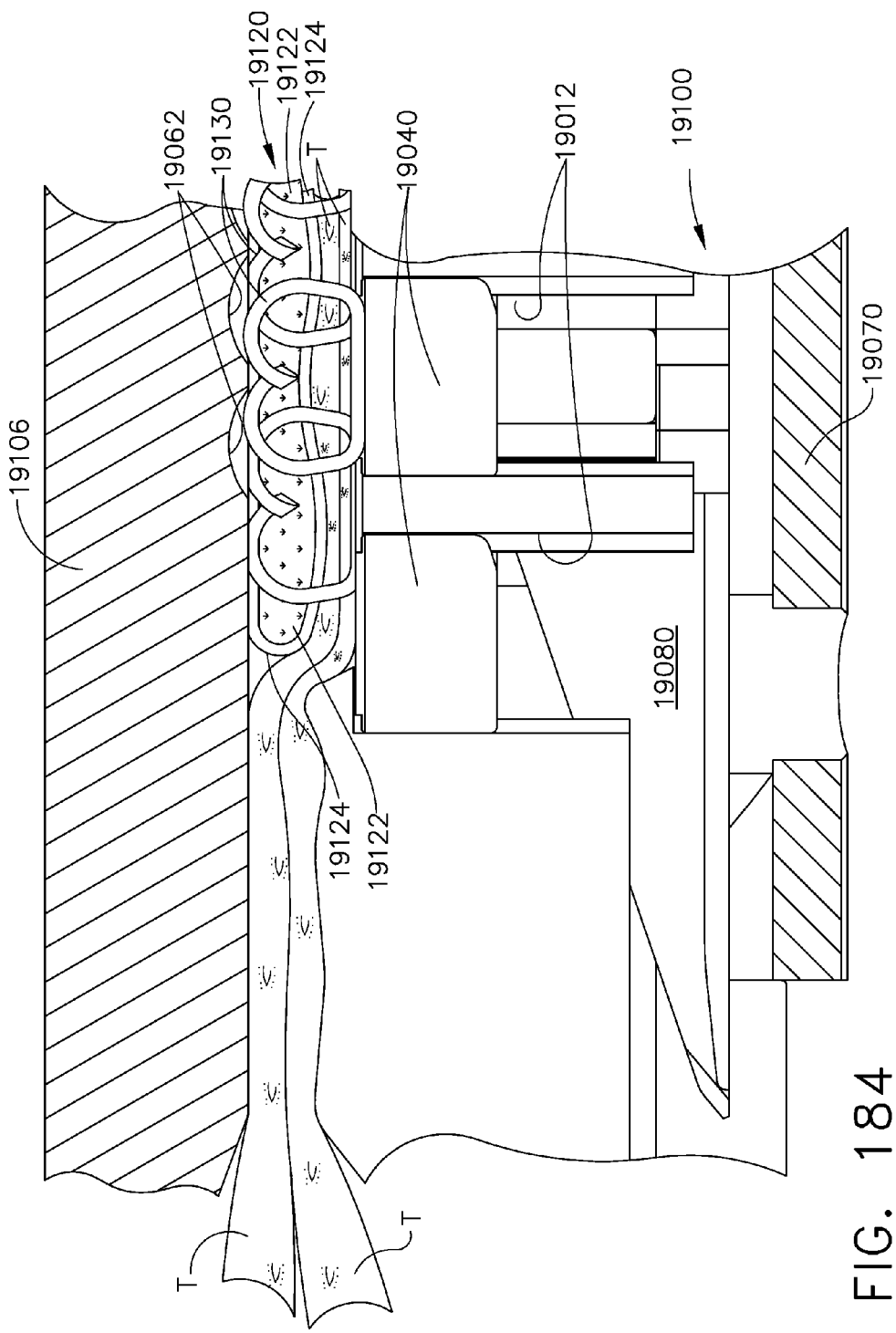
Figure 185:
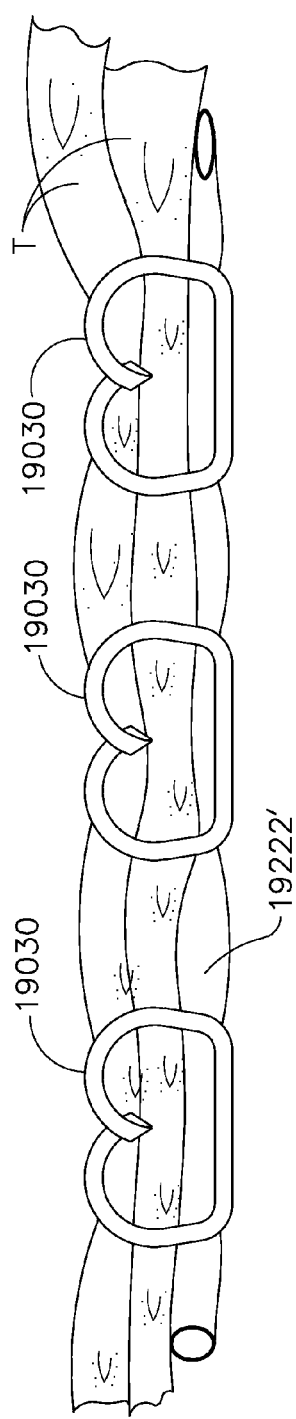
Figure 186:
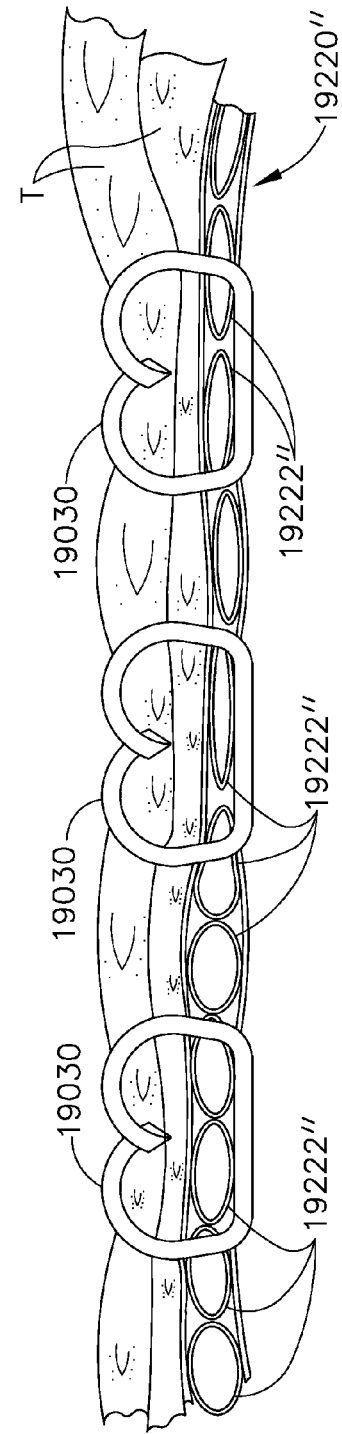
Figure 189A:
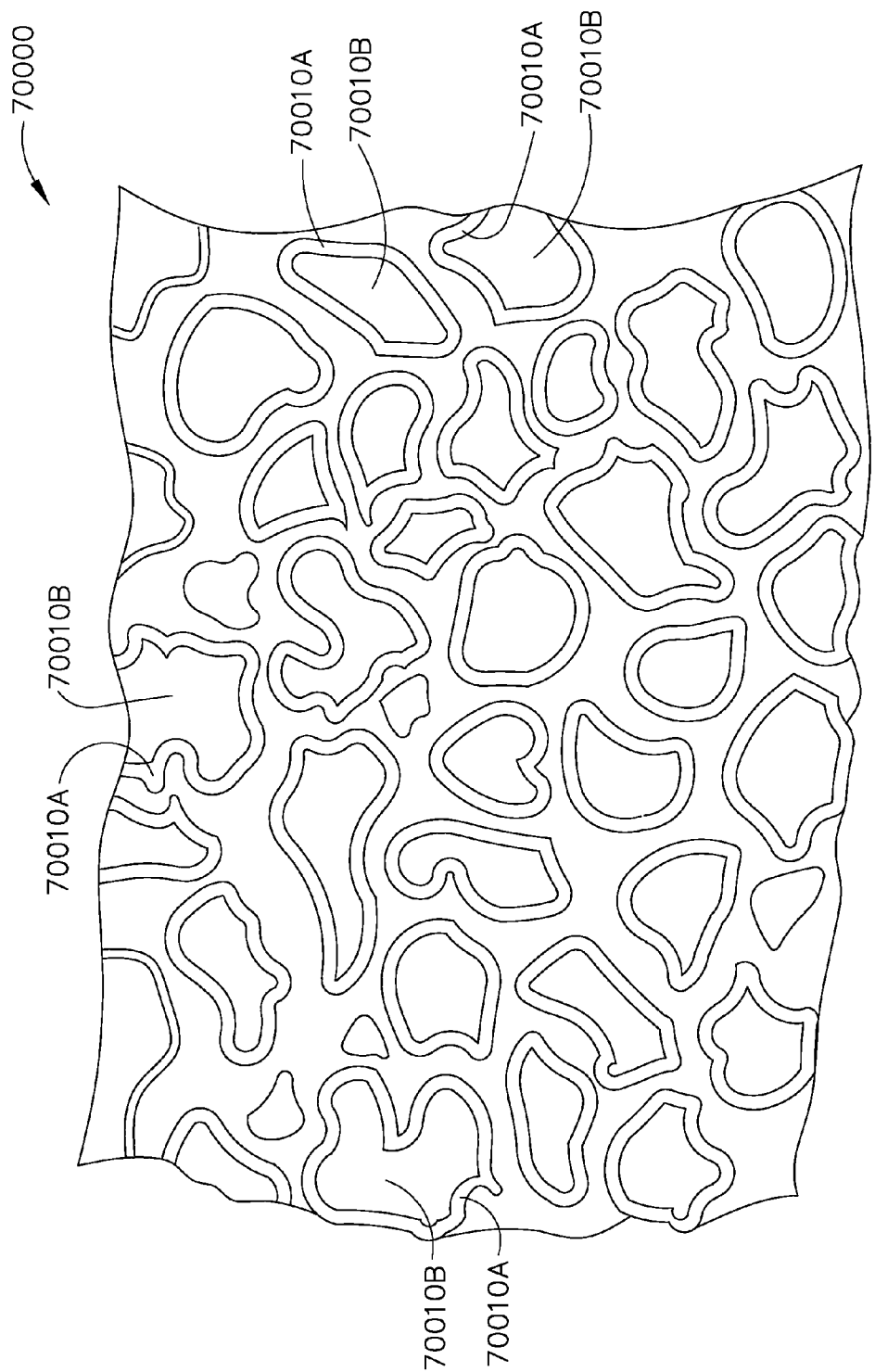
Figure 189B:
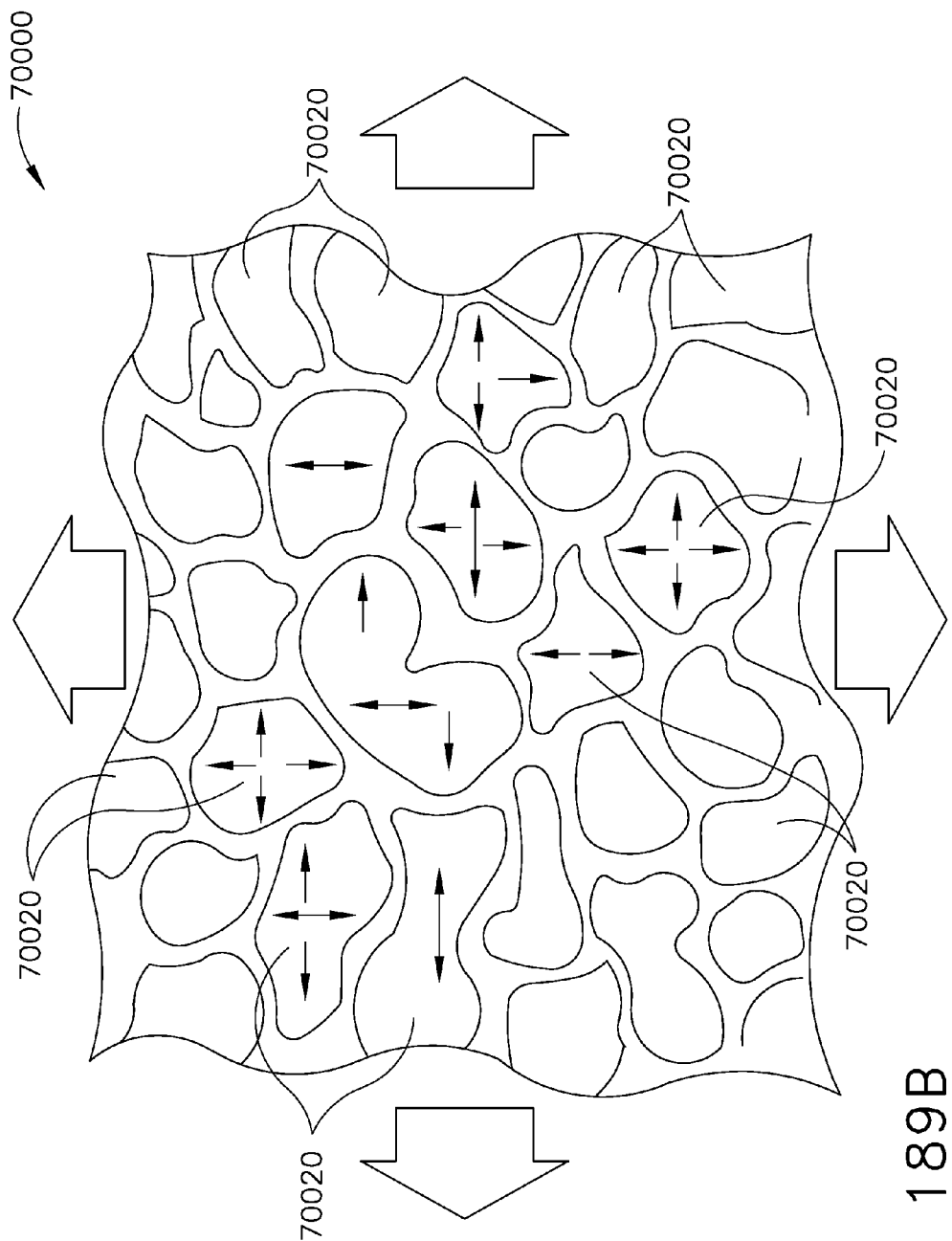
Figure 191:
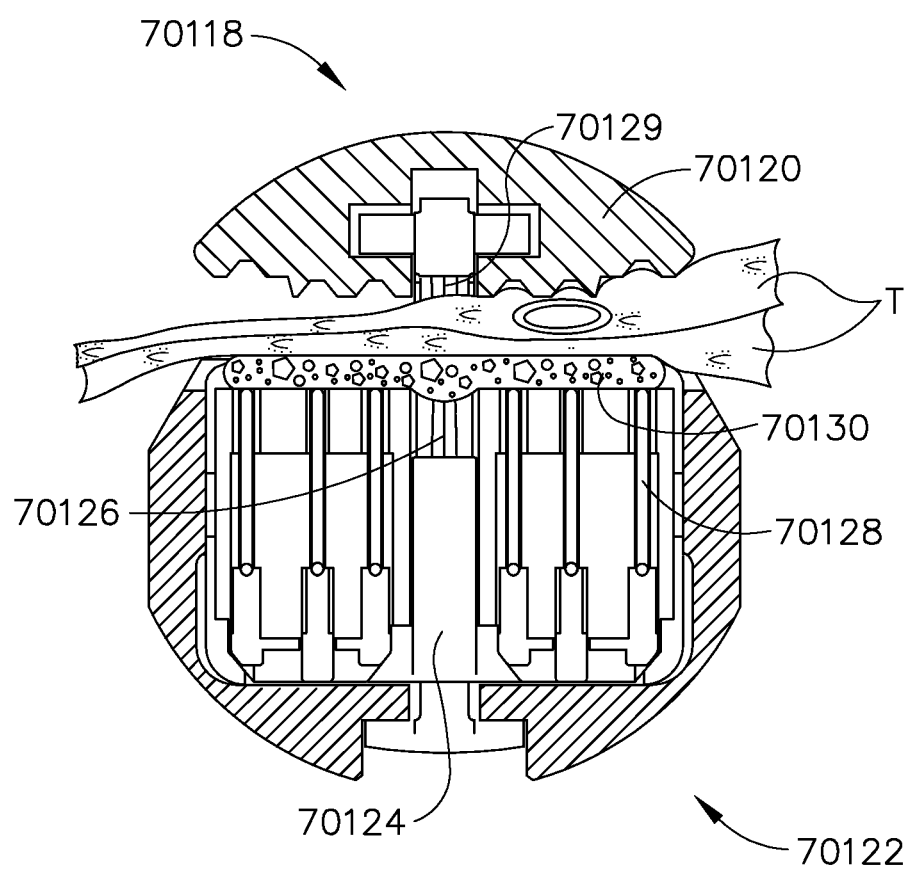
Figure 192:
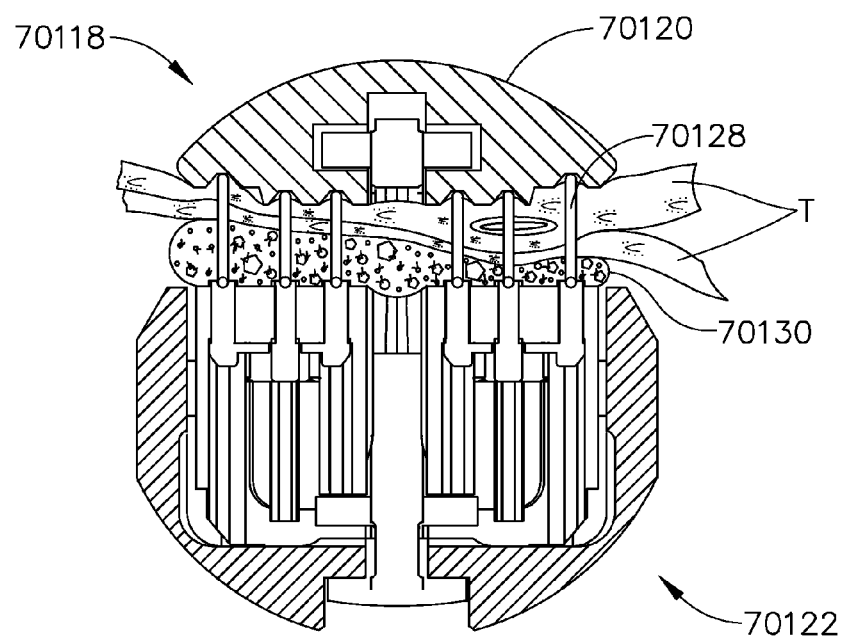
Figure 193:
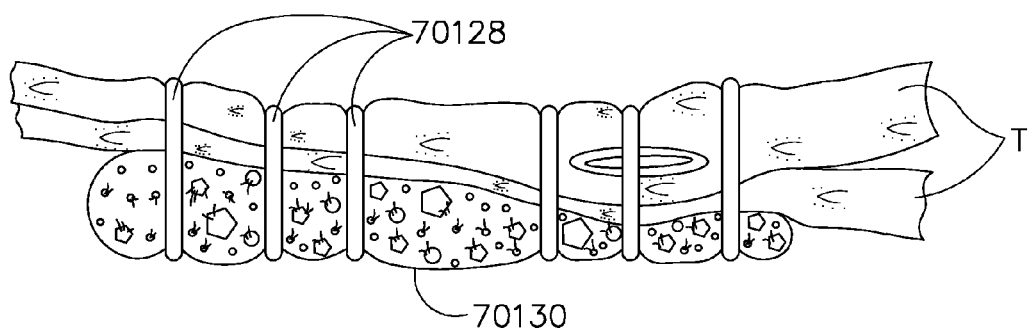
Figure 196:
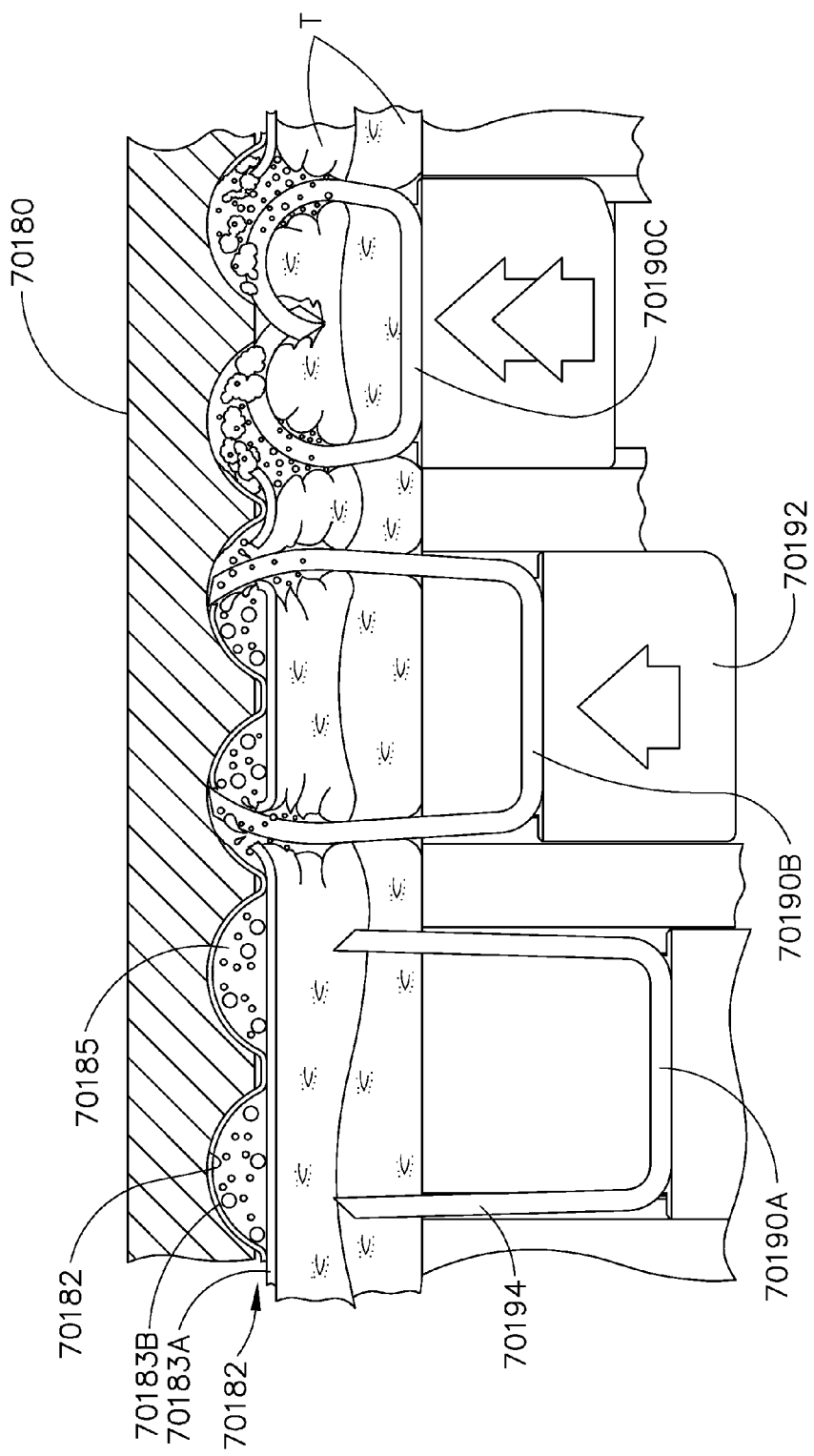
Figure 197:
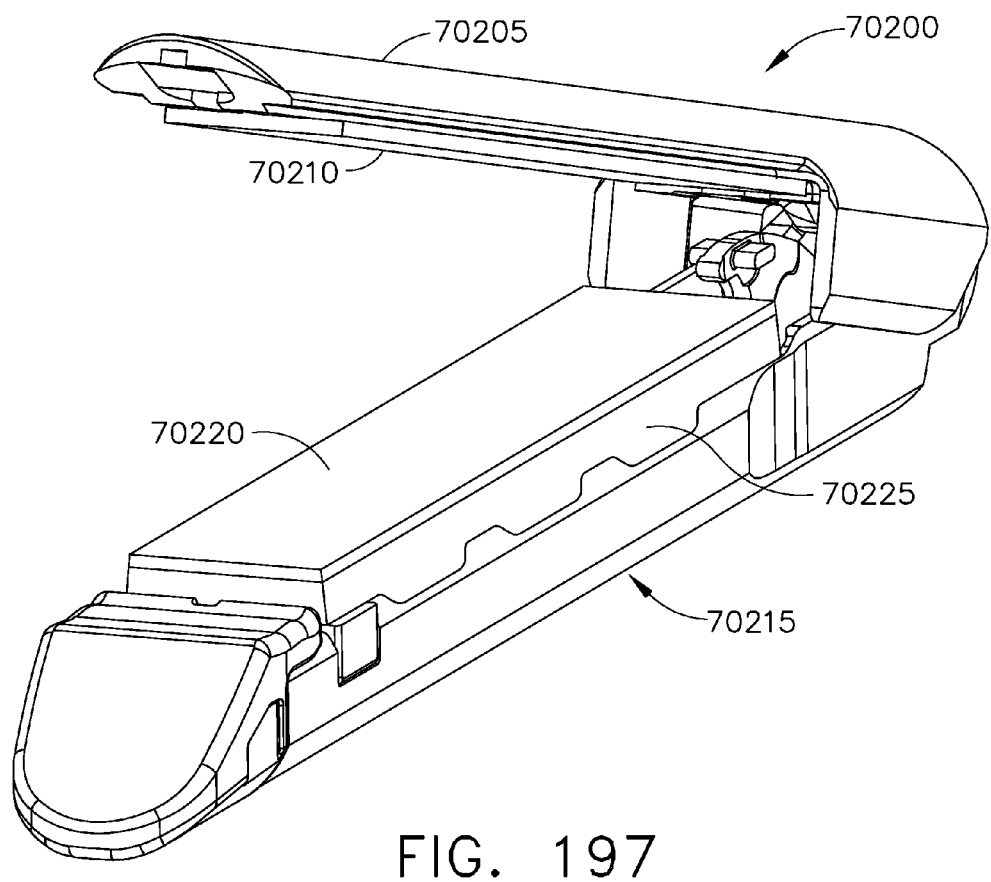
Figure 198A:
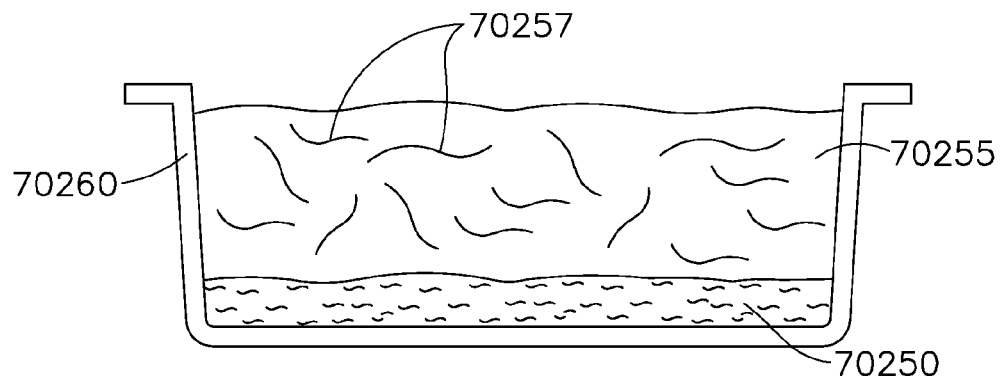
Figure 198B:
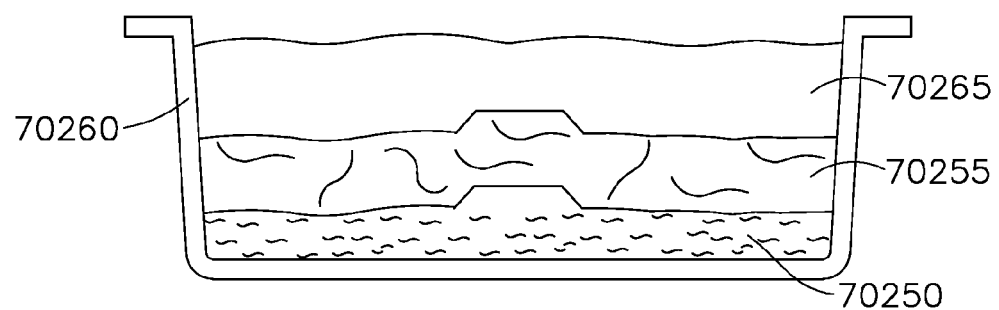
Figure 199:
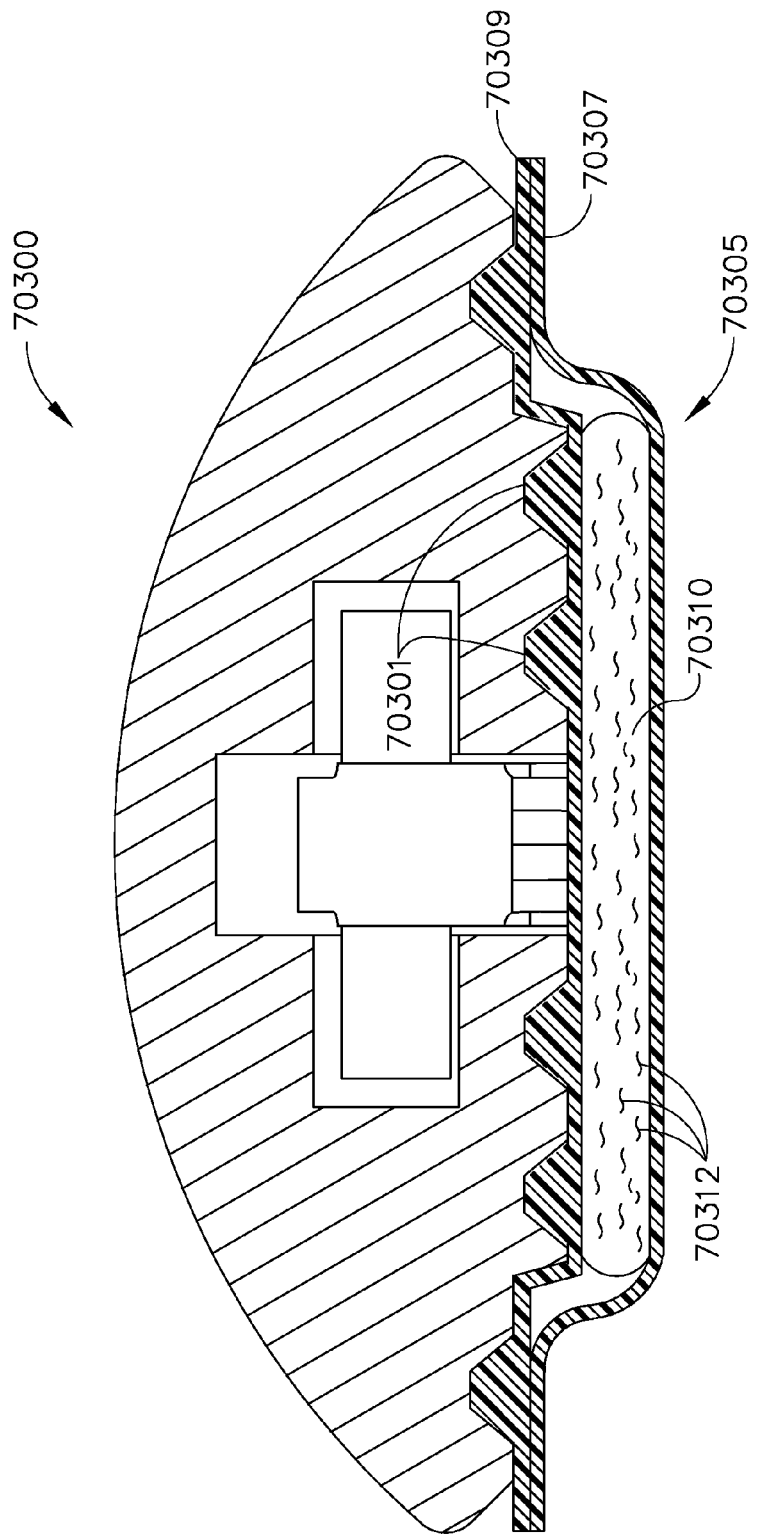
Figure 200:
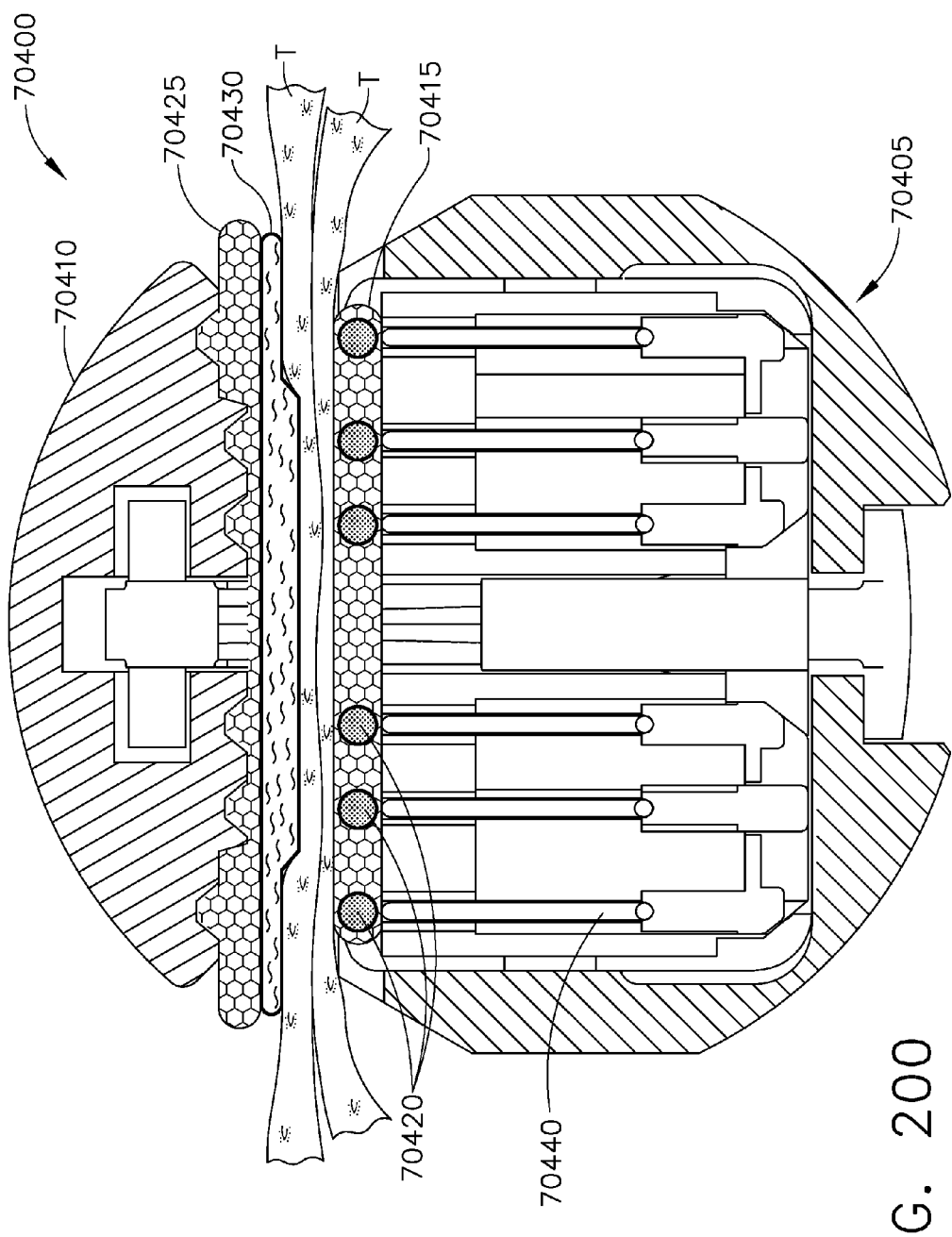
Figure 201:
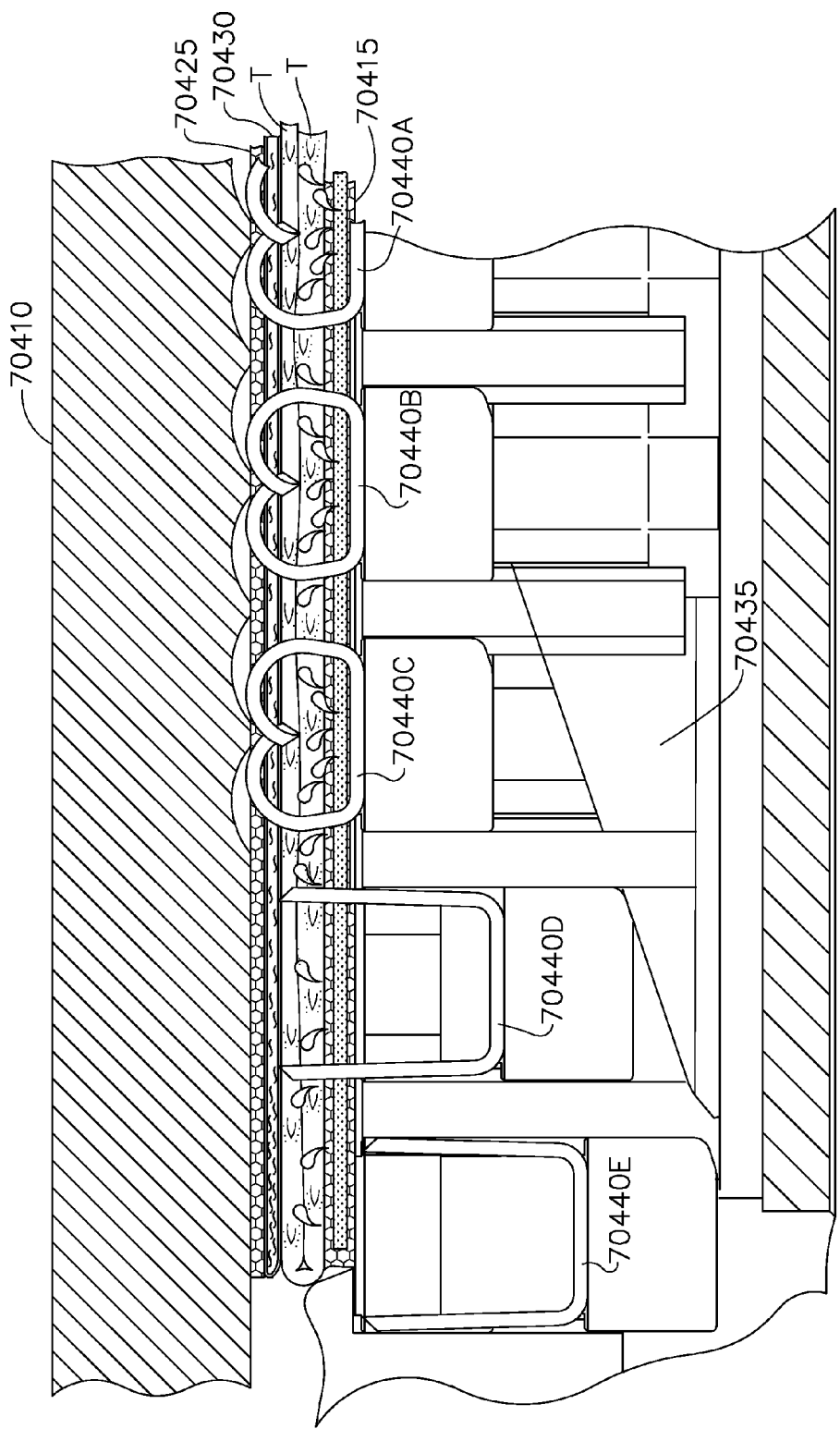
Figure 202:
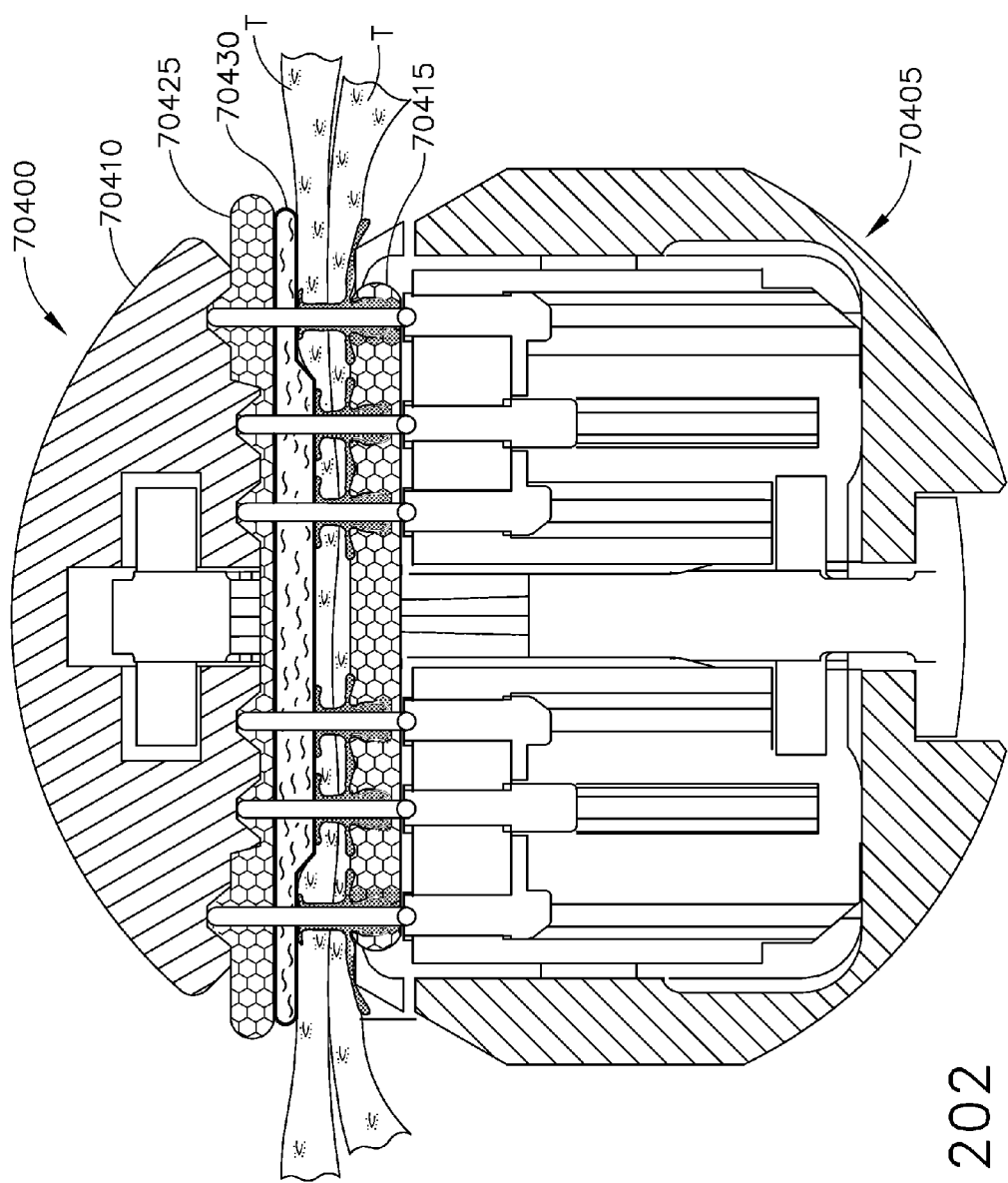
Figure 203:
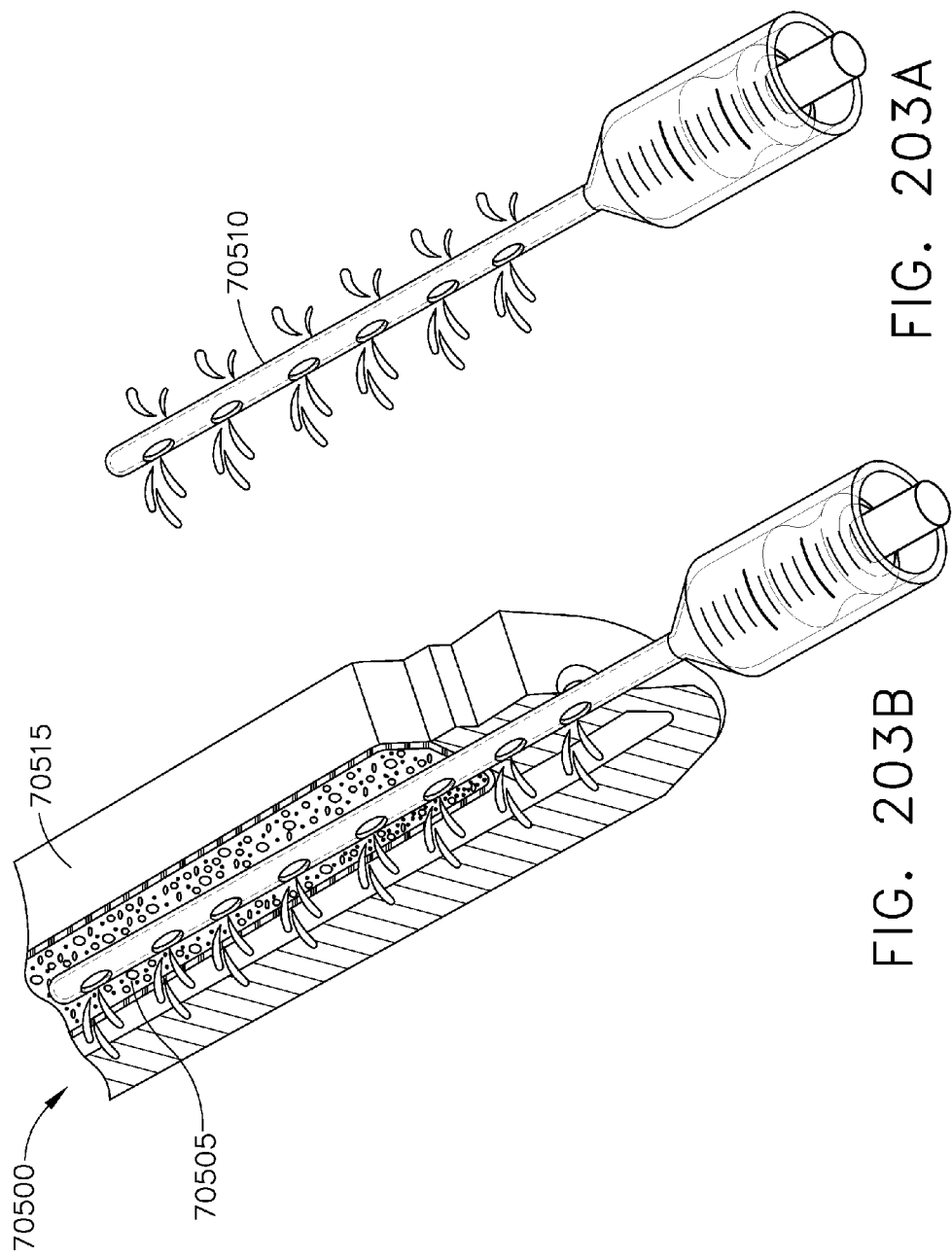
Figure 204:
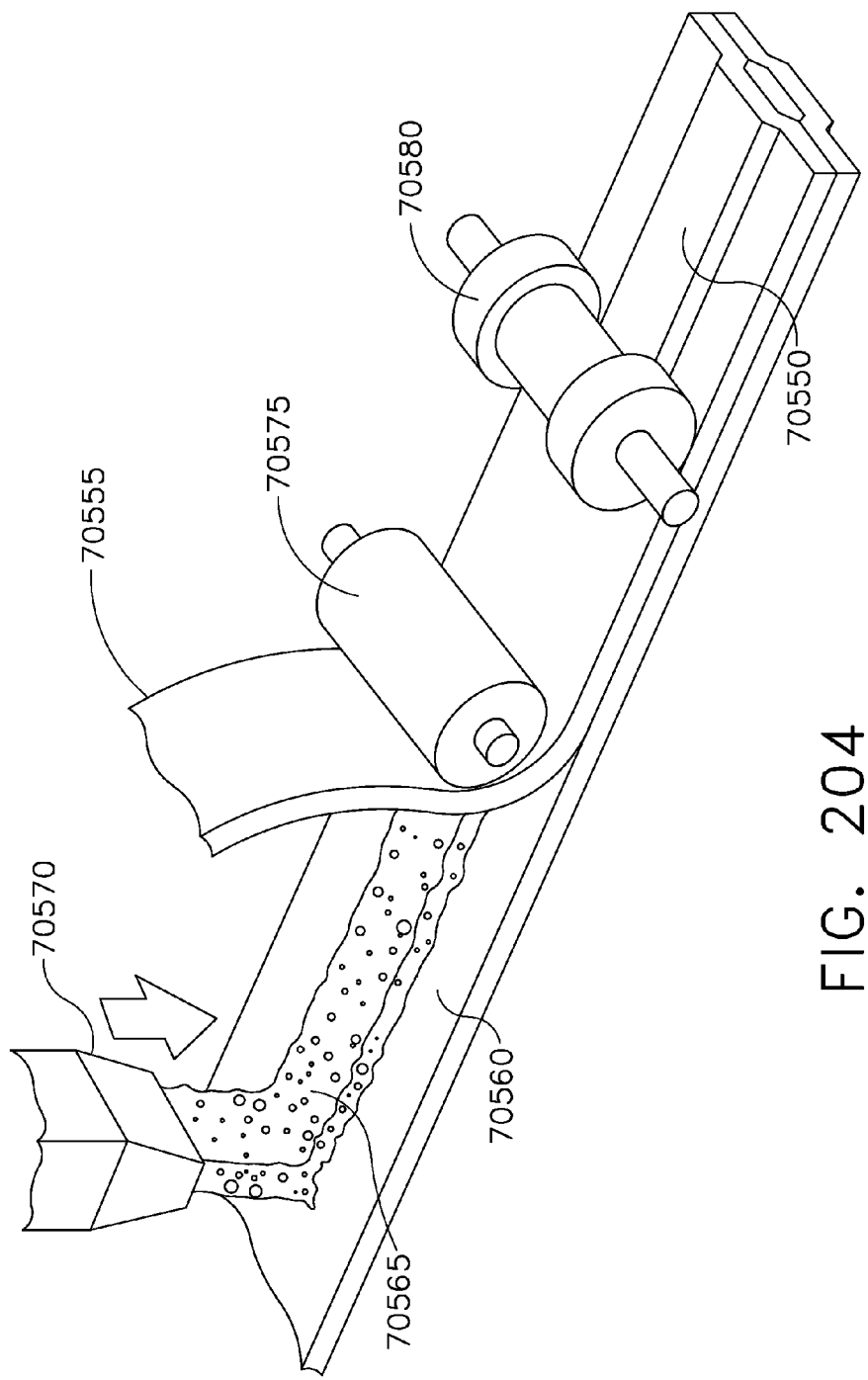
Figure 205:
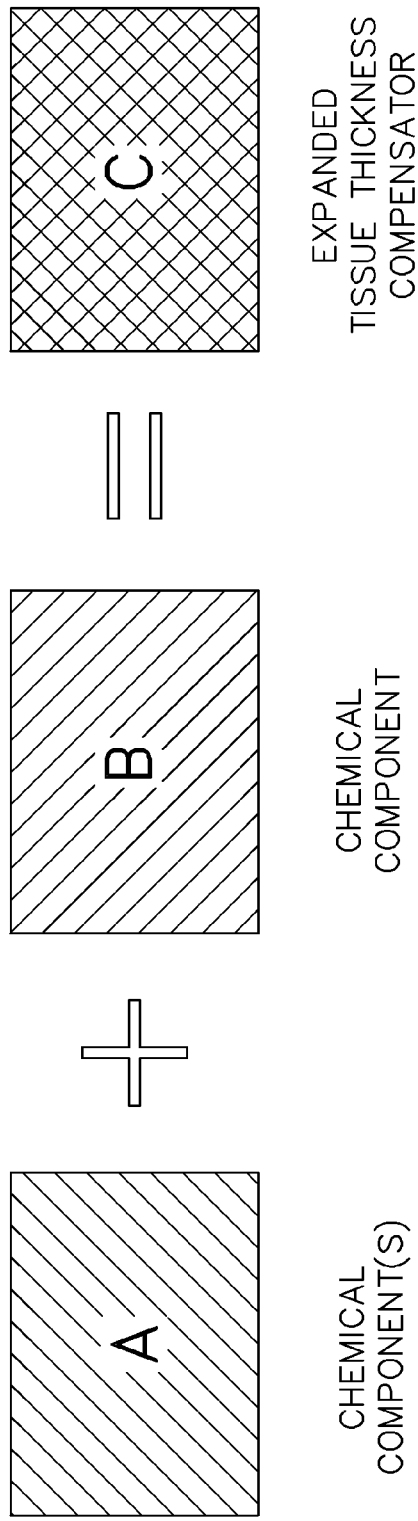
Figure 206:
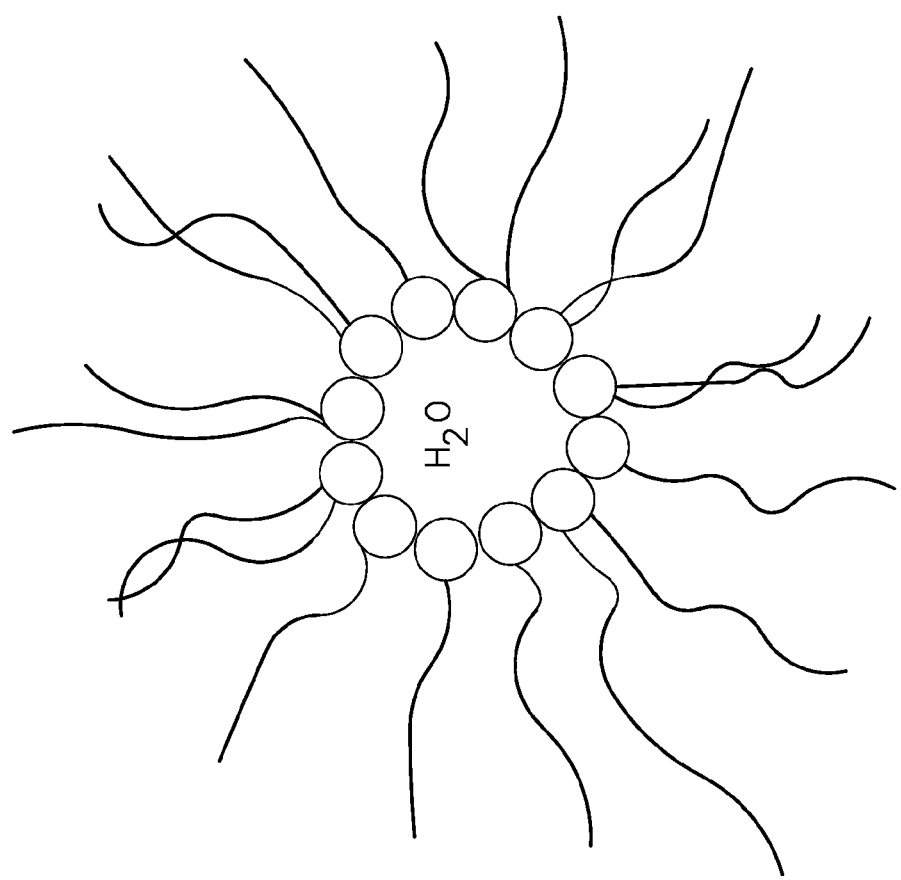

FIG. 123 is an elevational view of the tissue thickness compensator and the end effector of FIG. 120 depicting the end effector in a clamped configuration;

FIG. 124 is an elevational cross-sectional view of tubular elements of the tissue thickness compensator of FIG. 120 in an undeformed configuration;

FIG. 125 is an elevational cross-sectional view of tubular elements of the tissue thickness compensator of FIG. 120 in a deformed configuration;

FIG. 126 is a perspective view of a tissue thickness compensator in an end effector of a surgical instrument according to at least one embodiment;

FIG. 127 is an elevational cross-sectional view of the tissue thickness compensator and the end effector of FIG. 126 depicting the end effector in a clamped configuration;

FIG. 128 is an elevational cross-sectional view of the tissue thickness compensator and the end effector of FIG. 126 depicting the end effector in a fired and partially unclamped configuration;

FIG. 129 is a perspective view of a tissue thickness compensator positioned in an end effector of a surgical instrument according to at least one embodiment;

FIG. 130 is an elevational cross-sectional view of a tissue thickness compensator secured to an anvil of an end effector of a surgical instrument according to at least one embodiment;

FIG. 131 is an elevational cross-sectional view of the tissue thickness compensator and the end effector of FIG. 130 depicting the end effector in a clamped configuration;

FIG. 132 is an elevational cross-sectional view of the tissue thickness compensator and the end effector of FIG. 130 depicting the end effector in a fired and partially unclamped configuration;

FIG. 133 is a detail view of the tissue thickness compensator and the end effector of FIG. 132;

FIG. 134 is an elevational cross-sectional view of a tissue thickness compensator clamped in an end effector of a surgical instrument depicting deployment of staples by a staple-firing sled according to at least one embodiment;

FIG. 135 is an elevational cross-sectional view of the tissue thickness compensator and the end effector of FIG. 134 depicting the end effector in a clamped configuration;

FIG. 136 is an elevational cross-sectional view of the tissue thickness compensator and the end effector of FIG. 134 depicting the end effector in a fired configuration;

FIG. 137 is a perspective view of a tissue thickness compensator in an end effector of a surgical instrument according to at least one embodiment;

FIG. 138 is a perspective view of a tubular element of the tissue thickness compensator of FIG. 137;

FIG. 139 is a perspective view of the tubular element of FIG. 138 severed between a first and second end;

FIG. 140 is a perspective view of the tissue thickness compensator of FIG. 137 depicting a cutting element severing the tissue thickness compensator and staples engaging the tissue thickness compensator;

FIG. 141 is perspective view of a frame configured to make the tissue thickness compensator of FIG. 137 according to at least one embodiment;

FIG. 142 is an elevational cross-sectional view of the frame of FIG. 141 depicting the tissue thickness compensator of FIG. 137 curing in the frame;

FIG. 143 is an elevational cross-sectional view of the tissue thickness compensator removed from the frame of FIG. 142 and prepared for trimming by at least one cutting instrument;

FIG. 144 is an elevational cross-sectional view of the tissue thickness compensator of FIG. 143 after at least one cutting instrument has trimmed the tissue thickness compensator;

FIG. 145 is an elevational cross-sectional view of the tissue thickness compensator formed in the frame of FIG. 142 depicting severable tubes having various cross-sectional geometries;

FIG. 146 is a perspective view of a tissue thickness compensator in an end effector of a surgical instrument according to at least one embodiment;

FIG. 147 is a detail view of the tissue thickness compensator of FIG. 146 according to at least one embodiment;

FIG. 148 is a partial perspective view of a tissue thickness compensator according to at least one embodiment;

FIG. 149 is a partial perspective view of a tissue thickness compensator according to at least one embodiment;

FIG. 150A is an elevational cross-sectional view of the tissue thickness compensator and the end effector of FIG. 146 depicting the end effector in an unclamped configuration;

FIG. 150B is an elevational cross-sectional view of the tissue thickness compensator and the end effector of FIG. 146 depicting the end effector in a clamped configuration;

FIG. 150C is an elevational cross-sectional view of the tissue thickness compensator and the end effector of FIG. 146 depicting the end effector in a clamped and fired configuration;

FIG. 150D is an elevational cross-sectional view of the tissue thickness compensator of FIG. 146 captured in fired staples;

FIG. 150E is an elevational cross-sectional view of the tissue thickness compensator of FIG. 146 captured in fired staples depicting further expansion of the tissue thickness compensator;

FIG. 151 is a perspective cross-sectional view of a tissue thickness compensator in an end effector of a surgical instrument according to at least one embodiment;

FIG. 152 is a partial elevational view of the tissue thickness compensator of FIG. 151 captured in a fired staple;

FIG. 153 is an elevational view of a deformable tube of the tissue thickness compensator of FIG. 151;

FIG. 154 is an elevational view of a deformable tube according to at least one embodiment;

FIG. 155 is a perspective cross-sectional view of the tissue thickness compensator of FIG. 151;

FIG. 156 is a perspective cross-sectional view of a tissue thickness compensator in an end effector of a surgical instrument according to at least one embodiment;

FIG. 157 is a perspective view of a tissue thickness compensator according to at least one embodiment;

FIG. 158 is a partial elevational cross-sectional view of the tissue thickness compensator of FIG. 157 depicting a fastener engaged with tissue and with the tissue thickness compensator;

FIG. 159 is a perspective cross-sectional view of a tissue thickness compensator according to at least one embodiment;

FIG. 160 is an elevational view of a tissue thickness compensator according to at least one embodiment;

FIG. 161 is an elevational view of a tissue thickness compensator according to at least one embodiment;

FIG. 162 is an elevational view of a tissue thickness compensator positioned in a circular end effector of a surgical instrument according to at least one embodiment;

FIG. 163 is an elevational view of a tissue thickness compensator according to at least one embodiment;

FIG. 164 is an elevational view of a tissue thickness compensator according to at least one embodiment;

FIG. 165 is an elevational view of a tissue thickness compensator according to at least one embodiment;

FIG. 166 is an elevational view of a tissue thickness compensator according to at least one embodiment;

FIG. 167 is an elevational view of a tissue thickness compensator according to at least one embodiment;

FIG. 168 is a partial perspective view of a tissue thickness compensator according to at least one embodiment;

FIG. 169 is a partial perspective view of a tissue thickness compensator positioned in an end effector of a surgical instrument according to at least one embodiment;

FIG. 170 is a partial perspective view of a tissue thickness compensator with a fastener positioned in the apertures thereof according to at least one embodiment;

FIG. 171 is a partial perspective view of the tissue thickness compensator of FIG. 169 depicting the tissue thickness compensator in an undeformed configuration;

FIG. 172 is a partial perspective view of the tissue thickness compensator of FIG. 169 depicting the tissue thickness compensator in a partially deformed configuration;

FIG. 173 is a partial perspective view of the tissue thickness compensator of FIG. 169 depicting the tissue thickness compensator in a deformed configuration;

FIG. 174 is a perspective view of a tissue thickness compensator according to at least one embodiment;

FIG. 175 is a perspective view of an end effector of a stapling instrument comprising an anvil and a staple cartridge in accordance with at least one embodiment;

FIG. 176 is a cross-sectional view of the end effector of FIG. 175 illustrating staples positioned within the staple cartridge in an unfired state and a tissue thickness compensator comprising a sealed vessel in an unpunctured state, wherein the vessel is depicted with portions thereof removed for the purposes of illustration;

FIG. 177 is a cross-sectional view of the end effector of FIG. 175 illustrating the staples of FIG. 176 in an at least partially fired state and the vessel in an at least partially punctured state;

FIG. 178 is a perspective view of an end effector of a stapling instrument comprising an anvil and a staple cartridge in accordance with at least one embodiment;

FIG. 179 is a cross-sectional view of the end effector of FIG. 178 illustrating staples positioned within the staple cartridge in an unfired state and sealed vessels positioned within a tissue thickness compensator of the staple cartridge in an unpunctured state, wherein the vessels are depicted with portions thereof removed for the purposes of illustration;

FIG. 180 is a cross-sectional view of the end effector of FIG. 178 illustrating the staples of FIG. 179 in an at least partially fired state and the vessels in the staple cartridge in an at least partially punctured state;

FIG. 181 is a perspective view of an end effector of a stapling instrument comprising an anvil and a sealed vessel attached to the anvil in accordance with at least one alternative embodiment wherein the vessel is depicted with portions thereof removed for the purposes of illustration;

FIG. 182 is a cross-sectional view of the end effector of FIG. 181 illustrating staples at least partially fired from a staple cartridge and the vessels attached to the anvil in an at least partially punctured state;

FIG. 183 is a cross-sectional view of the vessel attached to the anvil of FIG. 181 illustrated in an expanded state;

FIG. 184 is a detail view of the vessel attached to the anvil of FIG. 183 illustrated in an expanded state;

FIG. 185 illustrates a vessel extending in a direction transverse to a line of staples;

FIG. 186 illustrates a plurality of vessels extending in directions which are transverse to a line of staples;

FIG. 187 is a cross-sectional view of a staple cartridge in accordance with various embodiments;

FIG. 188 is a partial cross-section view of FIG. 187 in an implanted condition;

FIG. 189A is a partial perspective view of a tissue thickness compensator prior to expansion;

FIG. 189B is a partial perspective view of a tissue thickness compensator of FIG. 189 during expansion;

FIG. 190 is a partial perspective view of a tissue thickness compensator comprising a fluid swellable composition according to various embodiments;

FIG. 191 is a cross-sectional view of tissue positioned adjacent a tissue thickness compensator according to various embodiments;

FIG. 192 is a partial cross-sectional view of FIG. 191 after the staple cartridge has been fired;

FIG. 193 is a diagram illustrating the tissue thickness compensator of FIG. 191 implanted adjacent the tissue;

FIG. 194 is a partial perspective view of a tissue thickness compensator according to various embodiments;

FIG. 195 is a perspective view of a jaw configured to receive the tissue thickness compensator of FIG. 194;

FIG. 196 is a partial cross-sectional view of a staple cartridge illustrating staples being deployed from the staple cartridge;

FIG. 197 is a perspective view of an upper tissue thickness compensator and a lower tissue thickness compensator positioned within an effector of a disposable loading unit;

FIG. 198A is a cross-sectional view of the lower tissue thickness compensator of FIG. 197 being manufactured in a mold in accordance with various embodiments;

FIG. 198B is a cross-sectional view of a trilayer tissue thickness compensator being manufactured in a mold in accordance with various embodiments;

FIG. 199 is a cross-sectional view of an anvil comprising a tissue thickness compensator comprising reinforcement material in accordance with various embodiments;

FIG. 200 is cross-sectional view of a tissue positioned intermediate the upper tissue thickness compensator and lower tissue thickness compensator in accordance with various embodiments;

FIG. 201 is a cross-sectional view of FIG. 200 illustrating staples being deployed from the staple cartridge;

FIG. 202 is a cross-sectional view of FIG. 200 after the staple cartridge has been fired;

FIG. 203A illustrates a needle configured to deliver a fluid to a tissue thickness compensator attached to a staple cartridge according to various embodiments;

FIG. 203B is a cross-sectional view of a staple cartridge comprising a tissue thickness compensator configured to receive the needle of FIG. 203A;

FIG. 204 illustrates a method of manufacturing a tissue thickness compensator according to various embodiments;

FIG. 205 is a diagram and a method of forming an expanding thickness compensator according to various embodiments;

FIG. 206 illustrates a micelle comprising a hydrogel precursor; and

Figure 207:
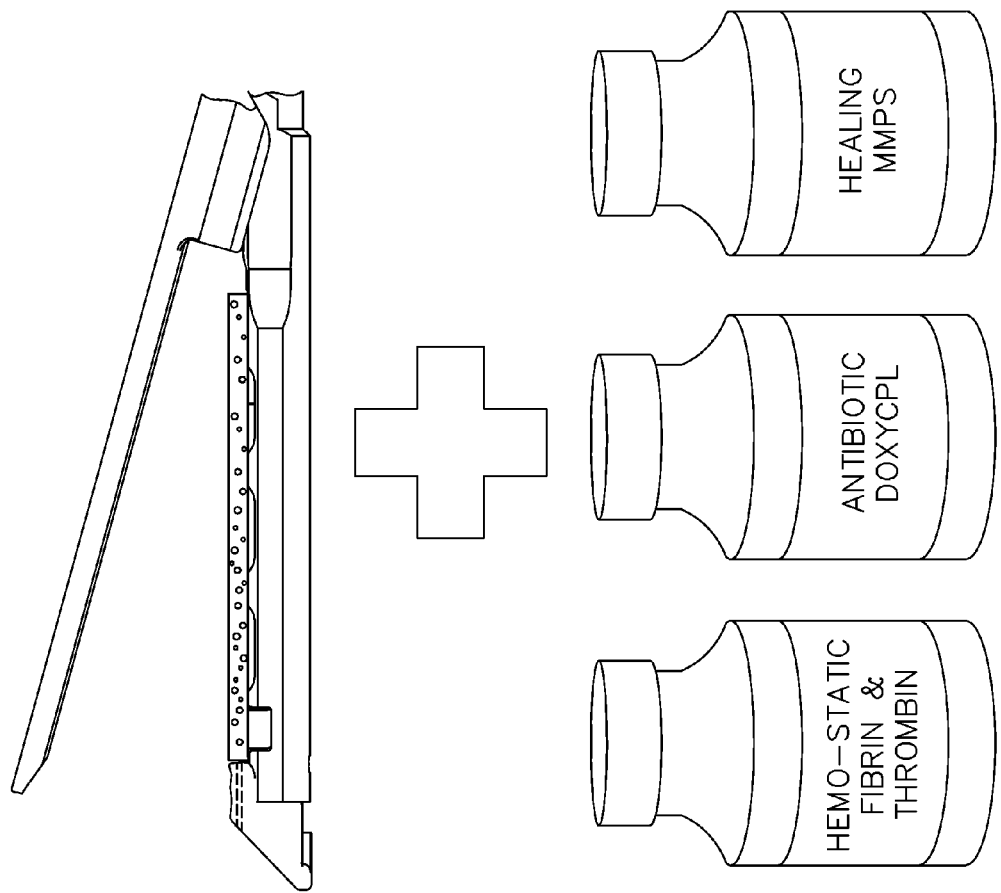

FIG. 207 is a diagram of a surgical instrument comprising a tissue thickness compensator and fluids that may be delivered to the tissue thickness compensator according to various embodiments.

FIG. 208 is a partial perspective view of a tissue thickness compensator secured to an anvil of an end effector of a surgical instrument according to at least one embodiment.

FIG. 209 is a perspective view of a tubular element of the tissue thickness compensator of FIG. 208.

FIG. 210 is a perspective view of the tubular element of FIG. 209 depicting the tubular element severed into two halves and fluid contacting the hydrophilic substance within each half.

FIG. 211 is a perspective view of a half of the severed tubular element of FIG. 210 depicting expansion of the severed tubular element.

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

The Applicant of the present application also owns the U.S. Patent Applications identified below which are each herein incorporated by reference in their respective entirety:

U.S. patent application Ser. No. 12/894,311, entitled SURGICAL INSTRUMENTS WITH RECONFIGURABLE SHAFT SEGMENTS, now U.S. Patent Application Publication No. 2012/0080496;

U.S. patent application Ser. No. 12/894,340, entitled SURGICAL STAPLE CARTRIDGES SUPPORTING NON-LINEARLY ARRANGED STAPLES AND SURGICAL STAPLING INSTRUMENTS WITH COMMON STAPLE-FORMING POCKETS, now U.S. Patent Application Publication No. 2012/0080482;

U.S. patent application Ser. No. 12/894,327, entitled JAW CLOSURE ARRANGEMENTS FOR SURGICAL INSTRUMENTS, now U.S. Patent Application Publication No. 2012/0080499;

U.S. patent application Ser. No. 12/894,351, entitled SURGICAL CUTTING AND FASTENING INSTRUMENTS WITH SEPARATE AND DISTINCT FASTENER DEPLOYMENT AND TISSUE CUTTING SYSTEMS, now U.S. Patent Application Publication No. 2012/0080502;

U.S. patent application Ser. No. 12/894,338, entitled IMPLANTABLE FASTENER CARTRIDGE HAVING A NON-UNIFORM ARRANGEMENT, now U.S. Patent Application Publication No. 2012/0080481;

U.S. patent application Ser. No. 12/894,369, entitled IMPLANTABLE FASTENER CARTRIDGE COMPRISING A SUPPORT RETAINER, now U.S. Patent Application Publication No. 2012/0080344;

U.S. patent application Ser. No. 12/894,312, entitled IMPLANTABLE FASTENER CARTRIDGE COMPRISING MULTIPLE LAYERS, now U.S. Patent Application Publication No. 2012/0080479;

U.S. patent application Ser. No. 12/894,377, entitled SELECTIVELY ORIENTABLE IMPLANTABLE FASTENER CARTRIDGE, now U.S. Pat. No. 8,393,514;

U.S. patent application Ser. No. 12/894,339, entitled SURGICAL STAPLING INSTRUMENT WITH COMPACT ARTICULATION CONTROL ARRANGEMENT, now U.S. Patent Application Publication No. 2012/0080500;

U.S. patent application Ser. No. 12/894,360, entitled SURGICAL STAPLING INSTRUMENT WITH A VARIABLE STAPLE FORMING SYSTEM, now U.S. Patent Application Publication No. 2012/0080484;

U.S. patent application Ser. No. 12/894,322, entitled SURGICAL STAPLING INSTRUMENT WITH INTERCHANGEABLE STAPLE CARTRIDGE ARRANGEMENTS, now U.S. Patent Application Publication No. 2012/0080501;

U.S. patent application Ser. No. 12/894,350, entitled SURGICAL STAPLE CARTRIDGES WITH DETACHABLE SUPPORT STRUCTURES AND SURGICAL STAPLING INSTRUMENTS WITH SYSTEMS FOR PREVENTING ACTUATION MOTIONS WHEN A CARTRIDGE IS NOT PRESENT, now U.S. Patent Application No. 2012/0080478;

U.S. patent application Ser. No. 12/894,383, entitled IMPLANTABLE FASTENER CARTRIDGE COMPRISING BIOABSORBABLE LAYERS, now U.S. Patent Application No. 2012/0080345;

U.S. patent application Ser. No. 12/894,389, entitled COMPRESSIBLE FASTENER CARTRIDGE, now U.S. Patent Application Publication No. 2012/0080335;

U.S. patent application Ser. No. 12/894,345, entitled FASTENERS SUPPORTED BY A FASTENER CARTRIDGE SUPPORT, now U.S. Patent Application Publication No. 2012/0080483;

U.S. patent application Ser. No. 12/894,306, entitled COLLAPSIBLE FASTENER CARTRIDGE, now U.S. Patent Application Publication No. 2012/0080332;

U.S. patent application Ser. No. 12/894,318, entitled FASTENER SYSTEM COMPRISING A PLURALITY OF CONNECTED RETENTION MATRIX ELEMENTS, now U.S. Patent Application Publication No. 2012/0080480;

U.S. patent application Ser. No. 12/894,330, entitled FASTENER SYSTEM COMPRISING A RETENTION MATRIX AND AN ALIGNMENT MATRIX, now U.S. Patent Application Publication No. 2012/0080503;

U.S. patent application Ser. No. 12/894,361, entitled FASTENER SYSTEM COMPRISING A RETENTION MATRIX, now U.S. Pat. No. 8,529,600;

U.S. patent application Ser. No. 12/894,367, entitled FASTENING INSTRUMENT FOR DEPLOYING A FASTENER SYSTEM COMPRISING A RETENTION MATRIX, now U.S. Patent Application Publication No. 2012/0080485;

U.S. patent application Ser. No. 12/894,388, entitled FASTENER SYSTEM COMPRISING A RETENTION MATRIX AND A COVER, now U.S. Pat. No. 8,474,677;

U.S. patent application Ser. No. 12/894,376, entitled FASTENER SYSTEM COMPRISING A PLURALITY OF FASTENER CARTRIDGES, now U.S. Patent Application Publication No. 2012/0080486;

U.S. patent application Ser. No. 13/097,865, entitled SURGICAL STAPLER ANVIL COMPRISING A PLURALITY OF FORMING POCKETS, now U.S. Patent Application Publication No. 2012/0080488;

U.S. patent application Ser. No. 13/097,936, entitled TISSUE THICKNESS COMPENSATOR FOR A SURGICAL STAPLER, now U.S. Patent Application Publication No. 2012/0080339;

U.S. patent application Ser. No. 13/097,954, entitled STAPLE CARTRIDGE COMPRISING A VARIABLE THICKNESS COMPRESSIBLE PORTION, now U.S. Patent Application Publication No. 2012/0080340;

U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336;

U.S. patent application Ser. No. 13/097,928, entitled TISSUE THICKNESS COMPENSATOR COMPRISING DETACHABLE PORTIONS, now U.S. Patent Application Publication No. 2012/0080490;

U.S. patent application Ser. No. 13/097,891, entitled TISSUE THICKNESS COMPENSATOR FOR A SURGICAL STAPLER COMPRISING AN ADJUSTABLE ANVIL, now U.S. Patent Application Publication No. 2012/0080489;

U.S. patent application Ser. No. 13/097,948, entitled STAPLE CARTRIDGE COMPRISING AN ADJUSTABLE DISTAL PORTION, now U.S. Patent Application Publication No. 2012/0083836;

U.S. patent application Ser. No. 13/097,907, entitled COMPRESSIBLE STAPLE CARTRIDGE ASSEMBLY, now U.S. Patent Application Publication No. 2012/0080338;

U.S. patent application Ser. No. 13/097,861, entitled TISSUE THICKNESS COMPENSATOR COMPRISING PORTIONS HAVING DIFFERENT PROPERTIES, U.S. Patent Application Publication No. 2012/0080337;

U.S. patent application Ser. No. 13/097,869, entitled STAPLE CARTRIDGE LOADING ASSEMBLY, now U.S. Patent Application Publication No. 2012/0160721;

U.S. patent application Ser. No. 13/097,917, entitled COMPRESSIBLE STAPLE CARTRIDGE COMPRISING ALIGNMENT MEMBERS, now U.S. Patent Application No. 2012/0083834;

U.S. patent application Ser. No. 13/097,873, entitled STAPLE CARTRIDGE COMPRISING A RELEASABLE PORTION, now U.S. Patent Application Publication No. 2012/0083833;

U.S. patent application Ser. No. 13/097,938, entitled STAPLE CARTRIDGE COMPRISING COMPRESSIBLE DISTORTION RESISTANT COMPONENTS, now U.S. Patent Application Publication No. 2012/0080491;

U.S. patent application Ser. No. 13/097,924, entitled STAPLE CARTRIDGE COMPRISING A TISSUE THICKNESS COMPENSATOR, now U.S. Patent Application Publication No. 2012/0083835;

U.S. patent application Ser. No. 13/242,029, entitled SURGICAL STAPLER WITH FLOATING ANVIL, now U.S. Patent Application Publication No. 2012/0080493;

U.S. patent application Ser. No. 13/242,066, entitled CURVED END EFFECTOR FOR A STAPLING INSTRUMENT, now U.S. Patent Application Publication No. 2012/0080498;

U.S. patent application Ser. No. 13/242,086, entitled STAPLE CARTRIDGE INCLUDING COLLAPSIBLE DECK, now U.S. Patent Application Publication No. 2013/0075450;

U.S. patent application Ser. No. 13/241,912, entitled STAPLE CARTRIDGE INCLUDING COLLAPSIBLE DECK ARRANGEMENT, now U.S. Patent Application Publication No. 2013/0075448;

U.S. patent application Ser. No. 13/241,922, entitled SURGICAL STAPLER WITH STATIONARY STAPLE DRIVERS, now U.S. Patent Application Publication No. 2013/0075449;

U.S. patent application Ser. No. 13/241,637, entitled SURGICAL INSTRUMENT WITH TRIGGER ASSEMBLY FOR GENERATING MULTIPLE ACTUATION MOTIONS, now U.S. Patent Application Publication No. 2012/0074201; and U.S. patent application Ser. No. 13/241,629, entitled SURGICAL INSTRUMENT WITH SELECTIVELY ARTICULATABLE END EFFECTOR, now U.S. Patent Application Publication No. 2012/0074200.

The Applicant of the present application also owns the U.S. Patent Applications identified below which were filed on Mar. 28, 2012 and which are each herein incorporated by reference in their respective entirety:

U.S. patent application Ser. No. 13/433,096, entitled TISSUE THICKNESS COMPENSATOR COMPRISING A PLURALITY OF CAPSULES, now U.S. Patent Application Publication No. 2012/0241496;

U.S. patent application Ser. No. 13/433,103, entitled TISSUE THICKNESS COMPENSATOR COMPRISING A PLURALITY OF LAYERS, now U.S. Patent Application Publication No. 2012/0241498;

U.S. patent application Ser. No. 13/433,098, entitled EXPANDABLE TISSUE THICKNESS COMPENSATOR, now U.S. Patent Application Publication No. 2012/0241491;

U.S. patent application Ser. No. 13/433,102, entitled TISSUE THICKNESS COMPENSATOR COMPRISING A RESERVOIR, now U.S. Patent Application Publication No. 2012/0241497;

U.S. patent application Ser. No. 13/433,114, entitled RETAINER ASSEMBLY INCLUDING A TISSUE THICKNESS COMPENSATOR, now U.S. Patent Application Publication No. 2012/0241499;

U.S. patent application Ser. No. 13/433,136, entitled TISSUE THICKNESS COMPENSATOR COMPRISING AT LEAST ONE MEDICAMENT, now U.S. Patent Application Publication No. 2012/0241492;

U.S. patent application Ser. No. 13/433,141, entitled TISSUE THICKNESS COMPENSATOR COMPRISING CONTROLLED RELEASE AND EXPANSION, now U.S. Patent Application Publication No. 2012/0241493;

U.S. patent application Ser. No. 13/433,144, entitled TISSUE THICKNESS COMPENSATOR COMPRISING FIBERS TO PRODUCE A RESILIENT LOAD, now U.S. Patent Application Publication Serial No. 2012/0241500;

U.S. patent application Ser. No. 13/433,155, entitled TISSUE THICKNESS COMPENSATOR COMPRISING RESILIENT MEMBERS, now U.S. Patent Application Publication No. 2012/0241502;

U.S. patent application Ser. No. 13/433,163, entitled METHODS FOR FORMING TISSUE THICKNESS COMPENSATOR ARRANGEMENTS FOR SURGICAL STAPLERS, now U.S. Patent Application Publication No. 2012/0248169;

U.S. patent application Ser. No. 13/433,167, entitled TISSUE THICKNESS COMPENSATORS, now U.S. Patent Application Publication No. 2012/0241503;

U.S. patent application Ser. No. 13/433,175, entitled LAYERED TISSUE THICKNESS COMPENSATOR, now U.S. Patent Application Publication No. 2012/0253298;

U.S. patent application Ser. No. 13/433,179, entitled TISSUE THICKNESS COMPENSATORS FOR CIRCULAR SURGICAL STAPLERS, now U.S. Patent Application Publication No. 2012/0241505;

U.S. patent application Ser. No. 13/433,115, entitled TISSUE THICKNESS COMPENSATOR COMPRISING CAPSULES DEFINING A LOW PRESSURE ENVIRONMENT, now U.S. Patent Application Publication No. 2013/0256372;

U.S. patent application Ser. No. 13/433,118, entitled TISSUE THICKNESS COMPENSATOR COMPRISED OF A PLURALITY OF MATERIALS, now U.S. Patent Application Publication No. 2013/0256365;

U.S. patent application Ser. No. 13/433,135, entitled MOVABLE MEMBER FOR USE WITH A TISSUE THICKNESS COMPENSATOR, U.S. Patent Application Publication No. 2013/0256382;

U.S. patent application Ser. No. 13/433,129, entitled TISSUE THICKNESS COMPENSATOR COMPRISING A PLURALITY OF MEDICAMENTS, now U.S. Patent Application Publication No. 2013/0256367;

U.S. patent application Ser. No. 13/433,140, entitled TISSUE THICKNESS COMPENSATOR AND METHOD FOR MAKING THE SAME, now U.S. Patent Application Publication No. 2013/0256368;

U.S. patent application Ser. No. 13/433,147, entitled TISSUE THICKNESS COMPENSATOR COMPRISING CHANNELS, now U.S. Patent Application Publication No. 2013/0256369;

U.S. patent application Ser. No. 13/433,126, entitled TISSUE THICKNESS COMPENSATOR COMPRISING TISSUE INGROWTH FEATURES, now U.S. Patent Application Publication No. 2013/0256366; and U.S. patent application Ser No. 13/433,132, entitled DEVICES AND METHODS FOR ATTACHING TISSUE THICKNESS COMPENSATING MATERIALS TO SURGICAL STAPLING INSTRUMENTS, now U.S. Patent Application Publication No. 2013/0256373.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 1:
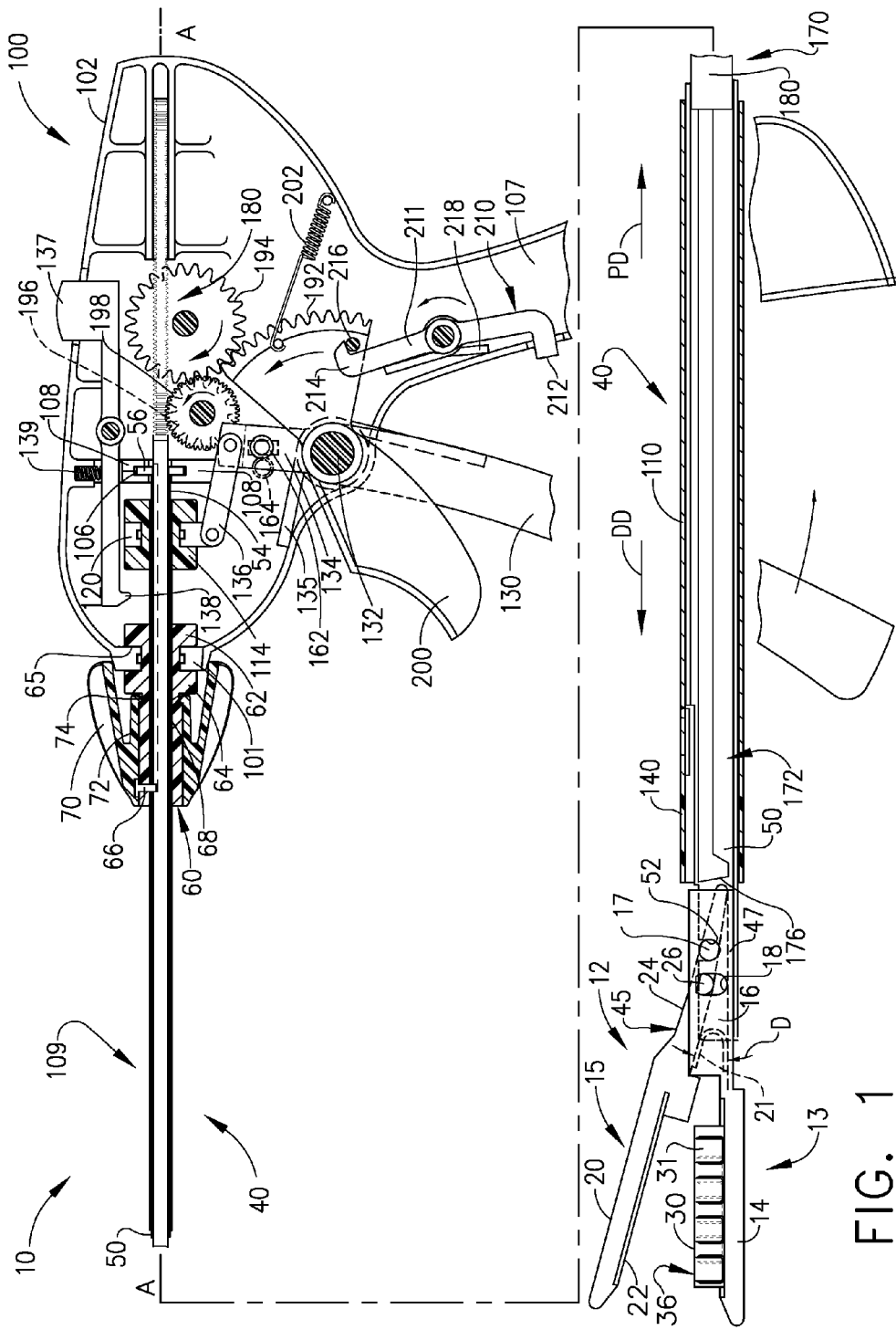
FIG. 1 is a cross-sectional view of a surgical instrument embodiment.

Turning to the Drawings wherein like numerals denote like components throughout the several views, FIG. 1 depicts a surgical instrument 10 that is capable of practicing several unique benefits. The surgical stapling instrument 10 is designed to manipulate and/or actuate various forms and sizes of end effectors 12 that are operably attached thereto. In the embodiment depicted in FIGS. 1-1E, for example, the end effector 12 includes an elongated channel 14 that forms a lower jaw 13 of the end effector 12. The elongated channel 14 is configured to support an "implantable" staple cartridge 30 and also movably support an anvil 20 that functions as an upper jaw 15 of the end effector 12.

In various embodiments, the elongated channel 14 may be fabricated from, for example, 300 & 400 Series, 17-4 & 17-7 stainless steel, titanium, etc. and be formed with spaced side walls 16. The anvil 20 may be fabricated from, for example, 300 & 400 Series, 17-4 & 17-7 stainless steel, titanium, etc. and have a staple forming undersurface, generally labeled as 22 that has a plurality of staple forming pockets 23 formed therein. See FIGS. 1B-1E. In addition, the anvil 20 has a bifurcated ramp assembly 24 that protrudes proximally therefrom. An anvil pin 26 protrudes from each lateral side of the ramp assembly 24 to be received within a corresponding slot or opening 18 in the side walls 16 of the elongated channel 14 to facilitate its movable or pivotable attachment thereto.

Figure 1A:
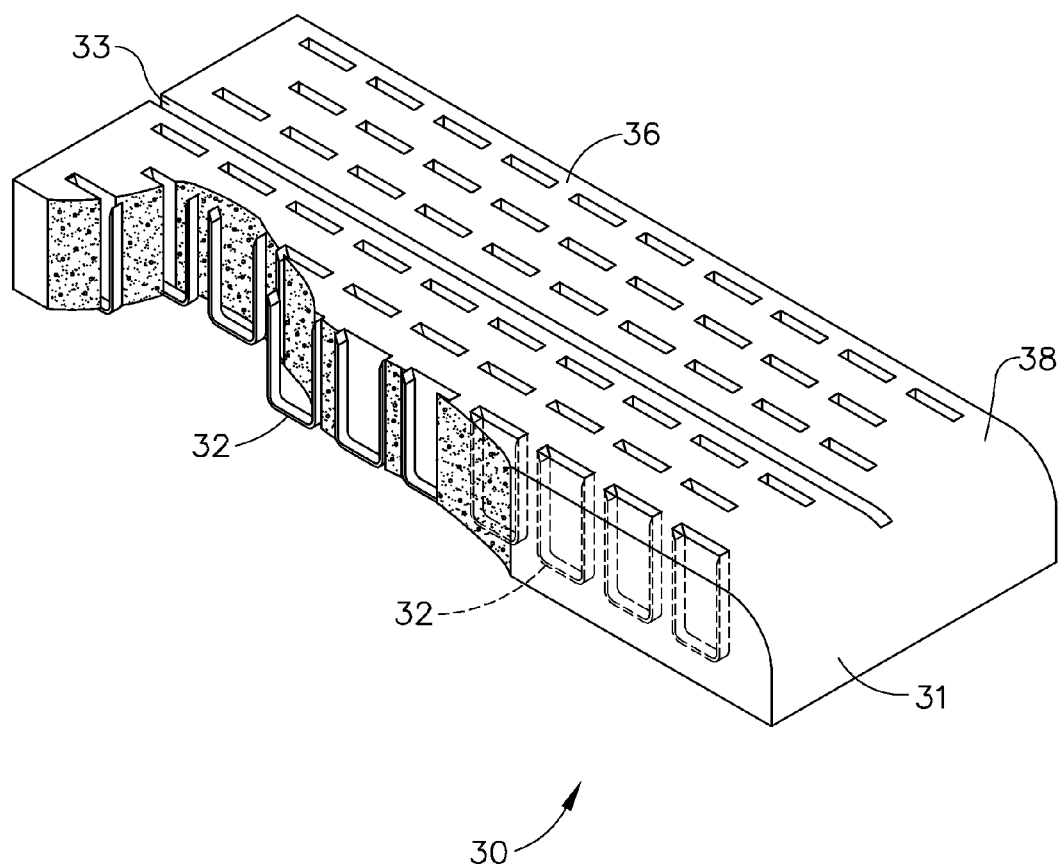
FIG. 1A is a perspective view of one embodiment of an implantable staple cartridge.

Various forms of implantable staple cartridges may be employed with the various embodiments of the surgical instruments disclosed herein. Specific staple cartridge configurations and constructions will be discussed in further detail below. However, in the embodiment depicted in FIG. 1A, an implantable staple cartridge 30 is shown. In at least one embodiment, the staple cartridge 30 has a body portion 31 that consists of a compressible hemostat material such as, for example, oxidized regenerated cellulose ("ORC") or a bioabsorbable foam in which lines of unformed metal staples 32 are supported. In at least some embodiments, in order to prevent the staple from being affected and the hemostat material from being activated during the introduction and positioning process, the entire cartridge may be coated or wrapped in a biodegradable film 38 such as a polydioxanon film sold under the trademark PDS® or with a Polyglycerol sebacate (PGS) film or other biodegradable films formed from PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured. The body 31 of staple cartridge 30 is sized to be removably supported within the elongated channel 14 as shown such that each staple 32 therein is aligned with corresponding staple forming pockets 23 in the anvil when the anvil 20 is driven into forming contact with the staple cartridge 30.

In use, once the end effector 12 has been positioned adjacent the target tissue, the end effector 12 is manipulated to capture or clamp the target tissue between an upper face 36 of the staple cartridge 30 and the staple forming surface 22 of the anvil 20. The staples 32 are formed by moving the anvil 20 in a path that is substantially parallel to the elongated channel 14 to bring the staple forming surface 22 and, more particularly, the staple forming pockets 23 therein into substantially simultaneous contact with the upper face 36 of the staple cartridge 30. As the anvil 20 continues to move into the staple cartridge 30, the legs 34 of the staples 32 contact a corresponding staple forming pocket 23 in anvil 20 which serves to bend the staple legs 34 over to form the staples 32 into a "B shape". Further movement of the anvil 20 toward the elongated channel 14 will further compress and form the staples 32 to a desired final formed height "FF".

The above-described staple forming process is generally depicted in FIGS. 1B-1E. For example, FIG. 1B illustrates the end effector 12 with target tissue "T" between the anvil 20 and the upper face 36 of the implantable staple cartridge 30. FIG. 1C illustrates the initial clamping position of the anvil 20 wherein the anvil has 20 been closed onto the target tissue "T" to clamp the target tissue "T" between the anvil 20 and the upper face 36 of the staple cartridge 30. FIG. 1D illustrates the initial staple formation wherein the anvil 20 has started to compress the staple cartridge 30 such that the legs 34 of the staples 32 are starting to be formed by the staple forming pockets 23 in the anvil 20. FIG. 1E illustrates the staple 32 in its final formed condition through the target tissue "T" with the anvil 20 removed for clarity purposes. Once the staples 32 have been formed and fastened to the target tissue "T", the surgeon will move the anvil 20 to the open position to enable the cartridge body 31 and the staples 32 to remain affixed to the target tissue while the end effector 12 is being withdrawn from the patient. The end effector 12 forms all of the staples simultaneously as the two jaws 13, 15 are clamped together. The remaining "crushed" body materials 31 act as both a hemostat (the ORC) and a staple line reinforcement (PGA, PDS or any of the other film compositions mentioned above 38). Also, since the staples 32 never have to leave the cartridge body 31 during forming, the likelihood of the staples 32 being malformed during forming is minimized. As used herein the term "implantable" means that, in addition to the staples, the cartridge body materials that support the staples will also remain in the patient and may eventually be absorbed by the patient's body. Such implantable staple cartridges are distinguishable from prior cartridge arrangements that remain positioned within the end effector in their entirety after they have been fired.

In various implementations, the end effector 12 is configured to be coupled to an elongated shaft assembly 40 that protrudes from a handle assembly 100. The end effector 12 (when closed) and the elongated shaft assembly 40 may have similar cross-sectional shapes and be sized to operably pass through a trocar tube or working channel in another form of access instrument. As used herein, the term "operably pass" means that the end effector and at least a portion of the elongated shaft assembly may be inserted through or passed through the channel or tube opening and can be manipulated therein as needed to complete the surgical stapling procedure. In some embodiments, when in a closed position, the jaws 13 and 15 of the end effector 12 may provide the end effector with a roughly circular cross-sectional shape that facilitates its passage through a circular passage/opening. However, the end effectors of various embodiments of the present invention, as well as the elongated shaft assembly embodiments, could conceivably be provided with other cross-sectional shapes that could otherwise pass through access passages and openings that have non-circular cross-sectional shapes. Thus, an overall size of a cross-section of a closed end effector will be related to the size of the passage or opening through which it is intended to pass. Thus, one end effector for example, may be referred to as a "5 mm" end effector which means it can operably pass through an opening that is at least approximately 5 mm in diameter.

In various embodiments, the elongated shaft assembly 40 may have an outer diameter that is substantially the same as the outer diameter of the end effector 12 when in a closed position. For example, a 5 mm end effector may be coupled to an elongated shaft assembly 40 that has 5 mm cross-sectional diameter. However, as the present Detailed Description proceeds, it will become apparent that various embodiments of the present may be effectively used in connection with different sizes of end effectors. For example, a 10 mm end effector may be attached to an elongated shaft that has a 5 mm cross-sectional diameter. Conversely, for those applications wherein a 10 mm or larger access opening or passage is provided, the elongated shaft assembly 40 may have a 10 mm (or larger) cross-sectional diameter, but may also be able to actuate a 5 mm or 10 mm end effector. Accordingly, the outer shaft 40 may have an outer diameter that is the same as or is different from the outer diameter of a closed end effector 12 attached thereto.

As depicted, the elongated shaft assembly 40 extends distally from the handle assembly 100 in a generally straight line to define a longitudinal axis A-A. In various embodiments, for example, the elongated shaft assembly 40 may be approximately 9-16 inches (229-406 mm) long. However, the elongated shaft assembly 40 may be provided in other lengths and, in other embodiments, may have joints therein or be otherwise configured to facilitate articulation of the end effector 12 relative to other portions of the shaft or handle assembly as will be discussed in further detail below. In various embodiments, the elongated shaft assembly 40 includes a spine member 50 that extends from the handle assembly 100 to the end effector 12. The proximal end of the elongated channel 14 of the end effector 12 has a pair of retention trunnions 17 protruding therefrom that are sized to be received within corresponding trunnion openings or cradles 52 that are provided in a distal end of the spine member 50 to enable the end effector 12 to be removably coupled the elongated shaft assembly 40. The spine member 50 may be fabricated from, for example, 6061 or 7075 aluminum, stainless steel, titanium, etc.

In various embodiments, the handle assembly 100 comprises a pistol grip-type housing that may be fabricated in two or more pieces for assembly purposes. For example, the handle assembly 100 as shown comprises a right hand case member 102 and a left hand case member (not illustrated) that are molded or otherwise fabricated from a polymer or plastic material and are designed to mate together. Such case members may be attached together by snap features, pegs and sockets molded or otherwise formed therein and/or by adhesive, screws, etc. The spine member 50 has a proximal end 54 that has a flange 56 formed thereon. The flange 56 is configured to be rotatably supported within a groove 106 formed by mating ribs 108 that protrude inwardly from each of the case members 102, 104. Such arrangement facilitates the attachment of the spine member 50 to the handle assembly 100 while enabling the spine member 50 to be rotated relative to the handle assembly 100 about the longitudinal axis A-A in a 360° path.

As can be further seen in FIG. 1, the spine member 50 passes through and is supported by a mounting bushing 60 that is rotatably affixed to the handle assembly 100. The mounting bushing 60 has a proximal flange 62 and a distal flange 64 that define a rotational groove 65 that is configured to rotatably receive a nose portion 101 of the handle assembly 100 therebetween. Such arrangement enables the mounting bushing 60 to rotate about longitudinal axis A-A relative to the handle assembly 100. The spine member 50 is non-rotatably pinned to the mounting bushing 60 by a spine pin 66. In addition, a rotation knob 70 is attached to the mounting bushing 60. In one embodiment, for example, the rotation knob 70 has a hollow mounting flange portion 72 that is sized to receive a portion of the mounting bushing 60 therein. In various embodiments, the rotation knob 70 may be fabricated from, for example, glass or carbon filled Nylon, polycarbonate, Ultem®, etc. and is affixed to the mounting bushing 60 by the spine pin 66 as well. In addition, an inwardly protruding retention flange 74 is formed on the mounting flange portion 72 and is configured to extend into a radial groove 68 formed in the mounting bushing 60. Thus, the surgeon may rotate the spine member 50 (and the end effector 12 attached thereto) about longitudinal axis A-A in a 360° path by grasping the rotation knob 70 and rotating it relative to the handle assembly 100.

In various embodiments, the anvil 20 is retained in an open position by an anvil spring 21 and/or another biasing arrangement. The anvil 20 is selectively movable from the open position to various closed or clamping and firing positions by a firing system, generally designated as 109. The firing system 109 includes a "firing member" 110 which, in various embodiments, comprises a hollow firing tube 110. The hollow firing tube 110 is axially movable on the spine member 50 and thus forms the outer portion of the elongated shaft assembly 40. The firing tube 110 may be fabricated from a polymer or other suitable material and have a proximal end that is attached to a firing yoke 114 of the firing system 109. In various embodiments for example, the firing yoke 114 may be over-molded to the proximal end of the firing tube 110. However, other fastener arrangements may be employed.

As can be seen in FIG. 1, the firing yoke 114 may be rotatably supported within a support collar 120 that is configured to move axially within the handle assembly 100. In various embodiments, the support collar 120 has a pair of laterally extending fins that are sized to be slidably received within fin slots formed in the right and left hand case members. Thus, the support collar 120 may slide axially within the handle housing 100 while enabling the firing yoke 114 and firing tube 110 to rotate relative thereto about the longitudinal axis A-A. In various embodiments, a longitudinal slot is provided through the firing tube 110 to enable the spine pin 66 to extend therethrough into the spine member 50 while facilitating the axial travel of the firing tube 110 on the spine member 50.

The firing system 109 further comprises a firing trigger 130 which serves to control the axial travel of the firing tube 110 on the spine member 50. See FIG. 1. Such axial movement in the distal direction of the firing tube 110 into firing interaction with the anvil 20 is referred to herein as "firing motion". As can be seen in FIG. 1, the firing trigger 130 is movably or pivotally coupled to the handle assembly 100 by a pivot pin 132. A torsion spring 135 is employed to bias the firing trigger 130 away from the pistol grip portion 107 of the handle assembly 100 to an un-actuated "open" or starting position. As can be seen in FIG. 1, the firing trigger 130 has an upper portion 134 that is movably attached to (pinned) firing links 136 that are movably attached to (pinned) the support collar 120. Thus, movement of the firing trigger 130 from the starting position (FIG. 1) toward an ending position adjacent the pistol grip portion 107 of the handle assembly 100 will cause the firing yoke 114 and the firing tube 110 to move in the distal direction "DD". Movement of the firing trigger 130 away from the pistol grip portion 107 of the handle assembly 100 (under the bias of the torsion spring 135) will cause the firing yoke 114 and firing tube 110 to move in the proximal direction "PD" on the spine member 50.

Various embodiments of the present invention may be employed with different sizes and configurations of implantable staple cartridges. For example, the surgical instrument 10, when used in connection with a first firing adapter 140, may be used with a 5 mm end effector 12 that is approximately 20 mm long (or in other lengths) which supports an implantable staple cartridge 30. Such end effector size may be particularly well-suited, for example, to complete relatively fine dissection and vascular transactions. However, as will be discussed in further detail below, the surgical instrument 10 may also be employed, for example, in connection with other sizes of end effectors and staple cartridges by replacing the first firing adapter 140 with a second firing adapter. In still other embodiments, the elongated shaft assembly 40 may configured to be attached to only one form or size of end effector.

One method of removably coupling the end effector 12 to the spine member 50 will now be explained. The coupling process is commenced by inserting the retention trunnions 17 on the elongated channel 14 into the trunnion cradles 52 in the spine member 50. Thereafter, the surgeon advances the firing trigger 130 toward the pistol grip 107 of the housing assembly 100 to distally advance the firing tube 110 and the first firing adapter 140 over a proximal end portion 47 of the elongated channel 14 to thereby retain the trunnions 17 in their respective cradles 52. Such position of the first firing adapter 140 over the trunnions 17 is referred to herein as the "coupled position". Various embodiments of the present invention may also have an end effector locking assembly for locking the firing trigger 130 in position after an end effector 12 has been attached to the spine member 50.

More specifically, one embodiment of the end effector locking assembly 160 includes a retention pin 162 that is movably supported in the upper portion 134 of the firing trigger 130. As discussed above, the firing tube 110 must initially be advanced distally to the coupled position wherein the first firing adapter 140 retains the retention trunnions 17 of the end effector 12 in the trunnion cradles 52 in the spine member 50. The surgeon advances the firing adapter 140 distally to the coupled position by pulling the firing trigger 130 from the starting position toward the pistol grip 107. As the firing trigger 130 is initially actuated, the retention pin 162 is moved distally until the firing tube 110 has advanced the first firing adapter 140 to the coupled position at which point the retention pin 162 is biased into a locking cavity 164 formed in the case member. In various embodiments, when the retention pin 162 enters into the locking cavity 164, the pin 162 may make an audible "click" or other sound, as well as provide a tactile indication to the surgeon that the end effector 12 has been "locked" onto the spine member 50. In addition, the surgeon cannot inadvertently continue to actuate the firing trigger 130 to start to form staples 32 in the end effector 12 without intentionally biasing the retention pin 162 out of the locking cavity 164. Similarly, if the surgeon releases the firing trigger 130 when in the coupled position, it is retained in that position by the retention pin 162 to prevent the firing trigger 130 from returning to the starting position and thereby releasing the end effector 12 from the spine member 50.

Various embodiments of the present invention may further include a firing system lock button 137 that is pivotally attached to the handle assembly 100. In one form, the firing system lock button 137 has a latch 138 formed on a distal end thereof that is oriented to engage the firing yoke 114 when the firing release button is in a first latching position. As can be seen in FIG. 1, a latch spring 139 serves to bias the firing system lock button 137 to the first latching position. In various circumstances, the latch 138 serves to engage the firing yoke 114 at a point where the position of the firing yoke 114 on the spine member 50 corresponds to a point wherein the first firing adapter 140 is about to distally advance up the clamping ramp 28 on the anvil 20. It will be understood that, as the first firing adapter 140 advances axially up the clamping ramp 28, the anvil 20 will move in a path such that its staple forming surface portion 22 is substantially parallel to the upper face 36 of the staple cartridge 30.

After the end effector 12 has been coupled to the spine member 50, the staple forming process is commenced by first depressing the firing system lock button 137 to enable the firing yoke 114 to be further moved distally on the spine member 50 and ultimately compress the anvil 20 into the staple cartridge 30. After depressing the firing system lock button 137, the surgeon continues to actuate the firing trigger 130 towards the pistol grip 107 thereby driving the first staple collar 140 up the corresponding staple forming ramp 29 to force the anvil 20 into forming contact with the staples 32 in the staple cartridge 30. The firing system lock button 137 prevents the inadvertent forming of the staples 32 until the surgeon is ready to start that process. In this embodiment, the surgeon must depress the firing system lock button 137 before the firing trigger 130 may be further actuated to begin the staple forming process.

The surgical instrument 10 may be solely used as a tissue stapling device if so desired. However, various embodiments of the present invention may also include a tissue cutting system, generally designated as 170. In at least one form, the tissue cutting system 170 comprises a knife member 172 that may be selectively advanced from an un-actuated position adjacent the proximal end of the end effector 12 to an actuated position by actuating a knife advancement trigger 200. The knife member 172 is movably supported within the spine member 50 and is attached or otherwise protrudes from a knife rod 180. The knife member 172 may be fabricated from, for example, 420 or 440 stainless steel with a hardness of greater than 38HRC (Rockwell Hardness C-scale) and have a tissue cutting edge 176 formed on the distal end 174 thereof and be configured to slidably extend through a slot in the anvil 20 and a centrally disposed slot 33 in the staple cartridge 30 to cut through tissue that is clamped in the end effector 12. In various embodiments, the knife rod 180 extends through the spine member 50 and has a proximal end portion which drivingly interfaces with a knife transmission that is operably attached to the knife advance trigger 200. In various embodiments, the knife advance trigger 200 is attached to pivot pin 132 such that it may be pivoted or otherwise actuated without actuating the firing trigger 130. In various embodiments, a first knife gear 192 is also attached to the pivot pin 132 such that actuation of the knife advance trigger 200 also pivots the first knife gear 192. A firing return spring 202 is attached between the first knife gear 192 and the handle housing 100 to bias the knife advancement trigger 200 to a starting or un-actuated position.

Various embodiments of the knife transmission also include a second knife gear 194 that is rotatably supported on a second gear spindle and in meshing engagement with the first knife gear 192. The second knife gear 194 is in meshing engagement with a third knife gear 196 that is supported on a third gear spindle. Also supported on the third gear spindle 195 is a fourth knife gear 198. The fourth knife gear 198 is adapted to drivingly engage a series of annular gear teeth or rings on a proximal end of the knife rod 180. Thus, such arrangement enables the fourth knife gear 198 to axially drive the knife rod 180 in the distal direction "DD" or proximal direction "PD" while enabling the firing rod 180 to rotate about longitudinal axis A-A with respect to the fourth knife gear 198. Accordingly, the surgeon may axially advance the firing rod 180 and ultimately the knife member 172 distally by pulling the knife advancement trigger 200 towards the pistol grip 107 of the handle assembly 100.

Various embodiments of the present invention further include a knife lockout system 210 that prevents the advancement of the knife member 172 unless the firing trigger 130 has been pulled to the fully fired position. Such feature will therefore prevent the activation of the knife advancement system 170 unless the staples have first been fired or formed into the tissue. As can be seen in FIG. 1, various implementations of the knife lockout system 210 comprise a knife lockout bar 211 that is pivotally supported within the pistol grip portion 107 of the handle assembly 100. The knife lockout bar 211 has an activation end 212 that is adapted to be engaged by the firing trigger 130 when the firing trigger 130 is in the fully fired position. In addition, the knife lockout bar 211 has a retaining hook 214 on its other end that is adapted to hookingly engage a latch rod 216 on the first cut gear 192. A knife lock spring 218 is employed to bias the knife lockout bar 211 to a "locked" position wherein the retaining hook 214 is retained in engagement with the latch rod 216 to thereby prevent actuation of the knife advancement trigger 200 unless the firing trigger 130 is in the fully fired position.

After the staples have been "fired" (formed) into the target tissue, the surgeon may depress the firing trigger release button 167 to enable the firing trigger 130 to return to the starting position under the bias of the torsion spring 135 which enables the anvil 20 to be biased to an open position under the bias of spring 21. When in the open position, the surgeon may withdraw the end effector 12 leaving the implantable staple cartridge 30 and staples 32 behind. In applications wherein the end effector was inserted through a passage, working channel, etc. the surgeon will return the anvil 20 to the closed position by activating the firing trigger 130 to enable the end effector 12 to be withdrawn out through the passage or working channel. If, however, the surgeon desires to cut the target tissue after firing the staples, the surgeon activates the knife advancement trigger 200 in the above-described manner to drive the knife bar 172 through the target tissue to the end of the end effector. Thereafter, the surgeon may release the knife advancement trigger 200 to enable the firing return spring 202 to cause the firing transmission to return the knife bar 172 to the starting (un-actuated) position. Once the knife bar 172 has been returned to the starting position, the surgeon may open the end effector jaws 13, 15 to release the implantable cartridge 30 within the patient and then withdraw the end effector 12 from the patient. Thus, such surgical instruments facilitate the use of small implantable staple cartridges that may be inserted through relatively smaller working channels and passages, while providing the surgeon with the option to fire the staples without cutting tissue or if desired to also cut tissue after the staples have been fired.

Various unique and novel embodiments of the present invention employ a compressible staple cartridge that supports staples in a substantially stationary position for forming contact by the anvil. In various embodiments, the anvil is driven into the unformed staples wherein, in at least one such embodiment, the degree of staple formation attained is dependent upon how far the anvil is driven into the staples. Such an arrangement provides the surgeon with the ability to adjust the amount of forming or firing pressure applied to the staples and thereby alter the final formed height of the staples. In other various embodiments of the present invention, surgical stapling arrangements can employ staple driving elements which can lift the staples toward the anvil. Such embodiments are described in greater detail further below.

In various embodiments, with regard to the embodiments described in detail above, the amount of firing motion that is applied to the movable anvil is dependent upon the degree of actuation of the firing trigger. For example, if the surgeon desires to attain only partially formed staples, then the firing trigger is only partially depressed inward towards the pistol grip 107. To attain more staple formation, the surgeon simply compresses the firing trigger further which results in the anvil being further driven into forming contact with the staples. As used herein, the term "forming contact" means that the staple forming surface or staple forming pockets have contacted the ends of the staple legs and have started to form or bend the legs over into a formed position. The degree of staple formation refers to how far the staple legs have been folded over and ultimately relates to the forming height of the staple as referenced above. Those of ordinary skill in the art will further understand that, because the anvil 20 moves in a substantially parallel relationship with respect to the staple cartridge as the firing motions are applied thereto, the staples are formed substantially simultaneously with substantially the same formed heights.

FIGS. 2 and 3 illustrate an alternative end effector 12" that is similar to the end effector 12' described above, except with the following differences that are configured to accommodate a knife bar 172'. The knife bar 172' is coupled to or protrudes from a knife rod 180 and is otherwise operated in the above described manner with respect to the knife bar 172. However, in this embodiment, the knife bar 172' is long enough to traverse the entire length of the end effector 12" and therefore, a separate distal knife member is not employed in the end effector 12". The knife bar 172' has an upper transverse member 173' and a lower transverse member 175' formed thereon. The upper transverse member 173' is oriented to slidably transverse a corresponding elongated slot 250 in anvil 20" and the lower transverse member 175' is oriented to traverse an elongated slot 252 in the elongated channel 14" of the end effector 12". A disengagement slot (not shown) is also provided in the anvil 20" such that when the knife bar 172' has been driven to an ending position within end effector 12", the upper transverse member 173' drops through the corresponding slot to enable the anvil 20" to move to the open position to disengage the stapled and cut tissue. The anvil 20" may be otherwise identical to anvil 20 described above and the elongated channel 14" may be otherwise identical to elongated channel 14 described above.

In these embodiments, the anvil 20" is biased to a fully open position (FIG. 2) by a spring or other opening arrangement (not shown). The anvil 20" is moved between the open and fully clamped positions by the axial travel of the firing adapter 150 in the manner described above. Once the firing adapter 150 has been advanced to the fully clamped position (FIG. 3), the surgeon may then advance the knife bar 172" distally in the manner described above. If the surgeon desires to use the end effector as a grasping device to manipulate tissue, the firing adapter may be moved proximally to allow the anvil 20" to move away from the elongated channel 14" as represented in FIG. 4 in broken lines. In this embodiment, as the knife bar 172" moves distally, the upper transverse member 173' and the lower transverse member 175' draw the anvil 20" and elongated channel 14" together to achieve the desired staple formation as the knife bar 172" is advanced distally through the end effector 12". See FIG. 5. Thus, in this embodiment, staple formation occurs simultaneously with tissue cutting, but the staples themselves may be sequentially formed as the knife bar 172" is driven distally.

The unique and novel features of the various surgical staple cartridges and the surgical instruments of the present invention enable the staples in those cartridges to be arranged in one or more linear or non-linear lines. A plurality of such staple lines may be provided on each side of an elongated slot that is centrally disposed within the staple cartridge for receiving the tissue cutting member therethrough. In one arrangement, for example, the staples in one line may be substantially parallel with the staples in adjacent line(s) of staples, but offset therefrom. In still other embodiments, one or more lines of staples may be non-linear in nature. That is, the base of at least one staple in a line of staples may extend along an axis that is substantially transverse to the bases of other staples in the same staple line. For example, the lines of staples on each side of the elongated slot may have a zigzag appearance.

In various embodiments, a staple cartridge can comprise a cartridge body and a plurality of staples stored within the cartridge body. In use, the staple cartridge can be introduced into a surgical site and positioned on a side of the tissue being treated. In addition, a staple-forming anvil can be positioned on the opposite side of the tissue. In various embodiments, the anvil can be carried by a first jaw and the staple cartridge can be carried by a second jaw, wherein the first jaw and/or the second jaw can be moved toward the other. Once the staple cartridge and the anvil have been positioned relative to the tissue, the staples can be ejected from the staple cartridge body such that the staples can pierce the tissue and contact the staple-forming anvil. Once the staples have been deployed from the staple cartridge body, the staple cartridge body can then be removed from the surgical site. In various embodiments disclosed herein, a staple cartridge, or at least a portion of a staple cartridge, can be implanted with the staples. In at least one such embodiment, as described in greater detail further below, a staple cartridge can comprise a cartridge body which can be compressed, crushed, and/or collapsed by the anvil when the anvil is moved from an open position into a closed position. When the cartridge body is compressed, crushed, and/or collapsed, the staples positioned within the cartridge body can be deformed by the anvil. Alternatively, the jaw supporting the staple cartridge can be moved toward the anvil into a closed position. In either event, in various embodiments, the staples can be deformed while they are at least partially positioned within the cartridge body. In certain embodiments, the staples may not be ejected from the staple cartridge while, in some embodiments, the staples can be ejected from the staple cartridge along with a portion of the cartridge body.

Referring now to FIGS. 6A-6D, a compressible staple cartridge, such as staple cartridge 1000, for example, can comprise a compressible, implantable cartridge body 1010 and, in addition, a plurality of staples 1020 positioned in the compressible cartridge body 1010, although only one staple 1020 is depicted in FIGS. 6A-6D. FIG. 6A illustrates the staple cartridge 1000 supported by a staple cartridge support, or staple cartridge channel, 1030, wherein the staple cartridge 1000 is illustrated in an uncompressed condition. In such an uncompressed condition, the anvil 1040 may or may not be in contact with the tissue T. In use, the anvil 1040 can be moved from an open position into contact with the tissue T as illustrated in FIG. 6B and position the tissue T against the cartridge body 1010. Even though the anvil 1040 can position the tissue T against a tissue-contacting surface 1019 of staple cartridge body 1010, referring again to FIG. 6B, the staple cartridge body 1010 may be subjected to little, if any, compressive force or pressure at such point and the staples 1020 may remain in an unformed, or unfired, condition. As illustrated in FIGS. 6A and 6B, the staple cartridge body 1010 can comprise one or more layers and the staple legs 1021 of staples 1020 can extend upwardly through these layers. In various embodiments, the cartridge body 1010 can comprise a first layer 1011, a second layer 1012, a third layer 1013, wherein the second layer 1012 can be positioned intermediate the first layer 1011 and the third layer 1013, and a fourth layer 1014, wherein the third layer 1013 can be positioned intermediate the second layer 1012 and the fourth layer 1014. In at least one embodiment, the bases 1022 of the staples 1020 can be positioned within cavities 1015 in the fourth layer 1014 and the staple legs 1021 can extend upwardly from the bases 1022 and through the fourth layer 1014, the third layer 1013, and the second layer 1012, for example. In various embodiments, each deformable leg 1021 can comprise a tip, such as sharp tip 1023, for example, which can be positioned in the second layer 1012, for example, when the staple cartridge 1000 is in an uncompressed condition. In at least one such embodiment, the tips 1023 may not extend into and/or through the first layer 1011, wherein, in at least one embodiment, the tips 1023 may not protrude through the tissue-contacting surface 1019 when the staple cartridge 1000 is in an uncompressed condition. In certain other embodiments, the sharp tips 1023 may be positioned in the third layer 1013, and/or any other suitable layer, when the staple cartridge is in an uncompressed condition. In various alternative embodiments, a cartridge body of a staple cartridge may have any suitable number of layers such as less than four layers or more than four layers, for example.

In various embodiments, as described in greater detail below, the first layer 1011 can be comprised of a buttress material and/or plastic material, such as polydioxanone (PDS) and/or polyglycolic acid (PGA), for example, and the second layer 1012 can be comprised of a bioabsorbable foam material and/or a compressible haemostatic material, such as oxidized regenerated cellulose (ORC), for example. In various embodiments, one or more of the first layer 1011, the second layer 1012, the third layer 1013, and the fourth layer 1014 may hold the staples 1020 within the staple cartridge body 1010 and, in addition, maintain the staples 1020 in alignment with one another. In various embodiments, the third layer 1013 can be comprised of a buttress material, or a fairly incompressible or inelastic material, which can be configured to hold the staple legs 1021 of the staples 1020 in position relative to one another. Furthermore, the second layer 1012 and the fourth layer 1014, which are positioned on opposite sides of the third layer 1013, can stabilize, or reduce the movement of, the staples 1020 even though the second layer 1012 and the fourth layer 1014 can be comprised of a compressible foam or elastic material. In certain embodiments, the staple tips 1023 of the staple legs 1021 can be at least partially embedded in the first layer 1011. In at least one such embodiment, the first layer 1011 and the third layer 1013 can be configured to co-operatively and firmly hold the staple legs 1021 in position. In at least one embodiment, the first layer 1011 and the third layer 1013 can each be comprised of a sheet of bioabsorbable plastic, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example, and the second layer 1012 and the fourth layer 1014 can each be comprised of at least one haemostatic material or agent.

Although the first layer 1011 can be compressible, the second layer 1012 can be substantially more compressible than the first layer 1011. For example, the second layer 1012 can be about twice as compressible, about three times as compressible, about four times as compressible, about five times as compressible, and/or about ten times as compressible, for example, as the first layer 1011. Stated another way, the second layer 1012 may compress about two times, about three times, about four times, about five times, and/or about ten times as much as first layer 1011, for a given force. In certain embodiments, the second layer 1012 can be between about twice as compressible and about ten times as compressible, for example, as the first layer 1011. In at least one embodiment, the second layer 1012 can comprise a plurality of air voids defined therein, wherein the amount and/or size of the air voids in the second layer 1012 can be controlled in order to provide a desired compressibility of the second layer 1012. Similar to the above, although the third layer 1013 can be compressible, the fourth layer 1014 can be substantially more compressible than the third layer 1013. For example, the fourth layer 1014 can be about twice as compressible, about three times as compressible, about four times as compressible, about five times as compressible, and/or about ten times as compressible, for example, as the third layer 1013. Stated another way, the fourth layer 1014 may compress about two times, about three times, about four times, about five times, and/or about ten times as much as third layer 1013, for a given force. In certain embodiments, the fourth layer 1014 can be between about twice as compressible and about ten times as compressible, for example, as the third layer 1013. In at least one embodiment, the fourth layer 1014 can comprise a plurality of air voids defined therein, wherein the amount and/or size of the air voids in the fourth layer 1014 can be controlled in order to provide a desired compressibility of the fourth layer 1014. In various circumstances, the compressibility of a cartridge body, or cartridge body layer, can be expressed in terms of a compression rate, i.e., a distance in which a layer is compressed for a given amount of force. For example, a layer having a high compression rate will compress a larger distance for a given amount of compressive force applied to the layer as compared to a layer having a lower compression rate. This being said, the second layer 1012 can have a higher compression rate than the first layer 1011 and, similarly, the fourth layer 1014 can have a higher compression rate than the third layer 1013. In various embodiments, the second layer 1012 and the fourth layer 1014 can be comprised of the same material and can comprise the same compression rate. In various embodiments, the second layer 1012 and the fourth layer 1014 can be comprised of materials having different compression rates. Similarly, the first layer 1011 and the third layer 1013 can be comprised of the same material and can comprise the same compression rate. In certain embodiments, the first layer 1011 and the third layer 1013 can be comprised of materials having different compression rates.

As the anvil 1040 is moved toward its closed position, the anvil 1040 can contact tissue T and apply a compressive force to the tissue T and the staple cartridge 1000, as illustrated in FIG. 6C. In such circumstances, the anvil 1040 can push the top surface, or tissue-contacting surface 1019, of the cartridge body 1010 downwardly toward the staple cartridge support 1030. In various embodiments, the staple cartridge support 1030 can comprise a cartridge support surface 1031 which can be configured to support the staple cartridge 1000 as the staple cartridge 1000 is compressed between the cartridge support surface 1031 and the tissue-contacting surface 1041 of anvil 1040. Owing to the pressure applied by the anvil 1040, the cartridge body 1010 can be compressed and the anvil 1040 can come into contact with the staples 1020. More particularly, in various embodiments, the compression of the cartridge body 1010 and the downward movement of the tissue-contacting surface 1019 can cause the tips 1023 of the staple legs 1021 to pierce the first layer 1011 of cartridge body 1010, pierce the tissue T, and enter into forming pockets 1042 in the anvil 1040. As the cartridge body 1010 is further compressed by the anvil 1040, the tips 1023 can contact the walls defining the forming pockets 1042 and, as a result, the legs 1021 can be deformed or curled inwardly, for example, as illustrated in FIG. 6C. As the staple legs 1021 are being deformed, as also illustrated in FIG. 6C, the bases 1022 of the staples 1020 can be in contact with or supported by the staple cartridge support 1030. In various embodiments, as described in greater detail below, the staple cartridge support 1030 can comprise a plurality of support features, such as staple support grooves, slots, or troughs 1032, for example, which can be configured to support the staples 1020, or at least the bases 1022 of the staples 1020, as the staples 1020 are being deformed. As also illustrated in FIG. 6C, the cavities 1015 in the fourth layer 1014 can collapse as a result of the compressive force applied to the staple cartridge body 1010. In addition to the cavities 1015, the staple cartridge body 1010 can further comprise one or more voids, such as voids 1016, for example, which may or may not comprise a portion of a staple positioned therein, that can be configured to allow the cartridge body 1010 to collapse. In various embodiments, the cavities 1015 and/or the voids 1016 can be configured to collapse such that the walls defining the cavities and/or walls deflect downwardly and contact the cartridge support surface 1031 and/or contact a layer of the cartridge body 1010 positioned underneath the cavities and/or voids.

Upon comparing FIG. 6B and FIG. 6C, it is evident that the second layer 1012 and the fourth layer 1014 have been substantially compressed by the compressive pressure applied by the anvil 1040. It may also be noted that the first layer 1011 and the third layer 1013 have been compressed as well. As the anvil 1040 is moved into its closed position, the anvil 1040 may continue to further compress the cartridge body 1010 by pushing the tissue-contacting surface 1019 downwardly toward the staple cartridge support 1030. As the cartridge body 1010 is further compressed, the anvil 1040 can deform the staples 1020 into their completely-formed shape as illustrated in FIG. 6D. Referring to FIG. 6D, the legs 1021 of each staple 1020 can be deformed downwardly toward the base 1022 of each staple 1020 in order to capture at least a portion of the tissue T, the first layer 1011, the second layer 1012, the third layer 1013, and the fourth layer 1014 between the deformable legs 1021 and the base 1022. Upon comparing FIGS. 6C and 6D, it is further evident that the second layer 1012 and the fourth layer 1014 have been further substantially compressed by the compressive pressure applied by the anvil 1040. It may also be noted upon comparing FIGS. 6C and 6D that the first layer 1011 and the third layer 1013 have been further compressed as well. After the staples 1020 have been completely, or at least sufficiently, formed, the anvil 1040 can be lifted away from the tissue T and the staple cartridge support 1030 can be moved away, and/or detached from, the staple cartridge 1000. As depicted in FIG. 6D, and as a result of the above, the cartridge body 1010 can be implanted with the staples 1020. In various circumstances, the implanted cartridge body 1010 can support the tissue along the staple line. In some circumstances, a haemostatic agent, and/or any other suitable therapeutic medicament, contained within the implanted cartridge body 1010 can treat the tissue over time. A haemostatic agent, as mentioned above, can reduce the bleeding of the stapled and/or incised tissue while a bonding agent or tissue adhesive can provide strength to the tissue over time. The implanted cartridge body 1010 can be comprised of materials such as ORC (oxidized regenerated cellulose), extracellular proteins such as collagen, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain circumstances, the cartridge body 1010 can comprise an antibiotic and/or antimicrobial material, such as colloidal silver and/or triclosan, for example, which can reduce the possibility of infection in the surgical site.

In various embodiments, the layers of the cartridge body 1010 can be connected to one another. In at least one embodiment, the second layer 1012 can be adhered to the first layer 1011, the third layer 1013 can be adhered to the second layer 1012, and the fourth layer 1014 can be adhered to the third layer 1013 utilizing at least one adhesive, such as fibrin and/or protein hydrogel, for example. In certain embodiments, although not illustrated, the layers of the cartridge body 1010 can be connected together by interlocking mechanical features. In at least one such embodiment, the first layer 1011 and the second layer 1012 can each comprise corresponding interlocking features, such as a tongue and groove arrangement and/or a dovetail joint arrangement, for example. Similarly, the second layer 1012 and the third layer 1013 can each comprise corresponding interlocking features while the third layer 1013 and the fourth layer 1014 can each comprise corresponding interlocking features. In certain embodiments, although not illustrated, the staple cartridge 1000 can comprise one or more rivets, for example, which can extend through one or more layers of the cartridge body 1010. In at least one such embodiment, each rivet can comprise a first end, or head, positioned adjacent to the first layer 1011 and a second head positioned adjacent to the fourth layer 1014 which can be either assembled to or formed by a second end of the rivet. Owing to the compressible nature of the cartridge body 1010, in at least one embodiment, the rivets can compress the cartridge body 1010 such that the heads of the rivets can be recessed relative to the tissue-contacting surface 1019 and/or the bottom surface 1018 of the cartridge body 1010, for example. In at least one such embodiment, the rivets can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain embodiments, the layers of the cartridge body 1010 may not be connected to one another other than by the staples 1020 contained therein. In at least one such embodiment, the frictional engagement between the staple legs 1021 and the cartridge body 1010, for example, can hold the layers of the cartridge body 1010 together and, once the staples have been formed, the layers can be captured within the staples 1020. In certain embodiments, at least a portion of the staple legs 1021 can comprise a roughened surface or rough coating which can increase the friction forces between the staples 1020 and the cartridge body 1010.

As described above, a surgical instrument can comprise a first jaw including the staple cartridge support 1030 and a second jaw including the anvil 1040. In various embodiments, as described in greater detail further below, the staple cartridge 1000 can comprise one or more retention features which can be configured to engage the staple cartridge support 1030 and, as a result, releasably retain the staple cartridge 1000 to the staple cartridge support 1030. In certain embodiments, the staple cartridge 1000 can be adhered to the staple cartridge support 1030 by at least one adhesive, such as fibrin and/or protein hydrogel, for example. In use, in at least one circumstance, especially in laparoscopic and/or endoscopic surgery, the second jaw can be moved into a closed position opposite the first jaw, for example, such that the first and second jaws can be inserted through a trocar into a surgical site. In at least one such embodiment, the trocar can define an approximately 5 mm aperture, or cannula, through which the first and second jaws can be inserted. In certain embodiments, the second jaw can be moved into a partially-closed position intermediate the open position and the closed position which can allow the first and second jaws to be inserted through the trocar without deforming the staples 1020 contained in the staple cartridge body 1010. In at least one such embodiment, the anvil 1040 may not apply a compressive force to the staple cartridge body 1010 when the second jaw is in its partially-closed intermediate position while, in certain other embodiments, the anvil 1040 can compress the staple cartridge body 1010 when the second jaw is in its partially-closed intermediate position. Even though the anvil 1040 can compress the staple cartridge body 1010 when it is in such an intermediate position, the anvil 1040 may not sufficiently compress the staple cartridge body 1010 such that the anvil 1040 comes into contact with the staples 1020 and/or such that the staples 1020 are deformed by the anvil 1040. Once the first and second jaws have been inserted through the trocar into the surgical site, the second jaw can be opened once again and the anvil 1040 and the staple cartridge 1000 can be positioned relative to the targeted tissue as described above.

Figure 7A:
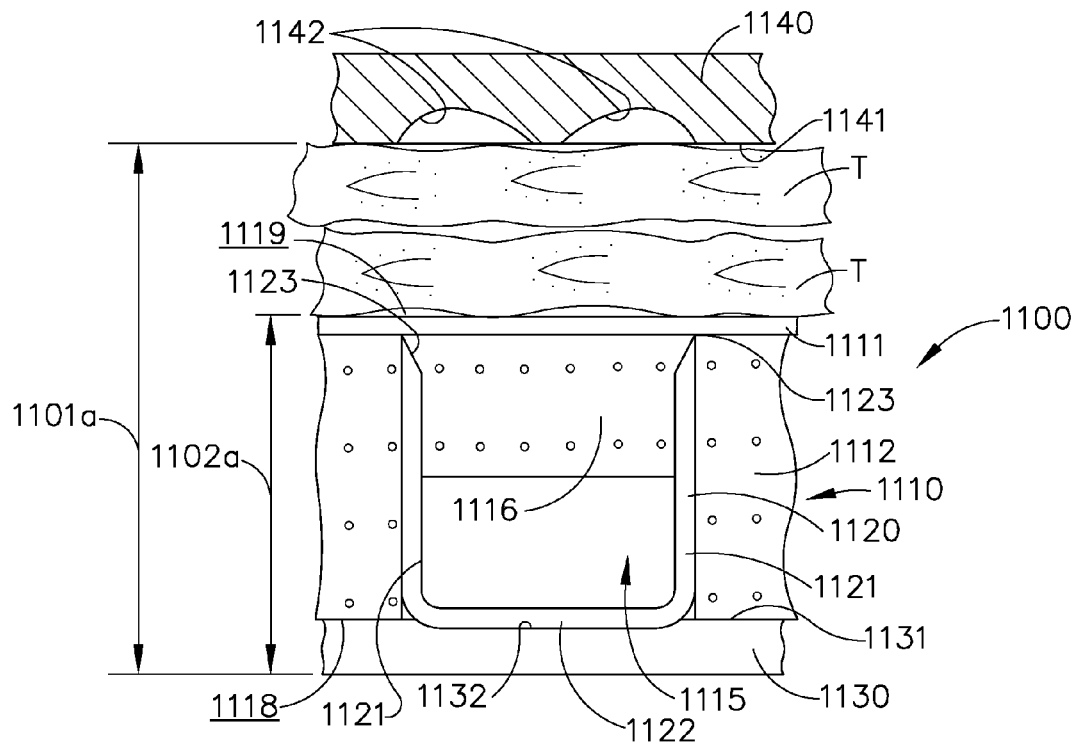
FIG. 7A is a diagram illustrating a staple positioned in a crushable staple cartridge body.
Figure 7B:
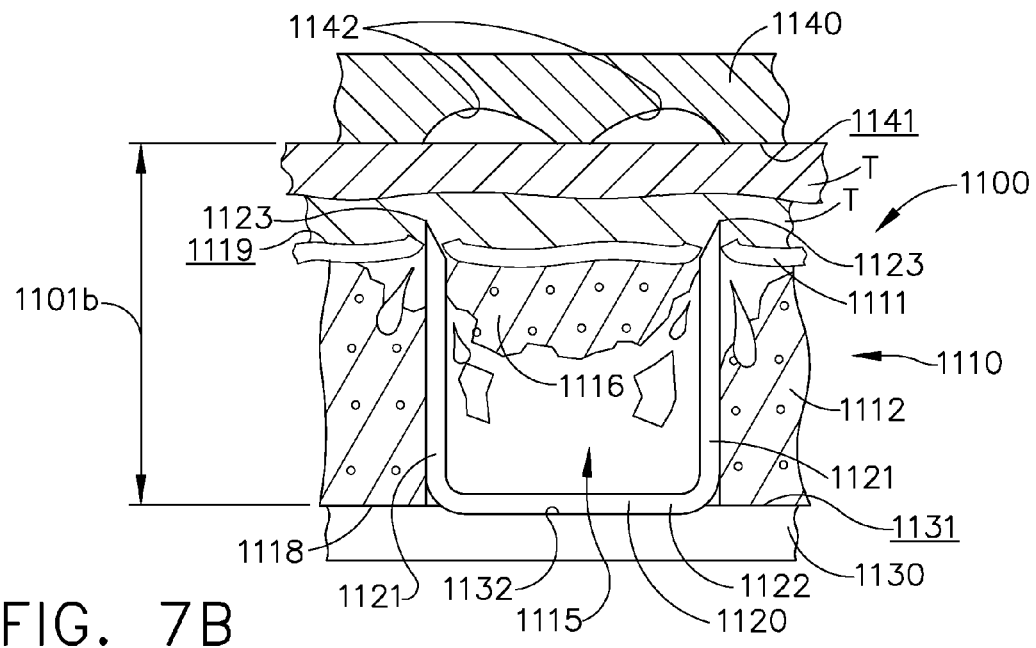
FIG. 7B is a diagram illustrating the crushable staple cartridge body of FIG. 7A being crushed by an anvil.
Figure 7C:
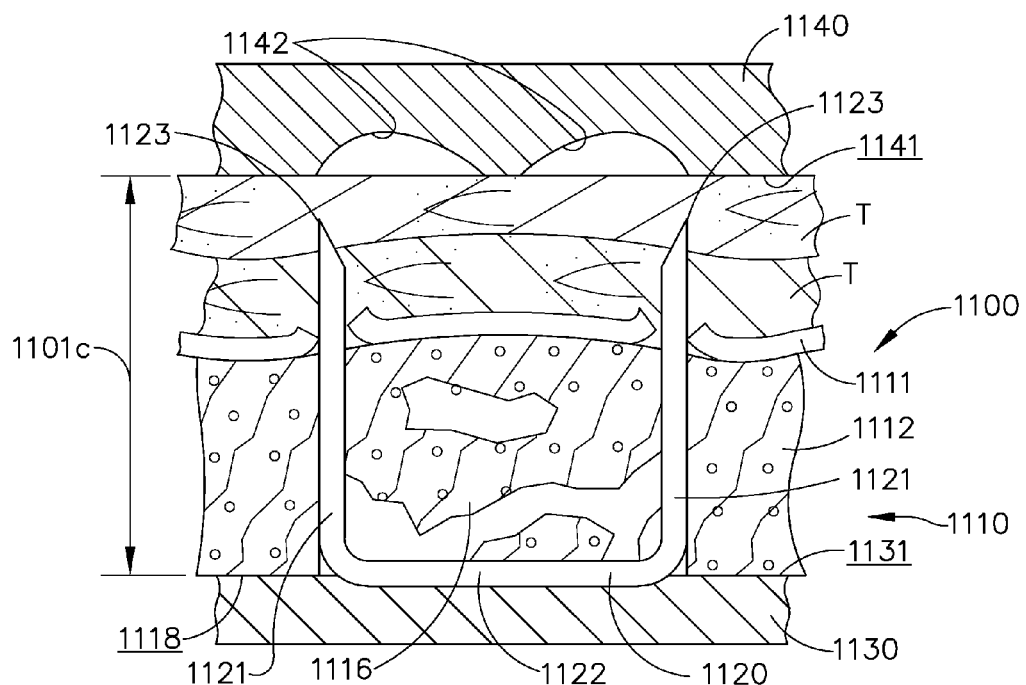
FIG. 7C is a diagram illustrating the crushable staple cartridge body of FIG. 7A being further crushed by the anvil.

In various embodiments, referring now to FIGS. 7A-7D, an end effector of a surgical stapler can comprise an implantable staple cartridge 1100 positioned intermediate an anvil 1140 and a staple cartridge support 1130. Similar to the above, the anvil 1140 can comprise a tissue-contacting surface 1141, the staple cartridge 1100 can comprise a tissue-contacting surface 1119, and the staple cartridge support 1130 can comprise a support surface 1131 which can be configured to support the staple cartridge 1100. Referring to FIG. 7A, the anvil 1140 can be utilized to position the tissue T against the tissue contacting surface 1119 of staple cartridge 1100 without deforming the staple cartridge 1100 and, when the anvil 1140 is in such a position, the tissue-contacting surface 1141 can be positioned a distance 1101a away from the staple cartridge support surface 1131 and the tissue-contacting surface 1119 can be positioned a distance 1102a away from the staple cartridge support surface 1131. Thereafter, as the anvil 1140 is moved toward the staple cartridge support 1130, referring now to FIG. 7B, the anvil 1140 can push the top surface, or tissue-contacting surface 1119, of staple cartridge 1100 downwardly and compress the first layer 1111 and the second layer 1112 of cartridge body 1110. As the layers 1111 and 1112 are compressed, referring again to FIG. 7B, the second layer 1112 can be crushed and the legs 1121 of staples 1120 can pierce the first layer 1111 and enter into the tissue T. In at least one such embodiment, the staples 1120 can be at least partially positioned within staple cavities, or voids, 1115 in the second layer 1112 and, when the second layer 1112 is compressed, the staple cavities 1115 can collapse and, as a result, allow the second layer 1112 to collapse around the staples 1120. In various embodiments, the second layer 1112 can comprise cover portions 1116 which can extend over the staple cavities 1115 and enclose, or at least partially enclose, the staple cavities 1115. FIG. 7B illustrates the cover portions 1116 being crushed downwardly into the staple cavities 1115. In certain embodiments, the second layer 1112 can comprise one or more weakened portions which can facilitate the collapse of the second layer 1112. In various embodiments, such weakened portions can comprise score marks, perforations, and/or thin cross-sections, for example, which can facilitate a controlled collapse of the cartridge body 1110. In at least one embodiment, the first layer 1111 can comprise one or more weakened portions which can facilitate the penetration of the staple legs 1121 through the first layer 1111. In various embodiments, such weakened portions can comprise score marks, perforations, and/or thin cross-sections, for example, which can be aligned, or at least substantially aligned, with the staple legs 1121.

Figure 7D:
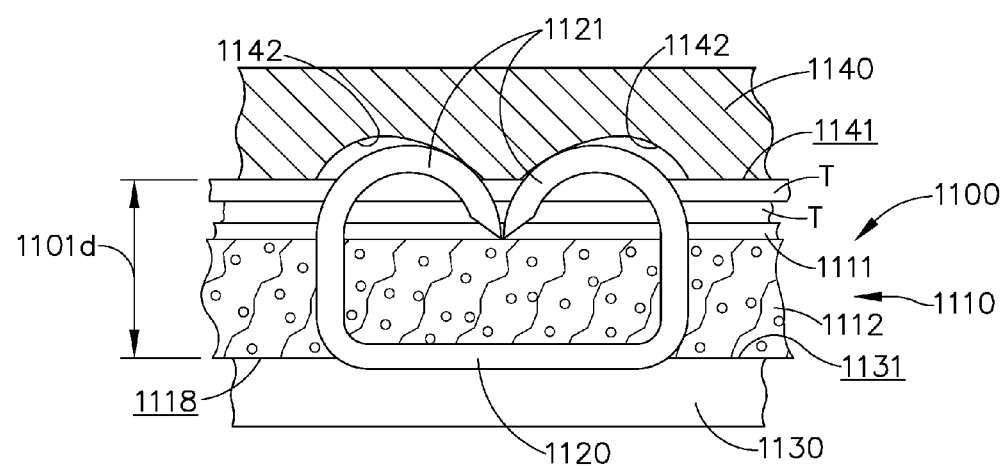
FIG. 7D is a diagram illustrating the staple of FIG. 7A in a fully formed configuration and the crushable staple cartridge of FIG. 7A in a fully crushed condition.

When the anvil 1140 is in a partially closed, unfired position, referring again to FIG. 7A, the anvil 1140 can be positioned a distance 1101a away from the cartridge support surface 1131 such that a gap is defined therebetween. This gap can be filled by the staple cartridge 1100, having a staple cartridge height 1102a, and the tissue T. As the anvil 1140 is moved downwardly to compress the staple cartridge 1100, referring again to FIG. 7B, the distance between the tissue contacting surface 1141 and the cartridge support surface 1131 can be defined by a distance 1101b which is shorter than the distance 1101a. In various circumstances, the gap between the tissue-contacting surface 1141 of anvil 1140 and the cartridge support surface 1131, defined by distance 1101b, may be larger than the original, undeformed staple cartridge height 1102a. As the anvil 1140 is moved closer to the cartridge support surface 1131, referring now to FIG. 7C, the second layer 1112 can continue to collapse and the distance between the staple legs 1121 and the forming pockets 1142 can decrease. Similarly, the distance between the tissue-contacting surface 1141 and the cartridge support surface 1131 can decrease to a distance 1101c which, in various embodiments, may be greater than, equal to, or less than the original, undeformed cartridge height 1102a. Referring now to FIG. 7D, the anvil 1140 can be moved into a final, fired position in which the staples 1120 have been fully formed, or at least formed to a desired height. In such a position, the tissue-contacting surface 1141 of anvil 1140 can be a distance 1101d away from the cartridge support surface 1131, wherein the distance 1101d can be shorter than the original, undeformed cartridge height 1102a. As also illustrated in FIG. 7D, the staple cavities 1115 may be fully, or at least substantially, collapsed and the staples 1120 may be completely, or at least substantially, surrounded by the collapsed second layer 1112. In various circumstances, the anvil 1140 can be thereafter moved away from the staple cartridge 1100. Once the anvil 1140 has been disengaged from the staple cartridge 1100, the cartridge body 1110 can at least partially re-expand in various locations, i.e., locations intermediate adjacent staples 1120, for example. In at least one embodiment, the crushed cartridge body 1110 may not resiliently re-expand. In various embodiments, the formed staples 1120 and, in addition, the cartridge body 1110 positioned intermediate adjacent staples 1120 may apply pressure, or compressive forces, to the tissue T which may provide various therapeutic benefits.

As discussed above, referring again to the embodiment illustrated in FIG. 7A, each staple 1120 can comprise staple legs 1121 extending therefrom. Although staples 1120 are depicted as comprising two staple legs 1121, various staples can be utilized which can comprise one staple leg or, alternatively, more than two staple legs, such as three staple legs or four staple legs, for example. As illustrated in FIG. 7A, each staple leg 1121 can be embedded in the second layer 1112 of the cartridge body 1110 such that the staples 1120 are secured within the second layer 1112. In various embodiments, the staples 1120 can be inserted into the staple cavities 1115 in cartridge body 1110 such that the tips 1123 of the staple legs 1121 enter into the cavities 1115 before the bases 1122. After the tips 1123 have been inserted into the cavities 1115, in various embodiments, the tips 1123 can be pressed into the cover portions 1116 and incise the second layer 1112. In various embodiments, the staples 1120 can be seated to a sufficient depth within the second layer 1112 such that the staples 1120 do not move, or at least substantially move, relative to the second layer 1112. In certain embodiments, the staples 1120 can be seated to a sufficient depth within the second layer 1112 such that the bases 1122 are positioned or embedded within the staple cavities 1115. In various other embodiments, the bases 1122 may not be positioned or embedded within the second layer 1112. In certain embodiments, referring again to FIG. 7A, the bases 1122 may extend below the bottom surface 1118 of the cartridge body 1110. In certain embodiments, the bases 1122 can rest on, or can be directly positioned against, the cartridge support surface 1130. In various embodiments, the cartridge support surface 1130 can comprise support features extending therefrom and/or defined therein wherein, in at least one such embodiment, the bases 1122 of the staples 1120 may be positioned within and supported by one or more support grooves, slots, or troughs, 1132, for example, in the staple cartridge support 1130, as described in greater detail further below.

In various embodiments, referring now to FIGS. 8 and 9, a staple cartridge, such as staple cartridge 1200, for example, can comprise a compressible, implantable cartridge body 1210 comprising an outer layer 1211 and an inner layer 1212. Similar to the above, the staple cartridge 1200 can comprise a plurality of staples 1220 positioned within the cartridge body 1210. In various embodiments, each staple 1220 can comprise a base 1222 and one or more staple legs 1221 extending therefrom. In at least one such embodiment, the staple legs 1221 can be inserted into the inner layer 1212 and seated to a depth in which the bases 1222 of the staples 1220 abut and/or are positioned adjacent to the bottom surface 1218 of the inner layer 1212, for example. In the embodiment depicted in FIGS. 8 and 9, the inner layer 1212 does not comprise staple cavities configured to receive a portion of the staples 1220 while, in other embodiments, the inner layer 1212 can comprise such staple cavities. In various embodiments, further to the above, the inner layer 1212 can be comprised of a compressible material, such as bioabsorbable foam and/or oxidized regenerated cellulose (ORC), for example, which can be configured to allow the cartridge body 1210 to collapse when a compressive load is applied thereto. In various embodiments, the inner layer 1212 can be comprised of a lyophilized foam comprising polylactic acid (PLA) and/or polyglycolic acid (PGA), for example. The ORC may be commercially available under the trade name Surgical and can comprise a loose woven fabric (like a surgical sponge), loose fibers (like a cotton ball), and/or a foam. In at least one embodiment, the inner layer 1212 can be comprised of a material including medicaments, such as freeze-dried thrombin and/or fibrin, for example, contained therein and/or coated thereon which can be water-activated and/or activated by fluids within the patient's body, for example. In at least one such embodiment, the freeze-dried thrombin and/or fibrin can be held on a Vicryl (PGA) matrix, for example. In certain circumstances, however, the activatable medicaments can be unintentionally activated when the staple cartridge 1200 is inserted into a surgical site within the patient, for example. In various embodiments, referring again to FIGS. 8 and 9, the outer layer 1211 can be comprised of a water impermeable, or at least substantially water impermeable, material such that liquids do not come into contact with, or at least substantially contact, the inner layer 1212 until after the cartridge body 1210 has been compressed and the staple legs have penetrated the outer layer 1211 and/or after the outer layer 1211 has been incised in some fashion. In various embodiments, the outer layer 1211 can be comprised of a buttress material and/or plastic material, such as polydioxanone (PDS) and/or polyglycolic acid (PGA), for example. In certain embodiments, the outer layer 1211 can comprise a wrap which surrounds the inner layer 1212 and the staples 1220. More particularly, in at least one embodiment, the staples 1220 can be inserted into the inner layer 1212 and the outer layer 1211 can be wrapped around the sub-assembly comprising the inner layer 1212 and the staples 1220 and then sealed.

Figure 10:
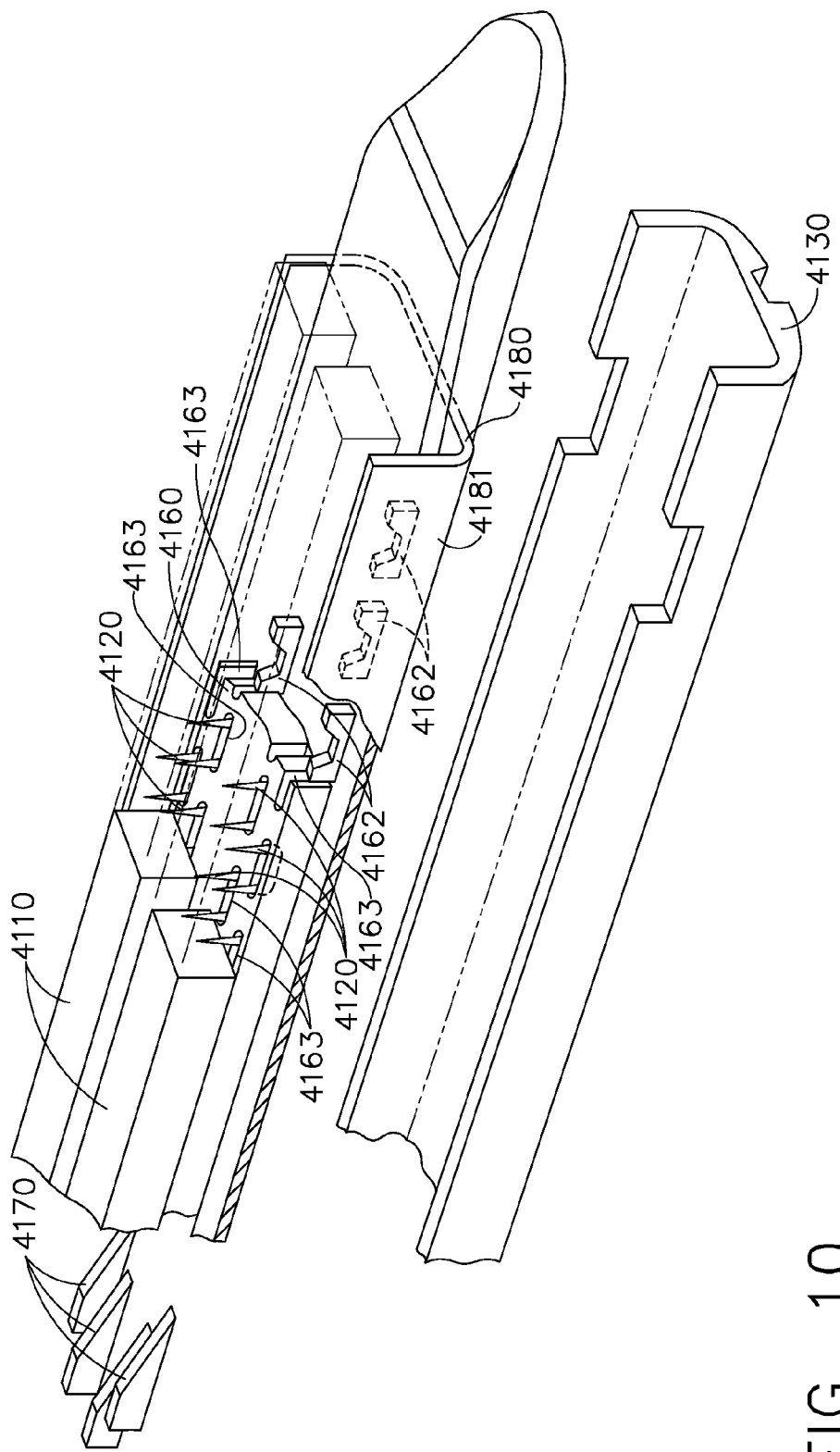
FIG. 10 is an exploded perspective view of an alternative embodiment of a compressible staple cartridge comprising staples therein and a system for driving the staples against an anvil.
Figure 10A:
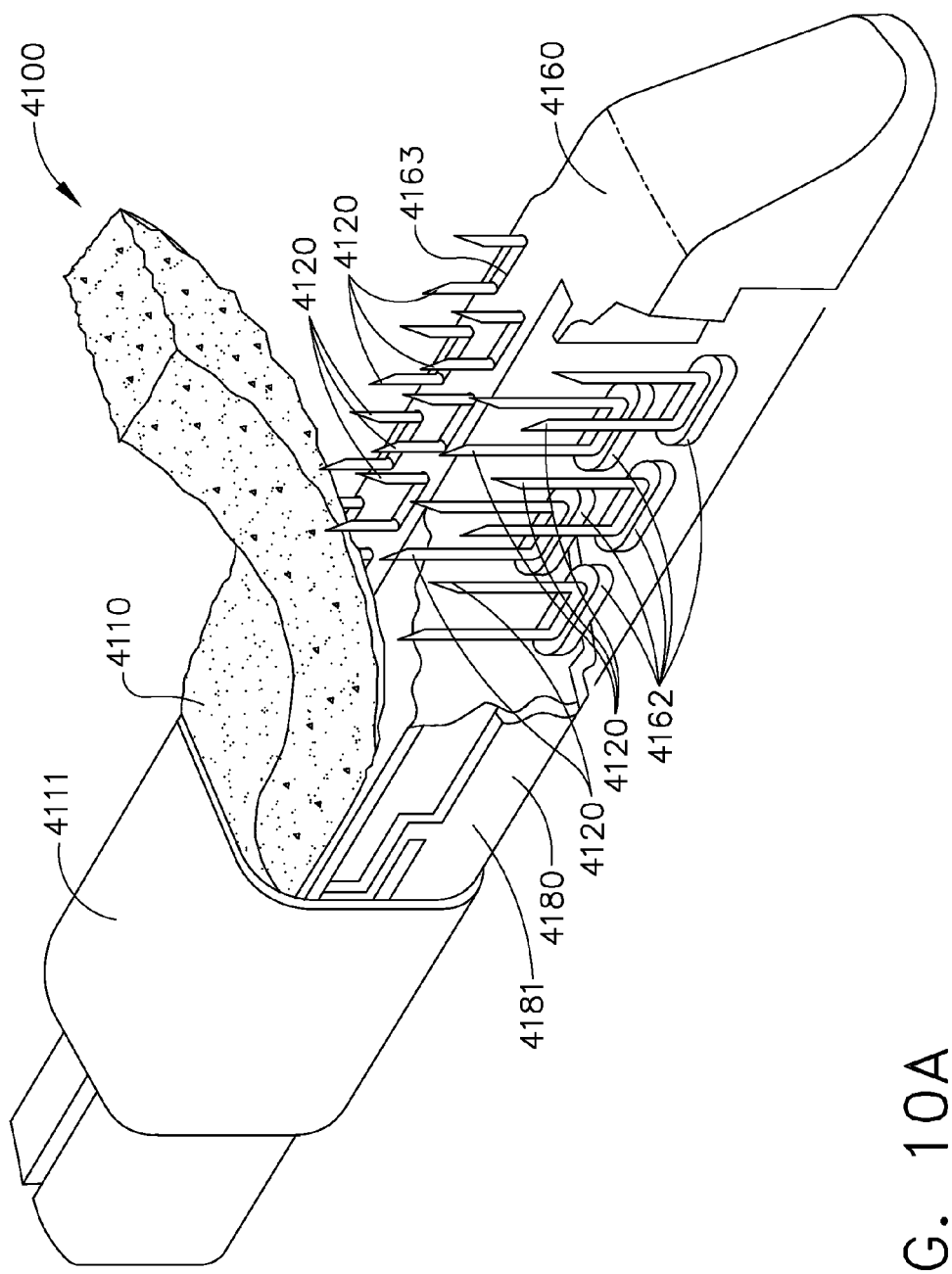
FIG. 10A is a partial cut-away view of an alternative embodiment of the staple cartridge of FIG. 10.
Figure 11:
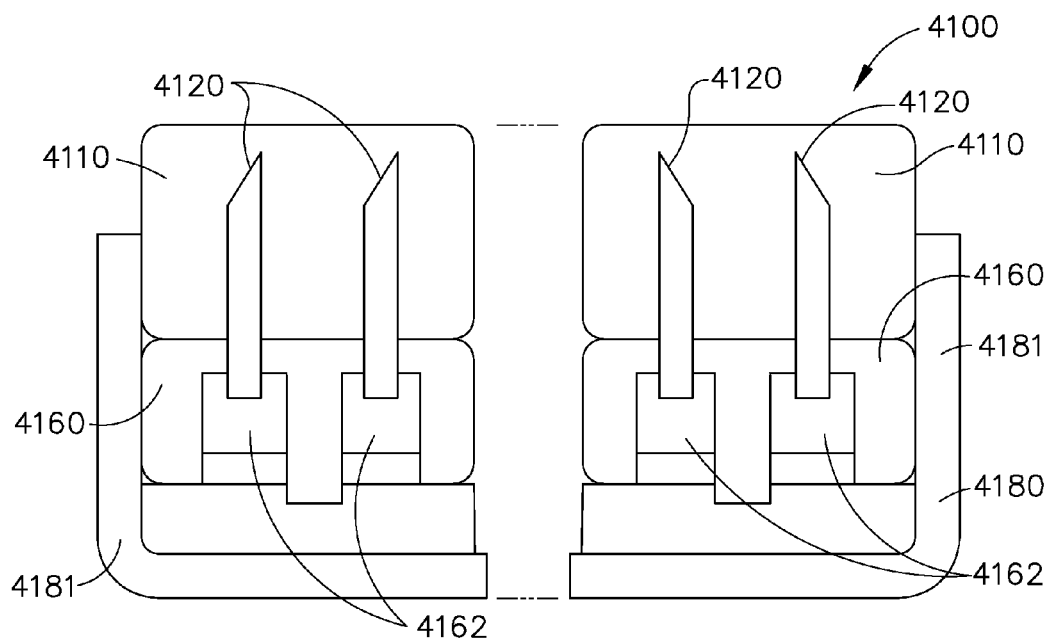
FIG. 11 is a cross-sectional view of the staple cartridge of FIG. 10.
Figure 12:
FIG. 12 is an elevational view of a sled configured to traverse the staple cartridge of FIG. 10 and move the staples to toward the anvil.

In various embodiments described herein, the staples of a staple cartridge can be fully formed by an anvil when the anvil is moved into a closed position. In various other embodiments, referring now to FIGS. 10-13, the staples of a staple cartridge, such as staple cartridge 4100, for example, can be deformed by an anvil when the anvil is moved into a closed position and, in addition, by a staple driver system which moves the staples toward the closed anvil. The staple cartridge 4100 can comprise a compressible cartridge body 4110 which can be comprised of a foam material, for example, and a plurality of staples 4120 at least partially positioned within the compressible cartridge body 4110. In various embodiments, the staple driver system can comprise a driver holder 4160, a plurality of staple drivers 4162 positioned within the driver holder 4160, and a staple cartridge pan 4180 which can be configured to retain the staple drivers 4162 in the driver holder 4160. In at least one such embodiment, the staple drivers 4162 can be positioned within one or more slots 4163 in the driver holder 4160 wherein the sidewalls of the slots 4163 can assist in guiding the staple drivers 4162 upwardly toward the anvil. In various embodiments, the staples 4120 can be supported within the slots 4163 by the staple drivers 4162 wherein, in at least one embodiment, the staples 4120 can be entirely positioned in the slots 4163 when the staples 4120 and the staple drivers 4162 are in their unfired positions. In certain other embodiments, at least a portion of the staples 4120 can extend upwardly through the open ends 4161 of slots 4163 when the staples 4120 and staple drivers 4162 are in their unfired positions. In at least one such embodiment, referring primarily now to FIG. 11, the bases of the staples 4120 can be positioned within the driver holder 4160 and the tips of the staples 4120 can be embedded within the compressible cartridge body 4110. In certain embodiments, approximately one-third of the height of the staples 4120 can be positioned within the driver holder 4160 and approximately two-thirds of the height of the staples 4120 can be positioned within the cartridge body 4110. In at least one embodiment, referring to FIG. 10A, the staple cartridge 4100 can further comprise a water impermeable wrap or membrane 4111 surrounding the cartridge body 4110 and the driver holder 4160, for example.

Figure 13:
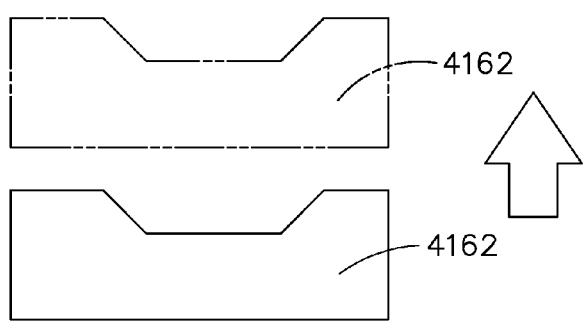
FIG. 13 is a diagram of a staple driver which can be lifted toward the anvil by the sled of FIG. 12.

In use, the staple cartridge 4100 can be positioned within a staple cartridge channel, for example, and the anvil can be moved toward the staple cartridge 4100 into a closed position. In various embodiments, the anvil can contact and compress the compressible cartridge body 4110 when the anvil is moved into its closed position. In certain embodiments, the anvil may not contact the staples 4120 when the anvil is in its closed position. In certain other embodiments, the anvil may contact the legs of the staples 4120 and at least partially deform the staples 4120 when the anvil is moved into its closed position. In either event, the staple cartridge 4100 can further comprise one or more sleds 4170 which can be advanced longitudinally within the staple cartridge 4100 such that the sleds 4170 can sequentially engage the staple drivers 4162 and move the staple drivers 4162 and the staples 4120 toward the anvil. In various embodiments, the sleds 4170 can slide between the staple cartridge pan 4180 and the staple drivers 4162. In embodiments where the closure of the anvil has started the forming process of the staples 4120, the upward movement of the staples 4120 toward the anvil can complete the forming process and deform the staples 4120 to their fully formed, or at least desired, height. In embodiments where the closure of the anvil has not deformed the staples 4120, the upward movement of the staples 4120 toward the anvil can initiate and complete the forming process and deform the staples 4120 to their fully formed, or at least desired, height. In various embodiments, the sleds 4170 can be advanced from a proximal end of the staple cartridge 4100 to a distal end of the staple cartridge 4100 such that the staples 4120 positioned in the proximal end of the staple cartridge 4100 are fully formed before the staples 4120 positioned in the distal end of the staple cartridge 4100 are fully formed. In at least one embodiment, referring to FIG. 12, the sleds 4170 can each comprise at least one angled or inclined surface 4711 which can be configured to slide underneath the staple drivers 4162 and lift the staple drivers 4162 as illustrated in FIG. 13.

In various embodiments, further to the above, the staples 4120 can be formed in order to capture at least a portion of the tissue T and at least a portion of the compressible cartridge body 4110 of the staple cartridge 4100 therein. After the staples 4120 have been formed, the anvil and the staple cartridge channel 4130 of the surgical stapler can be moved away from the implanted staple cartridge 4100. In various circumstances, the cartridge pan 4180 can be fixedly engaged with the staple cartridge channel 4130 wherein, as a result, the cartridge pan 4180 can become detached from the compressible cartridge body 4110 as the staple cartridge channel 4130 is pulled away from the implanted cartridge body 4110. In various embodiments, referring again to FIG. 10, the cartridge pan 4180 can comprise opposing side walls 4181 between which the cartridge body 4110 can be removably positioned. In at least one such embodiment, the compressible cartridge body 4110 can be compressed between the side walls 4181 such that the cartridge body 4110 can be removably retained therebetween during use and releasably disengaged from the cartridge pan 4180 as the cartridge pan 4180 is pulled away. In at least one such embodiment, the driver holder 4160 can be connected to the cartridge pan 4180 such that the driver holder 4160, the drivers 4162, and/or the sleds 4170 can remain in the cartridge pan 4180 when the cartridge pan 4180 is removed from the surgical site. In certain other embodiments, the drivers 4162 can be ejected from the driver holder 4160 and left within the surgical site. In at least one such embodiment, the drivers 4162 can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, the drivers 4162 can be attached to the staples 4120 such that the drivers 4162 are deployed with the staples 4120. In at least one such embodiment, each driver 4162 can comprise a trough configured to receive the bases of the staples 4120, for example, wherein, in at least one embodiment, the troughs can be configured to receive the staple bases in a press-fit and/or snap-fit manner.

In certain embodiments, further to the above, the driver holder 4160 and/or the sleds 4170 can be ejected from the cartridge pan 4180. In at least one such embodiment, the sleds 4170 can slide between the cartridge pan 4180 and the driver holder 4160 such that, as the sleds 4170 are advanced in order to drive the staple drivers 4162 and staples 4120 upwardly, the sleds 4170 can move the driver holder 4160 upwardly out of the cartridge pan 4180 as well. In at least one such embodiment, the driver holder 4160 and/or the sleds 4170 can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, the sleds 4170 can be integrally formed and/or attached to a drive bar, or cutting member, which pushes the sleds 4170 through the staple cartridge 4100. In such embodiments, the sleds 4170 may not be ejected from the cartridge pan 4180 and may remain with the surgical stapler while, in other embodiments in which the sleds 4170 are not attached to the drive bar, the sleds 4170 may be left in the surgical site. In any event, further to the above, the compressibility of the cartridge body 4110 can allow thicker staple cartridges to be used within an end effector of a surgical stapler as the cartridge body 4110 can compress, or shrink, when the anvil of the stapler is closed. In certain embodiments, as a result of the staples being at least partially deformed upon the closure of the anvil, taller staples, such as staples having an approximately 0.18" staple height, for example, could be used, wherein approximately 0.12" of the staple height can be positioned within the compressible layer 4110 and wherein the compressible layer 4110 can have an uncompressed height of approximately 0.14", for example.

In many embodiments described herein, a staple cartridge can comprise a plurality of staples therein. In various embodiments, such staples can be comprised of a metal wire deformed into a substantially U-shaped configuration having two staple legs. Other embodiments are envisioned in which staples can comprise different configurations such as two or more wires that have been joined together having three or more staple legs. In various embodiments, the wire, or wires, used to form the staples can comprise a round, or at least substantially round, cross-section. In at least one embodiment, the staple wires can comprise any other suitable cross-section, such as square and/or rectangular cross-sections, for example. In certain embodiments, the staples can be comprised of plastic wires. In at least one embodiment, the staples can be comprised of plastic-coated metal wires. In various embodiments, a cartridge can comprise any suitable type of fastener in addition to or in lieu of staples. In at least one such embodiment, such a fastener can comprise pivotable arms which are folded when engaged by an anvil. In certain embodiments, two-part fasteners could be utilized. In at least one such embodiment, a staple cartridge can comprise a plurality of first fastener portions and an anvil can comprise a plurality of second fastener portions which are connected to the first fastener portions when the anvil is compressed against the staple cartridge. In certain embodiments, as described above, a sled or driver can be advanced within a staple cartridge in order to complete the forming process of the staples. In certain embodiments, a sled or driver can be advanced within an anvil in order to move one or more forming members downwardly into engagement with the opposing staple cartridge and the staples, or fasteners, positioned therein.

In various embodiments described herein, a staple cartridge can comprise four rows of staples stored therein. In at least one embodiment, the four staple rows can be arranged in two inner staple rows and two outer staple rows. In at least one such embodiment, an inner staple row and an outer staple row can be positioned on a first side of a cutting member, or knife, slot within the staple cartridge and, similarly, an inner staple row and an outer staple row can be positioned on a second side of the cutting member, or knife, slot. In certain embodiments, a staple cartridge may not comprise a cutting member slot; however, such a staple cartridge may comprise a designated portion configured to be incised by a cutting member in lieu of a staple cartridge slot. In various embodiments, the inner staple rows can be arranged within the staple cartridge such that they are equally, or at least substantially equally, spaced from the cutting member slot. Similarly, the outer staple rows can be arranged within the staple cartridge such that they are equally, or at least substantially equally, spaced from the cutting member slot. In various embodiments, a staple cartridge can comprise more than or less than four rows of staples stored within a staple cartridge. In at least one embodiment, a staple cartridge can comprise six rows of staples. In at least one such embodiment, the staple cartridge can comprise three rows of staples on a first side of a cutting member slot and three rows of staples on a second side of the cutting member slot. In certain embodiments, a staple cartridge may comprise an odd number of staple rows. For example, a staple cartridge may comprise two rows of staples on a first side of a cutting member slot and three rows of staples on a second side of the cutting member slot. In various embodiments, the staple rows can comprise staples having the same, or at least substantially the same, unformed staple height. In certain other embodiments, one or more of the staple rows can comprise staples having a different unformed staple height than the other staples. In at least one such embodiment, the staples on a first side of a cutting member slot may have a first unformed height and the staples on a second side of a cutting member slot may have a second unformed height which is different than the first height, for example.

In various embodiments, as described above, a staple cartridge can comprise a cartridge body including a plurality of staple cavities defined therein. The cartridge body can comprise a deck and a top deck surface wherein each staple cavity can define an opening in the deck surface. As also described above, a staple can be positioned within each staple cavity such that the staples are stored within the cartridge body until they are ejected therefrom. Prior to being ejected from the cartridge body, in various embodiments, the staples can be contained with the cartridge body such that the staples do not protrude above the deck surface. As the staples are positioned below the deck surface, in such embodiments, the possibility of the staples becoming damaged and/or prematurely contacting the targeted tissue can be reduced. In various circumstances, the staples can be moved between an unfired position in which they do not protrude from the cartridge body and a fired position in which they have emerged from the cartridge body and can contact an anvil positioned opposite the staple cartridge. In various embodiments, the anvil, and/or the forming pockets defined within the anvil, can be positioned a predetermined distance above the deck surface such that, as the staples are being deployed from the cartridge body, the staples are deformed to a predetermined formed height. In some circumstances, the thickness of the tissue captured between the anvil and the staple cartridge may vary and, as a result, thicker tissue may be captured within certain staples while thinner tissue may be captured within certain other staples. In either event, the clamping pressure, or force, applied to the tissue by the staples may vary from staple to staple or vary between a staple on one end of a staple row and a staple on the other end of the staple row, for example. In certain circumstances, the gap between the anvil and the staple cartridge deck can be controlled such that the staples apply a certain minimum clamping pressure within each staple. In some such circumstances, however, significant variation of the clamping pressure within different staples may still exist. Surgical stapling instruments are disclosed in U.S. Pat. No. 7,380,696, which issued on Jun. 3, 2008, the entire disclosure of which is incorporated by reference herein. An illustrative multi-stroke handle for the surgical stapling and severing instrument is described in greater detail in the co-pending and co-owned U.S. patent application entitled SURGICAL STAPLING INSTRUMENT INCORPORATING A MULTISTROKE FIRING POSITION INDICATOR AND RETRACTION MECHANISM, Ser. No. 10/674,026, now U.S. Pat. No. 7,364,061, the disclosure of which is hereby incorporated by reference in its entirety. Other applications consistent with the present invention may incorporate a single firing stroke, such as described in co-pending and commonly owned U.S. patent application SURGICAL STAPLING INSTRUMENT HAVING SEPARATE DISTINCT CLOSING AND FIRING SYSTEMS, Ser. No. 10/441,632, now U.S. Pat. No. 7,000,818, the disclosure of which is hereby incorporated by reference in its entirety.

In various embodiments described herein, a staple cartridge can comprise means for compensating for the thickness of the tissue captured within the staples deployed from the staple cartridge. In various embodiments, referring to FIG. 14, a staple cartridge, such as staple cartridge 10000, for example, can include a rigid first portion, such as support portion 10010, for example, and a compressible second portion, such as tissue thickness compensator 10020, for example. In at least one embodiment, referring primarily to FIG. 16, the support portion 10010 can comprise a cartridge body, a top deck surface 10011, and a plurality of staple cavities 10012 wherein, similar to the above, each staple cavity 10012 can define an opening in the deck surface 10011. A staple 10030, for example, can be removably positioned in each staple cavity 10012. In at least one such embodiment, each staple 10030 can comprise a base 10031 and one or more legs 10032 extending from the base 10031. Prior to the staples 10030 being deployed, as also described in greater detail below, the bases 10031 of the staples 10030 can be supported by staple drivers positioned within the support portion 10010 and, concurrently, the legs 10032 of the staples 10030 can be at least partially contained within the staple cavities 10012. In various embodiments, the staples 10030 can be deployed between an unfired position and a fired position such that the legs 10032 move through the tissue thickness compensator 10020, penetrate through a top surface of the tissue thickness compensator 10020, penetrate the tissue T, and contact an anvil positioned opposite the staple cartridge 10000. As the legs 10032 are deformed against the anvil, the legs 10032 of each staple 10030 can capture a portion of the tissue thickness compensator 10020 and a portion of the tissue T within each staple 10030 and apply a compressive force to the tissue. Further to the above, the legs 10032 of each staple 10030 can be deformed downwardly toward the base 10031 of the staple to form a staple entrapment area 10039 in which the tissue T and the tissue thickness compensator 10020 can be captured. In various circumstances, the staple entrapment area 10039 can be defined between the inner surfaces of the deformed legs 10032 and the inner surface of the base 10031. The size of the entrapment area for a staple can depend on several factors such as the length of the legs, the diameter of the legs, the width of the base, and/or the extent in which the legs are deformed, for example.

In previous embodiments, a surgeon was often required to select the appropriate staples having the appropriate staple height for the tissue being stapled. For example, a surgeon could select tall staples for use with thick tissue and short staples for use with thin tissue. In some circumstances, however, the tissue being stapled did not have a consistent thickness and, thus, some staples were unable to achieve the desired fired configuration. For example, FIG. 48 illustrates a tall staple used in thin tissue. Referring now to FIG. 49, when a tissue thickness compensator, such as tissue thickness compensator 10020, for example, is used with thin tissue, for example, the larger staple may be formed to a desired fired configuration.

Figure 43:
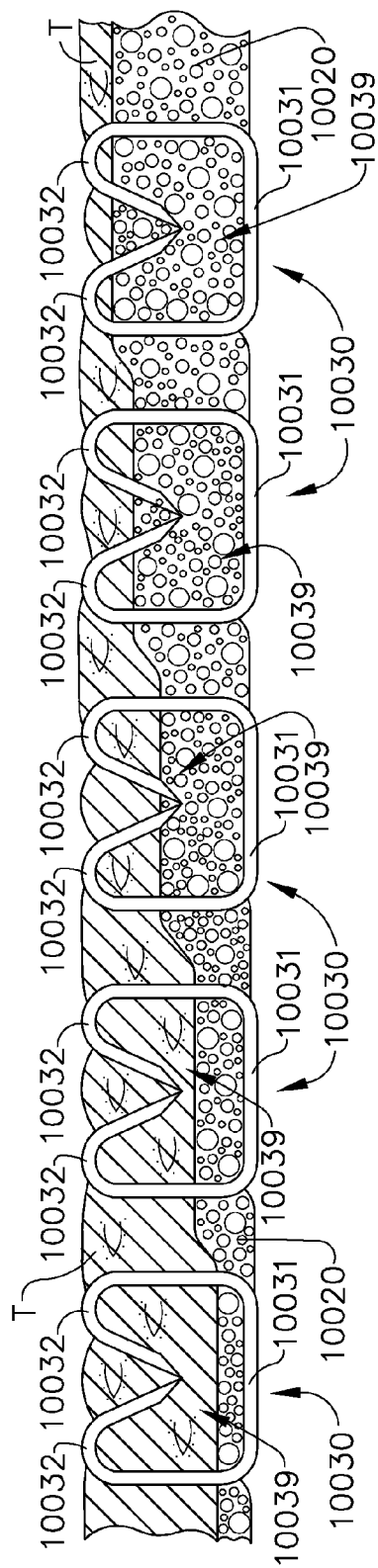
FIG. 43 is a diagram illustrating a tissue thickness compensator which is compensating for different tissue thickness captured within different staples.
Figure 44:
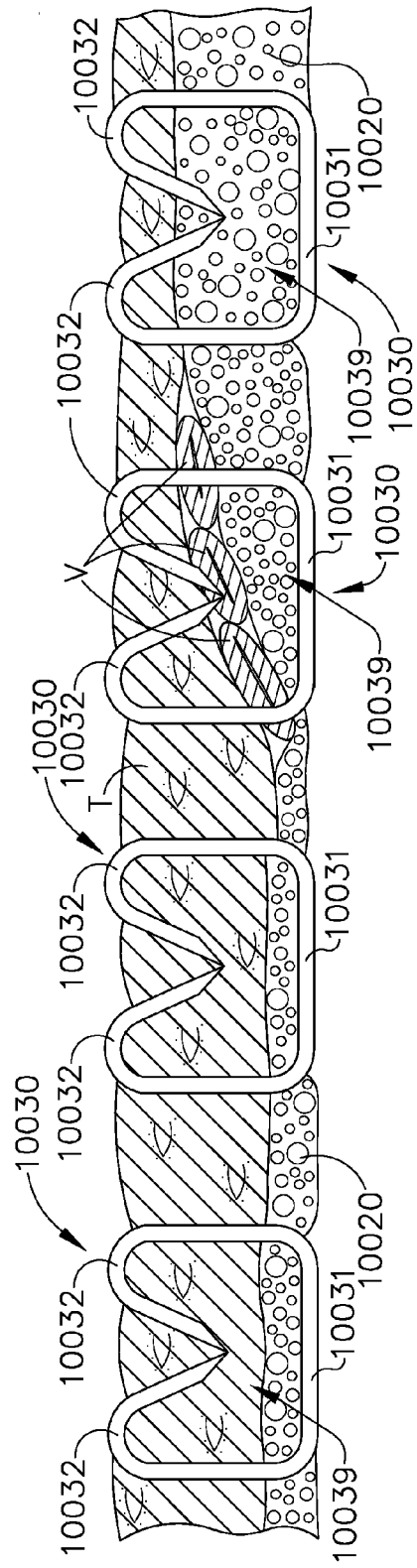
FIG. 44 is a diagram illustrating a tissue thickness compensator applying a compressive pressure to one or more vessels that have been transected by a staple line.
Figure 45:
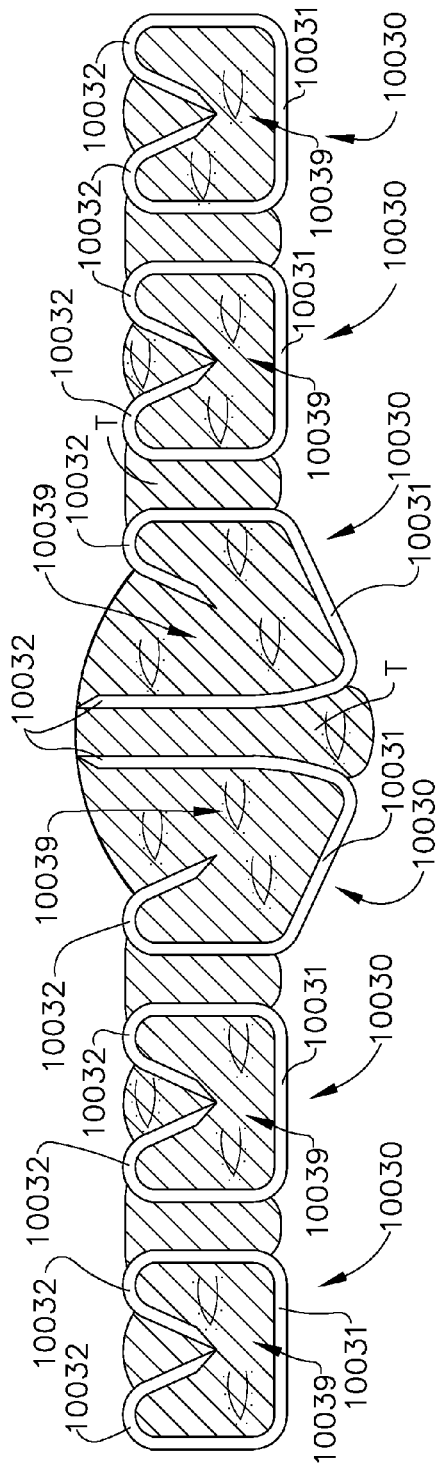
FIG. 45 is a diagram illustrating a circumstance wherein one or more staples have been improperly formed.
Figure 46:
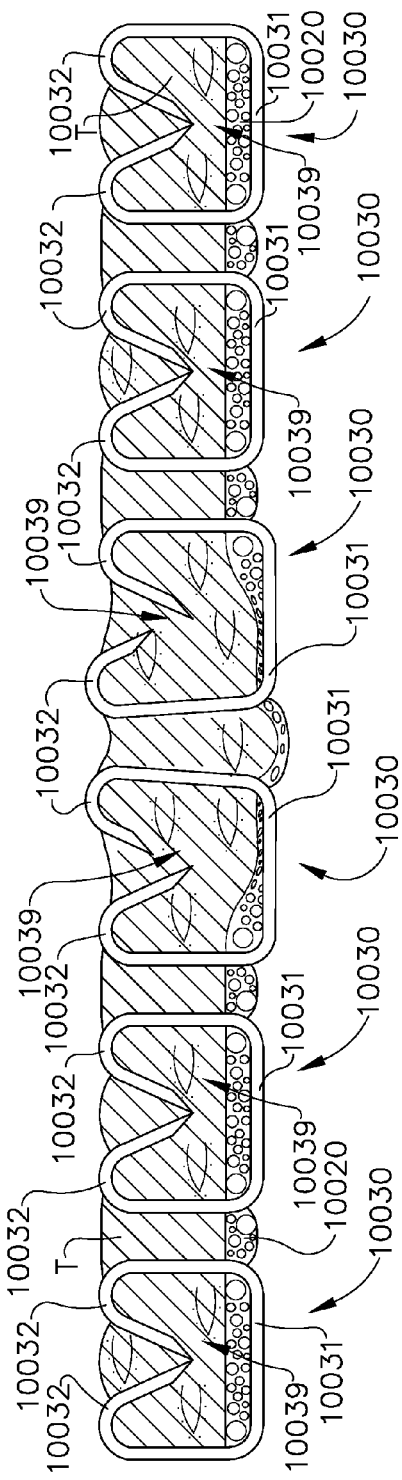
FIG. 46 is a diagram illustrating a tissue thickness compensator which could compensate for improperly formed staples.

Owing to the compressibility of the tissue thickness compensator, the tissue thickness compensator can compensate for the thickness of the tissue captured within each staple. More particularly, referring now to FIGS. 43 and 44, a tissue thickness compensator, such as tissue thickness compensator 10020, for example, can consume larger and/or smaller portions of the staple entrapment area 10039 of each staple 10030 depending on the thickness and/or type of tissue contained within the staple entrapment area 10039. For example, if thinner tissue T is captured within a staple 10030, the tissue thickness compensator 10020 can consume a larger portion of the staple entrapment area 10039 as compared to circumstances where thicker tissue T is captured within the staple 10030. Correspondingly, if thicker tissue T is captured within a staple 10030, the tissue thickness compensator 10020 can consume a smaller portion of the staple entrapment area 10039 as compared to the circumstances where thinner tissue T is captured within the staple 10030. In this way, the tissue thickness compensator can compensate for thinner tissue and/or thicker tissue and assure that a compressive pressure is applied to the tissue irrespective, or at least substantially irrespective, of the tissue thickness captured within the staples. In addition to the above, the tissue thickness compensator 10020 can compensate for different types, or compressibilities, of tissues captured within different staples 10030. Referring now to FIG. 44, the tissue thickness compensator 10020 can apply a compressive force to vascular tissue T which can include vessels V and, as a result, restrict the flow of blood through the less compressible vessels V while still applying a desired compressive pressure to the surrounding tissue T. In various circumstances, further to the above, the tissue thickness compensator 10020 can also compensate for malformed staples. Referring to FIG. 45, the malformation of various staples 10030 can result in larger staple entrapment areas 10039 being defined within such staples. Owing to the resiliency of the tissue thickness compensator 10020, referring now to FIG. 46, the tissue thickness compensator 10020 positioned within malformed staples 10030 may still apply a sufficient compressive pressure to the tissue T even though the staple entrapment areas 10039 defined within such malformed staples 10030 may be enlarged. In various circumstances, the tissue thickness compensator 10020 located intermediate adjacent staples 10030 can be biased against the tissue T by properly-formed staples 10030 surrounding a malformed staple 10030 and, as a result, apply a compressive pressure to the tissue surrounding and/or captured within the malformed staple 10030, for example. In various circumstances, a tissue thickness compensator can compensate for different tissue densities which can arise due to calcifications, fibrous areas, and/or tissue that has been previously stapled or treated, for example.

In various embodiments, a fixed, or unchangeable, tissue gap can be defined between the support portion and the anvil and, as a result, the staples may be deformed to a predetermined height regardless of the thickness of the tissue captured within the staples. When a tissue thickness compensator is used with these embodiments, the tissue thickness compensator can adapt to the tissue captured between the anvil and the support portion staple cartridge and, owing to the resiliency of the tissue thickness compensator, the tissue thickness compensator can apply an additional compressive pressure to the tissue. Referring now to FIGS. 50-55, a staple 10030 has been formed to a predefined height H. With regard to FIG. 50, a tissue thickness compensator has not been utilized and the tissue T consumes the entirety of the staple entrapment area 10039. With regard to FIG. 57, a portion of a tissue thickness compensator 10020 has been captured within the staple 10030, compressed the tissue T, and consumed at least a portion of the staple entrapment area 10039. Referring now to FIG. 52, thin tissue T has been captured within the staple 10030. In this embodiment, the compressed tissue T has a height of approximately ⅖H and the compressed tissue thickness compensator 10020 has a height of approximately ⅗H, for example. Referring now to FIG. 53, tissue T having an intermediate thickness has been captured within the staple 10030. In this embodiment, the compressed tissue T has a height of approximately ⅘H and the compressed tissue thickness compensator 10020 has a height of approximately ⅗H, for example. Referring now to FIG. 54, tissue T having an intermediate thickness has been captured within the staple 10030. In this embodiment, the compressed tissue T has a height of approximately ⅔H and the compressed tissue thickness compensator 10020 has a height of approximately ⅓H, for example. Referring now to FIG. 53, thick tissue T has been captured within the staple 10030. In this embodiment, the compressed tissue T has a height of approximately ⅝H and the compressed tissue thickness compensator 10020 has a height of approximately ⅛H, for example. In various circumstances, the tissue thickness compensator can comprise a compressed height which comprises approximately 10% of the staple entrapment height, approximately 20% of the staple entrapment height, approximately 30% of the staple entrapment height, approximately 40% of the staple entrapment height, approximately 50% of the staple entrapment height, approximately 60% of the staple entrapment height, approximately 70% of the staple entrapment height, approximately 80% of the staple entrapment height, and/or approximately 90% of the staple entrapment height, for example.

In various embodiments, the staples 10030 can comprise any suitable unformed height. In certain embodiments, the staples 10030 can comprise an unformed height between approximately 2 mm and approximately 4.8 mm, for example. The staples 10030 can comprise an unformed height of approximately 2.0 mm, approximately 2.5 mm, approximately 3.0 mm, approximately 3.4 mm, approximately 3.5 mm, approximately 3.8 mm, approximately 4.0 mm, approximately 4.1 mm, and/or approximately 4.8 mm, for example. In various embodiments, the height H to which the staples can be deformed can be dictated by the distance between the deck surface 10011 of the support portion 10010 and the opposing anvil. In at least one embodiment, the distance between the deck surface 10011 and the tissue-contacting surface of the anvil can be approximately 0.097", for example. The height H can also be dictated by the depth of the forming pockets defined within the anvil. In at least one embodiment, the forming pockets can have a depth measured from the tissue-contacting surface, for example. In various embodiments, as described in greater detail below, the staple cartridge 10000 can further comprise staple drivers which can lift the staples 10030 toward the anvil and, in at least one embodiment, lift, or "overdrive", the staples above the deck surface 10011. In such embodiments, the height H to which the staples 10030 are formed can also be dictated by the distance in which the staples 10030 are overdriven. In at least one such embodiment, the staples 10030 can be overdriven by approximately 0.028", for example, and can result in the staples 10030 being formed to a height of approximately 0.189", for example. In various embodiments, the staples 10030 can be formed to a height of approximately 0.8 mm, approximately 1.0 mm, approximately 1.5 mm, approximately 1.8 mm, approximately 2.0 mm, and/or approximately 2.25 mm, for example. In certain embodiments, the staples can be formed to a height between approximately 2.25 mm and approximately 3.0 mm, for example. Further to the above, the height of the staple entrapment area of a staple can be determined by the formed height of the staple and the width, or diameter, of the wire comprising the staple. In various embodiments, the height of the staple entrapment area 10039 of a staple 10030 can comprise the formed height H of the staple less two diameter widths of the wire. In certain embodiments, the staple wire can comprise a diameter of approximately 0.0089", for example. In various embodiments, the staple wire can comprise a diameter between approximately 0.0069" and approximately 0.0119", for example. In at least one exemplary embodiment, the formed height H of a staple 10030 can be approximately 0.189" and the staple wire diameter can be approximately 0.0089" resulting in a staple entrapment height of approximately 0.171", for example.

In various embodiments, further to the above, the tissue thickness compensator can comprise an uncompressed, or pre-deployed, height and can be configured to deform to one of a plurality of compressed heights. In certain embodiments, the tissue thickness compensator can comprise an uncompressed height of approximately 0.125", for example. In various embodiments, the tissue thickness compensator can comprise an uncompressed height of greater than or equal to approximately 0.080", for example. In at least one embodiment, the tissue thickness compensator can comprise an uncompressed, or pre-deployed, height which is greater than the unfired height of the staples. In at least one embodiment, the uncompressed, or pre-deployed, height of the tissue thickness compensator can be approximately 10% taller, approximately 20% taller, approximately 30% taller, approximately 40% taller, approximately 50% taller, approximately 60% taller, approximately 70% taller, approximately 80% taller, approximately 90% taller, and/or approximately 100% taller than the unfired height of the staples, for example. In at least one embodiment, the uncompressed, or pre-deployed, height of the tissue thickness compensator can be up to approximately 100% taller than the unfired height of the staples, for example. In certain embodiments, the uncompressed, or pre-deployed, height of the tissue thickness compensator can be over 100% taller than the unfired height of the staples, for example. In at least one embodiment, the tissue thickness compensator can comprise an uncompressed height which is equal to the unfired height of the staples. In at least one embodiment, the tissue thickness compensator can comprise an uncompressed height which is less than the unfired height of the staples. In at least one embodiment, the uncompressed, or pre-deployed, height of the thickness compensator can be approximately 10% shorter, approximately 20% shorter, approximately 30% shorter, approximately 40% shorter, approximately 50% shorter, approximately 60% shorter, approximately 70% shorter, approximately 80% shorter, and/or approximately 90% shorter than the unfired height of the staples, for example. In various embodiments, the compressible second portion can comprise an uncompressed height which is taller than an uncompressed height of the tissue T being stapled. In certain embodiments, the tissue thickness compensator can comprise an uncompressed height which is equal to an uncompressed height of the tissue T being stapled. In various embodiments, the tissue thickness compensator can comprise an uncompressed height which is shorter than an uncompressed height of the tissue T being stapled.

As described above, a tissue thickness compensator can be compressed within a plurality of formed staples regardless of whether thick tissue or thin tissue is captured within the staples. In at least one exemplary embodiment, the staples within a staple line, or row, can be deformed such that the staple entrapment area of each staple comprises a height of approximately 2.0 mm, for example, wherein the tissue T and the tissue thickness compensator can be compressed within this height. In certain circumstances, the tissue T can comprise a compressed height of approximately 1.75 mm within the staple entrapment area while the tissue thickness compensator can comprise a compressed height of approximately 0.25 mm within the staple entrapment area, thereby totaling the approximately 2.0 mm staple entrapment area height, for example. In certain circumstances, the tissue T can comprise a compressed height of approximately 1.50 mm within the staple entrapment area while the tissue thickness compensator can comprise a compressed height of approximately 0.50 mm within the staple entrapment area, thereby totaling the approximately 2.0 mm staple entrapment area height, for example. In certain circumstances, the tissue T can comprise a compressed height of approximately 1.25 mm within the staple entrapment area while the tissue thickness compensator can comprise a compressed height of approximately 0.75 mm within the staple entrapment area, thereby totaling the approximately 2.0 mm staple entrapment area height, for example. In certain circumstances, the tissue T can comprise a compressed height of approximately 1.0 mm within the staple entrapment area while the tissue thickness compensator can comprise a compressed height of approximately 1.0 mm within the staple entrapment area, thereby totaling the approximately 2.0 mm staple entrapment area height, for example. In certain circumstances, the tissue T can comprise a compressed height of approximately 0.75 mm within the staple entrapment area while the tissue thickness compensator can comprise a compressed height of approximately 1.25 mm within the staple entrapment area, thereby totaling the approximately 2.0 mm staple entrapment area height, for example. In certain circumstances, the tissue T can comprise a compressed height of approximately 1.50 mm within the staple entrapment area while the tissue thickness compensator can comprise a compressed height of approximately 0.50 mm within the staple entrapment area, thereby totaling the approximately 2.0 mm staple entrapment area height, for example. In certain circumstances, the tissue T can comprise a compressed height of approximately 0.25 mm within the staple entrapment area while the tissue thickness compensator can comprise a compressed height of approximately 1.75 mm within the staple entrapment area, thereby totaling the approximately 2.0 mm staple entrapment area height, for example.

In various embodiments, further to the above, the tissue thickness compensator can comprise an uncompressed height which is less than the fired height of the staples. In certain embodiments, the tissue thickness compensator can comprise an uncompressed height which is equal to the fired height of the staples. In certain other embodiments, the tissue thickness compensator can comprise an uncompressed height which is taller than the fired height of the staples. In at least one such embodiment, the uncompressed height of a tissue thickness compensator can comprise a thickness which is approximately 110% of the formed staple height, approximately 120% of the formed staple height, approximately 130% of the formed staple height, approximately 140% of the formed staple height, approximately 150% of the formed staple height, approximately 160% of the formed staple height, approximately 170% of the formed staple height, approximately 180% of the formed staple height, approximately 190% of the formed staple height, and/or approximately 200% of the formed staple height, for example. In certain embodiments, the tissue thickness compensator can comprise an uncompressed height which is more than twice the fired height of the staples. In various embodiments, the tissue thickness compensator can comprise a compressed height which is from approximately 85% to approximately 150% of the formed staple height, for example. In various embodiments, as described above, the tissue thickness compensator can be compressed between an uncompressed thickness and a compressed thickness. In certain embodiments, the compressed thickness of a tissue thickness compensator can be approximately 10% of its uncompressed thickness, approximately 20% of its uncompressed thickness, approximately 30% of its uncompressed thickness, approximately 40% of its uncompressed thickness, approximately 50% of its uncompressed thickness, approximately 60% of its uncompressed thickness, approximately 70% of its uncompressed thickness, approximately 80% of its uncompressed thickness, and/or approximately 90% of its uncompressed thickness, for example. In various embodiments, the uncompressed thickness of the tissue thickness compensator can be approximately two times, approximately ten times, approximately fifty times, and/or approximately one hundred times thicker than its compressed thickness, for example. In at least one embodiment, the compressed thickness of the tissue thickness compensator can be between approximately 60% and approximately 99% of its uncompressed thickness. In at least one embodiment, the uncompressed thickness of the tissue thickness compensator can be at least 50% thicker than its compressed thickness. In at least one embodiment, the uncompressed thickness of the tissue thickness compensator can be up to one hundred times thicker than its compressed thickness. In various embodiments, the compressible second portion can be elastic, or at least partially elastic, and can bias the tissue T against the deformed legs of the staples. In at least one such embodiment, the compressible second portion can resiliently expand between the tissue T and the base of the staple in order to push the tissue T against the legs of the staple. In certain embodiments, discussed in further detail below, the tissue thickness compensator can be positioned intermediate the tissue T and the deformed staple legs. In various circumstances, as a result of the above, the tissue thickness compensator can be configured to consume any gaps within the staple entrapment area.

In various embodiments, the tissue thickness compensator may comprise materials characterized by one or more of the following properties: biocompatible, bioabsorbable, bioresorbable, biodurable, biodegradable, compressible, fluid absorbable, swellable, self-expandable, bioactive, medicament, pharmaceutically active, anti-adhesion, haemostatic, antibiotic, anti-microbial, anti-viral, nutritional, adhesive, permeable, hydrophilic and/or hydrophobic, for example. In various embodiments, a surgical instrument comprising an anvil and a staple cartridge may comprise a tissue thickness compensator associated with the anvil and/or staple cartridge comprising at least one of a haemostatic agent, such as fibrin and thrombin, an antibiotic, such as doxycpl, and medicament, such as matrix metalloproteinases (MMPs).

In various embodiments, the tissue thickness compensator may comprise synthetic and/or non-synthetic materials. The tissue thickness compensator may comprise a polymeric composition comprising one or more synthetic polymers and/or one or more non-synthetic polymers. The synthetic polymer may comprise a synthetic absorbable polymer and/or a synthetic non-absorbable polymer. In various embodiments, the polymeric composition may comprise a biocompatible foam, for example. The biocompatible foam may comprise a porous, open cell foam and/or a porous, closed cell foam, for example. The biocompatible foam may have a uniform pore morphology or may have a gradient pore morphology (i.e. small pores gradually increasing in size to large pores across the thickness of the foam in one direction). In various embodiments, the polymeric composition may comprise one or more of a porous scaffold, a porous matrix, a gel matrix, a hydrogel matrix, a solution matrix, a filamentous matrix, a tubular matrix, a composite matrix, a membranous matrix, a biostable polymer, and a biodegradable polymer, and combinations thereof. For example, the tissue thickness compensator may comprise a foam reinforced by a filamentous matrix or may comprise a foam having an additional hydrogel layer that expands in the presence of bodily fluids to further provide the compression on the tissue. In various embodiments, a tissue thickness compensator could also be comprised of a coating on a material and/or a second or third layer that expands in the presence of bodily fluids to further provide the compression on the tissue. Such a layer could be a hydrogel that could be a synthetic and/or naturally derived material and could be either biodurable and/or biodegradable, for example. In various embodiments, the tissue thickness compensator may comprise a microgel or a nanogel. The hydrogel may comprise carbohydrate-derived microgels and/or nanogels. In certain embodiments, a tissue thickness compensator may be reinforced with fibrous non-woven materials or fibrous mesh type elements, for example, that can provide additional flexibility, stiffness, and/or strength. In various embodiments, a tissue thickness compensator that has a porous morphology which exhibits a gradient structure such as, for example, small pores on one surface and larger pores on the other surface. Such morphology could be more optimal for tissue in-growth or haemostatic behavior. Further, the gradient could be also compositional with a varying bio-absorption profile. A short term absorption profile may be preferred to address hemostasis while a long term absorption profile may address better tissue healing without leakages.

Examples of non-synthetic materials include, but are not limited to, lyophilized polysaccharide, glycoprotein, bovine pericardium, collagen, gelatin, fibrin, fibrinogen, elastin, proteoglycan, keratin, albumin, hydroxyethyl cellulose, cellulose, oxidized cellulose, oxidized regenerated cellulose (ORC), hydroxypropyl cellulose, carboxyethyl cellulose, carboxymethylcellulose, chitan, chitosan, casein, alginate, and combinations thereof.

Examples of synthetic absorbable materials include, but are not limited to, poly(lactic acid) (PLA), poly(L-lactic acid) (PLLA), polycaprolactone (PCL), polyglycolic acid (PGA), poly(trimethylene carbonate) (TMC), polyethylene terephthalate (PET), polyhydroxyalkanoate (PHA), a copolymer of glycolide and $\epsilon$-caprolactone (PGCL), a copolymer of glycolide and -trimethylene carbonate, poly(glycerol sebacate) (PGS), poly(dioxanone) (PDS), polyesters, poly(orthoesters), polyoxaesters, polyetheresters, polycarbonates, polyamide esters, polyanhydrides, polysaccharides, poly(esteramides), tyrosine-based polyarylates, polyamines, tyrosine-based polyiminocarbonates, tyrosine-based polycarbonates, poly(D,L-lactide-urethane), poly(hydroxybutyrate), poly(B-hydroxybutyrate), poly($\epsilon$-caprolactone), polyethyleneglycol (PEG), poly[bis(carboxylatophenoxy)phosphazene]poly (amino acids), pseudo-poly(amino acids), absorbable polyurethanes, poly(phosphazine), polyphosphazenes, polyalkyleneoxides, polyacrylamides, polyhydroxyethylmethylacrylate, polyvinylpyrrolidone, polyvinyl alcohols, poly(caprolactone), polyacrylic acid, polyacetate, polypropylene, aliphatic polyesters, glycerols, copoly(ether-esters), polyalkylene oxalates, polyamides, poly(iminocarbonates), polyalkylene oxalates, and combinations thereof. In various embodiments, the polyester is may be selected from the group consisting of polylactides, polyglycolides, trimethylene carbonates, polydioxanones, polycaprolactones, polybutesters, and combinations thereof.

In various embodiments, the synthetic absorbable polymer may comprise one or more of 90/10 poly(glycolide-L-lactide) copolymer, commercially available from Ethicon, Inc. under the trade designation VICRYL (polyglactic 910), polyglycolide, commercially available from American Cyanamid Co. under the trade designation DEXON, polydioxanone, commercially available from Ethicon, Inc. under the trade designation PDS, poly(glycolide-trimethylene carbonate) random block copolymer, commercially available from American Cyanamid Co. under the trade designation MAXON, 75/25 poly(glycolide-$\epsilon$-caprolactone-poliglecaprolactone 25) copolymer, commercially available from Ethicon under the trade designation MONOCRYL, for example.

Examples of synthetic non-absorbable materials include, but are not limited to, polyurethane, polypropylene (PP), polyethylene (PE), polycarbonate, polyamides, such as nylon, polyvinylchloride (PVC), polymethylmethacrylate (PMMA), polystyrene (PS), polyester, polyetheretherketone (PEEK), polytetrafluoroethylene (PTFE), polytrifluorochloroethylene (PTFCE), polyvinylfluoride (PVF), fluorinated ethylene propylene (FEP), polyacetal, polysulfone, silicons, and combinations thereof. The synthetic non-absorbable polymers may include, but are not limited to, foamed elastomers and porous elastomers, such as, for example, silicone, polyisoprene, and rubber. In various embodiments, the synthetic polymers may comprise expanded polytetrafluoroethylene (ePTFE), commercially available from W. L. Gore & Associates, Inc. under the trade designation GORE-TEX Soft Tissue Patch and co-polyetherester urethane foam commercially available from Polyganics under the trade designation NASOPORE.

In various embodiments, the polymeric composition may comprise from approximately 50% to approximately 90% by weight of the polymeric composition of PLLA and approximately 50% to approximately 10% by weight of the polymeric composition of PCL, for example. In at least one embodiment, the polymeric composition may comprise approximately 70% by weight of PLLA and approximately 30% by weight of PCL, for example. In various embodiments, the polymeric composition may comprise from approximately 55% to approximately 85% by weight of the polymeric composition of PGA and 15% to 45% by weight of the polymeric composition of PCL, for example. In at least one embodiment, the polymeric composition may comprise approximately 65% by weight of PGA and approximately 35% by weight of PCL, for example. In various embodiments, the polymeric composition may comprise from approximately 90% to approximately 95% by weight of the polymeric composition of PGA and approximately 5% to approximately 10% by weight of the polymeric composition of PLA, for example.

In various embodiments, the synthetic absorbable polymer may comprise a bioabsorbable, biocompatible elastomeric copolymer. Suitable bioabsorbable, biocompatible elastomeric copolymers include but are not limited to copolymers of ε-caprolactone and glycolide (preferably having a mole ratio of ε-caprolactone to glycolide of from about 30:70 to about 70:30, preferably 35:65 to about 65:35, and more preferably 45:55 to 35:65); elastomeric copolymers of ε-caprolactone and lactide, including L-lactide, D-lactide blends thereof or lactic acid copolymers (preferably having a mole ratio of ε-caprolactone to lactide of from about 35:65 to about 65:35 and more preferably 45:55 to 30:70) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of ε-caprolactone and p-dioxanone (preferably having a mole ratio of ε-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. In one embodiment, the elastomeric copolymer is a copolymer of glycolide and ε-caprolactone. In another embodiment, the elastomeric copolymer is a copolymer of lactide and ε-caprolactone.

The disclosures of U.S. Pat. No. 5,468,253, entitled ELASTOMERIC MEDICAL DEVICE, which issued on Nov. 21, 1995, and U.S. Pat. No. 6,325,810, entitled FOAM BUTTRESS FOR STAPLING APPARATUS, which issued on Dec. 4, 2001, are hereby incorporated by reference in their respective entireties.

In various embodiments, the tissue thickness compensator may comprise an emulsifier. Examples of emulsifiers may include, but are not limited to, water-soluble polymers, such as, polyvinyl alcohol (PVA), polyvinyl pyrrolidone (PVP), polyethylene glycol (PEG), polypropylene glycol (PPG), PLURONICS, TWEENS, polysaccharides and combinations thereof.

In various embodiments, the tissue thickness compensator may comprise a surfactant. Examples of surfactants may include, but are not limited to, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy)ethanol, and polyoxamers.

In various embodiments, the polymeric composition may comprise a pharmaceutically active agent. The polymeric composition may release a therapeutically effective amount of the pharmaceutically active agent. In various embodiments, the pharmaceutically active agent may be released as the polymeric composition is desorbed/absorbed. In various embodiments, the pharmaceutically active agent may be released into fluid, such as, for example, blood, passing over or through the polymeric composition. Examples of pharmaceutically active agents may include, but are not limited to, haemostatic agents and drugs, such as, for example, fibrin, thrombin, and oxidized regenerated cellulose (ORC); anti-inflammatory drugs, such as, for example, diclofenac, aspirin, naproxen, sulindac, and hydrocortisone; antibiotic and antimicrobial drug or agents, such as, for example, triclosan, ionic silver, ampicillin, gentamicin, polymyxin B, chloramphenicol; and anticancer agents, such as, for example, cisplatin, mitomycin, adriamycin.

In various embodiments, the polymeric composition may comprise a haemostatic material. The tissue thickness compensator may comprise haemostatic materials comprising poly(lactic acid), poly(glycolic acid), poly(hydroxybutyrate), poly(caprolactone), poly(dioxanone), polyalkyleneoxides, copoly(ether-esters), collagen, gelatin, thrombin, fibrin, fibrinogen, fibronectin, elastin, albumin, hemoglobin, ovalbumin, polysaccharides, hyaluronic acid, chondroitin sulfate, hydroxyethyl starch, hydroxyethyl cellulose, cellulose, oxidized cellulose, hydroxypropyl cellulose, carboxyethyl cellulose, carboxymethyl cellulose, chitan, chitosan, agarose, maltose, maltodextrin, alginate, clotting factors, methacrylate, polyurethanes, cyanoacrylates, platelet agonists, vasoconstrictors, alum, calcium, RGD peptides, proteins, protamine sulfate, ε-amino caproic acid, ferric sulfate, ferric subsulfates, ferric chloride, zinc, zinc chloride, aluminum chloride, aluminum sulfates, aluminum acetates, permanganates, tannins, bone wax, polyethylene glycols, fucans and combinations thereof. The tissue thickness compensator may be characterized by haemostatic properties.

The polymeric composition of a tissue thickness compensator may be characterized by percent porosity, pore size, and/or hardness, for example. In various embodiments, the polymeric composition may have a percent porosity from approximately 30% by volume to approximately 99% by volume, for example. In certain embodiments, the polymeric composition may have a percent porosity from approximately 60% by volume to approximately 98% by volume, for example. In various embodiments, the polymeric composition may have a percent porosity from approximately 85% by volume to approximately 97% by volume, for example. In at least one embodiment, the polymeric composition may comprise approximately 70% by weight of PLLA and approximately 30% by weight of PCL, for example, and can comprise approximately 90% porosity by volume, for example. In at least one such embodiment, as a result, the polymeric composition would comprise approximately 10% copolymer by volume. In at least one embodiment, the polymeric composition may comprise approximately 65% by weight of PGA and approximately 35% by weight of PCL, for example, and can have a percent porosity from approximately 93% by volume to approximately 95% by volume, for example. In various embodiments, the polymeric composition may comprise greater than 85% porosity by volume. The polymeric composition may have a pore size from approximately 5 micrometers to approximately 2000 micrometers, for example. In various embodiments, the polymeric composition may have a pore size between approximately 10 micrometers to approximately 100 micrometers, for example. In at least one such embodiment, the polymeric composition can comprise a copolymer of PGA and PCL, for example. In certain embodiments, the polymeric composition may have a pore size between approximately 100 micrometers to approximately 1000 micrometers, for example. In at least one such embodiment, the polymeric composition can comprise a copolymer of PLLA and PCL, for example.

According to certain aspects, the hardness of a polymeric composition may be expressed in terms of the Shore Hardness, which can defined as the resistance to permanent indentation of a material as determined with a durometer, such as a Shore Durometer. In order to assess the durometer value for a given material, a pressure is applied to the material with a durometer indenter foot in accordance with ASTM procedure D2240-00, entitled, "Standard Test Method for Rubber Property-Durometer Hardness", the entirety of which is incorporated herein by reference. The durometer indenter foot may be applied to the material for a sufficient period of time, such as 15 seconds, for example, wherein a reading is then taken from the appropriate scale. Depending on the type of scale being used, a reading of 0 can be obtained when the indenter foot completely penetrates the material, and a reading of 100 can be obtained when no penetration into the material occurs. This reading is dimensionless. In various embodiments, the durometer may be determined in accordance with any suitable scale, such as Type A and/or Type OO scales, for example, in accordance with ASTM D2240-00. In various embodiments, the polymeric composition of a tissue thickness compensator may have a Shore A hardness value from approximately 4 A to approximately 16 A, for example, which is approximately 45 OO to approximately 65 OO on the Shore OO range. In at least one such embodiment, the polymeric composition can comprise a PLLA/PCL copolymer or a PGA/PCL copolymer, for example. In various embodiments, the polymeric composition of a tissue thickness compensator may have a Shore A Hardness value of less than 15 A. In various embodiments, the polymeric composition of a tissue thickness compensator may have a Shore A Hardness value of less than 10 A. In various embodiments, the polymeric composition of a tissue thickness compensator may have a Shore A Hardness value of less than 5 A. In certain embodiments, the polymeric material may have a Shore OO composition value from approximately 35 OO to approximately 75 OO, for example.

In various embodiments, the polymeric composition may have at least two of the above-identified properties. In various embodiments, the polymeric composition may have at least three of the above-identified properties. The polymeric composition may have a porosity from 85% to 97% by volume, a pore size from 5 micrometers to 2000 micrometers, and a Shore A hardness value from 4 A to 16 A and Shore OO hardness value from 45 OO to 65 OO, for example. In at least one embodiment, the polymeric composition may comprise 70% by weight of the polymeric composition of PLLA and 30% by weight of the polymeric composition of PCL having a porosity of 90% by volume, a pore size from 100 micrometers to 1000 micrometers, and a Shore A hardness value from 4 A to 16 A and Shore OO hardness value from 45 OO to 65 OO, for example. In at least one embodiment, the polymeric composition may comprise 65% by weight of the polymeric composition of PGA and 35% by weight of the polymeric composition of PCL having a porosity from 93% to 95% by volume, a pore size from 10 micrometers to 100 micrometers, and a Shore A hardness value from 4 A to 16 A and Shore OO hardness value from 45 OO to 65 OO, for example.

In various embodiments, the tissue thickness compensator may comprise a material that expands. As discussed above, the tissue thickness compensator may comprise a compressed material that expands when uncompressed or deployed, for example. In various embodiments, the tissue thickness compensator may comprise a self-expanding material formed in situ. In various embodiments, the tissue thickness compensator may comprise at least one precursor selected to spontaneously crosslink when contacted with at least one of other precursor(s), water, and/or bodily fluids. Referring to FIG. 205, in various embodiments, a first precursor may contact one or more other precursors to form an expandable and/or swellable tissue thickness compensator. In various embodiments, the tissue thickness compensator may comprise a fluid-swellable composition, such as a water-swellable composition, for example. In various embodiments, the tissue thickness compensator may comprise a gel comprising water.

Referring to FIGS. 189A and B, for example, a tissue thickness compensator 70000 may comprise at least one hydrogel precursor 70010 selected to form a hydrogel in situ and/or in vivo to expand the tissue thickness compensator 70000. FIG. 189A illustrates a tissue thickness compensator 70000 comprising an encapsulation comprising a first hydrogel precursor 70010A and a second hydrogel precursor 70010B prior to expansion. In certain embodiments, as shown in FIG. 189A, the first hydrogel precursor 70010A and second hydrogel precursor 70010B may be physically separated from other in the same encapsulation. In certain embodiments, a first encapsulation may comprise the first hydrogel precursor 70010A and a second encapsulation may comprise the second hydrogel precursor 70010B. FIG. 189B illustrates the expansion of the thickness tissue compensator 70000 when the hydrogel is formed in situ and/or in vivo. As shown in FIG. 189B, the encapsulation may be ruptured, and the first hydrogel precursor 70010A may contact the second hydrogel precursor 70010B to form the hydrogel 70020. In certain embodiments, the hydrogel may comprise an expandable material. In certain embodiments, the hydrogel may expand up to 72 hours, for example.

In various embodiments, the tissue thickness compensator may comprise a biodegradable foam having an encapsulation comprising dry hydrogel particles or granules embedded therein. Without wishing to be bound to any particular theory, the encapsulations in the foam may be formed by contacting an aqueous solution of a hydrogel precursor and an organic solution of biocompatible materials to form the foam. As shown in FIG. 206, the aqueous solution and organic solution may form micelles. The aqueous solution and organic solution may be dried to encapsulate dry hydrogel particles or granules within the foam. For example, a hydrogel precursor, such as a hydrophilic polymer, may be dissolved in water to form a dispersion of micelles. The aqueous solution may contact an organic solution of dioxane comprising poly(glycolic acid) and polycaprolactone. The aqueous and organic solutions may be lyophilized to form a biodegradable foam having dry hydrogel particles or granules dispersed therein. Without wishing to be bound to any particular theory, it is believed that the micelles form the encapsulation having the dry hydrogel particles or granules dispersed within the foam structure. In certain embodiments, the encapsulation may be ruptured, and the dry hydrogel particles or granules may contact a fluid, such as a bodily fluid, and expand.

In various embodiments, the tissue thickness compensator may expand when contacted with an activator, such as a fluid, for example. Referring to FIG. 190, for example, a tissue thickness compensator 70050 may comprise a swellable material, such as a hydrogel, that expands when contacted with a fluid 70055, such as bodily fluids, saline, water and/or an activator, for example. Examples of bodily fluids may include, but are not limited to, blood, plasma, peritoneal fluid, cerebral spinal fluid, urine, lymph fluid, synovial fluid, vitreous fluid, saliva, gastrointestinal luminal contents, bile, and/or gas (e.g., $CO_2$). In certain embodiments, the tissue thickness compensator 70050 may expand when the tissue thickness compensator 70050 absorbs the fluid. In another example, the tissue thickness compensator 70050 may comprise a non-crosslinked hydrogel that expands when contacted with an activator 70055 comprising a cross-linking agent to form a crosslinked hydrogel. In various embodiments, the tissue thickness compensator may expand when contacted with an activator. In various embodiments, the tissue thickness compensator may expand or swell from contact up to 72 hours, such as from 24-72 hours, up to 24 hours, up to 48 hours, and up to 72 hours, for example, to provide continuously increasing pressure and/or compression to the tissue. As shown in FIG. 190, the initial thickness of the tissue thickness compensator 70050 may be less than an expanded thickness after the fluid 70055 contacts the tissue thickness compensator 70050.

Referring to FIGS. 187 and 188, in various embodiments, a staple cartridge 70100 may comprise a tissue thickness compensator 70105 and a plurality of staples 70110 each comprising staple legs 70112. As shown in FIG. 187, tissue thickness compensator 70105 may have an initial thickness or compressed height that is less than the fired height of the staples 70110. The tissue thickness compensator 70100 may be configured to expand in situ and/or in vivo when contacted with a fluid 70102, such as bodily fluids, saline, and/or an activator for example, to push the tissue T against the legs 70112 of the staple 70110. As shown in FIG. 188, the tissue thickness compensator 70100 may expand and/or swell when contacted with a fluid 70102. The tissue thickness compensator 70105 can compensate for the thickness of the tissue T captured within each staple 70110. As shown in FIG. 188, tissue thickness compensator 70105 may have an expanded thickness or an uncompressed height that is less than the fired height of the staples 70110.

In various embodiments, as described above, the tissue thickness compensator may comprise an initial thickness and an expanded thickness. In certain embodiments, the initial thickness of a tissue thickness compensator can be approximately 0.001% of its expanded thickness, approximately 0.01% of its expanded thickness, approximately 0.1% of its expanded thickness, approximately 1% of its expanded thickness, approximately 10% of its expanded thickness, approximately 20% of its expanded thickness, approximately 30% of its expanded thickness, approximately 40% of its expanded thickness, approximately 50% of its expanded thickness, approximately 60% of its expanded thickness, approximately 70% of its expanded thickness, approximately 80% of its expanded thickness, and/or approximately 90% of its expanded thickness, for example. In various embodiments, the expanded thickness of the tissue thickness compensator can be approximately two times, approximately five times, approximately ten times, approximately fifty times, approximately one hundred times, approximately two hundred times, approximately three hundred times, approximately four hundred times, approximately five hundred times, approximately six hundred times, approximately seven hundred times, approximately eight hundred times, approximately nine hundred times, and/or approximately one thousand times thicker than its initial thickness, for example. In various embodiments, the initial thickness of the tissue thickness compensator can be up to 1% its expanded thickness, up to 5% its expanded thickness, up to 10% its expanded thickness, and up to 50% its expanded thickness. In various embodiments, the expanded thickness of the tissue thickness compensator can be at least 50% thicker than its initial thickness, at least 100% thicker than its initial thickness, at least 300% thicker than its initial thickness, and at least 500% thicker than its initial thickness. As described above, in various circumstances, as a result of the above, the tissue thickness compensator can be configured to consume any gaps within the staple entrapment area.

As discussed above, in various embodiments, the tissue thickness compensator may comprise a hydrogel. In various embodiments, the hydrogel may comprise homopolymer hydrogels, copolymer hydrogels, multipolymer hydrogels, interpenetrating polymer hydrogels, and combinations thereof. In various embodiments, the hydrogel may comprise microgels, nanogels, and combinations thereof. The hydrogel may generally comprise a hydrophilic polymer network capable of absorbing and/or retaining fluids. In various embodiments, the hydrogel may comprise a non-crosslinked hydrogel, a crosslinked hydrogel, and combinations thereof. The hydrogel may comprise chemical crosslinks, physical crosslinks, hydrophobic segments and/or water insoluble segments. The hydrogel may be chemically crosslinked by polymerization, small-molecule crosslinking, and/or polymer-polymer crosslinking. The hydrogel may be physically crosslinked by ionic interactions, hydrophobic interactions, hydrogen bonding interactions, sterocomplexation, and/or supramolecular chemistry. The hydrogel may be substantially insoluble due to the crosslinks, hydrophobic segments and/or water insoluble segments, but be expandable and/or swellable due to absorbing and/or retaining fluids. In certain embodiments, the precursor may crosslink with endogenous materials and/or tissues.

In various embodiments, the hydrogel may comprise an environmentally sensitive hydrogel (ESH). The ESH may comprise materials having fluid-swelling properties that relate to environmental conditions. The environmental conditions may include, but are not limited to, the physical conditions, biological conditions, and/or chemical conditions at the surgical site. In various embodiments, the hydrogel may swell or shrink in response to temperature, pH, electric fields, ionic strength, enzymatic and/or chemical reactions, electrical and/or magnetic stimuli, and other physiological and environmental variables, for example. In various embodiments, the ESH may comprise multifunctional acrylates, hydroxyethylmethacrylate (HEMA), elastomeric acrylates, and related monomers.

In various embodiments, the tissue thickness compensator comprising a hydrogel may comprise at least one of the non-synthetic materials and synthetic materials described above. The hydrogel may comprise a synthetic hydrogel and/or a non-synthetic hydrogel. In various embodiments, the tissue thickness compensator may comprise a plurality of layers. The plurality of the layers may comprise porous layers and/or non-porous layers. For example, the tissue thickness compensator may comprise a non-porous layer and a porous layer. In another example, the tissue thickness compensator may comprise a porous layer intermediate a first non-porous layer and a second non-porous layer. In another example, the tissue thickness compensator may comprise a non-porous layer intermediate a first porous layer and a second porous layer. The non-porous layers and porous layers may be positioned in any order relative to the surfaces of the staple cartridge and/or anvil.

Examples of the non-synthetic material may include, but are not limited to, albumin, alginate, carbohydrate, casein, cellulose, chitin, chitosan, collagen, blood, dextran, elastin, fibrin, fibrinogen, gelatin, heparin, hyaluronic acid, keratin, protein, serum, and starch. The cellulose may comprise hydroxyethyl cellulose, oxidized cellulose, oxidized regenerated cellulose (ORC), hydroxypropyl cellulose, carboxyethyl cellulose, carboxymethylcellulose, and combinations thereof. The collagen may comprise bovine pericardium. The carbohydrate may comprise a polysaccharide, such as lyophilized polysaccharide. The protein may comprise glycoprotein, proteoglycan, and combinations thereof.

Examples of the synthetic material may include, but are not limited to, poly(lactic acid), poly(glycolic acid), poly(hydroxybutyrate), poly(phosphazine), polyesters, polyethylene glycols, polyethylene oxide, polyethylene oxide-co-polypropylene oxide, co-polyethylene oxide, polyalkyleneoxides, polyacrylamides, polyhydroxyethylmethylacrylate, poly(vinylpyrrolidone), polyvinyl alcohols, poly(caprolactone), poly(dioxanone), polyacrylic acid, polyacetate, polypropylene, aliphatic polyesters, glycerols, poly(amino acids), copoly(ether-esters), polyalkylene oxalates, polyamides, poly(iminocarbonates), polyoxaesters, polyorthoesters, polyphosphazenes and combinations thereof. In certain embodiments, the above non-synthetic materials may be synthetically prepared, e.g., synthetic hyaluronic acid, utilizing conventional methods.

In various embodiments, the hydrogel may be made from one or more hydrogel precursors. The precursor may comprise a monomer and/or a macromer. The hydrogel precursor may comprise an electrophile functional group and/or a nucleophile electrophile functional group. In general, electrophiles may react with nucleophiles to form a bond. The term "functional group" as used herein refers to electrophilic or nucleophilic groups capable of reacting with each other to form a bond. Examples of electrophilic functional groups may include, but are not limited to, N-hydroxysuccinimides ("NHS"), sulfosuccinimides, carbonyldiimidazole, sulfonyl chloride, aryl halides, sulfosuccinimidyl esters, N-hydroxysuccinimidyl esters, succinimidyl esters such as succinimidyl succinates and/or succinimidyl propionates, isocyanates, thiocyanates, carbodiimides, benzotriazole carbonates, epoxides, aldehydes, maleimides, imidoesters, combinations thereof, and the like. In at least one embodiment, the electrophilic functional group may comprise a succinimidyl ester. Examples of nucleophile functional groups may include, but are not limited to, $-NH_2$, $-SH$, $-OH$, $-PH_2$, and $-CO-NH-NH_2$.

In various embodiments, the hydrogel may be formed from a single precursor or multiple precursors. In certain embodiments, the hydrogel may be formed from a first precursor and a second precursor. The first hydrogel precursor and second hydrogel precursor may form a hydrogel in situ and/or in vivo upon contact. The hydrogel precursor may generally refer to a polymer, functional group, macromolecule, small molecule, and/or crosslinker that can take part in a reaction to form a hydrogel. The precursor may comprise a homogeneous solution, heterogeneous, or phase separated solution in a suitable solvent, such as water or a buffer, for example. The buffer may have a pH from about 8 to about 12, such as, about 8.2 to about 9, for example. Examples of buffers may include, but are not limited to borate buffers. In certain embodiments, the precursor(s) may be in an emulsion. In various embodiments, a first precursor may react with a second precursor to form a hydrogel. In various embodiments, the first precursor may spontaneously crosslink when contacted with the second precursor. In various embodiments, a first set of electrophilic functional groups on a first precursor may react with a second set of nucleophilic functional groups on a second precursor. When the precursors are mixed in an environment that permits reaction (e.g., as relating to pH, temperature, and/or solvent), the functional groups may react with each other to form covalent bonds. The precursors may become crosslinked when at least some of the precursors react with more than one other precursor.

In various embodiments, the tissue thickness compensator may comprise at least one monomer selected from the group consisting of 3-sulfopropyl acrylate potassium salt ("KSPA"), sodium acrylate ("NaA"), N-(tris(hydroxylmethyl)methyl)acrylamide ("tris acryl"), and 2-acrylamido-2-methyl-1-propane sulfonic acid (AMPS). The tissue thickness compensator may comprise a copolymer comprising two or more monomers selected from the group consisting of KSPA, NaA, tris acryl, AMPS. The tissue thickness compensator may comprise homopolymers derived from KSPA, NaA, trisacryl and AMPS. The tissue thickness compensator may comprise hydrophilicity modifying monomers copolymerizable therewith. The hydrophilicity modifying monomers may comprise methylmethacrylate, butylacrylate, cyclohexylacrylate, styrene, styrene sulphonic acid.

In various embodiments, the tissue thickness compensator may comprise a crosslinker. The crosslinker may comprise a low molecular weight di- or polyvinylic crosslinking agent, such as ethyleneglycol diacrylate or dimethacrylate, di-, tri- or tetraethylen-glycol diacrylate or dimethacrylate, allyl (meth)acrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol A diacrylate or dimethacrylate, methylene bisacrylamide or bismethacrylamide, ethylene bisacrylamide or ethylene bismethacrylamide, triallyl phthalate or diallyl phthalate. In at least one embodiment, the crosslinker may comprise N,N'-methylenebisacrylamide ("MBAA").

In various embodiments, the tissue thickness compensator may comprise at least one of acrylate and/or methacrylate functional hydrogels, biocompatible photoinitiator, alkyl-cyanoacrylates, isocyanate functional macromers, optionally comprising amine functional macromers, succinimidyl ester functional macromers, optionally comprising amine and/or sulfhydryl functional macromers, epoxy functional macromers, optionally comprising amine functional macromers, mixtures of proteins and/or polypeptides and aldehyde crosslinkers, Genipin, and water-soluble carbodiimides, anionic polysaccharides and polyvalent cations.

In various embodiments, the tissue thickness compensator may comprise unsaturated organic acid monomers, acrylic substituted alcohols, and/or acrylamides. In various embodiments, the tissue thickness compensator may comprise methacrylic acids, acrylic acids, glycerolacrylate, glycerolmethacryulate, 2-hydroxyethylmethacrylate, 2-hydroxyethylacrylate, 2-(dimethylaminoethyl) methacrylate, N-vinyl pyrrolidone, methacrylamide, and/or N,N-dimethylacrylamide poly(methacrylic acid).

In various embodiments, the tissue thickness compensator may comprise a reinforcement material. In various embodiments, the reinforcement material may comprise at least one of the non-synthetic materials and synthetic materials described above. In various embodiments, the reinforcement material may comprise collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethylcellulose, chitan, chitosan, alginate, poly(lactic acid), poly(glycolic acid), poly(hydroxybutyrate), poly(phosphazine), polyesters, polyethylene glycols, polyalkyleneoxides, polyacrylamides, polyhydroxyethylmethylacrylate, polyvinylpyrrolidone, polyvinyl alcohols, poly(caprolactone), poly(dioxanone), polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and combinations thereof.

In various embodiments, the tissue thickness compensator may comprise a layer comprising the reinforcement material. In certain embodiments, a porous layer and/or a non-porous layer of a tissue thickness compensator may comprise the reinforcement material. For example, the porous layer may comprise the reinforcement material and the non-porous layer may not comprise the reinforcement material. In various embodiments, the reinforcement layer may comprise an inner layer intermediate a first non-porous layer and a second non-porous layer. In certain embodiments, the reinforcement layer may comprise an outer layer of the tissue thickness compensator. In certain embodiments, the reinforcement layer may comprise an exterior surface of the tissue thickness compensator.

In various embodiments, the reinforcement material may comprise meshes, monofilaments, multifilament braids, fibers, mats, felts, particles, and/or powders. In certain embodiments, the reinforcement material may be incorporated into a layer of the tissue thickness compensator. The reinforcement material may be incorporated into at least one of a non-porous layer and a porous layer. A mesh comprising the reinforcement material may be formed using conventional techniques, such as, for example, knitting, weaving, tatting, and/or knipling. In various embodiments, a plurality of reinforcement materials may be oriented in a random direction and/or a common direction. In certain embodiments, the common direction may be one of parallel to the staple line and perpendicular to the staple line, for example. For example, the monofilaments and/or multifilament braids may be oriented in a random direction and/or a common direction. The monofilaments and multifilament braids may be associated with the non-porous layer and/or the porous layer. In various embodiments, the tissue thickness compensator may comprise a plurality of reinforcement fibers oriented in a random direction within a non-porous layer. In various embodiments, the tissue thickness compensator may comprise a plurality of reinforcement fibers oriented in a common direction within a non-porous layer.

In various embodiments, referring to FIG. 199, an anvil 70300 may comprise a tissue thickness compensator 70305 comprising a first non-porous layer 70307 and a second non-porous layer 70309 sealingly enclosing a reinforcement layer 70310. In various embodiments, the reinforcement layer 70310 may comprise a hydrogel comprising ORC particles or fibers embedded therein, and the non-porous layers may comprise ORC. As shown in FIG. 199, the tissue thickness compensator 70305 may be configured to conform to the contour of the anvil 70300. The inner layer of the tissue thickness compensator 70305 may conform to the inner surface of the anvil 70300, which includes the forming pockets 70301.

The fibers may form a non-woven material, such as, for example, a mat and a felt. The fibers may have any suitable length, such as, for example from 0.1 mm to 100 mm and 0.4 mm to 50 mm. The reinforcement material may be ground to a powder. The powder may have a particle size from 10 micrometers to 1 cm, for example. The powder may be incorporated into the tissue thickness compensator.

In various embodiments, the tissue thickness compensator may be formed in situ. In various embodiments, the hydrogel may be formed in situ. The tissue thickness compensator may be formed in situ by covalent, ionic, and/or hydrophobic bonds. Physical (non-covalent) crosslinks may result from complexation, hydrogen bonding, desolvation, Van der Waals interactions, ionic bonding, and combinations thereof. Chemical (covalent) crosslinking may be accomplished by any of a number of mechanisms, including: free radical polymerization, condensation polymerization, anionic or cationic polymerization, step growth polymerization, electrophile-nucleophile reactions, and combinations thereof.

In various embodiments, in situ formation of the tissue thickness compensator may comprise reacting two or more precursors that are physically separated until contacted in situ and/or react to an environmental condition to react with each other to form the hydrogel. In situ polymerizable polymers may be prepared from precursor(s) that can be reacted to form a polymer at the surgical site. The tissue thickness compensator may be formed by crosslinking reactions of the precursor(s) in situ. In certain embodiments, the precursor may comprise an initiator capable of initiating a polymerization reaction for the formation of the in situ tissue thickness compensator. The tissue thickness compensator may comprise a precursor that can be activated at the time of application to create, in various embodiments, a crosslinked hydrogel. In situ formation of the tissue thickness compensator may comprise activating at least one precursor to form bonds to form the tissue thickness compensator. In various embodiments, activation may be achieved by changes in the physical conditions, biological conditions, and/or chemical conditions at the surgical site, including, but not limited to temperature, pH, electric fields, ionic strength, enzymatic and/or chemical reactions, electrical and/or magnetic stimuli, and other physiological and environmental variables. In various embodiments, the precursors may be contacted outside the body and introduced to the surgical site.

In various embodiments, the tissue thickness compensator may comprise one or more encapsulations, or cells, which can be configured to store at least one component therein. In certain embodiments, the encapsulation may be configured to store a hydrogel precursor therein. In certain embodiments, the encapsulation may be configured to store two components therein, for example. In certain embodiments, the encapsulation may be configured to store a first hydrogel precursor and a second hydrogel precursor therein. In certain embodiments, a first encapsulation may be configured to store a first hydrogel precursor therein and a second encapsulation may be configured to store a second hydrogel precursor therein. As described above, the encapsulations can be aligned, or at least substantially aligned, with the staple legs to puncture and/or otherwise rupture the encapsulations when the staple legs contact the encapsulation. In certain embodiments, the encapsulations may be compressed, crushed, collapsed, and/or otherwise ruptured when the staples are deployed. After the encapsulations have been ruptured, the component(s) stored therein can flow out of the encapsulation. The component stored therein may contact other components, layers of the tissue thickness compensator, and/or the tissue. In various embodiments, the other components may be flowing from the same or different encapsulations, provided in the layers of the tissue thickness compensator, and/or provided to the surgical site by the clinician. As a result of the above, the component(s) stored within the encapsulations can provide expansion and/or swelling of the tissue thickness compensator.

In various embodiments, the tissue thickness compensator may comprise a layer comprising the encapsulations. In various embodiments, the encapsulation may comprise a void, a pocket, a dome, a tube, and combinations thereof associated with the layer. In certain embodiments, the encapsulations may comprise voids in the layer. In at least one embodiment, the layer can comprise two layers that can be attached to one another wherein the encapsulations can be defined between the two layers. In certain embodiments, the encapsulations may comprise domes on the surface of the layer. For example, at least a portion of the encapsulations can be positioned within domes extending upwardly from the layer. In certain embodiments, the encapsulations may comprise pockets formed within the layer. In certain embodiments, a first portion of the encapsulations may comprise a dome and a second portion of the encapsulations may comprise a pocket. In certain embodiments, the encapsulations may comprise a tube embedded within the layer. In certain embodiments, the tube may comprise the non-synthetic materials and/or synthetic materials described herein, such as PLA. In at least one embodiment, the tissue thickness compensator may comprise a bioabsorbable foam, such as ORC, comprising PLA tubes embedded therein, and the tube may encapsulate a hydrogel, for example. In certain embodiments, the encapsulations may comprise discrete cells that are unconnected to each other. In certain embodiments, one or more of the encapsulations can be in fluid communication with each other via one or more passageways, conduits, and/or channels, for example, extending through the layer.

The rate of release of a component from the encapsulation may be controlled by the thickness of the tissue thickness compensator, the composition of tissue thickness compensator, the size of the component, the hydrophilicity of the component, and/or the physical and/or chemical interactions among the component, the composition of the tissue thickness compensator, and/or the surgical instrument, for example. In various embodiments, the layer can comprise one or more thin sections or weakened portions, such as partial perforations, for example, which can facilitate the incision of the layer and the rupture of the encapsulations. In various embodiments, the partial perforations may not completely extend through a layer while, in certain embodiments, perforations may completely extend through the layer.

Referring to FIGS. 194 and 195, in various embodiments, a tissue thickness compensator 70150 may comprise an outer layer 70152A and an inner layer 70152B comprising encapsulations 70154. In certain embodiments, the encapsulation may comprise a first encapsulated component and a second encapsulated component. In certain embodiments, the encapsulations may independently comprise one of a first encapsulated component and a second encapsulated component. The first encapsulated component may be separated from the second encapsulated component. The outer layer 70152A may comprise a tissue-contacting surface. The inner layer 70152B may comprise an instrument-contacting surface. The instrument-contacting surface 70152B may be releasably attached to the anvil 70156. The outer layer 70152A may be attached to the inner layer 70152B to define a void between the outer layer 70152A and inner layer 70152B. As shown in FIG. 194, each encapsulation 70154 may comprise a dome on the instrument-contacting surface of the inner layer 70152B. The dome may comprise partial perforations to facilitate the incision of the layer by the staple legs and the rupture of the encapsulation. As shown in the FIG. 195, the anvil 70156 can comprise a plurality of forming pocket rows 70158 wherein the domes of the encapsulations 70154 may be aligned with the forming pocket 70158. The tissue-contacting surface may comprise a flat surface lacking domes. In certain embodiments, the tissue-contacting surface may comprise one or more encapsulations, such as encapsulations 70154, for example, extending therefrom.

In various embodiments, an anvil may comprise a tissue thickness compensator comprising an encapsulated component comprising at least one microsphere particle. In certain embodiments, the tissue thickness compensator may comprise an encapsulation comprising a first encapsulated component and a second encapsulated component. In certain embodiments, the tissue thickness compensator may comprise an encapsulation comprising a first microsphere particle and a second microsphere particle.

In various embodiments, referring to FIG. 196, a stapling apparatus may comprise an anvil 70180 and a staple cartridge (illustrated in other figures). The staples 70190 of a staple cartridge can be deformed by an anvil 70180 when the anvil 70180 is moved into a closed position and/or by a staple driver system 70192 which moves the staples 70190 toward the closed anvil 70180. The legs 70194 of the staples may contact the anvil 70180 such that the staples 70190 are at least partially deformed. The anvil 70180 may comprise a tissue thickness compensator 70182 comprising an outer layer 70183A, an inner layer 70183B. The tissue thickness compensator 70182 may comprise a first encapsulated component and a second encapsulated component. In certain embodiments, the encapsulations 210185 can be aligned, or at least substantially aligned, such that, when the staple legs 70194 are pushed through the tissue T and the outer layer 70183A, the staple legs 70194 can puncture and/or otherwise rupture the encapsulations 70185. As shown in FIG. 196, the staple 70190C is in its fully fired position, the staple 70190B is in the process of being fired, and the staple 70190A is in its unfired position. The legs of staples 70190C and 70190B have moved through the tissue T, the outer layer 70183A, and the inner layer 70183B of the tissue thickness compensator 70182, and have contacted an anvil 70180 positioned opposite the staple cartridge. After the encapsulations 70185 have been ruptured, the encapsulated components can flow out and contact each other, bodily fluids, and/or the tissue T, for example. The encapsulated components may react to form a reaction product such as a hydrogel, for example, to expand between the tissue T and the base of the staple and to push the tissue T against the legs of the staple. In various circumstances, as a result of the above, the tissue thickness compensator can be configured to consume any gaps within the staple entrapment area.

In various embodiments, the tissue thickness compensator may be suitable for use with a surgical instrument. As described above the tissue thickness compensator may be associated with the staple cartridge and/or the anvil. The tissue thickness compensator may be configured into any shape, size and/or dimension suitable to fit the staple cartridge and/or anvil. As described herein, the tissue thickness compensator may be releasably attached to the staple cartridge and/or anvil. The tissue thickness compensator may be attached to the staple cartridge and/or anvil in any mechanical and/or chemical manner capable of retaining the tissue thickness compensator in contact with the staple cartridge and/or anvil prior to and during the stapling process. The tissue thickness compensator may be removed or released from the staple cartridge and/or anvil after the staple penetrates the tissue thickness compensator. The tissue thickness compensator may be removed or released from the staple cartridge and/or anvil as the staple cartridge and/or anvil is moved away from the tissue thickness compensator.

Referring to FIGS. 191-193, stapling apparatus 70118 may comprise an anvil 70120 and a staple cartridge 70122 comprising a firing member 70124, a plurality of staples 70128, a knife edge 70129, and a tissue thickness compensator 70130. The tissue thickness compensator 70130 may comprise at least one encapsulated component. The encapsulated component may be ruptured when the tissue thickness compensator is compressed, stapled, and/or cut. Referring to FIG. 192, for example, the staples 70128 can be deployed between an unfired position and a fired position such that the staple legs move through the tissue thickness compensator 70130, penetrate through a bottom surface and a top surface of the tissue thickness compensator 70130, penetrate the tissue T, and contact an anvil 70120 positioned opposite the staple cartridge 70118. The encapsulated components may react with each other, a hydrophilic powder embedded or dispersed in the tissue thickness compensator, and/or bodily fluids to expand or swell the tissue thickness compensator 70130. As the legs are deformed against the anvil, the legs of each staple can capture a portion of the tissue thickness compensator 70130 and a portion of the tissue T within each staple 70128 and apply a compressive force to the tissue T. As shown in FIGS. 192 and 193, the tissue thickness compensator 70130 can compensate for the thickness of the tissue T captured within each staple 70128.

Referring to FIG. 197, a surgical instrument 70200 may comprise an anvil 70205 comprising an upper tissue thickness compensator 70210 and a staple cartridge 70215 comprising a lower tissue thickness compensator comprising an outer layer 70220 and an inner layer 70225. The upper tissue thickness compensator 70210 can be positioned on a first side of the targeted tissue and the lower tissue thickness compensator can be positioned on a second side of the tissue. In certain embodiments, the upper tissue thickness compensator 70210 may comprise ORC, the outer layer of the lower tissue thickness compensator may comprise a hydrogel having ORC particles embedded therein, and the inner layer of the lower tissue thickness compensator may comprise ORC, for example.

Referring to FIGS. 200-202, in various embodiments, a surgical instrument 70400 may comprise a staple cartridge 70405 and an anvil 70410. The staple cartridge 70405 may comprise a tissue thickness compensator 70415 including bioabsorbable foam. In various embodiments, the bioabsorbable foam can comprise an encapsulation which comprises an encapsulated component 70420. The bioabsorbable foam may comprise ORC and the encapsulated component may comprise a medicament, for example. The tissue thickness compensator 70415 of the anvil 70410 may comprise an inner layer 70425 and an outer layer 70430. The inner layer 70425 may comprise a bioabsorbable foam, and the outer layer 70430 may comprise a hydrogel, optionally comprising reinforcement materials, for example. During an exemplary firing sequence, referring primarily to FIG. 201, a sled 70435 can first contact staple 70440A and begin to lift the staple upwardly. As the sled 70435 is advanced further distally, the sled 70435 can begin to lift staples 70440B-D, and any other subsequent staples, in a sequential order. The sled 70435 can drive the staples 70440 upwardly such that the legs of the staples contact the opposing anvil 70410 and are deformed to a desired shape. With regard to the firing sequence illustrated in FIG. 201, the staples 70440A-C have been moved into their fully fired positions, the staple 70440D is in the process of being fired, and the staple 70420E is still in its unfired position. The encapsulated component 70470 may be ruptured by the staple legs during the exemplary firing sequence. The encapsulated component 70420 may flow from the encapsulation around the staple legs to contact the tissue T. In various circumstances, additional compression of the tissue thickness compensator can squeeze additional medicament out of the encapsulation. In various embodiments, the medicament can immediately treat the tissue and can reduce bleeding from the tissue.

In various circumstances, a surgeon, or other clinician, may deliver a fluid to the tissue thickness compensator to manufacture a tissue thickness compensator comprising at least one medicament stored and/or absorbed therein. In various embodiments, a staple cartridge and/or anvil may comprise a port configured to provide access to the tissue thickness compensator. Referring to FIG. 203B, a staple cartridge 70500 may comprise a port 70505 at a distal end thereof, for example. The port 70505 may be configured to receive a needle 70510, such as a fenestrated needle shown in FIG. 203A. In at least one embodiment, the clinician may insert a needle 70510 through the port 70505 into the tissue thickness compensator 70515 to deliver the fluid to the tissue thickness compensator 70515. In various embodiments, the fluid may comprise a medicament and hydrogel precursor, for example. As described above, the fluid may be released from tissue thickness compensator to the tissue when the tissue thickness compensator is ruptured and/or compressed. For example, the medicament may be released from the tissue thickness compensator 70515 as the tissue thickness compensator 70515 biodegrades.

Figure 14:
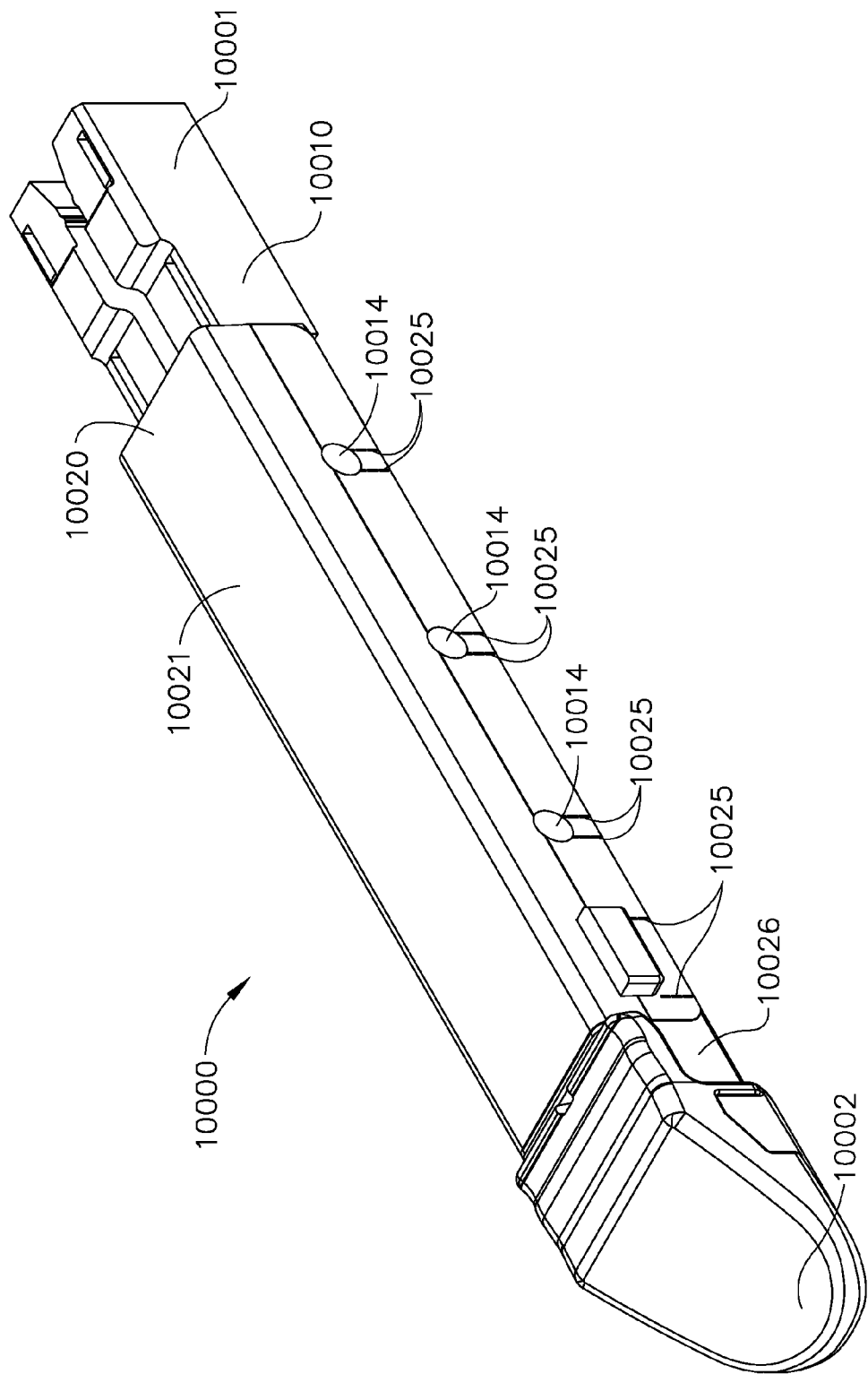
FIG. 14 is a perspective view of a staple cartridge comprising a rigid support portion and a compressible tissue thickness compensator for use with a surgical stapling instrument in accordance with at least one embodiment of the invention.
Figure 16:
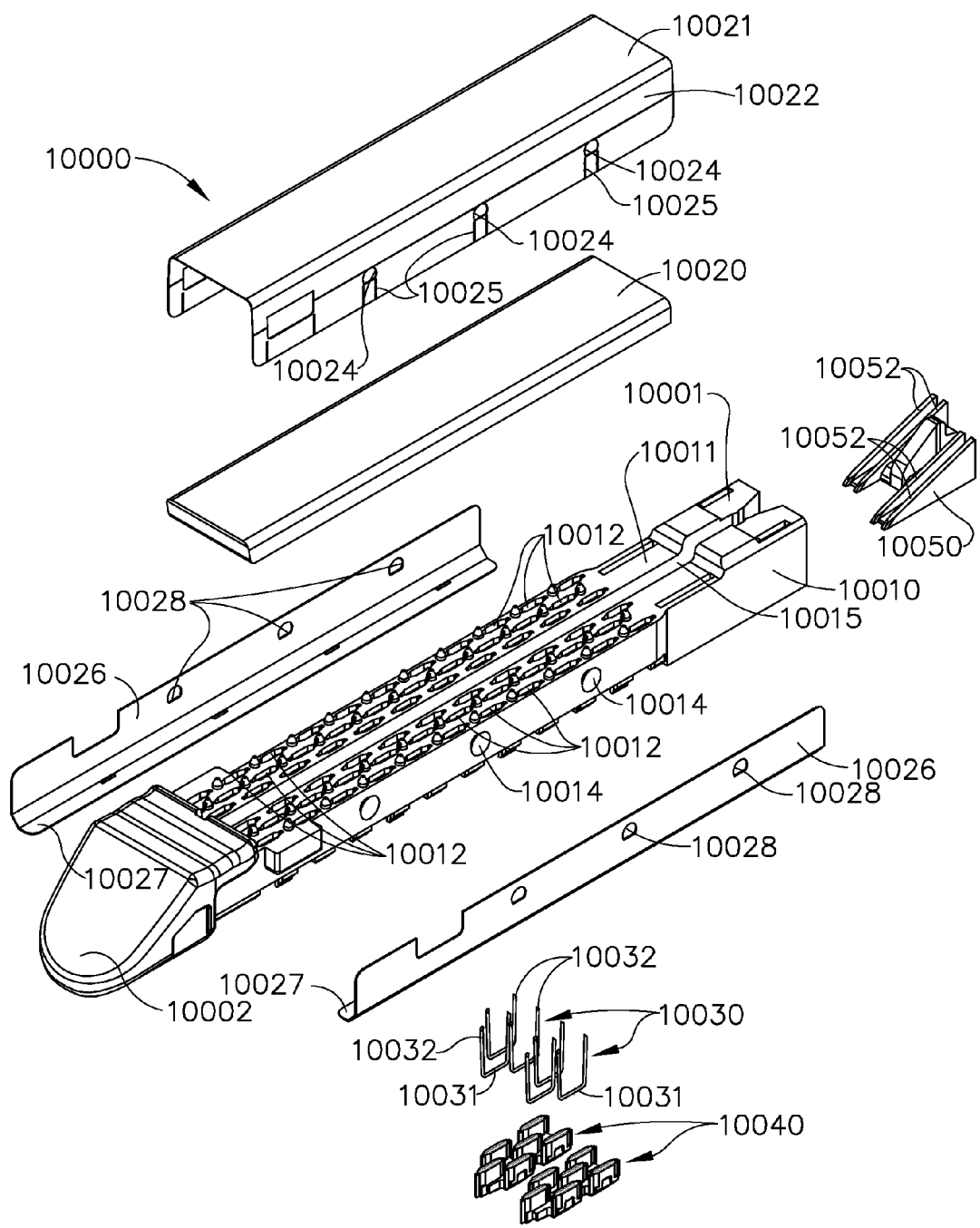
FIG. 16 is a fully exploded view of the staple cartridge of FIG. 14.
Figure 17:
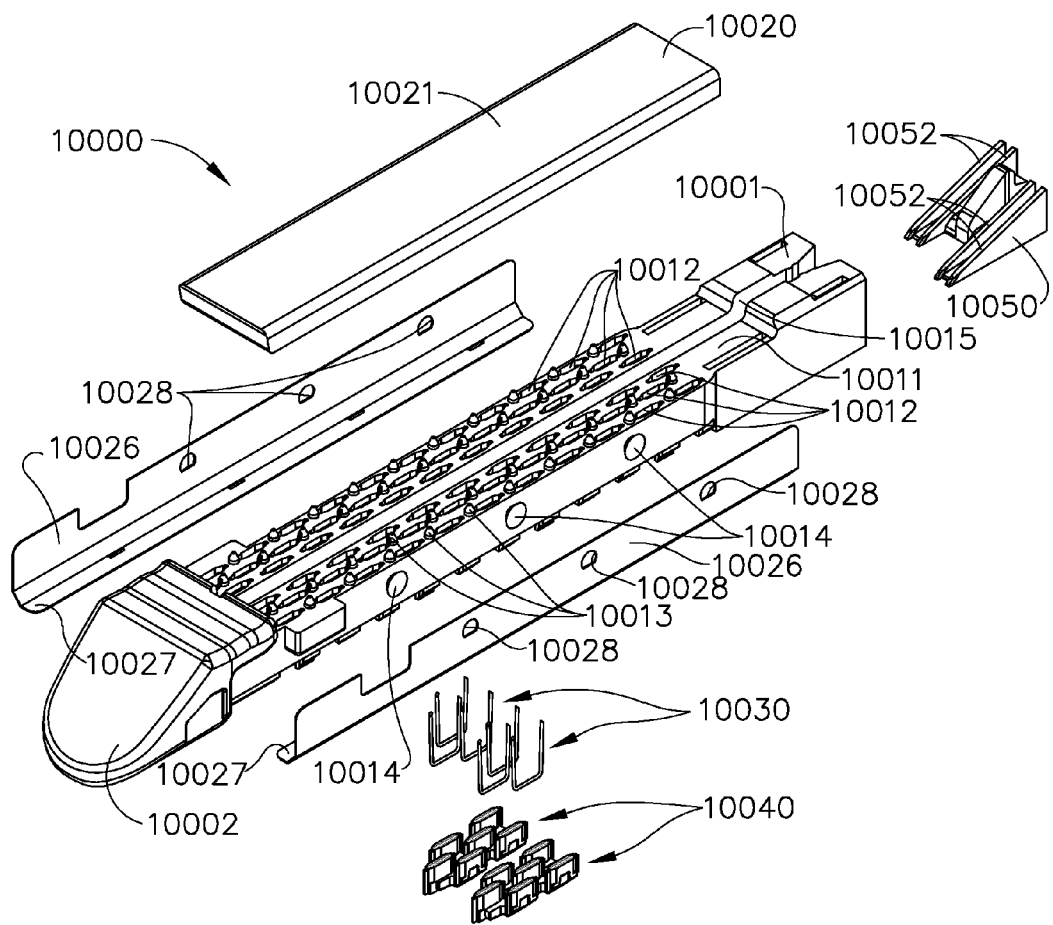
FIG. 17 is another exploded view of the staple cartridge of FIG. 14 without a warp covering the tissue thickness compensator.
Figure 18:
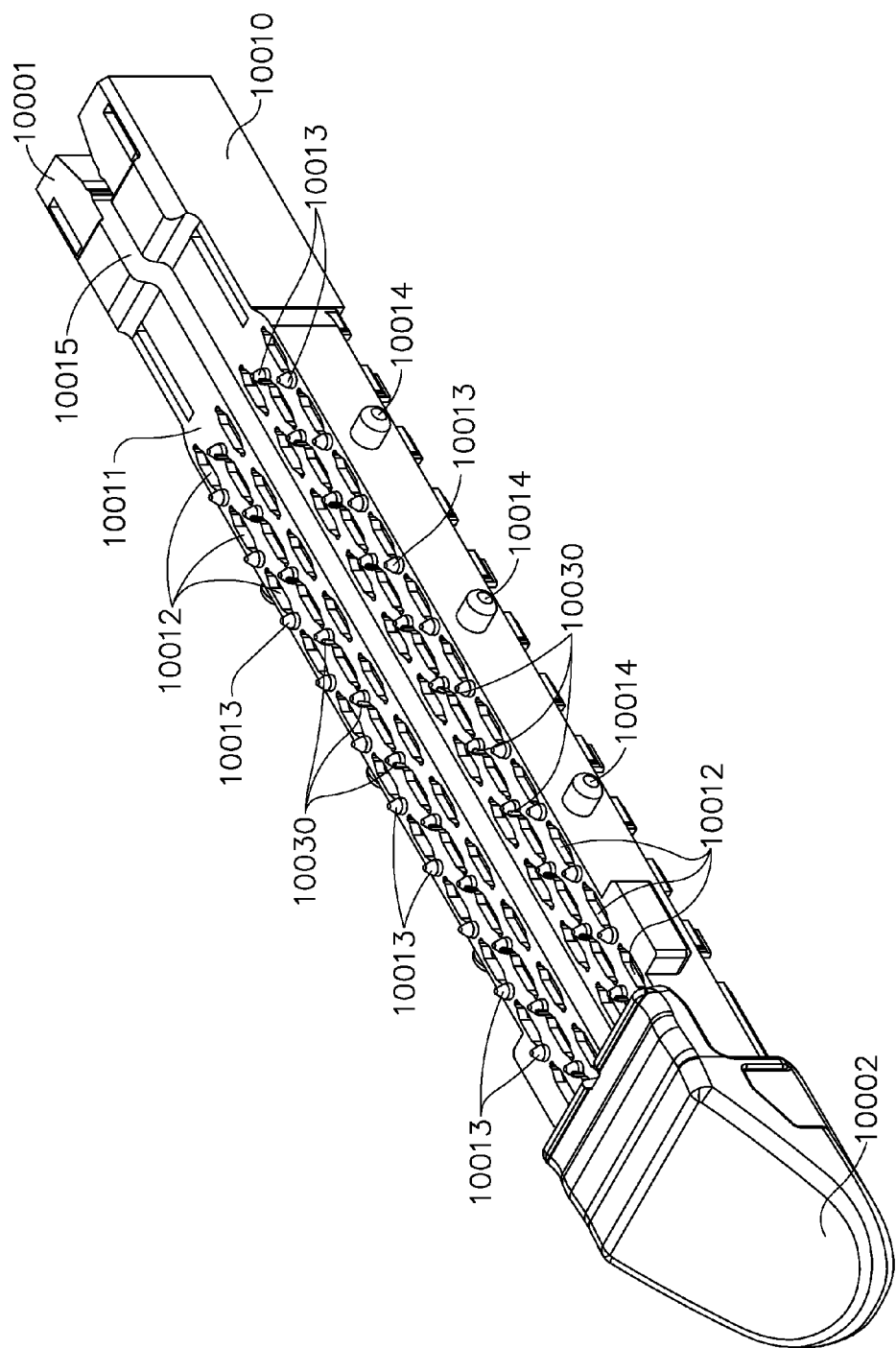
FIG. 18 is a perspective view of a cartridge body, or support portion, of the staple cartridge of FIG. 14.
Figure 19:
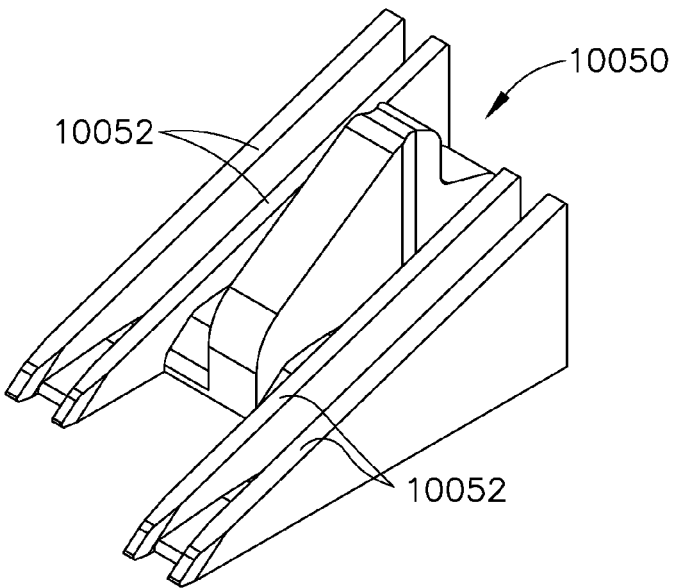
FIG. 19 is a top perspective view of a sled movable within the staple cartridge of FIG. 14 to deploy staples from the staple cartridge.
Figure 20:
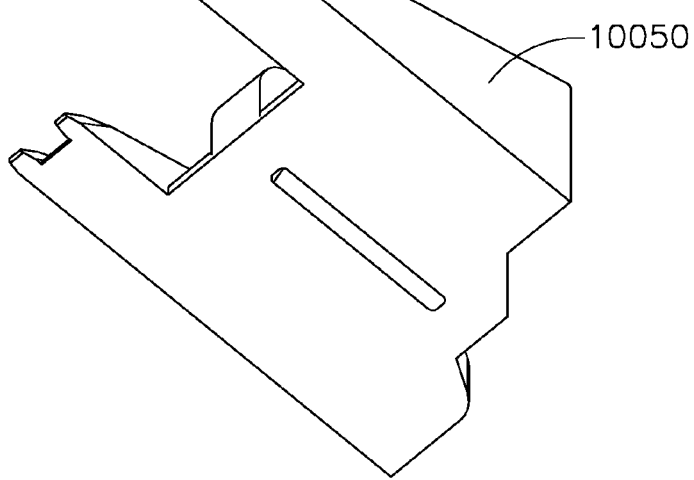
FIG. 20 is a bottom perspective view of the sled of FIG. 19.
Figure 21:
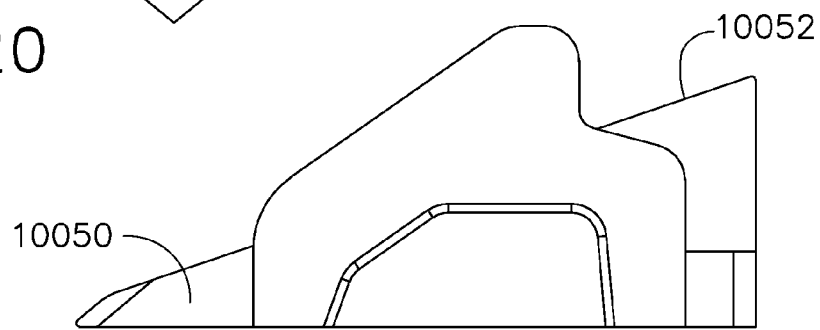
FIG. 21 is an elevational view of the sled of FIG. 19.
Figure 22:
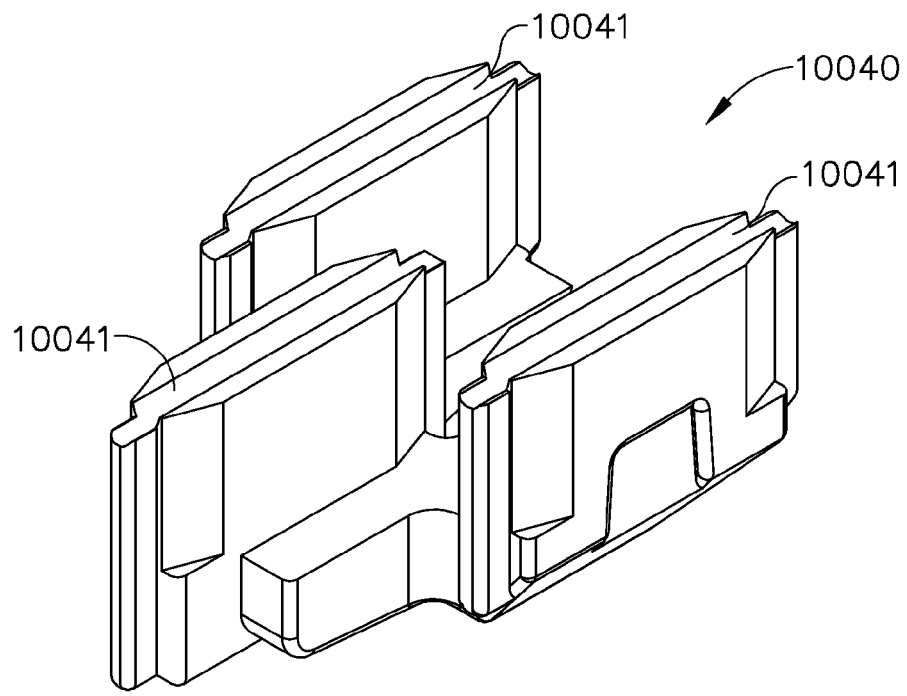
FIG. 22 is a top perspective view of a driver configured to support one or more staples and to be lifted upwardly by the sled of FIG. 19 to eject the staples from the staple cartridge.
Figure 23:
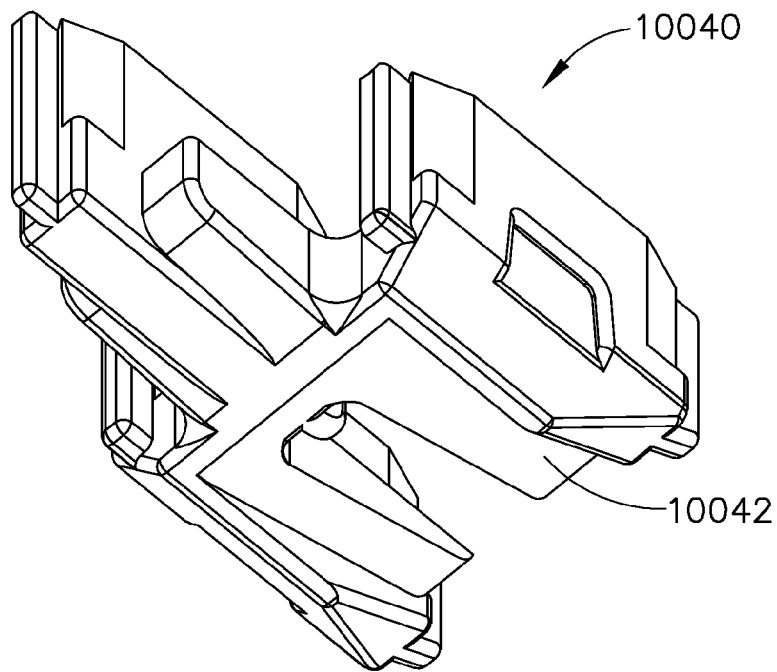
FIG. 23 is a bottom perspective view of the driver of FIG. 22.

In various embodiments, referring now to FIG. 14, a staple cartridge, such as staple cartridge 10000, for example, can comprise a support portion 10010 and a compressible tissue thickness compensator 10020. Referring now to FIGS. 16-18, the support portion 10010 can comprise a deck surface 10011 and a plurality of staple cavities 10012 defined within the support portion 10010. Each staple cavity 10012 can be sized and configured to removably store a staple, such as a staple 10030, for example, therein. The staple cartridge 10000 can further comprise a plurality of staple drivers 10040 which can each be configured to support one or more staples 10030 within the staple cavities 10012 when the staples 10030 and the staple drivers 10040 are in their unfired positions. In at least one such embodiment, referring primarily to FIGS. 22 and 23, each staple driver 10040 can comprise one or more cradles, or troughs, 10041, for example, which can be configured to support the staples and limit relative movement between the staples 10030 and the staple drivers 10040. In various embodiments, referring again to FIG. 16, the staple cartridge 10000 can further comprise a staple-firing sled 10050 which can be moved from a proximal end 10001 to a distal end 10002 of the staple cartridge in order to sequentially lift the staple drivers 10040 and the staples 10030 from their unfired positions toward an anvil positioned opposite the staple cartridge 10000. In certain embodiments, referring primarily to FIGS. 16 and 18, each staple 10030 can comprise a base 10031 and one or more legs 10032 extending from the base 10031 wherein each staple can be at least one of substantially U-shaped and substantially V-shaped, for example. In at least one embodiment, the staples 10030 can be configured such that the tips of the staple legs 10032 are recessed with respect to the deck surface 10011 of the support portion 10010 when the staples 10030 are in their unfired positions. In at least one embodiment, the staples 10030 can be configured such that the tips of the staple legs 10032 are flush with respect to the deck surface 10011 of the support portion 10010 when the staples 10030 are in their unfired positions. In at least one embodiment, the staples 10030 can be configured such that the tips of the staple legs 10032, or at least some portion of the staple legs 10032, extend above the deck surface 10011 of the support portion 10010 when the staples 10030 are in their unfired positions. In such embodiments, the staple legs 10032 can extend into and can be embedded within the tissue thickness compensator 10020 when the staples 10030 are in their unfired positions. In at least one such embodiment, the staple legs 10032 can extend above the deck surface 10011 by approximately 0.075", for example. In various embodiments, the staple legs 10032 can extend above the deck surface 10011 by a distance between approximately 0.025" and approximately 0.125", for example. In certain embodiments, further to the above, the tissue thickness compensator 10020 can comprise an uncompressed thickness between approximately 0.08" and approximately 0.125", for example.

Figure 25:
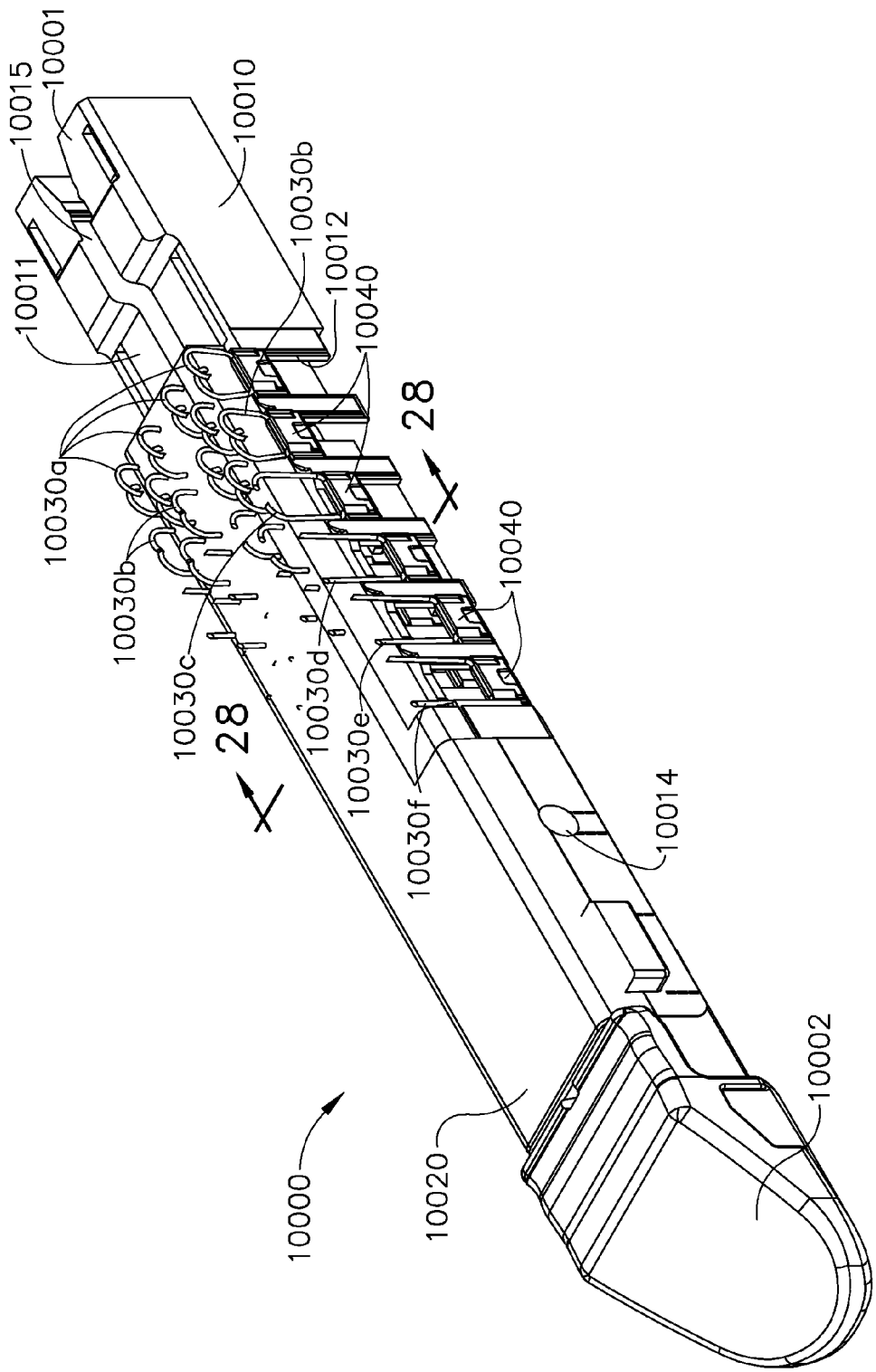
FIG. 25 is a partial cut away view of a staple cartridge comprising a rigid support portion and a compressible tissue thickness compensator illustrated with staples being moved from an unfired position to a fired position during a first sequence.
Figure 28:
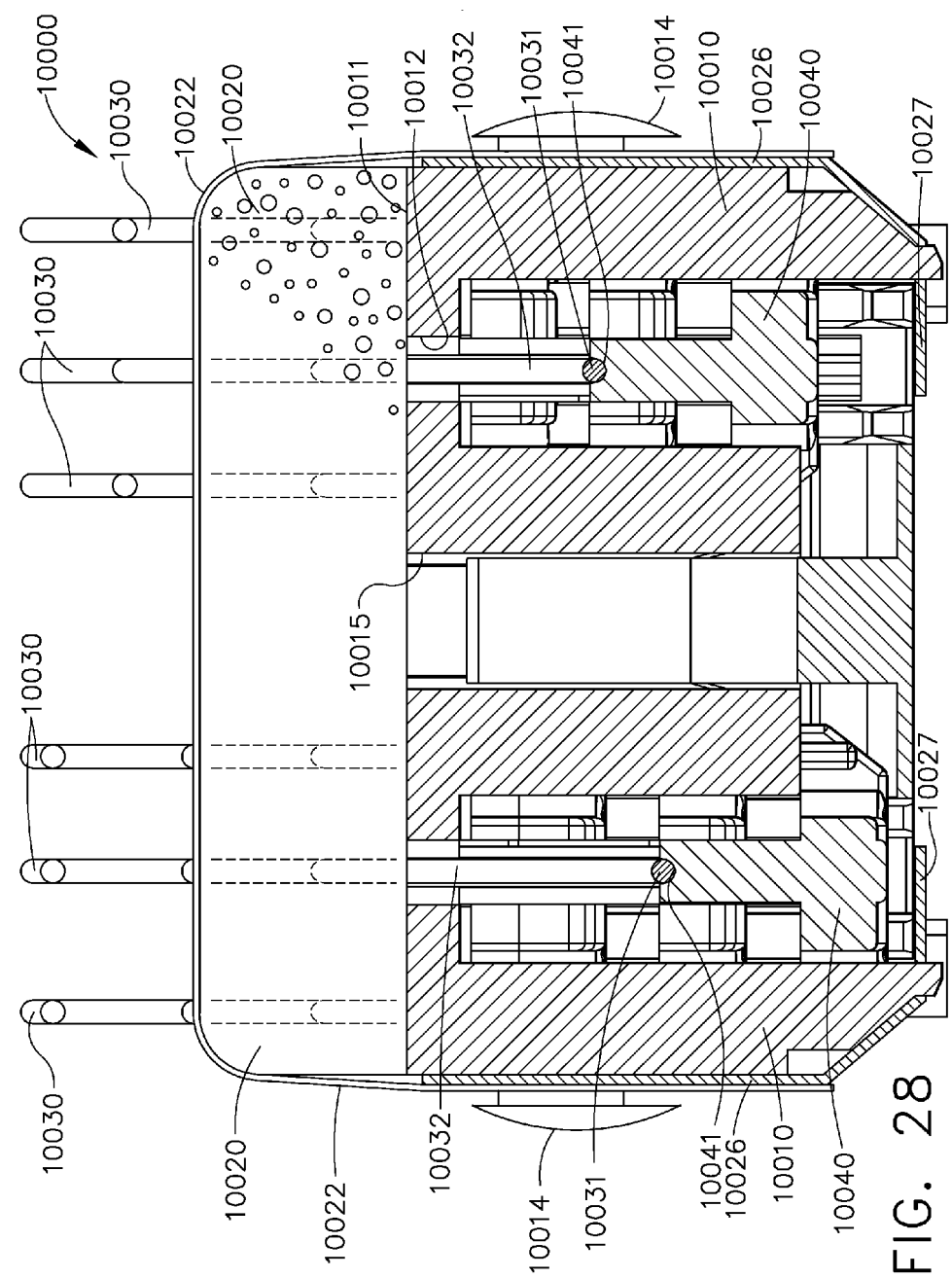
FIG. 28 is a cross-sectional end view of the staple cartridge of FIG. 25.
Figure 29:
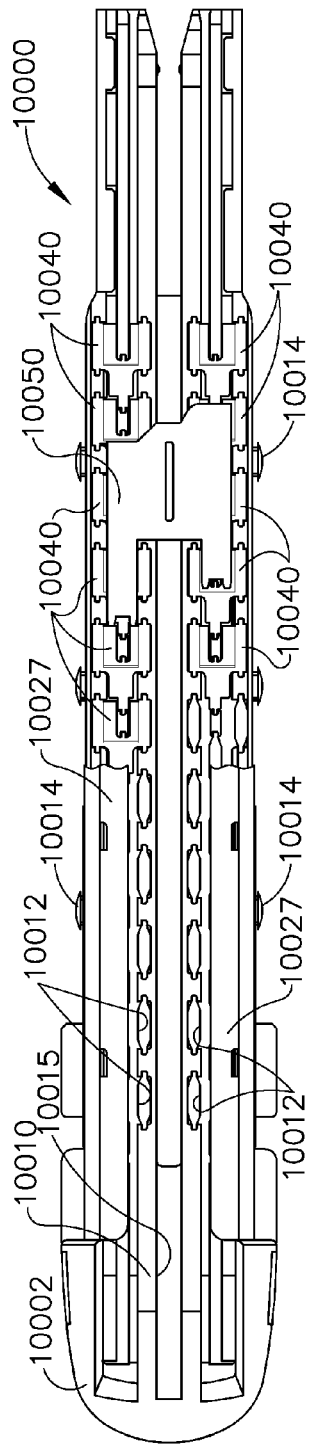
FIG. 29 is a bottom view of the staple cartridge of FIG. 25.
Figure 30:
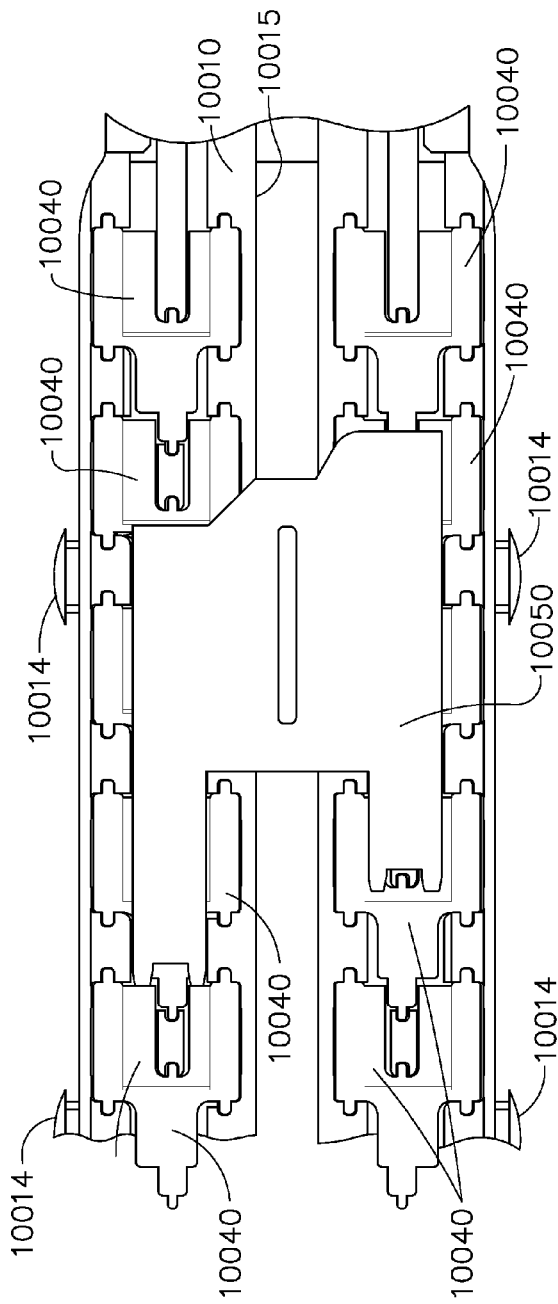
FIG. 30 is a detail bottom view of the staple cartridge of FIG. 25.

In use, further to the above and referring primarily to FIG. 31, an anvil, such as anvil, 10060, for example, can be moved into a closed position opposite the staple cartridge 10000. As described in greater detail below, the anvil 10060 can position tissue against the tissue thickness compensator 10020 and, in various embodiments, compress the tissue thickness compensator 10020 against the deck surface 10011 of the support portion 10010, for example. Once the anvil 10060 has been suitably positioned, the staples 10030 can be deployed, as also illustrated in FIG. 31. In various embodiments, as mentioned above, the staple-firing sled 10050 can be moved from the proximal end 10001 of the staple cartridge 10000 toward the distal end 10002, as illustrated in FIG. 32. As the sled 10050 is advanced, the sled 10050 can contact the staple drivers 10040 and lift the staple drivers 10040 upwardly within the staple cavities 10012. In at least one embodiment, the sled 10050 and the staple drivers 10040 can each comprise one or more ramps, or inclined surfaces, which can co-operate to move the staple drivers 10040 upwardly from their unfired positions. In at least one such embodiment, referring to FIGS. 19-23, each staple driver 10040 can comprise at least one inclined surface 10042 and the sled 10050 can comprise one or more inclined surfaces 10052 which can be configured such that the inclined surfaces 10052 can slide under the inclined surface 10042 as the sled 10050 is advanced distally within the staple cartridge. As the staple drivers 10040 are lifted upwardly within their respective staple cavities 10012, the staple drivers 10040 can lift the staples 10030 upwardly such that the staples 10030 can emerge from their staple cavities 10012 through openings in the staple deck 10011. During an exemplary firing sequence, referring primarily to FIGS. 25-27, the sled 10050 can first contact staple 10030*a* and begin to lift the staple 10030*a* upwardly. As the sled 10050 is advanced further distally, the sled 10050 can begin to lift staples 10030*b*, 10030*c*, 10030*d*, 10030*e*, and 10030*f*, and any other subsequent staples, in a sequential order. As illustrated in FIG. 27, the sled 10050 can drive the staples 10030 upwardly such that the legs 10032 of the staples contact the opposing anvil, are deformed to a desired shape, and ejected therefrom the support portion 10010. In various circumstances, the sled 10030 can move several staples upwardly at the same time as part of a firing sequence. With regard to the firing sequence illustrated in FIG. 27, the staples 10030*a* and 10030*b* have been moved into their fully fired positions and ejected from the support portion 10010, the staples 10030*c* and 10030*d* are in the process of being fired and are at least partially contained within the support portion 10010, and the staples 10030*e* and 10030*f* are still in their unfired positions.

Figure 33:
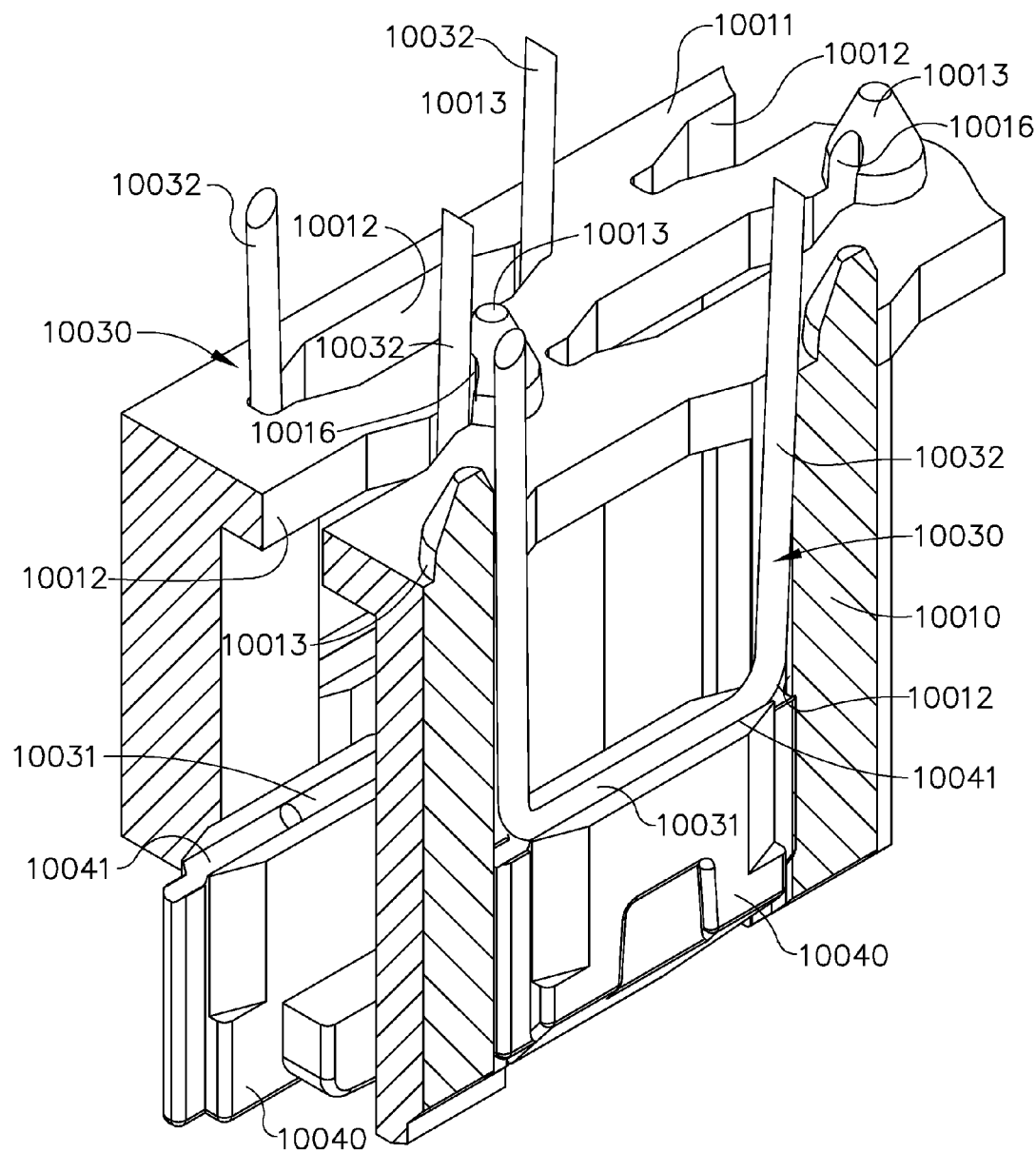
FIG. 33 is a partial detail view of the staple cartridge of FIG. 31 illustrating the staples in an unfired position.
Figure 34:
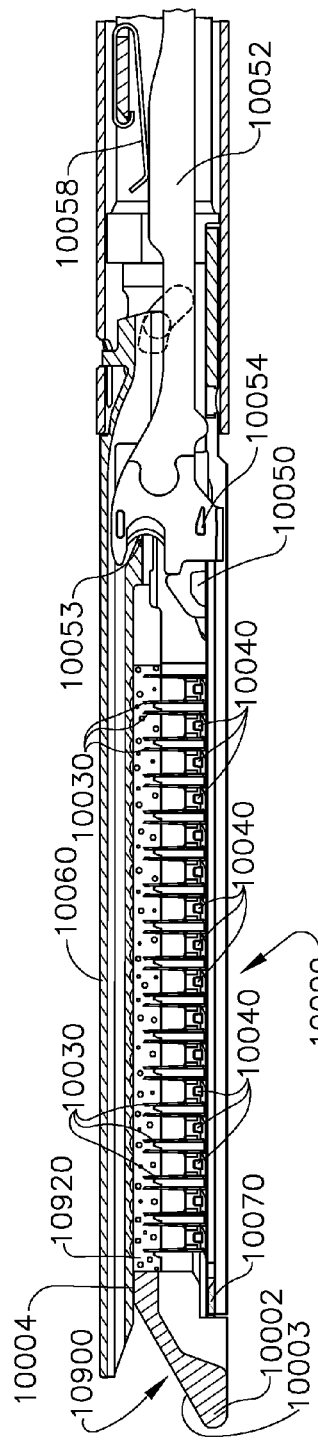
FIG. 34 is a cross-sectional elevational view of a staple cartridge comprising a rigid support portion and a compressible tissue thickness compensator illustrating the staples in an unfired position.
Figure 35:
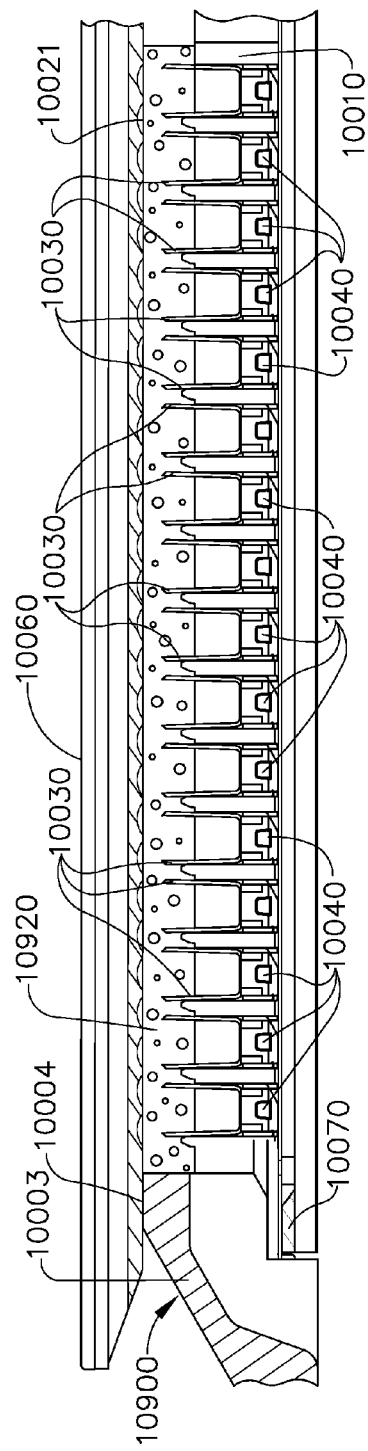
FIG. 35 is a detail view of the staple cartridge of FIG. 34.
Figure 36:
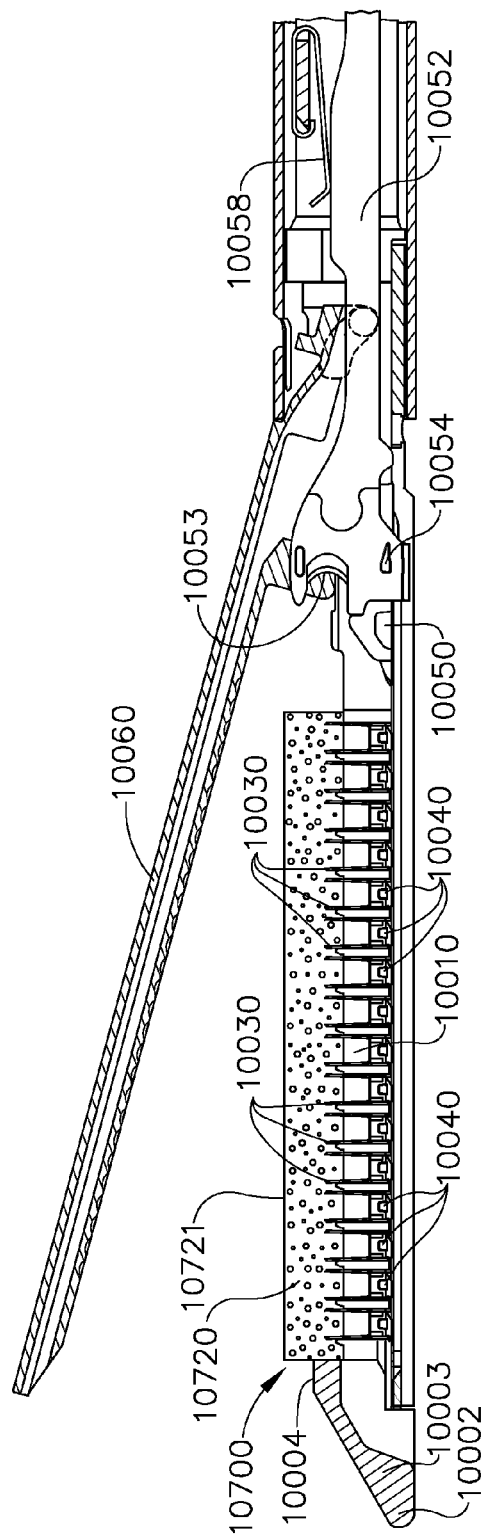
FIG. 36 is an elevational view of an anvil in an open position and a staple cartridge comprising a rigid support portion and a compressible tissue thickness compensator illustrating the staples in an unfired position.

As discussed above, and referring to FIG. 33, the staple legs 10032 of the staples 10030 can extend above the deck surface 10011 of the support portion 10010 when the staples 10030 are in their unfired positions. With further regard to this firing sequence illustrated in FIG. 27, the staples 10030*e* and 10030*f* are illustrated in their unfired position and their staple legs 10032 extend above the deck surface 10011 and into the tissue thickness compensator 10020. In various embodiments, the tips of the staple legs 10032, or any other portion of the staple legs 10032, may not protrude through a top tissue-contacting surface 10021 of the tissue thickness compensator 10020 when the staples 10030 are in their unfired positions. As the staples 10030 are moved from their unfired positions to their fired positions, as illustrated in FIG. 27, the tips of the staple legs can protrude through the tissue-contacting surface 10032. In various embodiments, the tips of the staple legs 10032 can comprise sharp tips which can incise and penetrate the tissue thickness compensator 10020. In certain embodiments, the tissue thickness compensator 10020 can comprise a plurality of apertures which can be configured to receive the staple legs 10032 and allow the staple legs 10032 to slide relative to the tissue thickness compensator 10020. In certain embodiments, the support portion 10010 can further comprise a plurality of guides 10013 extending from the deck surface 10011. The guides 10013 can be positioned adjacent to the staple cavity openings in the deck surface 10011 such that the staple legs 10032 can be at least partially supported by the guides 10013. In certain embodiments, a guide 10013 can be positioned at a proximal end and/or a distal end of a staple cavity opening. In various embodiments, a first guide 10013 can be positioned at a first end of each staple cavity opening and a second guide 10013 can be positioned at a second end of each staple cavity opening such that each first guide 10013 can support a first staple leg 10032 of a staple 10030 and each second guide 10013 can support a second staple leg 10032 of the staple. In at least one embodiment, referring to FIG. 33, each guide 10013 can comprise a groove or slot, such as groove 10016, for example, within which a staple leg 10032 can be slidably received. In various embodiments, each guide 10013 can comprise a cleat, protrusion, and/or spike that can extend from the deck surface 10011 and can extend into the tissue thickness compensator 10020. In at least one embodiment, as discussed in greater detail below, the cleats, protrusions, and/or spikes can reduce relative movement between the tissue thickness compensator 10020 and the support portion 10010. In certain embodiments, the tips of the staple legs 10032 may be positioned within the guides 10013 and may not extend above the top surfaces of the guides 10013 when the staples 10030 are in their unfired position. In at least such embodiment, the guides 10013 can define a guide height and the staples 10030 may not extend above this guide height when they are in their unfired position.

Figure 15:
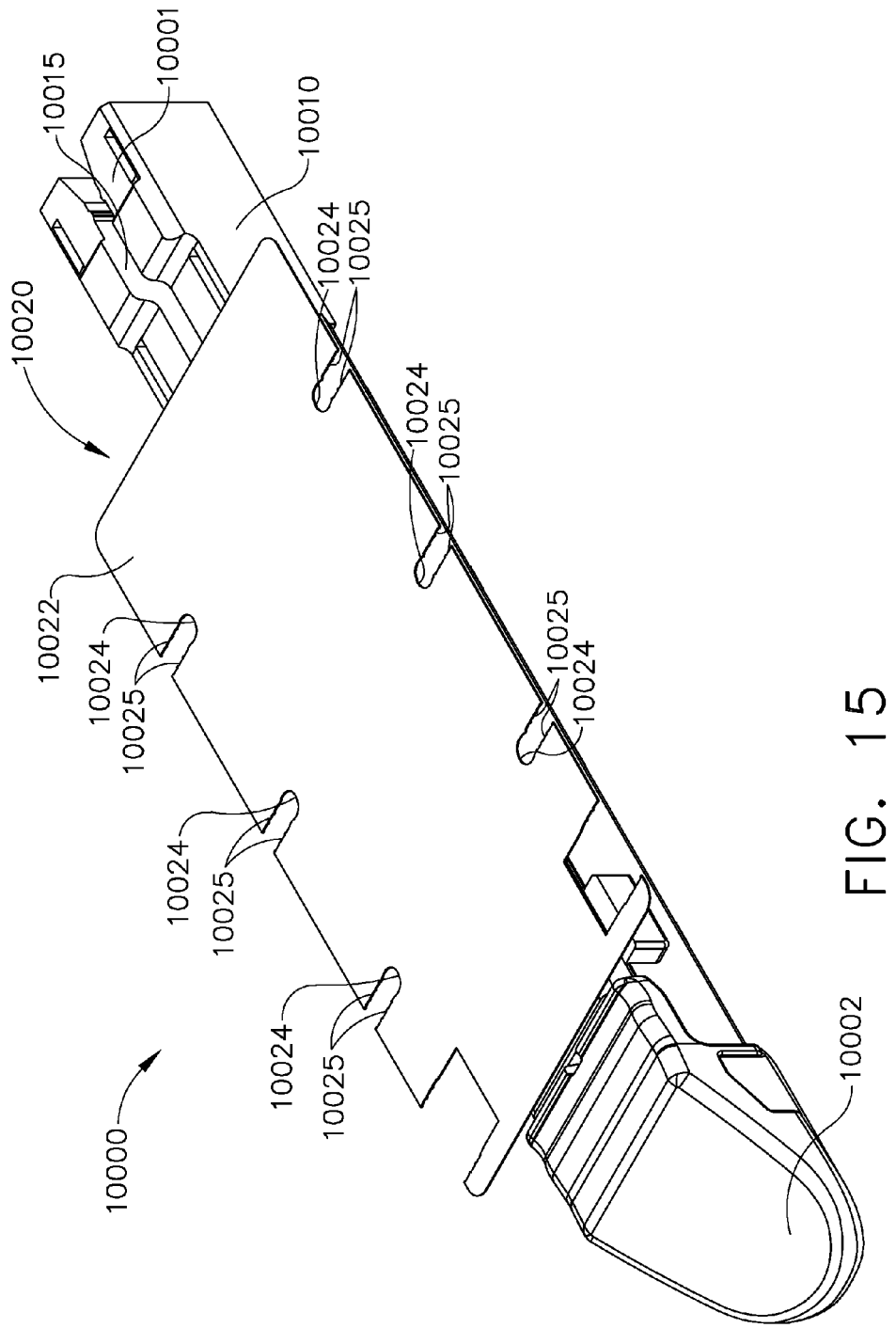
FIG. 15 is a partially exploded view of the staple cartridge of FIG. 14.
Figure 24:
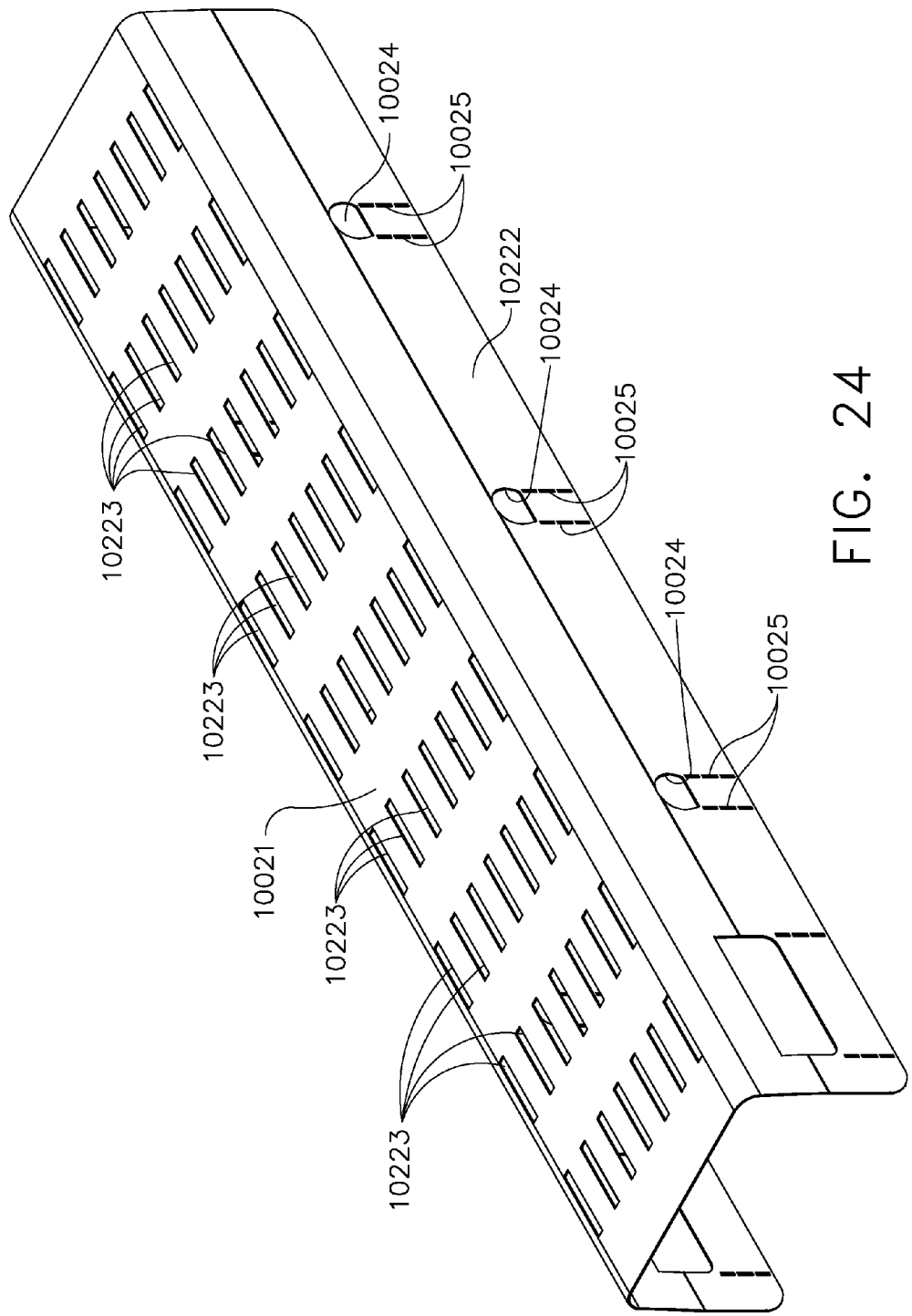
FIG. 24 is a wrap configured to at least partially surround a compressible tissue thickness compensator of a staple cartridge.

In various embodiments, a tissue thickness compensator, such as tissue thickness compensator 10020, for example, can be comprised of a single sheet of material. In at least one embodiment, a tissue thickness compensator can comprise a continuous sheet of material which can cover the entire top deck surface 10011 of the support portion 10010 or, alternatively, cover less than the entire deck surface 10011. In certain embodiments, the sheet of material can cover the staple cavity openings in the support portion 10010 while, in other embodiments, the sheet of material can comprise openings which can be aligned, or at least partially aligned, with the staple cavity openings. In various embodiments, a tissue thickness compensator can be comprised of multiple layers of material. In some embodiments, referring now to FIG. 15, a tissue thickness compensator can comprise a compressible core and a wrap surrounding the compressible core. In certain embodiments, a wrap 10022 can be configured to releasably hold the compressible core to the support portion 10010. In at least one such embodiment, the support portion 10010 can comprise one or more projections, such as projections 10014 (FIG. 18), for example, extending therefrom which can be received within one or more apertures and/or slots, such as apertures 10024, for example, defined in the wrap 10022. The projections 10014 and the apertures 10024 can be configured such that the projections 10014 can retain the wrap 10022 to the support portion 10010. In at least one embodiment, the ends of the projections 10014 can be deformed, such as by a heat-stake process, for example, in order to enlarge the ends of the projections 10014 and, as a result, limit the relative movement between the wrap 10022 and the support portion 10010. In at least one embodiment, the wrap 10022 can comprise one or more perforations 10025 which can facilitate the release of the wrap 10022 from the support portion 10010, as illustrated in FIG. 15. Referring now to FIG. 24, a tissue thickness compensator can comprise a wrap 10222 including a plurality of apertures 10223, wherein the apertures 10223 can be aligned, or at least partially aligned, with the staple cavity openings in the support portion 10010. In certain embodiments, the core of the tissue thickness compensator can also comprise apertures which are aligned, or at least partially aligned, with the apertures 10223 in the wrap 10222. In other embodiments, the core of the tissue thickness compensator can comprise a continuous body and can extend underneath the apertures 10223 such that the continuous body covers the staple cavity openings in the deck surface 10011.

In various embodiments, as described above, a tissue thickness compensator can comprise a wrap for releasably holding a compressible core to the support portion 10010. In at least one such embodiment, referring to FIG. 16, a staple cartridge can further comprise retainer clips 10026 which can be configured to inhibit the wrap, and the compressible core, from prematurely detaching from the support portion 10010. In various embodiments, each retainer clip 10026 can comprise apertures 10028 which can be configured to receive the projections 10014 extending from the support portion 10010 such that the retainer clips 10026 can be retained to the support portion 10010. In certain embodiments, the retainer clips 10026 can each comprise at least one pan portion 10027 which can extend underneath the support portion 10010 and can support and retain the staple drivers 10040 within the support portion 10010. In certain embodiments, as described above, a tissue thickness compensator can be removably attached to the support portion 10010 by the staples 10030. More particularly, as also described above, the legs of the staples 10030 can extend into the tissue thickness compensator 10020 when the staples 10030 are in their unfired position and, as a result, releasably hold the tissue thickness compensator 10020 to the support portion 10010. In at least one embodiment, the legs of the staples 10030 can be in contact with the sidewalls of their respective staple cavities 10012 wherein, owing to friction between the staple legs 10032 and the sidewalls, the staples 10030 and the tissue thickness compensator 10020 can be retained in position until the staples 10030 are deployed from the staple cartridge 10000. When the staples 10030 are deployed, the tissue thickness compensator 10020 can be captured within the staples 10030 and held against the stapled tissue T. When the anvil is thereafter moved into an open position to release the tissue T, the support portion 10010 can be moved away from the tissue thickness compensator 10020 which has been fastened to the tissue. In certain embodiments, an adhesive can be utilized to removably hold the tissue thickness compensator 10020 to the support portion 10010. In at least one embodiment, a two-part adhesive can be utilized wherein, in at least one embodiment, a first part of the adhesive can be placed on the deck surface 10011 and a second part of the adhesive can be placed on the tissue thickness compensator 10020 such that, when the tissue thickness compensator 10020 is placed against the deck surface 10011, the first part can contact the second part to active the adhesive and detachably bond the tissue thickness compensator 10020 to the support portion 10010. In various embodiments, any other suitable means could be used to detachably retain the tissue thickness compensator to the support portion of a staple cartridge.

Figure 59:
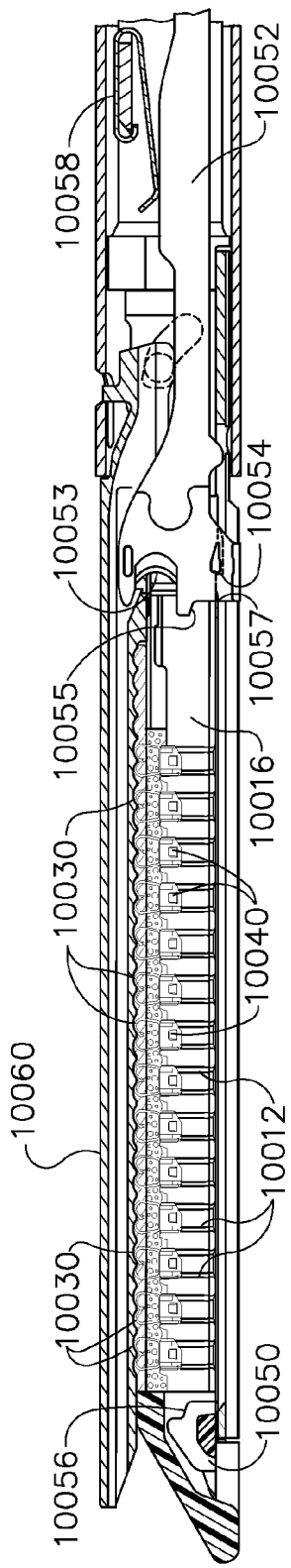
FIG. 59 is a cross-sectional view of the end effector of FIG. 56 illustrating the firing bar in a retracted position after being fired and the staple-firing sled left in its fully fired position.

In various embodiments, further to the above, the sled 10050 can be advanced from the proximal end 10001 to the distal end 10002 to fully deploy all of the staples 10030 contained within the staple cartridge 10000. In at least one embodiment, referring now to FIGS. 56-60, the sled 10050 can be advanced distally within a longitudinal cavity 10016 within the support portion 10010 by a firing member, or knife bar, 10052 of a surgical stapler. In use, the staple cartridge 10000 can be inserted into a staple cartridge channel in a jaw of the surgical stapler, such as staple cartridge channel 10070, for example, and the firing member 10052 can be advanced into contact with the sled 10050, as illustrated in FIG. 56. As the sled 10050 is advanced distally by the firing member 10052, the sled 10050 can contact the proximal-most staple driver, or drivers, 10040 and fire, or eject, the staples 10030 from the cartridge body 10010, as described above. As illustrated in FIG. 56, the firing member 10052 can further comprise a cutting edge 10053 which can be advanced distally through a knife slot in the support portion 10010 as the staples 10030 are being fired. In various embodiments, a corresponding knife slot can extend through the anvil positioned opposite the staple cartridge 10000 such that, in at least one embodiment, the cutting edge 10053 can extend between the anvil and the support portion 10010 and incise the tissue and the tissue thickness compensator positioned therebetween. In various circumstances, the sled 10050 can be advanced distally by the firing member 10052 until the sled 10050 reaches the distal end 10002 of the staple cartridge 10000, as illustrated in FIG. 58. At such point, the firing member 10052 can be retracted proximally. In some embodiments, the sled 10050 can be retracted proximally with the firing member 10052 but, in various embodiments, referring now to FIG. 59, the sled 10050 can be left behind in the distal end 10002 of the staple cartridge 10000 when the firing member 10052 is retracted. Once the firing member 10052 has been sufficiently retracted, the anvil can be re-opened, the tissue thickness compensator 10020 can be detached from the support portion 10010, and the remaining non-implanted portion of the expended staple cartridge 10000, including the support portion 10010, can be removed from the staple cartridge channel 10070.

Figure 60:
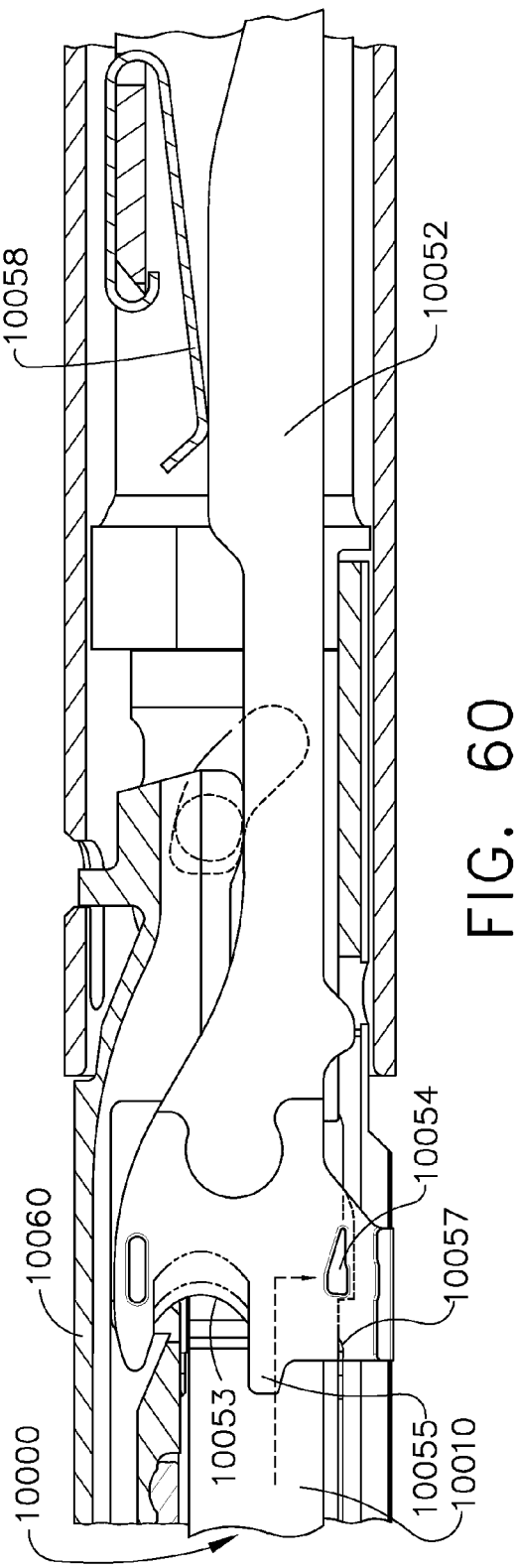
FIG. 60 is a detail view of the firing bar in the retracted position of FIG. 59.

After the expended staple cartridge 10000 has been removed from the staple cartridge channel, further to the above, a new staple cartridge 10000, or any other suitable staple cartridge, can be inserted into the staple cartridge channel 10070. In various embodiments, further to the above, the staple cartridge channel 10070, the firing member 10052, and/or the staple cartridge 10000 can comprise co-operating features which can prevent the firing member 10052 from being advanced distally a second, or subsequent, time without a new, or unfired, staple cartridge 10000 positioned in the staple cartridge channel 10070. More particularly, referring again to FIG. 56, as the firing member 10052 is advanced into contact with the sled 10050 and, when the sled 10050 is in its proximal unfired position, a support nose 10055 of the firing member 10052 can be positioned on and/or over a support ledge 10056 on the sled 10050 such that the firing member 10052 is held in a sufficient upward position to prevent a lock, or beam, 10054 extending from the firing member 10052 from dropping into a lock recess defined within the staple cartridge channel. As the lock 10054 will not drop into the lock recess, in such circumstances, the lock 10054 may not abut a distal sidewall 10057 of the lock recess as the firing member 10052 is advanced. As the firing member 10052 pushes the sled 10050 distally, the firing member 10052 can be supported in its upward firing position owing to the support nose 10055 resting on the support ledge 10056. When the firing member 10052 is retracted relative to the sled 10050, as discussed above and illustrated in FIG. 59, the firing member 10052 can drop downwardly from its upward position as the support nose 10055 is no longer resting on the support ledge 10056 of the sled 10050. In at least one such embodiment, the surgical staple can comprise a spring 10058, and/or any other suitable biasing element, which can be configured to bias the firing member 10052 into its downward position. Once the firing member 10052 has been completely retracted, as illustrated in FIG. 60, the firing member 10052 cannot be advanced distally through the spent staple cartridge 10000 once again. More particularly, the firing member 10052 can't be held in its upper position by the sled 10050 as the sled 10050, at this point in the operating sequence, has been left behind at the distal end 10002 of the staple cartridge 10000. Thus, as mentioned above, in the event that the firing member 10052 is advanced once again without replacing the staple cartridge, the lock beam 10054 will contact the sidewall 10057 of the lock recess which will prevent the firing member 10052 from being advanced distally into the staple cartridge 10000 once again. Stated another way, once the spent staple cartridge 10000 has been replaced with a new staple cartridge, the new staple cartridge will have a proximally-positioned sled 10050 which can hold the firing member 10052 in its upper position and allow the firing member 10052 to be advanced distally once again.

As described above, the sled 10050 can be configured to move the staple drivers 10040 between a first, unfired position and a second, fired position in order to eject staples 10030 from the support portion 10010. In various embodiments, the staple drivers 10040 can be contained within the staple cavities 10012 after the staples 10030 have been ejected from the support portion 10010. In certain embodiments, the support portion 10010 can comprise one or more retention features which can be configured to block the staple drivers 10040 from being ejected from, or falling out of, the staple cavities 10012. In various other embodiments, the sled 10050 can be configured to eject the staple drivers 10040 from the support portion 10010 with the staples 10030. In at least one such embodiment, the staple drivers 10040 can be comprised of a bioabsorbable and/or biocompatible material, such as Ultem, for example. In certain embodiments, the staple drivers can be attached to the staples 10030. In at least one such embodiment, a staple driver can be molded over and/or around the base of each staple 10030 such that the driver is integrally formed with the staple. U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, filed on Sep. 29, 2006, is hereby incorporated by reference in its entirety.

As described above, a surgical stapling instrument can comprise a staple cartridge channel configured to receive a staple cartridge, an anvil rotatably coupled to the staple cartridge channel, and a firing member comprising a knife edge which is movable relative to the anvil and the staple cartridge channel. In use, a staple cartridge can be positioned within the staple cartridge channel and, after the staple cartridge has been at least partially expended, the staple cartridge can be removed from the staple cartridge channel and replaced with a new staple cartridge. In some such embodiments, the staple cartridge channel, the anvil, and/or the firing member of the surgical stapling instrument may be re-used with the replacement staple cartridge. In certain other embodiments, a staple cartridge may comprise a part of a disposable loading unit assembly which can include a staple cartridge channel, an anvil, and/or a firing member, for example, which can be replaced along with the staple cartridge as part of replacing the disposable loading unit assembly. Certain disposable loading unit assemblies are disclosed in U.S. patent application Ser. No. 12/031,817, entitled END EFFECTOR COUPLING ARRANGEMENTS FOR A SURGICAL CUTTING AND STAPLING INSTRUMENT, which was filed on Feb. 15, 2008, now U.S. Patent Application Publication No. 2009/0206131, the entire disclosure of which is incorporated by reference herein.

In various embodiments, the tissue thickness compensator may comprise an extrudable, a castable, and/or moldable composition comprising at least one of the synthetic and/or non-synthetic materials described herein. In various embodiments, the tissue thickness compensator may comprise a film or sheet comprising two or more layers. The tissue thickness compensator may be obtained using conventional methods, such as, for example, mixing, blending, compounding, spraying, wicking, solvent evaporating, dipping, brushing, vapor deposition, extruding, calendaring, casting, molding and the like. In extrusion, an opening may be in the form of a die comprising at least one opening to impart a shape to the emerging extrudate. In calendering, an opening may comprise a nip between two rolls. Conventional molding methods may include, but are not limited to, blow molding, injection molding, foam injection, compression molding, thermoforming, extrusion, foam extrusion, film blowing, calendaring, spinning, solvent welding, coating methods, such as dip coating and spin coating, solution casting and film casting, plastisol processing (including knife coating, roller coating and casting), and combinations thereof. In injection molding, an opening may comprise a nozzle and/or channels/runners and/or mold cavities and features. In compression molding, the composition may be positioned in a mold cavity, heated to a suitable temperature, and shaped by exposure to compression under relatively high pressure. In casting, the composition may comprise a liquid or slurry that may be poured or otherwise provided into, onto and/or around a mold or object to replicate features of the mold or object. After casting, the composition may be dried, cooled, and/or cured to form a solid.

In various embodiments, a method of manufacturing a tissue thickness compensator may generally comprise providing a tissue thickness compensator composition, liquifying the composition to make it flowable, and forming the composition in the molten, semi-molten, or plastic state into a layer and/or film having the desired thickness. Referring to FIG. 198A, a tissue thickness compensator may be manufactured by dissolving a hydrogel precursor in an aqueous solution, dispersing biocompatible particles and/or fibers therein, providing a mold having biocompatible particles therein, providing the solution into the mold, contacting an activator and the solution, and curing the solution to form the tissue thickness compensator comprising an outer layer comprise biocompatible particles and an inner layer comprising biocompatible particles embedded therein. A shown in FIG. 198A, a biocompatible layer 70250 may be provided in the bottom of a mold 70260, and an aqueous solution of a hydrogel precursor 70255 having biocompatible particles 70257 disposed therein may be provided to the mold 70260, and the aqueous solution may be cured to form a tissue thickness compensator having a first layer comprising a biocompatible material, such as ORC, for example, and a second layer comprising a hydrogel having biocompatible fibers, such as ORC fibers, disposed therein. The tissue thickness compensator may comprise a foam comprising an outer layer comprise biocompatible particles and an inner layer comprising biocompatible particles embedded therein. In at least one embodiment, a tissue thickness compensator may be manufactured by dissolving a sodium alginater in water, dispersing ORC particles therein, providing a mold having ORC particles therein, pouring the solution into the mold, spraying or infusing calcium chloride to contact the solution to initiate crosslinking of the sodium alginater, freeze drying the hydrogel to form the tissue thickness compensator comprising an outer layer comprising ORC and an inner layer comprising a hydrogel and ORC particles embedded therein.

Referring to FIG. 198B, in various embodiments, a method of manufacturing a trilayer tissue thickness compensator may generally comprise by dissolving a first hydrogel precursor in a first aqueous solution, dispersing biocompatible particles and/or fibers in the first aqueous solution, providing a mold 70260 having a first layer 70250 of biocompatible particles therein, providing the first aqueous solution into the mold, contacting an activator and the first aqueous solution, curing the first aqueous solution to form a second layer 70255, dissolving a second hydrogel precursor in a second aqueous solution, providing the second aqueous solution into the mold, curing the second aqueous solution to form a third layer 70265. In at least one embodiment, a trilayer tissue thickness compensator may be manufactured by dissolving a sodium alginater in water to form a first aqueous solution, dispersing ORC particles in the first aqueous solution, providing a mold having a first layer of ORC particles therein, pouring the first aqueous solution into the mold, spraying or infusing calcium chloride to contact the first aqueous solution to initiate crosslinking of the sodium alginater, freeze drying the first aqueous solution to form a second layer comprising a hydrogel having ORC particles embedded therein, dissolving a sodium alginater in water to form a second aqueous solution, pouring the second aqueous solution into the mold, spraying or infusing calcium chloride to contact the second aqueous solution to initiate crosslinking of the sodium alginater, freeze drying the second aqueous solution to form a third layer comprising a hydrogel.

In various embodiments, a method of manufacturing a tissue thickness compensator comprising at least one medicament stored and/or absorbed therein may generally comprise providing a tissue thickness compensator and contacting the tissue thickness compensator and the medicament to retain the medicament in the tissue thickness compensator. In at least one embodiment, a method of manufacturing a tissue thickness compensator comprising an antibacterial material may comprise providing a hydrogel, drying the hydrogel, swelling the hydrogel in an aqueous solution of silver nitrate, contacting the hydrogel and a solution of sodium chloride to form the tissue thickness compensator having antibacterial properties. The tissue thickness compensator may comprise silver dispersed therein.

Figure 78:
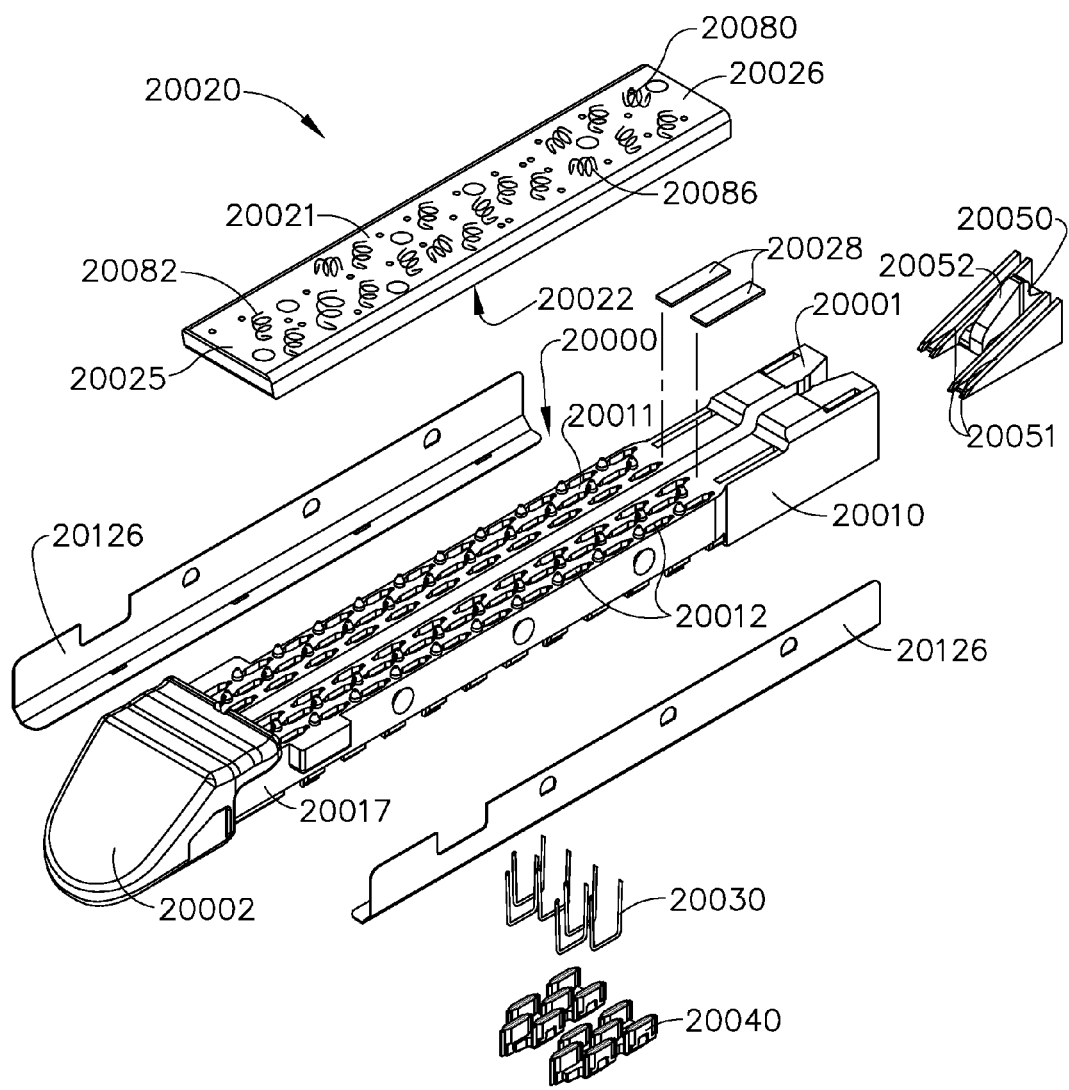
FIG. 78 is an exploded view of the fastener cartridge assembly of the end effector and tissue thickness compensator of FIG. 61.
Figure 79:
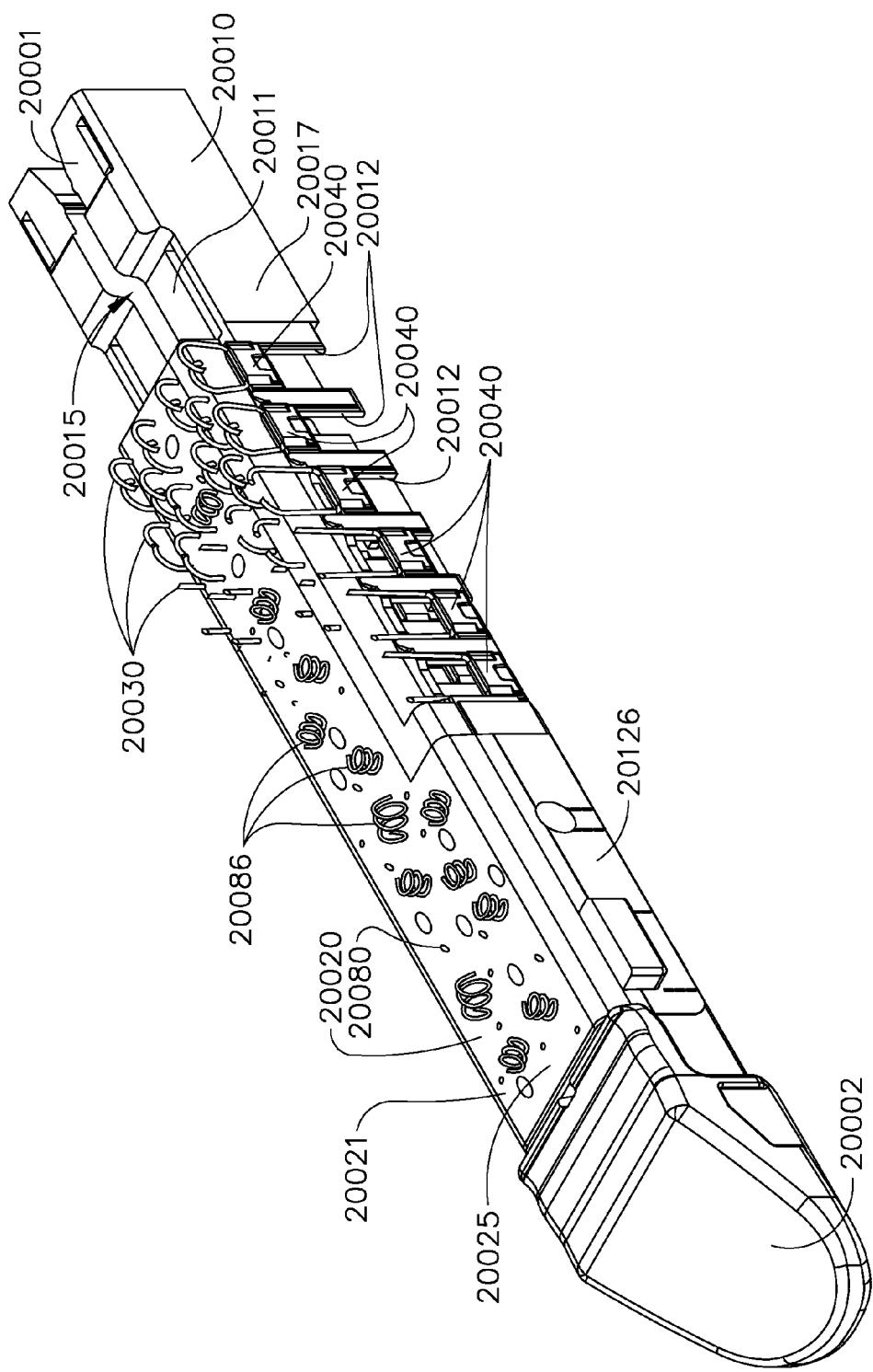
FIG. 79 is a partial cross-sectional view of the fastener cartridge assembly of FIG. 78 depicting unfired, partially fired, and fired fasteners.

Referring to FIG. 204, in various embodiments, a method for manufacturing a tissue thickness compensator may comprise co-extrusion and/or bonding. In various embodiments, the tissue thickness compensator 70550 may comprise a laminate comprising a first layer 70555 and a second layer 70560 sealingly enclosing an inner layer 70565 comprising a hydrogel, for example. The hydrogel may comprise a dry film, a dry foam, a powder, and/or granules, for example. The hydrogel may comprise super absorbent materials, such as, for example, polyvinylpyrrolidone, carboxy methylcellulose, poly sulfur propyl acrylate. The first and/or second layers may be made in-line by feeding raw materials of the first and second layers, respectively, into an extruder from a hopper, and thereafter supplying the first and second layers. The raw materials of the inner layer 70565 may be added to a hopper of an extruder. The raw materials can be dispersively mixed and compounded at an elevated temperature within the extruder. As the raw materials exit the die 70570 at an opening, the inner layer 70565 may be deposited onto a surface of the first layer 70555. In various embodiments, the tissue thickness compensator may comprise a foam, film, powder, and/or granule. The first and second layers 70555 and 70560 may be positioned in the face-to-face relationship. The second layer 70560 may be aligned with the first layer 70555 in a face-to-face relationship by a roller 70575. The first layer 70555 may adhere to the second layer 70560 wherein the first and second layers 70555, 70560 may physically entrap the inner layer 70565. The layers may be joined together under light pressure, under conventional calendar bonding processes, and/or through the use of adhesives, for example, to form the tissue thickness compensator 70550. In at least one embodiment, as shown in FIG. 78, the first and second layers 70555 and 70560 may be joined together through a rolling process utilizing a grooved roller 70580, for example. In various embodiments, as a result of the above, the inner layer 70565 may be contained and/or sealed by the first and second layers 70555 and 70560 which can collectively form an outer layer, or barrier. The outer layer may prevent or reduce moisture from contacting the inner layer 70565 until the outer layer is ruptured.

Figure 61:
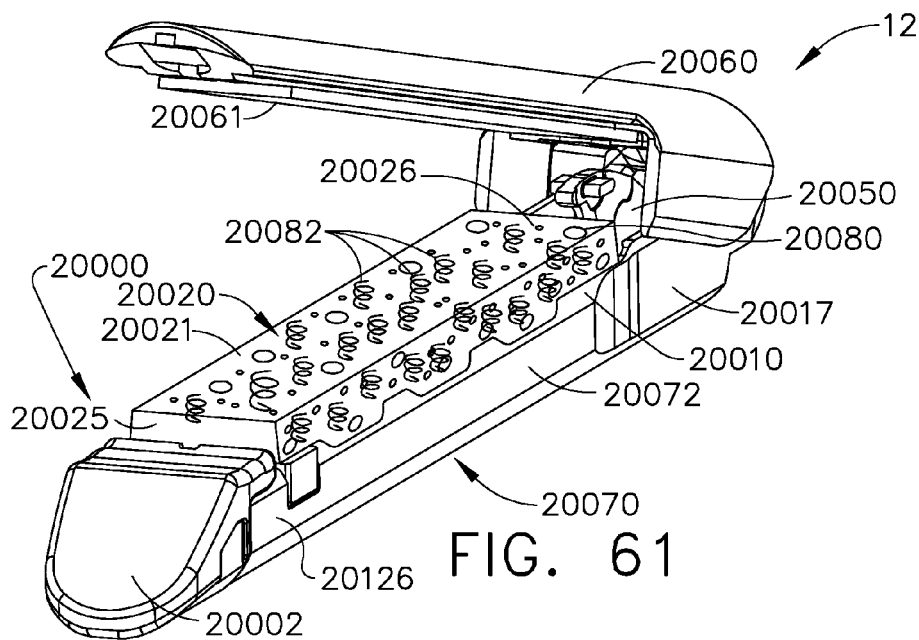
FIG. 61 is a perspective view of a tissue thickness compensator in an end effector of a surgical instrument according to at least one embodiment.

Referring to FIG. 61, an end effector 12 for a surgical instrument 10 (FIG. 1) can be configured to receive a fastener cartridge assembly, such as staple cartridge 20000, for example. As illustrated in FIG. 61, the staple cartridge 20000 can be configured to fit in a cartridge channel 20072 of a jaw 20070 of the end effector 12. In other embodiments, the staple cartridge 20000 can be integral to the end effector 12 such that the staple cartridge 20000 and the end effector 12 are formed as a single unit construction. The staple cartridge 20000 can comprise a first body portion, such as rigid support portion 20010, for example. The staple cartridge 20000 can also comprise a second body portion, such as a compressible portion or a tissue thickness compensator 20020, for example. In other embodiments, the tissue thickness compensator 20020 may not comprise an integral part of the staple cartridge 20000 but may be otherwise positioned relative to the end effector 12. For example, the tissue thickness compensator 20020 can be secured to an anvil 20060 of the end effector 12 or can be otherwise retained in the end effector 12. In at least one embodiment, referring to FIG. 78, the staple cartridge can further comprise retainer clips 20126 which can be configured to inhibit the tissue thickness compensator 20020 from prematurely detaching from the support portion 20010. The reader will appreciate that the tissue thickness compensators described herein can be installed in or otherwise engaged with a variety of end effectors and that such embodiments are within the scope of the present disclosure.

Figure 63:
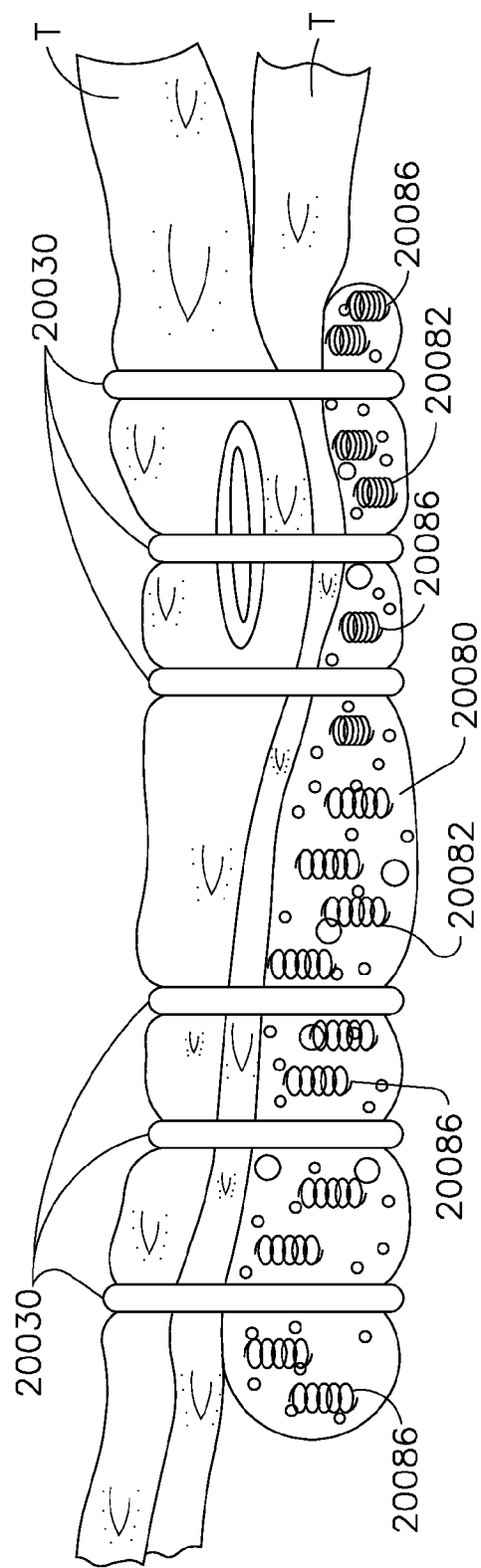
FIG. 63 is an elevational view depicting the tissue thickness compensator of FIG. 61 implanted against tissue and released from the end effector.

Similar to the tissue thickness compensators described herein, referring now to FIG. 78, the tissue thickness compensator 20020 can be released from or disengaged with the surgical end effector 12. For example, in some embodiments, the rigid support portion 20010 of the staple cartridge 20000 can remain engaged with the fastener cartridge channel 20072 of the end effector jaw 20070 while the tissue thickness compensator 20020 disengages from the rigid support portion 20010. In various embodiments, the tissue thickness compensator 20020 can release from the end effector 12 after staples 20030 (FIGS. 78-83) are deployed from staple cavities 20012 in the rigid support portion 2010, similar to various embodiments described herein. Staples 20030 can be fired from staple cavities 20012 such that the staples 20030 engage the tissue thickness compensator 20020. Also similar to various embodiments described herein, referring generally to FIGS. 63, 82 and 83, a staple 20030 can capture a portion of the tissue thickness compensator 20020 along with stapled tissue T. In some embodiments, the tissue thickness compensator 20020 can be deformable and the portion of the tissue thickness compensator 20020 that is captured within a fired staple 20030 can be compressed. Similar to the tissue thickness compensators described herein, the tissue thickness compensator 20020 can compensate for different thicknesses, compressibilities, and/or densities of tissue T captured within each staple 20030. Further, as also described herein, the tissue thickness compensator 20020 can compensate for gaps created by malformed staples 20030.

The tissue thickness compensator 20020 can be compressible between non-compressed height(s) and compressed height(s). Referring to FIG. 78, the tissue thickness compensator 20020 can have a top surface 20021 and a bottom surface 20022. The height of the tissue thickness compensator can be the distance between the top surface 20021 and the bottom surface 20022. In various embodiments, the non-compressed height of the tissue thickness compensator 20020 can be the distance between the top surface 20021 and the bottom surface 20022 when minimal or no force is applied to the tissue thickness compensator 20020, i.e., when the tissue thickness compensator 20020 is not compressed. The compressed height of the tissue thickness compensator 20020 can be the distance between the top surface 20021 and the bottom surface 20022 when a force is applied to the tissue thickness compensator 20020, such as when a fired staple 20030 captures a portion of the tissue thickness compensator 20020, for example. The tissue thickness compensator 20020 can have a distal end 20025 and a proximal end 20026. As illustrated in FIG. 78, the non-compressed height of the tissue thickness compensator 20020 can be uniform between the distal end 20025 and the proximal end 20026 of the tissue thickness compensator 20020. In other embodiments, the non-compressed height can vary between the distal end 20025 and the proximal end 20026. For example, the top surface 20021 and/or bottom surface 20022 of the tissue thickness compensator 20020 can be angled and/or stepped relative to the other such that the non-compressed height varies between the proximal end 20026 and the distal end 20025. In some embodiments, the non-compressed height of the tissue thickness compensator 20020 can be approximately 0.08 inches, for example. In other embodiments, the non-compressed height of the tissue thickness compensator 20020 can vary between approximately 0.025 inches and approximately 0.10 inches, for example.

As described in greater detail herein, the tissue thickness compensator 20020 can be compressed to different compressed heights between the proximal end 20026 and the distal end 20025 thereof. In other embodiments, the tissue thickness compensator 20020 can be uniformly compressed throughout the length thereof. The compressed height(s) of the tissue thickness compensator 20020 can depend on the geometry of the end effector 12, characteristics of the tissue thickness compensator 20020, the engaged tissue T and/or the staples 20030, for example. In various embodiments, the compressed height of the tissue thickness compensator 20020 can relate to the tissue gap in the end effector 12. In various embodiments, when the anvil 20060 is clamped towards the staple cartridge 20000, the tissue gap can be defined between a top deck surface 20011 (FIG. 78) of the staple cartridge 20000 and a tissue contacting surface 20061 (FIG. 61) of the anvil 20060, for example. The tissue gap can be approximately 0.025 inches or approximately 0.100 inches, for example. In some embodiments, the tissue gap can be approximately 0.750 millimeters or approximately 3.500 millimeters, for example. In various embodiments, the compressed height of the tissue thickness compensator 20020 can equal or substantially equal the tissue gap, for example. When tissue T is positioned within the tissue gap of the end effector 12, the compressed height of the tissue thickness compensator can be less in order to accommodate the tissue T. For example, where the tissue gap is approximately 0.750 millimeters, the compressed height of the tissue thickness compensator can be approximately 0.500 millimeters. In embodiments where the tissue gap is approximately 3.500 millimeters, the compressed height of the tissue thickness compensator 20020 can be approximately 2.5 mm, for example. Furthermore, the tissue thickness compensator 20020 can comprise a minimum compressed height. For example, the minimum compressed height of the tissue thickness compensator 20020 can be approximately 0.250 millimeters. In various embodiments, the tissue gap defined between the deck surface of the staple cartridge and the tissue contacting surface of the anvil can equal, or at least substantially equal, the uncompressed height of the tissue thickness compensator, for example.

Figure 62:
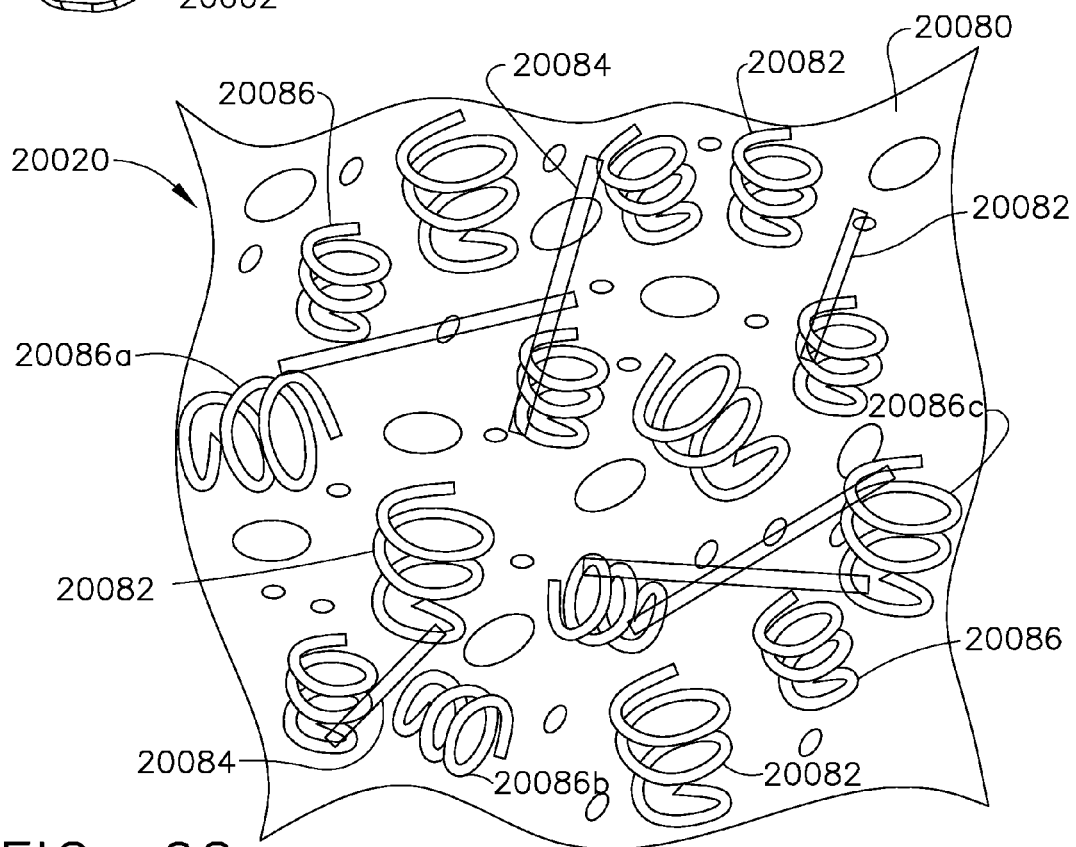
FIG. 62 is a detail view of nonwoven material of the tissue thickness compensator of FIG. 61.

Referring primarily to FIG. 62, the tissue thickness compensator 20020 can comprise a fibrous, nonwoven material 20080 including fibers 20082. In some embodiments, the tissue thickness compensator 20020 can comprise felt or a felt-like material. Fibers 20082 in the nonwoven material 20080 can be fastened together by any means known in the art, including, but not limited to, needle-punching, thermal bonding, hydro-entanglement, ultrasonic pattern bonding, chemical bonding, and meltblown bonding. Further, in various embodiments, layers of nonwoven material 20080 can be mechanically, thermally, or chemically fastened together to form the tissue thickness compensator 20020. As described in greater detail herein, the fibrous, nonwoven material 20080 can be compressible, which can enable compression of the tissue thickness compensator 20020. In various embodiments, the tissue thickness compensator 20020 can comprise a non-compressible portion as well. For example, the tissue thickness compensator 20020 can comprise a compressible nonwoven material 20080 and a non-compressible portion.

Still referring primarily to FIG. 62, the nonwoven material 20080 can comprise a plurality of fibers 20082. At least some of the fibers 20082 in the nonwoven material 20080 can be crimped fibers 20086. The crimped fibers 20086 can be, for example, crimped, twisted, coiled, bent, crippled, spiraled, curled, and/or bowed within the nonwoven material 20080. As described in greater detail herein, the crimped fibers 20086 can be formed in any suitable shape such that deformation of the crimped fibers 20086 generates a spring load or restoring force. In some embodiments, the crimped fibers 20086 can be heat-shaped to form a coiled or substantially coil-like shape. The crimped fibers 20086 can be formed from non-crimped fibers 20084. For example, non-crimped fibers 20084 can be wound around a heated mandrel to form a substantially coil-like shape.

In various embodiments, the tissue thickness compensator 20020 can comprise a homogeneous absorbable polymer matrix. The homogenous absorbable polymer matrix can comprise a foam, gel, and/or film, for example. Further, the plurality of fibers 20082 can be dispersed throughout the homogenous absorbable polymer matrix. At least some of the fibers 20082 in the homogenous absorbable polymer matrix can be crimped fibers 20086, for example. As described in greater detail herein, the homogeneous absorbable polymer matrix of the tissue thickness compensator 2002 can be compressible.

Figure 65:
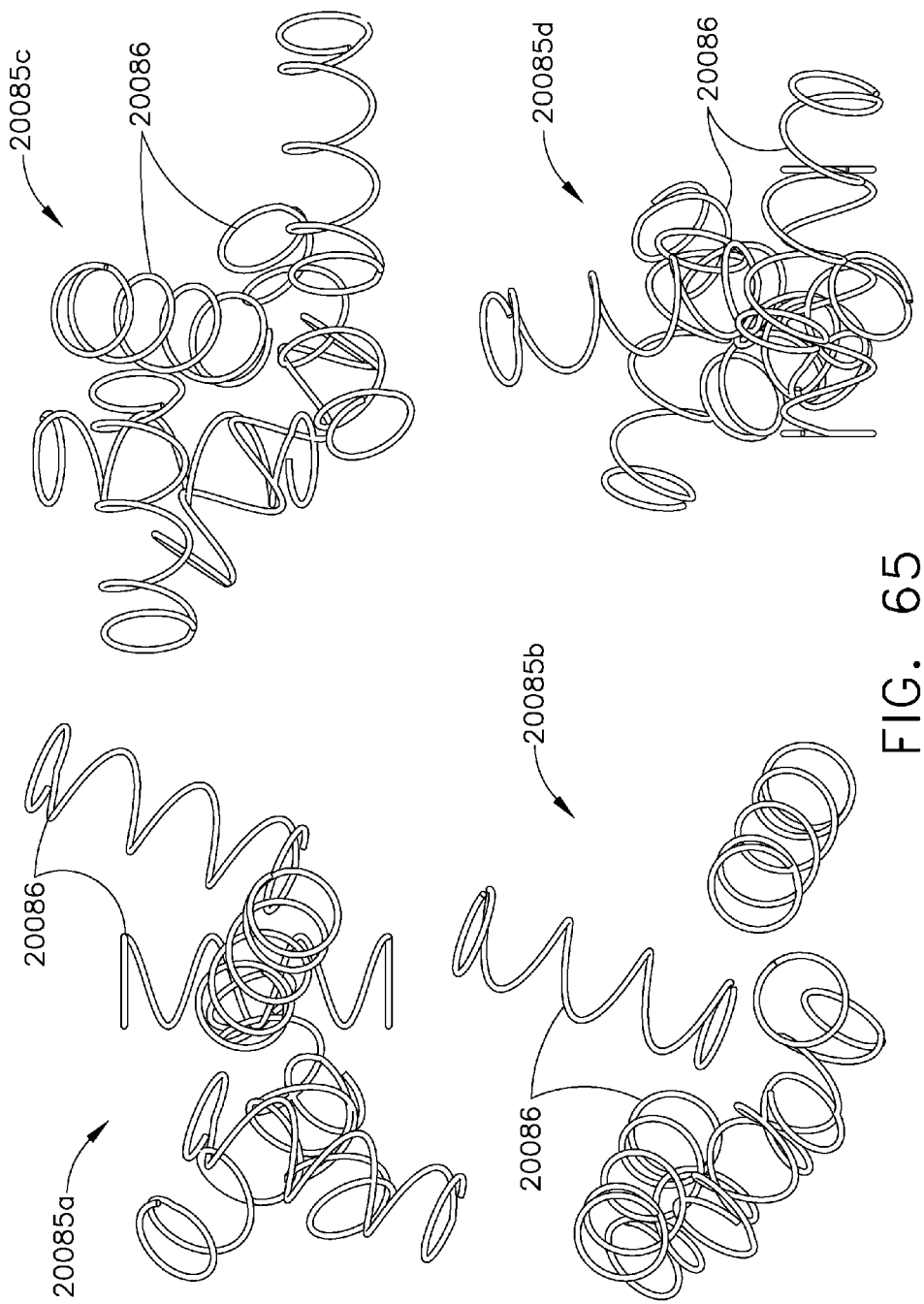
FIG. 65 is a schematic depicting clusters of randomly oriented crimped fibers according to at least one embodiment.
Figure 66:
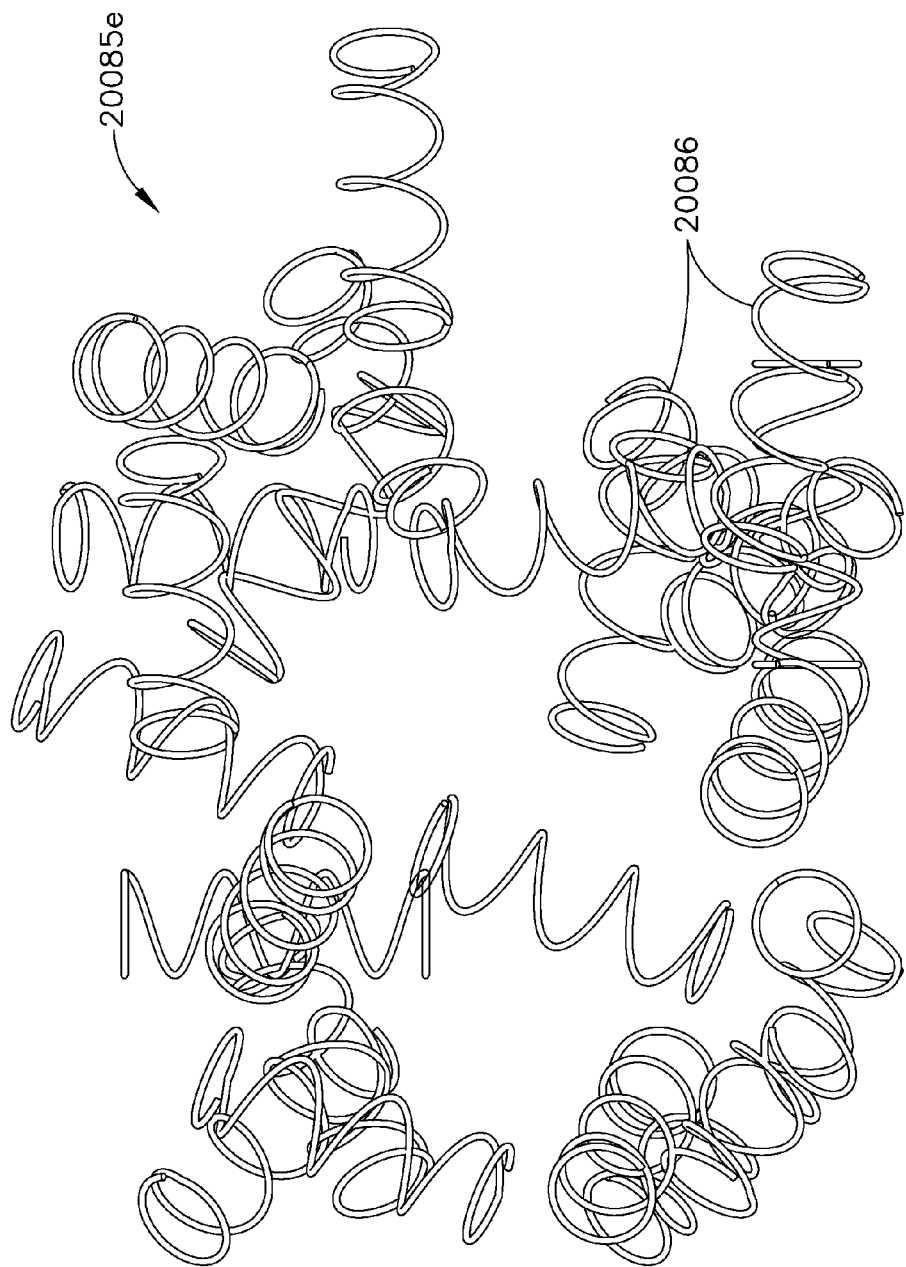
FIG. 66 is a schematic depicting a cluster of randomly oriented crimped fibers according to at least one embodiment.

In various embodiments, referring to FIGS. 65 and 66, crimped fibers 20086 can be randomly dispersed throughout at least a portion of the nonwoven material 20080. For example, crimped fibers 20086 can be randomly dispersed throughout the nonwoven material 20080 such that a portion of the nonwoven material 20080 comprises more crimped fibers 20086 than other portions of the nonwoven material 20080. Further, the crimped fibers 20086 can congregate in fiber clusters 20085a, 20085b, 20085c, 20085d and 20085e, for example, in the nonwoven material 20080. The shape of the crimped fibers 20086 can cause entanglement of the fibers 20086 during manufacturing of the nonwoven material 20080; entanglement of the crimped fibers 20086 can, in turn, result in the formation of the fiber clusters 20085a, 20085b, 20085c, 20085d and 20085e. Additionally or alternatively, crimped fibers 20086 can be randomly oriented throughout the nonwoven material 20080. For example, referring to FIG. 62, a first crimped fiber 20086a can be oriented in a first direction, a second crimped fiber 20086b can be oriented in a second direction, and a third crimped fiber 20086c can be oriented in a third direction.

In some embodiments, the crimped fibers 20086 can be systematically distributed and/or arranged throughout at least a portion of the nonwoven material 20080. For example, referring now to FIG. 67, crimped fibers 20186 can be positioned in an arrangement 20185, in which a plurality of crimped fibers 20186a are arranged in a first direction and another plurality of crimped fibers 20186b are arranged in a second direction. The crimped fibers 20186 can overlap such that they become entangled or interconnected with each other. In various embodiments, the crimped fibers 20186 can be systematically arranged such that a crimped fiber 20186a is substantially parallel to another crimped fiber 20186a. Still another crimped fiber 20186b can be substantially transverse to some crimped fibers 20186a. In various embodiments, crimped fibers 20186a can be substantially aligned with a first axis Y and crimped fibers 20186b can be substantially aligned with a second axis X. In some embodiments the first axis Y can be perpendicular or substantially perpendicular to the second axis X, for example.

Referring primarily to FIG. 68, in various embodiments, crimped fibers 20286 can be arranged in an arrangement 20285. In some embodiments, each crimped fibers 20286 can comprise a longitudinal axis defined between a first end 20287 and a second end 20289 of the crimped fiber 20286. In some embodiments, the crimped fibers 20286 can be systematically distributed in the nonwoven material 20080 such that a first end 20287 of one crimped fiber 20286 is positioned adjacent to a second end 20289 of another crimped fiber 20286. In another embodiment, referring now to FIG. 69, a fiber arrangement 20385 can comprise a first crimped fiber 20386a oriented in a first direction, a second crimped fiber 20386b oriented in a second direction, and a third crimped fiber 20386c oriented in a third direction, for example. In various embodiments, a single pattern or arrangement of crimped fibers 20286 can be repeated throughout the nonwoven material 20080. In at least one embodiment, crimped fibers can be arranged in different patterns throughout the nonwoven material 20080. In still other embodiments, the nonwoven material 20080 can comprise at least one pattern of crimped fibers, as well as a plurality of randomly oriented and/or randomly distributed crimped fibers.

Referring again to FIG. 62, the plurality of fibers 20082 in the nonwoven material 20080 can comprise at least some non-crimped fibers 20084. The non-crimped fibers 20084 and crimped fibers 20086 in the nonwoven material 20080 can be entangled or interconnected. In one embodiment, the ratio of crimped fibers 20086 to non-crimped fibers 20084 can be approximately 25:1, for example. In another embodiment, the ratio of crimped fibers 20086 to non-crimped fibers 20084 can be approximately 1:25, for example. In other embodiments, the ratio of crimped fibers 20086 to non-crimped fibers 20084 can be approximately 1:1, for example. As described in greater detail herein, the number of crimped fibers 20086 per unit volume of nonwoven material 20080 can affect the restoring force generated by the nonwoven material 20080 when the nonwoven material 20080 has been deformed. As also described in greater detail herein, the restoring force generated by the nonwoven material 20080 can also depend on, for example, the material, shape, size, position and/or orientation of crimped and non-crimped fibers 20086, 20084 in the nonwoven material 20080.

In various embodiments, the fibers 20082 of the nonwoven material 20080 can comprise a polymeric composition. The polymeric composition of the fibers 20082 can comprise non-absorbable polymers, absorbable polymers, or combinations thereof. In some embodiments, the absorbable polymers can include bioabsorbable, biocompatible elastomeric polymers. Furthermore, the polymeric composition of the fibers 20082 can comprise synthetic polymers, non-synthetic polymers, or combinations thereof. Examples of synthetic polymers include, but are not limited to, polyglycolic acid (PGA), poly (lactic acid) (PLA), polycaprolactone (PCL), polydioxanone (PDO), and copolymers thereof. For example, the fibers 20082 can comprise a 90/10 poly(glycolide-L-lactide) copolymer, such as, for example, the copolymer commercially available from Ethicon, Inc. under the trade designation "VICRYL (polyglactic 910)." Examples of non-synthetic polymers include, but are not limited to, lyophilized polysaccharide, glycoprotein, elastin, proteoglycan, gelatin, collagen, and oxidized regenerated cellulose (ORC). In various embodiments, similar to the polymeric compositions in tissue thickness compensators described herein, the polymeric composition of the fibers 20082 can include varied amounts of absorbable polymers, non-absorbable polymers, synthetic polymers, and/or non-synthetic polymers, for example, by weight percentage.

In some embodiments, the crimped fibers 20086 of the nonwoven material 20080 can comprise a first polymeric composition and the non-crimped fibers 20084 of the nonwoven material 20080 can comprise a different polymeric composition. For example, the crimped fibers 20086 can comprise synthetic polymer(s), such as, for example, 90/10 poly(glycolide-L-lactide), while the non-crimped fibers 20084 can comprise non-synthetic polymer(s), such as, for example, oxidized regenerated cellulose. In other embodiments, the crimped fibers 20086 and the non-crimped fibers 20084 can comprise the same polymeric composition.

As described herein, crimped fibers 20086 and non-crimped fibers 20084 can be fastened together, for example, by needle-punching, thermal bonding, hydro-entanglement, ultrasonic pattern bonding, chemical bonding, and meltblown bonding. In some embodiments, crimped fibers 20086 comprising synthetic polymers such as, for example, "VICRYL (polyglactic 910)", and non-crimped fibers 20084 comprising oxidized regenerated cellulose can be needle-punched together to form the nonwoven material 20080. In various embodiments, the nonwoven material 20080 can comprise approximately 5% to 50% crimped "VICRYL (polyglactic 910)" fibers 20086 by weight and approximately 5% to 50% non-crimped oxidized regenerated cellulose (ORC) fibers 20084 by weight, for example. When the nonwoven material 20080 contacts tissue T, the non-crimped ORC fibers 20084 can rapidly react with plasma in the tissue to form a gelatinous mass, for example. In various embodiments, the formation of the gelatinous ORC mass can be instantaneous or nearly instantaneous with the tissue contact. Further, after the formation of the gelatinous ORC mass, the crimped "VICRYL (polyglactic 910)" fibers 20086 can remain dispersed throughout the nonwoven material 20080. For example, the crimped fibers 20086 can be suspended in the gelatinous ORC mass. As the gelatinous ORC mass is bioabsorbed, the crimped "VICRYL (polyglactic 910)" fibers 20086 can exert a springback force on adjacent tissue, as described in greater detail herein. Further, the tissue can begin to heal around the "VICRYL (polyglactic 910)" fibers and/or the formed staples 30030, as also described in greater detail herein.

In at least one embodiment, referring primarily to FIGS. 78-81, the support portion 20010 of the staple cartridge 20000 can comprise a cartridge body 20017, a top deck surface 20011, and a plurality of staple cavities 20012. Similar to the embodiments described herein, each staple cavity 20012 can define an opening in the deck surface 20011. A staple 20030 can be removably positioned in a staple cavity 20012. In various embodiments, a single staple 20030 is disposed in each staple cavity 20012. In at least one embodiment, referring primarily to FIGS. 82 and 83 and similar to the staples described herein, each staple 20030 can comprise a base 20031 having a first end 20035 and a second end 20036. A staple leg 20032 can extend from the first end 20035 of the base 20031 and another staple leg 20032 can extend from the second end 20036 of the base 20031. Referring again to FIGS. 78-81, prior to the deployment of the staples 20030, the base 20031 of each staple 20030 can be supported by a staple driver 20040 positioned within the rigid support portion 20010 of the staple cartridge 20000. Also prior to deployment of the staples 20030, the legs 20032 of each staple 20030 can be at least partially contained within a staple cavity 20012.

In various embodiments, the staples 20030 can be deployed between an initial position and a fired position. For example, referring primarily to FIG. 81, staples 20030 can be in an initial position (staples 20030e, 20030f), a partially fired or intermediate position (staples 20030c, 20030d), or a fired position (staples 20030a, 20030b). A driver 20040 can motivate the staples between the initial position and the fired position. For example, the base 20031 of each staple 20030 can be supported by a driver 20040. The legs 20032 of a staple (staples 20030e, 20030f in FIG. 80, for example) can be positioned within a staple cavity 20012. As the firing member or staple-firing sled 20050 translates from the proximal end 20001 to the distal end 20002 of the staple cartridge 20000, an inclined surface 20051 on the sled 20050 can contact an inclined surface 20042 on a driver 20040 to deploy the staple 20030 positioned above to the contacted driver 20040. In various embodiments, the staples 20030 can be deployed between an initial position and a fired position such that the legs 20032 move through the nonwoven material 20080 of the tissue thickness compensator 20020, penetrate the top surface 20021 of the tissue thickness compensator 20020, penetrate tissue T, and contact an anvil 20060 (FIG. 61) positioned opposite the staple cartridge 20000 in the end effector 12. The staple legs 20032 can be deformed against the anvil 20060 and the legs 20032 of each staple 20030 can capture a portion of the nonwoven material 20080 and a portion of the tissue T.

Figure 80:
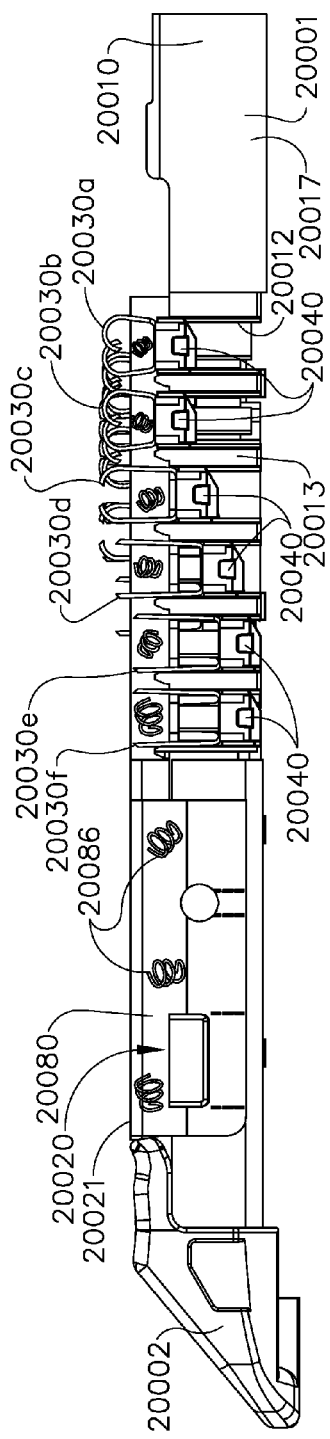
FIG. 80 is an elevational view of the fastener cartridge assembly of FIG. 78 depicting a driver firing fasteners from staple cavities of the fastener cartridge assembly into the tissue thickness compensator.
Figure 81:
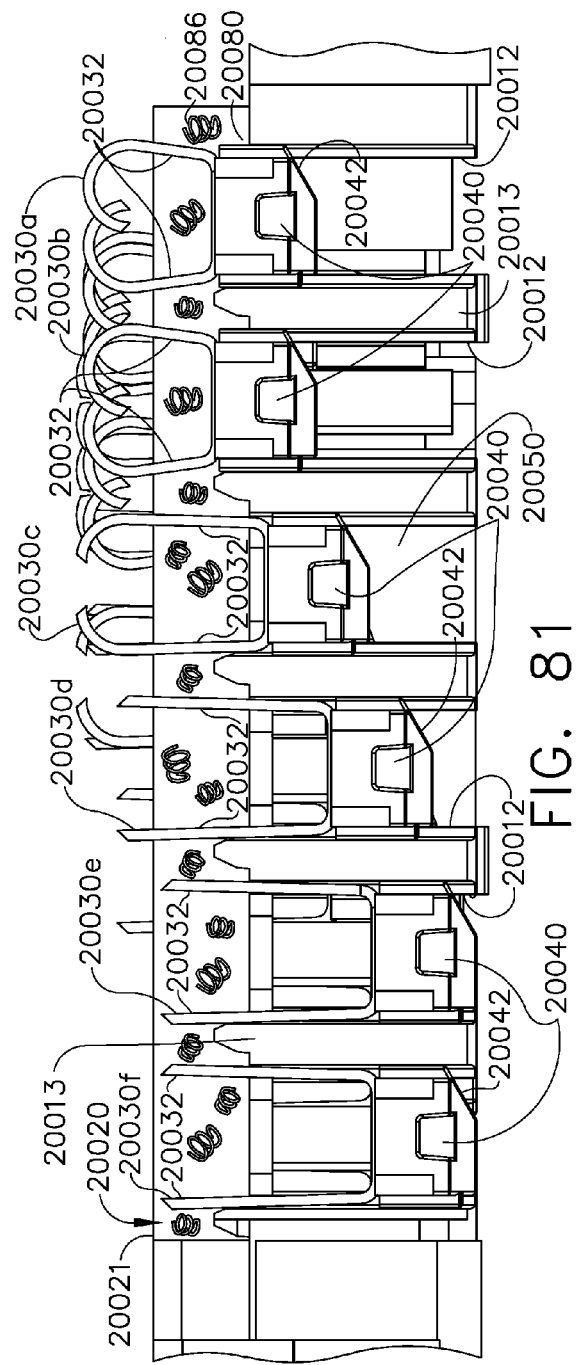
FIG. 81 is a detail view of the fastener cartridge assembly of FIG. 80.
Figure 82:
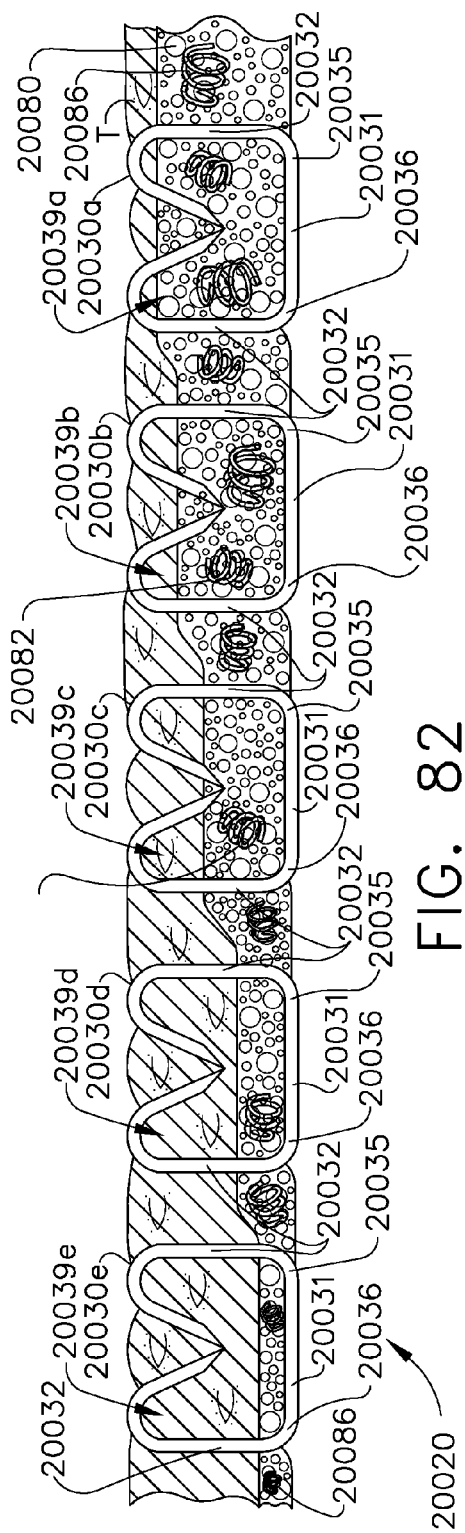
FIG. 82 is an elevational view of the tissue thickness compensator of FIG. 61 and tissue captured within fired fasteners.

In the fired configuration (FIGS. 82 and 83), each staple 20030 can apply a compressive force to the tissue T and to the tissue thickness compensator 20020 captured within the staple 20030. Referring primarily to FIGS. 80 and 81, the legs 20032 of each staple 20030 can be deformed downwardly toward the base 20031 of the staple 20030 to form a staple entrapment area 20039. The staple entrapment area 20039 can be the area in which the tissue T and the tissue thickness compensator 20020 can be captured by a fired staple 20030. In various circumstances, the staple entrapment area 20039 can be defined between the inner surfaces of the deformed legs 20032 and the inner surface of the base 20031 of a staple 20030. The size of the entrapment area 20039 for a staple 20030 can depend on several factors such as the length of the legs, the diameter of the legs, the width of the base, and/or the extent in which the legs are deformed, for example.

Figure 83:
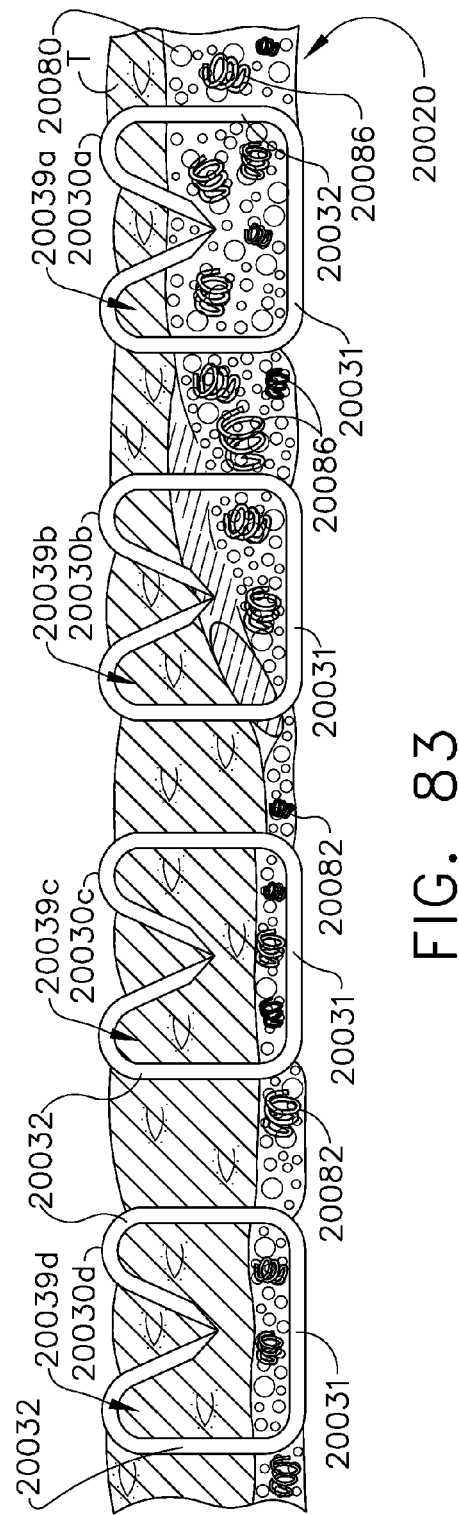
FIG. 83 is an elevational view of the tissue thickness compensator of FIG. 61 and tissue captured within fired fasteners.

In various embodiments, when a nonwoven material 20080 is captured in a staple entrapment area 20039, the captured portion of the nonwoven material 20080 can be compressed. The compressed height of the nonwoven material 20080 captured in a staple entrapment area 20039 can vary within the staple cartridge 20000 depending on the tissue T in that same staple entrapment area 20039. For example, where the tissue T is thinner, the staple entrapment area 20039 may have more room for the nonwoven material 20080 and, as a result, the nonwoven material 20080 may not be as compressed as it would be if the tissue T were thicker. Where the tissue T is thicker, the nonwoven material 20080 can be compressed more to accommodate the thicker tissue T, for example. For example, referring to FIG. 82, the nonwoven material 20080 can be compressed to a first height in a first staple entrapment area 20039a, a second height in a second staple entrapment area 20039b, a third height in a third staple entrapment area 20039c, a fourth height in a fourth staple entrapment area 20039d, and a fifth height in a fifth staple entrapment area 20039e, for example. Similarly, as illustrated in FIG. 83, the nonwoven material 20080 can be compressed to a first height in the first staple entrapment area 20039a, a second height in the second staple entrapment area 20039b, a third height in the third staple entrapment area 20039c, and a fourth height in the fourth staple entrapment area 20039d. In other embodiments, the compressed height of the nonwoven material 20080 can be uniform throughout the staple cartridge 20010.

In various embodiments, an applied force can move the nonwoven material 20080 from an initial uncompressed configuration to a compressed configuration. Further, the nonwoven material 20080 can be resilient, such that, when compressed, the nonwoven material 20080 can generate a springback or restoring force. When deformed, the nonwoven material 20080 can seek to rebound from the compressed or deformed configuration. As the nonwoven material 20080 seeks to rebound, it can exert a springback or restoring force on the tissue also captured in the staple entrapment area 30039, as described in greater detail herein. When the applied force is subsequently removed, the restoring force can cause the nonwoven material to rebound from the compressed configuration. In various embodiments, the nonwoven material 20080 can rebound to the initial, uncompressed configuration or may rebound to a configuration substantially similar to the initial, uncompressed configuration. In various embodiments, the deformation of the nonwoven material 20080 can be elastic. In some embodiments, the deformation of the nonwoven material can be partially elastic and partially plastic.

When a portion of the nonwoven material 20080 is compressed in a staple entrapment area 20039, the crimped fibers 20086 in that portion of the nonwoven compensator 20039 can also be compressed or otherwise deformed. The amount a crimped fiber 20086 is deformed can correspond to the amount that the captured portion of the nonwoven material 20080 is compressed. For example, referring to FIG. 63, the nonwoven material 20080 can be captured by deployed staples 20030. Where the nonwoven material 20080 is more compressed by a deployed staple 20030, the average deformation of crimped fibers 20086 can be greater. Further, where the nonwoven material 20080 is less compressed by a deployed staple, the average deformation of crimped fibers 20086 can be smaller. Similarly, referring to FIGS. 82 and 83, in a staple entrapment area 20039*d* where the nonwoven material 20080 is more compressed, the crimped fibers 20086 in that staple entrapment area 20039*d* can be, on average, more deformed. Further, in a staple entrapment area 20039*a* where the nonwoven material 20080 is less compressed, the crimped fibers 20086 in that staple entrapment area 20039*a* can be, on average, less deformed.

The ability of the nonwoven material 20080 to rebound from the deformed configuration, i.e., the resiliency of the nonwoven material 20080, can be a function of the resiliency of the crimped fibers 20086 in the nonwoven material 20080. In various embodiments, the crimped fibers 20086 can deform elastically. In some embodiments, deformation of the crimped fibers 20086 can be partially elastic and partially plastic. In various embodiments, compression of each crimped fiber 20086 can cause the compressed crimped fibers 20086 to generate a springback or restoring force. For example, the compressed crimped fibers 20086 can generate a restoring force as the fibers 20086 seek to rebound from their compressed configuration. In various embodiments, the fibers 20086 can seek to return to their initial, uncompressed configuration or to a configuration substantially similar thereto. In some embodiments, the crimped fibers 20086 can seek to partially return to their initial configuration. In various embodiments, only a portion of the crimped fibers 20086 in the nonwoven material 20080 can be resilient. When a crimped fiber 20086 is comprised of a linear-elastic material, the restoring force of the compressed crimped fiber 20086 can be a function of the amount the crimped fiber 20086 is compressed and the spring rate of the crimped fiber 20086, for example. The spring rate of the crimped fiber 20086 can at least depend on the orientation, material, shape and/or size of the crimped fiber 20086, for example.

In various embodiments, the crimped fibers 20086 in the nonwoven material 20080 can comprise a uniform spring rate. In other embodiments, the spring rate of the crimped fibers 20086 in the nonwoven material 20080 can vary. When a crimped fiber 20086 having a large spring rate is greatly compressed, the crimped fiber 20086 can generate a large restoring force. When a crimped fiber 20086 having the same large spring rate is less compressed, the crimped fiber 20086 can generate a smaller restoring force. The aggregate of restoring forces generated by compressed crimped fibers 20086 in the nonwoven material 20080 can generate a combined restoring force throughout the nonwoven material 20080 of the tissue thickness compensator 20020. In various embodiments, the nonwoven material 20080 can exert the combined restoring force on tissue T captured within a fired staple 20030 with the compressed nonwoven material 20080.

Furthermore, the number of crimped fibers 20086 per unit volume of nonwoven material 20080 can affect the spring rate of the nonwoven material 20080. For example, the resiliency in a nonwoven material 20080 can be low when the number of crimped fibers 20086 per unit volume of nonwoven material 20080 is low, for example; the resiliency of the nonwoven material 20080 can be higher when the number of crimped fibers 20086 per unit volume of nonwoven material 20080 is higher, for example; and the resiliency of the nonwoven material 20080 can be higher still when the number of crimped fibers 20086 per unit volume of nonwoven material 20080 is even higher, for example. When the resiliency of the nonwoven material 20080 is low, such as when the number of crimped fibers 20086 per unit volume of nonwoven material 20080 is low, the combined restoring force exerted by the tissue thickness compensator 20020 on captured tissue T can also be low. When the resiliency of the nonwoven material 20080 is higher, such as when the number of crimped fibers 20086 per unit volume of nonwoven material 20080 is higher, the aggregate restoring force exerted by the tissue thickness compensator 20020 on captured tissue T can also be higher.

Figure 64:
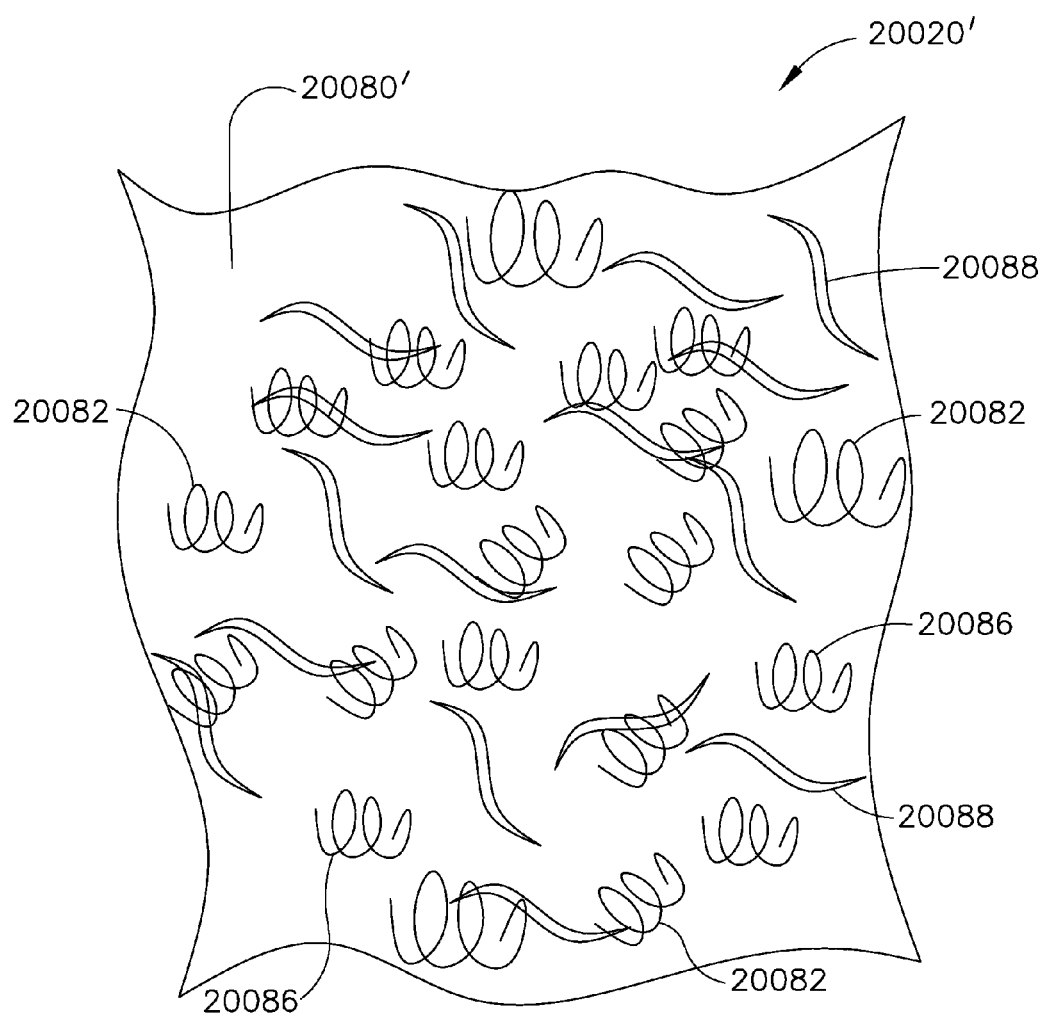
FIG. 64 is a detail view of nonwoven material of a tissue thickness compensator according to at least one embodiment.

In various embodiments, referring primarily to FIG. 64, a nonwoven material 20080' of a tissue thickness compensator 20020' can comprise a therapeutic agent 20088, such as a medicament and/or pharmaceutically active agent, for example. In various embodiments, the nonwoven material 20080' can release a therapeutically effective amount of the therapeutic agent 20088. For example, the therapeutic agent 20088 can be released as the nonwoven material 20080' is absorbed. In various embodiments, the therapeutic agent 20088 can be released into fluid, such as blood, for example, passing over or through the nonwoven material 20080'. Examples of therapeutic agents 20088 can include, but are not limited to, haemostatic agents and drugs such as, for example, fibrin, thrombin, and/or oxidized regenerated cellulose (ORC); anti-inflammatory drugs such as, for example, diclofenac, aspirin, naproxen, sulindac, and/or hydrocortisone; antibiotic and antimicrobial drugs or agents such as, for example, triclosan, ionic silver, ampicillin, gentamicin, polymyxin B, and/or chloramphenicol; and anticancer agents such as, for example, cisplatin, mitomycin, and/or adriamycin. In various embodiments, the therapeutic agent 20088 can comprise a biologic, such as a stem cell, for example. In some embodiments, the fibers 20082 of the nonwoven material 20080' can comprise the therapeutic agent 20088. In other embodiments, the therapeutic agent 20088 can be added to the nonwoven material 20080' or otherwise integrated into the tissue thickness compensator 20020'.

In some embodiments, primarily referring to FIGS. 70-70B, a tissue thickness compensator 20520 for an end effector 12 (FIG. 61) can comprise a plurality of springs or coiled fibers 20586. Similar to the crimped fibers 20086 described herein, the coiled fibers 20586 can be, for example, crimped, twisted, coiled, bent, crippled, spiraled, curled, and/or bowed within the tissue thickness compensator 20520. In some embodiments, the coiled fibers 20586 can be wound around a mandrel to form a coiled or substantially coil-like shape. Similar to the embodiments described herein, the coiled fibers 20586 can be randomly oriented and/or randomly distributed throughout the tissue thickness compensator 20520. In other embodiments, the coiled fibers 20586 can be systematically arranged and/or uniformly distributed throughout the tissue thickness compensator 20520. For example, referring to FIG. 70, the coiled fibers 20586 can comprise a longitudinal axis between a first end 20587 and a second end 20589 of the coiled fiber 20586. The longitudinal axes of the coiled fibers 20520 in the tissue thickness compensator 20520 can be parallel or substantially parallel. In some embodiments, the first end 20587 of each coiled fiber 20520 can be positioned along a first longitudinal side 20523 of the tissue thickness compensator 20520 and the second end 20589 of each coiled fiber 20586 can be positioned along a second longitudinal side 20524 of the tissue thickness compensator 20520. In such an arrangement, the coiled fibers 20586 can laterally traverse the tissue thickness compensator. In other embodiments, the coiled fibers 20586 can longitudinally or diagonally traverse the tissue thickness compensator 20520.

In various embodiments, similar to the crimped fibers 20086 described herein, the coiled fibers 20586 can comprise a polymeric composition. The crimped fibers 20586 can be at least partially elastic such that deformation of the crimped fibers 20586 generates a restoring force. In some embodiments, the polymeric composition of the coiled fibers 20586 can comprise polycaprolactone (PCL), for example, such that the coiled fibers 20586 are not soluble in a chlorophyll solvent. Referring to FIG. 70A, the springs or coiled fibers 20520 can be retained in a compensation material 20580. In various embodiments, the compensation material 20580 can hold the coiled fibers 20586 in a loaded position such that the coiled fibers 20586 exert a spring load on, or within, the compensation material 20580. In certain embodiments, the compensation material 20580 can hold the coiled fibers 20586 in a neutral position where the coiled fibers 20586 are not exerting a spring load on, or within, the compensation material 20580. The compensation material 20580 can be bioabsorbable and, in some embodiments, can comprise a foam, such as, for example, polyglycolic acid (PGA) foam. Furthermore, the compensation material 20580 can be soluble in a chlorophyll solvent, for example. In some embodiments the tissue thickness compensator can comprise coiled fibers 20586 that comprise polycaprolactone (PCL) and compensation material 20580 that comprises polyglycolic acid (PGA) foam, for example, such that the coiled fibers 20520 are not soluble in a chlorophyll solvent while the compensation material 20580 is soluble in the chlorophyll solvent. In various embodiments, the compensation material 20580 can be at least partially elastic, such that compression of the compensation material 20580 generates a restoring force. Further, similar to the embodiments described herein, referring to FIG. 70B, the compensation material 20580 of the tissue thickness compensator 20520 can comprise a therapeutic agent 20588, such as stem cells, for example. The compensation material 20580 can release a therapeutically effective amount of the therapeutic agent 20588 as the compensation material 20580 is absorbed.

Similar to the tissue thickness compensator 20020 described herein, the tissue thickness compensator 20520 can be compressible. For example, as staples 20030 (FIGS. 78-81) are deployed from an initial position to a fired position, the staples 20030 can engage a portion of tissue thickness compensator 20520. In various embodiments, a staple 20030 can capture a portion of the tissue thickness compensator 20520 and adjacent tissue T. The staple 20030 can apply a compressive force to the captured portion of the tissue thickness compensator 20520 and tissue T such that the tissue thickness compensator 20520 is compressed from a non-compressed height to a compressed height. Similar to the embodiments described herein, compression of the tissue thickness compensator 20520 can result in a corresponding deformation of the coiled fibers 20586 therein. As described in greater detail herein, deformation of each coiled fiber 20586 can generate a restoring force that can depend on the resiliency of the coiled fiber, for example, the amount the coiled fiber 20586 is deformed and/or the spring rate of the coiled fiber 20586. The spring rate of the coiled fiber 20586 can at least depend on the orientation, material, shape and/or size of the coiled fiber 20586, for example. Deformation of the coiled fibers 20586 in the tissue thickness compensator 20520 can generate restoring forces throughout the tissue thickness compensator 20520. Similar to the embodiments described herein, the tissue thickness compensator 20520 can exert the aggregate restoring force generated by the deformed coiled fibers 20586 and/or the resilient compensation material 20586 on the captured tissue T in the fired staples 20030.

In some embodiments, primarily referring to FIGS. 71 and 72, a tissue thickness compensator 20620 for an end effector 12 can comprise a plurality of spring coils 20686. Similar to the crimped fibers 20086 and coiled fibers 20586 described herein, spring coils 20686 can be, for example, crimped, twisted, coiled, bent, crippled, spiraled, curled, and/or bowed within the tissue thickness compensator 20620. In various embodiments, similar to the fibers and coils described herein, the spring coils 20686 can comprise a polymeric composition. Further, the spring coils 20686 can be at least partially elastic such that deformation of the spring coils 20686 generates a restoring force. The spring coils 20686 can comprise a first end 20687, a second end 20689, and a longitudinal axis therebetween. Referring to FIG. 71, the first end 20686 of a spring coil 20686 can be positioned at or near a proximal end 20626 of the tissue thickness compensator and the second end 20689 of the same spring coil 20686 can be positioned at or near a distal end 20625 of the tissue thickness compensator 20620 such that the spring coil 20686 longitudinally traverses the tissue thickness compensator 20620, for example. In other embodiments, the coiled fibers 20686 can laterally or diagonally traverse the tissue thickness compensator 20620.

The tissue thickness compensator 20620 can comprise an outer film 20680 that at least partially surrounds at least one spring coil 20686. In various embodiments, referring to FIG. 71, the outer film 20680 can extend around the perimeter of multiple spring coils 20686 in the tissue thickness compensator 20620. In other embodiments, the outer film 20680 can completely encapsulate the spring coils 20686 or at least one spring coil 20686 in the tissue thickness compensator 20620. The outer film 20680 can retain the spring coils 20686 in the end effector 12. In various embodiments, the outer film 20680 can hold the spring coils 20686 in a loaded position such that the spring coils 20686 generate a spring load and exert a springback force on the outer film 20680. In other embodiments, the outer film 20680 can hold the spring coils 20686 in a neutral position. The tissue thickness compensator 20620 can also comprise a filling material 20624. In some embodiments, the filling material 20624 can be retained within and/or around the spring coils 20686 by the outer film 20680. In some embodiments, the filling material 20624 can comprise a therapeutic agent 20688, similar to the therapeutic agents described herein. Further, the filling material 20624 can support the spring coils 20686 within the tissue thickness compensator 20620. The filling material 20624 can be compressible and at least partially resilient, such that the filling material 20624 contributes to the springback or restoring force generated by the tissue thickness compensator 20620, as described in greater detail herein.

Similar to the tissue thickness compensators described herein, the tissue thickness compensator 20620 can be compressible. As staples 20030 (FIGS. 78-81) are deployed from an initial position to a fired position, in various embodiments, the staples 20030 can engage a portion of the tissue thickness compensator 20620. In various embodiments, each staple 20030 can capture a portion of the tissue thickness compensator 20620 along with adjacent tissue T. The staple 20030 can apply a compressive force to the captured portion of the tissue thickness compensator 20620 and the captured tissue T such that the tissue thickness compensator 20620 is compressed between a non-compressed height and a compressed height. Similar to the embodiments described herein, compression of the tissue thickness compensator 20620 can result in a corresponding deformation of the spring coils 20686 retained therein (FIG. 72). As described in greater detail herein, deformation of each spring coils 20686 can generate a restoring force that depends on the resiliency of the spring coil 20686, for example, the amount the spring coil 20686 is deformed and/or the spring rate of the spring coil 20686. The spring rate of a spring coil 20686 can at least depend on the material, shape and/or dimensions of the spring coil 20686, for example. Furthermore, depending on the resiliency of the filling material 20624 and the outer film 20680, compression of the filling material 20624 and/or the outer film 20680 can also generate restoring forces. The aggregate of restoring forces generated at least by the deformed spring coils 20686, the filling material 20624 and/or the outer film 20680 in the tissue thickness compensator 20620 can generate restoring forces throughout the tissue thickness compensator 20620. Similar to the embodiments described herein, the tissue thickness compensator 20620 can exert the aggregate restoring force generated by the deformed spring coils 20686 on the captured tissue T in a fired staple 20030.

In various embodiments, primarily referring to FIGS. 73-75, a tissue thickness compensator 20720 for an end effector 12 can comprise a plurality of spring coils 20786. Similar to the coiled fibers and springs described herein, spring coils 20786 can be, for example, crimped, twisted, coiled, bent, crippled, spiraled, curled, and/or bowed within the tissue thickness compensator 20720. The spring coils 20786 can be at least partially elastic such that deformation of the spring coils 20786 generates a restoring force. Further, the spring coils 20786 can comprise a first end 20787, a second end 20789, and a longitudinal axis therebetween. Referring primarily to FIG. 75, the first end 20787 of the spring coil 20786 can be positioned at or near a proximal end 20726 of the tissue thickness compensator 20720 and the second end 20789 of the spring coil 20786 can be positioned at or near a distal end 20725 of the tissue thickness compensator 20720 such that the spring coil 20786 longitudinally traverses the tissue thickness compensator 20720. In some embodiments, the spring coil 20786 can longitudinally extend in two parallel rows in the tissue thickness compensator 20720. The tissue thickness compensator 20720 can be positioned in an end effector 12 such that a sled 20050 (FIG. 61) or cutting element 20052 can translate along a slot 20015 between the parallel rows of spring coils 20786. In other embodiments, similar to various embodiments described herein, the spring coils 20786 can laterally or diagonally traverse the tissue thickness compensator 20720.

Referring again to FIG. 75, the spring coils 20786 can be retained or embedded in a compensation material 20780. The compensation material 20780 can be bioabsorbable and, in some embodiments, can comprise foam, such as, for example, polyglycolic acid (PGA) foam. In various embodiments, the compensation material 20780 can be resilient such that deformation of the compensation material 20780 generates a springback force. The compensation material 20780 can be soluble in a chlorophyll solvent, for example. In some embodiments, for example, the tissue thickness compensator can comprise spring coils 20786 that comprise polycaprolactone (PCL) and compensation material 20780 that comprises polyglycolic acid (PGA) foam such that the spring coils 20786 are not soluble in a chlorophyll solvent while the compensation material 20780 is soluble in a chlorophyll solvent, for example. The compensation material 20780 can be at least partially resilient such that deformation of the compensation material 20780 generates a spring load or restoring force.

In various embodiments, the tissue thickness compensator 20720 can comprise interwoven threads 20790, which can extend between parallel rows of spring coils 20786. For example, referring to FIG. 75, a first interwoven thread 20790 can diagonally traverse the two parallel rows of spring coils 20786 and a second interwoven thread 20790 can also diagonally traverse the two parallel rows of spring coils 20786. In some embodiments, the first and second interwoven threads 20790 can crisscross. In various embodiments, the interwoven threads 20790 can crisscross multiple times along the length of the tissue thickness compensator 20720. The interwoven threads 20790 can hold the spring coils 20786 in a loaded configuration such that the spring coils 20786 are held in a substantially flat position in the tissue thickness compensator 20720. In some embodiments, the interwoven threads 20790 that traverse the tissue thickness compensator 20720 can be directly attached to the spring coils 20786. In other embodiments, the interwoven threads 20790 can be coupled to the spring coils 20786 via a support 20792 that extends through each spring coil 20786 along the longitudinal axis thereof.

As described in greater detail herein, in various embodiments, a staple cartridge 20000 can comprise a slot 20015 configured to receive a translating sled 20050 comprising a cutting element 20052 (FIG. 61). As the sled 20050 translates along the slot 20015, the sled 20050 can eject staples 20030 from fastener cavities 20012 in the staple cartridge 20000 and the cutting element 20052 can simultaneously or nearly simultaneously sever tissue T. In various embodiments, referring again to FIG. 75, as the cutting element 20052 translates, it can also sever the interwoven threads 20790 that crisscross between the parallel rows of spring coils 20786 in the tissue thickness compensator 20720. As the interwoven threads 20790 are severed, each spring coil 20786 can be released from its loaded configuration such that each spring coil 20786 reverts from the loaded, substantially flat position to an expanded position in the tissue thickness compensator 20720. In various embodiments, when a spring coil 20786 is expanded, the compensation material 20780 surrounding the spring coil 20786 can also expand.

In various embodiments, as staples 20030 (FIGS. 78-81) are deployed from an initial position to a fired position, the staples 20030 can engage a portion of the tissue thickness compensator 20720 and the tissue thickness compensator 20720 can expand, or attempt to expand, within the staples 20030 and can apply a compressive force to the tissue T. In various embodiments, at least one staple 20030 can capture a portion of the tissue thickness compensator 20720, along with adjacent tissue T. The staple 20030 can apply a compressive force to the captured portion of the tissue thickness compensator 20720 and the captured tissue T, such that the tissue thickness compensator 20720 is compressed between a non-compressed height and a compressed height. Similar to the embodiments described herein, compression of the tissue thickness compensator 20720 can result in a corresponding deformation of the spring coils 20786 and compensation material 20780 retained therein. As described in greater detail herein, deformation of each spring coils 20786 can generate a restoring force that can depend on the resiliency of the spring coil, for example, the amount the spring coil 20786 is deformed and/or the spring rate of the spring coil 20786. The spring rate of a spring coil 20786 can at least depend on the orientation, material, shape and/or size of the spring coil 20786, for example. The aggregate of restoring forces generated by at least the deformed spring coils 20786 and/or the compensation material 30380 in the tissue thickness compensator 20720 can generate restoring forces throughout the tissue thickness compensator 20720. Similar to the embodiments described herein, the tissue thickness compensator 20720 can exert the aggregate restoring force generated by the deformed spring coils 20786 in the tissue thickness compensator 20720 on the captured tissue T and fired staples 20030.

Figure 76:
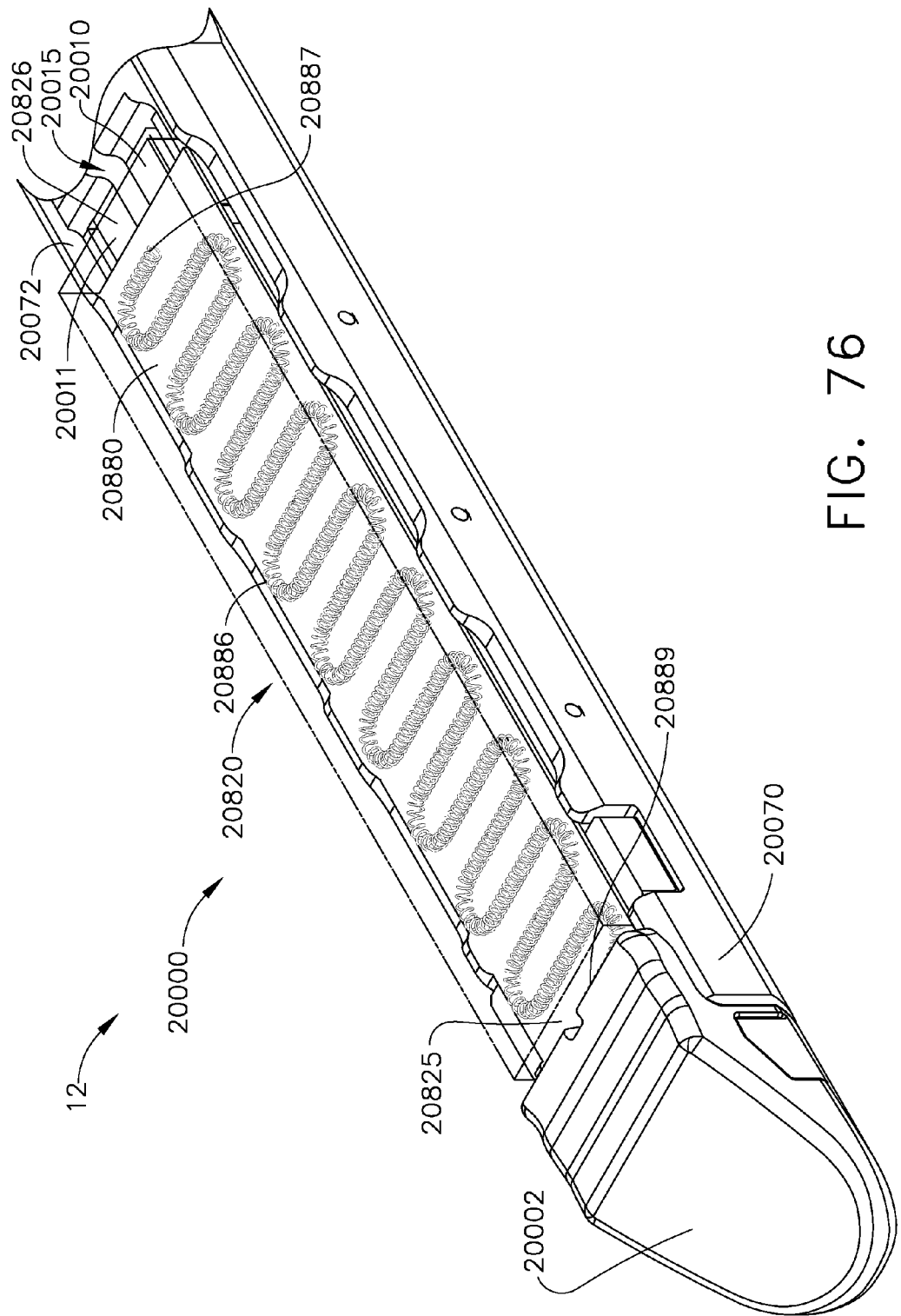
FIG. 76 is a perspective view of a tissue thickness compensator in an end effector of a surgical instrument according to at least one embodiment.
Figure 77:
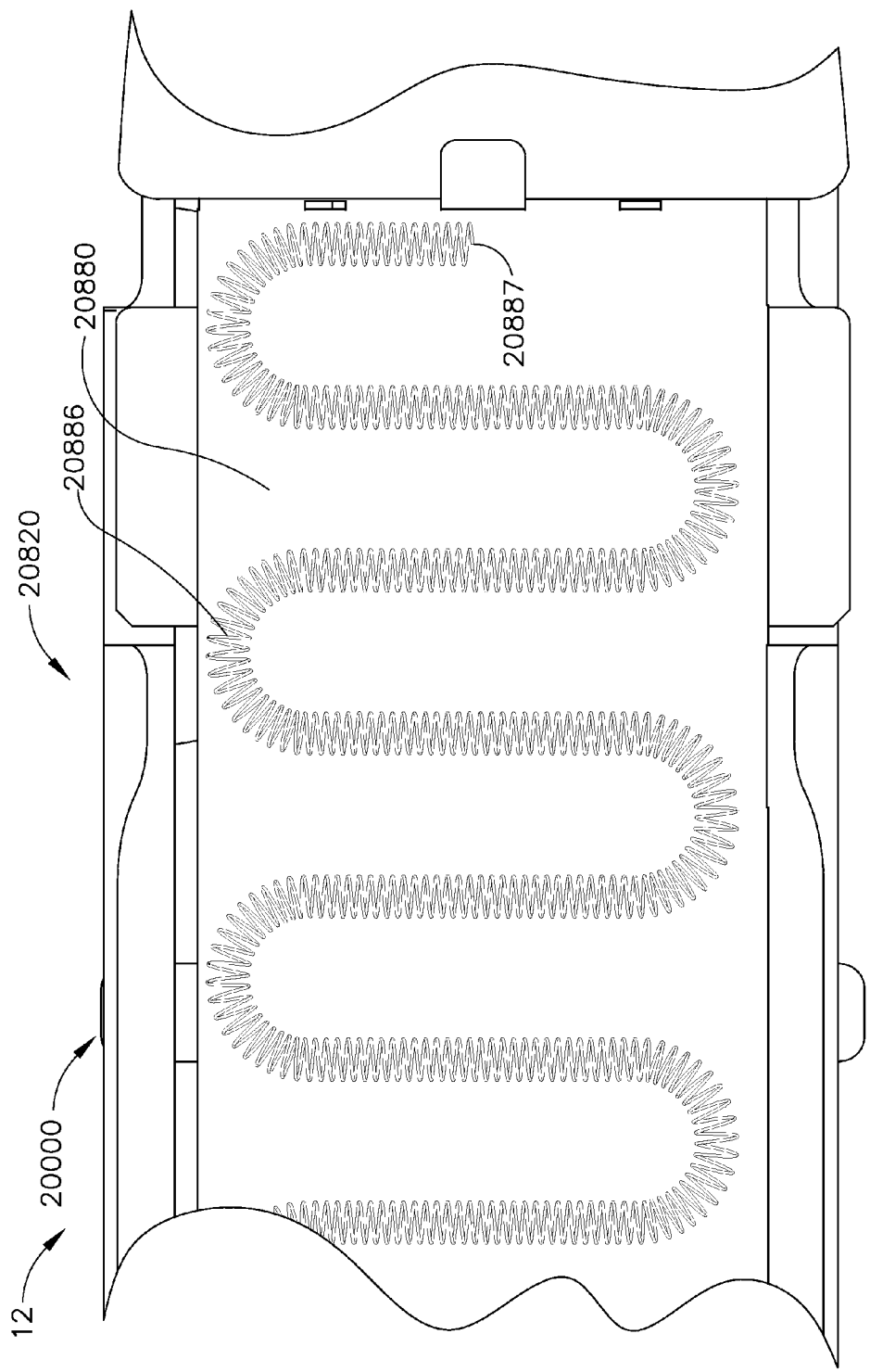
FIG. 77 is a partial plan view of the tissue thickness compensator of FIG. 76.

In various embodiments, primarily referring to FIGS. 76 and 77, a tissue thickness compensator 20820 for a surgical end effector 12 can comprise a spring coil 20886. Similar to the fibers and coils described herein, spring coil 20886 can be, for example, crimped, twisted, coiled, bent, crippled, spiraled, curled, and/or bowed within the tissue thickness compensator 20820. The spring coil 20886 can comprise a polymeric composition and can be at least partially elastic, such that deformation of the spring coil 20886 generates a springback force. Further, the spring coil 20886 can comprise a first end 20887 and a second end 20889. Referring to FIG. 76, the first end 20887 can be positioned at or near a proximal end 20826 of the tissue thickness compensator 20820 and the second end 20889 can be positioned at or near a distal end 20825 of the tissue thickness compensator 20820. The spring coil 20886 can wind or meander from the proximal end 20825 to the distal end 20826 of the tissue thickness compensator 20820.

Referring again to FIG. 76, the spring coil 20886 can be retained or embedded in a compensation material 20880. The compensation material 20880 can be bioabsorbable and, in some embodiments, can comprise a foam, such as, for example, polyglycolic acid (PGA) foam. The compensation material 20880 can be soluble in a chlorophyll solvent, for example. In some embodiments, the tissue thickness compensator can comprise spring coils 20886 comprising polycaprolactone (PCL) and compensation material 20880 comprising polyglycolic acid (PGA) foam, for example, such that the spring coil 20886 is not soluble in a chlorophyll solvent while the compensation material 20880 is soluble in a chlorophyll solvent. The compensation material 20880 can be at least partially resilient such that deformation of the compensation material 20880 generates a spring load or restoring force.

Similar to tissue thickness compensators described herein, for example, the tissue thickness compensator 20820 can be compressible. Compression of the tissue thickness compensator 20820 can result in a deformation of at least a portion of the spring coil 20886 retained or embedded in the compensation material 20880 of the tissue thickness compensator 20820. As described in greater detail herein, deformation of the spring coil 20886 can generate restoring forces that can depend on the resiliency of the spring coil 20886, the amount the spring coil 20886 is deformed, and/or the spring rate of the spring coil 20886, for example. The aggregate of restoring forces generated by the deformed spring coil 20886 and/or deformed compensation material 20880 can generate restoring forces throughout the tissue thickness compensator 20820. The tissue thickness compensator 20820 can exert the aggregate restoring force on the captured tissue T in the fired staples 20030.

Figure 84:
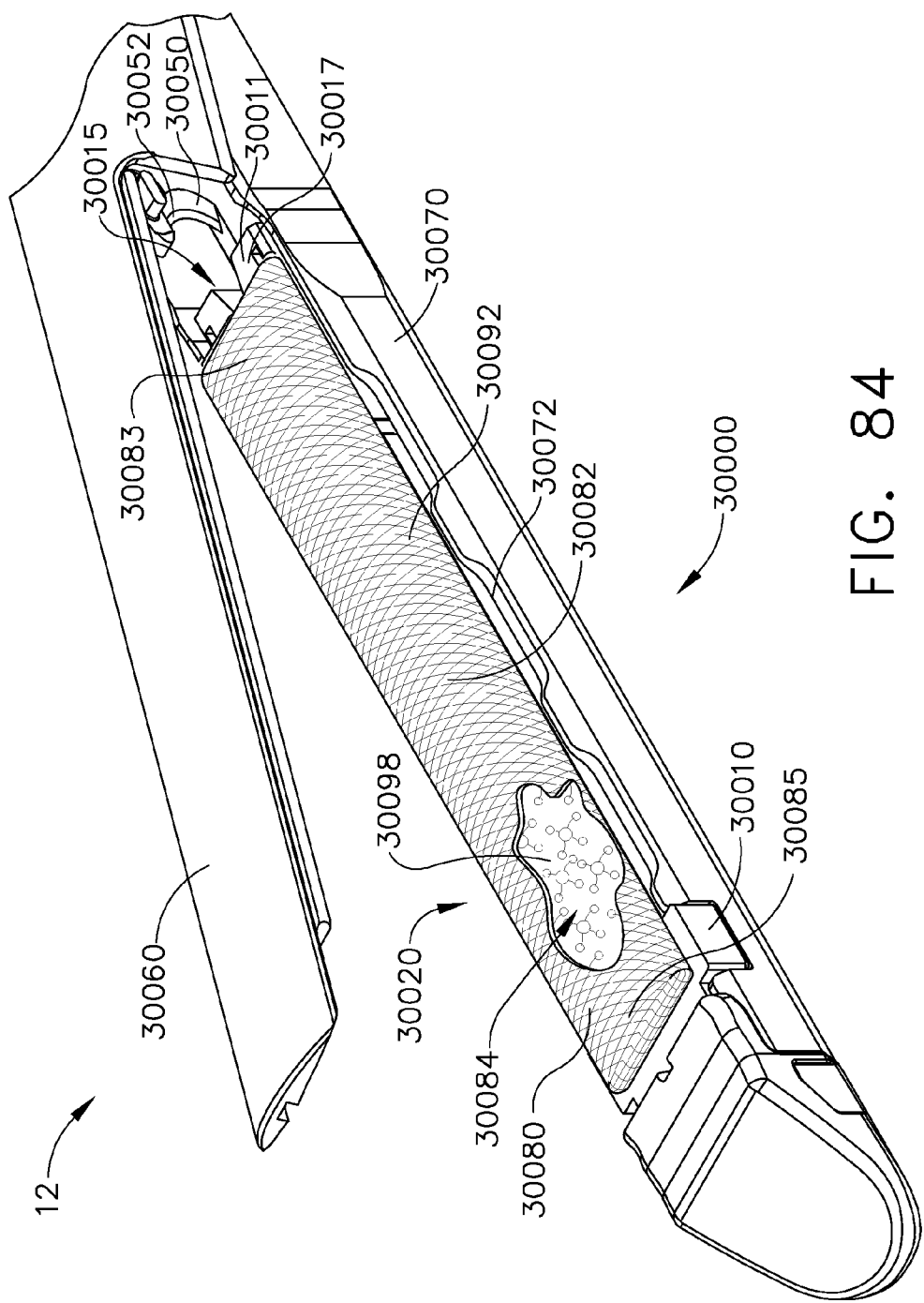
FIG. 84 is a perspective view of a tissue thickness compensator in an end effector of a surgical instrument according to at least one embodiment.

Referring now to FIG. 84, a surgical end effector 12 can comprise a tissue thickness compensator 30020 having at least one tubular element 30080. The tissue thickness compensator 30020 can be retained in the surgical end effector 12. As described in greater detail herein, a fastener in the end effector 12 can be deployed such that the fastener moves to a fired position and deforms at least a portion of the tubular element 30080 in the tissue thickness compensator 30020. The reader will appreciate that tissue thickness compensators comprising at least one tubular element as described herein can be installed in or otherwise engaged with a variety of surgical end effectors and that such embodiments are within the scope of the present disclosure.

In various embodiments, still referring to FIG. 84, the tissue thickness compensator 30020 can be positioned relative to the anvil 30060 of the end effector 12. In other embodiments, the tissue thickness compensator 30020 can be positioned relative to a fastener cartridge assembly, such as staple cartridge 30000, of the end effector 12. In various embodiments, the staple cartridge 30000 can be configured to fit in a cartridge channel 30072 of a jaw 30070 of the end effector 12. For example, the tissue thickness compensator 30020 can be releasably secured to the staple cartridge 30000. In at least one embodiment, the tubular element 30080 of the tissue thickness compensator 30020 can be positioned adjacent to a top deck surface 30011 of a rigid support portion 30010 of the staple cartridge 30000. In various embodiments, the tubular element 30080 can be secured to the top deck surface 30011 by an adhesive or by a wrap, similar to at least one of the wraps described herein (e.g., FIG. 16). In various embodiments, the tissue thickness compensator 30020 can be integral to an assembly comprises the staple cartridge 30000 such that the staple cartridge 30000 and the tissue thickness compensator 30020 are formed as a single unit construction. For example, the staple cartridge 30000 can comprise a first body portion, such as the rigid support portion 30010, and a second body portion, such as the tissue thickness compensator 30020, for example.

Figure 86:
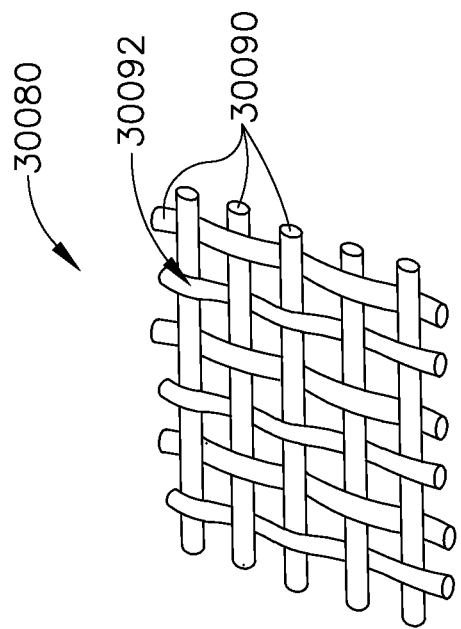
FIG. 86 is a detail view of the deformable tube of the tissue thickness compensator of FIG. 84.
Figure 85:
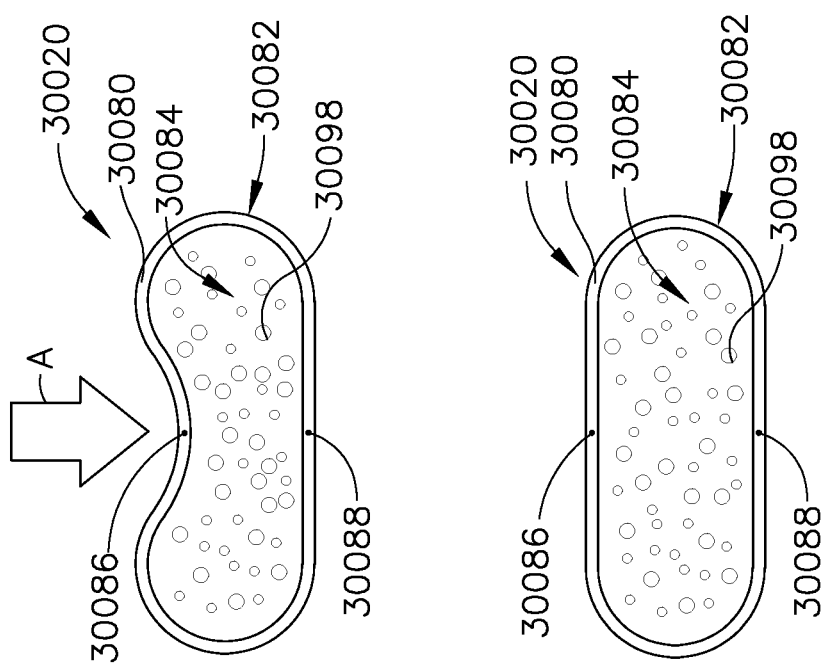
FIG. 85 is a diagram depicting deformation of a deformable tube of the tissue thickness compensator of FIG. 84.

Referring to FIGS. 84-86, the tubular element 30080 in the tissue thickness compensator 30020 can comprise an elongate portion 30082 having at least one lumen 30084 that extends at least partially therethrough. Referring primarily to FIG. 86, the elongate portion 30082 of the tubular element 30080 can comprise woven or braided strands 30090, as described in greater detail herein. In other embodiments, the elongate portion 30082 can comprise a solid structure, such as a polymer extrusion, rather than woven strands 30090. The elongate portion 30082 of the tubular element 30080 can comprise a thickness. In various embodiments, the thickness of the elongate portion 30082 can be substantially uniform throughout the length and around the diameter thereof; in other embodiments, the thickness can vary. The elongate portion 30082 can be elongated such that the length of the elongate portion 30082 is greater than the diameter of the elongate portion 30082, for example. In various embodiments, the elongate portion can comprise a length of approximately 1.20 inches to approximately 2.60 inches and a diameter of approximately 0.10 inches to approximately 0.15 inches, for example. In some embodiments, the length of the tubular element 20080 can be approximately 1.40 inches, for example, and the diameter of the tubular element 20080 can be approximately 0.125 inches, for example. Furthermore, the elongate portion 30082 can define a substantially circular or elliptical cross-sectional shape, for example. In other embodiments, the cross-sectional shape can comprise a polygonal shape, such as, for example, a triangle, a hexagon and/or an octagon. Referring again to FIG. 84, the tubular element 30080 can comprise a first distal end 30083 and a second proximal end 30085. In various embodiments, the cross-sectional shape of the elongate portion 30082 can narrow at the first and/or second end 30083, 30085 wherein at least one end 30083, 30085 of the tubular element 30080 can be closed and/or sealed. In other embodiments, a lumen 30084 can continue through the distal ends 30083, 30085 of the tubular element 30080 such that the ends 30083, 30085 are open.

In various embodiments, the tubular element 30080 can comprise a single central lumen 30084 that extends at least partially through the elongate portion 30084. In some embodiments, the lumen 30084 can extend through the entire length of the elongate portion 30084. In still other embodiments, the tubular element 30080 can comprise multiple lumens 30084 extending therethrough. Lumens 30084 extending through the tubular element 30080 can be circular, semi-circular, wedge-shaped, and/or combinations thereof. In various embodiments, a tubular element 30080 can also comprise support webs that can form a modified "T" or "X" shape, for example, within the lumen 30084. In various embodiments, the dimensions, lumen(s), and/or support web(s) within the tubular element 30080 can define the cross-sectional shape of the tubular element 30080. The cross-sectional shape of the tubular element 30080 can be consistent throughout the length thereof or, in other embodiments, the cross-sectional shape of the tubular element 30080 can vary along the length thereof. As described in greater detail herein, the cross-sectional shape of the tubular element 30080 can affect the compressibility and resiliency of the tubular element 30080.

In various embodiments, the tubular element 30080 can comprise a vertical diameter and a horizontal diameter; the dimensions thereof can be selected depending on the arrangement of the tubular element 30080 in the end effector 12, the dimensions of the end effector 12, including the tissue gap of the end effector 12, and the expected geometry of the staple entrapment areas 30039. For example, the vertical diameter of the tubular element 30080 can relate to the expected height of a formed staple. In such embodiments, the vertical diameter of the tubular element 30080 can be selected such that the vertical diameter can be reduced approximately 5% to approximately 20% when the tubular element 30080 is captured within a formed staple 30030. For example, a tubular element 30080 having a vertical diameter of approximately 0.100 inches may be used for staples having an expected formed height of approximately 0.080 inches to approximately 0.095 inches. As a result, the vertical diameter of the tubular element 30080 can be reduced approximately 5% to approximately 20% when captured within the formed staple 30030 even when no tissue T is captured therein. When tissue T is captured within the formed staple 30030, the compression of the tubular element 30080 may be even greater. In some embodiments, the vertical diameter can be uniform throughout the length of the tubular element 30080 or, in other embodiments, the vertical diameter can vary along the length thereof.

In some embodiments, the horizontal diameter of the tubular element 30080 can be greater than, equal to, or less than the vertical diameter of the tubular element 30080 when the tubular element 30080 is in an undeformed or rebounded configuration. For example, referring to FIG. 85, the horizontal diameter can be approximately three times larger than the vertical diameter, for example. In some embodiments the horizontal diameter can be approximately 0.400 inches and the vertical diameter can be approximately 0.125 inches, for example. In other embodiments, referring now to FIG. 87, the horizontal diameter of a tubular element 31080 can be equal to or substantially equal to the vertical diameter of the tubular element 31080 when the tubular element 31080 is in an undeformed or rebounded configuration. In some embodiments the horizontal diameter can be approximately 0.125 inches and the vertical diameter can also be approximately 0.125 inches, for example. In various embodiments, the tubular element 30080 can comprise a vertical diameter of approximately 0.125 inches, a horizontal diameter of approximately 0.400 inches, and a length of approximately 1.400 inches. As described in greater detail herein, when a force A is applied to the tubular element 30080 and/or 31080, the tubular element can deform such that the cross-sectional geometry, including the horizontal and vertical diameters, can change.

Referring again to FIGS. 84-86, the tubular element 30080 in the tissue thickness compensator 30020 can be deformable. In various embodiments, the entire tubular element 30080 can be deformable. For example, the tubular element 30080 can be deformable from the proximal end 30083 to the distal end 30085 of the elongate portion 30082 and around the entire circumference thereof. In other embodiments, only a portion of the tubular element 30080 can be deformable. For example, in various embodiments, only an intermediate length of the elongate portion 30082 and/or only a portion of the circumference of the tubular element 30080 can be deformable.

When a compressive force is applied to a contact point on the elongate portion 30082 of the tubular element 30080, the contact point can shift, which can alter the cross-sectional dimensions of the tubular element 30080. For example, referring again to FIG. 85, the tubular element 30080 can comprise a top apex 30086 and a bottom apex 30088 on the elongate portion 30082. In the initial, undeformed configuration, the tubular element 30080 can comprise undeformed cross-sectional dimensions, including an undeformed vertical diameter between the top apex 30086 and the bottom apex 30088. When a compressive force A is applied to the top apex 30086, the tubular element 30080 can move to a deformed configuration. In the deformed configuration, the cross-sectional dimensions of the tube 30080 can be altered. For example, the tube 30086 can comprise a deformed vertical diameter between the top apex 30086 and the bottom apex 30088, which can be less than the undeformed vertical diameter. In some embodiments, referring to FIG. 87, the horizontal diameter of the deformed tube 30080 can be lengthened, for example, when the tubular element 30080 moves from an undeformed configuration to a deformed configuration. The deformed cross-sectional dimensions of the deformed tube 30080 can at least depend on the position, angular orientation, and/or magnitude of the applied force A. As described in greater detail herein, deformation of a tubular element 30080 can generate a springback or restoring force that can depend on the resiliency of the tubular element 30080.

Referring still to FIG. 85, the tubular element 30080 can generate a springback or restoring force when compressed. In such embodiments, as described herein, the tubular element 30080 can move from an initial undeformed configuration to a deformed configuration when a force A is applied to a contact point on the elongate portion 30082 of the tubular element 30080. When the applied force A is removed, the deformed tube 30080 can rebound from the deformed configuration. The deformed tube 30080 may rebound to the initial, undeformed configuration or may rebound to a configuration substantially similar to the initial, undeformed configuration. The ability of the tubular element 30080 to rebound from a deformed configuration relates to the resiliency of the tubular element 30080.

Referring again to FIG. 85, a tubular element 30080 can exert a springback or restoring force. The restoring force can be generated by the tubular element 30080 when an applied force A is exerted on the tubular element 30080, for example, by a staple 30030 (FIGS. 88 and 89), as described in greater detail herein. An applied force A can alter the cross-sectional dimensions of the tubular element 30080. Furthermore, in linear-elastic materials, the restoring force of each deformed portion of the tubular element 30080 can be a function of the deformed dimensions of the tubular element 30080 and the spring rate of that portion of the tubular element 30080. The spring rate of a tubular element 30080 can at least depend on the orientation, material, cross-sectional geometry and/or dimensions of the tubular element 30080, for example. In various embodiments, the tubular element 30080 in a tissue thickness compensator 30020 can comprise a uniform spring rate. In other embodiments, the spring rate can vary along the length and/or around the diameter of the tubular element 30080. When a portion of a tubular element 30080 having a first spring rate is greatly compressed, the tubular element 30080 can generate a large restoring force. When a portion of the tubular element 30080 having the same first spring rate is less compressed, the tubular element 30080 can generate a smaller restoring force.

Referring again to FIG. 84, the tubular element 30080 in the tissue thickness compensator 30020 can comprise a polymeric composition. In some embodiments, the elongate portion 30082 of the tubular element 30080 can comprise the polymeric composition. Further, in various embodiments, the polymeric composition can comprise an at least partially elastic material such that deformation of the tubular element 30080 generates a restoring force. The polymeric composition can comprise non-absorbable polymers, absorbable polymers, or combinations thereof, for example. Examples of synthetic polymers include, but are not limited to, polyglycolic acid (PGA), poly(lactic acid) (PLA), polycaprolactone (PCL), polydioxanone (PDO), and copolymers thereof. In some embodiments, the absorbable polymers can include bioabsorbable, biocompatible elastomeric polymers, for example. Furthermore, the polymeric composition of the tubular element 30080 can comprise synthetic polymers, non-synthetic polymers, or combinations thereof, for example. In various embodiments, similar to the polymeric compositions in embodiments described herein, the polymeric composition of the tubular element 30080 can include varied amounts of absorbable polymers, non-absorbable polymers, synthetic polymers, and/or non-synthetic polymers, for example, by weight percentage.

Referring to FIGS. 84 and 85, the tubular element 30080 can comprise a therapeutic agent 30098 such as a pharmaceutically active agent or medicament, for example. In various embodiments, the therapeutic agent 30098 can be retained in the lumen 30084 of the tubular element 30080. The elongate portion 30082 can encapsulate or partially encapsulate the therapeutic agent 30098. Additionally or alternatively, the polymeric composition of the elongate portion 30082 can comprise the therapeutic agent 30098. The tubular element 30080 can release a therapeutically effective amount of the therapeutic agent 30098. In various embodiments, the therapeutic agent 30098 can be released as the tubular element 30080 is absorbed. For example, the therapeutic agent 30098 can be released into fluid (such as blood) passing over or through the tubular element 30080. In still other embodiments, the therapeutic agent 30098 can be released when a staple 30030 (FIGS. 88 and 89) pierces the tubular element 30080 and/or when the cutting element 30052 on the staple-firing sled 30050 (FIG. 84) cuts a portion of the tubular element 30080, for example. Examples of therapeutic agents 30098 can include, but are not limited to, haemostatic agents and drugs such as, for example, fibrin, thrombin, and/or oxidized regenerated cellulose (ORC), anti-inflammatory drugs such as, for example, diclofenac, aspirin, naproxen, sulindac, and/or hydrocortisone, antibiotic and antimicrobial drugs or agents such as, for example, triclosan, ionic silver, ampicillin, gentamicin, polymyxin B, and/or chloramphenicol, anticancer agents such as, for example, cisplatin, mitomycin, and/or adriamycin, and/or biologics such as, for example, stem cells.

Figure 104:
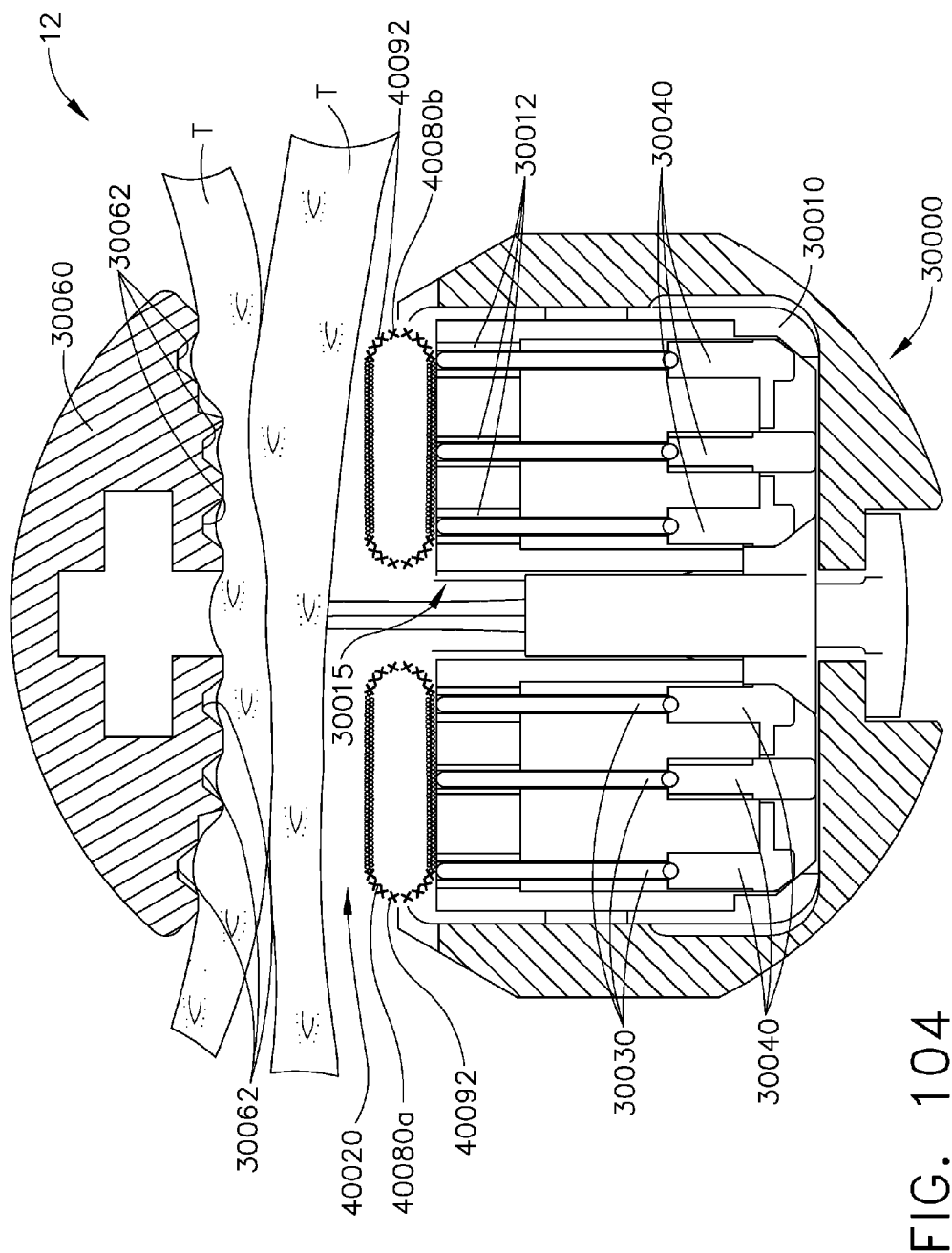
FIG. 104 is an elevational cross-sectional view of the tissue thickness compensator and the end effector of FIG. 102 depicting the end effector in an unclamped configuration.

In various embodiments, referring again to FIGS. 84, 88 and 89, fasteners such as staples 30030, for example, can be deployed from a staple cartridge 30000 such that the staples 30030 engage a tissue thickness compensator 30020 and apply a force A to a tubular element 32080 therein. As described herein, application of a force A to the tubular element 30080 can cause deformation of the tubular element 30080. Similar to the end effectors 12 described herein, the rigid support portion 30010 of the staple cartridge 30000 can comprise a cartridge body 30017, a deck surface 30011, and a plurality of staple cavities 30012 therein. Each staple cavity 30012 can define an opening in the deck surface 30011 and a staple 30030 can be removably positioned in a staple cavity 30012 (FIG. 104). In at least one embodiment, referring primarily to FIGS. 88 and 89, each staple 30030 can comprise a base 30031 and two staple legs 30032 extending from the base 30031. Prior to the deployment of the staples 30030, the base 30031 of each staple 30030 can be supported by a staple driver 30040 (FIG. 104) positioned within the rigid support portion 30010 of the staple cartridge 30000. Also prior to the deployment of the staples 30030, the legs 30032 of each staple 30030 can be at least partially contained within the staple cavity 30012 (FIG. 104).

In various embodiments, as described in greater detail herein, the staples 30030 can be deployed between an initial position and a fired position. For example, a staple-firing sled 30050 can engage a driver 30040 (FIG. 104) to move at least one staple 30030 between the initial position and the fired position. In various embodiments, referring primarily to FIG. 88, the staple 30030 can be moved to a fired position, wherein the legs 30032 of the staple 30030 engage a tubular element 32080 of a tissue thickness compensator 32020, penetrate tissue T, and contact an anvil 30060 (FIG. 104) positioned opposite the staple cartridge 30000 in the surgical end effector 12. Staple forming pockets 30062 in the anvil 30060 can bend the staple legs 30032 such that the fired staple 30030 captures a portion of the tubular element 32080 and a portion of the tissue T in a staple entrapment area 30039. As described in greater detail herein, at least one staple leg 30032 can pierce the tubular element 32080 of the tissue thickness compensator 32020 when the staple 30030 moves between the initial position and the fired position. In other embodiments, the staple legs 30032 can move around the perimeter of the tubular element 32080 such that the staple legs 30032 avoid piercing the tubular element 32080. Similar to the fasteners described herein, the legs 30032 of each staple 30030 can be deformed downwardly toward the base 30031 of the staple 30030 to form a staple entrapment area 30039 therebetween. The staple entrapment area 30039 can be the area in which tissue T and a portion of the tissue thickness compensator 32020 can be captured by a fired staple 30030. In the fired position, each staple 30030 can apply a compressive force to the tissue T and to the tissue thickness compensator 32020 captured within the staple entrapment area 30039 of the staple 30030.

Figure 88:
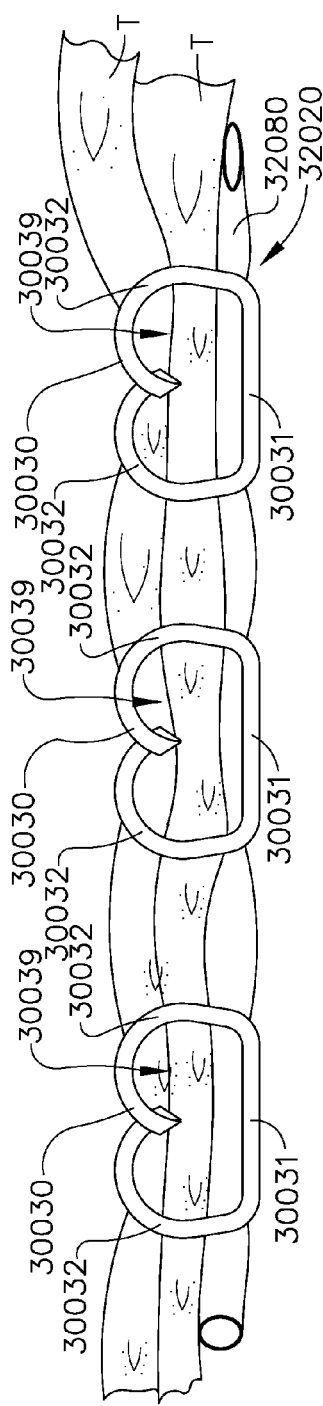
FIG. 88 is an elevational view of a tissue thickness compensator comprising a tubular element implanted against tissue according to at least one embodiment.
Figure 89:
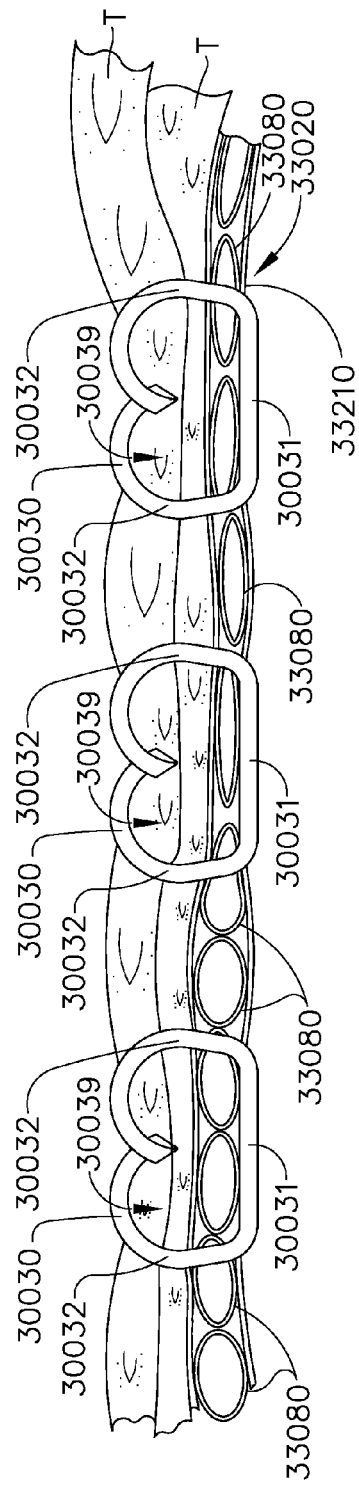
FIG. 89 is an elevational view of a tissue thickness compensator comprising tubular elements implanted against tissue according to at least one embodiment.

In various embodiments, referring still to FIG. 88, when the tubular element 32080 is captured in a staple entrapment area 30039, the captured portion of the tubular element 32080 can be deformed, as described herein. Furthermore, the tubular element 32080 can be deformed to different deformed configurations in different staple entrapment areas 30039 depending on, for example, the thickness, compressibility, and/or density of the tissue T captured in that same staple entrapment area 30039. In various embodiments, the tubular element 32080 in the tissue thickness compensator 32080 can extend longitudinally through successive staple entrapment areas 30039. In such an arrangement, the tubular element 32080 can be deformed to different deformed configurations in each staple entrapment area 30039 along a row of fired staples 30030. Referring now to FIG. 89, tubular elements 33080 in a tissue thickness compensator 33020 can be laterally arranged in the staple entrapment areas 30039 along a row of fired staples 30030. In various embodiments, the tubular elements 33080 can be retained by a flexible shell 33210. In such arrangements, the tubular elements 33080 and flexible shell 33210 can be deformed to different deformed configurations in each staple entrapment area 30039. For example, where the tissue T is thinner, the tubular elements 33080 can be compressed less and where the tissue T is thicker, the tubular elements 33080 can be compressed more to accommodate the thicker tissue T. In other embodiments, the deformed dimensions of the tubular elements 33080 can be uniform throughout the entire length and/or width of the tissue thickness compensator 33020.

Figure 90:
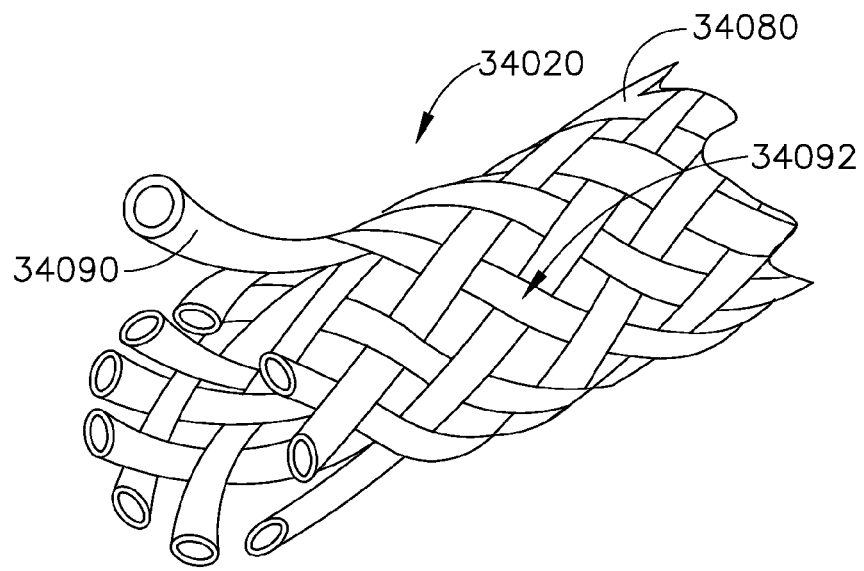
FIG. 90 is a partial perspective view of a deformable tube comprising a tubular lattice according to at least one embodiment.
Figure 91:
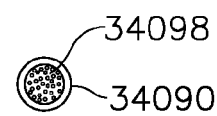
FIG. 91 is an elevational view of a tubular strand of the deformable tube of FIG. 90.
Figure 92:
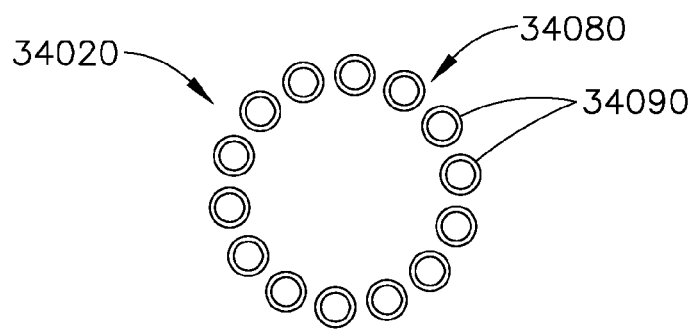
FIG. 92 is an elevational view of the deformable tube of FIG. 90.
Figure 93:
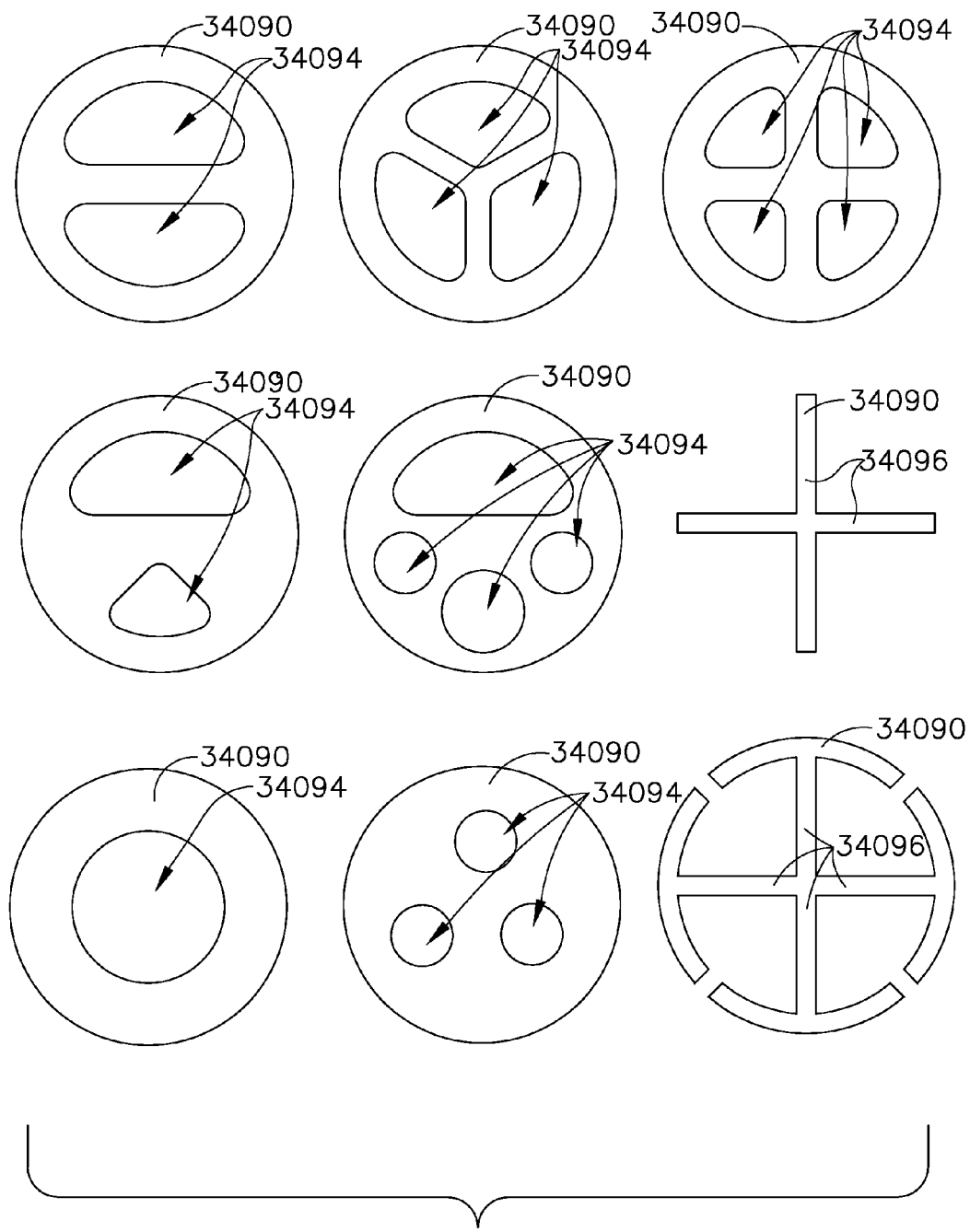
FIG. 93 is an elevational view of multiple tubular strands for the deformable tube of FIG. 90 according to various embodiments.

Referring to FIGS. 90-92, in various embodiments, a tubular element 34080 in a tissue thickness compensator 34020 can comprise a plurality of strands 34090. Referring primarily to FIG. 90, in some embodiments, the strands 34090 can be woven or braided into a tubular lattice 34092 forming the tubular element 34080. The tubular lattice 34092 formed by the strands 34090 can be substantially hollow. The strands 34090 of the tubular element 34080 can be solid strands, tubular strands, and/or another other suitable shape. For example, referring to FIG. 91, a single strand 34090 of the tubular lattice 34092 can be a tube. In various embodiments, referring to FIG. 93, a strand 34090 can comprise at least one lumen 34094 extending therethrough. The number, geometry and/or dimensions(s) of the lumens 34094 can determine the cross-sectional shape of the strand 34090. For example, a strand 34090 can comprise circular lumen(s), semi-circular lumen(s), wedge-shaped lumen(s), and/or combinations thereof. In various embodiments, a strand 34090 can also comprise support webs 34096 that can form a modified "T" or "X" shape, for example. At least the diameter of the strand 34090, the lumen(s) extending therethrough, and the support web(s) can characterize the cross-sectional shape of a strand 34090. The cross-sectional shape of each strand 34090, as discussed in greater detail herein, can affect the springback or restoring force generated by the strand 34090 and the corresponding springback or restoring force generated by the tubular element 34080.

Figure 94:
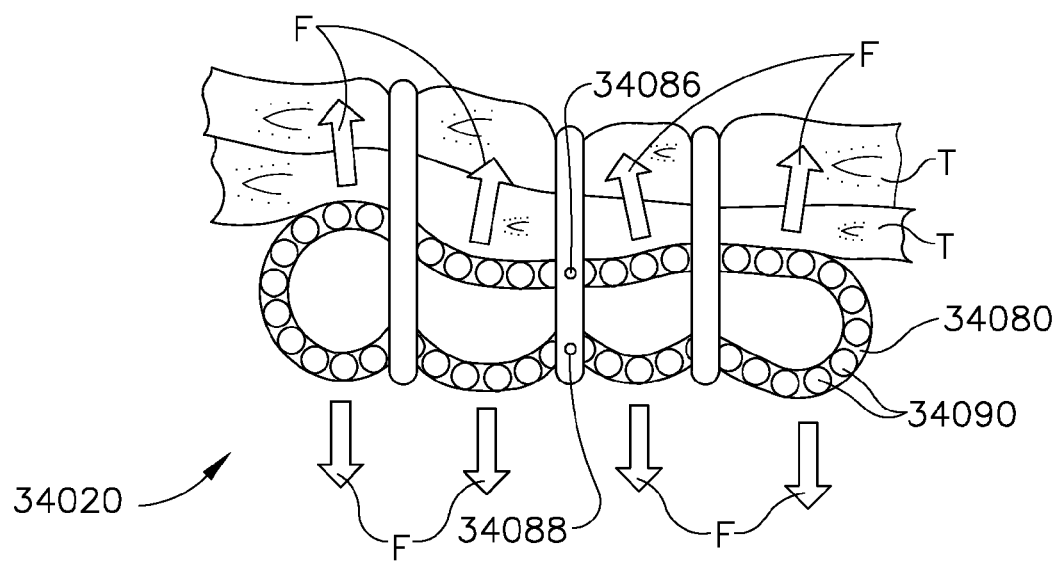
FIG. 94 is an elevational view of the tubular lattice of FIG. 90 implanted against tissue.

Referring to FIG. 94, a tubular lattice 34092 of strands 34090 can be deformable. In various embodiments, the tubular lattice 34092 can produce or contribute to the deformability and/or the resiliency of the tubular element 34080. For example, the strands 34090 of the tubular lattice 34092 can be woven together such that the strands 34090 are configured to slide and/or bend relative to each other. When a force is applied to the elongate portion 34082 of the tubular element 34080, the strands 34090 therein may slide and/or bend such that the tubular lattice 34092 moves to a deformed configuration. For example, referring still to FIG. 94, a staple 30030 can compress the tubular lattice 34092 and the tissue T captured in a staple entrapment area 34039 which can cause the strands 34090 of the tubular lattice 34092 to slide and/or bend relative to each other. A top apex 34086 of the tubular lattice 34092 can move towards a bottom apex 34088 of the tubular lattice 34092 when the tubular lattice 34092 is compressed to the deformed configuration in order to accommodate the captured tissue T in a staple entrapment area 30039. In various circumstances, the tubular lattice 34092 captured in a fired stapled 30030 will seek to regain its undeformed configuration and can apply a restoring force to the captured tissue T. Further, the portions of the tubular lattice 34092 positioned between staple entrapment areas 30039, i.e., not captured within a fired staple 30030, can also be deformed due to the deformation of adjacent portions of the tubular lattice 34092 that are within the staple entrapment areas 30039. Where the tubular lattice 34092 is deformed, the tubular lattice 34092 can seek to rebound or partially rebound from the deformed configuration. In various embodiments, portions of the tubular lattice 34092 can rebound to their initial configurations and other portions of the tubular lattice 34092 can only partially rebound and/or remain fully compressed.

Similar to the description of the tubular elements herein, each strand 34090 can also be deformable. Further, deformation of a strand 34090 can generate a restoring force that depends on the resiliency of each strand 34090. In some embodiments, referring primarily to FIGS. 91 and 92, each strand 34090 of a tubular lattice 34092 can be tubular. In other embodiments, each strand 34090 of a tubular lattice 34092 can be solid. In still other embodiments, the tubular lattice 30092 can comprise at least one tubular strand 34090, at least one solid strand 34090, at least one "X"- or "T"-shaped strand 34090, and/or a combination thereof.

In various embodiments, the strands 34090 in the tubular element 34080 can comprise a polymeric composition. The polymeric composition of a strand 34090 can comprise non-absorbable polymers, absorbable polymers, or combinations thereof. Examples of synthetic polymers include, but are not limited to, polyglycolic acid (PGA), poly(lactic acid) (PLA), polycaprolactone (PCL), polydioxanone (PDO), and copolymers thereof. In some embodiments, the absorbable polymers can include bioabsorbable, biocompatible elastomeric polymers, for example. Furthermore, the polymeric composition of the strand 34090 can comprise synthetic polymers, non-synthetic polymers, and/or combinations thereof. In various embodiments, similar to the polymeric compositions in embodiments described herein, the polymeric composition of the strand 34090 can include varied amounts of absorbable polymers, non-absorbable polymers, synthetic polymers, and/or non-synthetic polymers, for example, by weight percentage.

The strands 34090 in the tubular element 34080 can further comprise a therapeutic agent 34098 (FIG. 91) such as a pharmaceutically active agent or medicament, for example. In some embodiments, the strand 34090 can release a therapeutically effective amount of the therapeutic agent 34098. In various embodiments, the therapeutic agent 34098 can be released as the tubular strand 34090 is absorbed. For example, the therapeutic agent 30098 can be released into fluid, such as blood for example, passing over or through the strand 34090. In still other embodiments, the therapeutic agent 34098 can be released when a staple 30030 pierces the strand 34090 and/or when the cutting element 30052 on the staple-firing sled 30050 (FIG. 84) cuts a portion of the tubular lattice 34092, for example. Examples of therapeutic agents 34098 can include, but are not limited to, haemostatic agents and drugs such as, for example, fibrin, thrombin, and/or oxidized regenerated cellulose (ORC), anti-inflammatory drugs such as, for example, diclofenac, aspirin, naproxen, sulindac, and/or hydrocortisone, antibiotic and antimicrobial drugs or agents such as, for example, triclosan, ionic silver, ampicillin, gentamicin, polymyxin B, and/or chloramphenicol, anticancer agents such as, for example, cisplatin, mitomycin, and/or adriamycin; and/or biologics such as, for example, stem cells.

Figure 95:
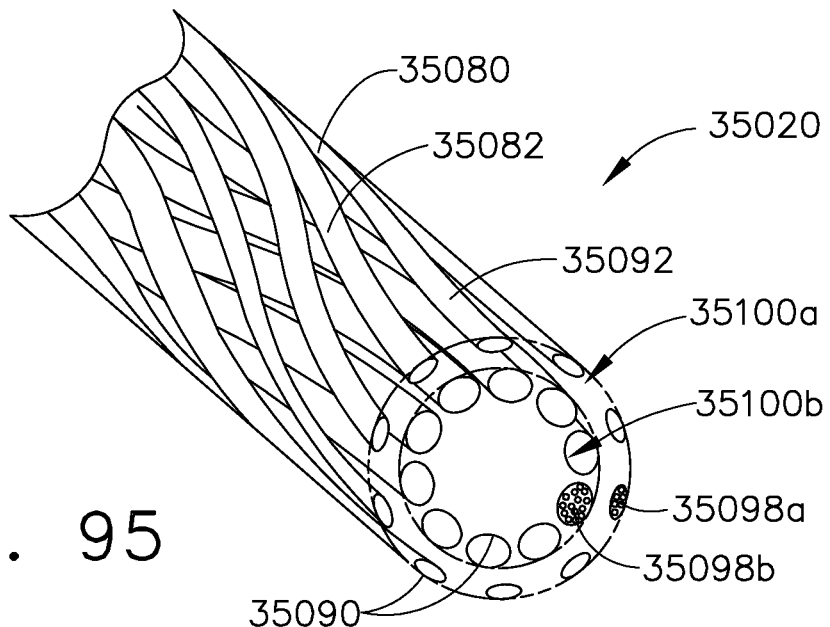
FIG. 95 is a partial perspective view of a deformable tube according to at least one embodiment.
Figure 96:
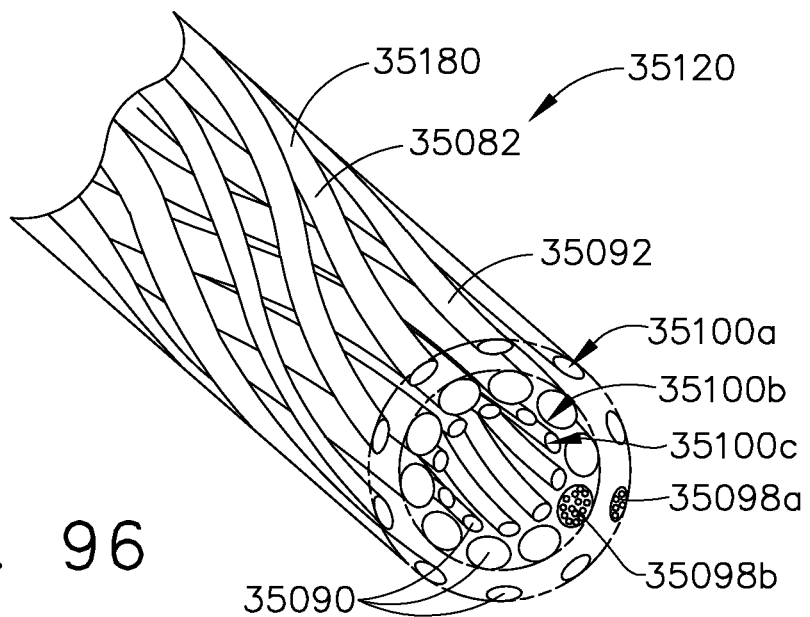
FIG. 96 is a partial perspective view of a deformable tube according to at least one embodiment.

Referring to FIGS. 95 and 96, a tubular element 35080 can comprise multiple layers 35100 of strands 35090. In some embodiments, the tubular element 35080 can comprise multiple layers 35100 of tubular lattices 35092. Referring to FIG. 95, the tubular element 35080 can comprise a first layer 35100a and a second layer 35100b of strands 35090, for example. Referring now to FIG. 96, a tubular element 35180 of a tissue thickness compensator 35120 can comprise a third layer 35100c of strands 35090, for example. Furthermore, different layers 35100 in the tubular element 35180 can comprise different materials. In some embodiments, each layer 35100a, 35100b, 35100c can be bioabsorbable, wherein, in at least one embodiment, each layer 35100a, 35100b, 35100c can comprise a different polymeric composition. For example, the first layer 35100a can comprise a first polymeric composition; the second layer 35100b can comprise a second polymeric composition; and the third layer 35100c can comprise a third polymeric composition. In such embodiments, layers 35100a, 35100b, 35100c of the tubular element 35180 can be bioabsorbed at different rates. For example, the first layer 35100a can absorb quickly, the second layer 35100b can absorb slower than the first layer 35100a, and the third layer 35100c can absorb slower than the first layer 35100a and/or the second layer 35100b. In other embodiments, the first layer 35100a can absorb slowly, the second layer 35100b can absorb faster than the first layer 35100a, and the third layer 35100c can absorb faster than the first layer 35100a and/or the second layer 35100b.

Similar to strands 34090 described herein, the strands 35090 in the tubular element 35180 can comprise a medicament 35098. In various embodiments, referring again to FIG. 95, to control elusion or release of the medicament(s) 35098, the first layer 35100a of strands 35090 comprising a medicament 35098a can be bioabsorbed at a first rate and the second layer 35100b of strands 35090 comprising a medicament 30098b can be bioabsorbed at a second rate. For example, the first layer 35100a can absorb quickly to allow for a rapid initial release of the medicament 35098a and the second layer 35100b can absorb slower to allow controlled release of the medicament 30098b. The medicament 35098a in the strands 35090 of the first layer 30100a can be different than the medicament 35098b in the strands 35090 of the second layer 35100b. For example, the strands 35090 in the first layer 35100a can comprise oxidized regenerated cellulose (ORC) and the strands 35090 in the second layer 35100b can comprise a solution comprising hyaluronic acid. In such embodiments, initial absorption of the first layer 35100a can release oxidized regenerated cellulose to help control bleeding while subsequent absorption of the second layer 35100b can release a solution comprising hyaluronic acid to can help prevent the adhesion of tissue. In other embodiments, the layers 35100a, 35100b can comprise the same medicament 35098a, 35098b. For example, referring again to FIG. 96, strands 35090 in layers 35100a, 35100b and 35100c can comprise an anticancer agent, such as, for example, cisplatin. Furthermore, the first layer 35100a can absorb quickly to allow for a rapid initial release of cisplatin, the second layer 35100b can absorb slower to allow for a controlled release of cisplatin, and the third layer 35100c can absorb slowest to allow for a more extended, controlled release of cisplatin.

Figure 97:
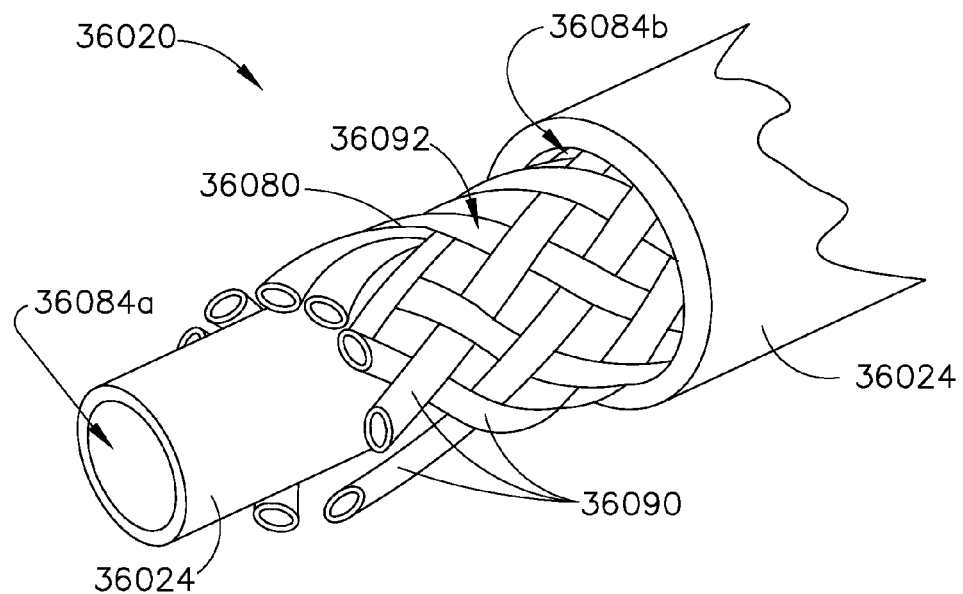
FIG. 97 is a partial perspective view of a deformable tube according to at least one embodiment.
Figure 98:
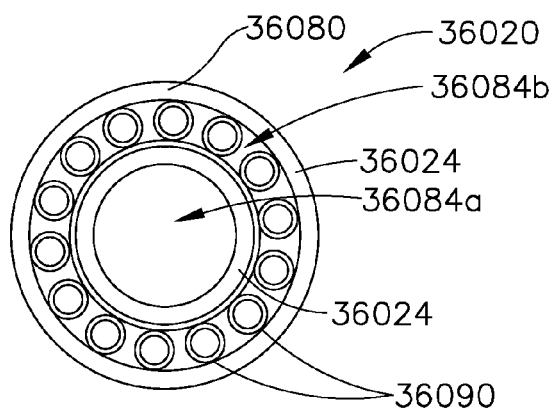
FIG. 98 is an elevational view of the deformable tube of FIG. 97.

In various embodiments, referring to FIGS. 97 and 98, a tissue thickness compensator 36020 can comprise an overmold material 36024. The overmold material 36024 can be formed outside a tubular element 36080, inside a tubular element 36080, or both inside and outside a tubular element 36080. In some embodiments, referring to FIG. 97, the overmold material 36024 can be coextruded both inside and outside the tubular element 36080 and, in at least one embodiment, the tubular element 36080 can comprise a tubular lattice 36092 of strands 36090. Similar to the polymeric composition described herein, the overmold material 36024 can comprise polyglycolic acid (PGA), poly(lactic acid) (PLA), and/or any other suitable, bioabsorbable and biocompatible elastomeric polymers, for example. Further, the overmold material 36024 can be non-porous such that the overmold material 36024 forms a fluid-impervious layer in the tubular element 36080. In various embodiments, the overmold material 36024 can define a lumen 36084 therethrough.

Figure 99:
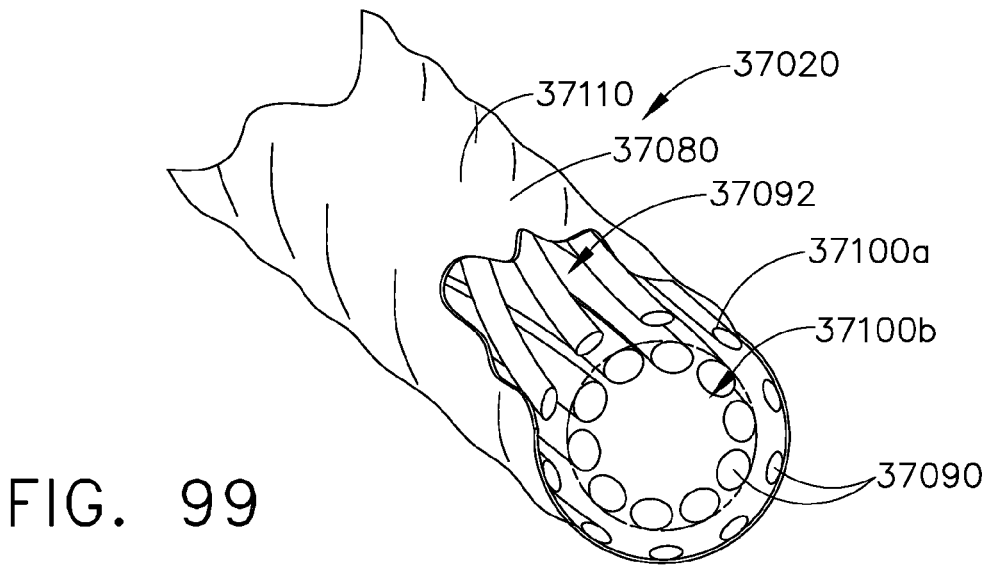
FIG. 99 is a partial perspective view of a deformable tube according to at least one embodiment.

Further to the discussion above, the tubular element 36080 and/or the strands 36090 in a tubular lattice 36092 can comprise a therapeutic agent 36098. In some embodiments, referring still to FIGS. 97 and 98, a non-porous overmold material 36024 can contain the medicament 36098 within an inner lumen 36084a. Alternatively or additionally, the non-porous, overmold material 36024 can contain the medicament 36098 within an intermediate lumen 36084b, such as, for example, the intermediate lumen 36084b that contains the tubular lattice 36092 of medicament-comprising strands 36090. Similar to the above, the tubular element 36080 can be positioned relative to staple cavities 30012 and a cutting element 30052 in staple cartridge 30000 (FIG. 84). In several such embodiments, the deployment of the staples 30030 and/or the translation of the cutting element 30052 can be configured to pierce or rupture the non-porous, overmold material 36024 such that the medicament 36098 contained in at least one lumen 36084 of the tubular element 30080 can be released from the lumen 30084. In various embodiments, referring to FIG. 99, a tubular element 37080 can comprise a non-porous film 37110. The non-porous film 37110 can at least partially surround a tubular lattice 37092 or a first layer 37100a and a second layer 37100b of tubular lattices 30092 to provide a fluid-impervious cover similar to the overmold material 36024 described herein.

Figure 100:
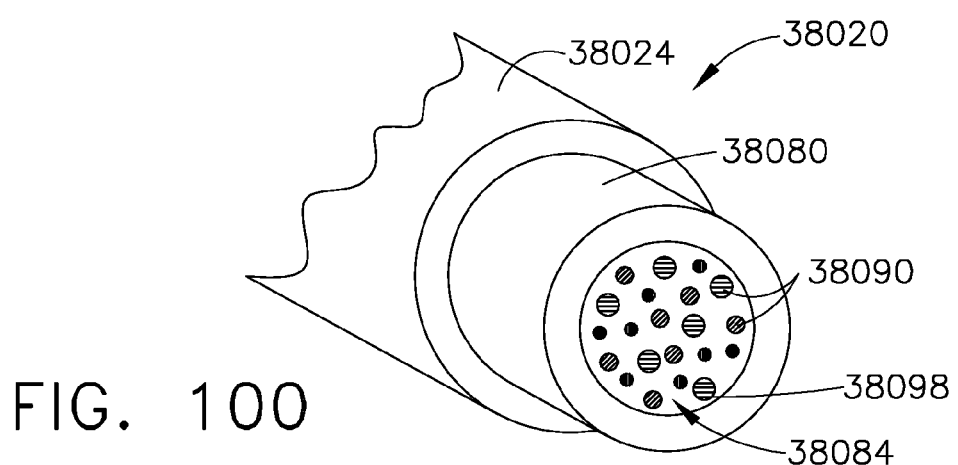
FIG. 100 is a partial perspective view of a deformable tube according to at least one embodiment.
Figure 101:
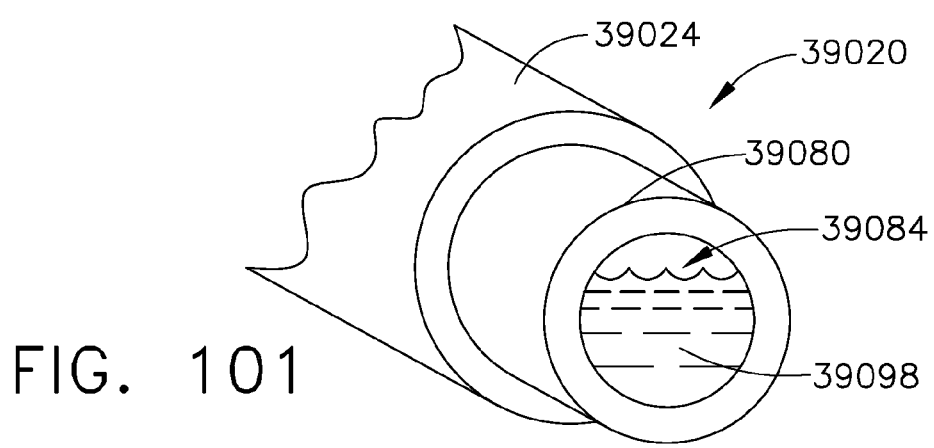
FIG. 101 is a partial perspective view of a deformable tube according to at least one embodiment.

As described herein, a tubular element can comprise at least one of a bioabsorbable material, a therapeutic agent, a plurality of strands, a tubular lattice, layers of tubular lattices, an overmold material, a non-porous film, or combinations thereof. For example, referring to FIG. FIG. 100, a tubular element 38080 can comprise an overmold material 38024 and a plurality of strands 38090 positioned through a central lumen 38084 of the tubular element 38080. In some embodiments, the strands 38090 can comprise a therapeutic agent 38098. In other embodiments, for example, referring to FIG. 101, a tubular element 39080 can comprise an overmold material 39024 and a therapeutic agent 39098 positioned in a central lumen 39084 of the tubular element 39080, for example. In various embodiments, at least one of the tubular element 39080 and overmold material 39024 can comprise a fluidic therapeutic agent 39098.

In various embodiments, referring again primarily FIG. 84, the tubular element 30080 can be positioned relative to the rigid support portion 30010 of the staple cartridge 30000. The tubular element 30080 can be longitudinally positioned adjacent to the rigid support portion 30010. In some embodiments, the tubular element 30080 can be substantially parallel to or aligned with a longitudinal slot or cavity 30015 in the rigid support portion 30010. The tubular element 30080 can be aligned with the longitudinal slot 30015 such that a portion of the tubular element 30080 overlaps a portion of the longitudinal slot 30015. In such embodiments, a cutting element 30052 on the staple-firing sled 30050 can sever a portion of the tubular element 30080 as the cutting edge 30052 translates along the longitudinal slot 30015. In other embodiments, the tubular element 30080 can be longitudinally positioned on a first or second side of the longitudinal slot 30015. In still other embodiments, the tubular element 30080 can be positioned relative to the rigid support portion 30010 of the staple cartridge 30000 such that the tubular element 30080 laterally or diagonally traverses at least a portion of the rigid support portion 30010.

In various embodiments, referring to FIG. 102 for example, a tissue thickness compensator 40020 can comprise multiple tubular elements 40080. In some embodiments, the tubular elements 40080 can comprise different lengths, cross-sectional shapes, and/or materials, for example. Further, the tubular elements 40080 can be positioned relative to the rigid support portion 40010 of the staple cartridge 30000 such that the tubular axes of the tubular elements 40080 are parallel to each other. In some embodiments, the tubular axes of tubular elements 40080 can be longitudinally aligned such that a first tubular element 40080 is positioned within another tubular element 40080. In other embodiments, parallel tubular elements 40080 can longitudinally traverse the staple cartridge 30000, for example. In still other embodiments, parallel tubular elements 40080 can laterally or diagonally traverse the staple cartridge 30000. In various other embodiments, non-parallel tubular elements 40080 can be angularly-oriented relative to each other such that their tubular axes intersect and/or are not parallel to each other.

Referring to FIGS. 102-105, a tissue thickness compensator 40020 can have two tubular elements 40080; a first tubular element 40080a can be longitudinally positioned on a first side of the longitudinal slot 30015 in the rigid support portion 30010 and a second tubular element 40080b can be longitudinally positioned on a second side of the longitudinal slot 30015. Each tubular element 40080 can comprise a tubular lattice 40092 of strands 40090. In various embodiments, the staple cartridge 30000 can comprise a total of six rows of staple cavities 30012, wherein three rows of staple cavities 30012 are positioned on each side of the longitudinal slot 30015, for example. In such embodiments, the cutting edge 30052 on the translating staple-firing sled 30050 may not be required to sever a portion of the tubular element 40080.

Figure 106:
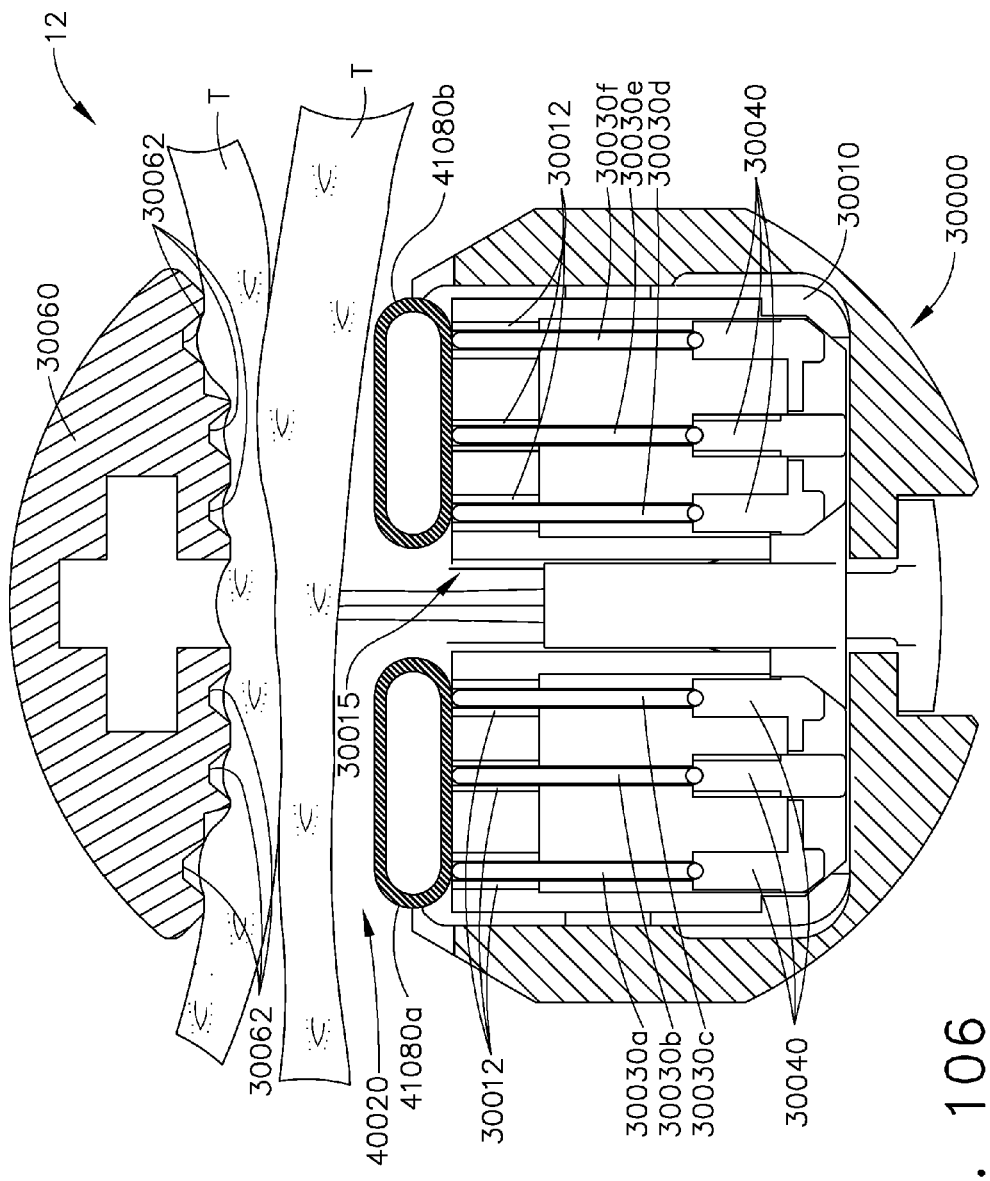
FIG. 106 is an elevational cross-sectional view of a tissue thickness compensator positioned in an end effector of a surgical instrument according to at least one embodiment.
Figure 107:
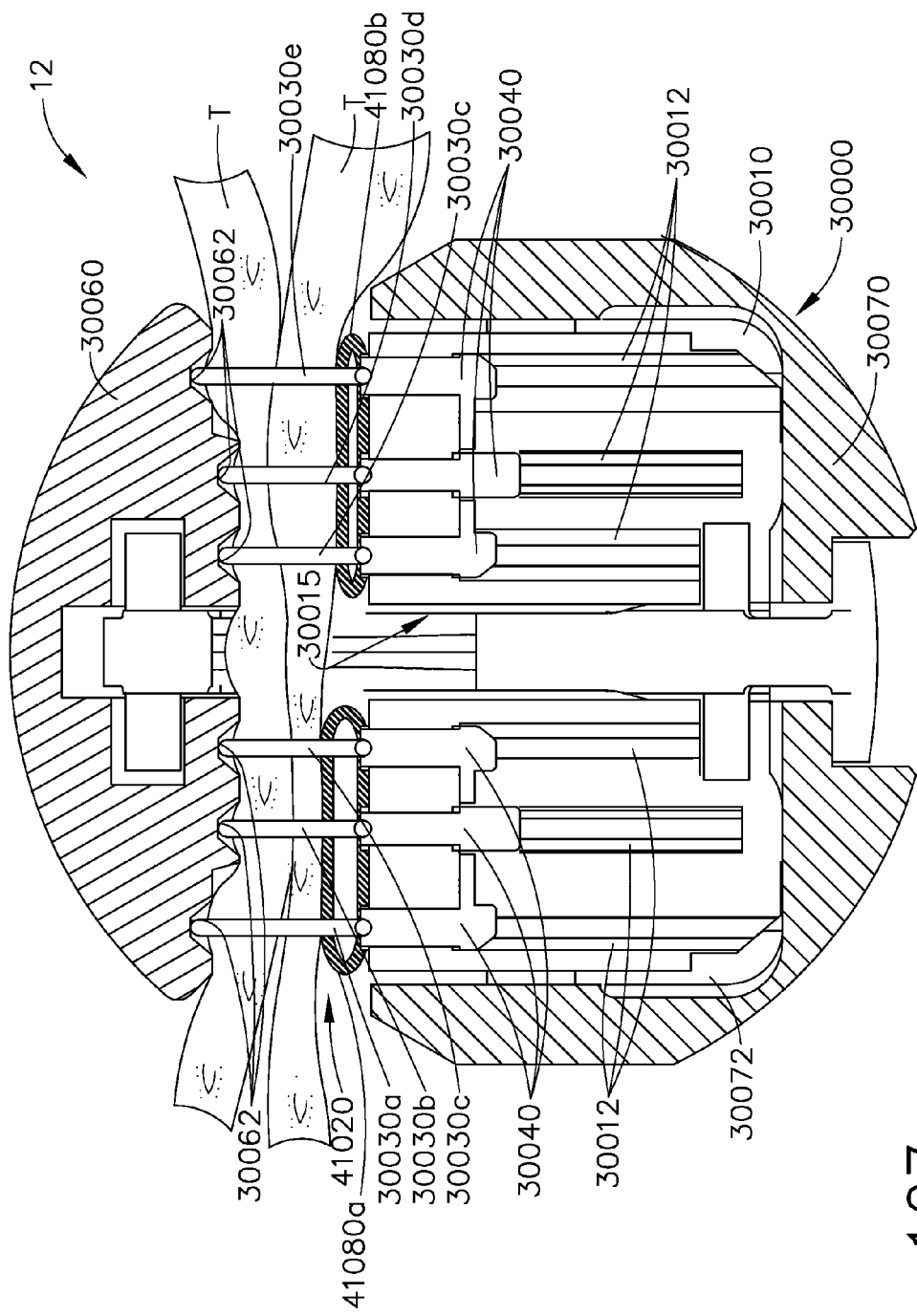
FIG. 107 is an elevational cross-sectional view of the tissue thickness compensator and the end effector of FIG. 106 depicting the end effector in a clamped and fired configuration.

Similarly, referring now to FIGS. 106-107, a tissue thickness compensator 41020 can comprise two tubular elements 41080a, 41080b longitudinally arranged in the staple cartridge 30000. Similar to the above, staples 30030 from three rows of staple cavities 30012 can engage one tubular element 41080a and staples 30030 from three different rows of staple cavities 30012 can engage another tubular element 41080b. In various embodiments, referring still to FIGS. 106-107, deployed staples 30030 can engage the tubular element 40080 at different locations across the cross-section of the tubular element 40080. As discussed herein, the springback resiliency and corresponding restoring force exerted by the tubular element 41080 can depend on the cross-sectional shape of the tubular element 41080, among other things. In some embodiments, a staple 30030 positioned in a staple entrapment area 30039 located at or near an arced portion of the tubular element 41080 can experience a greater restoring force than a staple 30030 in a staple entrapment area 30039 positioned near a non-arced portion. Similarly, a staple 30030 positioned in staple entrapment area 30039 in the non-arced portion of the tubular element 41080 can experience a lesser restoring force than the restoring force experienced by a staple 30030 positioned at or nearer to the arced portion of the tubular element 30080. In other words, the arced portions of a tubular element 41080 can have a greater spring rate than the non-arced portion of the tubular element 41080 owing to the possibility that a larger quantity of elastic material may be captured by the staples 30030 along such portions. In various embodiments, as a result, referring primarily to FIG. 107, the restoring force generated by the tissue thickness compensator 41020 can be greater near staples 30030a and 30030c and less near staple 30030b in tubular element 30080a. Correspondingly, the restoring force generated by the tissue thickness compensator 41020 can be greater near staples 30030d and 30030f than near staple 30030e in tubular element 30080b.

Figure 105:
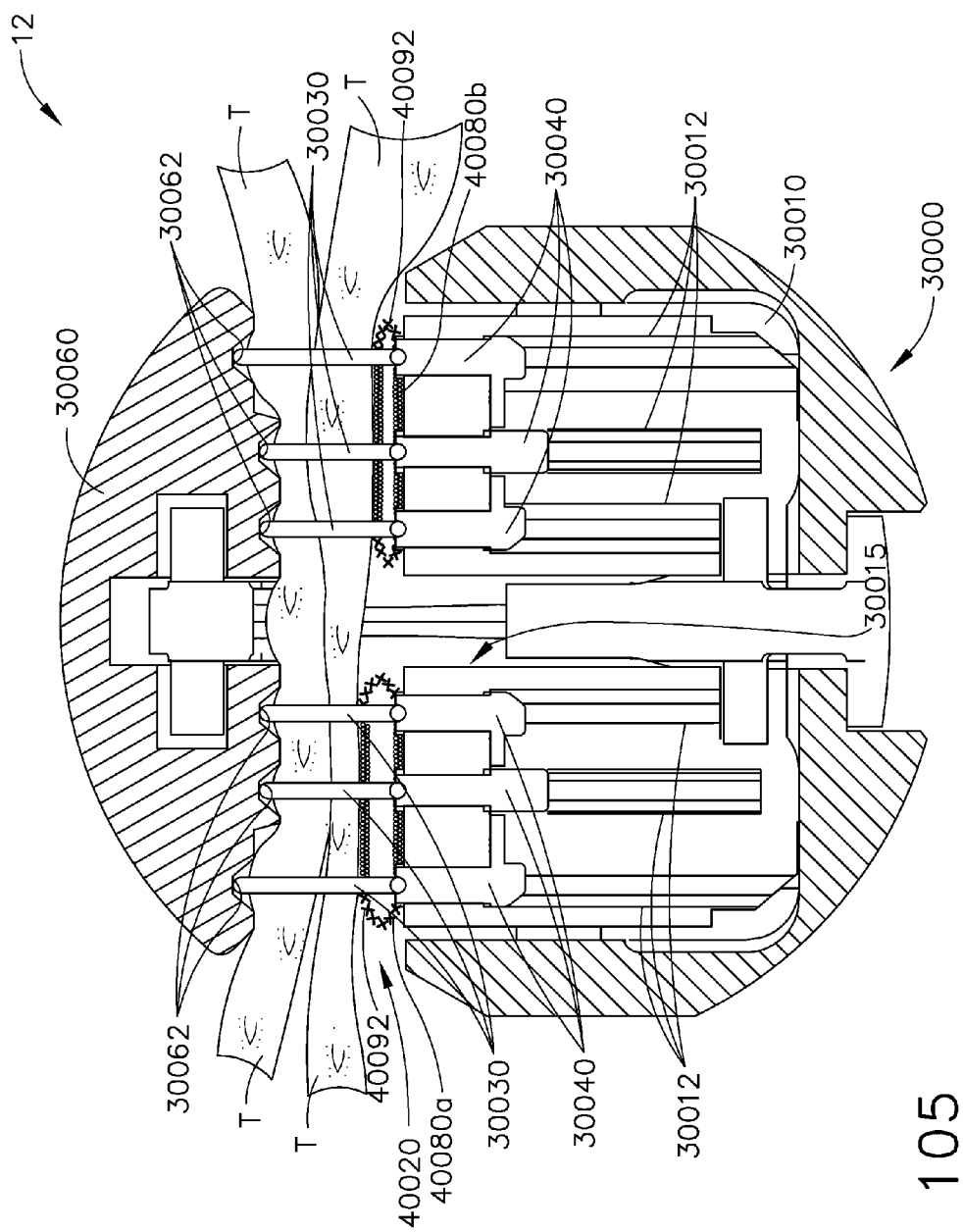
FIG. 105 is an elevational cross-sectional view of the tissue thickness compensator and the end effector of FIG. 102 depicting the end effector in a clamped and fired configuration.

Referring again to FIGS. 102-105, in various embodiments, the cross-sectional geometries of strands 40090 comprising the tubular lattice 40092 can be selected in order to provide a desired springback resiliency and corresponding restoring force exerted by the tubular lattice 40092. For example, referring again to FIG. 103, strands 40090a positioned in arced portions of the tubular element 40080 can comprise X-shaped cross-sections, whereas strands 40090b positioned in non-arced portions of the tubular element 40080 can comprise tubular cross-sections. In some embodiments, strands 40090a and 40090b comprising different cross-sectional geometries can be woven together to form the tubular lattice 40092. In other embodiments, the strands 40090a and 40090b can be attached to one another with an adhesive, for example. Referring to FIGS. 104 and 105, the different cross-sectional geometries of strands 40090 in the tubular element 40080 can optimize the restoring force experienced in staple entrapment areas 30039 across the staple cartridge 30000. In some embodiments, specific cross-sectional geometries can be selected such that the springback constant in staple entrapment areas 30039 across the staple cartridge is substantially balanced or equal.

Figure 108:
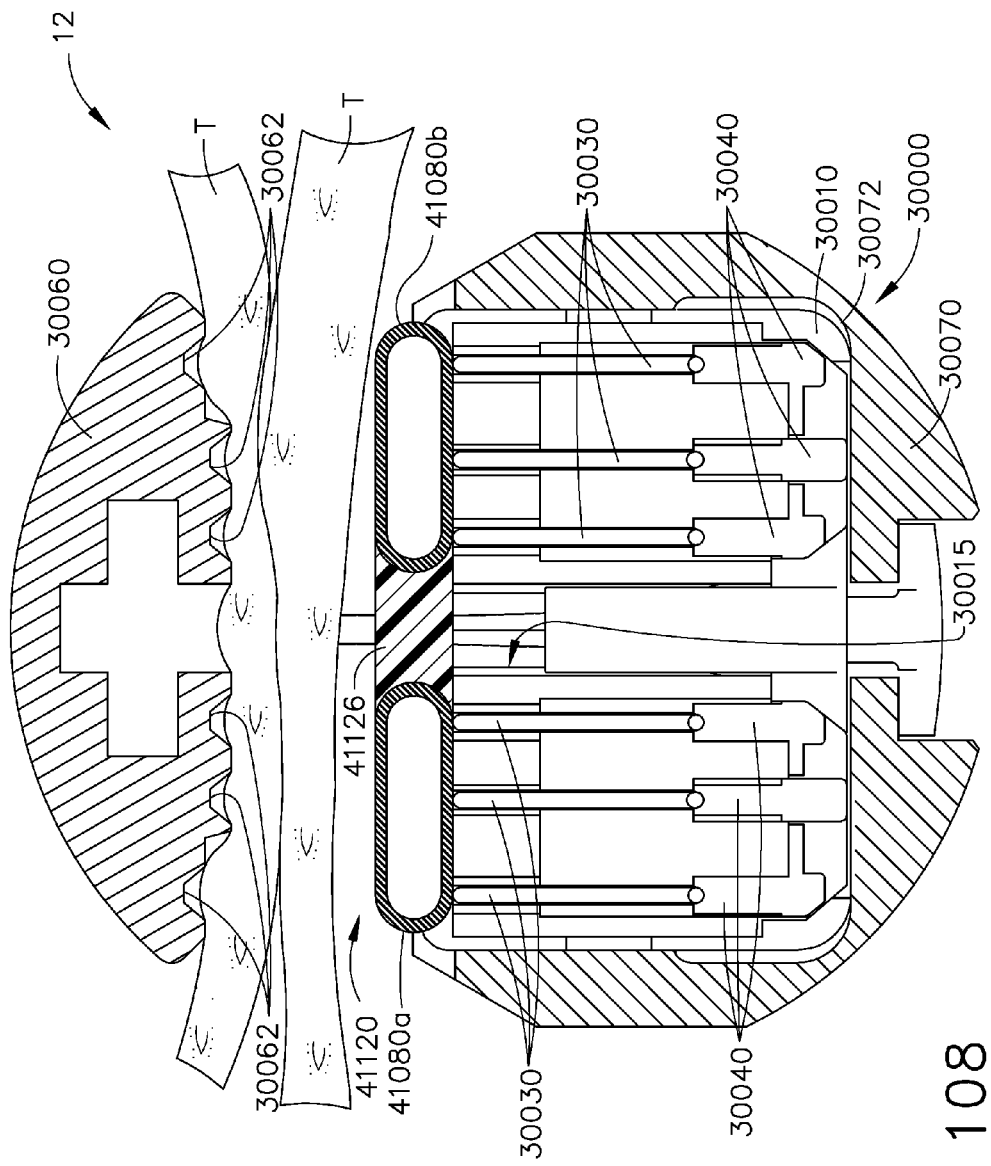
FIG. 108 is an elevational cross-sectional view of a tissue thickness compensator in the end effector of a surgical instrument according to at least one embodiment.

In some embodiments, referring to FIG. 108, the tubular elements 41080a, 41080b of a tissue thickness compensator 41120 can be fastened together by an adjoining portion 41126. Though the translating cutting element 30052 can be configured to pass between tubular elements 41080a and 41080b, the cutting element 30052 can be required to sever at least a portion of the adjoining portion 41126. In some embodiments, the adjoining portion 41126 can comprise a soft material, such as, for example, a foam or gel, which is easily severed by the translating cutting element 30052. In various embodiments, the adjoining portion 41026 can releasably secure the tissue thickness compensator 41120 to the surgical end effector 12. In at least one embodiment, the adjoining portion 41126 can be fixed to the top deck surface 30011 of the rigid support portion 30010 such that the adjoining portion 41126 remains retained in the surgical end effector 12 after the tubular elements 41080a, 41080b are released therefrom.

Figure 109:
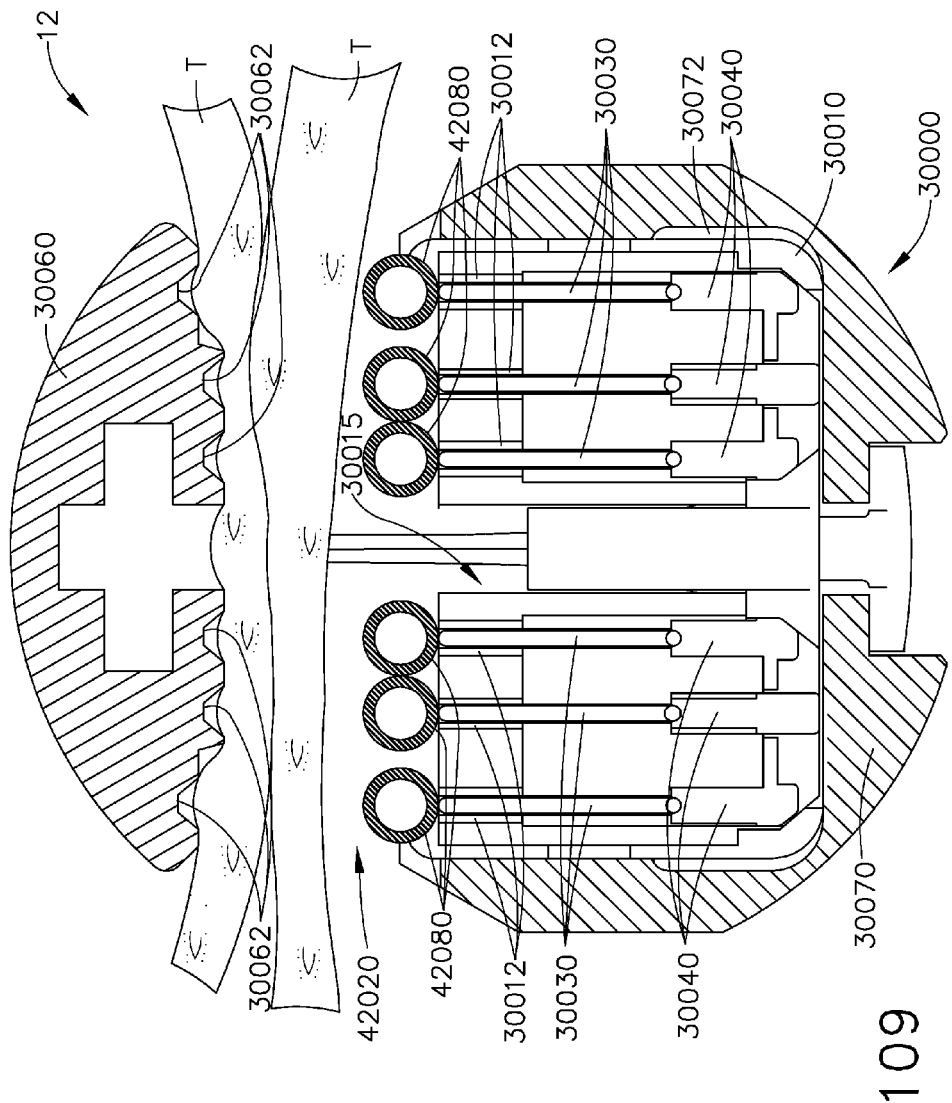
FIG. 109 is a cross-sectional elevational view of a tissue thickness compensator positioned in an end effector of a surgical instrument according to at least one embodiment.
Figure 110:
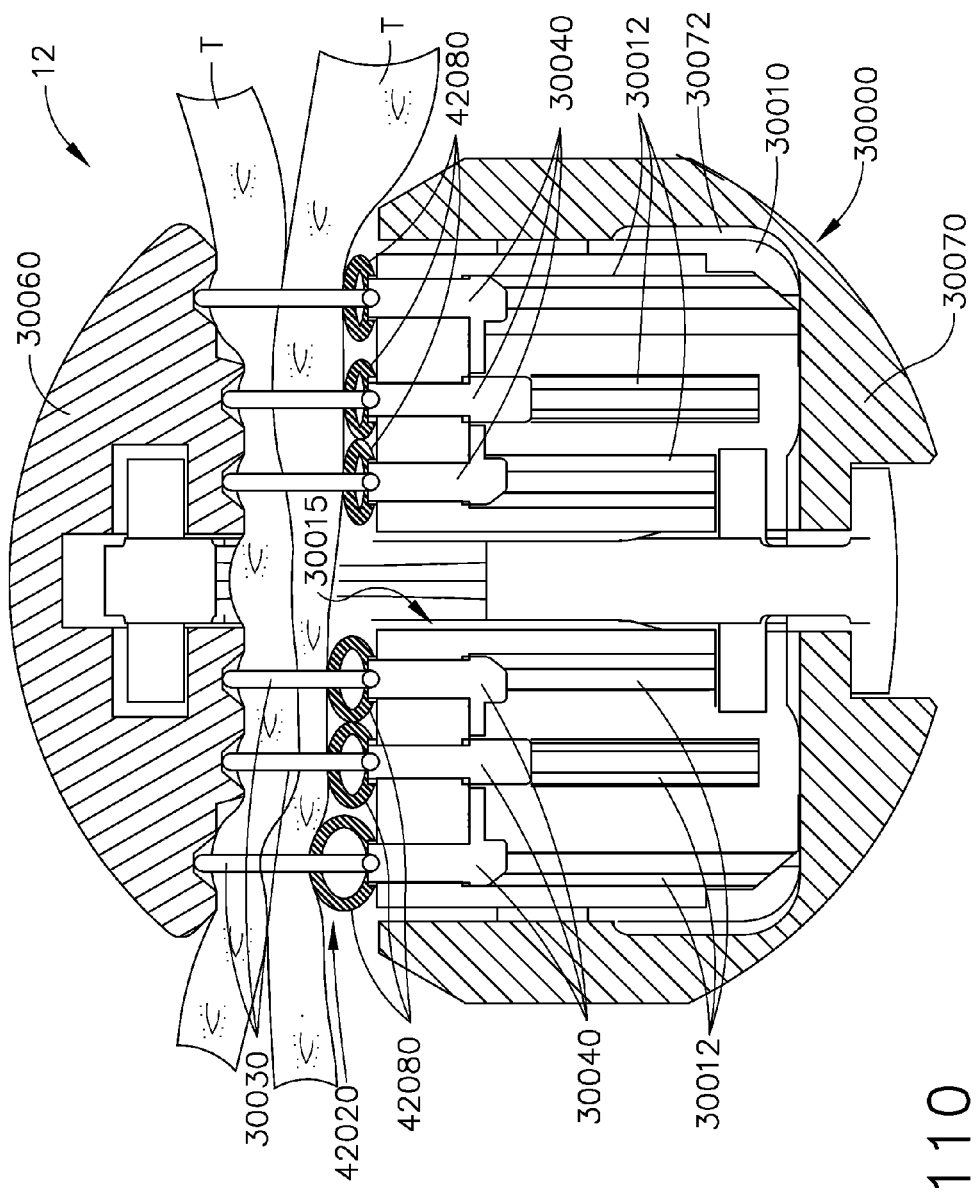
FIG. 110 is a cross-sectional elevational view of the tissue thickness compensator and the end effector of FIG. 109 depicting the end effector in a clamped and fired configuration.
Figure 111:
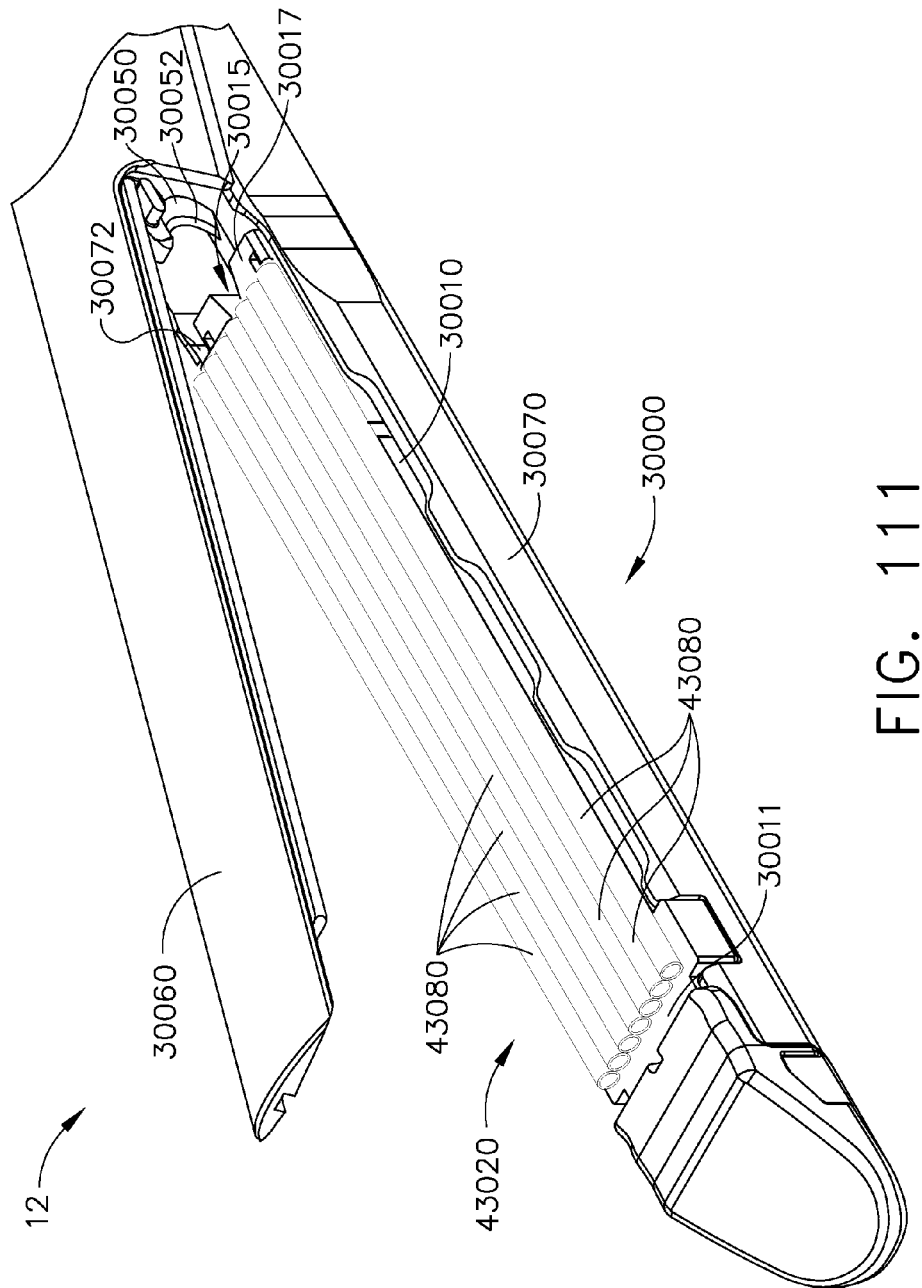

In various embodiments, referring to FIGS. 109-110, a tissue thickness compensator 42020 can comprise multiple tubular elements 42080 such that the number of tubular elements 42080 is the same as the number of rows of staple cavities 30012 in the staple cartridge 30000, for example. In at least one embodiment, the staple cartridge 30000 can comprise six rows of staple cavities 30012 and the tissue thickness compensator 42020 can comprise six tubular elements 42080. Each tubular element 42080 can be substantially aligned with a row of staple cavities 30012. When staples 30030 are ejected from a row of staple cavities 30012, each staple 30030 from that row can pierce the same tubular element 42080 (FIG. 110). In various embodiments, the deformation of one tube 42080 can have little or no impact on the deformation of an adjacent tube 42080. Accordingly, the tubular elements 42080 can exert a substantially discrete and customized springback force in staple entrapment areas 30039 across the width of the staple cartridge 30030. In some embodiments, where staples 30030 fired from multiple rows of staple cavities 30012 engage the same tubular element 35080 (FIG. 107), the deformation of the tubular element 35080 can be less customized. For example, the deformation of a tubular element 35080 in a staple entrapment area 30039 in a first row can impact the deformation of that tubular element 35080 in staple entrapment area 30039 in another row. In at least one embodiment, the translating cutting edge 30052 can avoid severing the tubular elements 42080. In other embodiments, referring to FIG. 111, a tissue thickness compensator 43020 can comprise more than six tubular elements 43080, such as, for example, seven tubular elements 44080. Further, the tubular elements 43080 can be symmetrically or non-symmetrically arranged in the end effector 12. When an odd number of tubular elements 43080 are longitudinally and symmetrically arranged in the end effector 12, the translating cutting element 30052 can be configured to sever the middle tubular element that overlies the longitudinal channel 30015.

Figure 112:
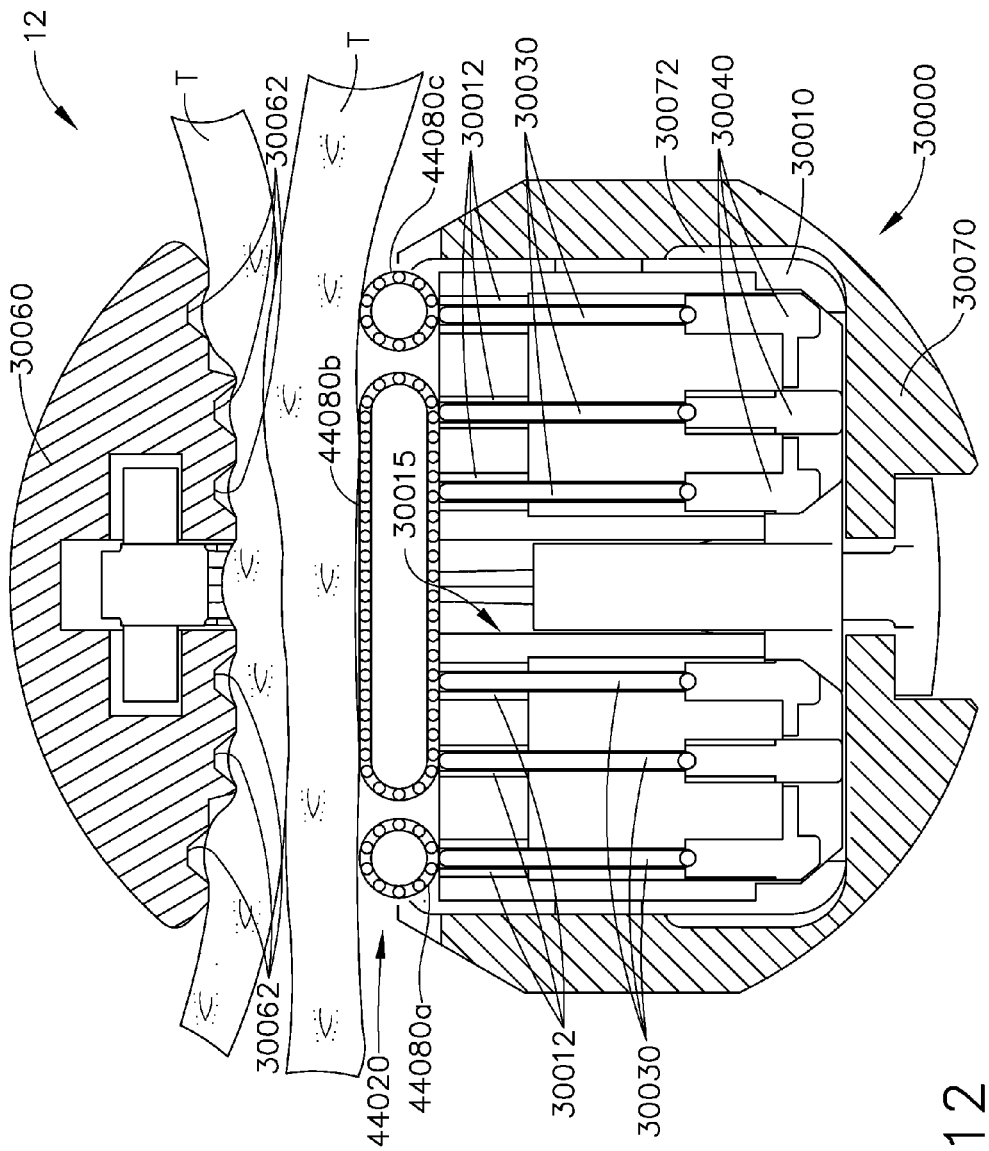
Figure 113:
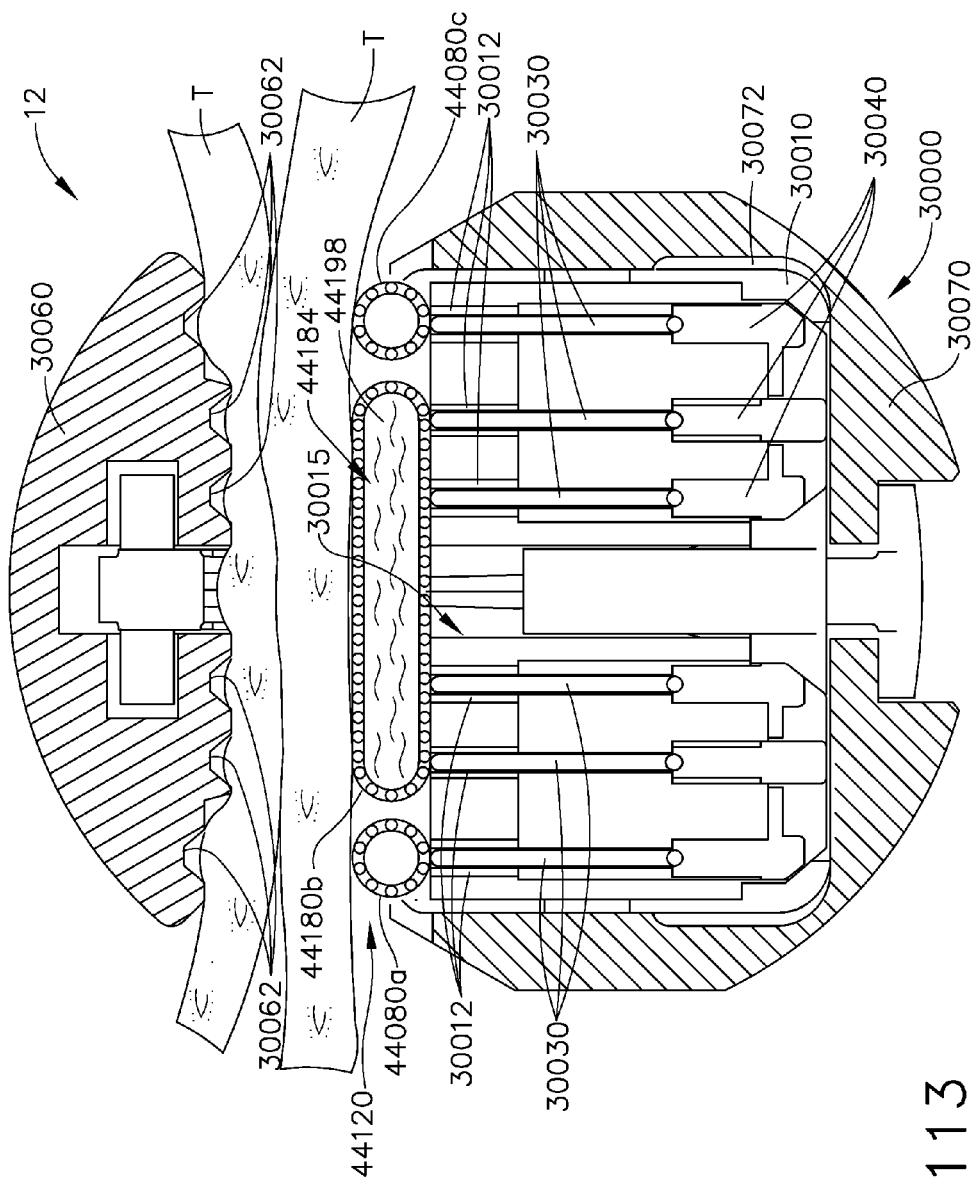

In various embodiments, referring to FIG. 112, a tissue thickness compensator 44020 can comprise a central tubular element 44080b that is at least partially aligned with the longitudinal slot 30015 in the rigid support portion 33010 of the staple cartridge 30000. The tissue thickness compensator 44020 can further comprise at least one peripheral tubular element 44080a, 44080c located on a side of the longitudinal slot 30015. For example, the tissue thickness compensator 44020 can comprise three tubular elements 44080: a first peripheral tubular element 44080a can be longitudinally positioned on a first side of the longitudinal slot 30015 of the staple cartridge 30000, a central tubular element 44080b can be substantially positioned over and/or aligned with the longitudinal slot 30015, and a second peripheral tubular element 44080c can be longitudinally positioned on a second side of the longitudinal slot 30015. In some embodiments, the central tubular element 44080b can comprise a horizontal diameter that is substantially elongated relative to the vertical diameter. In various embodiments, the central tubular element 44080b, and/or any other tubular element, can overlap multiples rows of staple cavities 30012. Referring still to FIG. 112, the central tubular element 44080b can overlap four staple rows of staple cavities 30012 and each peripheral tubular element 44080a, 44080c can overlap a single row of staple cavities 30012, for example. In other embodiments, the central tubular element 44080b can overlap less than four rows of staple cavities 30012, such as, for example, two rows of staple cavities 30012, for example. Further, peripheral tubular elements 44080a, 44080c can overlap more than one row of staple cavities 30012, such as, for example, two rows of staple cavities 30012. Referring now to FIG. 113, a central tubular element 44180b of a tissue thickness compensator 44120 can comprise a therapeutic agent 44198 in a lumen 44184 of the central tubular element 44180b. In various embodiments, central tubular element 44180b and/or at least one peripheral tubular element 44080a, 44080c can comprise the therapeutic agent 44198 and/or any other suitable therapeutic agent.

Figure 114:
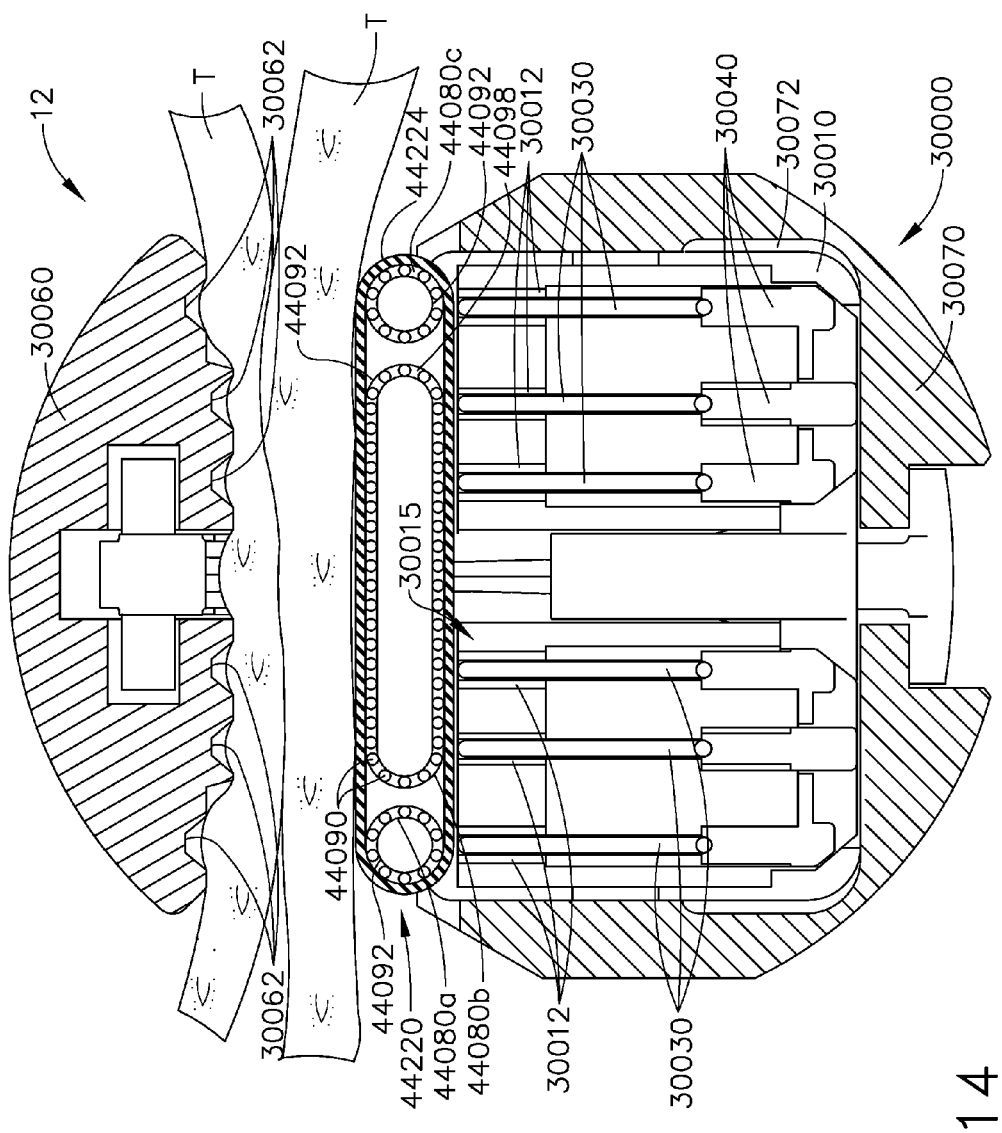

In various embodiments, referring to FIG. 114, the tissue thickness compensator 44220 can comprise a shell 44224, which can be similar to overmold material 32024 described herein. In various embodiments, the shell 44224 retains multiple tubular elements 44080 in position in the end effector 12. The shell 44224 can be coextruded with the tubular elements 44080. In some embodiments, the tubular elements 44080 can comprise a tubular lattice 44092 of strands 44090. Similar to the polymeric compositions described in embodiments herein, the shell 44224 can comprise polyglycolic acid (PGA), poly(lactic acid) (PLA), and/or any other suitable bioabsorbable, biocompatible elastomeric polymers, for example. Further, the shell 44224 can be non-porous such that the shell 44224 forms a fluid-impervious layer in the tissue thickness compensator 44220, for example. Further to the discussion herein, the tubular element 44080 and/or the strands 44090 in the tubular lattice 44092 can comprise a therapeutic agent 44098. In some embodiments, the non-porous shell 44224 can contain the therapeutic agent 44098 within the tissue thickness compensator. As described herein, the tubular element 44080 can be positioned relative to staple cavities 30012 and a cutting element 30052 in staple cartridge 30000. In several such embodiments, deployment of the staples 30030 and/or translation of the cutting element 30052 can be configured to pierce or rupture the non-porous, shell 44224 such that the therapeutic agent 44198 contained therein can be released from the tissue thickness compensator 44020.

Figure 115:
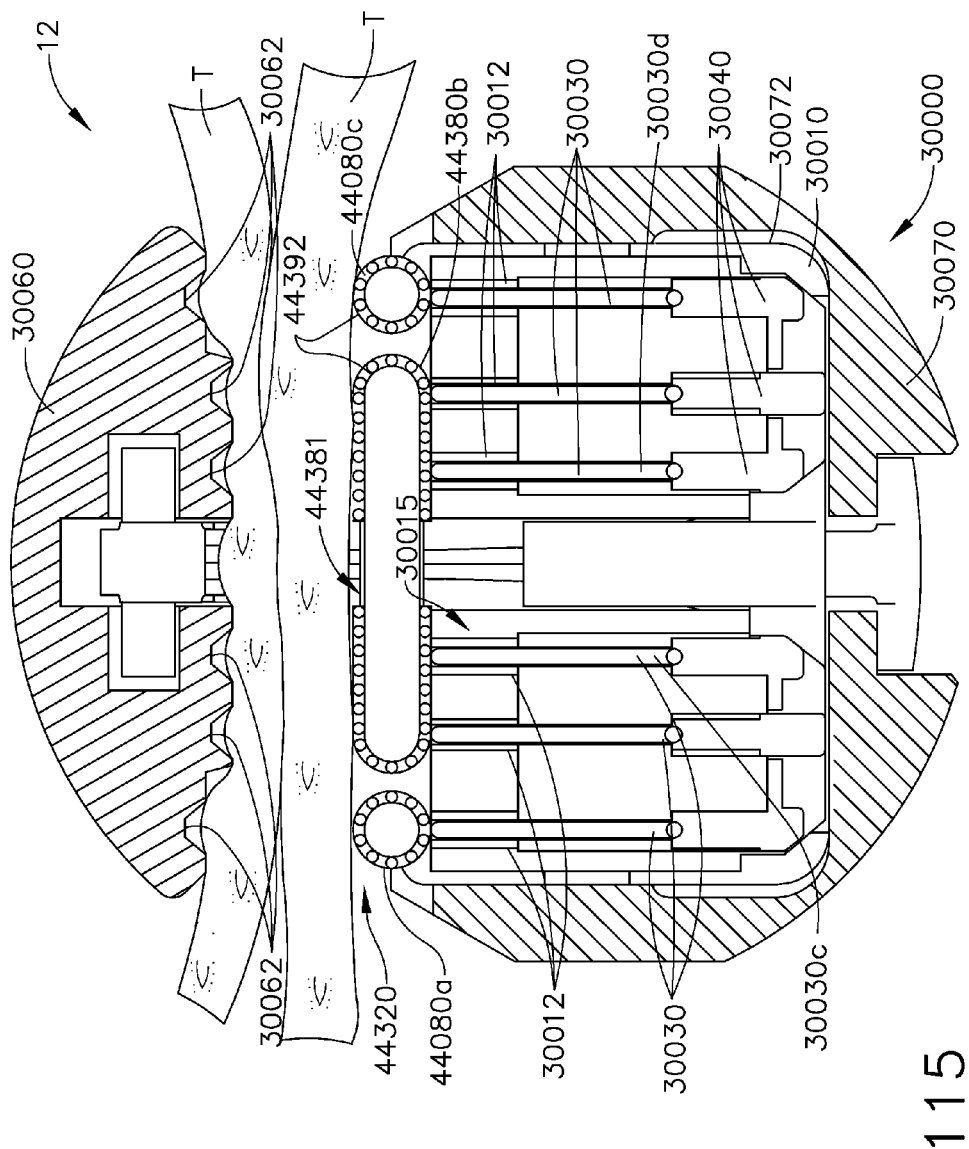

Referring to FIG. 115, a tissue thickness compensator 44320 can comprise a central tubular element 44380b comprising a tubular lattice 44392. The tubular lattice 44392 can have a non-woven portion or a gap 44381 that is substantially aligned with the longitudinal slot 30015 of the rigid support portion 30010. In such embodiments, a woven portion of the tubular lattice 44092 of the tubular element 44380b does not overlap the longitudinal slot 30015. Accordingly, the cutting element 30052 on the translating staple-fire sled 30052 can translate along the longitudinal slot 30015 without severing an overlapping a woven portion of the tubular lattice 44392. Though staples 30030c and 30030d positioned adjacent to the gap 44381 in tubular element 44380b may receive less support from the tubular lattice 44392 structure, in some embodiments, additional features can provide support for those staples 30030 and/or additional restoring force in the staple entrapment areas 30039 thereof. For example, as described in greater detail herein, additional tubular elements, support webbing, springs and/or buttressing material can be positioned at least one of inside and outside tubular element 44380b near gap 44381, for example.

Referring now to FIGS. 116-119, in various embodiments, a tissue thickness compensator 45020 can comprise multiple tubular elements 45080 that laterally traverse the staple cartridge 30000. The tubular elements 45080 can be positioned perpendicular to the rows of staple cavities 30012 and/or the longitudinal axis of the rigid support portion 30010 of the staple cartridge 30000. In some embodiments, referring to FIG. 116, the tubular elements 45080 can traverse the longitudinal slot 30015 in the staple cartridge 30000 such that the cutting element 30052 on the staple-firing sled 30050 is configured to sever the tubular elements 45080 as the staple-firing sled 30050 translates along the longitudinal slot 30015. In other embodiments, referring now to FIG. 117, the tissue thickness compensator 46020 can comprise two sets of laterally traversing tubular elements 46080. The first set of laterally traversing tubular elements 46080*a* can be positioned on a first side of the longitudinal slot 30015 and the second set of laterally traversing tubular elements 46080*b* can be positioned on a second side of the longitudinal slot 30015. In such an arrangement, the cutting element 30052 can be configured to pass between the two sets of tubular elements 46080 without severing a portion of the tubular elements 46080. In other embodiments, the cutting element 30052 can sever at least one tubular element 46080 that traverses the longitudinal slot 30015 while at least one other tubular element 46080 does not traverse the longitudinal slot 30015 and is not severed by the cutting element 30052.

As the tubular elements 45080 laterally traverse the staple cartridge 30000, referring to FIGS. 118 and 119, a staple 30030 can engage at least one tubular element 45080 in each staple entrapment area 30039. In such an arrangement, each tubular element 45080 can provide a discrete restoring force along the length of the staple cartridge 30000. For example, referring primarily to FIG. 119, the tubular elements 45080 positioned near the proximal end of the tissue thickness compensator 45020 where the tissue is thicker can be greatly compressed compared to the tubular elements 45080 positioned near to the distal end of the tissue thickness compensator 45020 where the tissue is thinner. As a result, the tubular elements 45080 positioned closer to the proximal end of the tissue thickness compensator 45020 can provide a greater restoring force than the restoring force that could be generated by the tubular elements 46080 positioned closer to the distal end of the tissue thickness compensator 45020. Further, referring still to FIG. 119, the deformation of one tube 45080 can have little or no impact on the deformation of an adjacent tube 45080. Accordingly, the tubular elements 45080 can exert a substantially discrete and customized springback force in staple entrapment areas 30039 along the length of the staple cartridge 30030. In some embodiments, where multiple staples 30030 fired from a single row of staple cavities 30012 engage the same tubular element 35080, the deformation of the tubular element 35080 can be less customized. For example, the deformation of a tubular element 35080 in one staple entrapment area 30039 can impact the deformation of that tubular element 35080 in another staple entrapment area 30039.

In still other embodiments, referring to FIGS. 120-125, tubular elements 47080 of the tissue thickness compensator 47020 can diagonally traverse the staple cartridge 30000. The tubular elements 47080 can traverse the longitudinal slot 30015 of the staple cartridge 30000 such that the cutting element 30052 on the staple-firing sled 30050 is configured to sever the diagonally traversing tubular elements 47080 as the staple-firing sled 30052 translates along the longitudinal slot 30015. In other embodiments, the tissue thickness compensator 47020 can comprise two sets of diagonally traversing tubular elements 47080. A first set of diagonally traversing tubular elements 47080 can be positioned on a first side of the longitudinal slot 30015 and a second set of diagonally traversing tubular elements 47080 can be positioned on a second side of the longitudinal slot 30015. In such an arrangement, the cutting element 30052 can pass between the two sets of tubular elements 47080 and may not sever any tubular element 47080.

Referring still to FIGS. 120-123, the diagonally traversing tubular elements 47080 can be positioned in the staple cartridge 30000 such that a gap is defined between the tubular elements 47080. A gap between adjacent tubular elements 47080 can provide space for horizontal expansion of the tubular elements 47080 when a compressive force is applied thereto, such as, for example, by tissue T captured within the staple entrapment area 30039 of the formed staple 30030. The tubular elements 47080 can be connected across a gap by a film or sheet of material 47024. The sheet of material can be positioned on at least one of the deck surface 30011 of the rigid support portion 30010 and/or the tissue contacting side of the tubular elements 47080.

In various embodiments, referring to FIGS. 124 and 125, at least one diagonally traversing tubular element 47080 can be positioned relative to the staple cavities 30012 in the staple cartridge 30000 such that the tubular element 47080 is positioned between the legs 30032 of the staples 30030 deployed from multiple rows of staple cavities 30012. As the staples 30030 are moved from the initial position to the fired position, as described in greater detail herein, the staple legs 30032 can remain positioned around the tubular element 47080. Further, the staples can be deformed such that the staple legs 30032 wrap around the perimeter of the tubular element 47080, for example. In such an arrangement, the staples 30030 can be configured to move to the fired or formed position without piercing the tubular element 47080. Movement of the staple legs 30032 around the tubular element 47080 could in some embodiments, prevent the inadvertent release of a therapeutic agent 47098 retained therein. The selected angular orientation of each tubular element 47080 relative to the longitudinal slot 30015 of the staple cartridge 30000 can depend on the position of the staple cavities 30012 in the staple cartridge 30000. For example, in some embodiments, the tubular elements 47080 can be positioned at an approximately forty-five (45) degree angle relative to the longitudinal slot 30015 of the staple cartridge 30000. In other embodiments, the tubular elements 47080 can be positioned at a fifteen (15) to seventy-five (75) degree angle relative to the longitudinal slot 30015 of the staple cartridge 30000, for example.

Similar to descriptions throughout the present disclosure, multiple tubular elements in a tissue thickness compensator can be connected by a binding agent, wrap, webbing, overmold, compensation material, and/or any other suitable connecting adhesive or structure, for example. In various embodiments, referring to FIGS. 126-128, a flexible shell 48024 may surround or encapsulate tubular elements 48080 in a tissue thickness compensator 48020. In various embodiments, the flexible shell 48024 can restrain the tubular elements 48080 in the end effector 12 and can hold each tubular element 48080 in position, such as, for example, in longitudinal alignment with a row of staple cavities 30012. In at least one embodiment, the tissue thickness compensator 48020 can comprise six tubular elements 48080, for example. In various embodiments, the flexible shell 48024 can be sufficiently deformable and resilient to restrain the tubular elements 48020 encased therein while permitting deformation and rebound of the tubular elements 48080. Further, in some embodiments, the flexible shell 48024 can tautly surround the tubular elements 48080 and can remain tautly engaged with the tubular elements 48080 as they deform and/or rebound.

Referring to FIG. 127, prior to the deployment of staples 30030, the anvil 30060 can be pivoted or rotated downwardly to compress the tissue thickness compensator 48020 and tissue T between the anvil 30060 and the staple cartridge 30000. Compression of the tissue thickness compensator 48020 can include a corresponding compression of the flexible shell 48024 and the tubular elements 48020 therein. As the tubular elements 48020 deform, the flexible shell 48024 can similarly deform. In various embodiments, the tubular elements 48020 can be uniformly compressed across the width of the staple cartridge 30000 and the flexible shell 48024 can experience a similarly uniform compression across the tubular elements 48080. Referring to FIG. 128, when the anvil 30060 is opened after the staples 30030 have been deployed from the staple cartridge 30000, the tubular elements 48080 can rebound or partially rebound from the compressed configurations (FIG. 127). In various embodiments, a tubular element 48080 can rebound such that the tubular element 48080 returns to its initial, undeformed configuration. In some embodiments, a tubular element 48080 can partially rebound such that the tubular element 48080 partially returns to its initial undeformed configuration. For example, the deformation of the tubular element 48080 can be partially elastic and partially plastic. As the tubular elements 48080 rebound, the flexible shell 48024 can remain tautly engaged with each tubular element 48080. The tubular elements 48080 and flexible shell 48024 can rebound to such a degree that the tubular elements 48080 and tissue T fill the staple entrapment areas 30039 while the tubular elements 48080 exert an appropriate restoring force on the tissue T therein. Referring to FIG. 129, in other embodiments, a tissue thickness compensator 48120 comprising six tubular elements 48180 retained in a flexible shell 48124 can be positioned on the anvil 30060 of the end effector 12, for example.

Referring to FIGS. 130-133, a tissue thickness compensator 49020 can comprise a tubular element 49080 longitudinally positioned along the longitudinal axis of the anvil 30060. In various embodiments, the tissue thickness compensator 49020 can be secured to the anvil 30060 of the end effector 12 by a compressible compensation material 49024. Further, the compressible compensation material 49024 can surround or encapsulate the tubular element 49080. Similar to the descriptions herein, the tubular element 49080 can comprise at least one therapeutic agent 49098 which may be released by the absorption of various components of the tissue thickness compensator 49020, the piercing of the tubular element 49080 by staples 30030 fired from the staple cartridge 30000, and/or by the cutting element 30052.

Referring to FIG. 131, a staple cartridge 30000 can comprise staples 30030 positioned in staple cavities 30012, wherein, prior to deployment of the staples 30030, the anvil 30060 and the tissue thickness compensator 49020 attached thereto can pivot toward the staple cartridge 30000 and compress tissue T captured therebetween. In some embodiments, the tubular element 49080 of the tissue thickness compensator 49020 can be uniformly deformed along the length of the staple cartridge 30000 by the pivoting anvil 30060 (FIG. 131). Referring to FIGS. 132 and 133, the staple-firing sled 30050 can translate along the longitudinal slot 30015 in the staple cartridge 30000 and engage each driver 30040 positioned beneath a staple 30030 in a staple cavity 30010, wherein each engaged driver 30040 can fire or eject the staple 30030 from the staple cavity 30012. When the anvil 30060 releases pressure on the tissue T and the tissue thickness compensator 49020, the tissue thickness compensator 49020, including the tubular element 49080 and the compressible compensation material 49024, can rebound or partially rebound from the compressed configurations (FIG. 131) to a rebounded configuration (FIGS. 132 and 133). The tubular element 49080 and compressible compensation material 49024 can rebound to such a degree that the tissue thickness compensator 49020 and tissue T fill the staple entrapment areas 30039 while the tissue thickness compensator 49020 exert an a restoring force on the captured tissue T.

In various embodiments, referring to FIGS. 124-126, two tissue thickness compensators 50020a, 50020b can be positioned in the end effector 12 of a surgical instrument. For example, a first tissue thickness compensator 50020a can be attached to the staple cartridge 30000 in the lower jaw 30070 and a second tissue thickness compensator 50020b can be attached to the anvil 30060. In at least one embodiment, the first tissue thickness compensator 50020a can comprise a plurality of tubular elements 50080 longitudinally arranged and retained in a first compensation material 50024a. At least one tubular element 50080 can comprise a therapeutic agent 50098, similar to the therapeutic agents described herein. The first compensation material 50024a can be deformable or substantially rigid. Further, in some embodiments, the first compensation material 50024a can hold the tubular elements 50080 in position relative to the staple channel 30000. For example, the first compensation material 50024a can hold each tubular element 50080 in longitudinal alignment with a row of staple cavities 30012. In at least one embodiment, the second tissue thickness compensator 50020b can comprise the first compensation material 50024a, a second compensation material 50024b and/or a third compensation material 50024c. The second and third compensation material 50024b, 50024c can be deformable or substantially rigid.

Similar to at least one embodiment described herein, the anvil 30060 can pivot and apply a compressive force to the tissue thickness compensators 50020a, 50020b and the tissue T between the anvil 30060 and the staple cartridge 30000. In some embodiments, neither the first tissue thickness compensators 50020a nor the second tissue thickness compensators 50020b can be compressible. In other embodiments, at least one component of the first tissue thickness compensators 50020a and/or the second tissue thickness compensators 50020b can be compressible. When the staples 30030 are fired from the staple cartridge 30000, referring now to FIGS. 135 and 136, each staple 30030 can pierce a tubular element 50080 retained in the first tissue thickness compensator 50020a. As shown in FIG. 135, the therapeutic agent 50098 retained in the tubular element 50080 can be released when a staple 30030 pierces the tubular element 50080. When released, the therapeutic agent 50098 can coat the staple legs 30032 and tissue T surrounding the fired staple 30030. In various embodiments, the staples 30030 can also pierce the second tissue thickness compensator 50020b when the staples 30030 are fired from the staple cartridge 30000.

Referring to FIGS. 137-140, a tissue thickness compensator 51020 can comprise at least one tubular element 51080 that laterally traverses the tissue thickness compensator 51020. For example, referring to FIG. 137, the tissue thickness compensator 51020 can be positioned relative to the staple cartridge 30000 such that a first end 51083 of the laterally traversing tubular element 51080 can be positioned near a first longitudinal side of the staple cartridge 30000 and a second end 51085 of the laterally traversing tubular element 51080 can be positioned near a second longitudinal side of the staple cartridge 30000. In various embodiments, the tubular element 51080 can comprise a capsule-like shape, for example. As illustrated in FIG. 138, the tubular element 51080 can be perforated between the first end 51083 and the second end 51085 and, in some embodiments, the tubular element 51080 can be perforated at or near the center 51087 of the tubular element 51080. The tubular element 51080 can comprise a polymeric composition, such as a bioabsorbable, biocompatible elastomeric polymer, for example. Further, referring again to FIG. 137, the tissue thickness compensator 51020 can comprise a plurality of laterally traversing tubular elements 51080. In at least one embodiment, thirteen tubular elements 51080 can be laterally arranged in the tissue thickness compensator 51020, for example.

Referring again to FIG. 137, the tissue thickness compensator 51020 can further comprise a compensation material 51024 that at least partially surrounds the tubular elements 51080. In various embodiments, the compensation material 51024 can comprise a bioabsorbable polymer, such as, for example, lyophilized polysaccharide, glycoprotein, elastin, proteoglycan, gelatin, collagen, and/or oxidized regenerated cellulose (ORC). The compensation material 51024 can hold the tubular elements 51080 in position in the tissue thickness compensator 51020. Further, the compensation material 51024 can be secured to the top deck surface 30011 of the rigid support portion 30010 of the staple cartridge 30000 such that the compensation material 51020 is securely positioned in the end effector 12. In some embodiments, the compensation material 51024 can comprise at least one medicament 51098.

Still referring to FIG. 137, laterally positioned tubular elements 51080 can be positioned relative to the translating cutting element 30052 such that the cutting element 30052 is configured to sever the tubular elements 51080. In various embodiments, the cutting element 30052 can sever the tubular elements 51080 at or near the perforation therein. When the tubular elements 51080 are severed in two halves, the severed portions of the tubular elements 51080 can be configured to swell or expand, as illustrated in FIG. 139. For example, in various embodiments, the tubular element 51080 can comprise a hydrophilic substance 51099 that can be released and/or exposed when the tubular element 51080 is severed. Furthermore, when the hydrophilic substance 51099 contacts bodily fluids in tissue T, the hydrophilic substance 51099 can attract the fluid, which can cause the tubular element 51080 to swell or expand. As the tubular element 51080 expands, the compensation material 51024 surrounding the tubular element 51080 can shift or adjust to accommodate the swollen tubular element 51080. For example, when the compensation material 51024 comprises gelatin, the gelatin can shift to accommodate the swollen tubular elements 51080. Referring now to FIG. 140, expansion of the tubular elements 51080 and shifting of the compensation material 51024 can cause a corresponding expansion of the tissue thickness compensator 51020.

Similar to other tissue thickness compensators discussed throughout the present disclosure, the tissue thickness compensator 51020 can be deformed or compressed by an applied force. Further, the tissue thickness compensator 51020 can be sufficiently resilient such that it produces a springback force when deformed by the applied force and can subsequently rebound or partially rebound when the applied force is removed. In various embodiments, when the tissue thickness compensator 51020 is captured in a staple entrapment area 30039, the staple 30030 can deform the tissue thickness compensator 51020. For example, the staple 30030 can deform the tubular elements 51080 and/or the compensation material 51024 of the tissue thickness compensator 51020 that are captured within the fired staple 30030. In various embodiments, non-captured portions of the tissue thickness compensator 51020 can also be deformed due to the deformation in the staple entrapment areas 30039. When deformed, the tissue thickness compensator 51020 can seek to rebound from the deformed configuration. In various embodiments, such a rebound may occur prior to the hydrophilic expansion of the tubular element 51080, simultaneously with the hydrophilic expansion of the tubular element 51080, and/or after the hydrophilic expansion of the tubular element 51080. As the tissue thickness compensator 51020 seeks to rebound, it can exert a restoring force on the tissue also captured in the staple entrapment area 30039, as described in greater detail herein.

In various embodiments, at least one of the tubular elements 51080 and/or the compensation material 51024 in the tissue thickness compensator 51020 can comprise a therapeutic agent 51098. When the tubular element 51080 that contains a therapeutic agent 51098 is severed, the therapeutic agent 51098 contained within the tubular elements 51080 can be released. Furthermore, when the compensation material 51024 comprises the therapeutic agent 51098, the therapeutic agent 51098 can be released as the bioabsorbable compensation material 51024 is absorbed. In various embodiments, the tissue thickness compensator 51020 can provide for a rapid initial release of the therapeutic agent 51098 followed by a controlled release of the therapeutic agent 51098. For example, the tissue thickness compensator 51020 can provide a rapid initial release of the therapeutic agent 51098 from the tubular elements 51080 to the tissue T along the cut line when the tubular elements 51080 comprising the therapeutic agent 51098 are severed. Further, as the bioabsorbable compensation material 51024 comprising the therapeutic agent 51098 is absorbed, the tissue thickness compensator 51020 can provide an extended, controlled release of the therapeutic agent 51098. In some embodiments, at least some of the therapeutic agent 51098 can remain in the tubular element 51080 for a short period of time before the therapeutic agent 51098 flows into the compensation material 51024. In other embodiments, at least some of the therapeutic agent 51098 can remain in the tubular element 51080 until the tubular element 51080 is absorbed. In various embodiments, the therapeutic agent 51098 released from the tubular element 51080 and the compensation material 51024 can be the same. In other embodiments, the tubular element 51080 and the compensation material 51024 can comprise different therapeutic agents or different combinations of therapeutic agents, for example.

Referring still to FIG. 140, in various embodiments, the end effector 12 can cut tissue T and fire staples 30030 into the severed tissue T nearly simultaneously or in quick succession. In such embodiments, a staple 30030 can be deployed into the tissue T immediately after the cutting element 30052 has severed the tubular element 51080 adjacent to the tissue T. In other words, the staples 30030 can engage the tissue thickness compensator 51020 immediately following or simultaneously with the swelling of the tubular element 51080 and the expansion of the tissue thickness compensator 51020. In various embodiments, the tissue thickness compensator 51020 can continue to grow or expand after the staples 30030 have been fired into the tissue T. In various embodiments, the staples 30030 can be configured to puncture the tubular elements 51080 when the staples 30030 are deployed. In such embodiments, therapeutic agents 51098 still retained in the severed tubular elements 51080 can be released from the tubular elements 51080 and, in some embodiments, can cover the legs 30031 of the fired staples 30030.

Referring to FIG. 141, the tissue thickness compensator 51020 can be manufactured by a molding technique, for example. In various embodiments, a frame, or a mold, 51120 can comprise a first longitudinal side 51122 and a second longitudinal side 51124. Each longitudinal side 51124 can comprise one or more notches 51130, which can each be configured to receive the first or second end 50183, 50185 of a tubular element 51080. In some embodiments, the first end 50183 of the tubular element 51080 can be positioned in a first notch 51130a on the first longitudinal side 51122 and the second end 50183 of the tubular element 51080 can be positioned in a second notch 51130*b* on the second longitudinal side 51124 such that the tubular element 51080 laterally traverses the frame 51120. In various embodiments, the notch 51180 can comprise a semi-circular groove, which can securely fit the first or second end 50183, 50185 of the tubular element 51080 therein. In various embodiments, the first notch 51130*a* can be positioned directly across from the second notch 51130*b* and the tubular element 51080 can be positioned perpendicular, or at least substantially perpendicular, to the longitudinal axis of the frame 51120. In other embodiments, the first notch 51130*a* can be offset from the second notch 51130*b* such that the tubular element 51080 is angularly positioned relative to the longitudinal axis of the frame 51120. In still other embodiments, at least one tubular element 51080 can be longitudinally positioned within the frame 51120 such that the tubular element extends between the lateral sides 51126, 51128 of the frame 51120. Further, at least one tubular element can be angularly positioned in the frame between two notches on the lateral sides 51126, 51128 of the frame and/or between a notch on a lateral side 51126 and a notch on a longitudinal side 51124, for example. In various embodiments, the frame 51120 can comprise a support ledge 51136, which can support the tubular elements 51080 positioned within the frame 51120.

In various embodiments, the frame 51120 can comprise notches 51130 to accommodate twelve tubular elements 51080, for example. In some embodiments, the frame notches 51130 can be filled with tubular elements 51080 while, in other embodiments, less than all of the notches 51130 may be filled. In various embodiments, at least one tubular element 51080 can be positioned in the frame 51120. In some embodiments, at least half the notches 51130 can receive tubular elements 51080. In at least one embodiment, once the tubular elements 51080 are positioned in the frame 51120, compensation material 51024 can be added to the frame 51120. The compensation material 51024 can be fluidic when added to the frame 51120. For example, in various embodiments, the compensation material 51024 can be poured into the frame 51120 and can flow around the tubular elements 51080 positioned therein. Referring to FIG. 142, the fluidic compensation material 51024 can flow around the tubular element 51080 supported by notches 51130 in the frame 51120. After the compensation material 51024 cures, or at least sufficiently cures, referring now to FIG. 143, the tissue thickness compensator 51020 comprising the compensation material 51024 and tubular elements 51080 can be removed from the frame 51120. In at least one embodiment, the tissue thickness compensator 51020 can be trimmed. For example, excess compensation material 51024 can be removed from the tissue thickness compensator 51020 such that the longitudinal sides of the compensation material are substantially planar. Furthermore, in some embodiments, referring to FIG. 144, the first and second ends 50183, 50185 of the tubular elements 51080 can be pressed together, or closed, to seal the tubular element 51080. In some embodiments, the ends can be closed before the tubular elements 51080 are placed in the frame 51120. In other embodiments, the trimming process may transect the ends 51083, 51085 and a heat stacking process can be used to seal and/or close the ends 51083, 51085 of the tubular elements 51080.

In various embodiments, referring again to FIG. 141, a stiffening pin 51127 can be positioned within each tubular element 51080. For example, the stiffening pin 51127 can extend through a longitudinal lumen of the tubular element 51080. In some embodiments, the stiffening pin 51127 can extend beyond each tubular element 51080 such that the stiffening pin 51127 can be positioned in notches 51130 in the frame 51120. In embodiments having stiffening pins 51127, the stiffening pins 51127 can support the tubular elements 51080 when the compensation material 51204 is poured into the frame 51120 and as the fluidic compensation material 51024 flows around the tubular elements 51080, for example. Once the compensation material 51024 cures, solidifies, and/or lyophilizes or sufficiently cures, solidifies, and/or lyophilizes the tissue thickness compensator 51020 can be removed from the frame 51120 and the stiffening pins 51127 can be removed from the longitudinal lumens of the tubular elements 51080. In some embodiments, the tubular elements 51080 can then be filled with medicaments, for example. Similar to at least one embodiment described herein, after the tubular elements 51080 are filled with medicaments, the tissue thickness compensator 51020, including the ends 51083, 51085 of the tubular elements 51080, for example, can be trimmed. In various embodiments, the tissue thickness compensator 51020 can be die cut, for example, and/or sealed by heat and/or pressure, for example.

As discussed herein, the tissue thickness compensator 52020 can comprise multiple tubular elements 51080. Referring now to FIG. 145, the tubular elements 51080 can comprise different material properties, dimensions and geometries. For example, a first tubular element 51080*a* can comprise a first thickness and a first material and a second tubular element 51080*b* can comprise a second thickness and a second material. In various embodiments, at least two tubular elements 51080 in the tissue thickness compensator 52020 can comprise the same material. In other embodiments, each tubular element 51080 in the tissue thickness compensator 5202 can comprise different materials. Similarly, in various embodiments, at least two tubular elements 51080 in the tissue thickness compensator 52020 can comprise the same geometry. In other embodiments, each tubular element 51080 in the tissue thickness compensator 52020 can comprise different geometries.

Referring now to FIGS. 208-211, a tissue thickness compensator 51220 can comprise at least one tubular element 51280 that laterally traverses the tissue thickness compensator 51220. In various embodiments, referring to FIG. 208, the tissue thickness compensator 51220 can be positioned relative to the anvil 30060 of the end effector 12. The tissue thickness compensator 51220 can be secured to a securing surface 30061 of the anvil 30060 of the end effector 12, for example. In various embodiments, referring primarily to FIG. 209, the tubular element 51280 can comprise a capsule-like shape, for example. The tubular element 51280 can comprise a polymeric composition, such as a bioabsorbable, biocompatible elastomeric polymer, for example.

Referring again to FIG. 208, the tissue thickness compensator 51220 can further comprise a compensation material 51224 that at least partially surrounds the tubular elements 51280. In various embodiments, the compensation material 51224 can comprise a bioabsorbable polymer, such as, for example, lyophilized polysaccharide, glycoprotein, elastin, proteoglycan, gelatin, collagen, and/or oxidized regenerated cellulose (ORC), for example. Similar to the above, the compensation material 51024 can hold the tubular elements 51280 in position in the tissue thickness compensator 51220. Further, the compensation material 51224 can be secured to the securing surface 30061 of the anvil 30060 such that the compensation material 51220 is securely positioned in the end effector 12. In some embodiments, the compensation material 51224 can comprise at least one medicate.

Still referring to FIG. 208, the laterally positioned tubular elements 51280 can be positioned relative to the cutting element 30252 on a translating sled 30250 such that the translatable cutting element 30252 is configured to sever the tubular elements 51280. In various embodiments, the cutting element 30252 can sever the tubular elements 51280 at or near the center of each tubular element 51280, for example. When the tubular elements 51280 are severed in two halves, the severed portions of the tubular elements 51280 can be configured to swell or expand, as illustrated in FIG. 208. Referring primarily to FIG. 210, in various embodiments, a tubular element 51280 can comprise a hydrophilic substance 51099 that can be released and/or exposed when the tubular element 51280 is severed. Furthermore, referring now to FIG. 211, when the hydrophilic substance 51099 contacts bodily fluids in the tissue T, the hydrophilic substance 51099 can attract the fluid, which can cause the tubular element 51280 to swell or expand. As the tubular element 51280 expands, the compensation material 51224 surrounding the tubular element 51280 can shift or adjust to accommodate the swollen tubular element 51280. For example, when the compensation material 51224 comprises gelatin, the gelatin can shift to accommodate the swollen tubular element 51280. Referring again to FIG. 208, expansion of the tubular elements 51280 and shifting of the compensation material 51224 can cause a corresponding expansion of the tissue thickness compensator 51220.

Similar to other tissue thickness compensators discussed throughout the present disclosure, the tissue thickness compensator 51220 can be deformed or compressed by an applied force. Further, the tissue thickness compensator 51220 can be sufficiently resilient such that it produces a springback force when deformed by the applied force and can subsequently rebound or partially rebound when the applied force is removed. In various embodiments, when the tissue thickness compensator 51220 is captured in a staple entrapment area 30039 (FIG. 88), the staple 30030 can deform the tissue thickness compensator 51220. For example, the staple 30030 can deform the tubular elements 51280 and/or the compensation material 51224 of the tissue thickness compensator 51220 captured within the fired staple 30030. In various embodiments, non-captured portions of the tissue thickness compensator 51220 can also be deformed due to the deformation in the staple entrapment areas 30039. When deformed, the tissue thickness compensator 51220 can seek to rebound from the deformed configuration. In various embodiments, such a rebound may occur prior to the hydrophilic expansion of the tubular element 51280, simultaneously with the hydrophilic expansion of the tubular element 51280, and/or after the hydrophilic expansion of the tubular element 51280. As the tissue thickness compensator 51220 seeks to rebound, it can exert a restoring force on the tissue also captured in the staple entrapment area 30039, as described in greater detail herein.

Referring to FIGS. 146-149, a tissue thickness compensator 52020 can comprise one or more tubular elements 52080 that laterally traverse the tissue thickness compensator 52020, similar to at least one tissue thickness compensator described herein. In various embodiments, the tissue thickness compensator 52020 can comprise multiple laterally traversing tubular elements 52080. The tissue thickness compensator 52020 can further comprise one or more sheets of material 52024 that hold or retain at least one tubular element 52080 in the tissue thickness compensator 52020. In various embodiments, the one or more sheets of material 52024 can be positioned above and/or below the tubular elements 52080 and can securely retain each tubular element 52080 in the tissue thickness compensator 52020. Referring primarily to FIG. 146, the tissue thickness compensator can comprise a first sheet of material 52024a and a second sheet of material 52024b. In various embodiments, the tubular elements 52080 can be positioned between the first and second sheets of material 52024a, 52024b. Further, referring still to FIG. 146, the sheet of material 52024b can be secured to the top deck surface 30011 of the rigid support portion of the staple cartridge 30000 such that the tissue thickness compensator 52020 is securely positioned in the end effector 12. In other embodiments, one or more of the sheets of material 52024 can be secured to the anvil 30060 or otherwise retained in the end effector 12.

In various embodiments, referring primarily to FIG. 147, the tissue thickness compensator 52020 can be porous and/or permeable. For example, the sheet of material 52024 can comprise a plurality of apertures 52026. In various embodiments, the apertures 52026 can be substantially circular. In at least one embodiment, the apertures 52036 can be visible in the sheet of material 52024. In other embodiments, the apertures 52036 can be microscopic. Referring still to FIG. 147, the tubular elements 52080 can comprise a plurality of apertures 52026, as well. In various embodiments, referring to FIG. 148, a tissue thickness compensator 52120 can comprise a sheet of material 52124 that comprises a plurality of non-circular apertures 52126. For example, the apertures 52126 can comprise a diamond and/or slotted shape. In various other embodiments, referring to FIG. 149, a tissue thickness compensator 52220 can comprise a tubular element 52280 that comprises a permeable tubular lattice 52292. In various embodiments, the sheet of material 52224 can comprise a bioabsorbable, biocompatible elastomeric polymer and can comprise a medicament, for example.

Similar to at least one embodiment described herein, at least one tubular element 52080 can be configured to swell or expand, as illustrated in FIGS. 150A-150D. For example, referring to FIG. 150A, the tubular elements 52080 can be positioned intermediate the first and second sheet of material 52024a, 52024b in the tissue thickness compensator 52020. When the tissue thickness compensator 52020 contacts tissue T, as illustrated in FIG. 150B, the tissue thickness compensator 52020 can expand. In various embodiments, for example, the tubular elements 52080 can comprise a hydrophilic substance 52099 that expands when exposed to fluid in and/or on the tissue T. Further, the sheet of material 52024 and tubular elements 52080 can be permeable, as described herein, such that fluid from the tissue T can permeate the tissue thickness compensator 52020 thereby allowing the fluid to contact the hydrophilic substance 52099 within the tubular elements 52080. As the tubular elements 52080 expand, the sheet of material 52024 surrounding the tubular elements 52080 can shift or adjust to accommodate the swollen tubular elements 52080. Similar to various tissue thickness compensators discussed throughout the present disclosure, the expanded tissue thickness compensator 52020 can be deformed or compressed by an applied force, such as, for example, a compressive force applied by fired staples, as illustrated in FIG. 150C. Further, the tissue thickness compensator 52020 can be sufficiently resilient such that it produces a springback force when deformed by the applied force and can subsequently rebound when the applied force is removed. Referring now to FIGS. 150D and 150E, the tissue thickness compensator 52020 can rebound to different configurations in different staple entrapment areas 30039 to appropriately accommodate the captured tissue T.

Referring to FIGS. 151-156, a tissue thickness compensator 53020 can comprise a plurality of vertically positioned tubular elements 53080. In various embodiments, each tubular element 53080 can comprise a tubular axis that is substantially perpendicular to the top deck surface 30011 of the rigid support portion 30010 of the staple cartridge 30000. Further, the first end of each tubular element 53080 can be positioned adjacent to the top deck surface 30011, for example. Similar to at least one embodiment described herein, the tubular elements 53080 can be deformable and may comprise an elastomeric polymer, for example. In various embodiments, as illustrated in FIG. 152, the tubular elements 53080 can be compressed when captured in a staple entrapment area 30039 with stapled tissue T. A tubular element 53080 can comprise an elastic material such that deformation of the tubular element 53080 generates a restoring force as the tubular element 53080 seeks to rebound from the deformed configuration. In some embodiments, deformation of the tubular element 53080 can be at least partially elastic and at least partially plastic. The tubular element 53080 can be configured to act as a spring under an applied force and, in various embodiments, can be configured not to buckle. In various embodiments, referring to FIG. 153, the tubular elements 53080 can be substantially cylindrical. In some embodiments, referring to FIG. 154, a tubular element 53180 can comprise a buckling region 53112. The tubular element 53180 can be configured to buckle or deform at the buckling region 53112 when a compressive force is applied thereto. The tubular element 53180 can deform elastically and/or plastically and then be designed to buckle suddenly at the buckling region 53112 under a preselected buckling force.

Referring primarily to FIG. 155, a first tubular element 53080 can be positioned at a first end of a staple cavity 30012 and another tubular element 53080 can be positioned at a second end of the staple cavity 30012. As illustrated in FIG. 153, the tubular element 53080 can comprise a lumen 53084 extending therethrough. Referring again to FIG. 152, when the staple 30030 is moved from the initial position to the fired position, each staple leg 30032 can be configured to pass through a lumen 53084 of each tubular element 53080. In various other embodiments, referring primarily to FIG. 156, vertically positioned tubular elements 54080 can be arranged in a tissue thickness compensator 54020 such that the tubular elements 54080 abut or contact each other. In other words, the tubular elements 54080 can be clustered or gathered together. In some embodiments, the tubular elements 54080 can be systematically arranged in the tissue thickness compensator 54020; however, in other embodiments, the tubular elements 54080 can be randomly arranged.

Referring again to FIGS. 151, 155, and 156, the tissue thickness compensator 53020 can also comprise a sheet of material 53024 that holds or retains the tubular elements 53080 in the tissue thickness compensator 53020. In various embodiments, the sheet of material 53024 can be positioned above and/or below the tubular elements 53080 and can securely retain each tubular element 53080 in the tissue thickness compensator 53020. In various embodiments, the tissue thickness compensator 53020 can comprise a first and a second sheet of material 53024. In various embodiments, the tubular elements 53080 can be positioned between the first and second sheets of material 53024. Further, the sheet of material 53024 can be secured to the top deck surface 30011 of the rigid support portion of the staple cartridge 30000 such that the tissue thickness compensator 53020 is securely positioned in the end effector 12. In other embodiments, a sheet of material 53024 can be secured to the anvil 30060 or otherwise retained in the end effector 12. Similar to at least one embodiment described herein, the sheet of material 53024 can be sufficiently deformable such that the sheet of material 53024 deforms as springs 55080 within the tissue thickness compensator are deformed.

Referring to FIGS. 157 and 158, a tissue thickness compensator 55020 can comprise at least one spring 55080 that is sufficiently resilient such that it is capable of producing a springback force when deformed. Referring primarily to FIG. 157, the tissue thickness compensator 55020 can comprise a plurality of springs 55080, such as, for example, three rows of springs 55080. The springs 55080 can be systematically and/or randomly arranged in the tissue thickness compensator 55020. In various embodiments, the springs 55080 can comprise an elastomeric polymer, for example. In some embodiments, the shape of the springs 55080 can allow for deformation thereof. In various embodiments, the springs 55080 can be deformed from an initial configuration to a deformed configuration. For example, when a portion of the tissue thickness compensator 55020 is captured in a staple entrapment area 30039, the springs 55080 in and/or around the staple entrapment area 30039 can be deformed. In various embodiments, the springs 55080 can buckle or collapse under a compressive force applied for a fired staple 30030 and the springs 55080 may generate a restoring force that is a function of the spring rate of the deformed spring 55080 and/or the amount the spring 55080 is deformed, for example. In some embodiments, the spring 55080 can act as a sponge under a compressive force applied by a fired staple 30030. Further, the spring 55080 can comprise a compensation material, as described in greater detail throughout the present disclosure.

The tissue thickness compensator 55020 can further comprise one or more sheets of material 55024 that hold or retain at least one spring 55080 in the tissue thickness compensator 55020. In various embodiments, the sheets of material 55024 can be positioned above and/or below the springs 55080 and can securely retain the springs 55080 in the tissue thickness compensator 55020. In at least one embodiment, the tissue thickness compensator 55020 can comprise a first sheet of material 55024*a* and a second sheet of material 55024*b*. In various embodiments, the tubular elements 52080 can be positioned between the first and second sheets of material 55024*a*, 55024*b*. Referring primarily to FIG. 158, in various embodiments, the tissue thickness compensator 55020 can further comprise a third sheet of material 55024*c* positioned adjacent to either the first or second sheet of material 55024*a*, 55024*b*. In various embodiments, at least one sheet of material 55024 can be secured to the top deck surface 30011 of the rigid support portion of the staple cartridge 30000, such that the tissue thickness compensator 55020 is securely positioned in the end effector 12. In other embodiments, at least one sheet of material 55024 can be secured to the anvil 30060 or otherwise retained in the end effector 12.

Referring now to FIG. 158, when a staple 30030 is fired from the staple cartridge 30000 (FIG. 156), the staple 30030 can engage the tissue thickness compensator 55020. In various embodiments, the fired staple 30030 can capture tissue T and a portion of the tissue thickness compensator 55020 in the staple entrapment area 30039. The springs 55080 can be deformable such that the tissue thickness compensator 55020 compresses when captured by a fired staple 30030. In some embodiments, the springs 55080 can be positioned between fired staples 30030 in the tissue thickness compensator 55020. In other embodiments, at least one spring 55080 can be captured within the staple entrapment area 30039.

Referring to FIG. 159, a tissue thickness compensator 60020 can comprise at least two compensation layers 60022. In various embodiments, the tissue thickness compensator 60020 can comprise a plurality of compensation layers 60022 which can be stacked on top of each other, positioned side-by-side, or a combination thereof. As described in greater detail herein, the compensation layers 60022 of the tissue thickness compensator 60020 can comprise different geometric and/or material properties, for example. Furthermore, as described in greater detail herein, pockets and/or channels can exist between adjacently stacked compensation layers 60022. For example, a tissue thickness compensator 62020 can comprise six compensation layers 62022a, 62022b, 62022c, 62022d, 62022e, 62022f, which can be adjacently stacked on top of each other (FIG. 174).

Referring to FIGS. 160, 161, and 163-168, a tissue thickness compensator can comprise a first compensation layer 60122a and a second compensation layer 60122b. In various embodiments, the first compensation layer 60122a can be adjacently stacked on top of the second compensation layer 60122b. In at least one embodiment, adjacently stacked compensation layers 60122 can be separated by a separation gap or pocket 60132. Referring primarily to FIG. 160, a tissue thickness compensator 60120 can also comprise at least one cantilever beam or support 60124 positioned between the first and second compensation layers 60122a, 60122b. In various embodiments, the support 60124 can be configured to position the first compensation layer 60122a relative to the second compensation layer 60122b such that compensation layers 60122 are separated by the separation gap 60132. As described in greater detail herein, deformation of the support 60124 and/or the compensation layers 60122a, 60122b, for example, can reduce the separation gap 60132.

The support beam of a tissue thickness compensator can comprise various geometries and dimensions. For example, the support beam can be a simple I-beam, a centered, single-bend support beam 60124 (FIG. 160), an off-centered, single-bend support beam 60224 (FIG. 161), an elliptical support beam 60324 (FIG. 163), a multi-bend support beam 60424 (FIG. 164), and/or a symmetrical, dual-cantilevered support beam 60524 (FIG. 165). Furthermore, referring now to FIGS. 160, 166, and 167, a support beam 60624 can be thinner than at least one compensation layer 60122 (FIG. 166), a support beam 60724 can be thicker than at least one compensation layer 60122 (FIG. 167), and/or a support beam 60124 can be substantially the same thickness as at least one compensation layer 60122 (FIG. 160), for example. The material, geometry and/or dimensions of the support beam 60124, for example, can affect the deformability and springback resiliency of the tissue thickness compensator 60120.

Referring still to FIG. 160, the compensation layers 60122 and support beam 60124 of the tissue thickness compensator 60120 can comprise different materials, such as, for example, structural material, biological material, and/or electrical material, for example. For example, in various embodiments, at least one compensation layer 60122 can comprise a polymeric composition. The polymeric composition can comprise an at least partially elastic material such that deformation of the compensation layer 60122 and/or the support beam 60124 can generate a springback force. The polymeric composition of the compensation layer 60122 can comprise non-absorbable polymers, absorbable polymers, or combinations thereof. In some embodiments, the absorbable polymers can include bioabsorbable, biocompatible elastomeric polymers, for example. Furthermore, the polymeric composition of the compensation layer 60122 can comprise synthetic polymers, non-synthetic polymers, or combinations thereof. Examples of synthetic polymers include, but are not limited to, polyglycolic acid (PGA), poly(lactic acid) (PLA), polycaprolactone (PCL), polydioxanone (PDO), and copolymers thereof. Examples of non-synthetic polymers include, but are not limited to, polysaccharides, glycoprotein, elastin, proteoglycan, gelatin, collagen, and oxidized regenerated cellulose (ORC). In various embodiments, similar to the polymeric compositions in embodiments described herein, the polymeric composition of the compensation layers 60122 can include varied amounts of absorbable polymers, non-absorbable polymers, synthetic polymers, and non-synthetic polymers, for example, by weight percentage. In various embodiments, each compensation layer 60022 in the tissue thickness compensator 60120 can comprise a different polymeric composition or, in various other embodiments, at least two compensation layers 60122 can comprise the same polymeric composition.

Referring again to FIG. 159, in various embodiments, at least one compensation layer 60022 can comprise a therapeutic agent 60098 such as a medicament or pharmaceutically active agent, for example. The compensation layer 60022 can release a therapeutically effective amount of the therapeutic agent 60098. In various embodiments, the therapeutic agent 60098 can be released as the compensation layer 60022 is absorbed. Examples of therapeutic agents 60098 can include, but are not limited to, haemostatic agents and drugs, such as, for example, fibrin, thrombin, and/or oxidized regenerated cellulose (ORC), anti-inflammatory drugs such as, for example, diclofenac, aspirin, naproxen, sulindac, and/or hydrocortisone antibiotic and antimicrobial drugs or agents such as, for example, triclosan, ionic silver, ampicillin, gentamicin, polymyxin B, and/or chloramphenicol, and/or anti-cancer agents such as, for example, cisplatin, mitomycin, and/or adriamycin. In some embodiments, the therapeutic agent 60098 can comprise a biologic, such as a stem cell, for example. In various embodiments, each compensation layer 60022 in a tissue thickness compensator 60020 can comprise a different therapeutic agent 60098 or, in various other embodiments, at least two compensation layers 60022 can comprise the same therapeutic agent 60098. In at least one embodiment, a compensation layer 60022 comprising a therapeutic agent 60098, such as a biologic, for example, can be encased between two structural compensation layers 60022 comprising a polymeric composition, such as, for example, polyglycolic acid (PGA) foam, for example. In various embodiments, a compensation layer 60022 can also comprise an electrically conductive material, such as, for example, copper.

In various embodiments, referring again to FIG. 174, the compensation layers 62022 in the tissue thickness compensator 62020 can have different geometries. When layers 62022 are adjacently positioned in the tissue thickness compensator 62020, the compensation layers 62022 can form at least one three-dimensional conduit 62032 between the layers 62022. For example, when a second compensation layer 62022b comprising a channel is positioned above a substantially flat third compensation layer 62022c, the channel and flat surface of the third compensation layer 62022c can define a three-dimensional conduit 62032a therebetween. Similarly, for example, when a fifth compensation layer 62022e comprising a channel is positioned below a fourth compensation layer 62022d comprising a corresponding channel, the channels can form a three-dimensional conduit 62032b defined by the channels in the adjacently stacked compensation layers 62022d, 62022e. In various embodiments, the conduits 62032 can direct therapeutic agents and/or bodily fluids as the fluids flow through the tissue thickness compensator 62020.

In various embodiments, referring to FIG. 170, a tissue thickness compensator 61020 can comprise compensation layers 61022, such as layers 60122a and 21022b, configured to receive staples 30030 deployed from the staple cartridge 20000 (FIG. 169). As a staple 30030 is moved from an initial position to a fired position, the geometry of at least one compensation layer 61022 can guide the staple legs 30032 to the fired position. In various embodiments, at least one compensation layer 61022 can comprise apertures 61030 extending therethrough, wherein the apertures 61030 can be arranged to receive the staple legs 30032 of deployed staples 30030 when the staples 30030 are fired from the staple cartridge 20000 (FIG. 169), as described in greater detail herein. In various other embodiments, referring again to FIG. 174, staple legs 30032 can pierce through at least one compensation layer, such as compensation layer 62022*f*, for example, and can be received through apertures 62030 in at least one compensation layer, such as, for example, compensation layer 62022*a*.

Referring primarily to FIG. 170, the tissue thickness compensator 60120 can comprise at least one support tab 61026 on one of the compensation layers 61022*a*, 61022*b*. The support tab 61026 can protrude into the separation gap 61032 defined between adjacent compensation layers, such as the gap 61032 between the first compensation layer 61020*a* and second compensation layer 61020*b*. In various embodiments, the support tab 61026 can protrude from a longitudinal side of a first compensation layer 61022*a*. Further, the support tab 61026 can extend along the length of the longitudinal side or only along a portion thereof. In various embodiments, at least one support tab 61026 can protrude from two longitudinal sides of the compensation layer 61022*a*, 61022*b*. Further, adjacently positioned compensation layers 61022*a*, 61022*b* can comprise corresponding support tabs 60126, such that the support tab 60126 that extends from the first compensation layer 60122*a* can at least partially align with the support tab 60126 that extends from the second compensation layer 60122*b*. In at least one embodiment, referring again to FIG. 168, a tissue thickness compensator 60820 can comprise a limiter plate 60828 between adjacent compensation layers 60122*a*, 60122*b*. The limiter plate 60828 can be positioned in the gap 60132 defined between the first compensation layer 60122*a* and the second compensation layer 60122*b*, for example. As described in greater detail herein, support tab(s) 61026 and/or limiter plate(s) 60828 can control the deformation and/or deflection of a support 60124 and/or the compensation layers 60122*a*, 60122*b*.

As described herein, in various embodiments, the compensation layers 60022 of the tissue thickness compensator 60020 can comprise different materials, geometries and/or dimensions. Such tissue thickness compensators 60020 can be assembled by a variety of manufacturing techniques. Referring primarily to FIG. 159, the tissue thickness compensator 60022 can be manufactured by lithographic, stereolithographic (SLA), or silk screening processes. For example, a stereolithographic manufacturing process can create a tissue thickness compensator 60020 in which each compensation layer 60022 comprises different materials and/or geometric features. For example, an ultraviolet light in a stereolithography machine can draw the geometry of a first compensation layer 60022, such that the first compensation layer 60022 comprising a first material, geometry and/or dimensions is cured by the ultraviolet light. The ultraviolet light can subsequently draw the geometry of a second compensation layer 60022, such that the second compensation layer 60022 comprising a second material, geometry and/or dimensions is cured by the ultraviolet light. In various embodiments, a stereolithography machine can draw compensation layers 60022 on top of each other, side-by-side, or a combination thereof. Further, the compensation layers 60022 can be drawn such that pockets 60132 exist between adjacent compensation layers 60022. Because a stereolithography machine can create very thin layers having unique geometries, a tissue thickness compensator 60020 manufactured by a stereolithographic process can comprise a very complex three-dimensional geometry.

In various embodiments, referring to FIG. 169, the tissue thickness compensator 60920 can be positioned in the end effector 12 of a surgical instrument 10 (FIG. 1). The tissue thickness compensator 60920 can be positioned relative to the staple cartridge 20000 of the end effector 12. For example, the tissue thickness compensator 60920 can be releasably secured to the staple cartridge 20000. In at least one embodiment, at least one compensation layer 60922 of the tissue thickness compensator 60920 can be positioned adjacent to the top deck surface 20011 (FIG. 79) of the staple cartridge 20000. For example, a second compensation layer 60922*b* can be secured to the top deck surface 20011 by an adhesive or by a wrap, similar to at least one of the wraps described herein (FIG. 16). In various embodiments, the tissue thickness compensator 60920 can be integral to the staple cartridge 20000 such that the staple cartridge 20000 and the tissue thickness compensator 60920 are formed as a single unit construction. For example, the staple cartridge 20000 can comprise a first body portion, such as the rigid support portion 20010 (FIG. 79), and a second body portion, such the as tissue thickness compensator 60920.

Still referring to FIG. 169, the tissue thickness compensator 60920 can comprise a first compensator portion 60920*a* and a second compensator portion 60920*b*. The first compensator portion 60920*a* can be positioned on a first longitudinal side of the staple cartridge 20000 and the second compensator portion 60920*b* can be positioned on a second longitudinal side of the staple cartridge 20000. In various embodiments, when the tissue thickness compensator 60920 is positioned relative to the staple cartridge 20000, the longitudinal slot 20015 (FIG. 78) in the rigid support portion 20010 (FIG. 78) can extend between the first compensator portion 60920*a* and the second compensator portion 60920*b*. When the cutting element 20052 on the staple-firing sled 20050 (FIG. 78) translates through the end effector 12, the cutting element 20052 can pass through the longitudinal slot 20015 between the first compensator portion 60920*a* and the second compensator portion 60920*b* without severing a portion of the tissue thickness compensator 60920, for example. In other embodiments, the cutting element 20052 can be configured to sever a portion of the tissue thickness compensator 60920.

In various embodiments, referring now to FIG. 162, a tissue thickness compensator 63020 can be configured to fit in the end effector 12' of a circular surgical instrument. In various embodiments, the tissue thickness compensator 62030 can comprise a circular first compensation layer 63022*a* and a circular second compensation layer 63022*b*. The second compensation layer 63022*b* can be positioned on a circular top deck surface 20011' of a circular staple cartridge 20000', wherein the second compensation layer 63022*b* can comprise a geometry that corresponds to the geometry of the deck surface 20011'. For example, the deck surface 20011' can comprise a stepped portion and the second compensation layer 63022*b* can comprise a corresponding stepped portion. Similar to various embodiments described herein, the tissue thickness compensator can further comprise at least one support 63024 and/or support tabs 63026, for example, extending around the tissue thickness compensator 63020.

Referring again to FIG. 170, fired staples 30030 can be configured to engage the tissue thickness compensator 60920. As described throughout the present disclosure, a fired staple 30030 can capture a portion of the tissue thickness compensator 60920 and tissue T and apply a compressive force to the tissue thickness compensator 60920. Further, referring primarily to FIGS. 171-173, the tissue thickness compensator 60920 can be deformable. In various embodiments, as described herein, a first compensation layer 60920*a* can be separated from a second compensation layer 60920*b* by a separation gap 60932. Referring to FIG. 171, prior to compression of the tissue thickness compensator 60920, the gap 60932 can comprise a first distance. When a compressive force A is applied to the tissue thickness compensator 60920 and tissue T, for example, by a fired staple 30030 (FIG. 170), the support 60924 can be configured to deform. Referring now to FIG. 172, the single-bend support beam 60924 can bend under the compressive force A such that the separation gap 60932 between the first compensation layer 60920*a* and the second compensation layer 60920*b* is reduced to a second distance. Referring primarily to FIG. 173, the first and second compensation layers 60922*a*, 60922*b* can also deform under the compressive force A. In various embodiments, the support tabs 60926 can control deformation of the compensation layers 60920. For example, the support tabs 60926 can prevent excessive bending of the compensation layers 60920 by supporting the longitudinal sides of the compensation layer 60920 when they come into contact with one another. The support tabs 60926 can also be configured to bend or bow under the compressive force A. Additionally or alternatively, the limiter plate 60128 (FIG. 168) described in greater detail herein, can limit the deformation of the compensation layers 60920 when the compensation layers 60920 and/or support tabs 60926 contact the limiter plate 60128.

Furthermore, similar to various tissue thickness compensators described herein, tissue thickness compensator 60920 can generate a springback or restoring force when deformed. The restoring force generated by the deformed tissue thickness compensator can at least depend on the orientation, dimensions, material, and/or geometry of the tissue thickness compensator 60920, as well as the amount of the tissue thickness compensator 60920 that is deformed by the applied force. Furthermore, in various embodiments, at least a portion of the tissue thickness compensator 60920 can be resilient such that the tissue thickness compensator 60920 generates a spring load or restoring force when deformed by a fired staple 30030. In at least one embodiment, the support 60924 can comprise an elastic material and/or at least one compensation layer 60922 can comprise an elastic material such that the tissue thickness compensator 60920 is resilient.

In various embodiments, referring now to FIG. 175, an end effector of a surgical stapling instrument can comprise a first jaw and a second jaw, wherein at least one of the first jaw and the second jaw can be configured to be moved relative to the other. In certain embodiments, the end effector can comprise a first jaw including a staple cartridge channel 19070 and a second jaw including an anvil 19060, wherein the anvil 19060 can be pivoted toward and/or away from the staple cartridge channel 19070, for example. The staple cartridge channel 19070 can be configured to receive a staple cartridge 19000, for example, which, in at least one embodiment, can be removably retained within the staple cartridge channel 19070. In various embodiments, the staple cartridge 19000 can comprise a cartridge body 19010 and a tissue thickness compensator 19020 wherein, in at least one embodiment, the tissue thickness compensator 19020 can be removably attached to the cartridge body 19010. Similar to other embodiments described herein, referring now to FIG. 176, the cartridge body 19010 can comprise a plurality of staple cavities 19012 and a staple 19030 positioned within each staple cavity 19012. Also similar to other embodiments described herein, the staples 19030 can be supported by staple drivers 19040 positioned within the cartridge body 19010 wherein a sled and/or firing member, for example, can be advanced through the staple cartridge 19000 to lift the staple drivers 19040 upwardly within the staple cavities 19012, as illustrated in FIG. 177, and eject the staples 19030 from the staple cavities 19012.

In various embodiments, referring primarily to FIGS. 175 and 176, the tissue thickness compensator 19020 can comprise resilient members 19022 and a vessel 19024 encapsulating the resilient members 19022. In at least one embodiment, the vessel 19024 can be sealed and can define a cavity containing an inner atmosphere having a pressure which is different than the surrounding atmospheric pressure. In certain embodiments, the pressure of the inner atmosphere can be greater than the pressure of the surrounding atmosphere while, in other embodiments, the pressure of the inner atmosphere can be less than the pressure of the surrounding atmosphere. In the embodiments in which the vessel 19024 contains a pressure less than the pressure of the surrounding atmosphere, the sidewall of the vessel 19024 can enclose a vacuum. In such embodiments, the vacuum can cause the vessel 19024 to distort, collapse, and/or flatten wherein the resilient members 19022 positioned within the vessel 19024 can be resiliently compressed within the vessel 19024. When a vacuum is drawn on the vessel 19024, the resilient members 19022 can deflect or deform downwardly and can be held in position by the sidewalls of the vessel 19024 in a compressed, or vacuum-packed, state.

Resilient member 19022 and vessel 19024 are comprised of biocompatible materials. In various embodiments, resilient member 19022 and/or vessel 19024 can be comprised of bioabsorbable materials such as PLLA, PGA, and/or PCL, for example. In certain embodiments, resilient member 19022 can be comprised of a resilient material. Resilient member 19022 can also comprise structural resilience. For example, resilient member 19022 can be in the form of a hollow tube.

Further to the above, the tissue thickness compensator 19020 can be positioned against or adjacent to the deck surface 19011 of the cartridge body 19010. When the staples 19030 are at least partially fired, referring now to FIG. 177, the legs of the staples 19030 can puncture or rupture the vessel 19024. In certain embodiments, the vessel 19024 can comprise a central portion 19026 which can be positioned over a cutting slot 19016 of the cartridge body 19010 such that, when a cutting member 19080 is advanced to incise tissue T positioned between the staple cartridge 19000 and the anvil 19060, the cutting member 19080 can also incise the central portion 19026 of the vessel 19024 thereby puncturing or rupturing the vessel 19024. In either event, once the vessel 19024 has been ruptured, the inner atmosphere within the vessel 19024 can equalize with the atmosphere surrounding the tissue thickness compensator 19020 and allow the resilient members 19022 to resiliently expand to regain, or at least partially regain, their undistorted and/or unflattened configuration. In such circumstances, the resilient members 19022 can apply a biasing force to the tissue T captured within the deformed staples 19020. More specifically, after being deformed by the forming surfaces of pockets 19062 defined in the anvil 19060, the legs of the staples 19030 can capture tissue T and at least a portion of a resilient member 19022 within the staples 19030 such that, when the vessel 19024 ruptures, the tissue thickness compensator 19020 can compensate for the thickness of the tissue T captured within the staples 19030. For instance, when the tissue T captured within a staple 19030 is thinner, a resilient member 19022 captured within that staple 19030 can expand to fill gaps within the staple 19030 and apply a sufficient compression force to the tissue T. Correspondingly, when the tissue T captured within a staple 19030 is thicker, a resilient member 19022 captured within that staple 19030 can remain compressed to make room for the thicker tissue within the staple 19030 and, likewise, apply a sufficient compression force to the tissue T.

When the vessel 19024 is punctured, as outlined above, the resilient members 19022 can expand in an attempt to resiliently return to their original configuration. In certain circumstances, the portion of resilient members 19022 that have been captured within the staples 19030 may not be able to return to their original undistorted shape. In such circumstances, the resilient members 19022 can comprise a spring which can apply a compression force to the tissue T captured within the staples 19030. In various embodiments, a resilient member 19022 can emulate a linear spring wherein the compression force applied by the resilient member 19022 is linearly proportional to the amount, or distance, in which the resilient member 19022 remains deflected within the staple 19030. In certain other embodiments, a resilient member 19022 can emulate a non-linear spring wherein the compression force applied by the resilient member 19022 is not linearly proportional to the amount, or distance, in which the resilient member 19022 remains deflected within the staple 19030.

In various embodiments, referring primarily to FIGS. 178 and 179, a staple cartridge 19200 can comprise a tissue thickness compensator 19220 which can comprise one or more sealed vessels 19222 therein. In at least one embodiment, each of the vessels 19222 can be sealed and can contain an inner atmosphere. In certain embodiments, the pressure of the inner atmosphere within a sealed vessel 19222 can exceed atmospheric pressure while, in certain other embodiments, the pressure of the inner atmosphere within a sealed vessel 19222 can be below atmospheric pressure. In embodiments where the pressure of the inner atmosphere within a vessel 19222 is below atmospheric pressure, the vessel 19222 can be described as containing a vacuum. In various embodiments, one or more of the vessels 19222 can be wrapped or contained in an outer shroud, container, wrap, and/or film 19224, for example, wherein the tissue thickness compensator 19220 can be positioned above a deck surface 19011 of the cartridge body 19010. In certain embodiments, each vessel 19222 can be manufactured from a tube having a circular, or an at least substantially circular, cross-section, for example, having a closed end and an open end. A vacuum can be drawn on the open end of the tube and, when a sufficient vacuum has been reached within the tube, the open end can be closed and sealed. In at least one such embodiment, the tube can be comprised of a polymeric material, for example, wherein the open end of the tube can be heat staked in order to close and seal the same. In any event, the vacuum within each vessel 19222 can pull the sidewalls of the tube inwardly and resiliently distort and/or flatten the tube. The vessels 19222 are illustrated in an at least partially flattened state in FIG. 179.

When the staples 19030 are in their unfired position, as illustrated in FIG. 179, the tips of the staples 19030 can be positioned below the tissue thickness compensator 19220. In at least one such embodiment, the staples 19030 can be positioned within their respective staple cavities 19012 such that the staples 19030 do not contact the vessels 19222 until the staples 19030 are moved from the unfired positions, illustrated in FIG. 179, to their fired positions, illustrated in FIG. 180. In certain embodiments, the wrap 19224 of the tissue thickness compensator 19220 can protect the vessels 19222 from being prematurely punctured by the staples 19030. When the staples 19030 are at least partially fired, referring now to FIG. 180, the legs of the staples 19030 can puncture or rupture the vessels 19222. In such circumstances, the inner atmospheres within the vessels 19222 can equalize with the atmosphere surrounding the vessels 19222 and resiliently expand to regain, or at least partially regain, their undistorted and/or unflattened configuration. In such circumstances, the punctured vessels 19222 can apply a biasing force to the tissue captured within the deformed staples 19030. More specifically, after being deformed by the forming surfaces of pockets 19062 defined in the anvil 19060, the legs of the staples 19030 can capture tissue T and at least a portion of a vessel 19222 within the staples 19030 such that, when the vessels 19222 rupture, the vessels 19222 can compensate for the thickness of the tissue T captured within the staples 19030. For instance, when the tissue T captured within a staple 19030 is thinner, a vessel 19222 captured within that staple 19030 can expand to fill gaps within the staple 19030 and, concurrently, apply a sufficient compression force to the tissue T. Correspondingly, when the tissue T captured within a staple 19030 is thicker, a vessel 19222 captured within that staple 19030 can remain compressed to make room for the thicker tissue within the staple 19030 and, concurrently, apply a sufficient compression force to the tissue T.

When the vessels 19222 are punctured, as outlined above, the vessels 19222 can expand in an attempt to resiliently return to their original configuration. The portion of vessels 19222 that have captured within the staples 19030 may not be able to return to their original undistorted shape. In such circumstances, the vessel 19222 can comprise a spring which can apply a compression force to the tissue T captured within the staples 19030. In various embodiments, a vessel 19222 can emulate a linear spring wherein the compression force applied by the vessel 19222 is linearly proportional to the amount, or distance, in which the vessel 19222 remains deflected within the staple 19030. In certain other embodiments, a vessel 19222 can emulate a non-linear spring wherein the compression force applied by the vessel 19222 is not linearly proportional to the amount, or distance, in which the vessel 19222 remains deflected within the staple 19030. In various embodiments, the vessels 19222 can be hollow and, in at least one embodiment, empty when they are in their sealed configuration. In certain other embodiments, each of the vessels 19222 can define a cavity and can further include at least one medicament contained therein. In at least some embodiments, the vessels 19222 can be comprised of at least one medicament which can be released and/or bioabsorbed, for example.

In various embodiments, the vessels 19222 of the tissue thickness compensator 19220 can be arranged in any suitable manner. As illustrated in FIG. 178, the staple cavities 19012 defined in the cartridge body 19010, and the staples 19030 positioned in the staple cavities 19012, can be arranged in rows. In at least the illustrated embodiment, the staple cavities 19012 can be arranged in six longitudinal, linear rows, for example; however, any suitable arrangement of staple cavities 19012 could be utilized. As also illustrated in FIG. 178, the tissue thickness compensator 19220 can comprise six vessels 19222 wherein each of the vessels 19222 can be aligned with, or positioned over, a row of staple cavities 19012. In at least one embodiment, each of the staples 19030 within a row of staple cavities 19012 can be configured to puncture the same vessel 19222. In certain situations, some of the staple legs of the staples 19030 may not puncture the vessel 19222 positioned thereover; however, in embodiments where the vessel 19222 defines a continuous internal cavity, for example, the cavity can be sufficiently punctured by at least one of the staples 19030 in order to allow the pressure of the internal cavity atmosphere to equalize with the atmospheric pressure surrounding the vessel 19222. In various embodiments, referring now to FIG. 185, a tissue thickness compensator can comprise a vessel, such as vessel 19222', for example, which can extend in a direction which is transverse to a line of staples 19030. In at least one such embodiment, a vessel 19222' can extend across multiple staple rows. In certain embodiments, referring now to FIG. 186, a tissue thickness compensator 19220" can comprise a plurality of vessels 19222" which extend in a direction which is perpendicular, or at least substantially perpendicular, to a line of staples 19030. In at least one such embodiment, some of the vessels 19222" may be punctured by the staples 19030 while others may not be punctured by the staples 19030. In at least one embodiment, the vessels 19222" can extend across or through a cutting path in which a cutting member could transect and rupture the vessels 19222", for example.

In various embodiments, as described above, a tissue thickness compensator, such as tissue thickness compensator 19220, for example, can comprise a plurality of sealed vessels, such as vessels 19222, for example. As also described above, each of the sealed vessels 19222 can comprise a separate internal atmosphere. In certain embodiments, the vessels 19222 can have different internal pressures. In at least one embodiment, for example, a first vessel 19222 can comprise an internal vacuum having a first pressure and a second vessel 19222 can comprise an internal vacuum having a second, different pressure, for example. In at least one such embodiment, the amount of distortion or flattening of a vessel 19222 can be a function of the vacuum pressure of the internal atmosphere contained therein. For instance, a vessel 19222 having a greater vacuum can be distorted or flattened a greater amount as compared to a vessel 19222 having a smaller vacuum. In certain embodiments, the cavity of a vessel can be segmented into two or more separate, sealed cavities wherein each separate, sealed cavity can comprise a separate internal atmosphere. In at least one such embodiment, some of the staples within a staple row can be configured and arranged to puncture a first cavity defined in the vessel while other staples within the staple row can be configured and arranged to puncture a second cavity defined in the vessel, for example. In such embodiments, especially in embodiments in which the staples in a staple row are sequentially fired from one end of the staple row to the other, as described above, one of the cavities can remain intact and can maintain its internal atmosphere when another cavity is ruptured. In certain embodiments, the first cavity can have an inner atmosphere having a first vacuum pressure and the second cavity can have an inner atmosphere having a second, different vacuum pressure, for example. In various embodiments, a cavity that remains intact can maintain its inner pressure until the vessel is bioabsorbed thereby creating a timed pressure release.

In various embodiments, referring now to FIGS. 181 and 182, a tissue thickness compensator, such as tissue thickness compensator 19120, for example, can be attached to an anvil 19160. Similar to the above, the tissue thickness compensator 19120 can comprise a vessel 19124 and a plurality of resilient members 19122 positioned therein. Also similar to the above, the vessel 19124 can define a cavity containing an inner atmosphere having a pressure which is less than or greater than the pressure of the atmosphere surrounding the tissue thickness compensator 19120. In embodiments where the inner atmosphere within the vessel 19124 comprises a vacuum, the vessel 19124 and the resilient members 19122 positioned therein can be distorted, collapsed, and/or flattened by the difference in pressure between the vacuum in the vessel 19124 and the atmospheric pressure outside of the vessel 19124. In use, the anvil 19160 can be moved into a closed position in which it is positioned opposite a staple cartridge 19100 and in which a tissue engaging surface 19121 on the vessel 19124 can engage the tissue T positioned intermediate the tissue thickness compensator 19120 and a staple cartridge 19100. In use, the firing member 19080 can be advanced distally to fire the staples 19030, as described above, and, at the same time, incise the tissue T. In at least one embodiment, the tissue thickness compensator 19120 can further comprise an intermediate portion 19126 which can be aligned with a cutting slot defined in the anvil 19160 wherein, when the firing member 19080 is advanced distally through the tissue thickness compensator 19120, the firing member 19080 can puncture or rupture the vessel 19124. Also, similar to the above, the firing member 19080 can lift the staple drivers 19040 upwardly and fire the staples 19030 such that the staples 19030 can contact the anvil 19160 and be deformed into their deformed configuration, as illustrated in FIG. 183. When the staples 19030 are fired, the staples 19030 can pierce the tissue T and then pierce or rupture the vessel 19124 such that the resilient members 19122 positioned within the vessel 19124 can at least partially expand, as outlined above.

In various embodiments, further to the above, a tissue thickness compensator can be comprised of a biocompatible material. The biocompatible material, such as, a foam, may comprise tackifiers, surfactants, fillers, cross-linkers, pigments, dyes, antioxidants and other stabilizers and/or combinations thereof to provide desired properties to the material. In certain embodiments, a biocompatible foam may comprise a surfactant. The surfactant may be applied to the surface of the material and/or dispersed within the material. Without wishing to be bound to any particular theory, the surfactant applied to the biocompatible material may reduce the surface tension of the fluids contacting the material. For example, the surfactant may reduce the surface tension of water contacting the material to accelerate the penetration of water into the material. In various embodiments, the water may act as a catalyst. The surfactant may increase the hydrophilicity of the material.

In various embodiments, the surfactant may comprise an anionic surfactant, a cationic surfactant, and/or a non-ionic surfactant. Examples surfactants include, but are not limited to polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy)ethanol, and polyoxamers, and combinations thereof. In at least one embodiment, the surfactant may comprise a copolymer of polyethylene glycol and polypropylene glycol. In at least one embodiment, the surfactant may comprise a phospholipid surfactant. The phospholipid surfactant may provide antibacterial stabilizing properties and/or disperse other materials in the biocompatible material. In various embodiments, the tissue thickness compensator may comprise at least one medicament. The tissue thickness compensator may comprise one or more of the natural materials, non-synthetic materials, and/or synthetic materials described herein. In certain embodiments, the tissue thickness compensator may comprise a biocompatible foam comprising gelatin, collagen, hyaluronic acid, oxidized regenerated cellulose, polyglycolic acid, polycaprolactone, polylactic acid, polydioxanone, polyhydroxyalkanoate, poliglecaprone, and combinations thereof. In certain embodiments, the tissue thickness compensator may comprise a film comprising the at least one medicament. In certain embodiments, the tissue thickness compensator may comprise a biodegradable film comprising the at least one medicament. In certain embodiments, the medicament may comprise a liquid, gel, and/or powder. In various embodiments, the medicaments may comprise anti-cancer agents, such as, for example, cisplatin, mitomycin, and/or adriamycin.

In various embodiments, the tissue thickness compensator may comprise a biodegradable material to provide controlled elution of the at least one medicament as the biodegradable material degrades. In various embodiments, the biodegradable material may degrade may decompose, or loses structural integrity, when the biodegradable material contacts an activator, such as, for example an activator fluid. In various embodiments, the activator fluid may comprise saline or any other electrolyte solution, for example. The biodegradable material may contact the activator fluid by conventional techniques, including, but not limited to spraying, dipping, and/or brushing. In use, for example, a surgeon may dip an end effector and/or a staple cartridge comprising the tissue thickness compensator comprising the at least one medicament into an activator fluid comprising a salt solution, such as sodium chloride, calcium chloride, and/or potassium chloride. The tissue thickness compensator may release the medicament as the tissue thickness compensator degrades. In certain embodiments, the elution of the medicament from the tissue thickness compensator may be characterized by a rapid initial elution rate and a slower sustained elution rate.

In various embodiments, a tissue thickness compensator, for example, can be comprised of a biocompatible material which may comprise an oxidizing agent. In various embodiments, the oxidizing agent may an organic peroxide and/or an inorganic peroxide. Examples of oxidizing agents may include, but are not limited to, hydrogen peroxide, urea peroxide, calcium peroxide, and magnesium peroxide, and sodium percarbonate. In various embodiments, the oxidizing agent may comprise peroxygen-based oxidizing agents and hypohalite-based oxidizing agents, such as, for example, hydrogen peroxide, hypochlorous acid, hypochlorites, hypocrites, and percarbonates. In various embodiments, the oxidizing agent may comprise alkali metal chlorites, hypochlorites and perborates, such as, for example, sodium chlorite, sodium hypochlorite and sodium perborate. In certain embodiments, the oxidizing agent may comprise vanadate. In certain embodiments, the oxidizing agent may comprise ascorbic acid. In certain embodiments, the oxidizing agent may comprise an active oxygen generator. In various embodiments, a tissue scaffold may comprise the biocompatible material comprising an oxidizing agent.

In various embodiments, the biocompatible material may comprise a liquid, gel, and/or powder. In certain embodiments, the oxidizing agent may comprise microparticles and/or nanoparticles, for example. For example, the oxidizing agent may be milled into microparticles and/or nanoparticles. In certain embodiments, the oxidizing agent may be incorporated into the biocompatible material by suspending the oxidizing agent in a polymer solution. In certain embodiments, the oxidizing agent may be incorporated into the biocompatible material during the lyophilization process. After lyophilization, the oxidizing agent may be attached to the cell walls of the biocompatible material to interact with the tissue upon contact. In various embodiments, the oxidizing agent may not be chemically bonded to the biocompatible material. In at least one embodiment, a percarbonate dry power may be embedded within a biocompatible foam to provide a prolonged biological effect by the slow release of oxygen. In at least one embodiment, a percarbonate dry power may be embedded within a polymeric fiber in a non-woven structure to provide a prolonged biological effect by the slow release of oxygen. In various embodiments, the biocompatible material may comprise an oxidizing agent and a medicament, such as, for example, doxycycline and ascorbic acid.

In various embodiments, the biocompatible material may comprise a rapid release oxidizing agent and/or a slower sustained release oxidizing agent. In certain embodiments, the elution of the oxidizing agent from the biocompatible material may be characterized by a rapid initial elution rate and a slower sustained elution rate. In various embodiments, the oxidizing agent may generate oxygen when the oxidizing agent contacts bodily fluid, such as, for example, water. Examples of bodily fluids may include, but are not limited to, blood, plasma, peritoneal fluid, cerebral spinal fluid, urine, lymph fluid, synovial fluid, vitreous fluid, saliva, gastrointestinal luminal contents, and/or bile. Without wishing to be bound to any particular theory, the oxidizing agent may reduce cell death, enhance tissue viability and/or maintain the mechanical strength of the tissue to tissue that may be damaged during cutting and/or stapling. In various embodiments, the biocompatible material may comprise at least one microparticle and/or nanoparticle. The biocompatible material may comprise one or more of the natural materials, non-synthetic materials, and synthetic materials described herein. In various embodiments, the biocompatible material may comprise particles having a mean diameter of about 10 nm to about 100 nm and/or about 10 µm to about 100 µm, such as, for example, 45-50 nm and/or 45-50 µm. In various embodiments, the biocompatible material may comprise biocompatible foam comprising at least one microparticle and/or nanoparticle embedded therein. The microparticle and/or nanoparticle may not be chemically bonded to the biocompatible material. The microparticle and/or nanoparticle may provide controlled release of the medicament. In certain embodiments, the microparticle and/or nanoparticle may comprise at least one medicament. In certain embodiments, the microparticle and/or nanoparticle may comprise a hemostatic agent, an anti-microbial agent, and/or an oxidizing agent, for example. In certain embodiments, the tissue thickness compensator may comprise a biocompatible foam comprising an hemostatic agent comprising oxidized regenerated cellulose, an anti-microbial agent comprising doxycline and/or Gentamicin, and/or an oxidizing agent comprising a percarbant. In various embodiments, the microparticle and/or nanoparticle may provide controlled release of the medicament up to three days, for example.

In various embodiments, the microparticle and/or nanoparticle may be embedded in the biocompatible material during a manufacturing process. For example, a biocompatible polymer, such as, for example, a PGA/PCL, may contact a solvent, such as, for example, dioxane to form a mixture. The biocompatible polymer may be ground to form particles. Dry particles, with or without ORC particles, may be contacted with the mixture to form a suspension. The suspension may be lyophilized to form a biocompatible foam comprising PGA/PCL having dry particles and/or ORC particles embedded therein.

In various embodiments, the tissue thickness compensators or layers disclosed herein can be comprised of an absorbable polymer, for example. In certain embodiments, a tissue thickness compensator can be comprised of foam, film, fibrous woven, fibrous non-woven PGA, PGA/PCL (Poly(glycolic acid-co-caprolactone)), PLA/PCL (Poly(lactic acid-co-polycaprolactone)), PLLA/PCL, PGA/TMC (Poly(glycolic acid-co-trimethylene carbonate)), PDS, PEPBO or other absorbable polyurethane, polyester, polycarbonate, Polyorthoesters, Polyanhydrides, Polyesteramides, and/or Polyoxaesters, for example. In various embodiments, a tissue thickness compensator can be comprised of PGA/PLA (Poly (glycolic acid-co-lactic acid)) and/or PDS/PLA (Poly(p-dioxanone-co-lactic acid)), for example. In various embodiments, a tissue thickness compensator can be comprised of an organic material, for example. In certain embodiments, a tissue thickness compensator can be comprised of Carboxymethyl Cellulose, Sodium Alginate, Cross-linked Hyaluronic Acid, and/or Oxidized regenerated cellulose, for example. In various embodiments, a tissue thickness compensator can comprise a durometer in the 3-7 Shore A (30-50 Shore OO) ranges with a maximum stiffness of 15 Shore A (65 Shore OO), for example. In certain embodiments, a tissue thickness compensator can undergo 40% compression under 3 lbf load, 60% compression under 6 lbf load, and/or 80% compression under 20 lbf load, for example. In certain embodiments, one or more gasses, such as air, nitrogen, carbon dioxide, and/or oxygen, for example, can be bubbled through and/or contained within the tissue thickness compensator. In at least one embodiment, a tissue thickness compensator can comprise beads therein which comprise between approximately 50% and approximately 75% of the material stiffness comprising the tissue thickness compensator.

In various embodiments, a tissue thickness compensator can comprise hyaluronic acid, nutrients, fibrin, thrombin, platelet rich plasma, Sulfasalazine (Azulfidine®–5ASA+ Sulfapyridine diazo bond))–prodrug–colonic bacterial (Azoreductase), Mesalamine (5ASA with different prodrug configurations for delayed release), Asacol® (5ASA+ Eudragit-S coated–pH>7 (coating dissolution)), Pentasa® (5ASA+ethylcellulose coated–time/pH dependent slow release), Mesasal® (5ASA+Eudragit-L coated–pH>6), Olsalazine (5ASA+5ASA–colonic bacterial (Azoreductase)), Balsalazide (5ASA+4-Aminobenzoyl-B-alanine)–colonic bacterial (Azoreductase)), Granulated mesalamine, Lialda (delay and SR formulation of mesalamine), HMPL-004 (herbal mixture that may inhibit TNF-alpha, interleukin-1 beta, and nuclear-kappa B activation), CCX282-B (oral chemokine receptor antagonist that interferes with trafficking of T lymphocytes into the intestinal mucosa), Rifaximin (nonabsorbable broad-spectrum antibiotic), Infliximab, murine chymieric (monoclonal antibody directed against TNF-alpha-approved for reducing signs/symptoms and maintaining clinical remission in adult/pediatric patients with moderate/severe luminal and fistulizing Crohn's disease who have had inadequate response to conventional therapy), Adalimumab, Total Human IgG1 (anti-TNF-alpha monoclonal antibody-approved for reducing signs/symptoms of Crohn's disease, and for the induction and maintenance of clinical remission in adult patients with moderate/severe active Crohn's disease with inadequate response to conventional therapies, or who become intolerant to Infliximab), Certolizumab pegoll, humanized anti-TNF FAB' (monoclonal antibody fragment linked to polyethylene glycol-approved for reducing signs/symptoms of Crohn's disease and for the induction and maintenance of response in adult patients w/moderate/severe disease with inadequate response to conventional therapies), Natalizumab, First non-TNF-alpha inhibitor (biologic compound approved for Crohn's disease), Humanized monoclonal IgG4 antibody (directed against alpha-4 integrin-FDA approved for inducing and maintaining clinical response and remission in patients with moderate/severe disease with evidence of inflammation and who have had inadequate response to or are unable to tolerate conventional Crohn's therapies and inhibitors of TNF-alpha), concomitant Immunomodulators potentially given with Infliximab, Azathioprine 6-Mercaptopurine (purine synthesis inhibitor-prodrug), Methotrexate (binds dihydrofolate reductase (DHFR) enzyme that participates in tetrahydrofolate synthesis, inhibits all purine synthesis), Allopurinol and Thioprine therapy, PPI, H2 for acid suppression to protect the healing line, C-Diff-Flagyl, Vancomycin (fecal translocation treatment; probiotics; repopulation of normal endoluminal flora), and/or Rifaximin (treatment of bacterial overgrowth (notably hepatic encephalopathy); not absorbed in GI tract with action on intraluminal bacteria), for example.

As described herein, a tissue thickness compensator can compensate for variations in the thickness of tissue that is captured within the staples ejected from a staple cartridge and/or contained within a staple line, for example. Stated another way, certain staples within a staple line can capture thick portions of the tissue while other staples within the staple line can capture thin portions of the tissue. In such circumstances, the tissue thickness compensator can assume different heights or thicknesses within the staples and apply a compressive force to the tissue captured within the staples regardless of whether the captured tissue is thick or thin. In various embodiments, a tissue thickness compensator can compensate for variations in the hardness of the tissue. For instance, certain staples within a staple line can capture highly compressible portions of the tissue while other staples within the staple line can capture portions of the tissue which are less compressible. In such circumstances, the tissue thickness compensator can be configured to assume a smaller height within the staples that have captured tissue having a lower compressibility, or higher hardness, and, correspondingly, a larger height within the staples that have captured tissue having a higher compressibility, or lower hardness, for example. In any event, a tissue thickness compensator, regardless of whether it compensates for variations in tissue thickness and/or variations in tissue hardness, for example, can be referred to as a 'tissue compensator' and/or as a 'compensator', for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A fastener cartridge assembly for a surgical instrument, the fastener cartridge assembly comprising:
   a cartridge body comprising a longitudinal row of fastener cavities;
   a deformable tube positioned relative to said cartridge body, wherein said deformable tube comprises a resilient material, and wherein said deformable tube comprises:
      a top portion;
      a bottom portion;
      a first end;
      a second end; and
      a tubular channel intermediate said top portion and said bottom portion and extending between said first end and said second end, wherein said top portion and said bottom portion are positioned above said cartridge body; and
   a fastener moveable between an initial position and a fired position, wherein said fastener is positioned in a fastener cavity in said row of fastener cavities when said fastener is in said initial position, and wherein said fastener is configured to engage a portion of said deformable tube when said fastener is moved to said fired position.

2. The fastener cartridge assembly of claim 1, wherein said cartridge body further comprises a deck, wherein said deformable tube overlies at least a portion of said longitudinal row of fastener cavities.

3. The fastener cartridge assembly of claim 2, wherein said deformable tube is positioned adjacent to said deck of said cartridge body.

4. The fastener cartridge assembly of claim 2, wherein said cartridge body comprises a plurality of substantially parallel rows of fastener cavities, wherein said plurality of substantially parallel rows of fastener cavities comprises said longitudinal row of fastner cavities, and wherein said cartridge body further comprises:
   a slot extending between two said substantially parallel rows of fastener cavities; and
   a cutting element configured to translate within said slot, wherein at least a portion of said deformable tube overlies said slot such that said cutting element is configured to cut at least a portion of said deformable tube.

5. The fastener cartridge assembly of claim 2, wherein said deformable tube comprises a first deformable tube, wherein the fastener cartridge assembly further comprises a second deformable tube, wherein said second deformable tube is substantially parallel to said first deformable tube.

6. The fastener cartridge assembly of claim 5, wherein said second deformable tube is positioned within said first deformable tube.

7. The fastener cartridge assembly of claim 6, further comprising a third deformable tube, wherein said third deformable tube is positioned within said second deformable tube.

8. The fastener cartridge assembly of claim 5, further comprising a third deformable tube, wherein said first deformable tube is aligned with a longitudinal axis defined by said cartridge body, wherein said second deformable tube is positioned on a first side of said first deformable tube, and wherein said third deformable tube is positioned on a second side of said first deformable tube.

9. The fastener cartridge assembly of claim 5, wherein said first deformable tube and said second deformable tube are coextruded with an adjoining portion to form a single piece.

10. The fastener cartridge assembly of claim 1, wherein said deformable tube comprises a lattice of strands woven together to form a tube wall.

11. The fastener cartridge assembly of claim 10, wherein said lattice of strands comprises tubular strands.

12. The fastener cartridge assembly of claim 10, wherein said lattice of strands comprises bioabsorbable strands.

13. The fastener cartridge assembly of claim 10, wherein said deformable tube further comprises a non-porous tube positioned one of outside and inside said lattice of strands, and wherein said non-porous tube is coextruded with said lattice of strands.

14. The fastener cartridge assembly of claim 13, wherein said lattice of strands is at least partially filled with a therapeutic agent to treat tissue.

15. A fastener cartridge for a surgical instrument, the fastener cartridge comprising:
   a cartridge body defining a longitudinal axis;
   a first plurality of strands woven into a resilient lattice, wherein said resilient lattice is substantially parallel to said longitudinal axis, and wherein said resilient lattice comprises:
      a top wall;
      a bottom wall; and
      a channel intermediate said top wall and said bottom wall, wherein said top wall and said bottom wall are positioned above said cartridge body; and
   fasteners moveable between an initial position and a fired position, wherein at least one said fastener is configured to compress a portion of said resilient lattice when said at least one fastener is moved to said fired position.

16. The fastener cartridge of claim 15, wherein said resilient lattice comprises a first resilient lattice, wherein said fastener cartridge further comprises a second plurality of strands woven into a second resilient lattice, wherein said second resilient lattice is substantially parallel to said longitudinal axis, and wherein at least one of said first plurality of strands and said second plurality of strands comprises tubular strands.

17. An end effector assembly for a surgical instrument, the end effector assembly comprising:
   an anvil;
   a fastener cartridge, comprising:
      at least one row of fastener cavities; and
      fasteners moveable between an initial position and a fired position, wherein each said fastener is positioned in a said fastener cavity when each said fastener is in said initial position; and a tube, wherein said tube comprises a resilient material, wherein said tube is substantially parallel to said at least one row of fastener cavities, and wherein said tube comprises:
   a top portion;
   a bottom portion; and
   a tubular passage intermediate said top portion and said bottom portion, wherein said top portion and said bottom portion are positioned between said anvil and said fastener cartridge;
wherein at least one said fastener, when moved to said fired position, is configured to deform a portion of said tube.

18. The end effector assembly of claim 17, wherein said tube comprises a therapeutic agent to treat tissue.

19. The end effector assembly of claim 18, wherein said tube is bioabsorbable such that said tube releases said therapeutic agent as said tube is being bioabsorbed.

20. The end effector assembly of claim 18, further comprising a cutting element configured to translate along at least a portion of a slot in said fastener cartridge, wherein at least one of said cutting element and said fasteners is configured to penetrate said tube such that said therapeutic agent is released from said tube.

\* \* \* \* \*